US011299741B2

(12) United States Patent
Bruno et al.

(10) Patent No.: US 11,299,741 B2
(45) Date of Patent: *Apr. 12, 2022

(54) MANIPULATION OF GENES INVOLVED IN SIGNAL TRANSDUCTION TO CONTROL FUNGAL MORPHOLOGY DURING FERMENTATION AND PRODUCTION

(71) Applicant: Zymergen Inc., Emeryville, CA (US)

(72) Inventors: Kenneth S. Bruno, Walnut Creek, CA (US); Sachin Jain, Emeryville, CA (US); Brandon Pfannenstiel, Walnut Creek, CA (US); Edyta Szewczyk, Walnut Creek, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/245,928

(22) Filed: Apr. 30, 2021

(65) Prior Publication Data

US 2021/0254080 A1   Aug. 19, 2021

Related U.S. Application Data

(63) Continuation of application No. 16/433,624, filed on Jun. 6, 2019, now Pat. No. 11,028,401.

(60) Provisional application No. 62/681,604, filed on Jun. 6, 2018.

(51) Int. Cl.
| | |
|---|---|
| *C12N 15/80* | (2006.01) |
| *C12N 15/90* | (2006.01) |
| *C12N 1/18* | (2006.01) |
| *C12R 1/865* | (2006.01) |

(52) U.S. Cl.
CPC ............. *C12N 15/80* (2013.01); *C12N 1/185* (2021.05); *C12N 15/905* (2013.01); *C12R 2001/865* (2021.05)

(58) Field of Classification Search
None
See application file for complete search history.

(56) References Cited

U.S. PATENT DOCUMENTS

| | | | |
|---|---|---|---|
| 4,935,349 A | 6/1990 | Mcknight et al. |
| 5,198,345 A | 3/1993 | Gwynne et al. |
| 5,252,726 A | 10/1993 | Woldike |
| 5,516,670 A | 5/1996 | Kuehnle et al. |
| 5,578,463 A | 11/1996 | Berke et al. |
| 5,605,793 A | 2/1997 | Stemmer |
| 5,705,358 A | 1/1998 | Gouka et al. |
| 5,741,665 A | 4/1998 | Kato et al. |
| 5,753,477 A | 5/1998 | Chan |
| 5,837,458 A | 11/1998 | Minshull et al. |
| 5,876,988 A | 3/1999 | Selten et al. |
| 5,939,306 A | 8/1999 | Alex et al. |
| 5,965,384 A | 10/1999 | Boel et al. |
| 6,040,439 A | 3/2000 | Hayakawa |
| 6,716,625 B1 | 4/2004 | Selitrennikoff et al. |
| 9,744,533 B2 | 8/2017 | Breinlinger et al. |
| 9,815,056 B2 | 11/2017 | Wu et al. |
| 9,857,333 B2 | 1/2018 | Chapman et al. |
| 9,889,445 B2 | 2/2018 | Chapman et al. |
| 9,895,699 B2 | 2/2018 | Short et al. |
| 9,908,115 B2 | 3/2018 | Hobbs et al. |
| 9,988,624 B2 | 6/2018 | Berber et al. |
| 9,996,920 B2 | 6/2018 | Du et al. |
| 10,010,882 B2 | 7/2018 | White et al. |
| 10,047,358 B1 | 8/2018 | Berber et al. |
| 10,058,865 B2 | 8/2018 | Breinlinger et al. |
| 10,101,250 B2 | 10/2018 | White et al. |
| 10,239,058 B2 | 3/2019 | Lavieu et al. |
| D844,471 S | 4/2019 | Stone et al. |
| 10,245,588 B2 | 4/2019 | Khandros et al. |
| 10,252,907 B2 | 4/2019 | Breinlinger et al. |
| 10,336,998 B2 | 7/2019 | Serber et al. |
| 10,350,594 B2 | 7/2019 | Hobbs et al. |
| 10,384,204 B2 | 8/2019 | Mcfarland et al. |
| 10,407,658 B2 | 9/2019 | Newstrom et al. |
| 10,457,933 B2 | 10/2019 | Serber et al. |
| 10,569,271 B2 | 2/2020 | Wu et al. |
| 10,578,630 B2 | 3/2020 | Du |
| 10,646,871 B2 | 5/2020 | White et al. |
| D887,296 S | 6/2020 | Stone et al. |
| 10,675,625 B2 | 6/2020 | Lionberger et al. |

(Continued)

FOREIGN PATENT DOCUMENTS

| | | |
|---|---|---|
| EP | 0238023 A2 | 9/1987 |
| EP | 0635574 B1 | 4/2003 |

(Continued)

OTHER PUBLICATIONS

Hagiwara et al., "Characterization of NikA Histidine Kinase and Two Response Regulators with Special Reference to Osmotic Adaptation and Asexual Development in Aspergillus nidulans" 73(7) Bioscience, Biotechnology, and Biochemistry 1566-1571 (Year: 2009).*

Aoyama, et al., "Spy1, a Histidine-Containing Phosphotransfer Signaling Protein, Regulates the Fission Yeast Cell Cycle through the Mcs4 Response Regulator." Journal of Bacteriology (Sep. 2000); 182(17): 4868-4874.

Arentshorst, et al., "Efficient Generation of Aspergillus niger Knock Out Strains by Combining NHEJ Mutants and a Split Marker Approach". In: van den Berg M., Maruthachalam K. (eds) Genetic Transformation Systems in Fungi (2014), vol. 1. Fungal Biology, pp. 263-272, 10 pages.

(Continued)

*Primary Examiner* — Nancy J Leith
(74) *Attorney, Agent, or Firm* — Cooley LLP

(57) ABSTRACT

The present disclosure provides a microbial genomic engineering method and system for transforming, screening, and selecting filamentous fungal cells that have altered morphology and/or growth under specific growth conditions. The method and system utilize high-throughput (HTP) methods to produce filamentous fungal production strains with a desired morphological phenotype.

29 Claims, 25 Drawing Sheets

Specification includes a Sequence Listing.

(56) References Cited

U.S. PATENT DOCUMENTS

| | | |
|---|---|---|
| 10,690,628 B2 | 6/2020 | Chapman et al. |
| 10,705,082 B2 | 7/2020 | Beaumont et al. |
| 10,712,344 B2 | 7/2020 | Chapman et al. |
| 10,723,988 B2 | 7/2020 | Lowe, Jr. et al. |
| 10,751,715 B1 | 8/2020 | Guan et al. |
| 10,954,511 B2 | 3/2021 | SunSpiral et al. |
| 10,973,227 B2 | 4/2021 | White et al. |
| 11,007,520 B2 | 5/2021 | Lowe, Jr. et al. |
| 11,028,401 B2 | 6/2021 | Bruno et al. |
| 11,180,753 B2 | 11/2021 | SunSpiral et al. |
| 2008/0038201 A1 | 2/2008 | Klein et al. |
| 2009/0280529 A1 | 11/2009 | Berg et al. |
| 2009/0317798 A1 | 12/2009 | Heid et al. |
| 2010/0216648 A1 | 8/2010 | Staehler et al. |
| 2011/0272127 A1 | 7/2011 | Jacobson et al. |
| 2011/0223671 A1 | 9/2011 | Yoder et al. |
| 2013/0149742 A1 | 6/2013 | Bower et al. |
| 2013/0319861 A1 | 12/2013 | Khandros et al. |
| 2014/0017791 A1 | 1/2014 | Chapman et al. |
| 2014/0116881 A1 | 5/2014 | Chapman et al. |
| 2014/0120558 A1 | 5/2014 | Chapman |
| 2014/0124370 A1 | 5/2014 | Short et al. |
| 2014/0220689 A1 | 8/2014 | Bodie et al. |
| 2015/0111784 A1 | 4/2015 | Chapman |
| 2015/0151298 A1 | 6/2015 | Hobbs et al. |
| 2015/0151307 A1 | 6/2015 | Breinlinger et al. |
| 2015/0165436 A1 | 6/2015 | Chapman et al. |
| 2015/0166326 A1 | 6/2015 | Chapman et al. |
| 2015/0211013 A1 | 7/2015 | Emalfarb et al. |
| 2015/0306598 A1 | 10/2015 | Khandros et al. |
| 2015/0306599 A1 | 10/2015 | Khandros et al. |
| 2015/0352547 A1 | 12/2015 | Breinlinger et al. |
| 2016/0158748 A1 | 6/2016 | Wu et al. |
| 2016/0158757 A1 | 6/2016 | Breinlinger et al. |
| 2016/0160259 A1 | 6/2016 | Du |
| 2016/0171686 A1 | 6/2016 | Du et al. |
| 2016/0184821 A1 | 6/2016 | Hobbs et al. |
| 2016/0193604 A1 | 7/2016 | Mcfarland et al. |
| 2016/0199837 A1 | 7/2016 | Breinlinger et al. |
| 2016/0257918 A1 | 9/2016 | Chapman et al. |
| 2016/0304905 A1 | 10/2016 | Hansen et al. |
| 2016/0312165 A1 | 10/2016 | Lowe, Jr. et al. |
| 2016/0318038 A1 | 11/2016 | Short et al. |
| 2016/0338347 A1 | 11/2016 | White et al. |
| 2016/0340632 A1 | 11/2016 | Breinlinger et al. |
| 2016/0370266 A1 | 12/2016 | White et al. |
| 2017/0021366 A1 | 1/2017 | Chapman et al. |
| 2017/0043343 A1 | 2/2017 | Khandros et al. |
| 2017/0113231 A9 | 4/2017 | Breinlinger et al. |
| 2017/0114316 A1 | 4/2017 | Newstrom et al. |
| 2017/0159045 A1 | 6/2017 | Serber et al. |
| 2017/0165667 A1 | 6/2017 | Beaumont et al. |
| 2017/0173580 A1 | 6/2017 | Lowe, Jr. et al. |
| 2017/0184583 A1 | 6/2017 | Beaumont et al. |
| 2017/0224734 A1 | 8/2017 | Chapman et al. |
| 2017/0276679 A1 | 9/2017 | Chapman et al. |
| 2017/0316353 A1 | 11/2017 | Frewen et al. |
| 2017/0354969 A1 | 12/2017 | Lionberger et al. |
| 2017/0355595 A1 | 12/2017 | Breinlinger et al. |
| 2018/0037919 A1 | 2/2018 | Bodie et al. |
| 2018/0099282 A1 | 4/2018 | Breinlinger et al. |
| 2018/0126380 A1 | 5/2018 | Khandros et al. |
| 2018/0135011 A1 | 5/2018 | Bronevetsky et al. |
| 2018/0147576 A1 | 5/2018 | Lavieu et al. |
| 2018/0193835 A1 | 7/2018 | Hobbs et al. |
| 2018/0259482 A1 | 9/2018 | Chapman et al. |
| 2018/0272350 A1 | 9/2018 | Chapman et al. |
| 2018/0298318 A1 | 10/2018 | Kurz et al. |
| 2018/0362991 A1 | 12/2018 | Berber et al. |
| 2019/0060900 A1 | 2/2019 | Breinlinger et al. |
| 2019/0060907 A1 | 2/2019 | Bao et al. |
| 2019/0064038 A1 | 2/2019 | White et al. |
| 2019/0083983 A1 | 3/2019 | Breinlinger et al. |
| 2019/0085375 A1 | 3/2019 | Mcewen |
| 2019/0134630 A1 | 5/2019 | White |
| 2019/0152771 A1 | 5/2019 | Breinlinger et al. |
| 2019/0172196 A1 | 6/2019 | Du et al. |
| 2019/0194692 A1 | 6/2019 | Meijrink et al. |
| 2019/0217297 A1 | 7/2019 | Lavieu et al. |
| 2019/0240665 A1 | 8/2019 | Lionberger et al. |
| 2019/0275516 A1 | 9/2019 | Lowe, Jr. et al. |
| 2019/0283026 A1 | 9/2019 | Loutherback et al. |
| 2019/0323036 A1 | 10/2019 | Bruno et al. |
| 2019/0345488 A1 | 11/2019 | Soumillon et al. |
| 2019/0374944 A1 | 12/2019 | Lundguist et al. |
| 2019/0376070 A1 | 12/2019 | Bruno et al. |
| 2019/0384963 A1 | 12/2019 | Kim et al. |
| 2020/0017817 A1 | 1/2020 | Kelly-greene et al. |
| 2020/0032193 A1 | 1/2020 | Newstrom et al. |
| 2020/0038857 A1 | 2/2020 | Mcfarland et al. |
| 2020/0064337 A1 | 2/2020 | Park et al. |
| 2020/0071693 A1 | 3/2020 | SunSpiral et al. |
| 2020/0078785 A1 | 3/2020 | Hobbs et al. |
| 2020/0078788 A1 | 3/2020 | Chapman et al. |
| 2020/0115680 A1 | 4/2020 | Bronevetsky et al. |
| 2020/0123491 A1 | 4/2020 | Beemiller et al. |
| 2020/0123535 A1 | 4/2020 | SunSpiral et al. |
| 2020/0139362 A1 | 5/2020 | Beemiller et al. |
| 2020/0171501 A1 | 6/2020 | Mcewen et al. |
| 2020/0230601 A1 | 7/2020 | White et al. |
| 2021/0102150 A1 | 4/2021 | Kurz et al. |
| 2021/0114020 A1 | 4/2021 | Lowe, Jr. et al. |
| 2021/0115436 A1 | 4/2021 | Ramenani et al. |
| 2021/0129142 A1 | 5/2021 | Hobbs et al. |
| 2021/0284993 A1 | 9/2021 | SunSpiral et al. |

FOREIGN PATENT DOCUMENTS

| | | |
|---|---|---|
| JP | H11304666 A | 11/1999 |
| WO | WO 1993/007277 A1 | 4/1993 |
| WO | WO 1993/025663 A1 | 12/1993 |
| WO | WO 1997/006261 A2 | 2/1997 |
| WO | WO 1997/008332 A1 | 3/1997 |
| WO | WO 2000/020555 A2 | 4/2000 |
| WO | WO 2005/021772 A1 | 3/2005 |
| WO | WO 2005/095624 A2 | 10/2005 |
| WO | WO 2008/113847 A2 | 9/2008 |
| WO | WO 2009/085135 A2 | 7/2009 |
| WO | WO 2011/154147 A1 | 12/2011 |
| WO | WO 2013/135729 A1 | 9/2013 |
| WO | WO 2015/082535 A1 | 6/2015 |
| WO | WO 2015/168184 A1 | 11/2015 |
| WO | WO 2016/073990 A2 | 5/2016 |
| WO | WO 2016/100272 A1 | 6/2016 |
| WO | WO 2016/100568 A1 | 6/2016 |
| WO | WO 2016/100571 A1 | 6/2016 |
| WO | WO 2017/100376 A2 | 6/2017 |
| WO | WO 2017/100377 A1 | 6/2017 |
| WO | WO 2017/189784 A1 | 11/2017 |
| WO | WO 2018/126207 A1 | 12/2017 |
| WO | WO 2018/009372 A1 | 1/2018 |
| WO | WO 2018/050666 A1 | 3/2018 |
| WO | WO 2018/226900 A2 | 6/2018 |
| WO | WO 2018/123134 A1 | 7/2018 |
| WO | WO 2019/236848 A1 | 12/2019 |
| WO | WO 2021/081432 A1 | 4/2021 |
| WO | WO 2021/097449 A1 | 5/2021 |

OTHER PUBLICATIONS

Arras and Fraser, "Chemical Inhibitors of Non-Homologous End Joining Increase Targeted Construct Integration in Cryptococcus neoformans". PLoS One (Sep. 2016); 11(9): e0163049.

Barcellos, et al. "Genetic analysis of Aspergillus nidulans unstable transformants obtained by the biolistic process." Canadian Journal of Microbiology (1998); 44(12): 1137-1141.

Basu, et al., "Purification of specific cell population by fluorescence activated cell sorting (FACS)". J Vis Exp. (2010); (41):1546. Published Jul. 10, 2010.

Becker and Guarente, "[12] High-efficiency transformation of yeast by electroporation." Methods in Enzymology (1991); 194: 182-187.

(56) References Cited

OTHER PUBLICATIONS

Bégueret, et al., "Cloning gene ura5 for the orotidylic acid pyrophosphorylase of the filamentous fungus *Podospora anserina*: transformation of protoplasts". Gene (Dec. 1984); 32(3): 487-492.
Beydon, et al., "Microbiological High Throughput Screening: An Opportunity for the Lead Discovery Process". Journal of Biomolecular Screening (2000); 5(1): 13-22.
Bischof, et al., "A versatile platform for creating a comprehensive UAS-ORFeome library in *Drosophila*", Development (Jun. 2013); 140(11): 2434-2442. Epub May 1, 2013.
Blumhoff, et al., "Targeting enzymes to the right compartment: metabolic engineering for itaconic acid production by Aspergillus niger". Metab Eng. (2013); 19: 26-32.
Brown, et al., "Yeast Skn7p functions in a eukaryotic two-component regulatory pathway." The EMBO Journal (1994); 13(21): 5186-5194.
Casqueiro, et al., "Gene Targeting in Penicillium chrysogenum: Disruption of the lys2 Gene Leads to Penicillin Overproduction". Journal of Bacteriology (Feb. 1999); 181(4): 1181-1188.
Catlett, et al., "Split-Marker Recombination for Efficient Targeted Deletion of Fungal Genes". Fungal Genetics Reports (2003); 50(Article 4): 9-11.
Chakraborty and Kapoor, "Transformation of filamentous fungi by electroporation." Nucleic Acids Research (1990); 18(22): 6737.
Cheng and Belanger, "Protoplast preparation and regeneration from spores of the biocontrol fungus Pseudozyma flocculosa". FEMS Microbiology Letters (Sep. 2000); 190(2): 287-291.
Choi, et al., "Single spore isolation of fungi". Fungal Diversity (Oct. 1999); 3: 29-38.
Christiansen, et al., "Biolistic transformation of the obligate plant pathogenic fungus, *Erysiphe graminis* f. sp. *hordei*." Current Genetics (1995); 29(1): 100-102.
Christie and Gordon, "The Agrobacterium Ti plasmids." Microbiology Spectrum (2014); 2(6): 10.1128.
Collado, et al., "High-throughput culturing of fungi from plant litter by a dilution-to-extinction technique". FEMS Microbiol Ecol. (2007); 60(3): 521-533.
Crameri, et al. "DNA shuffling of a family of genes from diverse species accelerates directed evolution." Nature (1998); 391(6664): 288-291.
Crameri, et al. "Molecular evolution of an arsenate detoxification pathway by DNA shuffling." Nature Biotechnology (1997); 15(5): 436-438.
Dai, et al., "Impact of alg3 gene deletion on growth, development, pigment production, protein secretion, and functions of recombinant Trichoderma reesei cellobiohydrolases in Aspergillus niger". Fungal Genetics and Biology (Dec. 2013); 61: 120-132. Epub Sep. 25, 2013.
Dai, et al., "Identification of Genes Associated with Morphology in Aspergillus niger by Using Suppression Subtractive Hybridization". Applied and Environmental Microbiology (Apr. 2004); 70(4): 2474-2485.
De Almeida, et al. "Transgenic expression of two marker genes under the control of an *Arabidopsis* rbcS promoter: Sequences encoding the Rubisco transit peptide increase expression levels." Molecular and General Genetics MGG (1989); 218(1): 78-86.
De Boer, et al., "Highly efficient gene targeting in Penicillium chrysogenum using the bi-partite approach in Δlig4 or Δku70 mutants". Fungal Genet Biol. (Oct. 2010); 47(10): 839-846. Epub Jul. 24, 2010.
Durand, et al. "Transient expression of the β-glucuronidase gene after biolistic transformation of the anaerobic fungus *Neocallimastix frontalis*." Current Genetics (1997); 31(2) : 158-161.
Extended European Search Report for European Patent Application No. EP 17886439.3, dated Jul. 3, 2020, 12 pages.
Eyini, et al., "Isolation, Regeneration and PEG-Induced Fusion of Protoplasts of Pleurotus pulmonarius and Pleurotus florida." Mycobiology (Jun. 2006); 34(2): 73-78.
Fincham, J.R., "Transformation in fungi." Microbiological Reviews (Mar. 1989); 53(1): 148-170.

Goosen, et al., "Transformation of Aspergillus niger using the homologous orotidine-5'-phosphate-decarboxylase gene". Current Genetics (Mar. 1987); 11(6-7): 499-503.
Ho and Ko, "A simple method for obtaining single-spore isolates of fungi", Bot. Bull. Acad. Sin. (1997); 38(1): 41-43.
Huang, et al., "Microfluidic screening and whole-genome sequencing identifies mutations associated with improved protein secretion by yeast". PNAS (Aug. 25, 2015); 112 (34): E4689-E4696. Epub Aug. 10, 2015.
Hynes, M.J., "Genetic transformation of filamentous fungi". J. Genet. (Dec. 1996); 75(3): 297-311.
Ito, et al., "Transformation of intact yeast cells treated with alkali cations." Journal of Bacteriology (1983); 153(1): 163-168.
Ji, et al., "Iterative combinatorial mutagenesis as an effective strategy for generation of deacetoxycephalosporin C synthase with improved activity toward penicillin". G. Appl Environ Microbiol. (2012); 78(21): 7809-7812.
Jiang, et al., "Molecular tools for functional genomics in filamentous fungi: Recent advances and new strategies". Biotechnol Adv. (Dec. 2013); 31(8): 1562-1574. Epub Aug. 26, 2013.
Jones, et al., "High level expression of introduced chimaeric genes in regenerated transformed plants." The EMBO Journal (1985); 4(10): 2411-2418.
Khanna, N.C., et al. "Identification of the template binding polypeptide in the pea chloroplast transcriptional complex." Nucleic Acids Research (1992); 20.1: 69-74.
Krijgsheld, et al., "Development in Aspergillus". Studies in Mycology (Mar. 2013); 74: 1-29. Epub Sep. 12, 2012.
Li, et al., "Methods for genetic transformation of filamentous fungi". Microb Cell Fact. (Oct. 3, 2017); 16(1): 168, pp. 1-13.
Li, et al., "The yeast histidine protein kinase, Sln1p, mediates phosphotransfer to two response regulators, Ssk1p and Skn7p". The EMBO Journal (1998); 17(23): 6952-6962.
Liu, et al., "Improved Production of a Heterologous Amylase in *Saccharomyces cerevisiae* by Inverse Metabolic Engineering". Appl Environ Microbiol (Sep. 2014); 80(17): 5542-5550. Epub Jun. 27, 2014.
Liu, et al., "Efficient genome editing in filamentous fungus *Trichoderma reesei* using the CRISPR/Cas9 system". Cell Discov (2015); 1, 15007, 11 pages.
Loske, et al., "Tandem shock waves to enhance genetic transformation of Aspergillus niger". Ultrasonics (Aug. 2014); 54(6): 1656-1662.
Magaña-Ortíz, et al., "A novel and highly efficient method for genetic transformation of fungi employing shock waves". Fungal Genetics and Biology (Jul. 2013); 56: 9-16.
Moore, et al. "Strategies for the in vitro evolution of protein function: enzyme evolution by random recombination of improved sequences." Journal of Molecular Biology (1997); 272(3): 336-347.
Nakashima, et al., "Bacterial cellular engineering by genome editing and gene silencing." International Journal of Molecular Sciences (2014); 15(2): 2773-2793.
Nakasone, et al., "Preservation and distribution of fungal cultures". Biodiversity of Fungi, G.M. Mueller et al., (ED), (2004), Ch. 3, pp. 37-47, 13 pages.
Nielsen, et al., "Efficient PCR-based gene targeting with a recyclable marker for Aspergillus nidulans". Fungal Genet Biol. (Jan. 2006); 43(1): 54-64. Epub Nov. 11, 2005.
Nielsen, et al., "Transient disruption of non-homologous end-joining facilitates targeted genome manipulations in the filamentous fungus Aspergillus nidulans". Fungal Genet Biol. (Mar. 2008); 45(3): 165-170. Epub Jul. 20, 2007.
Nielsen, et al., "Transient Marker System for Iterative Gene Targeting of a Prototrophic Fungus". Appl Environ Microbiol. (Nov. 2007); 73(22): 7240-7245. Epub Oct. 5, 2007.
Nódvig, et al., "A CRISPR-Cas9 System for Genetic Engineering of Filamentous Fungi". PLoS One (Jul. 2015); 10(7): e0133085.
Park, et al., "High-throughput production of gene replacement mutants in Neurospora crassa". Methods Mol Biol. (2011); Ch. 13, 722: 179-189.
PCT/US2017/069086, International Preliminary Report on Patentability, dated Jul. 2, 2019, 10 pages.

(56) References Cited

OTHER PUBLICATIONS

PCT/US2017/069086, International Search Report and Written Opinion dated May 14, 2018, 13 pages.
PCT/US2017/069086, Invitation to Pay Additional Fees, dated Mar. 12, 2018, 2 pages.
PCT/US2018/036360, International Preliminary Report on Patentability dated Dec. 10, 2019, 20 pages.
PCT/US2018/036360, International Search Report and Written Opinion dated Nov. 23, 2018, 39 pages.
PCT/US2018/036360, Invitation to Pay Additional Fees, dated Sep. 21, 2018, 28 pages.
PCT/US2019/035793, Invitation to Pay Additional Fees, dated Aug. 22, 2019, 4 pages.
PCT/US2019/035793, International Search Report and Written Opinion dated Nov. 8, 2019, 16 pages.
PCT/US2019/035793, International Preliminary Report on Patentability dated Dec. 8, 2020, 9 pages.
Pohl, et al., "CRISPR/Cas9 Based Genome Editing of Penicillium chrysogenum". ACS Synth Biol. (Jul. 15, 2016); 5(7): 754-764. Epub May 3, 2016.
Ricciardelli, et al., "Development and characterization of primary cultures of smooth muscle cells from the fibromuscular stroma of the guinea pig prostate." In Vitro Cellular & Developmental Biology (1989); 25(11): 1016-1024.
Roncero, et al., "Mutagenesis in multinucleate cells: the effects of N-methyl-N'-nitro-N-nitrosoguanidine on phycomyces sporres". Mutation Research/Fundamental and Molecular Mechanisms of Mutagenesis (Feb. 1984); 125(2): 195-204.
Ruiz-Díez, B., "Strategies for the transformation of filamentous fungi". J. Appl. Microbiology (Jan. 2002); 92(2): 189-195.
Stemmer, Willem P.C., "Rapid evolution of a protein in vitro by DNA shuffling." Nature (1994); 370(6488): 389-391.
Stemmer, Willem P.C., "DNA shuffling by random fragmentation and reassembly: In vitro recombination for molecular evolution." Proceedings of the National Academy of Sciences (1994); 91(22): 10747-10751.
Szewczyk, et al., "Fusion PCR and gene targeting in Aspergillus nidulans". Nat Protoc. (Jan. 1, 2006); 1(6): 3111-3120.
Tear, et al., "Excision of Unstable Artificial Gene-Specific Inverted Repeats Mediates Scar-Free Gene Deletions in *Escherichia coli*." Applied Biochemistry and Biotechnology (2014); 175(4): 1858-1867.
Wyatt, et al., "Essential Roles for Polymerase θ-Mediated End Joining in the Repair of Chromosome Breaks". Molecular Cell (Aug. 2016); 63(4): 662-673.
Yabuki, et al., "Rapid method for converting fungal cells into protoplasts with a high regeneration frequency". Experimental Mycology (Dec. 1984); 8(4): 386-390.
Yelton, et al., "Transformation of Aspergillus nidulans by using a trpC plasmid." Proceedings of the National Academy of Sciences (1984); 81(5): 1470-1474.
Zhang, et al., "Directed evolution of a fucosidase from a galactosidase by DNA shuffling and screening." Proceedings of the National Academy of Sciences (1997); 94 (9): 4504-4509.

Zhang, et al., "An Optimized Protocol of Single Spore Isolation for Fungi". Cryptogamie, Mycologie (Dec. 2013); 34(4): 349-356.
U.S. Appl. No. 17/387,634, filed Jul. 28, 2021, Knox, et al.
Aslanidis, et al., "Ligation-independent cloning of PCR products (LIC-PCR)." Nucleic Acids Research 18.20 (1990): 6069-6074.
Azhayev, et al., "Amide group assisted 3'-dephosphorylation of oligonucleotides synthesized on universal A-supports." Tetrahedron 57.23 (2001): 4977-4986.
Czar, et al. "Gene synthesis demystified" Trends in biotechnology 27.2 (2009): 63-72.
Damha, et al., "An improved procedure for derivatization of controlled-pore glass beads for solid-phase oligonucleotide synthesis." Nucleic Acids Research 18.13 (1990): 3813-3821.
Engler, et al., "A one pot, one step, precision cloning method with high throughput capability." PLoS One 3.11 (2008): e3647.
Farrow and Arnold, "High Throughput Screening of Fungal Endoglucanase Activity in *Escherichia coli*". J. Vis. Exp. (54), e2942. Epub Aug. 13, 2011.
Gibson, et al., "Enzymatic assembly of DNA molecules up to several hundred kilobases." Nature Methods 6.5 (2009): 343-345.
Kotera, et al., "A high-throughput and single-tube recombination of crude PCR products using a DNA polymerase inhibitor and type IIS restriction enzyme." Journal of Biotechnology 137.1-4 (2008): 1-7.
Kozlov, et al., "Significant improvement of quality for long oligonucleotides by using controlled pore glass with large pores." Nucleosides, Nucleotides and Nucleic Acids 24.5-7 (2005): 1037-1041.
PCT/US2021/043704, Invitation to Pay Additional Fees, dated Oct. 13, 2021, 2 pages.
Reyrat, et al., "Counterselectable markers: untapped tools for bacterial genetics and pathogenesis." Infection and Immunity 66.9 (1998): 4011-4017.
Sierzchala, et al., "Solid-phase oligodeoxynucleotide synthesis: a two-step cycle using peroxy anion deprotection." Journal of the American Chemical Society 125.44 (2003): 13427-1344.
Tian, et al., "Advancing high-throughput gene synthesis technology." Molecular BioSystems 5.7 (2009): 714-722.
Weber, et al., "Assembly of designer TAL effectors by Golden Gate cloning." PLoS One 6.5 (2011): e19722.
Yu, et al., "Double-joint PCR: a PCR-based molecular tool for gene manipulations in filamentous fungi." Fungal Genetics and Biology 41.11 (2004): 973-981.
Alex, L.A. et al., "Hyphal Development in *Neurospora crassa*: Involvement of a Two-component Histidine Kinase (Filamentous Fungi/Signal Transduction/Osmoregulation)," Proceedings of the National Academy of Sciences USA, vol. 93(8), Apr. 1996, pp. 3416-3421.
DATABASE Geneseq [Online] Nov. 24, 2011 (Nov. 24, 2011),"Plasmid pUSAS-Fc Partial Nucleotide Sequence, SEQ ID 8.", XP002805516, Retrieved from EBI Accession No. GSN: AZN51021 Database Accession No. AZN51021, 1 page.
Gabaldon, T. et al., "Functional and Evolutionary Implications of Gene Orthology," Nature Reviews Genetics, vol. 14(5), May 2013, pp. 360-366. Epub Apr. 4, 2013.
Pel, H.J. et al., "Genome Sequencing and Analysis of the Versatile Cell Factory Aspergillus Niger CBS 513.88," Nature Biotechnology, vol. 25(2), Feb. 1, 2007, ☐ pp. 221-231. Epub Jan. 28, 2007.

* cited by examiner 24 hour timepoint     Parent     manB(p)snp18

Base

Production

Minimal MediapH2.0

Base strain dense tight colonies

Production strain less dense. More straight hyphae

SEQUENCE LISTING

```
<160> NUMBER OF SEQ ID NOS: 79

<210> SEQ ID NO 1
<211> LENGTH: 504
<212> TYPE: DNA
<213> ORGANISM: Aspergillus niger

<400> SEQUENCE: 1
ctgtctccat ccgtattccc cccttcactc tcgtttactc tccgttcctg ctggtcagtc    60
tcttccttga ccgtgtccct cgcttccaac actcgtttcc ttcaatttcc tccccccttt   120
tctctcgttg cccccctcct cccgctccct cccgccatgc gtctcgttcg agattgcctg   180 tatgggggt tattccttaa cacggcgctc ttctcccagc tctcccacgc catcgatatc    240
gatatcagca gtaccagtat gccttccccc cacttcttca atctctttcc cattatatac   300
accactgtct cggcccttgc tttattccgt catccttctc ctctcctaca tacttggacg   360
cagttgcgcc actatatcta agactccatg ccttccattc caacgacata cataaatacc   420
atgaattgac aactgataca catttttatt gtccgtatag gttcaattaa agatgccgcc   480
agtaagacgg cctacgggtc catg                                          504

<210> SEQ ID NO 2
<211> LENGTH: 620
<212> TYPE: DNA
<213> ORGANISM: Aspergillus oryzae

<400> SEQUENCE: 2
gaattcatgg tgttttgatc attttaaatt tttatatggc gggtggtggg caactcgctt    60
gcgcgggcaa ctcgcttacc gattacgtta gggctgatat ttacgtaaaa atcgtcaagg   120
gatgcaagac caaagtagta aaaccccgga gtcaacagca tccaagccca agtccttcac   180
ggagaaaccc cagcgtccac atcacgagcg aaggaccacc tctaggcatc ggacgcacca   240
tccaattaga agcagcaaag cgaaacagcc caagaaaaag gtcggcccgt cggccttttc   300
tgcaacgctg atcacgggca gcgatccaac caacaccctc cagagtgact aggggcggaa   360
atttaaaggg attaatttcc actcaaccac aaatcacagt cgtccccggt attgtcctgc   420
agaatgcaat ttaaactctt ctgcgaatcg cttggattcc ccgcccctgg ccgtagagct   480
taaagtatgt cccttgtcga tgcgatgtat cacaacatat aaatactagc aagggatgcc   540
atgcttggag gatagcaacc gacaacatca catcaagctc tcccttctct gaacaataaa   600
ccccacagaa ggcatttatg                                               620

<210> SEQ ID NO 3
<211> LENGTH: 1503
<212> TYPE: DNA
<213> ORGANISM: Aspergillus niger

<400> SEQUENCE: 3
gcttccatgg ttggcagggt cacgtagccg taattatttt cggggaaggt tggaatgcaa    60
tggaaggaga tttccgtagc tagggctttg atcgatgcgg ggagcactgc cggtaggagg   120
tctggggtga atggggtgat atgcaggcgc ttcgtatcgg acggtgtggt cgtcatttgc   180
```

| | |
|---|---|
| ccaatagata gttagataga tacctgagta cggtagcagt gcaggtgacg gctaagaagt | 240 |
| cggagggaaa aaggtgcagt cacaagcgca ttcagcctaa caagtgtctt tgatactcgg | 300 |
| tgagaaacaa acttgagtag aataagacag aaagttcttg tgaatggtca caatgggctt | 360 |
| ccaacgaagc atcaagcaga ccctgttgca atagatattc caagaccgaa aaattaatga | 420 |
| taggatcagt tattggccga gggatttttcc gggccgccaa gaccgggtta tggagatgtg | 480 |
| gcgcaggcat gccatcctca gccacaggtt tctgtgacat cccaaaagca ttgatcgaag | 540 |
| ttggtataag tttcattcta tctaccatgg tgacaaggaa gtacgggtgt agaaaagaaa | 600 |
| aatctggtag gaatagctca gcaacaaatg gcggaatgat tgatgtaaga ctcgatgtat | 660 |
| ccactggaac gagatgcaag ttgcaacagc aataaatgga tttcagcctc cattacaatg | 720 |
| taacagtcgg gccgatactc agccggagca ggatttggcg ggtgaatagt ggatccggag | 780 |
| agaaacgatc aggtaatctt tcgtacggga ccagacccga cccggcctgc tttttagtta | 840 |
| ccagctgtta cttgtgtaat ccccgtaaaa cgatcagtaa ctgccattga tcttcctgct | 900 |
| cttttcccctt attcccttttt ccccctttga aacttatttt cttcttcctc ttcatcgctt | 960 |
| aactacttaa gtactaggat tctcactcgc cactcttccc caatatctaa aagtagtctt | 1020 |
| gctacgaaga tcccttcccc ctacattact cctcctcctt caacacaccc accccccct | 1080 |
| gatccggccc cataccagtc ttcccgcggc taactaaagc ccgcacgtct gatctcatcg | 1140 |
| ccgcttccag cttcgacctc agtcgctcac atggccactc ggattcctta gcatcatctc | 1200 |
| ttttttttccc atcccctccc cgccctacca actgagggtc ctctgaagtg tgctccacat | 1260 |
| ttccttccct tcacttattt tggatcctca ttttctttct tcctctgttt cggggcgttc | 1320 |
| ttcaacatcg ctacttagtc acttctctcc tctcattacc ggacgggaac ttcgctccct | 1380 |
| tctccgcttt cttatccgga ccgcctcttg ccaatctcac catcgatcct aacccgtcat | 1440 |
| aatccagtca ctcaaccta ctattgtcga catacacgtc ggttcccatt ctcgttcgag | 1500 |
| atg | 1503 |

<210> SEQ ID NO 4
<211> LENGTH: 1503
<212> TYPE: DNA
<213> ORGANISM: Aspergillus niger

<400> SEQUENCE: 4

| | |
|---|---|
| acagtggcca tgaaatccaa tcatttcctt ctggccgccc tcgggcaaga gatagtgccg | 60 |
| cagaggtctc tcacagcatc tacatctgcg accgcaacag ccaccaagcg aggcgcacat | 120 |
| gagcttgtcc tcctcccatg ccaaagtttg gccctcttcg tttctgtgat gctgaaggaa | 180 |
| gtcaaactcg tcgatgatag gaccagatgg tttgtcaagg gtcaacgctt tccatgcctt | 240 |
| ctggcaccgg tagtaatgct cttctgcaag ggagacttga cgtttcggat ccgcgggccc | 300 |
| cgggacatgc tggaagggat tttctggctc aataccacgt ctgtatttga ccctttccag | 360 |
| acagttaatc cgctgcagga gggcgaactg tagctcctcg ttctccttgt agcgcttgat | 420 |
| ccagtctttt tggatgttgc acttgcttgg cctatgcttc tcatataatc ttgccctgtc | 480 |
| atagagacga cgtctgagat tgtagcgttc gtctttgatc acccggagcc agataggcct | 540 |
| gagtatatct gacattagat caaagggtct gtggatagtc tccttcagca tcagcgacgc | 600 |
| atgtgactcg catgtcggag agagcttgtg ggtggtcatc tttgatggcg tcctctgctt | 660 |
| tcccttgatt ttcgttgatt gtttttcgaa agttaagtct ggaagtcaag agaatccttc | 720 |
| tgccagacat tatatttacg tatactgacg tagtagaaac agcgtcagga tgaggacatg | 780 |

```
gtgtgtgctg gaccacggaa tcatagttca tcagtatatt gggttggaca aataacgctg    840
agcatgtata tgtctttaca cactataaaa gccagcgaac gccaataaaa tagggcatat    900
tgatgtgaaa atatgacacc agttaaaagc agtgtattga ttttatctct cttcacctcg    960
gacctatact accgtataca agactcaact tacttccaga tatagtaata tacaccctat   1020
ggacgaacca gcacaataat tacagccaaa caacaccacc caaatggcat attcctaatc   1080
agcactaagc acaaatacca ctgtcatcac agcataatca ataagaatcc cagacaaccg   1140
actcactctg actcacctta cacaaacccc caagcaaagc gcagcccaga acctcagcca   1200
acaatcgggc aacgtacggg gaaagattgg ccgatccatg atgtcagcag ccctaaccca   1260
aagcggacta gcgcataccg cccctctgac tccgccatcc cagggctcga gaagcttccg   1320
tggcgtcgat ataaattcag cgggccttga acatccctcc ttacgacaca cctcacgcga   1380
tcgattttga cactcacaca ccgccaccct cacatcctcc acccacacca caccccttaa   1440
tcaacccacc atcaccgcta gaacgtctat ctcatcaccg acttctcatc catcttcaaa   1500
atg                                                                 1503

<210> SEQ ID NO 5
<211> LENGTH: 1206
<212> TYPE: DNA
<213> ORGANISM: Aspergillus niger

<400> SEQUENCE: 5
atgagcttcc gtcaagccct cagacccttc cgtcgcacca tgtccggtga aaagatctac     60
gaaggcgtat tcgccgtcca caaaccccaa ggcgtctcct ccgccgacgt cgtccgcacc    120
ctccaaacgc acttcaaccc ctccacgctc ttcgccccct ggctcgctga cgagcgcgcc    180
cgtcgcgccc gcgaaagcac ctaccagcgc aagcgccgcc gcacccagcg tctcgacgtg    240
aagatcggcc acggaggcac cctcgacccc ctcgcgaccg gcattctcgt cgcgggagtc    300
ggcaagggca cgaaacacct gaacgagttc ctaggatgca cgaagcaata tgagaccgtt    360
gtgctgttcg gcgccgagac agataccctat gatcggctgg ggaaggtggt gcgcaaggcg    420
ccctacgagc atgtgacaag ggagatggtg gagaaggcac tggagcagtt ccgtgggaag    480
attatgcaga ggccgccaat tttctcggcg ctgaaggtga atggcaagaa gctttatgag    540
tatgcccgcg agggcaagga ccgccgatt gagatccaga agaggccggt cgaggtgacg    600
gatttgagga ttgtcgagtg gtacgagcct ggaacgcatg agtttaagtg gcctgaggtt    660
gaggcagacg gggaggagaa ggctgttgcg agaagttgt tggcgtagga ggatgagttg    720
ccgattgtgg agagggaggc ggatggtgaa ggagaggcct ctgcgaagag aaagtccccg    780
cctgcggagg atgctaagga ggagaaggta gagggtggtg atactgagtc tgctccctcg    840
gctaagaagc agaaggttgc tgatggcgag gctgcgcctg ttgcgccggc cgagcaggag    900
gcgtcggatc tcccaatgc tgaagccgtg gaatcctcgg aatccaagcc ccagtcccag    960
ccccagccgg ctgcggtgaa gatcaccatg acggtgtcat ctggcttcta tgtgcgctcc   1020
ttggcgcacg atctgggcaa ggcggtcgga agctgcgggc tgatgtcctc gctgatccgg   1080
tctcgtcagg ctcagttcga gcttcacccg gacaaggtgc tcgagtataa ggacctcgag   1140
gccggcgagg aggtctgggg ccccaaggtc cagcgattcc tcgaggactg ggaggagaag   1200
cgactg                                                             1206

<210> SEQ ID NO 6
```

<211> LENGTH: 3303
<212> TYPE: DNA
<213> ORGANISM: Aspergillus niger

<400> SEQUENCE: 6

| | |
|---|---:|
| atgactatcc cactgagtcg actatccacc gtggatccgc ggcaaccagg aattagtggc | 60 |
| cataatcggg gcctcttgaa cgccgacgtc gtcccgatca acgacaagca gaaagtcttt | 120 |
| cttgccggtt ctggccctcc gtcgccaatg catcgcgtac aacctctgga cggatcgcat | 180 |
| ggtccgccca gtgctccagc agtctacgag cagccatggc gccctccgta ctcgtcttct | 240 |
| tatgacggac atcccgcgga ccagcgtcgc acatcgaatg ctcctcagcc tgcgctccca | 300 |
| ccccacggat acccgatgaa cccaaaccgt gagctgccgc agctcccacc agaagtccca | 360 |
| tatggccgac agggcagttt gcctggcccc gtgcataccc ctccagaagc ccccactcct | 420 |
| catcccagct ttcgtcctat gaatggaact ccccatgagg ccgcccctca ttcagcaccc | 480 |
| cccgactatc gctcacggat gtcttttaca cctcaggagc ctcacagcaa tggggacgct | 540 |
| ccgctccccg cccacacgtt accccgact cagtatccca ctccggttcc gcatttgtcg | 600 |
| catactccta cgccgtacga ttcaggtctt tacggaaacc aggcgtacgg gatacgccag | 660 |
| cagcgaaagg ccgctcgggc gcaacaggcc tgcgatcagt gccgaacgag aaaggccaag | 720 |
| tgcgatgaag gccggcctgc ttgtagccat tgcaaggaga caacttgat atgtgtttat | 780 |
| aaagaagttc cccctcacaa gcaagaaaag gcaacacagc ttcttctgga ccgtatctct | 840 |
| cagttggaag acggtctcat cgaaaaaatc gatcgcatta atgcactcca ggtcgagcac | 900 |
| acgaatcaac tcactcagct gtatcctcgg ttgaaagagg ctaaagcgat aagcaccaag | 960 |
| gagacgacag agaagcaagc cattcctcgg atatcgaaag cggatatacc tgatatctta | 1020 |
| caaaaaacgg aaaccaaaga agaagacatg aacgcgatcg tcggacagga gcttgaaaga | 1080 |
| gccgaagggg aagtgattcc acagggtgaa gacggtgatc tttcaattcc cgttgagcat | 1140 |
| accactgcag cccacaagtt gctttcgtgg ccgtctatca aggctcttct cgaaccgaga | 1200 |
| gagtacgatg aagattatgt tatgaagctg aagaggagc gaggattgat tctcgtttac | 1260 |
| ggccgcggtg aaggacacga tactagtgaa agcccagcaa tgacattctc atcatcatcg | 1320 |
| tcccggtcca actgggatca aagttacagc aatggtgctc ctgctagcgg ccagtggaac | 1380 |
| ccaggcgctg tccaaaatgg cactcatctc aaaccactcg gacccagtat tgatgatttc | 1440 |
| gggatattca gcactgatgc caaaaccgtt cgtcgttatc atcaaagcta cctgaaccac | 1500 |
| atgcataagc ttcatccatt tatcaacctg accgaattga gcgcaagcat cgaatcattc | 1560 |
| attcagaaat actgctcacc tgacgtttct gttccggtaa acatcctgaa cagccatacg | 1620 |
| cccggcgaca ttccacgcgg tgcgaaaagg aagcgttctt gcgatacgct acatggtggc | 1680 |
| ggatgcgaca tccagttttc tcctggtgcc aaacacgaag gctctagcgg acgtcgcgtg | 1740 |
| gagaagtcac tggaaaatgc tattgttctc ttggttcttg cacttggcag tatttgtgaa | 1800 |
| gttccgggag ccatccctgg tccagttact gacacgcccg tggactttca aaaggagcgg | 1860 |
| attcctggac cctctacacg cagcatgcta tcatcggcag atacagaact agttatgcag | 1920 |
| tcccagggaa gttcttctc gcagacaagt aaccattcat tttcatctgc taccgggggg | 1980 |
| cagaaggctg cttccgatcg gtcgccatac ccggataata gtcacttaag gaacgtggat | 2040 |
| gtcattcctg gcttggcata ttatgcgtac gccgcacaga tcttggggag tttgcaaggc | 2100 |
| gcgaacgggc tgtaccatgt tcaagcagcc ttactagcag gactttatgc gggacaatta | 2160 |
| gcacatcctt tccagagcca tggatggatc taccaggcgg ccagagcatg ccaagtgctt | 2220 |

```
gtccgatcga aacggtatga acaaatgaat gacggcccgc tgaaagacct atataacttt    2280
gcgtactgga cctgcctgca gctcgagagc gacatccttg ccgaactaga tcttccggct    2340
agtggtatat ctcgcgcgga agcacggatt gagttgccaa agggccgaac tctctctcta    2400
cctaacgacc ctgctgctcc gaacaccatg atgatgtttt tctactctgc ccagatccat    2460
ttgagaaagg ttctgaaccg tgttcacacc gatctataca agtcgaaag taagttgatc    2520 ttaggcaggc aggagccctt ggctaatgag aacaggtggt ctgctaacgt acaggagatt    2580
ctgagcatga accttgaact gtggagaagc agcttacctg acataatgag atggaaggac    2640
acggaccctc cacatgagga tattaatgtg gctcggatgc gagctaagta ctacggtgca    2700
cgatacatta tccatcgtcc actccttaac tgggctctgc atcattcaca tcccaccgaa    2760
aacggtcgat cggcatcagt ggattcccct acaggatcag cgatgtcggg agccaagtcg    2820
cagcaggttt cgccctcaat ggcgcacagc caacgtgcta tcaatatggc acgattgtct    2880
agtgatgttg gccctatggg tcgatcggca ccgacgccaa ccccgctcc gacaggatcg    2940 cgaccagcac tcgcatatcg cgacctcaat ccgaagttac gaagagcgtg caaagtatgc    3000
atagactccg ccatattgag taccgaggcc tttgatggca tcacaggccg gccggtagta    3060
actaatatct tcggcacagc tcatgctcaa ttcggtaaca tgctggtatt gtcggccacg    3120
tatatgtcaa gtctctcaga gctggttgat cggaacgacc tcgatcggtt atttaagcga    3180
accatacgct ttctcctcca aagccgcgag atatcgccaa ccctacgagc cgatgcaaag    3240
attctcagcg agatatacga aagatctttt ggggagccag ctgatatcgt ggctccgtta    3300
taa                                                                  3303

<210> SEQ ID NO 7
<211> LENGTH: 3894
<212> TYPE: DNA
<213> ORGANISM: Aspergillus niger

<400> SEQUENCE: 7
atggctggcg cggacgaaac gctcgcggcc gctgctgcca ttttgagagg tcttgcgaaa      60
gaaactcctt cctccagcgc tcctcccttc gacttcgaat tctcccatcc tcccgccaat     120
ggctacgaca caaaactcgc aaaattaccc ggggaaacga gttcagcaaa ggcggctttt     180
gaacaggagt tggaagcttt ggtccgacga gtccgtcatc tggaattcca aaatacaaca     240
caacaacaac aacaacaaca accccatgga tccagacgat cggccatcga accggaagac     300
cacgaagtgg aggaagacat cgacgatgag gagagtgacg aagatgagga actgaattca     360
aggacacgtt tggtacgcga ggaggacatc agctacctac ggaatcatgt tcaaaaacaa     420
gcggaggaaa taagtttcca gaaggatatc attgctcagg tccgtgacga attacaacaa     480
caggaggagc aaaacgacg ggctttgacc aaggtcgaaa acgaagatgt ggtcttgctg     540 gagcggggagc tacgcaagca ccagcaggcc aacgaagcgt tccaaaaggc tctacgggaa      600
atcggcggca tcattaccca ggtcgcaaac ggtgacctgt ccatgaaggt gcagattcac     660
ccgttggaga tggaccccga aattgccact ttcaagcgta cgatcaacac catgatggac     720
caactacaag tcttcggtag cgaggtgtcg cgagtcgcac gagaggtcgg aacagagggc     780
atactcggtg gtcaggctca gatcaccggg gtgtatggta tctggaagga gttgacggag     840
aacgtcaaca taatgccaa gaatctcacc gatcaggtcc gtgagatcgc tgcagtcacg     900
acagcggtcg cccacggtga cctgagccag aagattgaaa gtcgggccca gggtgaaatc     960
```

```
ttggaactgc aacagactat caacaccatg gtggaccaac taaggacatt tgcaacggaa    1020
gtcacccgcg tcgcgcgtga tgtcggtacg gaaggtgtgc ttggtggaca ggcccaaatt    1080 gaagggtgc  aaggcatgtg gaacgaactc acggtgaatg tcaacgccat ggcgaacaat    1140
cttacgacgc aagtgcgtga tatcgccacg gttaccaagg ctgtggcgaa gggtgacttg    1200
acgcagaagg ttcaggcgaa ctgcaaggga gagatcgcag agttgaagaa tatcatcaat    1260
tccatggttg accaactaag gcagtttgca caagaagtca ccaagatcgc caaggaggtc    1320
ggtacggatg gtgtccttgg tggtcaagcc accgtcaacg atgtggaggg cacatggaag    1380
gatctgaccg aaaacgtcaa ccgtatggcc aacaatctga ccacccaggt cagggagatc    1440
gccgacgtga ccaccgccgt cgccaagggt gatttgacaa agaaggtgac ggctaatgtt    1500
caaggtgaaa tactggactt gaagagcacg atcaacggca tggtggaccg gctaaatacc    1560
tttgcctttg aagtcagcaa ggtcgcgcgt gaagtcggca cggatggtac actgggtggt    1620
caagccaagg ttgataatgt ggaaggaaaa tggaaggatc taaccgacaa tgtgaacacc    1680
atggcccaga atctgacgtc ccaggtgcgg agtatatcgg acgttacgca agcaattgca    1740
aagggtgacc ttagcaagaa gatcgaggtc catgcacaag gagagatact caccctgaag    1800
gtcaccatca accacatggt tgaccgacta gccaaattcg cgactgaact gaagaaggtg    1860
gcgcgcgatg ttgggggttga tggcaagatg ggtggtcagg ctaacgtcga agggatcgct    1920
ggaacatgga aggaaatcac ggaggacgtg aatacgatgg ccgagaacct gacgtctcag    1980
gtgcgcgcat tcggtgagat tacggatgcc gccacggacg gtgatttcac caagctcatc    2040
acggtcaacg catccggcga aatggatgag ttgaagcgga agatcaacaa gatggttttcc   2100 aacctccgag acagtatcca acgtaacacg gccgccaggg aagctgcaga attggcgaac    2160
cgcaccaaat ccgagttcct cgcaaacatg agtcacgaga tccggacgcc catgaacggt    2220
atcattggta tgacgcagtt gaccttggac acggatgatc tcaagcccta tacccgagag    2280
atgttgaatg tcgtgcacaa cctggccaac agcttgctca ccatcattga tgacatactc    2340
gatatctcca agatcgaagc gaaccgtatg gtgattgaga gcatcccgtt caccgtgagg    2400
ggaaccgtct tcaacgccct gaagacgtta gccgtcaagg ccaacgagaa gttcctgagt    2460
ttgacgtacc aggtggacaa caccgttcct gactatgtca tcggtgatcc cttccgtctg    2520
cggcagatta tccttaacct tgtcggcaat gccatcaagt tcaccgagca tggcgaagtc    2580
aaacttacta tctgcaaatc cgaccgagag cagtgcgcag cagacgaata tgcgtttgaa    2640
ttctccgtct cggatacagg tattggtatt gaggaagaca agctagatct catcttcgac    2700
accttccagc aggcggacgg atcgaccacg cggaggtttg gtggaactgg tcttggtctg    2760
tccatttcca agcgcctcgt gaacctgatg ggtggtgatg tctgggtcac ttcggaatac    2820
ggccatggca gtaccttcca cttcacttgc gttgttaaac tggcggacca gtctttgagc    2880
gtcatcgcct cgcagctgtt gccgtacaag aaccaccgtg tcctctttat cgacaagggc    2940
gagaatggtg gccaggccga gaatgtgatg aagatgctca agcaaatcga cctggaaccg    3000
ttagtggtgc ggaacgagga tcatgtcccg ccgcctgaga ttcaggaccc gtcgggcaag    3060
gagtccggcc atgcctatga tgtgataatc gtggactcgg tggccactgc tcggctgctg    3120
cggacgttcg atgacttcaa gtacgttcct attgtcttgg tgtgcccgct ggtctgcgtc    3180
agcttgaagt ctgcccttga cctcggtatc agctccctata tgaccacgcc atgccagcca    3240
attgatctcg gtaacggtat gctgcctgct cttgaaggac ggtctacgcc catcaccacg    3300
gaccactccc ggtcgttcga catccttctg gcggaggata acgacgtcaa tcagaagttg    3360
```

```
gctgtgaaga tacttgagaa acacaaccac aacgtttccg tcgtcagtaa cggtctcgaa   3420
gccgtagaag ccgtaaagca acggcgctac gatgtcattc tgatggatgt tcagatgcca   3480
gtcatgggtg gtttcgaagc cacaggcaag atccgcgagt atgagaggga aagtggtctc   3540
agccggacac cgatcatcgc gctaactgca cacgccatgc tgggcgatcg agagaagtgt   3600
attcaagccc agatggatga gtacttgtcg aaaccoctga agcagaacca gatgatgcag   3660
accattctca aatgtgctac attaggtggt tctcttttgg agaagagcag gagtcgcgaa   3720
tctcaagtag tggtgaaatg cacccggtcc atcacagtgg gcctgatggc aagagccaac   3780
agcgtccggg gttggaacct cgatccgtca ccgcaaccag cactattaac cgtggtggtg   3840
gcctcgcaag cccaaacgtt gaccgagcgg atgagcttgc cgtcgaaagg gtga         3894
```

<210> SEQ ID NO 8
<211> LENGTH: 6084
<212> TYPE: DNA
<213> ORGANISM: Aspergillus niger

<400> SEQUENCE: 8

```
atggctgctg ctacgattga gttaccgttt atttcgtcgc actacgccat tgccgagtcg     60
acattgagca ccctcaccac agctcctacg gtcgagctag tcaaccagct cttggaagct    120
atcactacga aagcacgcga gcatgacgag ctcaagtctg acaagatacg cctcgaggtg    180
gaactcgata atgccgttcg ctccagagac aacaaaatca aggttctgaa gagctcggtc    240
gagaaaggtc atgccgaagt cgaggaaaca aggaagaaac ttcacgagtc cgaaaacact    300
cgttctaccc tggaatccga gatcgctaca ctcaagtcgt cctccacgtc aaacgagtct    360
gaagccagct cattgaagtc tcgtatctcg tcgctcgaag cttctaacag agacactctc    420
tcactcctcg aatccaagtc cgcagcatat gacaagcttg ccgaggagct ctcaacacaa    480
cacaagaaga caatcgaatt gagacgcgaa cttttccaccg ccgagcagaa cctccaagcc    540
gccaactctg cttccgccag cgctaagttc cgtgagcaga gtctccagca ggatttggaa    600
ttgacaaaga aaacaacga gtggttcgag acggaattga agaccaagtc cgccgaatat    660
ctgaaatttc gcaaggagaa gagcgcccgg atttcggagc ttcagcgtga aaacgaggag    720
atcagtgcaa acgttgactc cttgagacga agcgagaatg ccottaagag ccgcctggat    780 gaggtggaac agcgttatga agaggctctt tccagcatca accagctcag agaagacgct    840
atcaaggcga ccgagtcgtt cagaatcgaa ttggacagtg caagtagact agccgagttg    900
cagtcgaatg ctgcagagac ttcgaagcag cgtgccaagg aatgtcaact cgctctggat    960
aaagcaaggg aagatgctgc ggagcagatt tcccgactcc gagtggagat tgaaaccgaa   1020
catgccgaca agaagctgc tgaacgccgc gttgctgagc ttgagctcac ggtcagccag   1080
ctcgaatccg atggttttgc tggaagaaga tccatgagcc tgcactgaa tggcgcaggg   1140 cccagcaccc caatgcgtcc cagtacccca gttggcgcgt tttcacctag agcgtcgcgc   1200
ggaaagggag gactcacact gacgcagatg tataccgagt acgacaagat gagaatttcg   1260
ctggccatgg agcaaaaaac aaaccaagaa cttcgagcaa ctctagcga gatggtccaa   1320 gatctcgagg ccagcaagcc tgaaatcgat gagctgcgtg cggaccacgg tagacttgaa   1380
aatgctgttg ttgagatgtc taacatactg gaaactgctg ggaaggaacg agacgatgca   1440
actaaggagg caagaaagtg gcaaggccag gtggagggat tggccccggga gggagacatt   1500 ttgcgccagc aactcagaga cctgagctcc cagattaagg tcttggtttt ggaaaatgca   1560
```

```
attctgaagg aaggcgaaac aacgtacgat agagaggaac tcgagaagat tgcgcgccag    1620
gagatcgatg actcctctgc tgatctcaac ccaaccggac ggttcatcag tcgcaatctg    1680
atgacgttca aggatctcca cgagctccaa gagcagaatg tcactctccg tcgtatgctg    1740
agagagcttg gggataagat ggagggtgca gaagctcgcg agcaggatgc catccgtcaa    1800
caagagcaag aagagttgaa ggacctgaga atccgggtgc agacttaccg tgacgagatc    1860
gctaacctcg tcgctcaaac aaagagctat gttaaggaga gagatacgtt ccggagcatg    1920
cttacccgcc gccgtcagac tgttggcgat gcttctgtct tctcccaatc tcttcctctg    1980
ggcgcagctc ctcccgcttc tgaagagcca gccaaggatg ttccagacta cgctgatctg    2040
ttgcgcaagg tgcaggcaca cttcgacagc ttccgcgagg agtccgccac cgaccatgca    2100
gctttgaagc aacaggtcaa tgagttgtcc aggaagaaca gtgaattgat gagcgaaatt    2160
agccgctcta gcagtcagct tgttgccgcc acacagagag cggagcttct tcagggtaac    2220
ttcgatatgc tcaagaacga aaacgcgaaa atgcagaaac gctacgctac cctcctggag    2280
aacgctaacc ggcaggatat caggactcag caagctgccg aagatctggt ggagacgaag    2340
ggcctcgttg agagccttca acgggaaaat gccaacctca aggcagaaaa ggatctctgg    2400
aagaatatcg agaagagact catcgaggat aacgagacac tacgtaacga gagaggtcga    2460
cttgattctc ttaacgcgaa cctccaaacc attctcaatg agcgggaaca taccgatgct    2520
gagagtcgcc gtcgtttgca aagcagtgtg gagtctctcg aatcggagct tcaatccacc    2580
aagcggaagc ttaacgatga ggttgaggaa ggaagaaagg catcgctgcg tagggaatac    2640
gaacatgagc aaagtcagaa gcgaattgac gacttggtga cgagcttggg cgcagctcgg    2700
gaggagttag tggctgcgaa gacgacaaga gatcacttgc aatcgagagt cgatgaactc    2760
actgtcgagc tgcgtagcgc cgaagagcgc ctccaggtcg tgcagactaa gcccagtgtg    2820
tctgctgctc ctactgaagc gcctgcggtt ccggaggaag gccaggagag tggcctgaca    2880
cgcgagcagg aacttggtat tgaagtttcc gagctccgtc gtgatttgga gttgacaaag    2940
aatgagcttc agcacgctga agagcgggtg gaggattata aggctatcag tcagcagagc    3000
gaagagcgtc tgcagtctgt cactgagacc caggaacagt atcgggagga aacggagcgt    3060
ctcatcgaag agaaggataa gaagattcag gacctcgaaa agcgcatcga agaaatttcc    3120
gccgagcttt cgactacgaa cggcgaactt accaaattgc gtgacgagca aggggaggct    3180
agccgacatt tggaggagca gaaggccgcg ctggaagcag agatcacaag gctgaaggac    3240
gagaatgaaa ggcagatcgc ttctgcccaa ttccaccagg aagatctcaa ggcacaagct    3300
gaaatcgcgc agcatgccca gcagaactat gagagcgaac tgctcaagca tgctgaagcc    3360
gcgaagaatc tacaattggt ccggtccgaa gctaaccagt tgaagctgga agttgtcgaa    3420
ctgcggacac aggccgacac tttcaagaag gaccttgctc agaaggagga aagctggacc    3480
gagatcaagg ataggtatga gagcgagctt acggaactgc aaaagcgccg cgaggaagtt    3540
ctccaccaga actctttgtt gcatacccaa ctcgagaata ttacaaacca gatcgcagcc    3600
ctccagcgtg accgggctaa cattcctgag ggagatgagg acggagaggc cggcgcgccc    3660
aacctcgaag gcctccagga ggtgatcaag ttcctgcgtc gggagaagga gatcgttgat    3720
gtgcagtacc atctgtcaac ccaggaaagc aagcgtcttc gtcagcaact cgactacact    3780
cagacccagc ttgacgaggc ccggcttaag ctcgagcagc agcgtcgcgc ggctgccgac    3840
agtgaacata cgcgccctcag ccacaacaag ctgatggaga ccctgaacga actgaatctg    3900
ttccgcgaga gtagtgttac gctgcgtaac caggttaagc aggcggaaac ctcacttgcg    3960
```

```
gagaagtcct ctcgcatcga agaacttgtt cagcaaatac agccgctaga gactagaatc    4020
agggaactgg agaacactgt agagacaaag gatggagagc tgaagttgct acaggatgat    4080
agggaccggt ggcagcaacg tacgcagaat atcctgcaga agtacgaccg ggtagatccc    4140
gcggaaatgg aaggtctgaa ggagaagctc gagactttgg aaaaggagcg ggatgaggcc    4200
attgctgccc gggacactct acagacccag gctgctgctt cccagaaaca gctgaagcat    4260
gcggaggatc gcgtgcaaga actgcgcacg aagctcacgg accaattcaa ggctcggtcc    4320
aaggagttga ctggccgtat aaacgctaaa caggtggagc tcaacacggt tatgcaggag    4380
aaggaagtca ttcaagaaga actcaagacg actcggagg aattgaatga gctgaagacg    4440
aagatggccg agcaacccgc agctcctgct gccccagctg ttgaaggagc tactggtgtt    4500
gactcaacgc ctgcctctca gttccctgcg ccaacaacgc agccgcctgc cgcttctgac    4560
gatcaacgcg tgaaggctct ggaagagaag gtgcagcgcc tcgaggcagc tcttgcggag    4620
aaggagacgc cgttgaccgc gaaggaaacg gagcacgagg cgaagatcaa ggagcggtcc    4680
gacaagctga aggagatgtt caacagtaag ctggctgaga ttcgagctgc gcaccggcaa    4740
gaagttgagc ggttgaaatc cagtcaacca gccgctcctc aagaacctgg aaccccagct    4800
cccaaacccg agcaggtgcc agcaacgccg gcgactcctg cggctgctcc tgcgacaccc    4860
tccaaggaca ctgggctgcc tgaactgaca gatgcgcaag ccagggagct cgttgccaag    4920
aacgagacga ttcgtaacat cattcggagc aacatccgca cccaggtggc taagcaaaag    4980
gaatccgaca gcaggaaag ccaggccaac caggaggcta tgagcacact ggagcagaag    5040
tttaacgaag agagaagc gttgaagaag gcccacgaag agggtgtgga ggagaagatc    5100
aaggctgctg tcgagttgtc ggacaagaaa tcactggcga aactaagcat gctggacacc    5160
cggtaccgga cagcccaggc caagatcgat gtggttcaga aggctgctac ggagacgcct    5220
cagaagcctg ttgtcgaagt ctgggaggtc gcaaagacca ctagagcgcc tccagcggcg    5280
caggccaagc ccgcccaggt ggcatctcct gcgcctgcac cgtctcccgc gcccgctgcg    5340
gcccaggcaa caccggtggt gccatcgccg tcgcctgccc caacggctac tcctgcggcc    5400 acaccgcag ctacgcctgc agctgcaccc caggcccagc ctgtggagcc tgcagcagca    5460
tccacagccg agccagcttc tgctgaatct acgccgcaga caggtgcccc agcgcagcag    5520
caaccgcagc aacaacctgc gcctgaacag gccgcacaac aacaagctgc acctgcgacg    5580
gctcagccag ctaccaatgc tcctccaaac ccattcggtc agagccagaa caagcagccc    5640
tcgtcgttgc ccagcaagcc cccagccggt aatgcttctg gccttatgcg agcactgacg    5700
tccggactgc ccgtcgcgcg aggcggcagg gccggcggcc gcgtggggtc gcaagcgaat    5760
actttcggtc agcaacaggg acaacagcaa caggcgcaag gtcaggctca agcccagcag    5820
caagctccta gccagcgcgg ctctggtcta ccccggggtc gtggcggacg cggaggccat    5880
ggacgcggcg gaaaccaaaa tgtacagccc acgaatgccg ctcagcaagg acaggctagc    5940
ccaggtcgct cgctgaatgc cggtgctcgc cagttcgtcc ctcagggcaa caagcgtgct    6000
cgcgaggatg gagaagctgg aggcgaagga gcaaccagtg gaggaaagcg catgagggga    6060
ggaggtcata cccgggggtc atag                                          6084
```

<210> SEQ ID NO 9
<211> LENGTH: 543
<212> TYPE: DNA
<213> ORGANISM: Aspergillus niger

<400> SEQUENCE: 9

```
atggcgccca ccactactac aaagaccgtg gaggagcctg taggtgtcgc gaagccgcac    60
actgaagcca aggttgaagc tgacctcccc aagcccaagg agactaagga gatccctct    120
acattggcgg agatgagtgg gagtatcgac cagagcacat tcgagcagat tttggagatg   180
gacgacgacg acagtgatag agatttcagc aagggtatcg tgtttgggtt cttcgaccag   240
gctgagagca cattcatcaa gatggaggat gctttgaagg cggaagatct gaatgatctg   300
tcttctctgg acactacct gaaaggttca tcagccacgc tcggactcac aaggtcaag    360
gatgcatgcg agaagattca acactacggc gccggcaagg atgagaccgg tacgacggac   420
gagccggaca agaagacctc cctttcgcgc attgagaaga ccctgaccca ggtgaaaaag   480
gattacaagg aagtagaggc cttcctgcgc aagtattatg gcgaagagga ggaatcctct   540
taa                                                                 543
```

<210> SEQ ID NO 10
<211> LENGTH: 2685
<212> TYPE: DNA
<213> ORGANISM: Aspergillus niger

<400> SEQUENCE: 10

```
atgccagacc gtcgctgggc caagctcaag gcaaagctgt tattgcgacg atcgtcgtcg    60
acctcgtccg ctcccgccgc caccagcgac attattgccg agaacaatcc ccatgatgtc   120
cacgcccagc aaagctgcgc ccccgaacaa ttggacgagt cgatcgcgaa ttttccccca   180
gcgcgaccca tcagttccaa tcggcgcgcg atatcattgc aggccgtgcc ccaagccttg   240
aagctgagga aggaggagga cgaggaggag gaggagaggc aggaagagga cgatcgggcg   300
agtgcagctg aagggacgcg gacatcggtg attggcccga aaggcgggcg gtcgagggga   360
tcattggagg aggaagagaa gttcgagaag ttggagaact gcaacttcaa atcgaaatcc   420
tcctctcgcc ccgaaccggt cgcagaacaa cgtgagggac aacggcactc gctcctcgtt   480
cctccaggtg ccggtgccgg tgctggtccc agtgcttccc gccagcgtca gcatcagcaa   540
ttggacgcga caacttcttg cgatcgtgtt cgccccgcgc cctgcaggcg tcacagtcac   600
ggtccctttt ccgagcacgt cctttccca cccccgacaa ctctatcgcc agatctgctc   660
ccttcgcctt ctccgacccc tcctccccct gtctctgatc gtggtgttgt ctcgccgtct   720
ttccaatttg gccacactca aggccttgat cgcctggggc ctacggtcgg ggagccgcag   780
ttgcccgtgt tggatgtcgt tgcggagaat ccgacggtcg aaccagaatt tcagtcctcc   840
tccaaccata ccccgctgc ttccttccca aagcgtccca gtttaggctc ccgtcgtcag   900
tcgctgctgg ccccgtctca tcaacacctg atcaacagct tgttggaccc cggtgtgact   960
gcagagcctg aaaccaacgg taacggtcgc tccgccacct acagcacagg catgtctcgc  1020
aagatctggg tcaagcggcc aggcgggtcg gccaccttgg tccccatctc gctcgattct  1080
ttggtggacg agctacggga ccaggtgatt ttgaagtact cgaactcgct tggcagaacc  1140
ttcgatgccc ccgatattgt cattcgcatt actccgcgag atggttcgaa caggcaggcc  1200
actcccgatc ggatgcttag ccccgaagag ccgctggcaa gcgtggtgga cacatattac  1260
ccgggaggtc aagctatcga ggaggctcta ataatcgata tcccttcgcg tcgcactccc  1320
aaaccctctc cacgccattc agtatactac aaccaccatc attccgaacc gggcgagcat  1380
ggcgagtact ccccgctcat gccggcgaat cccagccgttc ccacgccgcc gacgcatccg  1440
tcaaactcgt ctgccagtgt taatgctcat cccgcccat caatatcgat cctgacgaca  1500
```

-continued

```
ggaatggccc ctccgctacc atctccaggg agtcgcggga ctcgacatcc ccgtcggccg    1560
cccttgactc gtcatgccac aaactcaccc accatcctca atcaggcgcc aacagcgaaa    1620
gaccccggaa tcgtcccag tagtatccct ccgcagcctg ctccgtccat ccctactccg     1680
ccaggcccgc cgccagaatc ccctcaggcc aaatccctga ctcctccagc acgcggggca    1740
tcaccgcgtc cacgtccctc cacatcctcc gcgaagccga agaagaccag cgcagcacaa    1800
tcattgagcg gggtctttgg aggcctcatc gagggcacgg taccgcccat caacgtcttg    1860
atcgtggagg acaataacat caaccaacgt ctcttggaag cttttatgaa acgtctcagc    1920
gttcgctgga agtgtgcggc caatggtgaa gaggcggtga acaaatggcg ccagggtggt    1980
ttccatctcg tcttgatgga tatccagttg cccgtcatga acggtctgga tgcgacgaaa    2040
gagatccgca ggctcgaacg cctgaacggc gtcggtgtgt tcccaagac cgctgacggg     2100 cggtcgagcg ctgcaactgc caatgcggca tcgccctcgg caattgtggg cagtcgggaa    2160
cccctgaagg cagaggatac attacacgat ctgtctctgt tcaaaagtcc cgttattatt    2220
gtagccctga ccgcgagcag tctgcagagc gatcgtcacg aggctctggc agctggctgc    2280
aacgactttt tgaccaagcc ggttcgcttt gaatggctgg agcagaaagt gacagaatgg    2340
ggctgcatgc aagccttgat cgatttgaa ggctggcgca aatggcgcgg ttacgccgat     2400
gacactcagc cttcgcccac gtctgatggt catacgagtc ccatgcaaac tggcggggac    2460
ggaacttcgc ggaaacagtc tcctgttatt ccgctctcac catcctctac cttgagtcaa    2520
ggagccacca aaaaggaccg caaaaccccc agcttcccta aaccatcga cgttacaccc     2580 gaagactctt ccggcagtgg tagcggcgag ggcttggact cacctgccag tccggtgaca    2640
tcagtccctg ttccagatgg gcctgcagat cctgatgcac tctga                   2685
```

<210> SEQ ID NO 11
<211> LENGTH: 2379
<212> TYPE: DNA
<213> ORGANISM: Aspergillus niger

<400> SEQUENCE: 11

```
atggatctca acaaacgcct gttccatctc gatatcgaga ataagaccca agcgcaacct     60
ctcaacttct ctatggtaac cacaccaccg gatgatgagg atgatgacga ggtgaaccat    120
ctaaagctca aggtcgagtt gaaacaatct cctcacgatc atgacaagcc gcatcaccgt    180
caaaagaaga tgcccgatac cgatgcgcag caacctccag cggctctagg tcgaatatat    240
cgctataccc ccactcccag cgtcattctt gatccttcgt tacatgtcgt ggaggtatcg    300
gattcccacg tggcatttgc cgggctgtca agggcgctgt tgctcggccg gttcatctgt    360
gacatctgtc cacgcatcct gccggctcta gatgttgcta ttcttttgg cgcattgcgc     420 gccgccatca cgacgcagga cgtccagtcg attgacaaaa tctgtataga tgacgctagc    480
acttgctata ctcttcgcat cacccccatc tttgaaaact ctaacctgtt atacattgtc    540
ctggaggcac ttgatatcac caagcgtcag gctacatcgg tgtccaagcc ccatgagtct    600
tactccaatg agacttacaa agtcctactg gacacggtca aggactatgc catcttcatg    660
ctcgacacac atggccatat tgtaacttgg aacacggagc cggccctgct gaaagggtac    720
tcggccaagg agatcatcgg acgtcacttt tccaccttct atagcctgga ggatcgcatg    780
gcggataagc ccggcaaaga actggaggta tgtctccggg agggcaaagt ggaggacgaa    840
ggctggcggt accgcaagga cggttcgcgg ttctgggcca acgtgctgat cactcccatg    900
```

```
tacgccctgg gtcgccatat tggcttcacc aaggtcactc gcgatttaac ggaacgcaat    960
gcagccgaaa cccgcatgat cgcagccttt gaagaatcgt cgagattaaa gacagacttc   1020
ttggccaaca tgagccatga gattcgcacg ccaatgaacg gcatgctctt agcccttaca   1080
tcactgctgg ccacggactt gaacgaacag cagcgcgaat attcctctat catcgaagat   1140
tcgaccaatg ttttgctcca agtcatcaat gacgtcctcg actattcgaa attgtcatcc   1200
gggtctttta ctctgcatcc tgatactttc agtgtcgaca gtattaccaa cgccgtcgtg   1260
cgcaactgca agggcgctct gaaaaccggt gtccaactga ctagctctat ctcatccaac   1320
ttcccatccc aggtcgaggg tgatccgttg cggtaccgtc aggtccttca gaatcttgtc   1380
ggcaatgcag tcaagttcac cgaggagggc tacgtcaaga tcaacaccac cttctcggaa   1440
gatgcggagg atcctagtgt atattacatc cggacggagg ttgccgatac gggcgttggc   1500
gttcccgaag atgctcttgg ctcattgttc acaccgttca cacgcttcgc cgagactggt   1560
tcgaagagat accaaggcac gggccttggc ttatcgatct gcaaaagctt ggccgaactc   1620
atggacggaa gtgtcggata ccgacctaat cctgagagac atggcagtgt cttctgggtc   1680
acagccaaga tgcatcgggt gcgtgtgacg ccgcccgcta gaacgactgg gacagggaca   1740
cccgttgaag acgtcggtga cattgaacga aatatccacg acatcgctcc tcacaaacac   1800
gttctcctgg ttgaggacaa cctggttaac cagatgatga tgctcaagct tctccagaac   1860
atgggcttcg cgcggattga tactgcatgg gatggggcag aggcggttcg actggtgaag   1920
cagcagcctt tatcctacaa tacaattctt atggatatcg gcatgccggt gctggatggc   1980
gtacaggcga cacgacagat ccggcaaatg ggactagaga tgcctatcat tgcgcttacg   2040
gggaacgtca tgccgggaga tatagaggat tatacgaagc agggaatgag cgatcatatt   2100
gggaaaccaa tccaccagaa acagttaatg cgtttgctct ggaatccgac tccgcataag   2160
aaactgagcg ttactgacac cgctttcgcg ttgaaccaac cctgcccatt acactgcaaa   2220
gcagtacgct ctagggcaat cgccatgatg agctcaggtg ctcaagaaca cagaaccatt   2280
cctgtaaagt ggacaggttc cgaagattac aatatgcaag actcacgatc ttctcttctc   2340
atgaagttta cgatgggaac atactacctc gatttatga                          2379
```

<210> SEQ ID NO 12
<211> LENGTH: 2022
<212> TYPE: DNA
<213> ORGANISM: Aspergillus niger

<400> SEQUENCE: 12

```
atgttcctcg acggccattt ggccgctctt tccctcgagg agaagtccgc gacaacacac     60
agtgtacgtg tgcccgacga tgactcccca gcggtgtctc cctctctggc atgcatctat    120
cgccatactc cgactcccac gatcgtcctc gattcatcta tgaccatcgt cgaggtctct    180
gatagtcatc tcgctttatc cggcaagacg cgccaatcca tgctgcatgc gaccgttcgt    240
gatctcgacc ctgctgccgt acccgcccct aatatcgcta tcctctgtgg cgcattgcgt    300
gcagcctgct cgacgaagga aattcagata gtcgagagaa ttgtgtctag cgataaatct    360
ttgtacaacc tccgagttac tccgattttc aacgactta ccctgcttta cattgtgttg    420
gaggcgcaca agctatcggt ggagaccgcc agcattaacc atgcctatac gaacgaaacc    480
tacaagatcc tcgtggatac tgtcaaagag tacgccattt tcatgctgga tacacagggc    540
aatatccacca cctggaaccc gggcgctgcc atcatgaagg gatggccagc agaggagatc    600
cttggcagac atttctctgt cttttacagc ccggaggatc gcctggcagg aaagcctcta    660
```

-continued

```
agaggtcttg ctgtgtgctt gcgagaaggc cgtatggagg atgaggggtg gaggtatcgg      720
cgcgatggct cgcggttttg ggccaacgta cttatcaccc ccatctacca gtttggacag      780
catgttggtt ttgttaaagt gacccgagat ctcagcgagc gcaaagaagc agaggcgcgc      840
ataattgctc ccttcgaaga gtcatcacgc ctcaaaacag actttctcgc taatattagc      900
catgaaattc gaactccgat gaatgggatg aaacttgcca tgaccatgct ggccgacaca      960
ggtctgtctg cgacacagct cgagcatgcc gcaatcatcc aagactctat gtcactctta     1020
cttgagactg tgaacgatgt tctcgactac tcgaaacttt catctggctc tttctcgtta     1080
cattccgacg tcgtcgatgt caacgatgtg gtcggagcgg tcatacgaaa ttgtcgcccc     1140
tcattgaaga acggggtgga actgactacg gacattgcac ccgactttcc caggaatctt     1200
cgaggagatc ccctacgata tcgccagatt ctgcagaatt tggtcggcaa tgccgtcaag     1260
tttaccgaga gcggccatat tcgggtctcc acagtgtgtt ctccggatga acaagaggag     1320
ggctgctgcc tagtgcgtac agaggtcata gacaccggca ttggcgttcc tgacaatgca     1380
atgaataccc tattcacccc gttcacacgc tttgccaact cgagcactcg acaataccag     1440
gggactggat taggcctttc catttgcaaa agcctggccg aactcatgga cggagaagtg     1500
ggatattcgc caaatcccga aggccgaggc agtgtcttct ggtttactgc caaattagga     1560
gaacgatcca ttactacgtc gctaaagccc gcagtcctg tattaacacc cgtgggtgat     1620
gatctctgcg ataaaatgcg ggccattgca ccccacaaac atgtcttgtt ggttgaggac     1680
aacatggtca accataccat gatgctgaaa cttcttcgca gcatcggctt cacgcgagtg     1740
gatgggcct ggaatggtgc tgaggcactt tccaagataa agaagaagcc tttatcgtac     1800
aacgtcgttt tgatggatgt ctccatgccc atcatggacg gccttgtcgc caccgggcat     1860
atccgcgaca tggggttaca aatgccgatt atcgcagtca cgggtaatgc tatgcagggc     1920
gatgccgaaa gctacattgc caagggcatg agcgattgca tcggtaagcc ggttcaccga     1980
gatcaactac tgagtatttt atggaagtgg attggatctt ga                       2022
```

<210> SEQ ID NO 13
<211> LENGTH: 4110
<212> TYPE: DNA
<213> ORGANISM: Aspergillus niger

<400> SEQUENCE: 13

```
atggaatctc agcaggaccg cgggtttccg atcatggagc atcctgattt aaacaaccat       60
gattcggatg gctccgggtc ctccgatgag cttctgcagc agccatatgc tgtaagagcc      120
aactccagtt tcccggagaa tttcgacacc caggtccaaa ccccggcgac gaccatttcc      180
tcgtcccctc ccccatccat tgcgtctgcc ctgccatcat gggcaaccgg cacgcccaca      240
cgcgcccgcg gggccagtat aggtgcttct gctgctcttg agaaagctcc gccgatggat      300
ggccatccgg tgaccgatcg tgacttgagg ccgcaacgtc cgtccggccc cgctcggacg      360
ccctccaata cctacgcgcc ccaacgacgc ccacctcagt atatcagctt ccaaaatgac      420
cgccaacgga gctcatcaac gaaacgaact tctagacgcg atcccaatgc acagtaccga      480
gctcaggaga aggcgtatgt ccagcgcatt cgtgcgaccc tcaggcctg gtacagtcat      540
ttcgatgagg ctcaaaacat gagcatgacg gtcggggact cggacctaga agaaccctca      600
ccatcctcgg aggttccttt cgaagacgat gcctacgatc cggatattca actcttcctg      660
accgacgaca atcagccgac gatcgaggaa ctcaagaacc caagaaacca agagaggctg      720
```

-continued

```
gagtggcatt ctatgctttc gtctgtgtta aagggagacg tggtgaagca agagaaacag   780
cgattactcg gctctacaga atcaaaacga tcgtcggccc agaacaacgc aatatggttg   840
ggtgtcagag ccaggacctg tggaaggagt gttgcactgc agaggaaact cattgaagaa   900
gcgagggctg gccttggccc catcatcgaa gaaattatca agttcgagat caaaggtgaa   960
acagagatcg ggaagccacc catcaagcag gttgaggata ttgtcgcaca gatagaacgt  1020
tgtgaaagcc tctactctac tcacaaggag ctggagactg cccacccag agtcgcttca   1080
gaggagtatc actcgagtcg cgatgctgtt tttgcctggc acaacgac catcttgatc    1140
aacaccgagc tcgctatcct gcagaaatgg gttggaaacg atgagttgga tttcagcaaa  1200
tcgagaacga aatcaatcaa tagcgacctt tccgacgaaa catccttcct tgaccgcatc  1260
atgaaggagg atggcctcaa aacgctgcaa ggaaaacata acatgctcca cggcattgga  1320
gaagtcatcc aaaaagcaaa gaatacatta attgagaatg ccggttcctt cgccaaacgc  1380
cacttacctc cctatatcga agaacttctt actcttatca atttcccgtc tcgtctcata  1440
caggaaatta tacggttcg actatcttac gctaagaata tgaaagaccc agcttcgcaa   1500
tccgccatct tagtcgatca aatgatatcg cagttccaga ttttgatgaa ggtggcggtc  1560
gatatcaaac ggcattattt ggatatcgcc agacccgagc tgggtggga cctgccccct   1620
tgcattgatg acggtttcga cgcagtcgtc ttggatgcga tgaagtatta cttccggctt  1680
ctgaactgga agctgactgc aaataagaac acattcaaag aagcggagat ctagaacag   1740
gattgggaat tttccaacga ggtcggccga caacttgagg gcggagatat cgaggtcgcg  1800
gagcagttta gtgcactgac tgccaagtcg atccaacgct tgatgtacca cttcgagcgg  1860
gagttgcagc ctcgccatga cgaggatcct gccgacatgg acaagcgtta taaaagcgta  1920
ttggactcaa ctcggatccg gcaacggaag ctttaccgat tttcccgatt cttgcgccag  1980
ctgttcgaaa atgcaacgga atacaatttg ccggctgaca ttgcatacga ctttttggag  2040
tcgttgcttt tgtcggatca ttttatgatc aaatcaaacg tctctgttgg tcaaaagggc  2100
gtctatctct ttgcgcaccc tgcattgtgg gatcgccctg cagatatcca agctatccta  2160
ggcacatcat ttcgtgagga tgacaccagc aaggatacac cccatgcacc gtatatactc  2220
gtggttcgtc cggaaaagcc ccttttcctgg gctggcaaag aaatgcagct gggcatcatg  2280
gaacagccta cggacttgcg attgggcaaa ttgcgacttg tggttgaagg gacgcagcag  2340
cggctgtcta atgcgagaca tgagctgact catctcactg gtattcagct cgatatggcc  2400
atcgagcaac gtgccaatct tggtcgggtc aacgtggagc taaacaagat caagaagacg  2460
tcatttaagc tatcaatgac tatcatggat agtgttgccc ggatacggga gcaactcaag  2520
gatagagacg tggagaacca cgatctagtc caagcatgct atgcttttgc gaccgagttc  2580
gggaagcgtt cttcaaacgt tgatcccaat agacgcgcaa tgaacagtaa tagacttgtc  2640
gagttgtccc tcgactgggt ttcgttcatc tgtgatgatt gtgatgctgc tgacaggaaa  2700
accttcaagt gggccgttgc tgctctgaa tttgcaatgg ctatcacctc cagcaggcac  2760
ctcctgtcta tggatgatgc tcagtatagt cgactgaggc agaaggttgc cgggtgcatg  2820
tcgctcctta tatctcactt tgatatcatg ggtgctcgat cgtctcgtgc ggctcaagca  2880
gagaagcaac gcttggaaga gcgcggcggt tcgagacgaa tgggcgcagg gcgaatcctt  2940
acagatgaag aggcagccaa gcttgttcgg gagcagcgcg tggctcatct taccgagatc  3000
gaggagagac gcgttgacga agatgctaaa cgccaagcat tggaagggt tctagagggc  3060
tcaaacgaag cggacaggtc tcttacggtg cttcatcct cggctacgaa cgttactctg  3120
```

```
cgatggcaac agggccagtt cattggtgga ggaacctttg ggtccgttta cgctggaatt      3180
aaccttgaca gcaactacct catggctgtc aaggagatcc gtttgcaaga cccccaactt      3240
atccctaaaa ttgcccagca aatccgtgat gagatgggtg tgttggaagt cttggatcat      3300
cctaacatcg tctcttacca cggtattgaa gtgcaccgcg ataaggtcta catcttcatg      3360
gaatactgtt ctggtgggtc ccttgccagc ttgcttgagc acggacgtgt cgaggatgaa      3420
accgtcatta tggtctacgc tcttcagttg ctggagggat tagcgtacct gcaccaggct      3480
ggcattatcc atcgcgatat caagcctgaa aatatcctgc ttgatcataa cggtatcatc      3540
aaatacgtcg attttggagc tgcaaagatc atcgctcgtc agggcagaac cgttgtccct      3600
atggatgcct tcgctggcgc tggtcataag gacgctatag tgcccaagga cgcccagctg      3660
gctcacaaca attggggcaa gaaccagaaa acgatgaccg gcaccccaat gtacatgtca      3720
cccgaggtga ttcgcggcga taccacaaaa cttatccacc gccagggagc tgtcgacatc      3780
tggtcgttag gatgcgtgat cttagaaatg gccacgggtc gtcgcccttg gtccactctg      3840
gataacgaat gggccatcat gtacaacatt gcccagggca accaaccgca attgccatcc      3900
cgagaccagc tcagcgacct aggtatcgac ttcctccgac gatgcttcga gtgtgacccc      3960
aataaacggt ccactgcagc agaactcctc cagcatgaat ggatcgtctc catccgccag      4020
caagtcgtac tcgagccagc cacgcctggc agcgacaata gcggtggtag ttcccattca      4080
ggcagtcgcc agaactcagc gtatctatga                                      4110

<210> SEQ ID NO 14
<211> LENGTH: 4039
<212> TYPE: DNA
<213> ORGANISM: Aspergillus niger

<400> SEQUENCE: 14
atggctggcg cggacgaaac gctcgcggcc gctgctgcca ttttgagagg tcttgcgaaa        60
gaaactcctt cctccagcgc tcctcccttc gacttcgaat tctcccatcc tcccgccaat       120
ggctacgaca caaaactcgc aaaattaccc ggggaaacga gttcagcaaa ggcggctttt       180
gaacaggagt tggaagcttt ggtccgacga gtccgtcatc tggaattcca aaatgtcagt       240
caccaccagt caaccccaa atcctcccag tcttctctca ctcccggcga aaggacgct         300 gatttcctct ggtcctttgg tctctctcgt gtttcgtccc gtgacggttc tgactcttgc       360
ctctcacagc atcaaaagac aacacaacaa caacaacaac aacaacccca tggatccaga       420
cgatcggcca tcgaaccgga agaccacgaa gtggaggaag acatcgacga tgaggagagt       480
gacgaagatg aggaactgaa ttcaaggaca cgtttggtac gcgaggagga catcagctac       540
ctacggaatc atgttcaaaa acaagcgag gaaataagtt tccagaagga tatcattgct       600
caggtccgtg acgaattaca acaacaggag gagcaaacac gacgggcttt gaccaaggtc       660
gaaaacgaag atgtggtctt gctggagcgg gagctacgca agcaccagca ggccaacgaa       720
gcgttccaaa aggcactacg ggaaatcggc ggcatcatta cccaggtcgc aaacggtgac       780
ctgtccatga aggtgcagat tcacccgttg gagatggacc ccgaaattgc cacttttcaag      840 cgtacgatca acaccatgat ggaccaacta caagtcttcg gtagcgaggt gtcgcgagtc       900
gcacgagagg tcggaacaga gggcatactc ggtggtcagg ctcagatcac cggggtgcat       960
ggtatctgga aggagttgac ggagaacgtc aacataatgg ccaagaatct caccgatcag      1020
gtccgtgaga tcgctgcagt cacgacagcg gtcgcccacg gtgacctgag ccagaagatt      1080
```

```
gaaagtcggg cccagggtga atcttggaa ctgcaacaga ctatcaacac catggtggac       1140
caactaagga catttgcaac ggaagtcacc cgcgtcgcgc gtgatgtcgg tacggaaggt       1200
gtgcttggtg acaggccca aattgaaggg gtgcaaggca tgtggaacga actcacggtg       1260
aatgtcaacg ccatggcgaa caatcttacg acgcaagtgc gtgatatcgc cacggttacc       1320
aaggctgtgg cgaagggtga cttgacgcag aaggttcagg cgaactgcaa gggagagatc       1380
gcagagttga agaatatcat caattccatg gttgaccaac taaggcagtt tgcacaagaa       1440
gtcaccaaga tcgccaagga ggtcggtacg gatggtgtcc ttggtggtca agccaccgtc       1500
aacgatgtgg agggcacatg gaaggatctg accgaaaacg tcaaccgtat ggccaacaat       1560
ctgaccaccc aggtcaggga gatcgccgac gtgaccaccg ccgtcgccaa gggtgatttg       1620
acaaagaagg tgacggctaa tgttcaaggt gaaatactgg acttgaagag cacgatcaac       1680
ggcatggtgg accggctaaa tacctttgcc tttgaagtca gcaaggtcgc gcgtgaagtc       1740
ggcacggatg gtacactggg tggtcaagcc aaggttgata atgtggaagg aaaatggaag       1800
gatctaaccg acaatgtgaa caccatggcc cagaatctga cgtcccaggt gcggagtata       1860
tcggacgtta cgcaagcaat tgcaaagggt gaccttagca agaagatcga ggtccatgca       1920
caaggagaga tactcaccct gaaggtcacc atcaaccaca tggttgaccg actagccaaa       1980
ttcgcgactg aactgaagaa ggtggcgcgc gatgttgggg ttgatggcaa gatgggtggt       2040
caggctaacg tcgaagggat cgctggaaca tggaaggaaa tcacggagga cgtgaatacg       2100
atggccgaga acctgacgtc tcaggtgcgc gcattcggtg agattacgga tgccgccacg       2160
gacggtgatt tcaccaagct catcacggtc aacgcatccg gcgaaatgga tgagttgaag       2220
cggaagatca acaagatggt ttccaacctc cgagacagta tccaacgtaa cacggccgcc       2280
agggaagctg cagaattggc gaaccgcacc aaatccgagt tcctcgcaaa catgagtcac       2340
gagatccgga cgcccatgaa cggtatcatt ggtatgacgc agttgacctt ggacacggat       2400
gatctcaagc cctataccg agagatgttg aatgtcgtgc acaacctggc caacagcttg       2460
ctcaccatca ttgatgacat actcgatatc tccaagatcg aagcgaaccg tatggtgatt       2520
gagagcatcc cgttcaccgt gaggggaacc gtcttcaacg ccctgaagac gttagccgtc       2580
aaggccaacg agaagttcct gagtttgacg taccaggtgg acaacaccgt tcctgactat       2640
gtcatcggtg atcccttccg tctgcggcag attatcctta accttgtcgg caatgccatc       2700
aagttcaccg agcatggcga agtcaaactt actatctgca aatccgaccg agagcagtgc       2760
gcagcagacg aatatgcgtt tgaattctcc gtctcggata caggtattgg tattgaggaa       2820
gacaagctag atctcatctt cgacaccttc cagcaggcgg acggatcgac cacgcggagg       2880
tttggtggaa ctggtcttgg tctgtccatt tccaagcgcc tcgtgaacct gatgggtggt       2940
gatgtctggg tcacttcgga atacggccat ggcagtacct tccacttcac ttgcgttgtt       3000
aaactggcgg accagtcttt gagcgtcatc gcctcgcagc tgttgccgta caagaaccac       3060
cgtgtcctct ttatcgacaa gggcgagaat ggtggccagg ccgagaatgt gatgaagatg       3120
ctcaagcaaa tcgacctgga accgttagtg gtgcggaacg aggatcatgt cccgccgcct       3180
gagattcagc ccccgtcggg caaggagtcc ggccatgcct atgatgtgat aatcgtggac       3240
tcggtggcca ctgctcggct gctgcggacg ttcgatgact tcaagtacgt tcctattgtc       3300
ttggtgtgcc cgctggtctg cgtcagcttg aagtctgccc ttgacctcgg tatcagctcc       3360
tatatgacca cgccatgcca gccaattgat ctcggtaacg gtatgctgcc tgctcttgaa       3420
ggacggtcta cgcccatcac cacggaccac tcccggtcgt tcgacatcct tctggcggag       3480
```

| | |
|---|---|
| gataacgacg tcaatcagaa gttggctgtg aagatacttg agaaacacaa ccacaacgtt | 3540 |
| tccgtcgtca gtaacggtct cgaagccgta gaagccgtaa agcaacggcg ctacgatgtc | 3600 |
| attctgatgg atgttcagat gccagtcatg ggtggtttcg aagccacagg caagatccgc | 3660 |
| gagtatgaga gggaaagtgg tctcagccgg acaccgatca tcgcgctaac tgcacacgcc | 3720 |
| atgctgggcg atcgagagaa gtgtattcaa gcccagatgg atgagtactt gtcgaaaccc | 3780 |
| ctgaagcaga accagatgat gcagaccatt ctcaaatgtg ctacattagg tggttctctt | 3840 |
| ttggagaaga gcaaggagtc gcgaatctca gtagtggtg aaatgcaccc ggtccatcac | 3900 |
| agtgggcctg atggcaagag ccaacagcgt ccggggttgg aacctcgatc cgtcaccgca | 3960 |
| accagcacta ttaaccgtgg tggtggcctc gcaagcccaa acgttgaccg agcggatgag | 4020 |
| cttgccgtcg aaagggtga | 4039 |

<210> SEQ ID NO 15
<211> LENGTH: 2022
<212> TYPE: DNA
<213> ORGANISM: Aspergillus niger

<400> SEQUENCE: 15

| | |
|---|---|
| tcaagatcca atccacttcc ataaaatact cagtagttga tctcggtgaa ccggcttacc | 60 |
| gatgcaatcg ctcatgccct tggcaatgta gctttcggca tcgccctgca tagcattacc | 120 |
| cgtgactgcg ataatcggca tttgtaaccc catgtcgcgg atatgcccgg tggcgacaag | 180 |
| gccgtccatg atgggcatgg agacatccat caaaacgacg ttgtacgata aaggcttctt | 240 |
| ctttatcttg gaaagtgcct cagcaccatt ccaggcccca tccactcgcg tgaagccgat | 300 |
| gctgcgaaga gtttcagca tcatggtatg gttgaccatg ttgtcctcaa ccaacaagac | 360 |
| atgtttgtgg ggtgcaatgg cccgcatttt atcgcagaga tcatcaccca cgggtgttaa | 420 |
| tacaggactg cggggcttta gcgacgtagt aatggatcgt tctcctaatt tggcagtaaa | 480 |
| ccagaagaca ctgcctcggc cttcgggatt tggcgaatat cccacttctc cgtccatgag | 540 |
| ttcggccagg cttttgcaaa tggaaaggcc taatccagtc ccctggtatt gtcgagtgct | 600 |
| cgagttggca aagcgtgtga acggggtgaa tagggtattc attgcattgt caggaacgcc | 660 |
| aatgccggtg tctatgacct ctgtacgcac taggcagcag ccctcctctt gttcatccgg | 720 |
| agaacacact gtggagaccc gaatatggcc gctctcggta aacttgacgg cattgccgac | 780 |
| caaattctgc agaatctggc gatatcgtag gggatctcct cgaagattcc tgggaaagtc | 840 |
| gggtgcaatg tccgtagtca gttccacccc gttcttcaat gaggggcgac aatttcgtat | 900 |
| gaccgctccg accacatcgt tgacatcgac gacgtcggaa tgtaacgaga aagagccaga | 960 |
| tgaaagtttc gagtagtcga gaacatcgtt cacagtctca gtaagagtg acatagagtc | 1020 |
| ttggatgatt gcggcatgct cgagctgtgt cgcagacaga cctgtgtcgg ccagcatggt | 1080 |
| catggcaagt tcatcccat tcatcggagt tcgaatttca tggctaatat tagcgagaaa | 1140 |
| gtctgttttg aggcgtgatg actcttcgaa ggcagcaatt atgcgcgcct ctgcttcttt | 1200 |
| gcgctcgctg agatctcggg tcactttaac aaaaccaaca tgctgtccaa actggtagat | 1260 |
| gggggtgata agtacgttgg cccaaaaccg cgagccatcg cgccgatacc tccacccctc | 1320 |
| atcctccata cggccttctc gcaagcacac agcaagacct cttagaggct ttcctgccag | 1380 |
| gcgatcctcc gggctgtaaa agacagagaa atgtctgcca aggatctcct ctgctggcca | 1440 |
| tcccttcatg atggcagcgc ccgggttcca ggtggtgata ttgccctgtg tatccagcat | 1500 |

| | |
|---|---|
| gaaaatggcg tactctttga cagtatccac gaggatcttg taggtttcgt tcgtataggc | 1560 |
| atggttaatg ctggcggtct ccaccgatag cttgtgcgcc tccaacacaa tgtaaagcag | 1620 |
| ggtaaagtcg ttgaaaatcg gagtaactcg gaggttgtac aaagatttat cgctagacac | 1680 |
| aattctctcg actatctgaa tttccttcgt cgagcaggct gcacgcaatg cgccacagag | 1740 |
| gatagcgata ttaggggcgg gtacggcagc agggtcgaga tcacgaacgg tcgcatgcag | 1800 |
| catggattgg cgcgtcttgc cggataaagc gagatgacta tcagagacct cgacgatggt | 1860 |
| catagatgaa tcgaggacga tcgtgggagt cggagtatgg cgatagatgc atgccagaga | 1920 |
| gggagacacc gctggggagt catcgtcggg cacacgtaca ctgtgtgttg tcgcggactt | 1980 |
| ctcctcgagg gaaagagcgg ccaaatggcc gtcgaggaac at | 2022 |

<210> SEQ ID NO 16
<211> LENGTH: 3998
<212> TYPE: DNA
<213> ORGANISM: Aspergillus niger

<400> SEQUENCE: 16

| | |
|---|---|
| atggattcga acgatccccc cacctcgaca ggccggggca cggatctcga ccctcatgcc | 60 |
| cccgaagtac cgccgacatc caacaaagaa acgactgttc cggatcaagg ccataatacc | 120 |
| tccatggaca gtacgactgt aggcggcacg gatcgagtat atcctattcg gtcaatcatc | 180 |
| tcctttaatc ccgtttccac agacattacc cagcaaagca taccaaatga atgcgttct | 240 |
| ccgcgaagtg gtgctcgttc atattcaatt atcgacgccg atacttggga ccaattgagt | 300 |
| tcacaatctg ctagttcgcc acataccaat ccttctccca acgcgcctgt ccatagtcct | 360 |
| gagtcgaccg gtcggctctc gcagcagtct tctgatgtct tctcgccggc ctcgagcgct | 420 |
| gccgagcgag acgctccgcc ggatgaaagc tccacgtaca ggaaagtcgc gccggaagag | 480 |
| ggccatgcga gccttgttac ttcgcggttc cagcacgtgg tcacggcggc gggtcatgct | 540 |
| gttataacag gcaatacacc tgattctttt cgggcctgtg aagacgaacc gatccacatt | 600 |
| ccgggcgccg tgcaaacctt tggcgtcatg cttgttttgc gcgagacacc tgagggttca | 660 |
| ctagcagtcc atgtagctag tgaaaattct gaggctattt tgggtcattc gccaagtaac | 720 |
| cttttttgcgc tggagagttt ctctgacctc ctgcaagacg accagaccga catcctcctc | 780 |
| gatcatattg acttcatcag agacgatgga tatgaccccg ttagcgatgg cccagaggta | 840 |
| tttatccttg ctgttaagga tcgacttagc cgtcctcgac gcttttggtg tgccatccat | 900 |
| gtaaaccccg ctcaccggga tgtgctcatc tgtgagttcg aattggagga cgaccgcatt | 960 |
| aaccctctca cgttgctgg gcgcacaaca cctacatccc cgacggatac cttgggcttt | 1020 |
| gaaccaacac ctgatcaatt agcaagcagc actgtgaaca tcagccagcc gctacgagtg | 1080 |
| cttcggaatg cacgcagaag gagggggcgaa gcagctgcca tggaggtgtt cagtattgtt | 1140 |
| agccagattc aggatcagct tggtgatgcc caaaacatgg acgctttgct aaacattacg | 1200 |
| attggcatag ttaaggagtt aacgggattt caccgcgtga tgatatatca gtttgatagc | 1260 |
| gaggccaatg gagatgtggt ggcagaatta gtcgacacga gaatgaccaa ggacttgtat | 1320 |
| aagggattac atttcccatc gtcggatatt ccaaagcaag cccgcgacct gtatcgtctc | 1380 |
| aacaaagtac gcatactcta cgaccgtgag cagatgagct cacggttggt gtgtcgaggc | 1440 |
| atcgaggatc tcaagactcc tctagacatg acacatgcct acttgcgtgc aatgtcgcct | 1500 |
| atccacatca gtacctagc gaacatgggg gtccgtgcgt ccatgtcgat cagtatcaac | 1560 |
| aacacgcatg atctttgggg tctgatctcc tgccactcat atggagacgc cggcatgcga | 1620 |

```
gtacctttcc caattcggaa aatgtgtcgg ttgatcggtg atacactttc tcggaacatc    1680
gagcgtcttt cttacgcatc acgtctccag gcacgcaagc tcctcaacac catccctacg    1740
gatgcaaacc cctcgggtta cataattgcc tcatcggatg acttactgaa gcttttgat    1800 gcggactacg gcgcattgtc tatcagaggg gagaccaaga tcctcggaaa gtcaaccgag    1860
tcgcaggaga tgctggctct gctagagttt ctcaagatcc gccagctcaa ttccgtcgtt    1920
gcatcgcatc atgtgaagaa ggactttcca gacttgcgtt acccgccggg cttcaaggag    1980
atctcgggca tgttgtacgt gcctttgtcg gccgatggca aggactttat cgtcttcttc    2040
cgcaagggcg agctgacgca gatcaaatgg ggtggtaatc cttatactaa actcctgcaa    2100
aatggtcacc tcgaacctcg cgcgagtttc caggtctgga ctgagactgt catggaccgg    2160
gctcgtgaat ggagcgaatc ggaagtagag actgcagccg tttatgcct ggtctatggc     2220 aaatttatca agtatggag acaacaggag gctgcgttgg aaggttcgca gttgacgaag      2280
ctgcttctgg ctaattcagc ccacgaagtc cgaaccccgc tgaatgccat tgtcaattat    2340
ctagaaattg ctctcgaagg tgccttggac acggagactc gcgacaacct taccaaatca    2400
tactccgcct cgaaatcatt gatctacgtc atcaacgacc tattggacct gaccaacacc    2460
gaaaagggac acaatttgat caaagatgaa cccttcgatc ttcctttatg tttcaaggaa    2520
gcgaccggca tgttttccgg cgaggcgcac cggaaaggaa tagagtatac ggttcacgcc    2580
caccccgggc tcccgaagac cgttatgggt gatgaacggc gtgttcggca ggcaatctca    2640
aatctgatct caaatgccat ccagcataca tctacgggtg gcgtcactgt cgaaatgtgg    2700
cgagcccctg gcaatccaga gcctgggttt gcaaccatac acatgacagt gcttgatacg    2760
gggaccggaa tgtcgtccgc tatactggag acgatgttcc aggaattgga gcaggtctcc    2820
tcagaggacg acagctactt tttcgaccgg gatcctaaca ataattcgca gcatactgag    2880
agtgaacgcc agaaaggtgt cctcgggttg gggctcgcat tggtgtctcg cattgtacgg    2940
aatacccacg gtcagctcac agtgcgatcg gaggagggca agggtagtcg cttccagatt    3000
tcgctacaat ttgctacacc agaggatacg aattctgacc aacccgaaac cccgcaaacg    3060
tcaacgcagg acgatggcgc catcccttt gaggccaagg aagagtttat cttggtcgac     3120
agcagctcgt ctgcaccaag tgatggatgg cgacgcagtg gtagctatcg tggcgcgaat    3180
agcccgtctg cagacgagct ggacgccaaa ctggtagttg aggaatctat tgatcgtacg    3240
aaagacgaag ctgctggtct gcttccctct tcagatcgcc ggaaactcgt tacgctgcct    3300 tcaaccccctg aaagattgga tgatgtcaca cgtgctttgc agcagaacgt gcagaatctg    3360
tccatatcca caaaccggc aagcactatt gcaggccctg caggacccgc tccaacgagt     3420
gctcctgcag gctcggacac taaagccccg tctggcaagt atcgcgttct ggtggccgaa    3480
gacgacccta tcaatggcaa gattgtacag aagaggctcg ggaagctagg ccacaccgtc    3540
caactgacag taaacggtga agaatgcgca gctgcatacc gagccgattc tgcgcaatat    3600
gatgtcgtct tgatggatat ccaggtaggc cttccttagg tatttgttag tatagacatg    3660
ctaatgcaag atagatgccg attgtggatg gtatcaaatc gacggaaatg atccgcgagt    3720
tcgaaacgtc gtccgatcca acagagctct cgtcggtcgc aaagctgaac aatcgaatcc    3780
ccatatttgc agtttcagcc tctcttttag agaaggacat gtccttatat gttgatgcag    3840
gcttcgatgg ctgggtcatg aaacccatca acttcaaccg acttaatgtg cttttttgaag   3900 gccttcaaac gagggataca agaaacgctg ctacgtatca tccaggctgc gactgggaac    3960
```
aaggcggctg gttcacgcct attcccgaga agcagtag        3998

<210> SEQ ID NO 17
<211> LENGTH: 7301
<212> TYPE: DNA
<213> ORGANISM: Aspergillus niger

<400> SEQUENCE: 17

```
atggaggaca gccatatact gggtgacgac ctgccactcc caccggcacg ccttttcgag     60
aggttgggac atttgcctgg atatacatgg gatcagacta ttgagccgtt tcattcgaca    120
tataatcact ggcatgtctt tggcctccga catgccgcag agtcagatgt ctctacacct    180
gccgcgacct cgtcgggccc atctagcctg gctcgcaatt ccccgcgaac cgagtcccgc    240
cctccgtttc gacatcactg gagaagcagc ctaagcgaat ccagtagtga gctctctctt    300
tctcgcatgg atcacgagcc aatatggatc ccagtgctag ctcgagtctc gtctcacgtt    360
gtgagactgg agcgcgagtt ccatatgctc agatctattg tgcagacttc cgatccagac    420
tgcaaccata ctatacgtcc catagacctt atacgtttgc cctccgaccc gggtgatgca    480
ggccctctcc tcgtggctat ctttgaatct cccggccaga atatgctgcg agaaatggtc    540
gccttttggcc ctgcctggtt cgcggccggt ggtaggactg acagcaatga gccgaccccg    600
ggagaacaag tttctcttgc cacttttctc gattttgcga ttggggcatg cgattgcttg    660
gaacttctac actacggcct caaaacggtc catggcgaaa tccgcgggga tgccttccat    720
ttcaatcgag aggcagggtc tgtgaagctt accaacacgg ggaatggtgc taggtctttt    780
gataatattc tgagcgaagg ctggtcatcc ctctcaaaag agcttggtgt caagaataaa    840
ctacaattca tcgctccgga acaaacagga agaatgccta cggagccgga tagtcgaact    900
gacatttatg ccttgggcgt gcttttctgg acgatgttgg ttggtaaacc agccttcacg    960
ggcagcgacc ctgttgaagt cgtgcagaac gtactaggaa agaagctacc accgctctca   1020
gccaagagaa tggatattcc cgacgcagtg tcagctgtaa tccagaaaat gacacagaag   1080
gctgtcaatg aacgctacca cacaatctca tctgtcaagc gggatctggc acagatctcc   1140
cagttgctcg gggatggcga tagtgaagca ttgaaagatt tccagatcgc ccagcgtgat   1200
gtgtcgtcct ttttcacgct tccctctcgg atgtttgggc ggcgagagga atatgaaaag   1260
atcactaacg tcgtcgagaa ggtccatagg cgccaacaag ctgcgtatgc gagagcagcc   1320
gctcagacct ctagtggagt aggatccaac tcctcggtct cggacggccg ggttgatagc   1380
tttgagattg catctggctc gagcgactca ggctccttca atcttgcgtc cagggcagct   1440
tccaacggtg gcccttccaa cttaggacgc gtatctactc acgaatctct gcacagtacg   1500
gattcttctc cctcaactcc taaacccggt gactcatcag gtaaacccaa gagtcctgtg   1560
gagtctcgcg catcctggga gaatgtagac agagatggcc atccttctgc tggaacaagc   1620
acgcagagcc atggtgattc gatcggatct gttgccaggc cgaaggctgc acacaaggtt   1680
cgtcgcgcag gaaaatgcga agtaattacc ataagcggtg cagctggcat ggaaagacag   1740
gaccttttga accgtgttca gcccgcaatt cgtaaacttg gatatatcgg tatagcccgt   1800
ctggatcgcg ccaggcggat accgtttgaa cctttcgcca aaattctggc tagccttctc   1860
cgccagatct tctctgaacg tgatgtcaca actgagtacc acaataacat ccgcactgcg   1920
ttgagaccaa tgtggccgac attacaccgt gtgctggaac tcccggagca gctcatgtct   1980
tccggaggaa atgaacgaca aatttccccc agactctcag cagcgcaaca tatcttcaag   2040
gaagtttcga ccaagggcga accatccaag cgcgttgcac ttccaagtct ggatcatggt   2100
```

```
caaagctctg tggacttctt tctatccaat gctgcactga agaacatgcg tttgatggag    2160
acatttttgg agatcctgcg gacgctatcc cagtacaggt tgatatgcgc atgtgtggac    2220
gatttgcatt atgccgatga cgagaccctg gagttgatta tgaacatcgt gaaagctaaa    2280
attccatgtg tgttgatact cacgagccga aagtctgagt tggagtcgaa tataatcagg    2340
cctcttttcg aatctgagaa tcccagcgtg acgcgcgtgg tactcaagcc tcttggagag    2400
gaagagatta tgcaaatcgt ggccgctaca atgcatcagg aacccaaccc gatgttaacc    2460
ccgctcgccg ctgtcataca agagaagagt atgggcaacc cgttctttgt ccggatgatg    2520
ctcgaaacct gctatagcaa aaactgtatt tggtattcgt ggaaaaattc tgtgtgggaa    2580
ttcgacctgg atcggatctt caccgaattt gtggctccta ggtatggcga ggggcttgga    2640
ctagggttca tcgcaaggcg tctccaggag atcccggcag ctgccaggtc cataatggtc    2700
tggggcgcat tgctaggaag cccgtttgcg ttctctctgg tacaaaaact tctcacaagc    2760
gagttcttgt attccagcga ggacgatgag gctgtagacc tcacctgtcc tcagaatgca    2820
aatctaatcc gacaatctga agccgatata gttgtcggtc tgcagtatct ggtgcaagca    2880
aacctgatca ttccgggaaa gacggatgat gaattcaggt aggtgctcct gattgaattc    2940
atttcgtgtc cactaactag tattcttaga tttgtcaatg atcgattctc gcaagcggcc    3000
ttgtcgttga cggagggacg gaacgtggaa aaaatgcact tcatcatatc ccaagcaatg    3060
atgaagtact accatgacgg gcgcagtcga tacgcaatgg cgcgacatgt ggctctggcg    3120
tcccggataa tcaagtctcg tgtcgtggaa agacttgagt atagaaagat cttgtgggat    3180
gcggcgcaaa ccgctgcgca atcgggtgcg cgaccaacag cgctttggta cttccggcac    3240
tgcatcactt tccttcaaga caatccttgg gatgacaata acgctgatgt gtactaccgg    3300
gagactctgc gtctgcatat tgctacggct gaaatgtcat ggtcccaagg gcataacacg    3360
gaagctctgg acttgcttga taaagtcttc gaacatggaa agagtgccgt gtgcaaatca    3420
cgagcttgga tcgttaaagc caagatctac gctcagatgg gtaaccacct ccggtcgatg    3480
gattcactcc ttacgtgcct ggaagagctt ggtgtacatc tacgagagcc tacgacctat    3540
gacgaatgcg acgatgccta ccgtaacctt cgcgcatacc tcgagcaagc ggacttggaa    3600
gctattgtcc gtaagcccgt cagcaaggat gtcgacatga tcactattgg agaggtcatg    3660
gctgaggcga tggctgtcac gtactgggac gatgcactga cattctaccg gatggccatt    3720
gaaatgatga acctacatct tttcaaaggc ggttttgtgc aaatttccat cggctgttcg    3780
cacctggcga tgatatcgtt cagccgattc agggacttgg agctcgccgt gaggctgagc    3840
gatttcgcgc tcactctcct tgagcggtgt cccgaacagt ggacccaaag tcgggctct     3900 attgtgcata acctttatgt cggccacctg cgtgttccat tgtcctcgac gctcccgaat    3960
cttgaggcct ctgttgagac atccttctcg atgggtgatc cgtacatcac cttaatcagt    4020
ctgtcgtcga tggcgatgac aagactgtat ctggccatg atatggctca ggtgaggca     4080 ttctgcaatg aaagcccgga agatattccc gactgggtca atgatactcg gggaggcgct    4140
agtctgcttg cagttaggta aggttccctc gtctactcta ggagcactgg tgaatatgtc    4200
acctgctaac agctttgcct atagacaagt tgcacgtgct ctgcaaggta aaacggcatg    4260
tcgctctcct gatactatca tgtccgatga gcaccatcac acgaatgagt acatcgcttt    4320
cctggacaac aatgccagta acgccgaccg gccgcgggac atttactggg gccttgcaat    4380
gattccgctt tttgcatatg gacatcatac caaggctata cagctgggca tgcagatgat    4440
```

```
ggagactatg cccagactgt ggtctgctcg tgtttcatac gtagtctatt tctatctcgc    4500
cctttctctt ctgactcttc acaacgagta ccctgctcgc gggtatcttg acggaagcct    4560
gcatacggtc ttgaagtata aagccgaagt ggattttgcg cgcagtgctt gcgatgccaa    4620
ttatggaatg tggtccttaa tattggaggc actgatatgc gaagtccgga atgaccatac    4680
ttccgcgatt caatccttcg aagtaagttg caggactgcc ctggatggag tgaaagagaa    4740
gctaatcagg ccaggctgca atcgatcatt gtcaaatcca cgggtggccc ttggaagaag    4800
cgcttgctct agaactgcat ggtatgtaca ccgacgtccc aaatcgcagt acttttgggg    4860
ggaggggtta cccccacgtc ttggcccaaa ttaactttcg agtaggagag ttcttgatcc    4920
gtcgcggtgc caaaagggcg gcgcgttctg tcatgcaaga cgcaattgcc gcatgggccg    4980
cgataagcgc tgtgggcaag gcggcgcagc tgaccgagaa gcatgaatgg ctattgaaaa    5040
ccgccacatc ttcgaggaat gttgacactg gctgtcaaac tgtggactcg ctgcttggaa    5100
tcaaccgcaa taccgccaa  gaacatatgg gagtagcaca gaatatgaa  gaagatgaca    5160 gaaaacaacg ctggatagaa cagaatggtg ttactaccgg tgagcgttct ttcgacatat    5220
ctggcgtcgg tcttggtaag ctacactttt ctgacacttg cgagccgtgc taatatgaag    5280
cagatatcat tgatttgtca agcatcctcg aatctagcca agtgatgtct tcggagcttc    5340
agatcgacaa acttctgacg aagatgattg agattgtttt ggagtcctgc aatggctcag    5400
actctgcggt cattgcgacc aatttcgata caacttcac  ggtcgctgcg gctgggact     5460 tggagaaagg acagaagtct ttcgtagacg gccttccgtt ctccgaaatc gaggataaga    5520
tggcgcatca gatctctcac tatgtcatgc gcactaggga ggaagttctt gttcacaacg    5580
tcctggagga tgagcgtttc tcgaacgtca atgagggata ccaagccagg tatccccttg    5640
ggcggtccgt gatcgcattg cctatcatgc aggccgagca tctgctcggt gtcatccata    5700
ttgaaggcaa accgaattca ttcacccagc gcaatgttgt ggtcctccac ttgctctgca    5760
accagattgg tatctcgctt tccaatgcgt tgctcttccg ggaagtgcgc aaggttagcg    5820
ctaccaatgc ttccatggtg gaggctcaga gcgcgcact  tgcccaggct cgcgaggcgg    5880
agcagaaggc taaagtggcc gaggctgaag caaagcacaa cgtgaagctg aaagaagatg    5940
cagcgaaggc caagtccata ttcttggcta acatatctca cgatctacgc acaccgatga    6000
acggcgttat cggtttgtcg gaactactta agggtaccaa gttggacaga gagcaggacg    6060
aatacgtgga atcaatccgt gtctgcgctg acacgttgct cacactcatc aatgatatcc    6120
ttgacttctc caaattggaa gctggcaaga tgaagatctc tactgtaccc ctcaatatcc    6180
gagaaacaat ctcagaggtg gttcgcgcac ttcgctatac gcatcgcgat cgcggtttag    6240
agacaatcga ggacctggac aaagtccac  cagaacttgt ggtcctcggt gaccctgttc    6300
gcttgcatca gatcttcatg aaccttctca gcaacagtta caagttcacc cccaagggat    6360
ctgtgactgt gagagccaaa gtttcccggg aaggcaaggg gcgtgtccgt ttagagtgct    6420
ccgtatccga tacaggaatt ggaatttcag aagaacagaa atcacggctg ttccggccat    6480
tttcgcaggc tgataactcc acggcgcggt catatggcgg cagtgggctt ggattgagta    6540
tctgcaaggc aatcattgag gacgtcctag gcggcgctat ctggctcgat tcgacctcag    6600
gcgttggaac caccgtgacg ttccatctgg cattcaacaa ggtgaaagac gctgccgcca    6660
aagctgctaa aaacaaggcc gccaaccagg tggagaacaa ggctccggtt cctaccgctc    6720
gagacttgac catggtgcct cgggatcaaa tccgggtctg tatcgctgaa gacaatccga    6780
ttaatcagaa gattgccgtc aaatttgtca aggggcttaa tcttcagtgt gaagcttaca    6840
```

```
gcgatgggcg gcaggcggtt gaagccctcc gaacccggtc ccgcgagggt aacccgttcc    6900
atgtggtcct gatggatgtg caaatgccga ctctcgacgg ttacaacgcg actcgcgaaa    6960
tccggaaaga cccagacccc aatgtcaacg aagtgttggt catagccatg acggcgagtg    7020
ccatcgaggg agatcgcgag aaatgccttg gtgccggaat gaataactac ctgcccaagc    7080
cggtccgatc tacgatattg agtgagatgc ttgaccaata tcttgcgccg gtgccagcat    7140
atacaaggac gcgactagtg aaccgggaac gaggaagtgt gagcactgag gcagggacac    7200
cacggagcca ctccatatcg cctaatattg acggccaagc caccgctgtg acgccggagg    7260
aagagaagca attgcaagag cggcagccca cagtaaatta g                        7301

<210> SEQ ID NO 18
<211> LENGTH: 3373
<212> TYPE: DNA
<213> ORGANISM: Aspergillus niger

<400> SEQUENCE: 18
gtcagatcga catcttcaac ccctagtgca gcccagacct tggtcagagc ggcacaaagg      60
aggatcgggt ctttgaaagc agcacagacg ccctaccgca taccgtctcc tctttcgctt     120
ggatacgcct gtgatatcga ttcagcctga actgtaagtc atcatgttgt ccctccacag     180
gcgcccccac ggatacccca acccggtct ttgtcttcag ttggccgccg catgagggac      240
tgacagttac gcgacaatct tagaggtgta gttctggacc atgcattgaa cttcccaaca     300
tctctctgcc gagtcccgct ttccctccga gtcggtgttt cgaagacgtc aaggttatac     360
acactaggtg gcgatagccc agcctttacg gtatttatcc cagagtttgc cgccaaatct     420
gcagggctac agcagggaat ataatatacc caaggaaaac ctcgtccgcg ctctcgatat     480
ctcgcagcca tgcttgcaaa agcaacctac aacccgttgg gcgtgtctgc aacccagacc     540
cctacaactt cctactacac tgggtcctcg cagaagccca ccgcgattgg agattcacag     600 aagggggatga tgttcactag tcccactgag tcaagttttt ctgacgcgta cgacgggctt    660
gatgctgtac ggtaagtttt ggctctatcc atgtccgatg acaaagtctc aaaatactga    720
cggttacaag atcttgggat gagaagcagg ttattgcctg gcttcatagc ataaactgcg    780
gccaatacga ggcattgttc aaaggtacta agcgccaccg ttatccaggt caaattactc    840
tggcaacaaa tgctgatcag ctccagcgaa taactttaat ggtaataacc tcatcgaatg    900
cgatcagaaa atcctgcagg agatgggaat caagaagatt ggcgatcgtg tgcggatatt    960
tgttgccatc aagcaactca ggaacaagtc agttctcaac ggcaagtcga ggaatctggt   1020
aagttgaata cgccactagt aaactgaatt gaaactaacc atgggccaga atcaactggc   1080
tacactggaa gccgtatcct acacaaacac ttcatcggag ccatcacgtc cctccaatct   1140
ccggcagact tctgcaactt ctacgactcg tcgctcgtct cgagcagccg agactaatgc   1200
tctcaactat tccgctaaca ggccgtcatc acggcccgaa tcgcctctgc gtcctcagca   1260
gtatgtcgct aatagcccga tggaaatggg gcgtatggaa caggggcaaa gctacttcag   1320
ccatccgtcc tccggtagct cgatgaccag ccgaaaaccg ggaacgccca gcgaacgatc   1380
tgggtcgcat ttgaggcaaa acccatagttt ggatggcttg actatgggac aattaccgat   1440
gaactcgccc gttatcagag tgatctacac agggggcaa actaagatgc tggacatcaa    1500
acactgcagg gatgccgatg aggtcgttct ctgcgtgctg aagaaactac agctcccgga   1560
acatcaatac cgcaattatt gcttctacgt tttggatggc ctggagccaa atcctgccaa   1620
```

| | |
|---|---|
| ctgtagaaga ctgacagacc aagagctcat ggaggtgtgt gagagtactc acaggtccga | 1680 |
| gcggggtcgt cttatccttc gcaaaatcca tgctggggaa cccgatcccg atgagcttcg | 1740 |
| tcgtgcttct caactggcgg tagatgaaag ccaattagcg catatgaatg ctctgagcag | 1800 |
| ttcaaatgtt cgcaaccagc tcaagatcca gcagctgact ggggagccct ggcataatat | 1860 |
| cagacagccc atgtcacccg tctcttccag acacaatcag acacctagtg agcacgatat | 1920 |
| gcgaccgccc atgaatgtgg agcgccaggt gggcaagttg cggtccttct tcggtgcccg | 1980 |
| tcctccaagc gagatgatca tccacgagat cacgtcctac ttccctagtc accagcggga | 2040 |
| ggaaatcgaa aagaccatgc gcatgtccgt tcgcagatcc cagcgcctga gccgggccgc | 2100 |
| aagccgtttg agtgtcgtca gtaatacaag ttatgcgtct agcttgagag atgcgccccc | 2160 |
| gattcctagc attgcagata cctggcttaa tgctgggcca cagcctgctc gcggtcagcg | 2220 |
| gccgctctca gtttccaagt tcaaccttcc ttccgctacg tacagagatt cgattgcttc | 2280 |
| tagctccctt cagcctctcc aggaagagtc gcccatcgag cctaatcgca agtcatatgt | 2340 |
| ttctttcgat agtggctcgg atgacccac acgtcgcgc cagagccttg tggatgagaa | 2400 |
| cgcaagtgtt gctgcaacgg atggaggttc acttaatgaa cgattgagca tcctcgtggc | 2460 |
| agaagatggg gaagaggaag atgatggtct caatgacttc ttggctggaa caactttgc | 2520 |
| gcccaagaat tggatgaagg atccctaat tggagagggt tccttcggaa gtgttttcct | 2580 |
| cgctcttcat gccattactg gagagcttat ggctgtgaaa caagttgaga ttccgtctgc | 2640 |
| aaccaagggc accgaatttg acaagcggaa gaatagcatg gttaccgccc tcaagcatga | 2700 |
| gattgaactt ttgcaagggt tccatcaccc gaacattgtg cagtacttgg gcactgctgc | 2760 |
| tgacgaccag tacttgaaca ttttcttgga gtacgtgcca ggagggtcca ttgctaccat | 2820 |
| gctcaagcag tacaacacgt tccaagagcc tctgatcaag aacttcgtga ggcaaatcct | 2880 |
| tgccggtctc tcttatctcc acagccgtga tatcatccat cgtgatatca agggcgccaa | 2940 |
| catccttgtt gacaacaagg gcggcatcaa gatctccgat ttcggtatct ctaaacgggt | 3000 |
| agaggcctcg actcttcttg gtgcgcgggc tagtggtgga ggtggccacg cacaccgagt | 3060 |
| ctccatgcag ggtagcgttt actggatggc ccctgaagtg gttcaacaga caatccacac | 3120 |
| caagaaggcc gacatttgga gtctgggatg tcttgttgtc gagatgttca ccggcgcgca | 3180 |
| tccccttcccc tcctgcagtc aactgcaagc aatctacgct atcggcaaag agaaagccag | 3240 |
| acctcccgct cccgaacacg cgagcgacga agccgtggca ttcttggaca tgaccttcca | 3300 |
| agttgattac gaaaagagac cgagcgccga cgaacttctc aagtgcaaat ttttggccaa | 3360 |
| tcctcttgca tga | 3373 |

<210> SEQ ID NO 19
<211> LENGTH: 4900
<212> TYPE: DNA
<213> ORGANISM: Aspergillus niger

<400> SEQUENCE: 19

| | |
|---|---|
| atggacggtc aacgcccgca gcagtacatc cccgtacccc cgccttcgtc ggcgacgcag | 60 |
| ccctcccaat cgcacataat ccctttacca ccgccgccgc ctcggtaccc tcctactcag | 120 |
| tcgcagggtg ttatgcttcc cccgccccg ggactacctc cagggacagc ttatggcgcc | 180 |
| tccaaactta ccaatcccca attgcaacat cagaatacac tcgggtggca gcaacagagc | 240 |
| tgggcaagac aagcactctc acaagggtat cttccacctc ctccgcctcc ccccatggtg | 300 |
| cctgcgaatc aatctccata cgggcgtcct gcagctttgt cgattccctc cgcggaaact | 360 |

-continued

```
cggacgtctg caacttacgt tcctcaagct ggcactttcg ggccgggggt cgggatcccg    420
ccattcgacg tacactcgaa cacgtacgac ggtgcgggga caatgcagtc cagcgacaga    480
caacggaacc cctccactca agcctacgaa tattcagcca ccgactcttc tccgtataag    540
cgggatgcca atgtccctgc cactccttct actactcgca atctaccttc ctctctagct    600
gtccatgatg gtgctcatga tatggcttca gccagctacg ccgccacgaa cgtgcaaaac    660
tcgctacaac aggtgtctgc gccgtcttcc gaactcacca catcaggcag tcatcgccat    720
aatcacagta cattgcttgg tggcatgtcg ccaaatgagg cctcggtcca gtggcctctc    780
gatcgtgtcc tgcagtggct tgcgaataat ggattctcta cagactggca agaaaccttc    840
aggtccttgg aaattcaagg ggccgacttc ctcgagctag acatgggtc aaatggccgg     900 cctaatctgg gcaagatgca ccaggtggtc tatcctcatc ttgcaaaagt gtgcgaagca    960
agtggcactc cctgggatca gattcgtgaa cgggaagagg gaaaacgcat gcgccggttg   1020
attaagaaaa tccatgatga cggcagttat gataccgaga tctcgattca gaagcgacgc   1080
gattctcacc ctatgagcgc ccacgatggc gcgcctgacg cttcgccgaa attgacttac   1140
gagccaaggt ccgcgggtcc tgcttcaggg aacatcacaa acagccctaa tctcaaggcc   1200
ccccagcctg catatggaca aagacagagc gttcagatgc gttctttcac aaccccata    1260 ccgacaactc atgatcatgc gtcttccgag cttgctacaa gcgaagctaa tacaatgtgg   1320
tcccgatcgg actattcgcg agctgtttta tctagcatcg gtggtgagca tcacaggcag   1380
agcccttcta tgtccagtga tggcgggaca ttccagatac ctattagatc ctacgaggac   1440
agtcccaaga gcgggagccc agcggcgcag catgctactt tggcacatac aggaccctcg   1500
tcatccacgg gagatctcgg tgttaagttc gagcactcgc gcggcaacag ttcagattcg   1560
accactggtc gccggtatta tgaatccatc aagcaagacg gcgggatccg tccttcgccg   1620
caggagtcaa gcaatcgcca ttctggtggg gagacaccgt cctcgtaccc taaagaccac   1680
cgtaatgggc ttttagggtt cttcaagaaa cgttccaagg caggcgattc caaccacccg   1740
tccccagagg agccgttttt ggagtctccc accagcccag tcaacatgcg ccagaacagc   1800
tcacagctgc cttataatag gccaaatttc agtaccagtg agttgtcgtt gggcgagcgg   1860
ccgtcatctt catccatgtc ggatcatgaa cgattggcgt tgcgaggcac caagccaatg   1920
caaaagagca agaagtggac atttgtgact ctggacggat ggaactatcg cttagtcgac   1980
ataactgaga tggactccgt ggagacccta cgttctgcca tatgtcaaag ccttggaatc   2040
gctgattgga ctggggcgca gatcttcatg acggagcccg gcagactga acacgatgag    2100 cctttgaatg acactagcct ggcgttgtgt cgacggacaa agtcagacac ggttggctca   2160
ttgaagctgt ttgtacgagg gcctcatatg caactgggtg tgaatagctc cactcactac   2220
ggcctggggc tgtcaatccc agagaagggc acagcctcgc ccacatctgc acaccatgtg   2280
cacagaaagc cgcttgacga ggaagctctc agcaggatat ctcctcacaa cccggccaag   2340
cctacgtctc ctcaggtgtc ttcccgacag cagctcaagg ctcccagtgc taagctaccg   2400
gcctcgcaac catcaattac aacgtctcca gtcgacggtg gcgccgaagc cggactgcct   2460
actgatgccg agaaagcaga cctgttagct cgtcacgaag aacatatgcg tgaggttgag   2520
cggaagcaga gggcctaccg catctcaaag gtcccaccca tgccacaacc gagaaaggat   2580
gtttatggtg aaactggtta ccggcgtgaa ggcgtcattg attttgatca gccccgcacg   2640
tctccctacg aagacaagaa gtctgagcca cttgtgccac ttcgcaagcc tcctactgcg   2700
```

```
cctcacgagt caagcacact caccaaagtc aattcactaa ggaagaagga tattgagcgg    2760
ccccgcatac agactaccgc gcaaccacat ggtactcacg gtctaggagc agtattggcc    2820
agtgttggta ggatgaccag cgccattgga accccatctc catcggtccc tacgccacct    2880
gccgctagtc aggagctcag agggccatcg caatcgtcta cggagcagga taaccaaaca    2940
acgccgacag tgcattcgag tcagtctccg gcacaacccg gttctgcgac tcctcaagaa    3000
ccgaaaccgc ctctgcagtc tcgcaagtca tttggacccg agtttgactt tgaggagacc    3060
aaggtatctt tccaagggtc accggtgcca cagcagcccc aagaggactc tgatgatgat    3120
tccgatgatg gactcttcgc tattcccata gcgagtacca aaaccccggt aaagagaac    3180 ccgcctatga acgtctcgcc agagtcccaa aggcgagccg ggaaaccgtc cctcacgctg    3240
aacaccgaaa acagattacg aaaagggtta tccgtcagct tcaggtcacc tagtgctacc    3300
cgcgaaacgt tcgccagttc aagcggggag tctggcaaca ggaacccgtc cttccttgac    3360
atgagtgcgt cgccggagga agagaagcca cctcgcaggg attcttttgc ccaaggcgac    3420
ctgtgggcaa gcagacctcc agtcgagggc gtcattgatc acctcgatga cttcttcccg    3480
gacatcgacc ttgataccc ttaccttgac gggcagggca tgtcacctcc ctcatccccg    3540
gcctctaagg ttgcagctga aacgacata atccccaagg ataaaccaga tgccgtatca    3600
catcccaccc cacatacacc tgcgcccca agtgagaaca ccctcggctc tagtgagccc    3660
accatgaagc ctcaggaccc cggagtcgtc gctcggcgga acgtcagtcg ctctggcggt    3720
gggctaacac gaatgaagtc tatccgagaa gtggcaaaag gtgccaacca agctagtagg    3780
aatcggagtg tgacgtctca tactggaaac caaagatcag gtgatatttt gcgccgcaag    3840
agcacgaaga tgttcggcgc caagattatg caaatcagcc cgaagcgtgg cagccgtctt    3900
agccagctgg accctattcc acagaatcat gcgccgtctg gtaatattcc tcagagacag    3960
cccactttcc gcatcatccg tggtcagctg atcggcaagg gcacttatgg acgggtatac    4020
ctaggcatga acgctgacaa tggtgaggtc ttggctgtga agcaagtgga ggtcaatcct    4080
cggattgccg gaacagacaa ggaccgcatc aaggagatgg tcgcagcgat ggaccaggaa    4140
attgatacca tgcaacatct cgagcaccct aacatcgtgc agtacctcgg ttgtgaacga    4200
ggcgagttct ccatctcaat ctacctcgaa tatatctctg gtggctctat cggcagttgt    4260
cttcgcaagc atggcaagtt tgaggagagc gtggtgaagt ctcttacgca tcagactctg    4320
agcgggctgg catatcttca caaccaggga attctccatc gtgacctgaa agccgacaat    4380
atcctcctgg atctggacgg aacgtgcaag atctctgatt tcggaatttc gaagaaaaca    4440
gacaacatct atggaaacga ttcgaccaac tccatgcaag gctcggtctt ctggatggcg    4500
ccagaagtca tccaatccca aggacaaggg tacagcgcca aggtagacat ctggtctctg    4560
ggatgcgtgg tgttggagat gtttgcagga cgccgaccgt ggagcaagga agaggctatc    4620
ggtgcgatct tcaagctggg tagtttgagt caagcccctc cgattcccga agatgtttcc    4680
atgaacatca caccagcagc tctcgccttc atgtacgact gcttcacagt gtaagttgat    4740
attgcctttt ggaaccattt ccgccagact gacctgttat agggactcgc gtgatcgacc    4800
aactgctgag actctcctga cccatcccctt ctgcgaaccc gacccgaagt acaatttctt    4860
ggataccgag ctctacgcca aaatccgcca cgtcctgtaa                         4900
```

<210> SEQ ID NO 20
<211> LENGTH: 4163
<212> TYPE: DNA
<213> ORGANISM: Aspergillus niger

<400> SEQUENCE: 20

```
atggaatctc agcaggaccg cgggtttccg atcatggagc atcctgattt aaacaaccat      60
gattcggatg gctccgggtc ctccgatgag cttctgcagc agccatatgc tgtaagagcc     120
aactccagtt tcccggagaa tttcgacacc caggtccaaa ccccggcgac gaccatttcc     180
tcgtcccctc ccccatccat tgcgtctgcc ctgccatcat gggcaaccgg cacgcccaca     240
cgcgcccgcg gggccagtat aggtgcttct gctgctcttg agaaagctcc gccgatggat     300
ggccatccgg tgaccgatcg tgacttgagg ccgcaacgtc cgtccggccc cgctcggacg     360
ccctccaata cctacgcgcc caacgacgc ccacctcagt atatcagctt ccaaaatgac      420
cgccaacgga gctcatcaac gaaacgaact tctagacgcg atcccaatgc acagtaccga     480
gctcaggaga aggcgtatgt ccagcgcatt cgtgcggacc tcaggcctg gtacagtcat      540
ttcgatgagg ctcaaaacat gagcatgacg gtcggggact cggacctaga agaaccctca     600
ccatcctcgg aggttccttt cgaagacgat gcctacgatc cggatattca actcttcctg     660
accgacgaca atcagccgac gatcgaggaa ctcaagaacc caagaaacca agagaggctg     720
gagtggcatt ctatgctttc gtctgtgtta aagggagacg tggtgaagca agagaaacag     780
cgattactcg gctctacaga atcaaaacga tcgtcggccc agaacaacgc aatatggttg     840
ggtgtcagag ccaggacctg tggaaggagt gttgcactgc agaggaaact cattgaagaa     900
gcgagggctg gccttggccc catcatcgaa gaaattatca agttcgagat caaaggtgaa     960
acagagatcg ggaagccacc catcaagcag gttgaggata ttgtcgcaca gatagaacgt    1020
tgtgaaagcc tctactctac tcacaaggag ctggagactg cccaccccag agtcgcttca    1080
gaggagtatc actcgagtcg cgatgctgtt tttgcctggc acaacacgac catcttgatc    1140
aacaccgagc tcgctatcct gcagaaatgg gttggaaacg atgagttgga tttcagcaaa    1200
tcgagaacga aatcaatcaa tagcgaccit tccgacgaaa catccttcct tgaccgcatc    1260
atgaaggagg atggcctcaa aacgctgcaa ggaaaacata acatgctcca cggcattgga    1320
gaagtcatcc aaaaagcaaa gaatacatta attgagaatg ccggttcctt cgccaaacgc    1380
cacttacctc cctatatcga agaacttctt actcttatca atttcccgtc tcgtctcata    1440
caggaaatta tacgggttcg actatcttac gctaagaata tgaaagaccc agcttcgcaa    1500
tccgccatct tagtcgatca aatgatatcg cagttccaga ttttgatgaa ggtggcggtc    1560
gatatcaaac ggcattattt ggatatcgcc agacccgagc ctgggtggga cctgccccct    1620
tgcattgatg acgtttcga cgcagtcgtc ttggatgcga tgaagtatta cttccggctt    1680
ctgaactgga agctgactgc aaataagaac acattcaaag aagcggagat tctagaacag    1740
gattgggaat tttccaacga ggtcggccga caacttgagg gcggagatat cgaggtcgcg    1800
gagcagttta ggtacgaaca accttcacac tatgcgatat atcaatatgg ctaacctgag    1860
ctagtgcact gactgccaag tcgatccaac gcttgatgta ccactcgag cgggagttgc     1920
agcctcgcca tgacgaggat cctgccgaca tggacaagcg ttataaaagc gtattggact    1980
caactcggat ccggcaacgg aagctttacc gattttcccg attcttgcgc cagctgttcg    2040
aaaatgcaac ggaatacaat ttgccggctg acattgcata cgactttttg gagtcgttgc    2100
ttgtgtcgga tcattttatg atcaaatcaa acgtctctgt tggtcaaaag ggcgtctatc    2160
tctttgcgca ccctgcattg tgggatcgcc ctgcagatat ccaagctatc ctaggcacat    2220
catttcgtga ggatgacacc agcaaggata caccccatgc accgtatata ctcgtggttc    2280
```

```
gtccggaaaa gccccttttcc tgggctggca agaaatgca gctgggcatc atggaacagc    2340
ctacggactt gcgattgggc aaattgcgac ttgtggttga agggacgcag cagcggctgt    2400
ctaatgcgag acatgagctg actcatctca ctggtattca gctcgatatg ccatcgagc    2460 aacgtgccaa tcttggtcgg gtcaacgtgg agctaaacaa gatcaagaag acgtcattta    2520
agctatcaat gactatcatg gatagtgttg cccggatacg ggagcaactc aaggatagag    2580
acgtggagaa ccacgatcta gtccaagcat gctatgcttt tgcgaccgag ttcgggaagc    2640
gttcttcaaa cgttgatccc aatagacgcg caatgaacag taatagactt gtcgagttgt    2700
ccctcgactg ggtttcgttc atctgtgatg attgtgatgc tgctgacagg aaaaccttca    2760
agtgggccgt tgctgctctg gaatttgcaa tggctatcac ctccagcagg cacctcctgt    2820
ctatggatga tgctcagtat agtcgactga ggcagaaggt tgccgggtgc atgtcgctcc    2880
ttatatctca ctttgatatc atgggtgctc gatcgtctcg tgcggctcaa gcagagaagc    2940
aacgcttgga gagcgcggc ggttcgagac gaatgggcgc agggcgaatc cttacagatg    3000
aagaggcagc caagcttgtt cgggagcagc gcgtggctca tcttaccgag atcgaggaga    3060
gacgcgttga cgaagatgct aaacgccaag cattgggaag ggttctagag ggctcaaacg    3120
aagcggacag gtctcttacg gtgctttcat cctcggctac gaacgttact ctgcgatggc    3180
aacagggcca gttcattggt ggaggaacct ttgggtccgt ttacgctgga attaaccttg    3240
acagcaacta cctcatggct gtcaaggaga tccgtttgca agaccccaa cttatccta    3300 aaattgccca gcaaatccgt gatgagatgg gtgtgttgga agtcttggat catcctaaca    3360
tcgtctctta ccacggtatt gaagtgcacc gcgataaggt ctacatcttc atggaatact    3420
gttctggtgg gtcccttgcc agcttgcttg agcacggacg tgtcgaggat gaaaccgtca    3480
ttatggtcta cgctcttcag ttgctggagg gattagcgta cctgcaccag gctggcatta    3540
tccatcgcga tatcaagcct gaaaatatcc tgcttgatca taacggtatc atcaaatacg    3600 tcgatttttgg agctgcaaag atcatcgctc gtcagggcag aaccgttgtc cctatggatg    3660
ccttcgctgg cgctggtcat aaggacgcta tagtgcccaa ggacgcccag ctggctcaca    3720
acaattgggg caagaaccag aaaacgatga ccggcacccc aatgtacatg tcacccgagg    3780
tgattcgcgg cgataccaca aaacttatcc accgccaggg agctgtcgac atctggtcgt    3840
taggatgcgt gatcttagaa atggccacgg gtcgtcgccc ttggtccact ctggataacg    3900
aatgggccat catgtacaac attgcccagg gcaaccaacc gcaattgcca tcccgagacc    3960
agctcagcga cctaggtatc gacttcctcc gacgatgctt cgagtgtgac cccaataaac    4020
ggtccactgc agcagaactc ctccagcatg aatggatcgt ctccatccgc cagcaagtcg    4080
tactcgagcc agccacgcct ggcagcgaca atagcggtgg tagttcccat tcaggcagtc    4140
gccagaactc agcgtatcta tga    4163

<210> SEQ ID NO 21
<211> LENGTH: 1813
<212> TYPE: DNA
<213> ORGANISM: Aspergillus niger

<400> SEQUENCE: 21
atggccgatc aattcaaggc gcgaacgctg aagcgcaaga acgtcaaagg ccttgccctg     60
aacgcagctc cgaagcccgc ctccaataat tccgatggcg atgctcaggt tccaggcgcc    120
attgggaaca ccgacagcaa ccgcaccgat actctggaga tcggcctcga gtttcgtctt    180
gacctgcgta gcgaggatct ggttaccctg aaggagctgg gcgctggaaa tggtggtacg    240
```

```
gtctcaaagg tcatgcacgc ctccacgaag gtggtcatgg ctcgaaaggt gcgtgccttc      300
tggagaccct cgtcgtccgt gctttgccgt agacccggca ggtatgctga ccccgtcgtc      360
ctagataatc cgcgtcgacg caaaggagaa tgtgagaaag cagatcttgc gggaactcca      420
ggttggacac gactgcaatt ccccccacat tgtcaccttc tatggtgcct tccagaatga      480
agccagagat attgtcttgt gtatggagta catggattgc gggtaaggga gccgctgcct      540
ttcctttttct tctgttggtt ccaagctaac ctggaccctc gcatgatagc tcgctcgatc      600
gcatatccaa ggactttggt cccgtgcggg tagacgtgtt gggcaaaatc actgagtcgg      660
tcctggccgg tctggtgtac ctgtacgaag ctcatcgtat catgcatcgc gatatcaagc      720
catccaacat cctcgtcaac tcgcgcggca acatcaagct ctgcgacttt ggcgttgcga      780
ctgagacagt caactcgatc gctgatacgt tcgtcggcac ctccacctac atggcccccg      840
agcgtatcca gggtggtgcg tacactgtgc gctcggatgt gtggagtgtc gggttgacgg      900
tgatggaatt ggcggttggt cgcttcccct ttgacacgtc cgactcctca gcaggcgacc      960
gtgccagcgc cggtccgatg ggtattctgg atctgctgca gcagattgtg cacgagcctg     1020
ctccgaagtt gccaagagc gacgccttcc ctcccatcct gcacgagttt gtcgccaaat     1080
gtctcctcaa gaagtccgag gaacgcccca cgcctcgcga gctttatgta tgtctcaccc     1140
tttgtccgct tttggactac ggtcttgagc cggatccgac taacagccaa tttaggacaa     1200
ggatgcgttc ctgcaggccg ccaagcggac gccggttgat ctccaagaat gggccatcag     1260
catgatggag cgacacaacc gcaagtcgta tctggctccc ccgccgccca agtcgctcaa     1320
ggacgagccc ccagctgcgc gatcgactcc gtccccgaag cctcaacccc agcagcagcc     1380
cagcagcaag ccgatgcgca ctccccagta cgcccccagc gacattccct ccagcgtggg     1440
ccgcaacagc ccctcgcagt accagtacaa ctacgccccc gccaacccat ccccgcgtcc     1500
acccccggtca acacgctcgc ctcccatctc tctcgagcat ctgtcgttgg aagatgagta     1560
ccgctccggc cgtcgtccct cacggactcc cgtcgggggc ccctcttccg gattggaacc     1620
ccccatgaac ccgatgggat ctcgttccgc cagctcacac aacacgaagt cgcgaatgcc     1680
tctacagtca gcagcgctgc ccgtgcgaaa cgcgcctccc ccgagcgggc cttcgccctc     1740
tgctcctgga aatggatcct ggcagcgcca gccaaactcc atgcgcgggg accatatgac     1800
gggtgccgtc tag                                                         1813
```

<210> SEQ ID NO 22
<211> LENGTH: 2128
<212> TYPE: DNA
<213> ORGANISM: Aspergillus niger

<400> SEQUENCE: 22

```
cctctgtctt cattctctca cactctctcc ccctctccga tcagccaacc cctcttgtca       60
gccaaccgcc gctctgttca gccaattaac cccacggccc tctttgttcc gaccacctcg      120
tccaactcct cttcctctta cttatcacac cttctcctct tttctcctct ttcacttaat      180
ccctctcccc agagtccccc cgtccctctt tcaaagtgtc ctactcaaac accgccgatc      240
tggctacctt ggctgacccc aacgagttgt ttttgcctgg tgagaggcaa aacaatctcg      300
caatgtcatc ctcgccggtt cctctcctca agccgcccgt gcctggcaac cgcggcaaca      360
acaatggttc ccgacctccc aaactcacct tgggaatccc tccatctcca aatgttcgtc      420
cggtcacggg aacccggtgtt cctgtcgctg ccgccgccgc cgctcccgct cccgcgcctg      480
```

```
ctcctccaac agaggtccct cagctgcagc gtccagctgc tcgcccggcg cctccccagc      540
tacgtctgaa aaccccatg ggcagcagtc agaatgtgca acaagtgaag agtcgacccg       600
ctccaccacc gttggcgacg accggcttga acgaaccgaa tggacactcg aggtctggta      660
gcttcacgta cctggacggg aaggccagtg ggcccgcctc cgcatcatcc tccaactatt      720
cagccctatc attcgccatg ggccttcgcc agcctcacgg cagcactccg gatccctcgt      780
cagcgatttc cgtctactcc gaccgggaaa gtggtgtaca gatggagcgc gatagcagtg      840
tgaacagcct aatcccggat ctggacaaga tgagtctgga aaagggcagg ccctcgatg       900
tggatgactt ggatgatgaa gcctggcttg cagctagtga gcagaagaaa attgtggagt      960
tgggtagctt gggtgagggc gctggaggtg ccgtcactcg atgcaagctc aaggagggta     1020
agacggtgtt tgcgttgaag gtaggtttca ttggtggttt gcatcgtctg gtgttttggt     1080
atgttaacaa ctttctagat tattactacg accccaacc ccgatgtgaa aaagcagatt      1140
gttcgagaac tcaacttcaa taaagattgt gcctcggagc acatctgtcg ctactacggt     1200
gctttcatgg acaagtcaac ggggaccatc tccattgcaa tggaattttg cgaaggtggc     1260
agtttggaca gtatctacaa ggaggtcaag aagcttggtg gacggacggg agagaaagtg     1320
ctaggcaagg ttgccgaggg tgtcttgaac gggttgacct accttcatag cagaaagatc     1380
attcaccgag gtcagtcagg ttctagattt gtagttgttt atcatccagc taacgttaat     1440
cttagacatc aaaccgtcga acattctcct ctgccgaaat ggtcaggtca gctttgtga     1500
ttttggtgtc agtggagagt ttggcaccaa gggagacgcc aatacgttta tcggcacatc    1560
atactacatg gcccctgaac gcatcaccgg ccaatcatac accatcacct ctgacgtgtg    1620
gtcactcggt gtgaccttgc ttgaagtcgc ccaacatcgc ttccccttcc ctgccgacgg    1680
caccgaaatg cagccacgcg ccggtttgat cgatctgttg acctacattg tccgtcaacc    1740
gatccccaag ctgaaagacg aaccggacaa cggtattcga tggtccgaga acttcaaata    1800
cttcatcgag tgctggtacg tgttgatatg cctaatagta gatggattgt gctaactttt    1860
cgtctagttt ggagaaagaa cctccgcgac gagcgactcc ctggcggatg ctcgaacatc    1920
cctggatgct ggacatgaaa acaagaaagg tcaacatggc caatttcgta aggcaagtct    1980
gggactggaa agactagatt gcctgcatgc agcaactgga tctcggcaat cattcatgca    2040
ccttccggac gaaatgctcc acctctaata cgatcgcaca taacggtctc tcctttgatg    2100
cttacaagtg gctggcccctt ggttgacc                                       2128

<210> SEQ ID NO 23
<211> LENGTH: 1943
<212> TYPE: DNA
<213> ORGANISM: Aspergillus niger

<400> SEQUENCE: 23
atggacaacc ggtccgacac gaccgacgac gaccttcac cctccctcgc gacgacacaa       60
tcgtacgctt cagtgccctc cctccgcccg accctcgata aatccggtat tactgcgtcg      120
tcgacacatc tcggccaact caacgccgcc cgccgcggtg cgggaacccc tcctcgtcca      180
caagcttcaa tgagcggcgc gcaacctgga ggattgaatc aagatatttt agcgaagatg      240
aaggctttct ccttgtcccg acagggcgcc ccaccctctt tggcgcatgc caatacgact      300
ggcttggtgc ccagggcctc tccgtcggtg tcgggcggaa gtcccgtctc aggacaacct      360
tctccaggcg caaatggccc cttagcaggt gctcttgccg ccgtttaccc cccggcgct      420
gttcgtccaa ctactaaaaa ctgggtctcg tcgccttccg tgcctcatgg gtctcccggt      480
```

```
ggcagttctc ccaagcccgg tggtctggcc gcgaaacgta tgaagccggg gctgaagtta       540
tcggacgcta cgggtctgaa cggctcaccg tcgccaggcc agcccgccaa cggcggacct       600
gctcctacag aaaccgcatt tagcaaatat tcggaattta tcgatacaaa atcggggacg       660
ctaaatttca agaacaaggc tatcctccac ggtggcggta tcgaattctc atcaggtcac       720
agtttcagca tctccttaga cgaggtcgat cgtctggacg aattaggcaa gggtaactac       780
gggacagtgt acaaggttcg ccatagccgt cctcacatgc gcaaacccgg aatgggatta       840
cgggggataa taagccgcaa tgatgatgga gacagcacta cgacacccgg agtgaagtca       900
gaaggtaatc tttctggagt cgtcatggcg atgaaagaga ttcgcctgga attggacgag       960
agcaagttcg ctcagattat catggaattg gagattcttc accgctgcgt gtccccattc      1020
attatcgact tctacggtgc cttcttccaa gagggtgccg tctatatctg cgttgaatac      1080
atggatggcg gctcgatcga caaattatac aaggagggaa ttcccgagaa catccttcgc      1140
aaggtagcat tatccactgt catgggcttg aagaccctca aggacgacca caatattata      1200
catcgcgatg tcaagcccac aaacatcctc gtcaactccc gcggacaagt caagatctgc      1260
gatttcggtg tgagcggcaa cctggtcgct agtattgcca agacgaacat tggctgtcag      1320
agctacatgg cccccgagcg cattgcaggt gggggtgtgc agcagtccgg agcaagtgga      1380
ggcggaacct acagcgtcca gagcgatgtc tggagcttgg gcttgtccat aatcgagtgt      1440
gccattggtc ggtatccata tccgcccgag acattcaata acatcttcag ccagctacac      1500
gtaagtcatt gttttcatta catccttgcac gtcattgaag atactaaccg tccacaaagg      1560
ccattgttca cggtgacgcg cccacactcc ccgaaacggg ctactctgaa gaagcacact      1620
cctttgtccg cgcgtgcttg gacaaaaatc cgaacaaccg tccatcgtac agcatgctcc      1680
ttcgacatcc ctggctgtcg tcgctcatgc agcctcccac aaacaccgac gctgatgatg      1740
cacccaacgg ctcggcgaag gagggtgcgt ccaatgtaac ggaagatgag gaagtggcgg      1800
cgtgggtcaa ggaacagcta gaccgtcgcc agcgcggctt ggttcaagac gcaagcaagc      1860
ctgcactaca cgccgtcgcc ctggatgccg ttcctgggag ccccctcctt gatgacccct      1920
ccactatttc cgctcaatgt taa                                              1943

<210> SEQ ID NO 24
<211> LENGTH: 2623
<212> TYPE: DNA
<213> ORGANISM: Aspergillus niger

<400> SEQUENCE: 24
caccgagcaa gaacacttgt tcacctctct ctttctctat ttatcgtgat cgctattgtt        60
gttcgtgtta ttgatgacat acctttgcta ctcatctccc tcatcatctt tcatctctcc       120
ctctcttctt cttcttcttc ctcctgcccc accccactct ggccgatccg cgcccggttt       180
attaacttcc aactacgtac gctagtctcc tcattgtgtc ctactactgc cttcactatt       240
gctctgtgtc tctccatccc ctctccacat ctctcgaact gctcctgctg tctttttttcc      300 ctcctctgcg cttactcttc tgtttccccc ctccgatctg ccctggtgt gtttccactg       360 tccattcgag aaagctcaaa gaacccttg aaactgactc gcggttgcat agcgcaagct       420
acgagggaga caccatacaa cggaattaaa aatagaacgg aactgtgaaa cgccagacgg       480
agtgtgaaaa tagctcctca acattggtaa gtccatctcc ttttcagcga cgtcttgcct       540
cttgacctgg agtattacaa aaggttctct tcgctcgtgc tggatcggtt cattgacatc       600
```

```
ctccagttcc ttttcaggtc atcacataca tccaccccac gtccttgctg agcggttcgc    660
ccggcctgcc tcacgaccaa ccgcccctgg ttcccgaatc tacattgaat ccctcccatc    720
ccgaacgtac aggcgcctcc ggaactcctg gcggctactt gcgggtcctc cgtggtttcg    780
attgcagacg cgctgtaccc cgcttccgat ccttgacagc tcccgaacga ctgtcactcg    840
tctaccactc tcgccctagc atgcgcattg gcggttatta gcccccccaa cataaccaac    900
atcaattgag agccctcctg taagcgctag cctggcatct gttgcctgaa catgtggtgg    960
gtcgcggtgt tactcaatag gccatcttgt tgcatgtgac gggcctacct tgtcacttca   1020
ctcaggtgtc atggggtgtg atgagatagt ctactgagta cacgacccaa cacaactgaa   1080
tgcagcagat acgctcattg atttcgactg acacttgata gttcacaaac cgcaattatg   1140
gtgcagcaaa tgcctcctca aggggggtcg cgaaagatct ctttcaacgt ttccgaccag   1200
tatgagatcc aggatgtcat tggtgaggga gcttacggtg ttgtatggtg agtttgctca   1260
cttgctcggc gtgagtgatg gcagcatact aatgaaccga agctctgcta tccacaagcc   1320
ttctggccag aaggtcgcca tcaagaagat caccccttc gaccactcga tgttctgctt   1380
gcggactctg cgtgagatga agctgctgcg ctacttcaac catgaaaaca tcatttccat   1440
tctggatatc cagaggcctc ggaattatga gagcttcaac gaggtgtatc tgattcaggt   1500
aacgctcatc gtcattaatt cagcgaagat tggactgacg gatccaggaa ctgatggaga   1560
cggatatgca ccgggtcatt cgtactcagg acctctccga tgaccactgc caatacttta   1620
tctaccagac cttgcgtgcg ctcaaggcca tgcactccgc caacgtcctc caccgtgatc   1680 tcaagcccctc caaccttctc ctcaatgcaa actgcgacct gaaagtctgc gactttggtc   1740
tggcccggtc agccgcatca accgacgaca actctggatt catgacggaa tacgtcgcga   1800
cacggtggta ccgtgccccg gagatcatgt tgacgttcaa ggaataccc aaggcgatcg   1860 atgtctggag tgttggatgt atcctggcgg aaatgctgag tggaaagccg ctcttccccg   1920
gaaaggacta tcaccaccaa ctgactctga ttcttgatgt cctgggcacg ccaactatgg   1980
aggactacta cggcatcaag tctcgccggg ctcgggagta cattcgctca ttgcccttca   2040
agaagaagat tcccttccgc gcaatgttcc ccaagagcaa cgagctggcg ctggaccttt   2100
tggagaagct tctggcgttc aaccctgcga agcgtatcac tgtcgaggag gcgttgcgtc   2160
atccgtacct cgagccgtac catgaccctg atgacgagcc aacggcgccc ccgattcccg   2220
aaggcttctt tgattttgac aagaacaagg atgcactcag caaggagcaa ctgaagcgta   2280
agtaaaccgc atctgcattc gagactcttt actgacatgc gcagtcctga tctacgagga   2340
gattatgcgg taaaggcttc acgagtcgat gaatgcaatt gatataccac ccgacatgga   2400
acgaaggcag agcctgacat gatggacgga gttggcttag cacataccca tggatgcata   2460
gagaacaggc cgcggcacca ggcgcgctgg ccttgtacgc agtaatatat tgaatagccc   2520
aattgtgagg gagtcatgac tgcagcatct cgagattgtt gttgatgttg atgtggaagc   2580
ggcgtgcagt ttcagcgata gtccagcttg aatatacatt acg                    2623
```

<210> SEQ ID NO 25
<211> LENGTH: 2350
<212> TYPE: DNA
<213> ORGANISM: Aspergillus niger

<400> SEQUENCE: 25

```
gcctgacaga cgccattcct cgtgaattga ctggttctgt accttcaacc cgccgagctt     60
gtctggagag aagtgacaaa gagaaaataa aaagggagaa aaagcaacct cagccggagc    120
```

```
gaatttcctc tgtgtgagaa gcctgaatcc gccagggaaa agaaagagtc tcaatccacc    180
gccgggccag cccagcggct actttgctac cattaaatca cttaactcac taccccacct    240
ggtgccatcc atcggaacaa ctctctccct acctcatcga ttctcccaat cggcctcata    300
acttcccctt tacctccccc gccgtacctc gtctcgcttc tttctaccat cttctctgtt    360
ttcttctttg tacgagtgtt tatcatggcc gacttgcagg gtcgcaagat cttcaaggtc    420
ttcaaccagg actttatcgt cgatgagcgc tacaatgtca ccaaggagct gggccagggc    480
gcatacggca ttgtctggta ggtttgacat tctccgacag agtcactcat cgtggaggat    540
gcaatatcgg ttcaatggat cttatttttc taacaatttc agcgccgcga caaatgctca    600
cactggtgag ggtgtcgcca tcaagaaggt caccaacgtc ttcagcaaga agatcctagc    660
caaacgcgcc ctgagagaga tcaagctgct ccagcacttc agaggtcacc gtaacgtgcg    720
ttattattat acccattccg attattgctc cgagcctcga gtctgacgtg aaagtggctt    780
agatcacttg cttgtatgac atggacattc cccgcccgga caacttcaac gaaacgtacc    840
tgtacgaggg tgaggcttcc ttcggtaccc gcgggctact agttcctgat gctaacacca    900
tccttcatta gaattgatgg aatgcgattt ggccgctatt attcgctccg acagccccct    960
aaccgatgcc catttccaat ccttcattta ccaaatcctc tgcggtctca aatacatcca   1020
ttcggccaac gttctgcacc gtgatttgaa gcctggaaac cttctcgtca atgcggactg   1080
cgagctgaag atttgcgatt tcggtctggc ccgtggtttc tctatcgacc cggaggagaa   1140
tgcaggatac atgacggaat atgtcgccac aagatggtac cgtgcgccgg agatcatgct   1200
gagcttccag agctacacga aagccagtat gtgtctctca tcctcccctg ccccggcgct   1260
attgctaata tacccagtc cgatgtttgg tccgtgggtt gcattttggc cgagctgcta   1320
ggtggtcggc ccttcttcaa gggccgtgac tatgtcgacc agcttaacca gatcctccac   1380
tatctgggta ctcctaacga ggagactctg agccgcattg gctcacctcg tgcccaggag   1440
tacgttcgca acttgcccct catgcctaag attcccttcc agcgcctgtt ccccaatgcc   1500
aatcccgatg ccctcgatct gctcgatcgc atgcttgcat tcgacccgac atcgcgtatc   1560
tcggttgagg aggcccttga gcatccttac ttgcacatct ggcacgacgc ctcggatgag   1620
cccacctgcc cgacgacctt cgacttccac ttcgaggtgg tcgaggacgt gcaggagatg   1680
cgccacatga tttacgacga ggtagtgcgc ttccgggctc tggtccggca gcagtcgcag   1740
gcgcaggccg ccgcgcagca gcagcagatt gcccagcaga ccaatgtgcc catccccgac   1800
aaccaacaag gtggatggaa gacggaggaa cctaagcccc aggaagcgct cgccgcaggc   1860
ggtggccacc acaacgatct ggaatcgtcg ctgcagcggg gcatggatgt gcagtaggcc   1920
actactagtt ccagcctgcc gctgccttct tcaaatacag tgtacatgtg ttcagattaa   1980
gacaatggtg gggaggagag gcctgactat ttgagacgga ttataatcat tatcgttccg   2040
gaagtcgcgg gcgtttcctg gactacctac cgctgttata cgatatcatc catatcgcta   2100
tctatccgtt atgctgtcct gtgttatgcc cttactccct gtctgctggg attatgaatt   2160
cttgaaatgc aaacgtacgc tcttggtcgg ctgctgtcct ctcattggat gaggttttgt   2220
cattgatttt ccccccatgaa agaaagaact ggttttactc gcatcccgga agtgtctttg   2280
gagacatatc tcgccgggaa actgctgcct tgcaattgag cgctgattcg aacacggtct   2340
gccttggttg                                                          2350
```

<210> SEQ ID NO 26

<211> LENGTH: 1746
<212> TYPE: DNA
<213> ORGANISM: Aspergillus niger

<400> SEQUENCE: 26

```
cagatctcct gagaaagagc ttccgaggct cccacttccc ccctctttga gtgcggtgta      60
ccgtcatcct tgctccaaaa tggcggaatt cgtgcgtgcc cagatcttcg gcacaacctt     120
cgaaattaca agcaggtgcg actcttttg acgatttaaa aagatcagt atgatctatc       180
gaccatttac tcattctctc gcaggtacac agacctgcag cctgtgggaa tgggcgcttt     240
tggtcttgtc tggtaagttc gacaacccct cttctggatt tcgcccgcca cgcggatggc     300
ttctgtggcc cgcccgaaca gcacatggac tgacgcctgt catggtataa ttcagctctg     360
cgagggatca attgacagga caaccagtcg ccgtcaagaa gattatgaag ccgtttagca     420
caccagttct gtccaagaga acgtaccgcg agttgaaact gttgaagcat ctacgacacg     480
aaaatgtcag ccaaaatccc cccaccaaaa ggcggtccgc catccgccgt accgcaatgc     540
tgactatgag cagataatca gtctcagtga tatcttcatt tctccgctcg aagatatgta     600
agaaactttg cctgcttcga gctgtcactg agttgccttg tttttctgac gatcgccgca     660
gctatttcgt cacggaactc ctgggaaccg acctccatag actcctcact tcccgacctc     720
tggaaaagca gttcattcag tatttcctct accagatttt ggtacgccat tctgtcattt     780
atttccgcgt tttttctatc gtggatcttt cgcctggcgt acgctgacca ttcgcagcga     840
ggactaaaat atgtccactc ggccggtgtc gttcatcgcg atcttaagcc gagcaacatc     900
ctcatcaacg agaactgtga tttgaaaatc tgcgactttg ccttgcccg tattcaagac      960
ccccaaatga caggctatgt ctcgacccgg tattatcgcg ctcccgagat catgctcaca    1020
tggcaaaaat acgatgtgga agtcgatatc tggagtgcgg cctgcatctt tgcggagatg    1080
ctggagggaa agccactgtt cccaggaaag gatcatgtca accaattctc gattattaca    1140
gagcttttgg gcaccccgcc ggacgacgtt attcagacca tctgcagtga aacgtgagc     1200
atccactctc cgctactgtg aatcctgctc tttcgatgag atatcgctaa tattttaccg    1260
tgttagactt tgcgatttgt taagtcactg ccgaaacgcg aacggcaacc tttggctagc    1320
aagttcaaga atgccgaccc cgacggtatg tatattgcca atagtcaaat tagtcgacgc    1380
tgggccaatc tctaacatca tcatagctgt tgatcttctc gagagaatgc tagttttcga    1440
ccccaagaag cggatccgtg ccggcgaagc gcttgcacat gaatatctcg cccccctacca   1500
cgaccccacc gacgaacccg tgcggaagaa gaagttcgat tggtccttta atgacgccga    1560
cctgccggtg gatacttgga agatcatgat gtgggttttt gcgaattaga gctgttagag    1620
tgttgaatgc taacctagtg taggtactcg gagattcttg acttccacaa cattgatcaa    1680
gccaacgatg ctggccaagt gcttgtcgaa ggagcagtcg cagatggaca acaggccttc    1740
gcatga                                                              1746
```

<210> SEQ ID NO 27
<211> LENGTH: 7301
<212> TYPE: DNA
<213> ORGANISM: Aspergillus niger

<400> SEQUENCE: 27

```
atggaggaca gccatatact gggtgacgac ctgccactcc caccggcacg cctttttcgag     60
aggttgggac atttgcctgg atatacatgg gatcagacta ttgagccgtt tcattcgaca    120
tataatcact ggcatgtctt tggcctccga catgccgcag agtcagatgt ctctacacct    180
```

-continued

```
gccgcgacct cgtcgggccc atctagcctg gctcgcaatt ccccgcgaac cgagtcccgc    240
cctccgtttc gacatcactg gagaagcagc ctaagcgaat ccagtagtga gctctctctt    300
tctcgcatgg atcacgagcc aatatggatc ccagtgctag ctcgagtctc gtctcacgtt    360
gtgagactgg agcgcgagtt ccatatgctc agatctattg tgcagacttc cgatccagac    420
tgcaaccata ctatacgtcc catagacctt atacgtttgc cctccgaccc gggtgatgca    480
ggccctctcc tcgtggctat ctttgaatct cccggccaga atatgctgcg agaaatggtc    540
gcctttggcc ctgcctggtt cgcggccggt ggtaggactg acagcaatga gccgaccccg    600
ggagaacaag tttctcttgc cacttttctc gattttgcga ttggggcatg cgattgcttg    660
gaacttctac actacggcct caaaacggtc catggcgaaa tccgcgggga tgccttccat    720
ttcaatcgag aggcagggtc tgtgaagctt accaacacgg ggaatggtgc taggtctttt    780
gataatattc tgagcgaagg ctggtcatcc ctctcaaaag agcttggtgt caagaataaa    840
ctacaattca tcgctccgga acaaacagga agaatgccta cggagccgga tagtcgaact    900
gacatttatg ccttgggcgt gcttttctgg acgatgttgg ttggtaaacc agccttcacg    960
ggcagcgacc ctgttgaagt cgtgcagaac gtactaggaa agaagctacc accgctctca   1020
gccaagagaa tggatattcc cgacgcagtg tcagctgtaa tccagaaaat gacacagaag   1080
gctgtcaatg aacgctacca cacaatctca tctgtcaagc gggatctggc acagatctcc   1140
cagttgctcg gggatggcga tagtgaagca ttgaaagatt tccagatcgc ccagcgtgat   1200
gtgtcgtcct ttttcacgct tccctctcgg atgtttgggc ggcgagagga atatgaaaag   1260
atcactaacg tcgtcgagaa ggtccatagg cgccaacaag ctgcgtatgc gagagcagcc   1320
gctcagacct ctagtggagt aggatccaac tcctcggtct cggacggccg ggttgatagc   1380
tttgagattg catctggctc gagcgactca ggctccttca atcttgcgtc cagggcagct   1440
tccaacggtg gcccttccaa cttaggacgc gtatctactc acgaatctct gcacagtacg   1500
gattcttctc cctcaactcc taaacccggt gactcatcag gtaaacccaa gagtcctgtg   1560
gagtctcgcg catcctggga gaatgtagac agagatggcc atccttctgc tggaacaagc   1620
acgcagagcc atggtgattc gatcggatct gttgccaggc cgaaggctgc acacaaggtt   1680
cgtcgcgcag gaaaatgcga agtaattacc ataagcggtg cagctggcat tggaaagaca   1740
gaccttttga accgtgttca gcccgcaatt cgtaaacttg gatatatcgg tatagcccgt   1800
ctggatcgcg ccaggcggat accgtttgaa cctttcgcca aaattctggc tagccttctc   1860
cgccagatct tctctgaacg tgatgtcaca actgagtacc acaataacat ccgcactgcg   1920
ttgagaccaa tgtggccgac attacaccgt gtgctggaac tcccggagca gctcatgtct   1980 tccgaggaa atgaacgaca aatttccccc agactctcag cagcgcaaca tatcttcaag   2040
gaagtttcga ccaagggcga accatccaag cgcgttgcac ttccaagtct ggatcatggt   2100
caaagctctg tggacttctt tctatccaat gctgcactga gaacatgcg tttgatggag   2160 acatttttgg agatcctgcg gacgctatcc cagtacaggt tgatatgcgc atgtgtggac   2220
gatttgcatt atgccgatga cgagaccctg gagttgatta tgaacatcgt gaaagctaaa   2280
attccatgtg tgttgatact cacgagccga agtctgagt ggagtcgaa tataatcagg   2340 cctcttttcg aatctgagaa tcccagcgtg acgcgcgtgg tactcaagcc tcttggagag   2400
gaagagatta tgcaaatcgt ggccgctaca atgcatcagg aacccaaccc gatgttaacc   2460
ccgctcgccg ctgtcataca agagaagagt atgggcaacc cgttctttgt ccggatgatg   2520
```

```
ctcgaaacct gctatagcaa aaactgtatt tggtattcgt ggaaaaattc tgtgtgggaa    2580
ttcgacctgg atcggatctt caccgaattt gtggctccta ggtatggcga ggggcttgga    2640
ctagggttca tcgcaaggcg tctccaggag atcccggcag ctgccaggtc cataatggtc    2700
tggggcgcat tgctaggaag cccgtttgcg ttctctctgg tacaaaaact tctcacaagc    2760
gagttcttgt attccagcga ggacgatgag gctgtagacc tcacctgtcc tcagaatgca    2820
aatctaatcc gacaatctga agccgatata gttgtcggtc tgcagtatct ggtgcaagca    2880
aacctgatca ttccgggaaa gacggatgat gaattcaggt aggtgctcct gattgaattc    2940
atttcgtgtc cactaactag tattcttaga tttgtcaatg atcgattctc gcaagcggcc    3000
ttgtcgttga cggagggacg gaacgtggaa aaaatgcact tcatcatatc ccaagcaatg    3060
atgaagtact accatgacgg gcgcagtcga tacgcaatgg cgcgacatgt ggctctggcg    3120
tcccggataa tcaagtctcg tgtcgtggaa agacttgagt atagaaagat cttgtgggat    3180
gcggcgcaaa ccgctgcgca atcgggtgcg cgaccaacag cgctttggta cttccggcac    3240
tgcatcactt tccttcaaga caatccttgg gatgacaata acgctgatgt gtactaccgg    3300
gagactctgc gtctgcatat tgctacggct gaaatgtcat ggtcccaagg gcataacacg    3360
gaagctctgg acttgcttga taaagtcttc gaacatggaa agagtgccgt gtgcaaatca    3420
cgagcttgga tcgttaaagc caagatctac gctcagatgg gtaaccacct ccggtcgatg    3480
gattcactcc ttacgtgcct ggaagagctt ggtgtacatc tacgagagcc tacgacctat    3540
gacgaatgcg acgatgccta ccgtaacctt cgcgcatacc tcgagcaagc ggacttggaa    3600
gctattgtcc gtaagcccgt cagcaaggat gtcgacatga tcactattgg agaggtcatg    3660
gctgaggcga tggctgtcac gtactgggac gatgcactga cattctaccg gatggccatt    3720
gaaatgatga acctacatct tttcaaaggc ggttttgtgc aaatttccat cggctgttcg    3780
cacctggcga tgatatcgtt cagccgattc agggacttgg agctcgccgt gaggctgagc    3840
gatttcgcgc tcactctcct tgagcggtgt cccgaacagt ggacccaaag tcggggctct    3900
attgtgcata acctttatgt cggccacctg cgtgttccat tgtcctcgac gctcccgaat    3960
cttgaggcct ctgttgagac atccttctcg atgggtgatc cgtacatcac cttaatcagt    4020
ctgtcgtcga tggcgatgac aagactgtat ctgggccatg atatggctca ggtggaggca    4080
ttctgcaatg aaagcccgga agatattccc gactgggtca atgatactcg gggaggcgct    4140
agtctgcttg cagttaggta aggttccctc gtctactcta ggagcactgg tgaatatgtc    4200
acctgctaac agctttgcct atagacaagt tgcacgtgct ctgcaaggta aaacggcatg    4260
tcgctctcct gatactatca tgtccgatga gcaccatcac acgaatgagt acatcgcttt    4320
cctggacaac aatgccagta acgccgaccg gccgcgggac atttactggg gccttgcaat    4380
gattccgctt tttgcatatg gacatcatac caaggctata cagctgggca tgcagatgat    4440
ggagactatg cccagactgt ggtctgctcg tgtttcatac gtagtctatt tctatctcgc    4500
cctttctctt ctgactcttc acaacgagta ccctgctcgc gggtatcttg acggaagcct    4560
gcatacggtc ttgaagtata agccgaagt  ggattttgcg cgcagtgctt gcgatgccaa    4620
ttatggaatg tggtccttaa tattggaggc actgatatgc gaagtccgga atgaccatac    4680
ttccgcgatt caatccttcg aagtaagttg caggactgcc ctggatggag tgaaagagaa    4740
gctaatcagg ccaggctgca atcgatcatt gtcaaatcca cgggtggccc ttggaagaag    4800
cgcttgctct agaactgcat ggtatgtaca ccgacgtccc aaatcgcagt acttttggg     4860
ggaggggtta cccccacgtc ttggcccaaa ttaactttcg agtaggagag ttcttgatcc    4920
```

```
gtcgcggtgc caaaagggcg gcgcgttctg tcatgcaaga cgcaattgcc gcatgggccg    4980
cgataagcgc tgtgggcaag gcggcgcagc tgaccgagaa gcatgaatgg ctattgaaaa    5040
ccgccacatc ttcgaggaat gttgacactg gctgtcaaac tgtggactcg ctgcttggaa    5100
tcaaccgcaa taccggccaa gaacatatgg gagtagcaca gaatatgaaa gaagatgaca    5160
gaaaacaacg ctggatagaa cagaatggtg ttactaccgg tgagcgttct ttcgacatat    5220
ctggcgtcgg tcttggtaag ctacactttt ctgacacttg cgagccgtgc taatatgaag    5280
cagatatcat tgatttgtca agcatcctcg aatctagcca agtgatgtct tcggagcttc    5340
agatcgacaa acttctgacg aagatgattg agattgtttt ggagtcctgc aatggctcag    5400
actctgcggt cattgcgacc aatttcgata caacttcac ggtcgctgcg gctggggact    5460
tggagaaagg acagaagtct ttcgtagacg gccttccgtt ctccgaaatc gaggataaga    5520
tggcgcatca gatctctcac tatgtcatgc gcactaggga ggaagttctt gttcacaacg    5580
tcctggagga tgagcgtttc tcgaacgtca atgagggata ccaagccagg tatccccttg    5640
ggcggtccgt gatcgcattg cctatcatgc aggccgagca tctgctcggt gtcatccata    5700
ttgaaggcaa accgaattca ttcacccagc gcaatgttgt ggtcctccac ttgctctgca    5760
accagattgg tatctcgctt tccaatgcgt tgctcttccg ggaagtgcgc aaggttagcg    5820
ctaccaatgc ttccatggtg gaggctcaga agcgcgcact tgcccaggct cgcgaggcgg    5880
agcagaaggc taaagtggcc gaggctgaag caaagcacaa cgtgaagctg aaagaagatg    5940
cagcgaaggc caagtccata ttcttggcta acatatctca cgatctacgc acaccgatga    6000
acggcgttat cggtttgtcg gaactactta agggtaccaa gttggacaga gagcaggacg    6060
aatacgtgga atcaatccgt gtctgcgctg acacgttgct cacactcatc aatgatatcc    6120
ttgacttctc caaattggaa gctggcaaga tgaagatctc tactgtaccc ctcaatatcc    6180
gagaaacaat ctcagaggtg gttcgcgcac ttcgctatac gcatcgcgat cgcggtttag    6240
agacaatcga ggacctggac aaagtcccac cagaacttgt ggtcctcggt gaccctgttc    6300
gcttgcatca gatcttcatg aaccttctgc gcaacagtta caagttcacc cccaagggat    6360
ctgtgactgt gagagccaaa gtttcccggg aaggcaaggg gcgtgtccgt ttagagtgct    6420
ccgtatccga tacaggaatt ggaatttcag aagaacagaa atcacggctg ttccggccat    6480
tttcgcaggc tgataactcc acggcgcggt catatggcgg cagtgggctt ggattgagta    6540
tctgcaaggc aatcattgag gacgtcctag gcggcgctat ctggctcgat tcgacctcag    6600
gcgttggaac caccgtgacg ttccatctgg cattcaacaa ggtgaaagac gctgccgcca    6660
aagctgctaa aaacaaggcc gccaaccagg tggagaacaa ggctccggtt cctaccgctc    6720
gagacttgac catggtgcct cgggatcaaa tccgggtctg tatcgctgaa gacaatccga    6780
ttaatcagaa gattgccgtc aaatttgtca aggggcttaa tcttcagtgt gaagcttaca    6840
gcgatgggcg gcaggcggtt gaagccctcc gaacccggtc ccgcgagggt aacccgttcc    6900
atgtggtcct gatggatgtg caaatgccga ctctcgacgg ttacaacgcg actcgcgaaa    6960
tccggaaaga cccagacccc aatgtcaacg aagtgttggt catagccatg acggcgagtg    7020
ccatcgaggg agatcgcgag aaatgccttg gtgccggaat gaataactac ctgcccaagc    7080
cggtccgatc tacgatattg agtgagatgc ttgaccaata tcttgcgccg gtgccagcat    7140
atacaaggac gcgactagtg aaccgggaac gaggaagtgt gagcactgag gcagggacac    7200
cacggagcca ctccatatcg cctaatattg acggccaagc caccgctgtg acgccggagg    7260
```
aagagaagca attgcaagag cggcagccca cagtaaatta g        7301

<210> SEQ ID NO 28
<211> LENGTH: 5856
<212> TYPE: DNA
<213> ORGANISM: Aspergillus niger

<400> SEQUENCE: 28

| | | | | | |
|---|---|---|---|---|---|
| atgggggaag | ttcgcagcat | gaggacacct | ccgcttccat | cgccggccga | ggcccttcg | 60 |
| cctgtcgccg | catcccatcc | cctccgtcga | acctcctccc | aatcaactgg | ctttcttcct | 120 |
| gttcacagca | ctggatttgc | aatcgatgga | gacgcgatca | cggagaataa | cacgtggaat | 180 |
| gctaacgctt | attcttctat | tccgattgag | cagactacgg | acgcatgtca | tacctcaacg | 240 |
| cctgcgaaga | aagacagttc | cgaagcgggg | aagtacccag | aggaccaggg | acgaagcctg | 300 |
| caaacccta | aagagctccg | gaggcagatg | gaagagttgc | tcgtctatca | acagatgcaa | 360 |
| caatcacaga | accagacttc | ttcggctaat | cgcgaagccc | ctccatcgca | acccgatcct | 420 |
| gtcacctcaa | attcccctgg | gtcgacaagg | aaaagacccc | tcaatgtatc | cttccccaaa | 480 |
| gtcgcctcgt | ccacaggagc | gatgccctca | gcttccttct | ccgattctac | cgggtctggt | 540 |
| gggaccatcc | gggctatgga | ttctaccccc | gacaacctca | ccggccaaac | cccgtcctat | 600 |
| ccgttcccga | gaatgcagac | gcaaccttcg | acgcggccga | cacagagctc | cacactcaac | 660 |
| catagccctt | tcaagttgac | actgccggct | gagaaactga | agacgcacat | ggtgccatcg | 720 |
| caactttcgg | aggagcagca | gctgacaggg | gcagatacac | cgcacttgca | gagctttttc | 780 |
| ctaccagcgg | tacacaagaa | cgtgatcgag | gatccgaact | atcccagtcc | aaatttgtat | 840 |
| gatcttacgt | tgcaactgaa | cgcagatccg | ggtttagacg | catggtgggc | gaatgtggtt | 900 |
| catattctgc | aagcccatta | tggtgctgag | agagtgtcgc | ttgccgtacc | tggcgatgcg | 960 |
| actgacctag | aaaatgtccc | atggggccag | aaagcggttt | ttgatcagaa | catcgagacg | 1020 |
| gagtcgcagg | tacggcatct | gcacgatgag | acgagcacac | cccgcgataa | tatcccgaaa | 1080 |
| gagaatgaag | acccggagcg | aaagaaggaa | ctgtttctta | gggaagcgct | tgccaacgga | 1140 |
| acaagcgctt | cgaaatctcc | aaagcgaccc | tcgcttctat | cgccgacactc | cttcgccggg | 1200 |
| tttggcaagg | aaaggaagat | ctccactgtt | caggactcgg | aaattccgcg | cctacaacca | 1260 |
| aagtcttcgc | tcagaccaga | gctaaaacgc | acatctaccc | tcgccgagaa | ccccgccgct | 1320 |
| ccagaaaccg | agccgtcatc | cgggccacct | cattatacac | aggacaaccc | tcgacaagct | 1380 |
| gtcttcccga | tacctaggcc | gttggaagta | gaagcagacc | cgcttatcaa | gcggacagga | 1440 |
| gttgttaagc | tttttggccg | caccgacccc | gttgttctga | cccgtgaata | ctcccagggc | 1500 |
| ttgacacatg | atcagacgcc | ctgtgagacc | cccgaggaca | aaattcaagt | cacgccgacc | 1560 |
| gccgagccct | ccaataatca | ggcaccatac | gcagcccgcg | ctagatcgac | ttctaatccc | 1620 |
| gctgcgtcag | gcttgcaagc | acatcgtacg | tcgtctatgg | aattcttcga | cgagtacgag | 1680 |
| caaataccct | cttcgccgtg | gtcgcagtcg | ccagctcctt | cgcctgcgcc | ccgtgctcat | 1740 |
| gcggagcaaa | atcctttctt | cgtcagtcac | gctgtcgacg | aggaggcatt | tgcgaagcat | 1800 |
| cccccgcctc | atgattattc | caacctcaag | cccttggaag | ccataggtgt | cgacttggcc | 1860 |
| aagtcagtgg | tccatattcc | acttttgcac | gccggccgct | ctaaacaaac | atcaccgtct | 1920 |
| acgttacgat | ttcccgttgc | agtgatttcc | attctctcct | caataatgcc | ttatccctcc | 1980 |
| aacctgagga | agtctttggc | ctacctcatg | ccccatctaa | ccacttcctt | ttgcttggct | 2040 |
| caacaataca | gtcagcttga | gcgccaagtc | acttcccgac | tcgaggttcc | gcgctacgga | 2100 |

```
catcttcttg gccttggtgg aacattctcc gatgaaagta gcgagttgga gctcgtcgct    2160
ggactcagcg gccatgtaaa ctacacgata gcggatgatg gatcgctttc agcccgcgcc    2220
agtctttcta gtcccgaaga aagatcaaat tcggccaaat ttagccctgc agtatctgga    2280
cttggtacgc ctggattcga attgagcaat attgggcag  ggacaactgt gaatctctcc    2340
gaatcacccg gtgtggccgc acggctcagc aatgatggcg tggacagcta tttcaacgtt    2400
cagcagtcga agcaattcca gcagcgcatt aggctggcga aggtcaaaca aaacgttgca    2460
gcctcaactc ctacatcccc cggcaagttc cttgggaagc cctcggagga ggaggttgcc    2520
tcgcaggacc aaagcccggc aataatatca ccgccacaag aaattaaggc gcctccagtt    2580
atatcaccga cgcaaacttc ccggcaccca tcaacaaatt cattctacgc tcaattacaa    2640
cgcgaactac cgcgtccgtt caccgacact gtggctcagc tcatgttgaa ctcagttccc    2700
ctgcatctat tccttgcaaa gcctcaaagt ggcgaggtta tctggactaa ttcgaaattc    2760
gatgcttaca gcggagtca  accccaggaa cagaagctaa gggatccctg gcagaacatc    2820
cacagtagcg agcgcgacca cgtatctcag gaatgggcaa atgctttgcg tacggggtct    2880
caattcaccg aacgtgtacg cgtaaagcgt ttcaacgatg agtcggctta tcgttggttc    2940
atcttccggg caaatccgct actgtcttcc acaggagagg tgctatattg gatcgggtca    3000
ttccttgata tccatgaaca gcatattgcg gagctgaaag cagcacagga aagagagaaa    3060
tttgccactg atgccaagta tcgagcattc tccaattcta ttccgcagat cgtcttcgaa    3120
gcgacagaat accggggcct tatattcgtg aatgagcaat ggcatctgta cactggacag    3180
aagcttgaag atgcgcttaa ctttggcttt gcaaagcatg ttcatcatga tgatctagag    3240
aagtgtggct actttccct  ttacctccat gaatcacaga aaactggggg cgccattgac    3300
gcaggtgaag cgcctgcgga gacgacggcc gccaagaatt ctcaggagaa gcatctgggt    3360
cagggcgtca cacccgcact ggaagagctt gtcaaacgtg gagttgcgtc tgtgcagaga    3420
gatgagaatg gtcgcgtctt ctactcgaca gaactacgac tgcgttcgaa aggggtgat   3480 ttccgatggc accttgttcg tctggtctgt gtcgagacaa gtagttttgg cagtggcgaa    3540
gcgtcctggt acggaacgtg cacggatatc aacgaccgca agaatttaga gcgggaactg    3600
aacaaagcca tgcaacaact taacaaccag atggagtcca agacgaagtt ctttagcaat    3660
atgtcgcatg aaatccggac tccactaaac ggcatccttg gcaccattcc tttcattctt    3720
gatacccagt tggacactga tcagaggaga atgcttgata ccatccagaa tagctcgacc    3780
aacctacgtg agctagtcga caatattctg gatgtttcga gagtggaagc tggtaaaatg    3840
tcgctagtca actcgtggtt ccatgtacga tctgtgattg aagatgtgat cgacactgtt    3900
tcgtctaggg ccatcgacaa gggcctcgag atcaactact tgatggatgt ggatgtcccg    3960
ccgatggtca taggagacag attccgaatc cgacaggtgc tcatcaacct tgtcggtaat    4020
gcagtcaagt tcactgcgca gggggagatt cacatctgct gctccattta ccacgatgcc    4080
tcagcacaaa tcaagaagac tgaactctta ttgaacttcg atgtcgtgga tacgggcaaa    4140
ggcttcagcg cgagggatgc ggaacggttg atgcaacgat tcagtcagct tgggcagaat    4200
ggatcgcagc aacatgcggg tagtgggttg ggactgtttt tatccaagca gcttgttgag    4260
atgcatggcg gaaaattgac tccaagcagc aaggaaggcc aaggcgcaaa gttctccttc    4320
catgtcaaag tcgatgcccc cccaccaccg acgcccgaag aatcccggac ccttcgacaa    4380
gcacagggtg cctctgaaat gctcggagcg cagcccaagc ttaaccccct tgcacaaacta    4440
```

```
cttttcacga aagatacgct caataataag acgccagatc aagccgaact gtcttctgcc    4500
ctcgagtcat ccctctcgaa aacacaagcc aacccagaaa cccccctccg tttgacaaca    4560
accagtttct ccgagcggtc gtcactttcc tctgcccttc caacgcctga tcttagcacg    4620
gtagaccctc taactaagat cgatgcctcc gctgcggccg aacgaaacc cgtgactcca     4680 agtggtgaca gctcacgtcc agcgaccgag ccagtatccc aagagcagga atcccctct     4740 tcgactcagc caccgtcgtc gggtgttgca actgacgcga aacaattacc aagcgcattc    4800
tccattctta tcctgtgccc cttggacaac actcgcaaag ccatcaagca acacatcgag    4860
caggtggtcc ctcttgaggt cccattctct attacctcaa ctccagatat cgaagactgg    4920
cgggaccacg tgagtgatga aactggctcg aagctcactc acttggttct caacctgccc    4980
agtgtggacg acgtttcgga cgtgattcaa tatgtctcag agtgtgatcc cgcgaccgct    5040
ccaacccttg tcatcatttc cgacctttac cagaaacgac aagtcaacac ccggatcaaa    5100
gagctggctg ccaccggaag gcgtgtctac acagtaccaa aaccagtcaa gccctctgcc    5160
ttctctgcca tcttcgatcc tgacaaccga cgcgatctga gcaaggatag aaaccaagat    5220
atggctaggg agatcaacaa caacttcaag actatgtcta agatggttaa ggaggttatc    5280
ggcaacaaag gctacaggat attattagta gaggacgacg agacgaatcg catggtacgt    5340
ccttgcccat tactactcac cccattgcac ctctctttct gattttaacc catcttaggt    5400
gatgttgaaa tacctcgata agatcaaagt tatggcggag acagctacaa atggccaaga    5460
gtgtacagaa atggtctttt cgaaggaacc gggatactac tcgctcatca ttgtaagtgc    5520
aggatttccc gcttcgcgca gttgaatttc tcgctcaccc ttgtgcagtg tgatatccag    5580
atgcctgtta agaatgggta tgatacgtgt cgtgatatcc gcggttggga gttgaagaat    5640
cattatcctc aaatcccgat catggcgctc tcagcaaacg caatgaccga tcaaattgag    5700
gatgctgcac gagctggctt caacgactat gtcaccaagc ctatcaagca caatgagttg    5760
ggcaagatga tgatgggtct gctcgatcct aatcggcctt tgcttctcct tcgcgaccgc    5820
ctcagggccg atagtgagga ccaccaccgc gattaa                              5856
```

<210> SEQ ID NO 29
<211> LENGTH: 780
<212> TYPE: DNA
<213> ORGANISM: Aspergillus niger

<400> SEQUENCE: 29

```
atgagtggga gtatcgacca gagcacattc gagcagattt tggagatgga cgacgacgac     60
agtgatagag atttcagcaa gggtatcgtg tttgggttct tcgaccaggc tgagagcaca    120
ttcatcaaga tggaggatgc tttgtaagtg ttcgcgccgc ttgcggtttg gtaaatcgcg    180
ctaatcaagc atataggaag gcggaagatc tgaatgatct gtcttctctg ggacactacc    240
tgaaaggttc atcagccacg ctcggactca ccaaggtcaa ggatgcatgc gagaagattc    300
aacactacgg cgccggcaag gatgagaccg gtacgacgga cgagccggac aagaagacct    360
ccctttcgcg cattgagaag accctgaccc aggtgaaaaa ggattacaag gaagtagagg    420
ccttcctgcg caagtattat ggcgaagagg aggaatcctc ttaaacttag gacgaacaga    480
aacagaagga cagggtagaa tcaggcgaga attctgtgtc agttaactga atatacgcgc    540
gagagcgagg ccacacgctc cgcccaagat caatgcaatc gagatcacca gtgacagca    600 ccatcaccac acagctattt ctaagactgc ggaaacatgc aggaagacaa gacatccatc    660
ttgccgcgga aaaagatga tttcatttct atttttgccc cttgtcttgg ccggggctgt     720
```

```
ttgttcctag aactgtatga accatgaact aaagggaata tgaagaacca gaacaaaagg    780
```

<210> SEQ ID NO 30
<211> LENGTH: 1721
<212> TYPE: DNA
<213> ORGANISM: Aspergillus niger
<400> SEQUENCE: 30

```
ccagaatttc agtcctcctc caaccatacc cccgctgctt ccttcccaaa gcgtcccagt     60
ttaggctccc gtcgtcagtc gctgctggcc ccgtctcatc aacacctgat caacagcttg    120
ttggaccccg gtgtgactgc agagcctgaa accaacggta acgtcgctc cgccacctac     180 agcacaggca tgtctcgcaa gatctgggtc aagcggccag gcgggtcggc caccttggtc    240
cccatctcgc tcgattcttt ggtggacgag ctacgggacc aggtgatttt gaagtactcg    300
aactcgcttg gcagaaccct tcgatgcccc gatattgtca ttcgcattac tccgcgagat    360
ggttcgaaca ggcaggccac tcccgatcgg atgcttagcc ccgaagagcc gctggcaagc    420
gtggtggaca catattaccc gggaggtcaa gctatcgagg aggctctaat aatcgatatc    480
ccttcgcgtc gcactcccaa accctctcca cgccattcag tatactacaa ccaccatcat    540
tccgaaccgg gcgagcatgg cgagtacttc ccgctcatgc cggcgaatcc cagcgttccc    600
acgccgccga cgcatccgtc aaactcgtct gccagtgtta atgctcatcc cgccccatca    660
atatcgatcc tgacgacagg aatggcccct ccgctaccat ctccagggag tcgcgggact    720
cgacatcccc gtcggccgcc cttgactcgt catgccacaa actcacccac catcctcaat    780
caggcgccaa cagcgaaagg ttggtcaact ctcatcttaa tgagctgcaa gacgtaagat    840
tcctttgcta agaagcttgc taactttgag gagacccgg aatcgtcccc agtagtatcc     900
ctccgcagcc tgctccgtcc atccctactc cgccaggccc gccgcagaa tcccctcagg    960 ccaaatccct gactcctcca gcacgcgggg catcaccgcg tccacgtccc tccacatcct   1020
ccgcgaagcc gaagaagacc agcgcagcac aatcattgag cggggtcttt ggaggcctca   1080
tcgagggcac ggtaccgccc atcaacgtct tgatcgtgga ggacaataac atcaaccaac   1140
gtctcttgga agcttttatg aaacgtctca gcgttcgctg gaagtgtgcg gccaatggtg   1200
aagaggcggt gaacaaatgg cgccagggtg gtttccatct cgtcttgatg gatatccagt   1260
tgcccgtcat gaacggtctg gatgcgacga aagagatccg caggctcgaa cgcctgaacg   1320
gcgtcggtgt gtttcccaag accgctgacg ggcggtcgag cgctgcaact gccaatgcgg   1380
catcgccctc ggcaattgtg ggcagtcggg aaccctgaa gcagaggat acattacacg     1440 atctgtctct gttcaaaagt cccgttatta ttgtagccct gaccgcgagc agtctgcaga   1500
gcgatcgtca cgaggctctg gcagctgct gcaacgactt tttgaccaag gtatgcatat    1560
attctctcgg actattgttc attaccgggt cttctatcat accatgctaa cgaattgcga   1620
agccggttcg ctttgaatgg ctggagcaga aagtgacaga atggggctgc atgcaagcct   1680
tgatcgattt tgaaggctgg cgcaaatggc gcggttacgc c                       1721
```

<210> SEQ ID NO 31
<211> LENGTH: 2462
<212> TYPE: DNA
<213> ORGANISM: Aspergillus niger
<400> SEQUENCE: 31

```
atggacggtg gccagacctc gaccagcgcc gcccccgcgg gcaactccag cgattttgta     60
```

-continued

```
agtgtcgccc tcgatagcga ccgttgtgaa cctcatgatc gctgttattt ttctatgcga    120
ctatacttca ctttgctaac acgatggtta ggtacgaaaa ctctacaagt gagttcttcc    180
tcttttacta ttccctgta ccttgcctgc gcttcatcac tccggttcct cgtccgccgg    240
gttcacatcc tcgactcccc cgggctctcg ctgtccggtt gtcgctgcgc cctgatcaaa    300
cttagcgatg ctttgcataa tatcgacctg atcatgcgta ctaatactct tcgcaaagga    360
tgctcgaaga cccatcgtac gcggaaatcg tgcgatgggg tgacgaagga gacagttttg    420
tggtcttgga ggtacggcgc tctcttcgca tctcccaccc ccctcctcct ttcctgcggt    480
cgcaatcctc gaggctgacc aaaaactgca ttcagtgcga aaaatttacc aagaccatcc    540
ttccgaagca cttcaaacac agcaactttg ccagtttcgt gcgacagctg aacaagtacg    600
acttccacaa agtgagacag aacaacgagg aaaacggaca gtcgccatac ggccaaaacg    660
taagcaatct gcgcttggta gcagtcgatg cgataggtgt taactgtatt ggctcttcag    720
gcctgggagt tcaaacatcc tgaatttaga gcgaacagca aagagtccct cgataatatt    780
cgacggaagg ccccggctcc gcgcaaacag actcagagca acgaagactc ggtcccgaca    840
caacaaatag atctgctgaa ccagcaaata gtggctcaac aacaacagat tcatcaatta    900
cacgagcgac acacacggct cagtgtcgat caccaactca tgatgcagga agttatgagg    960
gtgcaaaaga ccatcctcaa ccatgaaaat gtcatccacc aggtgatgac ttacctgctc   1020
tctgttgatg cccgccagag gcgcgacagc aaagcggctg ccgtgccttt ccaagcccag   1080
ggtcaagcag gctcgacact gagcccttca caggtcgcat ccatggacga cgagccctcg   1140
tcgcccttgc agcatgcctc gaagctcctg aatgatatga acgccgaaat ccagttcaac   1200 ctaggggtc tagagtcgat gggcgagcca ccgaaaacta ccgctgtggt tcctacgcct   1260
gctctggaga ccgctcccg aaatggtgtc gcgcggccat ctgctgccga cgcaagtgcg   1320
aatactgcta tggtctattc caagatgaac ggagagatcg agcccgtcgt ctacccagtg   1380
ggcgccacca acggaatcga tcctatgtac agtgaacatg ttaacaacgt cccgtatccg   1440
atgcctccca aacaagagat tgacgaatct cgacggcaat tccccgacaa ccggaaaaag   1500
agcgcaaatg tcgatcccgg ttgggtacgc agccccata tcctgctagt ggaggacgat   1560
gcgacatgtc gtcaaattgg cggcaaattc ctgtattctt tctcatgtct gattgatacc   1620
gcggtatgtt atccctttcg ggttgctcgg attccgcccg actgacatag ctgcagtttg   1680
atggcctgga agcggtgaat aagatccagg atggttccaa atatgaccct attctcatgg   1740
acattatcat gcccaatttg gatggtgttt ctgcttgcca ccttattcgc caattcgaca   1800 ggaccctat catcgccatg acttccaaca tccgcagtga cgatatccag ctctacttcc   1860
aacatggtat gcccgccacc cctgaaactt cttcgtacgg tcactctcta ttgctatttt   1920
agtgactaac acaatttata ggaatggatg atgtccttcc aaaacctttc acaagaaaga   1980
gtcttctcga tatgcttgag aaacacttgg ttcacctgaa gacgatgccg cagagcatag   2040
aggctcctca atccgcagca gccgtaacga tggccgcgca aagctcggcc gcccagtcag   2100
tcaaggagga cagctctcct gggcagtcgc cagcaacatc gatgactgct tggcaatcac   2160
ccggccagtt tccaggcatg actgccgtgg ctcctaacgt cccgcaagtc caaagccaat   2220
atgtacccac cgcccctgct gcggctgcat atgctgtaga tcagaacgga gttcagtatc   2280
ccgcacccgc ggtggcgctt gctactacgg cgcctgcggc agtcaggccg caaccacctc   2340
ggcgacagct ttcggaaatg tcgagtgcta ccgaaacccc caatatggcc aaacggccac   2400
gcatgtacgc tcatcaaccg cagccaatgg tgaaccccat gcaagctgca cgaacgggct   2460
```

```
                                                                  ag                                                2462

<210> SEQ ID NO 32
<211> LENGTH: 6210
<212> TYPE: DNA
<213> ORGANISM: Aspergillus niger

<400> SEQUENCE: 32
atggcgggca atggcacaga tgatgctcag tacctcgctc ctccggccgt gactgcccta      60
cggcaggaag ctcggagtat cgatccgaga ttctctccta ctcgctcccc cagcgtcgat     120
cacatgcgac aggaacgtga agatctcaaa gaggcggcgg aacaaacctt gaacgtcatt     180
gttgatttgg atctcgatgg tcgcgtcaaa tgggtcagtc cgtcatggaa acaggtcgtc     240
ggcacgtcac cagtatcaat agaggggcgg atgatatcag agatcgtggt cggtaaccag     300
aatgtctttc acgatgccat agagagcatg aaggaggatg actcccgcag tcggtttatt     360
cggtttgcag ttcatatggg ccccgattcg gtcttgaagt actcgccaga gccacgacct     420
gcggagccag agcatgaagc tactgaaacg accgacattg cagaagaagc acaagcccct     480
gcagaggagg accgccatca tgacctcctt catctggaag acaaggtat catggtgttt     540 gatcggacag ccgatggagt tggacatgta ggtcaccgca attgtcgatg ctcggtatac     600
gtgatataaa ctgaccattc ttttctacat tggcagacca tgtggatgtt gcgaccgttt     660
acggaaccga gagaagtcac catcgacctt ccgcctttgc tagtagaatc cttaggcgtc     720
ggagcggaag tgttggcaaa ttacttgacc actctggctg aggctgctgc tagtgagcct     780
gatccttcaa agcatccagc tccgaatccg gtgttgtgtc gtatctgtga gcgacagatc     840
acaccatggt ggttcgagaa acattcggac ctctgtctac aggagcatcg ggccgagatg     900
gatgttcaaa tagcccagga gaatctcaac gagcaccgtc atgccatcgt caaggtgcta     960
gatgctctag aggccagaca aagcaggccg ttggtactcg gagagagcaa tcccccgcca    1020
acaccccagc ccgagtacaa aggcctacct attgggccat ctccagtggc ctccgcaccg    1080
tcgtcaggat cagtctctag tgctaattcc gctcctggca cgccacctcg gtccagagat    1140
cattcggcct caggaatcgg gcatactcgc gctcgatcat tcgcagtgcg gcgtccgtta    1200
gctcgcgtcg ttgagttgat ccttgacctt tgtgacactg ccctagaaat caacatgcct    1260
atgatcaagg aatctcgcgc ggacaacagt gatgattttc ggacattgtc accgcagtcc    1320
gaatcccgta tctcgcaggt tctccagtgg caatcaccca gctctaatac actagagcag    1380
gagcaaggac tcgcggccct atgcaacgat accgaacaag tcgccaaggc aaaagttgat    1440
gcggttatcc gccatagaag aattgtggag tatgctgagc ggattcgcat cgaatacacg    1500
attctggtag aggagtgcat caccgcagct ctcaccaaag ccgagcgaat tgcggccggt    1560
cagctcagtg attcgagtgc ctcagacgat gacgcccccc aagacaccga acccgccgtg    1620
accacaagta gcccgataat acgagggaag cgcgaatctg cagcaccgcc tacaatgtcc    1680
gctttaacga tgtccatgcg caattcgccc gaccgattcc agtccagcca ctcctccgaa    1740
ggcaaagcct cagtcgctgt gtcgaccggg tcgaacagcc caatggaatg tcccacaccc    1800
cgatcacaca agagtatagc cggcgtttta ggacatcgca gccatccag acggggtctc    1860 tctttgatag atttggatgc cggtgattac agtgacagca gcgctccttc ttctgctttt    1920
cccggtgccg tgcgaaccga ctctccctcg tccgaccgca gtatggacag gaagcgaagg    1980
agtctggtcc ttcccggtct ttctagctca cctcgcagac aacattctcc agccaggata    2040
```

```
tcggggccac attcaccatt acgaatgccc cgggctcgtc tttcgagcgg cgccgatagt    2100
ctaccgtcac ctatagtatc tccctctgca aatgcgatcg agctggcaca aattcactac    2160
cctcatcatc gccgtcaatc gtccgcaacg tcttccgata tcgtaaagcc gcccgtttca    2220
cctcatctat cttccgccag ccagccgcag ccgagaccag caccgccgtc gatcaaggac    2280
tttgagatca tcaagccaat cagtaaaggt gcctttggaa gtgtttactt ggccaaaaag    2340
aaagtaactg gggaatactt tgcgatcaag gtattgaaaa aggcggatat ggttgcgaag    2400
aatcaggtca ccaatgtcaa ggcggagcgt gcaatcatga tgtggcaagg cgaaagcgat    2460
tttgttgcta agctctactg gacatttttcc agcaaggact accttttacct ggtaatggaa    2520
tatctcaacg gcggcgattg tgcttcgctt gtcaaggttc ttggtggact gcccgaggac    2580
tgggcgaaaa agtacattgc ggaagtagtc cttggggtcg aacacctcca tggtaggggt    2640
atcgtccacc gtgatctcaa accagacaat cttcttatcg atcagacggg tcatctcaag    2700
ctgactgatt tcggactgtc acgcatgggc cttgttgggc gtcaaaaacg cgtcctcaag    2760
agtatgaaca atgagccggc acccgatctt ctgaaacagg gctcgtttcc tcgagcaact    2820
tcaatcacat cttccagatc agcctctttc gatttccaag gcagcggatc cccgggatcc    2880
actccgttga tcacgccaga tgttgctagt agcattcccc aaccttctta cttcagcctc    2940
aaccaaggtg gcggtctcag tcggcagact tcacgtcgag cgtccggcta ccgtagcgat    3000
agcggcgcca gcgagagtct gaatgccatg ttccgcactt tgtctatcaa cgagggtggt    3060
gaagcttccg gcaccatgcc tgtgcccgtc ccttcctcgg gccaacacca acatcaacac    3120
catctacctg aagaggaaag ccagagcgag gcgggtgagt ctcctcactt gtacccgctt    3180
caacccacga tgagcaattc cttctcctac agcactcctc cgcaacagtc aatgatgcct    3240
cccctaatgg cgctgtttga ccccgaggac cataacaggc ggtttgtggg tacgccagat    3300
tatctggctc cggaaactat caacggtgtt ggtcaggatg aaatgagtga ttggtggtcc    3360
ctgggctgca tcatgtttga gttcctcttc ggctatccgc cattcaatgc tgggactcca    3420
gacgaggttt tcgacaatat ccttcaccgg aggatcaact ggccggacga agccgaggaa    3480
ttcgcatccc ccgaagctat tgatcttgtg aacaggctca tgactatgaa tcctcgtgaa    3540
cggatagggg ctaatgtgga tgagaaatac ccaaatggtg gagcagagat ccggagccac    3600
ccttggtttt ctgatatcaa ctgggatacc ttactggagg acaaagcgca gtttgtaccc    3660
aacattgaga accccgaaga taccgaatac ttcgacgctc gtggcgccac gcttcaggcc    3720
tttgctgaag aactggaaga tgcaagcccc cctcaaccgc cgttaaccac tggcgcatac    3780
cctcaagatc ggcctcatga tgccttgttc aaagtccgct ctcatgttaa ttcgatgaag    3840
cgaccgttga tgcctctaca tattccacct catgtgcgtg agtcacgtag caggaggctg    3900
agcgagccta caatggccga cgattttggc aacttcgcct tcaagaatct ccctatgcta    3960
gagaaagcca acaaggacgt gattcagaaa ctacgccagg aggcaatgca agcacagcaa    4020
cgtcacgttc ctcctacggg ttctcagcaa caaggacatg cgcaaggcgg ccaggatcaa    4080
gcccccactc agcctgcacc acccactttg gagggaagcc cgttaccgat gtccctacag    4140
cggacattgt ctcaaaccaa aggcaacaac cgacctgcgt cccctttcaag catgagccag    4200
gcgaattcgt ctcccagtcg tccttctcaa ccctcgtctc cgcttcttgt tcaatttagc    4260
accggtcaaa atcacgagcg cagaaaaacg tccgggtcat cttctaataa ctcgcagtcc    4320
gccgaaagct ctcagcccgc aagtgtcgac ccaagccgga tggcgagtct taagcacggt    4380
tccgcctcat cgtctcctat aaaaccccct cgggccacgg ctcactcgcc tgacaagaca    4440
```

```
ccttctggac agcgccacgg cagtgctcct gcctcacgag caagatcaca gaccatcggc    4500
tcccaggacg gggacctctc atcatccta gccaaggaaa catacgccgt gggccactac    4560
aaacgccgca gccaattatt cgatatttcg ccctcctcgt cagacaatga ggatccgcgt    4620
acgaaagctt tgcttaaagt acagcgccgc cgccaaagct cgaggcgcat gtcacagatc    4680
aatttccccg atgggccatt tttccggcct ttggacgtgc tcatctgtga agatcatcct    4740
gtttctcgca tagtgatgga acgcctcttt gagaaactgc gctgtcgtac cattacggcc    4800
gtcaacggta acgaagctat gcgttacgct ctcagcgagg tgcagtttga cattatcatg    4860
acggagttta aactaccca ggtaaccggc gctgatgtcg cgcgtatggt gcgggaaaca    4920
cgtagtgcga atcggcatac tccaatcatt gcggttacag gctaccttaa ggatctgcca    4980
gaaacccacc attttgacgc gctcatcgag aagcctccaa ccctaacaaa attcacggaa    5040
gcactgtgta agttctgtca gtggaagccg cctccaaagg actacaaccc ttcccagtca    5100
atgagtgtcc cgccttctac gatgcgccag gctttcgtgc aagccgagca tagcccaagt    5160
tcaacagcct cgtcggggtt cgcacatgta cctcctagct cttacagagg atccagtcga    5220
gaggactcca tcgtcagcag ttactttggc gatatggagt caatcaaacc cgatgacggc    5280
cctgtcatcg tgagtcatca caatgaagaa tcggaacagg ataaaggtgg cctcgggatt    5340
tctgaagatg taattcgagt acaagaaacg acggatggca gtttcacatc tggctcggat    5400
acagtgcctt tcccaagcct acttcacgcc tcttcagcac cacccaccgt gcatccttct    5460
ggaaacatta cacctcgcaa acagcgatcc actgaagcga ttcgggcgaa gagagaatcg    5520
ctggaacgca agcgctacga gtgtgccgag tctggcgatg atgaagatga agagctcggt    5580
aattctcaaa cacgatcaag cagccccaa caaagatctc gtcgtcctgg ctctaagcta    5640
ggaatagaga tgatgagaac caatagcagg ggcagcgttg tcagtggaag tgaggagctt    5700
ctcaagagag agagggagtc tttggagcga cggagcagtg gaggttccgg tggcgccagt    5760
gactacagcg aggaacgtac tggcactcgc tctccgcaga gtccaagtct ggagagccgc    5820
ctcgagaacc tttcaattcc cgaggaggcg attgtggggt ccgttgaagg atacagccct    5880
aagcattcgc ccatcgtgga gctagggtcg aaaatggaca taccagcaat cttttcagat    5940
cggtcaccgt caccgtactc ggcagaaact gcttcgggtg cacaggctat ggaagacagc    6000
gtcgaaacac ccaaacttgg acatattaca ccacctattg ttttacgag agatggagag    6060 tctgagccct caggagacga cccggcgacc ccttacttca agactactgg ggacgattca    6120
gctgcgagat atggtgcaga agccgacaat gaccgatatc tggatgccga tgccacgcct    6180
cgaccattgc atacaccatc gccccatccg                                    6210
```

<210> SEQ ID NO 33
<211> LENGTH: 1279
<212> TYPE: DNA
<213> ORGANISM: Aspergillus niger

<400> SEQUENCE: 33

```
atggctccag ctcctattga ccccagaata gttgatgttg cggaaccttt gaagcaaacg      60
cttccgcttc caccagcatc ccaaaagcgc ctcgagaagg cggagtagac ctgtctgag     120 ggatacccctt acaggccgtc tcgtcctttg tatctagacg acgtctacaa gatccgtgat    180
tatgaccggc cccatgtgga tccaggcacc cgtgcggacc cagaaaagaa ggcgctattg    240
tcggcagcga aagaggtcat ccatctgacc agacacattg gcacggaaat cgtgggactg    300
```

| | |
|---|---|
| caattgaaag acctaacgga ccagcagaag gatgaactgg gcttgctgat cgctgaacgt | 360 |
| agcgttgtct tcttcagaga ccaggatatc tctccccagc agcagaagga gcttggcgaa | 420 |
| tggtttggcg agatcgagat ccatgtaagc ccactatgcc tctccatgtc agtaactagc | 480 |
| gaactcgctg actgatggtt ccgtccttct ccagccacaa gttccccaag tgcctggggt | 540 |
| cgccggggtg acggtcattt ggccagctct gcaggcaacg gagtctcctg ccaatttccg | 600 |
| ccgccctgga ggagcctcac gttggcacac tgatcttgta catgaacgtc aacctgcagg | 660 |
| tgtaactcat ttacataatg acaccatccc cagcatcggc ggagacacgc tctgggccag | 720 |
| tggctatgcg gcttatgaga agctgtcgcc tgcttttcgt aagataatcg acggtaaaac | 780 |
| tgccatctac cgatccgccc accgtatct tgatcgcaac caccccgaag aaggcccaaa | 840 |
| gtacgtcgaa cgtgagcatc cccttgttcg cgttcacccc gccacgggtt ggaaagcgct | 900 |
| gtgggtgaac cgagccatga ccgaccgcat tgttggtctc gacaaggcgg agagtgatgt | 960 |
| tatcctgggg tatttgtgcg acgtatatga aagaacatt gacatccagg ttcgcttcaa | 1020 |
| atggagtcct ggaacaagcg cgctatggga taaccggtca gttactttgc atccaataag | 1080 |
| gccttgaatg catctgacgt atggcagtat taccatccac aacgccagct gggactatga | 1140 |
| aggttccgag cctagacatg gtaccagagt gacggccctt gcggagaagc cattctttga | 1200 |
| tcccaatgct ccgactcgaa gggaagctct gggactgctt gatcgtgctg agaaggagga | 1260 |
| attggctcgc gcgaactga | 1279 |

<210> SEQ ID NO 34
<211> LENGTH: 720
<212> TYPE: DNA
<213> ORGANISM: Aspergillus niger

<400> SEQUENCE: 34

| | |
|---|---|
| atgatgcgga ctaagagaac caacacccaa ccgttagaag atgcctccat ctcgcccgcc | 60 |
| accttcaacg acggccttcc gctcccgaaa ctgatcgcct ttgatctcga ctatacactc | 120 |
| tggccattct gggtcgacac gcacgtcagc gccccaatca aaccccgcga caacaactcc | 180 |
| cgctgcacgg atcggtatgt ccccgaagcc ccaagcaaaa ccactgccat ataactcacc | 240 |
| atcttctccc gcagctggaa cgagtcgttc gccttctacc ccgccgtctc ctccatcgtc | 300 |
| tacgcctgta aaagcaagaa catccctctc gctctggcct cgcgcactca caccccgat | 360 |
| ctggcccgcg acatgctcaa agctctgcac atcattccta cgttctcgga taaccccgcc | 420 |
| gcgaagacga agtcggtgcg cgcactggat tacttcgact acgtgcagat cttcccagcg | 480 |
| aacaagacgc agcacttctc gcgcattcag caggcgagcg gggtggcgta tgaagagatg | 540 |
| ctgttctttg atgatgaggc gaggaatcga aatgttgaga ccgagttggg ggtgactttc | 600 |
| tgtttggtca aggatgggat gacgagggag gaggtggatc ggggcgtttg gcgtggcgg | 660 |
| aagaggaatg ggattaagca gcgcaaggag ggggaggcag agaatgggga tgaagagtga | 720 |

<210> SEQ ID NO 35
<211> LENGTH: 3820
<212> TYPE: DNA
<213> ORGANISM: Aspergillus niger

<400> SEQUENCE: 35

| | |
|---|---|
| atggagccgg aagggtcaag tggattcaaa cggaactctg tccatcaggg aatttacagt | 60 |
| cgtcctgtgg aacggcggcc cagcaagaag tcttcctcca aggaccggca tgggatggtt | 120 |
| tatcccgata gttttaggga cacgggaatt cgaacagtca ccccagactc tgaggctggc | 180 |

```
aaccactcac cttcctcgga ggcggagtat ctcgcatcaa gtgcagcagc ttcccctcgt      240
cccgccaccc ggacaagagc ctccgatcga gaatcccgtc gcgattatca ctcttaccac      300
tcggcaggcg acgaagaaga tacacatgtg gagatgaaaa gtcagcgcgc acggtcacgg      360
accaccaccc tagatgatca gcgcagcgag atctccccta acacattttt cagagcccgg      420
aatcgcctgg gatccatcaa caccgcagtt ccacaaccca aaaccccgga cgagtcgtca      480
tctattggct atccgtcgat tcagtccccc acctatttca gtcactccct tggtcgccaa      540
cggtcaagca agcccccagg gggttcgagc ttggtgacga gtgtatcagc caatcagacc      600
ccctccgcgc tgtcgactac cgatgcgtcc aagatcctgc agcttatgaa acgacttgt       660 ggaaggatgc acggcattct ttcgtttcgg actgcatcaa caacggcttg gtcctcgggc      720
tactgcgcca tcaacgtcgc cacgggcagt ctaatatatc aagccaaggg agagcccgca      780
ctggccaaga ccttgattcc tgatcttcgt ggctgtcagg ttcgctcgct tgtcgatccg      840
gaactacgga cgaattacct cagcgtgtcc acgtttactt cagggctagg tgtcgagcta      900
aggccccatg taagcgaaac attcgactcc tggcttgctg ccttgctgtg ctggcagcca      960
attcgtccca agggcgttca aaacaaaatg acaaagcccc agtcggttgc gattggtgac     1020
cgccgtttgg ccgaacgccg gcgaaactcg agagtacag  tccagaaaga ggcagcgatt     1080
atcaaggttg gcaagatgct cttatgggac aggcctagtg cttccggtgt tcgaccttcc     1140
tctggccgcc gagtgtcaac atatcgacaa caaagagctc tttcctcgtc gtggctgagg     1200
gtcagctgta cgttgcaaga aaacggcgcc ttcaagctgt ataccgagtc cgatatcacc     1260
cttgtaacgt gcatccaact ttcgcagctc tcgcgctgtt cggtgcagca attacactct     1320
tcggtcttgg aagatgaatt ttgcgtcgcc atttatcctc aatacgccgt tcactctgca     1380
tccggcatca ctcgacccgt atatttagcc ttggaaagtc gagtcctgtt cgaggtatgg     1440
ttcgtgctcc tgcgcgcctt cacgatacca gagctctatg ggcccgaaac ctgtgcagaa     1500
gacgacccga agagtccgtc cgatgcccct acagcatcta tggcagatat gtttcgaatc     1560
gagcgagtgc tcaatgtgag agtaacggaa gctaagctcc tccgaaacaa agctgccgag     1620
aaagctcctc gaagccggaa gcagtcgcgg tcacatagca attcaacccc aacatctgcc     1680
gtgagcgatt actacacaga agtacttctt gatggggaaa tccgcgccaa gactgctgtc     1740
aagtaccgca cagccaaccc gttttggcga gaagacttta atttcagtga tcttccgcct     1800
gtcctgtcgc aagtgtcgat tctagtaaag acggtcaacc cgacacagaa ggattggaca     1860
cttatcgcac atggctccta tggccaggac catagtaatc cggcgcgttt gttagacgac     1920
gttgagctct cctcccagga tgctacgttc ggcagggtcg atttgaagct ggacgatcta     1980
cagcctggag tcgaaacgga aaaatggtgg ccgatcctag atgacaaaga tcagccggtg     2040
ggtgaaatgc tcatgcgagc ccgaatggag gagacagttg ttctgatgtc gcacgagtat     2100
acgccgatgt cggaaatcct acattcgttc accaatgggc tcacgattaa catgtctcaa     2160
gtcatgtcct cggagctcaa tcagttgtcc gaagctctcc taaatatta  ccaggtatca     2220 ggcacgactg tcgagtggat ttcagcattg gtcgaggatg agattgatgg gctgcacaaa     2280
gagtcgacag caaacaggct aaggtataca acgaggattc attccaacga ttcccgggag     2340
tcgggtcaag aaagagaagt gctcgtccga gacatgggcc gtactgccac cgttgaggca     2400
aacctccttt tccgagggaa ctcgcttctc accaaggcgc tcgactacca catgcgtcgc     2460
ctaggcaagg aatacttgga agaaacaatt ggcgagcgac ttcgcgatat cgatgaaacc     2520
```

-continued

| | |
|---|---|
| gacccggagt gcgaggtgga cccttcccgt gtacaccgat cggatgatct cgaccgcaac | 2580 |
| tggaggaacc tcgtctccct aagtacaggg gtctggaaat caattgcaag ctctgcttct | 2640 |
| agatgcccgg ctgaattgag gcttattttt cggcatatcc gggcttgtgc agaggaccgt | 2700 |
| tatgcgatt tcctccggtc agtcacatac agtagtgtat cgggcttctt gttttgcgg | 2760 |
| ttcttttgtc cagcaatcct gaatcccaaa ctatttggat tgctcaaagg tatttgttct | 2820 |
| cccctatcac atttctcata catgtcttct aatgcgcgca gatcatccgc gcccccgggc | 2880 |
| ccagcgcaca ctgacactga tcgccaaggc cctgcaaggc ctggccaata tgaccacgtt | 2940 |
| cggcagcaag gagccttgga tggagcctat gaacaaattt ctggtcagca accgcgccga | 3000 |
| ttttaagcaa ttcgtcgatt ccatttgtgc cattcctgcc gaccgtcccg cgcctatcgt | 3060 |
| cacacccttc tatgccacgc caatacagat tctgggtcgt ctccccccaa catcccgcga | 3120 |
| aggattcccc agcctaccct tcctcattga tcacgcgcga agctttgcca atctcatcag | 3180 |
| tatatggctc gagatcgcac cggagcgcct ggcggaattg gaggagattg acccagcagt | 3240 |
| cagcaaattc catgaaatgg ccgttcgtct ccaccaacgc accaaggaat gtttgagtag | 3300 |
| agccgaacag gcagaacgtc caaacggagg cctggaggtc aaatgggagg aactggttga | 3360 |
| cgcgatggaa cggtcggtga ccttctacga ggacagttcc aagcctacaa gcccggccac | 3420 |
| cgaggcagct attgcagggt cgacatcccct acaggcagc catcgcaatt cgatcggtta | 3480 |
| cttcgcgtcg aggccctctc taccgcgtcg gtctaccgat tacgctcctg aagcggacga | 3540 |
| tgacacgcct cccagttcct cttcggccac gtgggaccaa agcagagtcc ccttctcgat | 3600 |
| accacgatgg gcagatccca gggacagcac cggcagttcg aagaattcat ccacatattc | 3660 |
| gcttgaatat cccgaaccct cgaaatcgcg cagatctagc atcactagag agacgacaag | 3720 |
| caagtaccgg ttcttcgatt tcgtgcctcc gtctcgccgc aaagcgaagg atcgggaaca | 3780 |
| ggctcaaaat tcgcgtgagg aacagcgcaa cgagttatga | 3820 |

<210> SEQ ID NO 36
<211> LENGTH: 2233
<212> TYPE: DNA
<213> ORGANISM: Aspergillus niger
<400> SEQUENCE: 36

| | |
|---|---|
| cgcgtcgtca acctcacgat ggcacagttg cacatgcgac agacaaggcc aggattgtct | 60 |
| gtgggctgcg gaatcaaccg ggaccatgac tgtggccgtg tctgattggg atagaagcca | 120 |
| aaagtaaggg gaggcgtgca ggcctgaaaa tgcccgcatg ccaatccgc tttgggcctg | 180 |
| cgtcatcgcc gctcattgga acggccggca ctggtcctgt ttggattggc ttggattggg | 240 |
| cctcatcgtg atccattaag tcataggcag ttagtttaga atcatagtag tcagttagtc | 300 |
| actgcgtgtg tctctgttcc cccacttgct gcaattggcc tgggtatcgt gaaaaagtct | 360 |
| tggtcccatt caccgttgca ctttcccgtt gtttccatcg tgggtgcctc attctccctc | 420 |
| atttccctca attccctcat tatactttat ataccccctcc attcccctc ttctttctct | 480 |
| ccgtcttctg ctcttcaatt ctcaacccctt cctttgtctt cacaacacca ctcttctctt | 540 |
| tcgcgatatc aaacatcctt tcatactcct gatcatcttg ctttactttt gatcagtctt | 600 |
| ccaattacac tctatctccc ttctactatc agacttccac tacatcatgg gaaagaaggc | 660 |
| tatccagttc ggcggtggta acatcggccg tggcttcgtc gccgaattcc tccacaaggc | 720 |
| gggctacgaa gtagtcttcg tcgatgtcat ggacaagatg gtcgaggctc tgcagcagaa | 780 |
| caagtcgtac aaggtgaccg aggtcagtga ggagggtgag cacacaacga ctatcaccaa | 840 |

```
ctaccgtgcc atcaactcca agacccacga gagcgacgtc attcaagaga ttgcgacggc    900
tgatgtcgtg acctgtgccg tgggccccca cattctcaag ttcatcgccc ctgtcattgc    960
caagggtatc gatgctcgca cagagtctaa gcctgtcgct gttattgcct gtgagaatgc   1020
cattggcgct accgacaccc tgcacggctt catcaagcag cacaccagcc aggaccgcgt   1080
tgaatccctg tatgaccgcg ctcagtttgc caactctgcc attgaccgca tcgtccctca   1140
gcaagccccc aacagtggcc tcgacgtccg cattgagaag ttctacgaat gggctgtcga   1200
gaagactccc tttggctctg tcggccaccc agacattcct gccattcact gggtcgacaa   1260
cctggagcct acattgagc gcaaattgtt cactgtcaac accagccatg ctactactac    1320
tgcctacttt ggacacttcc ggggcaagaa gatgattgcc gacgctctgg aggacgagga   1380
gatccgtgga cttgttcaca aggttctcga ggagactgcc tcactcatcg tggctaagca   1440
cgacatctcg gaggaggagc agaaagagta tgtcaagaag atcgttagcc gcatctctaa   1500
cccctatctg gaggacaagg tcgaacgtgt gggccgtgct cccctgcgca agctgtctcg   1560
caaggaacgg ttcattggac cggcttcgca gctggccgag cgcggcatga agtatgactc   1620
cttgatggat gctgtcgaga tgctctctgcg cttccagaac gtgcctggtg acgacgagag   1680
tgcggagctc gccaacattc tcaacgaaca gcgggctgaa gatgccacca tccacctcac   1740
cggcctggat gaggaacacc cactgtatcc tgccgtgcta gagcgggtgc gcaaggtgca   1800
gcagggacg aagtaaaggc attgctactg tcgcaaactg tcttctttaa tgttcacgat    1860
tacgattacg aaaactgcga aagcattccg agtcgatcac ctgcatgtac aactggccac   1920
gccgcaggac ggtgacaggc catctgggat acggcgaaca ctggtcggcg cggatatgga   1980
gcatgggtat ggaaacggat tagcatagtc ataacatgat aattatgtac atagttgcag   2040
gcaactagca cgaatacatg actgaaacat gaacctatct tgctcaggta tttcttaaat   2100
actagttgat catagatctc aaaagtatca caacttacta tccctccaca caggcttcct   2160
cttctcgaca aacgccctca acccctcctt aatattctcc ccctgattca acttctccga   2220
ccactcttga atc                                                      2233
```

<210> SEQ ID NO 37
<211> LENGTH: 1864
<212> TYPE: DNA
<213> ORGANISM: Aspergillus niger

<400> SEQUENCE: 37

```
cgcttcgaac tttcagtctg cgttgtggaa aagcaagaca aaaatagtcc agagggccgc     60
tacggccgcg ccatcaccct gttcccacgg acgctggaac tcctcgatca attggacttg    120
gtccatacaa tgcttcaaca gggatttgct tgcagaagta gtgtgacata caaagatgga    180
gtgagacagc aagtatacct ctctgtctgt accaactatt tcggctaacc agactgggta    240
ggttccagaa aaagtatgg actttcatgg agaatatcca aggaacagtg tttgattttg     300
ccctcgtgct aaggcaaatg tacaccgagg gtatattgag aaagaggcta gataaggaaa    360
aggttactta tcatggttct atggagtgtg ttgcctttga aatcggtctg gacggtagtg    420
aatacccggt gactgtacat tgctcaggac ctggtggcat gatgacagca aaaaggtatg    480
ttttcacac gaagtgctgt tataggaagg atgattctga ttgaagtgct agtaagtacc     540
ttgttggagc agacggtggc catagtctcg ttcgcagata tgccaatatt cccttcgatg    600
gtgattcatc agaggatcag tggattcgca tcgatggcat agtcgagacg aatatgccca    660
```

```
taaatcgggc ctatgggtaa gctagaccct gaaatagtga tctcaacatg gtctgactgc    720
acatagggcc atagaaacaa caacacatgg aatgtcctc tgggcccctc ttgaccacgg     780
cgctacccgt atcggctacg catacacacc cgagatagca gccaaatacc cggaaggagt   840
aacagaggaa gttgctgtga acgaagcaat tgcgtgcttg cggccttca atttgaagtt    900 caaggaagtg cactggtgga cattgtaaga aacctaagca agtcactaga cgtccgacta   960
acgaatcgtc agatacaaaa tcggccagcg catggctcga acttttgcaa cgcacaacaa  1020
tcgcgtcttc atctgcggtg atgcagccca cacccacagc agtggcgccg ctcaaggcct  1080
gaacactggt atccatgatg ccgtgaacct cgcatggaag ctggctttgg aggtgcacgg  1140
actatctcat cccgaggtct tgaacaccta cacaaccgag cgccagtccg ccgtgcagag  1200
gttactcaac tatgatagag acatctctct attgatgacg cataaatggc cggtttggta  1260
cgatggggat cgaagcgcgg atctgaatgt tcttctcgga gagatattcc aagatgctgc  1320
acaattcaac acgggtctcg gtataagcta cgaggccaac gtgatcaacc aacccttgga  1380
gccatccacc gaggtggctg ttggagttca accggggagt cgggctccgg ataccgagtt  1440
gaccatgcca gggacattcc agtctgtgcg gatgcaccaa gttctgcgga accggtgcca  1500
gtttcttgcg gtagtgttta caggaggtga tattgagaca gcgaagttgg atttacttcc  1560
tcttcgggag tacttggata gccatccaga gctttcaacg cacccggcca ttgcttggct  1620
aacagtgtgc ggctcagccg gctgctcgcc gtacagggtg ctcggatga cgggcttcgg   1680 cgatacctac ttcgacgcga gggggatagc acacatcgcc tacaaactgg aaccacgcaa  1740
aggaagactc gtagtgatcc gaccggacgg gctgatagca ttcacatgta cattagacgg  1800
agaggcgatc cggcagcatt ttttccggat actgaagagc cagccagaga agacctgctc  1860
ttga                                                                1864

<210> SEQ ID NO 38
<211> LENGTH: 396
<212> TYPE: DNA
<213> ORGANISM: Aspergillus niger

<400> SEQUENCE: 38
caccggtggg atagagatgg gatggcccgc gatggaacat tgtcggacaa cttcactaga    60
tacggctggc gaattattag tcccgtccag tccgtaggga atgggttggc ttataccaga   120
ctggtcggca acgttgcatg atctttggac gcagggagat atggtggtag gcagatcagg   180
cttctggcaa tggcaagcaa agtctgtcaa ctgtgaacat ccatcacgct cgaatgcact   240
gatgaagcag tttatctaag agacaagttg taatgtcagt caggttaatc ccatcagctg   300
gacgttaaag cttacagagc atgaagggat atttgggagc tgtgcagtag caagggtgct   360
agcgagcaga acaaaaagtg cgttaaatag ctgcat                            396

<210> SEQ ID NO 39
<211> LENGTH: 1919
<212> TYPE: DNA
<213> ORGANISM: Aspergillus niger

<400> SEQUENCE: 39
atggaatccg ccaatcagca tacagtctct ttacttgaag cggagagaag aaagtttgat    60
tgtaaagact acaccccacc tcctcgtctc atgcagcgat gcagagctgc ttttcgacta   120
ttgaaaagtg atctctccaa gcagccaagg cagacacgtc aacggaatac caacgctcaa   180
caaaatttgg ccgcaatttt cgagaagagc gtggatattt tgttctccg ctctttgact    240
```

```
tcaacattgt cccagcttgg cttgaagcgc gagtatggac tcgccccgac attgatcaaa    300
tggtggactg gcgtgcaaca tccgcagagt ctcagcaata tatcacgggg cctctgcgcg    360
gagttcggcc tgcaatatct ggaaaacgca aatatctcaa agacgactta tcaggatgcc    420
agagttcctg aagtctccac cagtgatggg ctggacttgg ttacaacagg aacgggttct    480
aacgacgaca atctgtttta tgaaggtgaa aatccagaag actctcccag agaaggcttt    540
tcaaccaccc gccacccctt cggtatggcg agatttctgg attctgaata tggaaatcaa    600
agaatgccgg atcaatatca tgctcaattg gaccggcgag acgagaatcc tctacaagtg    660
accactccaa gaagtgcaca cggtatattt atagtacatc tatcctatga agcatgacta    720
accactattt agatatgaat caactgcccc gcccagaaaa ccagcctttg caatcggtcc    780
ttcctttcca gaagttcgaa ctgctcgagt tctttgattc tccggaaaat ccttggggaa    840
gaagcacact ttcaagtgtt cttccttctg ctcgtcagga cctaaggttg cttatgcctt    900
ggagtggtac acctcttcct tgcctggaag tcaaactgga agtgccaata gaattcactg    960
aagcatttat gaaattccgc caatctagac ttggcgtcgg aaatatcgaa cagaaggctg   1020
cccataaaaa cgacaactct ggccttgcct tagaataatg agccaccatt cagtgccccg   1080
atccggacct gtcatcataa tgtccaactc atttccgtga acatacacag cgcccactcc   1140
gccgtctatc tgaacaagaa ctgcacaagc cgtattccaa ttaacagaat ccaaatcatg   1200
tacctcggca tttgttgcag acactgtcac gtcttcgccc gtcaactcct tcactttggc   1260
cttaagaagc acatcatcat gcgcgatatc atccactcga actttctgtt cttttttgt    1320 ctcgcgcgtt ccgtccggtc ccccgccat ggccgcaaca acgggtttg ttaataggc     1380 gcagagtgca gataacgaag cggtcatata ctgcctttcg atatggcagg aaagaagtgc   1440
agaacttttg aatgattggg ccctgcatt atggagttag tcaatagaga acccgagttt    1500
tcttgacata ttgtggggac aatagtctca ctagtgataa ttttgcgact gcaatattct   1560
ctttggtatc tctgatctcg tcttgcaagt tcgccaacat gagcatcaag acatcttcaa   1620
ataccaagat agtctgaacg agaagactgt ttggagtgag aaatactcaa aatgctgttg   1680
ggcattcata catcattttt cagacgaaat aggataggt gaacttgcct agagccttcg    1740
acaagcggga attaggaggg gtaggtaacg tgacatgaaa cctgccggtt acttccggta   1800
agacgggggg gaccgggata gtacgttttt atatcacgtg tcagcgacgg aagagtaacc   1860
atctgcggca gcgctcaaat acctcttaat acactagtta taggcaatga acgggaatg    1919
```

<210> SEQ ID NO 40
<211> LENGTH: 938
<212> TYPE: DNA
<213> ORGANISM: Aspergillus niger

<400> SEQUENCE: 40

```
ttacttacca tcagagcccc aaaaatcgct tgccctttcc tggttccttc ttaaaaaatc     60 gggggggaggt ggtcctagtg cagcgataat ttgggctaga tgcgcagcat catacagatc    120
accatcttca tctcgtgctg tgaaaagctt gctcggctcg agaagatccc aggcctgcag    180
ttcatttcag ttagcacaaa aggctgtcac ggaaccatgc tggctaggag aaatcgtgac    240
ctacagttaa acctacactc cagatatcga caggataact ccaacctata tagagcaatg    300
tctcaggtgc ccgatactcc aggggcatga tatcactgcc gtgcggccct ggaccaattc    360
gtgtctcacc aaagtcagac aacaacattg gacctacttg aggacgcatc aggcgtgata    420
```

| | |
|---|---|
| aataaatagt ccgcgcggga gagaccggct tgcgaggtac tggtgacaca agttctttgt | 480 |
| gttccagtgc actcagcgac tggttatcat aggctccgag gagcaaattc ccaggatgta | 540 |
| tatctattat gaatttaatt agttcactta cttgcagctt acctgcacga aggaaagaat | 600 |
| tctttaccag tgtgaacact ctgtccttgt gtatgaagaa agtctaccgc ctgtaaaagc | 660 |
| tcggtaatag cacctttaac gagaccctca tcaaacccgc cctgttggaa cactatcttc | 720 |
| atgtcccgta gactcatctg cgcggcctcg aagataagga ctgtatgtat cccatcttga | 780 |
| ctggaaacag tgaaggaatt taacaacttg cgaatattgt atcgtccctg atgtgagctt | 840 |
| gtttgtagat gatgcttcaa gtgattatag aacgggactt cgcggtgaaa cgatgaagta | 900 |
| tgcacataga ctttcaatgc gacatagtgg ccgtttct | 938 |

<210> SEQ ID NO 41
<211> LENGTH: 2271
<212> TYPE: DNA
<213> ORGANISM: Aspergillus niger

<400> SEQUENCE: 41

| | |
|---|---|
| atggcgtcta caaagggtgt cgccgctggg cggaagaagg acgccattca cttcgtcaat | 60 |
| gcgcgcccag catctgagac ggagcggatc aaaatccagc ggctggtccg cgcccatgtg | 120 |
| ggcaaatgga tctccgacca gaccaaagat cgttcgtccg cccagaatc gcccgacagc | 180 |
| aatcaatccc agtcgtcttc ctcgtccca gatgcctcta gtcagtctcc gcctcagggc | 240 |
| gcagttccgc ccgctccagg ccttcattta ttgacgcctc cgaacggctc tccgtccccc | 300 |
| gctgctctca cgccttccgc ccttcccctg gccttcccct cacaccacag ccctccctcc | 360 |
| gagacaccta ttcgccgtag ttcatcggat ccttccacac cttccccaga gtatggattc | 420 |
| gctgactgtc cgcccttggt gccggggtg gtaggcgagt cgcatttcca ctttgatccg | 480 |
| gaagaaatgg agttatcccc cgataccgtc tggcagttcc agcaacaaac tctcgatgaa | 540 |
| acaccctatg atcacagcga aactacgaaa aggactacaa cttccgattc cttcagcgtg | 600 |
| ccggctccct cgtcagctac atccatgggg tttattgaga gttttggctg tgtcgccgtc | 660 |
| gatccgtttc atacgaaccc aatggatctg gcgagaacgg agattgcggc cacagaagaa | 720 |
| tactgttcgt gctcatctct tgttccttca ttacattct cttcacagag cactaacata | 780 |
| cggtatccgt aggtctctat gtcctgtggc ccggcctgac ccccgtctcc cccggtcagg | 840 |
| agacgcgacc agccagcacc agctggttac ccctcgcttt acaagaccgc actctattta | 900 |
| ccgccttcgt gttcggctct ctatctcaca aacgccttcg gtggctcaat ggctggattt | 960 |
| cacgggaatc cttcctgcca aagagcaac ggatcctgca atggtgtgag ctggaaacca | 1020 |
| tccagaacgt tacacgggaa gtcagtaatc ccagtcgagc ggtgtgcgat tcagtgattc | 1080 |
| tcgctgtcat ctgcatggca cataatgtcg cagaagacca cggacgcggc attcatcgga | 1140 |
| ctctgccgtt cgatgcgccg ctaccacgtt tgcagtggct ggacgtctat ggagcccttc | 1200 |
| cgccgaatct ggttcatatc aaaggtctgg tgcagatggt gcggttacgg ggaggcatcg | 1260 |
| agaacctgac tctgcccggg ctggctgcaa ctctgtcctt gttagtttta actccctcga | 1320 |
| gattcccgct ttcatgcta actcataatc ctcaattcta gctccgacat tgtgacctgc | 1380 |
| agcaccttcc tcatgccacc cgtgttcacg tttattcccc tcttccacga gcggcgaaac | 1440 |
| ttcagcctgc agaaaatgct cggcttcaca accgttgatg tagagcgccg atacgctccc | 1500 |
| ctccggggaca tcggcctcac tgcagaaatg gtggaagtct tatacgccat gcatctctac | 1560 |
| atgaggctcg tcgaagagca catcaaagcc cacctcgtca accccgacta ctccctcatc | 1620 |

```
tccgatcaac gcaacctcac ccaatatacc ctcctctccc tccccgcggc cagccaactc    1680
gacgggtttg ccgcctacaa gccgcacgaa atcatctacg aagcctgtcg tctcgcggcc    1740
ctcatctacg gcgtcggcgt cgtcttcccc ctcccctacc agagcactcc cctgggccaa    1800
ctcgccaagc tcatccagaa cgttctccaa atctccgacc tcgcctccac ctggagccac    1860
ccgcaagccc gcatcgccct tttctgggtc ctcgtcctcg gcggcatcgc cgcagacgac    1920
cggcccgaac gagcctggtt cgtccacgtc ctcagccaag ccgccgccag ccacggcatt    1980
agatcctggg tcgacgcccg caaacttctc ggcctgatgg tatggtctga tcgtgcctgc    2040
gaccgaccgg gtagcgatct ctgggcagaa gtgaaactgg ctatggttag aatggagtga    2100
actatacccc ccatacacat actctctcca cgtgccatct caattccatc tttccatttc    2160
tcttacctat ttacatttat ctttactcct ttcccatggc cttactcagt ggtctatcct    2220
ttgtttctct attctcttat tctatatttt aatattttat accccgctct g             2271

<210> SEQ ID NO 42
<211> LENGTH: 1409
<212> TYPE: DNA
<213> ORGANISM: Aspergillus niger

<400> SEQUENCE: 42
cagtcgcttc tcctcccagt cctcgaggaa tcgctggacc ttggggcccc agacctcctc      60
gccggcctcg aggtccttat actcgagcac cttgtccggg tgaagctcga actgagcctg     120
acgagaccgg atcagcgagg acatcagccc gcagcttccg accgcttgcc ccagatcgtg     180
cgccaaggag cgcacataga agccagatga caccgtcatg gtgatcttca ccgcagccgg     240
ctggggctgg gactgggct tggattccga ggattccacg gcttcagcat gggagcatc      300 cgacgcctcc tgctcggccg gcgcaacagg cgcagcctcg ccatcagcaa ccttctgctt     360
cttagccgag ggagcagact cagtatcacc accctctacc ttctcctcct tagcatcctc     420
cgcaggcggg gactttctct tcgcagaggc ctctccttca ccatccgcct ccctctccac     480
aatcggcaac tcatcctcct tcgccaacaa cttctccgca acagcttct cctcccgtc       540 tgcctcaacc tcaggccact taaactcatg cgttccaggc tcgtaccact cgacaatcct     600
caaatccgtc acctcgaccg gcctcttctg gatctcaatc ggcggctcct tgccctcgcg     660
ggcatactca taaagcttct tgccattcac cttcagcgcc gagaaaattg gcggcctctg     720
cataatcttc ccacggaact gctccagtgc cttctccacc atctcccttg tcacatgctc     780
gtagggcgcc ttgcgcacca ccttccccag ccgatcatag gtatctgtct cggcgccgaa     840
cagcacaacg gtctcatatt gcttcgtgca tcctaggaac tcgttcaggt gtttcgtgcc     900
cttgccgact cccgcgacga gaatgccggt cgcgagggg tcgagggtgc ctccgtggcc      960
gatcttcacg tcgagacgct gggtgcggcg gcgcttgcgc tggtaggtgc tttcgcgggc    1020
gcgacgggcg cgctcgtcag cgagccaggg ggcgaagagc gtggaggggt tgaagtgcgt    1080
ttggagggtg cggacgacgt cggcggagga gacgccttgg ggtttgtgga cggctattta    1140
tcattccata gtattagctt ggaggtaaat caaagcagaa atgctaggag tgaggtatac    1200
cgaatacgcc ttcgtagatc ttttcaccgg acatggtgcg acgaagggt ctgagggctt     1260 gacggaagct catcggcgag cgatgagtgt gagtggcggg gatttgattg agggagagcg    1320
gcaattgatc gactagcaca gctcagtgat gcgatcgtaa agagacaact gtagatatag    1380
ttgaacacaa ccgaaagaat agaagtgca                                       1409
```

<210> SEQ ID NO 43
<211> LENGTH: 1772
<212> TYPE: DNA
<213> ORGANISM: Aspergillus niger

<400> SEQUENCE: 43

| | | | | | |
|---|---|---|---|---|---|
| atggcgccct | tgaccatctc | ccgcacccgg | acaggctgct | gggcttgtag | ggcccggagg | 60 |
| gtaaagtgtg | atggtattat | agtttcctct | tggtttgaaa | agctagtgta | agctaacaca | 120 |
| ttagcaaaga | gacccacccc | gtctgccgtc | gctgcgcgcg | aaacaaccgg | tgctgcgaat | 180 |
| acagcttgca | gttgacttgg | cttgatgaat | caatcgccaa | gggcgtgtgt | catgggaggg | 240 |
| ccggagtatg | gtcgaagaat | ggccggaaga | gaaaggatgt | ctcaaatgag | cagagtctgg | 300 |
| agatggtgcg | acatactgtg | cctaaggcgt | cgcaccagca | gtggatgttt | ctaaacacgt | 360 |
| ccgctgacga | cgtgaaccgg | ctctgtatgc | agtaccaaac | ggtatatggc | gggattttac | 420 |
| ccagtcatca | acgacggctg | atactatcac | ccgcattgaa | tacaatgcca | gccacggcct | 480 |
| cgaatcgatc | cagagaggac | caaatgctac | tggcattctt | tgaggcagtc | atttgcagca | 540 |
| gctcaaccct | ggtcgacaat | gtgcaatcga | atccatatcg | atacttgatc | ctgcccatgg | 600 |
| ccctcaactc | cgacggcatc | tatcatgcgg | cgttggcgat | ctccgcaaat | accctgcgtc | 660 |
| tttccaaagt | acagtatcgt | gtccctgctt | tggagcacca | tcatcgtgcg | ctactctacc | 720 |
| tccaatctct | tctagatcga | gagagttggt | cgaattggga | gatggatgag | atcttggggc | 780 |
| ttgttttgat | gctctgttgg | tttgaggtat | tgaagccttt | tcaccataat | acagccaatt | 840 |
| agttgtgaga | attgacacca | ttagatctca | gatcatagtc | gttcatcgtg | ggtgacacac | 900 |
| cttaacgggt | tccaggatgt | catgtctgca | cgaaagcaac | gacattggaa | acatcatcg | 960 |
| cagcacagtc | aggagcttct | tggttttttc | gaccgctact | ttgctttcca | cctcgttctt | 1020 |
| gctcgaacgg | cctttcgatg | ggatgggcca | cgaacacacc | cgtgtctttc | tgccttgcct | 1080 |
| tcaagtccat | cctcagaaat | tattgaccct | tatatgggat | ttagccacgc | actacttctc | 1140 |
| ttaataaatg | aagtgactga | cttggcatgg | caagaacatg | agctggacat | tcagaaggtg | 1200 |
| tatgggctga | agcactcatt | ggaggtgctc | cgtcagacgc | cacctcatgg | ggatattaac | 1260 |
| ttacactcag | gacaggaatg | tatggtcatt | gctgaagcaa | accgcttggg | tgcaatactg | 1320 |
| ctcctgtacg | agatatgctc | gtcttctgaa | tcaatttctt | catgttcatc | atttagctcg | 1380 |
| gaggagaaac | tccgctatgt | tcggcagatt | ctcgatctta | ttcaggcgca | caagtccaac | 1440 |
| atgatgcgca | ctgccgtcct | ccctctatgg | cctctcttcc | tagcaggttg | ctgtgtctcg | 1500 |
| gacgacaacg | acagagtcat | tgttctgcaa | atcttccaag | agtgggaggc | cattcgtcgg | 1560 |
| tttggcgtac | gtctgtccac | ccatatatac | catgtcacaa | gctaatgatt | tagaatatcg | 1620 |
| caccggcaag | agaagtgata | gagatggtct | ggcgacgccg | tgaccttaac | caaaatgaat | 1680 |
| ttgccaacgg | cgccatgtca | gggaagacag | cgcgctttga | atgggaacat | gcgatgacga | 1740 |
| tgcttggagg | gttgaagcta | gcgctaacat | ag | | | 1772 |

<210> SEQ ID NO 44
<211> LENGTH: 1639
<212> TYPE: DNA
<213> ORGANISM: Aspergillus niger

<400> SEQUENCE: 44

| | | | | | |
|---|---|---|---|---|---|
| gcagccaagt | attcctcgac | tcttgtggct | cagattctca | cgcacaagtc | gaaatctgtc | 60 |
| tacgcaaacg | actatcttgg | gaattgttct | agcgtggatg | tcgtcaatgc | tttaaaaggc | 120 |

```
agacccttgg accatactca cgttgactat ttccagggct ttgagcgatt ccacgaaaat      180
gggcttattc gtcgattacc catagaagag gaacaaaaaa ttgacgaaga cccaagtctc      240
attgaaatta gcgcaaaact taaatgtgcg cagtcagagg acgaaaccag aaggctgcga      300
cgtgaatata gcattcagag gaggaagatc tattcgaaaa agttccagca ataccaaagt      360
gactgggtcc gaaaccgacg tgactggaaa attctgacca gaggtcgtga acgccctgaa      420
catattgaac aggctgcgga gaaacaagta ctgtgcaagc tcatgccgga gctgggtcgt      480
ctagcagcgg tgatatcgtc caatcaggct ctctcgttcg acgaaaaagc tagtgtggtc      540
aatgacatcc atacgcattg ccttcgacag ttcgacgtgg tttatctccc tggtgaggaa      600
ccacaggaag gacgatgccg cgtgcccgct tgtggtgaat cgtggaaca gtgagttgtc       660 tactgatact taaacagagc ctctgctaac gagccatagt atgaagaagc cgaaccgaaa      720
tacgcatgtc cacaagtgtc atctacaaca ttttgcttct gaacgaaatt tatcacctca      780
acaagtcaag tactgctggg aatgttacac ttgccatgg ggaaaaagtt gtgagtttga       840
agagcactgt gctggccatc ttccatcaat gaccagccaa cactacgagg tcatcaaata      900
tcgtcatgct accatccgtg ctggctactg cattgaatgc atgtggaatg acgggctttc      960
tgcggtgtgc agaatgagag cctttagccg aagcacggat cttcgaaacc acatggagga     1020
gcatctggtt cagaaatcat ggccttcgga atgcccctgat ccttcctgta accacatttc    1080
taaggaagag caagattatc gccgacacct tcacgacgtg caccattatc acaaaacgat     1140
atgtgtggca cccaaggagg ctcacaagaa acgaacgtct gcgatgctag acgagaaggc     1200
aatctcggac cgtactcagt cgatgcaaca caaacatcca cgcaagcgcc gcaagaacgc     1260
tcccgattca ccaccacgcg gatcgaagga gttgaaaatc aatttctgga agccttccac     1320
aatgcccaca gagcccatgt ttgaaactgc gatgcaaggc attatgcagg agagaccgca     1380
agaattggca tggcagattg agaactgcca aagcacaatt gcgttgggtg aaggtcggaa     1440
tagcgcggtt gtcccgtcgg tcacacttga cactccagat ctcacagatg atagcagcac     1500
gtgttcaagt ccttccgcag tgtgttcaac ttttagtgca gttgatatcg acccacagct     1560
attaaagttg tctcagcccg tcttgtccca gcaaaatgag aagattgatc aacctgatgc     1620
gtgtacccac ttggagcag                                                  1639
```

<210> SEQ ID NO 45
<211> LENGTH: 2242
<212> TYPE: DNA
<213> ORGANISM: Aspergillus niger

<400> SEQUENCE: 45

```
ctacagtggt agccgggcta ttgccactcg ctgcgcgtcc tccatcagtg ccttatacag       60
cttctggtcc tcggcactca tcccccctc ttgtgtcgaa ggcgacgctc ccagtatggg      120
cttaacgtct gctttgcata ctacaccaga aggcggaagc tcgcctgtct gaaaatattg      180
tcggatcttc ttatgaacac acacggacgg tgccgccaat gttgagtgct agaaagtcag      240
atcgcctgat caggctcgac atgtgaggtc acttacgcct tcggaatcct gctgcagaag      300
caccgagccg gggaagtttt cggacatttt gcgcgcactg caaaagatta gccctgatga      360
caggttgctg agaaaatatg gaaattacct gcgcagaggc gtcactgggt cgagcgtatt      420
gctcacaaac agcagtggat gggaggtgtt ggctgcaaat gggcctggaa acatcagcaa      480
tgaacgatcc agatcaatga gacactacct gtaagcttcc acttcggctt gagcttccac      540
```

| | |
|---|---|
| cctacgcagc tcatcagaag actggcccag taatccccaa gcatggcact atcttcctgc | 600 |
| aacgacgccc aggagcgctt gaactcttct cgtcggcat cctgcaaata ctccgcatcg | 660 |
| gcacaaagaa tggctgtgct cgaatacgcc tcattgtgcc cggacacttg acactcagca | 720 |
| gaccacggcc cagcttgaag gcattgatcg gaagggcatg atggggagcg cctccaact | 780 |
| ttgaagtcgg caagggcggc accactgccc agagataatt cggtcgctat ttctgccagc | 840 |
| tgaggaaatc cgtaaagtgg ttgatacaaa gcgattcgca agatgatctt cagatcactc | 900 |
| catgtcacga cttccggacc tcgtgtggct gatgcgggaa ccggtaatga gcgattgtag | 960 |
| agagcctctt ccagtgccaa atacgctttc ttgatggcag ccggtccgcc ttggacatag | 1020 |
| aaggggcaga catcccctcc agccgcatga cagtatcgcg tgaattggtc gaaaatggcg | 1080 |
| tcagcgtctt cgacagcatt gggcccttcc ccgaagtagt acttatcggc atctaccaca | 1140 |
| gcatcaagca cagcacgatg aatacgatcg ggaaacatag ttgcaaacgt ggaacctaga | 1200 |
| acggttccat acgaccgacc ccagtacagg agcttctccc gtccctgctg ccatcgtgtt | 1260 |
| cgcgctacta tactctgtcc cggatcatag ccatgcatat ggtcctgttg gcgttgctcc | 1320 |
| agcaatcctt gctctgcacg ccattcaccg tgtcgttcaa cgatctctag catatctcta | 1380 |
| gccacagggg gcgtgttgag atgttcgccc aaagcctcct ctccatctct cggaggagtg | 1440 |
| gacaaattgg cagcgcatcc agtattgagg gcagtcgagc gagcccagtt atgccagaat | 1500 |
| gcgtcctctg cgctaccgag tgtgccttcg gctgccactt gcagttccca gtttcgctga | 1560 |
| gcgaagagat gggggaagca gctgaaccct ggagtcgtgt tgttgacccc ccggggatca | 1620 |
| aatccgatga tgtcaaaata cttgtcccgc gaagcgcttt ctggatcgac aatacctggg | 1680 |
| tcattctccg agtctacggt cttttgcagg ctttgccgc tgacaagcac ctgcgcgacg | 1740 |
| cctgagccac ccgggccacc tgagacgcaa ttagtaaggg caaaatgaca tagaaatctt | 1800 |
| gaaccgtacc tgggtttgtc aaaaccgcgc caccatagcg ggaatctgtc accggaacct | 1860 |
| tggcgggaag acgagtaatg gcgatcgcga agcgccgtcc ttgaccatca gatcggttgt | 1920 |
| agtccatggg gacttcaaga cgggcgcatt ggaacccatc gaagcagtca tggtacacaa | 1980 |
| gtgattgcga aggagttatc tttaccggtt agacacctct ggcgacaaat gcaaagtctc | 2040 |
| tcacctgatc ccagctaaac tccgactgga tgataatctc agtatgcgct ccaggataga | 2100 |
| gacgtggcgt ccaccacgca agacccgcca aagctactac agcgattccc atgccatgga | 2160 |
| gtacattccg ccatgctcca tattttgcag gatgtacatg agtccgaaag gacccgtatt | 2220 |
| cagaggattt taagggttcc at | 2242 |

<210> SEQ ID NO 46
<211> LENGTH: 1958
<212> TYPE: DNA
<213> ORGANISM: Aspergillus niger

<400> SEQUENCE: 46

| | |
|---|---|
| atggtttact caacgctgtc tcctcccctg gacctgtcac atcacttctc ctcggtcacg | 60 |
| aagagacggg aggcgagcga acaaagagc ctgtataagt acttttttcat cccaggcatt | 120 |
| gcgaacttgg ctgtggtgc gttttttctc ctgcttgcta acttcctggc tcttgctcgg | 180 |
| gcataacacg acggttgcac ttgtgccact tgttaacct cttgcgacat caggcctgcc | 240 |
| aaatgcgtca tacttcccct atgatacccct cgaagctacc gttgctcatc ctcagcgttt | 300 |
| ccccgccacc tccgacaatg accagatcaa gcccccagt ggctcccctt caacggagcg | 360 |
| cagaatcgtc ccgaaagaaa gcccgactac caatctcctg aagaaaattg atcttaccac | 420 |

```
agccctccag tatggaacag ctgaaggcct ccccgttatg gccgatttcg tccggcagtt      480
cactcgcaat cacctccacc cgaatgtccc ctatgccggc ggccctggca cccttctcac      540
gtgcggtgcc accgacgggt tttccaaggc cattgaaacc tttactaacc cgtgggaccc      600
ccgtcgggat tggatcagtc aacgtgaggg catactatgc gaggaatttg tgtacatgaa      660
cgcaatccaa accgtgaagc gcgggggcct taacatcgtt ccggtagcca tagatgcgca      720
gggcatgctt gcgcatggta aaggaggatt ggccgacgtg cttgagaact gggatttcaa      780
gaagggccgt ctcccgcatc tgatgtacac aatcacgtaa gttcaaacct ctgtagcaac      840
actttgctgg catgttggct aatgttgcct tatctggttg cagtatcggc caaaacccga      900
cgggcgggac cttgtcggtc gagcgcagga gggagatcta cgctctctgt cgacaatttg      960
acatcatcat catagaagac gatccgtact ggaacttaca gtatccttct gcaactgcta     1020
tggaggccgg atttcgagga tcagatgccg tagatgtaat tccacgcaac tacaacgccc     1080
acggcaggtc ctccgggtac gattttctgg attccttggt gccatcgtat ctctccgttg     1140
atacggacgg gcgtgtcgtg cgtcttgaca ccttctcaaa gaccatagct cctggttgtc     1200
gcttaggatg gattaccgct cagccagcta taatcgaacg cctgactcgt ctcaccgaga     1260
catcgactca gcagccatca gggtttgtac aggccatggt ggccgaactg attgtgggtc     1320
agcaatccga ggatggccag aatgccacag gtgcaagtag gaataaatct aaaaagagcg     1380
aacaagcctg gcagatggac ggctgggttc gctggttgga aggcctccgt gcgggatacg     1440
aacaacgcat gacgacaatg tgtacaattc tcgaagaggg caagtacctc attgactccg     1500
gtagcgcatg ggacgatgta caacccatgg cagaggatga cactgcctgg gaagtcctgg     1560
ataagatgca gatgtacgag ttctcctggc ccaccggcgg tatgtttgtg tgggtcaagg     1620
tctgcatcga gacgcacccc ttgctggaga agtatggccc ggagaagctg atccaagctt     1680
tgtggctgca tttgatgcaa aagccgtatt tgtgcctttc gggtcccgga accatgtttg     1740
ctcctacaac ggagcttctg gaccgggcgc agacatatta caggttgtgc tttgcggcga     1800
tgcctgcgga ggatgtgttg ggcattactc ggaggttggt agatggattt cgcgcgtttt     1860
ggcaacggaa gaatctcgat ggcttggatg atgaggaggt tgctcttggt aggctgcagg     1920
caaagggttc aggcaacttg ttgggtttgg gctgctag                             1958
```

<210> SEQ ID NO 47
<211> LENGTH: 3689
<212> TYPE: DNA
<213> ORGANISM: Aspergillus niger

<400> SEQUENCE: 47

```
atgactatcc cactgagtcg actatccacc gtggatccgc ggcaaccagg aattagtggc       60
cataatcggg gcctcttgaa cgccgacgtc gtcccgatca acgacaagca gaaagtctttt    120
cttgccggtt ctggccctcc gtcgccaatg catcgcgtac aacctctgga cggatcgcat      180
ggtccgccca gtgctccagc agtctacgag cagccatggc gccctccgta tcgtcttct      240
tatgacggac atcccgcgga ccagcgtcgc acatcgaatg ctcctcagcc tgcgctccca      300
ccccacggat acccgatgaa cccaaaccgt gagctgccgc agctcccacc agaagtccca      360
tatggccgac agggcagttt gcctggcccc gtgcataccc tccagaagc ccccactcct       420
catcccagct ttcgtcctat gaatggaact cccatgaggg ccgcccctca ttcagcaccc      480
cccgactatc gctcacggat gtcttttaca cctcaggagc ctcacagcaa tggggacgct      540
```

| | |
|---|---|
| ccgctccccg cccacacgtt accccgact cagtatccca ctccggttcc gcatttgtcg | 600 |
| catactccta cgccgtacga ttcaggtctt tacggaaacc aggcgtacgg gatacgccag | 660 |
| cagcgaaagg ccgctcgggc gcaacaggtg aattgtctcc ttgcagcgaa gttagctgag | 720 |
| atattgatcg ggaaaccctg actaactcgt gagcttttgc tgtctttgaa ggcctgcgat | 780 |
| cagtgccgaa cgagaaaggc caagtgcgat gaaggccggc ctgcttgtag ccattgcaag | 840 |
| gagaacaact tgatatgtgt ttataaagaa gttcccctc acaagtccgt ggcccggcaa | 900 |
| ttgccactct aatagttcga tggacatgtg ctgacgacgt atccaggcaa gaaaaggcaa | 960 |
| cacagcttct tctggaccgt atctctcagt tggaagacgg tctcatcgaa aaatcgatc | 1020 |
| gcattaatgc actccaggtc gagcacacga atcaactcac tcagctgtat cctcggttga | 1080 |
| aagaggctaa agcgataagc accaaggaga cgacagagaa gcaagccatt cctcggatat | 1140 |
| cgaaagcgga tatacctgat atcttacaaa aaacggaaac caaagaagaa gacatgaacg | 1200 |
| cgatcgtcgg acaggagctt gaaagagccg aaggggaagt gattccacag ggtgaagacg | 1260 |
| gtgatctttc aattcccgtt gagcatacca ctgcagccca caagttgctt tcgtggccgt | 1320 |
| ctatcaaggc tcttctcgaa ccgagagagt acgatgaaga ttatgttatg aagctggaag | 1380 |
| aggagcgagg attgattctc gtttacggcc gcggtgaagg acacgatact agtgaaagcc | 1440 |
| cagcaatgac attctcatca tcatcgtccc ggtccaactg ggatcaaagt tacagcaatg | 1500 |
| gtgctcctgc tagcggccag tggaacccag cgctgtcca aaatggcact catctcaaac | 1560 |
| cactcggacc cagtattgat gatttcggga tattcagcac tgatgccaaa accgttcgtc | 1620 |
| gttatcatca aagctacctg aaccacatgc ataagcttca tccatttatc aacctgaccg | 1680 |
| aattgagcgc aagcatcgaa tcattcattc agaaatactg ctcacctgac gtttctgttc | 1740 |
| cggtaaacat cctgaacagc catacgcccg gcgacattcc acgcggtgcg aaaaggaagc | 1800 |
| gttcttgcga tacgctacat ggtggcggat gcgacatcca gttttctcct ggtgccaaac | 1860 |
| acgaaggctc tagcggacgt cgcgtggaga agtcactgga aaatgctatt gttctcttgg | 1920 |
| ttcttgcact tggcagtatt tgtgaagttc cgggagccat ccctggtcca gttactgaca | 1980 |
| cgcccgtgga ctttcaaaag gagcggattc ctggaccctc tacacgcagc atgctatcat | 2040 |
| cggcagatac agaactagtt atgcagtccc agggaagttt cttctcgcag acaagtaacc | 2100 |
| attcattttc atctgctacc gggggggcaga aggctgcttc cgatcggtcg ccatacccgg | 2160 |
| ataatagtca cttaaggaac gtggatgtca ttcctggctt ggcatattat gcgtacgccg | 2220 |
| cacagatctt ggggagtttg caaggcgcga acgggctgta ccatgttcaa gcagccttac | 2280 |
| tagcaggact ttatgcggga caattagcac atccttccca gagccatgga tggatctacc | 2340 |
| aggcggccag agcatgccaa gtgcttgtcc gatcgtatgt attttcctat tttactcttc | 2400 |
| tttctctttt tcaccctgaa caccaggagt ttgcaagaaa aatcccgtgc taaccagtct | 2460 |
| caggaaacgg tatgaacaaa tgaatgacgg cccgctgaaa gacctatata actttgcgta | 2520 |
| ctggacctgc ctgcagctcg agaggtaagc acgttgctct cattatgcga tccatgagta | 2580 |
| ctaataagtc attcatatag cgacatcctt gccgaactag atcttccggc tagtggtata | 2640 |
| tctcgcgcgg aagcacggat tgagttgcca aagggccgaa ctctctctct acctaacgac | 2700 |
| cctgctgctc cgaacaccat gatgatgttt ttctactctg cccagatcca tttgagaaag | 2760 |
| gttctgaacc gtgttcacac cgatctatac aaagtcgaaa gtaagttgat cttaggcagg | 2820 |
| caggagccct tggctgtact aacgcttctc tgcagaacag aatgagaaca ggtggtctgc | 2880 |
| taacgtacag gagattctga gcatgaacct tgaactgtgg agaagcagct acctgacat | 2940 |

| | |
|---|---:|
| aatgagatgg aaggacacgg accctccaca tgaggatatt aatgtggctc ggatgcgagc | 3000 |
| taagtactac ggtgcacgat acattatcca tcgtccactc ctttactggg ctctgcatca | 3060 |
| ttcacatccc accgaaaacg gtcgatcggc atcagtggat tccctacag gatcagcgat | 3120 |
| gtcgggagcc aagtcgcagc aggtttcgcc ctcaatggcg cacagccaac gtgctatcaa | 3180 |
| tatggcacga ttgtctagtg atgttggccc tatgggtcga tcggcaccga cgccaacccc | 3240 |
| cgctccgaca ggatcgcgac cagcactcgc atatcgcgac ctcaatccga agttacgaag | 3300 |
| agcgtgcaaa gtatgcatag actccgccat attgagtacc gaggcctttg atggcatcac | 3360 |
| aggccggccg gtagtaacta atatcttcgg cacagctcat gcgtaagtgg agcccaaaag | 3420 |
| ggagtgtgaa gccggatagt ggacgtcgct gaccttgctg atgctgtgct agtcaattcg | 3480 |
| gtaacatgct ggtattgtcg gccacgtata tgtcaagtct ctcagagctg gttgatcgga | 3540 |
| acgacctcga tcggttattt aagcgaacca tacgctttct cctccaaagc cgcgagatat | 3600 |
| cgccaaccct acgagccgat gcaaagattc tcagcgagat atacgagaag atctttgggg | 3660 |
| agccagctga tatcgtggct ccgttataa | 3689 |

<210> SEQ ID NO 48
<211> LENGTH: 5150
<212> TYPE: DNA
<213> ORGANISM: Aspergillus niger

<400> SEQUENCE: 48

| | |
|---|---:|
| ctatctgaaa ggagtgggtg agaactcacc gccaaggacc gctttctctc tctgattact | 60 |
| gacgaacttg ttcacatcgc gagcaaaatt gctgctgctc tcttccagcc gatccatgct | 120 |
| gtcgcctgca agttgagcc gctcggtgcg ttcctgcact tgccgttgca tgtaggaaaa | 180 |
| gtacccttcc tggctactcg acgacttgtt cgttggggtt ctgccttcgc ggaatgcttt | 240 |
| acggcgctcc tcttcctcta ggcgcatctg ctcctgcata cgcttggatg gtggccgatc | 300 |
| agggccgccg actgttatag aagttagctg ctgattgtag gccagtaggg gagtgtaacg | 360 |
| aactgaggat gtccatgtcg gctggggaaa cgtattgcgt tcctgagatc cactgaatgt | 420 |
| tggtgatcgt aggtcgtggg ggcataacga cttgcgggtt gtagagctgg tcttcggact | 480 |
| ggcgtctata tagtctgtta gtactcacgt ctatatttaa gatgataggt gctgcgtaca | 540 |
| gtccgtgtcc tcctccccat acactgaata agcccacttc agaaggactg gtccagacca | 600 |
| tgacggtccc attggaggag atcgtggcat ccgacaggcg tctcatatca gctatttgat | 660 |
| tgattggact tgcgccaatc tctttcagac cagggatgga gaatgctcgc gtgtatccgt | 720 |
| ctccgaaaag cccgacaaga ctgtagccgc gagcctcggt cttgacaacc gctgcggaat | 780 |
| cgcaaaggta gtcatcccag gacctatgag caccttgga agttgctggt ttaaagatcc | 840 |
| tgcacccgga aacagtcacc gcgacgacgg caccattcac acgcactccg tttctcaagc | 900 |
| ccccaacagc gttgggggtg gccaaggcaa gcccgccatc gtctgcattg atggggatga | 960 |
| tgttgataac cttgtcatcc agcaagcttg tgccgacaaa ctgagccacg tacgtccac | 1020 |
| cctccgaggg caggattttg aatgtggcca ggttacccct gttggtaccc acaaagcagc | 1080 |
| agatactgga ataatctgcg agctgttagt ataatccgca acacttagtt tagtatcctc | 1140 |
| accttcaccc tcaagagtca gcacaccaaa ctcgatgctg gtaggccatt caggagcagg | 1200 |
| gctctcggag ctgcgcttat tgaagatact gcctcgcttg ttcgccttga caattccga | 1260 |
| gaagtgggct gtgtggatga ttgcgggccc gcgcaaatcc aggattgcta gactgcctcc | 1320 |

-continued

```
ttcaaatcca acagccacaa agcccacttg actgtgcttc aaggcagtca ctgggccttg    1380
ctgcatgttt aggagtgtca gtgggaggat acctgtcttc aaaccagggt cgactctgtg    1440
agtgatcttg gtcaatgttc cagggccttc attggcacct gggggctctt cacgaccaaa    1500
gctctggttt ttccccatc gaaagacgac gagctcgccg gtccgcaaac cgactgagag    1560
ctcgcccgtt gagcctccaa aagacatctc ggtcacctct acgttcccaa cccggccaac    1620
agctcgggcc aagtccactt ggacgacgtc cccattctcg atctcatcat caatgccagc    1680
atcccagatg cggatagtgc catcagcatg agccgtcgta agaacgttgc gatcttcgaa    1740
gcgcttcaac ggtttcctta tctccgctcc tccgagtaaa aacttaggcc cctgtgatcg    1800
tttctccttc aggcccagcc acgccgaacg atcgactgac gtcagagtaa ccttgttcac    1860
gaacggatgc acgaaactaa ggtaaggatg gagcatgttt gtcggagtga tgggatgacc    1920
actggggaag ctcatcgtga tgacttctcc cgaggacaag agagcgagta atgcgatagg    1980
atcatgagcg ccgccatagt aaggggtgct acgcgggatg gggcagaagt cgaccacttc    2040
cgcaccggga ggagtaggta ggagtgcggt gcgtttcggg gtctcgaagt actttgcgat    2100
cattgcccac gaagaagtct gataattagg agacggtccc aggtcgatga aagtcagtcc    2160
tttgttggct tcagctttcg gtcgaccgcc agcgatcaag agcccactgt catcaccgtt    2220
gtctttgaca caccacgcga cgtttgtaat tgggtccttg agcccggtag ccgactgggg    2280
tcgttcgggg cttacgcccg gctggtcaat gttgggggta ttgatagatc tggccatgat    2340
tttgcggccg tccttcgagt cccagaaaac caagctatta tcatcatgca cagtcagcac    2400
gaagataccg tttgggtgcc agagggccct agtcagtcga ggcctgcgca tttccgacgc    2460
cggaacatct ccatttcctc ccaaagcacc tggtgggacc tcatattcga aatacttttg    2520
agcaacattc tgcttgaacg agaacgtcac agcaccttcc ggatacccaa ccaagatctt    2580
cccaatatcc cgaggcgaga aagagagact gagaacagga caaaggcgga cgcggggatt    2640
gcgctgagcc cacagattag gtacacggaa tggcgtcaag gtttcacgat ccagatcgta    2700
ggcaatgata tcacctagtt gagacgcctc gtcagcacga aaaagacgt cacgatccaa     2760
tatccccat accattttgt aacccaatga aagcataatc gagactcgga tcggtaagta    2820
aagcgctcgc atgactcggc ggagcatacg agacaagcgt tgtctagtt tctaaggaga     2880
aaatgctgat ttcacttttc gagtcgacac tgacgagctt gtcggcgcag aattgtatga    2940
atttggcaga cgccttccgc gggagcgcga acaccaccgc tactcgccgt tgaccgaaga    3000
cgtaaatctg accatggccg aattgcgtgt cgcttgttcc gacggcgagg agcgactgga    3060
cgggatcgta cgcgatcgca ctgatctggg agtttatacc gcatcgagcg aactataagc    3120
agcaacagca ggaaattagt atatgtcagt gcgtgatatg agcttgagag aaggaagaag    3180
aggatttgct gagagatata catcatcaag ggcgaacagg tccggcgaca agttctcgga    3240
gaagtccttt tggatgccgg cttgctttcc ccgcagaaaa tgcgccattc tggcggacac    3300
ggaactgaag ggataaggtc ggagagtaga ggaaagttga gaaaaagga agagagagag     3360
aaggcgctag aaatcaagta gataagagat tgttaagtca agcaatgaag ctaagaataa    3420
ggctgcaacg acccccgcg gtagaggagc aagtcgaaga agtggtgttt catgacaacc    3480
gcggaaatcc tccagacggt tgacgccatt aaggctgacc tttgaaggtg acttgtgact    3540
agttcagctt agtgtgtctt gccccgcccg accgctggat ttaatgggga tcccttgctg    3600
gctcgcgctt gttgaagatt acgaagatga tcagtctatc tatcataaat gattcttaat    3660
agggctctct ctacattgct atctcaaaac ggggctctcc gtatacattc cagcacggaa    3720
```

```
tgagttcgta ttttctcagg aaccagatct cttacatggg tggaaatcaa cttccaagga    3780
gaacctcgcc aatcttcgta ggcagcaaca aatcatcgcc aagacagctt ccatgccgac    3840
atgaccgaat cttgcattgg actattggct tttgttttca tatgatttct ccgaaaccga    3900
tcatattcat attcatcatg tagctcatgg tcgaacactg ctgtgtagca ctaaggaacc    3960
tttcccattc ttgagacttc catctgaagt ctaactgcag atcggtccgg ccgactgaac    4020
taactaaatc cgagtcattg ttcccatcta tataatcttc cagagatgtc cctggacatc    4080
ccatttcaac acaacgtgca gactccgtct acggaggcca tctcagctaa gactgacgtt    4140
agacgtctcc tagcatcgat ctctgcagcc atcccctgat cgcggtagta gtgtatcgta    4200
acctggtgca cagcacgata gcaggcatac ctaagggacc gacagtcagc tcatagactc    4260
tcccaccatt ttcagtctca tccagagatt gcatacagta gttgtcgggc cacctgggcc    4320
ttatttgtct tcggtcgagt accaaagccc tccaacacag ccggagacgg cgcctcaaag    4380
atctctgcca tatgcacatc gccccagaga gtgttctcta gccctaagag ccctgcaagc    4440
ttcttcgacc ccggattcag caccacctgc gacggccggc ctaacccaac aatcactagt    4500
tgcggtgacg taatttcctc gagcgcaggg gacagccgac gaacttggtt tcgaatctcc    4560
gcatatggaa gatgaacaaa agcgtcttcg gagtcccgga gaatgccttc tagaagcgtc    4620
acaaacgctt ctcgccagga ctgcttccct gatccacagg ctacctggtc tagtgaccca    4680
aaggagctgg agaaattctg tccgatctca cgagctaaag accccagagc ccggttgaga    4740
tcatcccgct cttgcatggt aagcgcggat tccagctcct gcattgtcgc cccattgata    4800
tagtgtctta ctaagaaggc agagcccagc ggtcccccgt ggagaccata atgcaggaat    4860
gacgggatgt atgggttttc ctgttgttct aggatggagt gggcacgggc ttcagtttca    4920
agtagcagct gttctcgccg taagagaggc gttgtcggcc ctggagagca cttcagaagc    4980
aggtggaccc cgttcgacag tacgaggcga ctaattgaat gtaggtggcc cttgagcgga    5040
tagattcctt tgacctgtac cgaagaagaa aagtggcgtt gaaggatgga gccgagagta    5100
taagaaggtt caatgtcagg gattaagatc ggtgataaag aaggcgacat              5150
```

<210> SEQ ID NO 49
<211> LENGTH: 6133
<212> TYPE: DNA
<213> ORGANISM: Aspergillus niger

<400> SEQUENCE: 49

```
atggctgctg ctacgattga gttaccgttt atttcgtcgc actacgccat tgccgagtcg      60
acattgagca ccctcaccac agctcctacg gtcgagctag tcaaccagct cttggaagct     120
atcactacga aagcacgcga gcatgacgag ctcaagtctg acaagatacg cctcgaggtg     180
gaactcgata atgccgttcg ctccagagac aacaaaatca aggttctgaa gagctcggtc     240
gagaaaggtc atgccgaagt cgaggaaaca aggaagaaac ttcacgagtc cggttagttc     300
ctatgcggac ccgccaatac gcgtctactt acgctctgca gaaaacactc gttctaccct     360
ggaatccgag atcgctacac tcaagtcgtc ctccacgtca aacgagtctg aagccagctc     420
attgaagtct cgtatctcgt cgctcgaagc ttctaacaga gacactctct cactcctcga     480
atccaagtcc gcagcatatg acaagcttgc cgaggagctc tcaacacaac acaagaagac     540
aatcgaattg agacgcgaac tttccaccgc cgagcagaac ctccaagccg ccaactctgc     600
ttccgccagc gctaagttcc gtgagcagag tctccagcag gatttggaat tgacaaagaa     660
```

| | |
|---|---|
| aaacaacgag tggttcgaga cggaattgaa gaccaagtcc gccgaatatc tgaaatttcg | 720 |
| caaggagaag agcgcccgga tttcggagct tcagcgtgaa aacgaggaga tcagtgcaaa | 780 |
| cgttgactcc ttgagacgaa gcgagaatgc ccttaagagc cgcctggatg aggtggaaca | 840 |
| gcgttatgaa gaggctcttt ccagcatcaa ccagctcaga gaagacgcta tcaaggcgac | 900 |
| cgagtcgttc agaatcgaat tggacagtgc aagtagacta gccgagttgc agtcgaatgc | 960 |
| tgcagagact tcgaagcagc gtgccaagga atgtcaactc gctctggata aagcaaggga | 1020 |
| agatgctgcg gagcagattt cccgactccg agtggagatt gaaaccgaac atgccgacaa | 1080 |
| agaagctgct gaacgccgcg ttgctgagct tgagctcacg gtcagccagc tcgaatccga | 1140 |
| tggttttgct ggaagaagat ccatgagccc tgcactgaat ggcgcagggc ccagcacccc | 1200 |
| aatgcgtccc agtaccccag ttggcgcgtt ttcacctaga gcgtcgcgcg aaagggagg | 1260 |
| actcacactg acgcagatgt ataccgagta cgacaagatg agaatttcgc tggccatgga | 1320 |
| gcaaaaaaca aaccaagaac ttcgagcaac tctagacgag atggtccaag atctcgaggc | 1380 |
| cagcaagcct gaaatcgatg agctgcgtgc ggaccacggt agacttgaaa atgctgttgt | 1440 |
| tgagatgtct aacatactgg aaactgctgg gaaggaacga gacgatgcaa ctaaggaggc | 1500 |
| aagaaagtgg caaggccagg tggagggatt ggcccgggag ggagacattt tgcgccagca | 1560 |
| actcagagac ctgagctccc agattaaggt cttggttttg gaaaatgcaa ttctgaagga | 1620 |
| aggcgaaaca acgtacgata gagaggaact cgagaagatt gcgcgccagg agatcgatga | 1680 |
| ctcctctgct gatctcaacc caaccggacg gttcatcagt cgcaatctga tgacgttcaa | 1740 |
| ggatctccac gagctccaag agcagaatgt cactctccgt cgtatgctga gagagcttgg | 1800 |
| ggataagatg gagggtgcag aagctcgcga gcaggatgcc atccgtcaac aagagcaaga | 1860 |
| agagttgaag gacctgagaa tccgggtgca gacttaccgt gacgagatcg ctaacctcgt | 1920 |
| cgctcaaaca aagagctatg ttaaggagag agatacgttc cggagcatgc ttacccgccg | 1980 |
| ccgtcagact gttggcgatg cttctgtctt ctcccaatct cttcctctgg gcgcagctcc | 2040 |
| tcccgcttct gaagagccag ccaaggatgt tccagactac gctgatctgt tgcgcaaggt | 2100 |
| gcaggcacac ttcgacagct tccgcgagga gtccgccacc gaccatgcag ctttgaagca | 2160 |
| acaggtcaat gagttgtcca ggaagaacag tgaattgatg agcgaaatta gccgctctag | 2220 |
| cagtcagctt gttgccgcca cacagagagc ggagcttctt cagggtaact tcgatatgct | 2280 |
| caagaacgaa aacgcagaaa tgcagaaacg ctacgctacc ctcctggaga acgctaaccg | 2340 |
| gcaggatatc aggactcagc aagctgccga agatctggtg gagacgaagg gcctcgttga | 2400 |
| gagccttcaa cgggaaaatg ccaacctcaa ggcagaaaag gatctctgga agaatatcga | 2460 |
| gaagagactc atcgaggata acgagacact acgtaacgag agaggtcgac ttgattctct | 2520 |
| taacgcgaac ctccaaacca ttctcaatga gcgggaacat accgatgctg agagtcgccg | 2580 |
| tcgtttgcaa agcagtgtgg agtctctcga atcggagctt caatccacca agcggaagct | 2640 |
| taacgatgag gttgaggaag gaaagaaggc atcgctgcgt agggaatacg aacatgagca | 2700 |
| aagtcagaag cgaattgacg acttggtgac gagcttgggc gcagctcggg aggagttagt | 2760 |
| ggctgcgaag acgacaagag atcacttgca atcgagagtc gatgaactca ctgtcgagct | 2820 |
| gcgtagcgcc gaagagcgcc tccaggtcgt gcagactaag cccagtgtgt ctgctgctcc | 2880 |
| tactgaagcg cctgcggttc cggaggaagg ccaggagagt ggcctgacac gcgagcagga | 2940 |
| acttggtatt gaagtttccg agctccgtcg tgatttggag ttgacaaaga atgagcttca | 3000 |
| gcacgctgaa gagcgggtgg aggattataa ggctatcagt cagcagagcg aagagcgtct | 3060 |

```
gcagtctgtc actgagaccc aggaacagta tcgggaggaa acggagcgtc tcatcgaaga    3120
gaaggataag aagattcagg acctcgaaaa gcgcatcgaa gaaatttccg ccgagctttc    3180
gactacgaac ggcgaactta ccaaattgcg tgacgagcaa ggggaggcta gccgacattt    3240
ggaggagcag aaggccgcgc tggaagcaga gatcacaagg ctgaaggacg agaatgaaag    3300
gcagatcgct tctgcccaat tccaccagga agatctcaag gcacaagctg aaatcgcgca    3360
gcatgcccag cagaactatg agagcgaact gctcaagcat gctgaagccc gaagaatct     3420 acaattggtc cggtccgaag ctaaccagtt gaagctggaa gttgtcgaac tgcggacaca    3480
ggccgacact ttcaagaagg accttgctca aggaggaa agctggaccg agatcaagga     3540
taggtatgag agcgagctta cggaactgca aaagcgccgc gaggaagttc tccaccagaa    3600
ctctttgttg catcccaac tcgagaatat tacaaaccag atcgcagccc tccagcgtga     3660
ccgggctaac attcctgagg gagatgagga cggagaggcc ggcgcgccca acctcgaagg    3720
cctccagggg gtgatcaagt tcctgcgtcg ggagaaggga atcgttgatg tgcagtacca    3780
tctgtcaacc caggaaagca agcgtcttcg tcagcaactc gactacactc agacccagct    3840
tgacgaggcc cggcttaagc tcgagcagca gcgtcgcgcg ctgccgaca gtgaacatag     3900 cgccctcagc cacaacaagc tgatggagac cctgaacgaa ctgaatctgt tccgcgagag    3960
tagtgttacg ctgcgtaacc aggttaagca ggcggaaacc tcacttgcgg agaagtcctc    4020
tcgcatcgaa gaacttgttc agcaaataca gccgctagag actagaatca gggaactgga    4080
gaacactgta gagacaaagg atggagagct gaagttgcta caggatgata gggaccggtg    4140
gcagcaacgt acgcagaata tcctgcagaa gtacgaccgg gtagatcccg cggaaatgga    4200
aggtctgaag gagaagctcg agactttgga aaaggagcgg gatgaggcca ttgctgcccg    4260
ggacactcta cagacccagg ctgctgcttt cccagaacag ctgaagcatg cggaggatcg    4320
cgtgcaagaa ctgcgcacga agctcacgga ccaattcaag gctcggtcca aggagttgac    4380
tggccgtata aacgctaaac aggtggagct caacacggtt atgcaggaga aggaagtcat    4440
tcaagaagaa ctcaagacga ctcgggagga attgaatgag ctgaagacga agatggccga    4500
gcaacccgca gctcctgctg ccccagctgt tgaaggagct actggtgttg actcaacgcc    4560
tgcctctcag ttccctgcgc caacaacgca gccgcctgcc gcttctgacg atcaacgcgt    4620
gaaggctctg gaagagaagg tgcagcgcct cgaggcagct cttgcggaga aggagacggc    4680
gttgaccgcg aaggaaacgg agcacgaggc gaagatcaag gagcggtccg acaagctgaa    4740
ggagatgttc aacagtaagc tggctgagat tcgagctgcg caccggcaag aagttgagcg    4800
gttgaaatcc agtcaaccag ccgctcctca agaacctgga accccagctc ccaaacccga    4860
gcaggtgcca gcaacgccgg cgactcctgc ggctgctcct gcgacaccct ccaaggacac    4920
tgggctgcct gaactgacag atgcgcaagc cagggagctc gttgccaaga acgagacgat    4980
tcgtaacatc attcggagca acatccgcac ccaggtggcc aagcaaaagg aatccgacaa    5040
gcaggaaagc caggccaacc aggaggctat gagcacactg gagcagaagt taacgaaga     5100 gagagaagcg ttgaagaagg cccacgaaga gggtgtggag gagaagatca aggctgctgt    5160
cgagttgtcg gacaagaaat cactggcgaa actaagcatg ctggacaccc ggtaccggac    5220
agcccaggcc aagatcgatg tggttcagaa ggctgctacg gagacgcctc agaagcctgt    5280
tgtcgaagtc tgggaggtcg caaagaccac tagagcgcct ccagcggcgc aggccaagcc    5340
cgcccaggtg gcatctcctg cgcctgcacc gtctcccgcg cccgctgcgg cccaggcaac    5400
```

| | |
|---|---|
| accggtggtg ccatcgccgt cgcctgcccc aacggctact cctgcggcca caccgcagc | 5460 |
| tacgcctgca gctgcacccc aggcccagcc tgtggagcct gcagcagcat ccacagccga | 5520 |
| gccagcttct gctgaatcta cgccgcagac aggtgcccca gcgcagcagc aaccgcagca | 5580 |
| acaacctgcg cctgaacagg ccgcacaaca acaagctgca cctgcgacgg ctcagccagc | 5640 |
| taccaatgct cctccaaacc cattcggtca gagccagaac aagcagccct cgtcgttgcc | 5700 |
| cagcaagccc ccagccggta atgcttctgg ccttatgcga gcactgacgt ccggactgcc | 5760 |
| cgtcgcgcga ggcggcaggg ccggcggccg cggtgggtcg caagcgaata ctttcggtca | 5820 |
| gcaacaggga caacagcaac aggcgcaagg tcaggctcaa gcccagcagc aagctcctag | 5880 |
| ccagcgcggc tctggtctac cccggggtcg tggcggacgc ggaggccatg gacgcggcgg | 5940 |
| aaaccaaaat gtacagccca cgaatgccgc tcagcaagga caggctagcc caggtcgctc | 6000 |
| gctgaatgcc ggtgctcgcc agttcgtccc tcagggcaac aagcgtgctc gcgaggatgg | 6060 |
| agaagctgga ggcgaaggag caaccagtgg aggaaagcgc atgaggggag gaggtcatac | 6120 |
| ccgggggtca tag | 6133 |

<210> SEQ ID NO 50
<211> LENGTH: 3663
<212> TYPE: DNA
<213> ORGANISM: Saccharomyces cerevisiae

<400> SEQUENCE: 50

| | |
|---|---|
| atgcgatttg gcctgccatc aaaattggaa ctcactcctc cgtttaggat aggcatccga | 60 |
| actcaactaa cggcactagt tagtatagtg gctttgggct cactgattat tctggctgta | 120 |
| acgacagggg tctatttac ctcgaactat aaaaatttaa ggtccgatag actgtacatt | 180 |
| gccgctcagt taaagtcatc acagattgac caaactctaa actacttata ttaccaggcg | 240 |
| tactatttgg catcaagaga cgccctgcaa agctcactaa caagttacgt tgcaggtaac | 300 |
| aagagtgcag ataattgggt agattccttg agtgtgattc aaaaatttt gagctcttca | 360 |
| aacttgtttt atgttgctaa agtttacgat tcttcattta atgctgtttt gaacgctacg | 420 |
| aataatggaa ctggtgatct aattccagaa gatgttttag acagtttgtt cccattatcc | 480 |
| accgatacac cgctaccttc ttcactggaa actataggta tattgacgga tccagtacta | 540 |
| aatagcaccg actatttgat gtctatgtct ttacctattt ttgccaatcc ttctattatc | 600 |
| ttgactgatt caagggttta cggatacatt actataataa tgtcggcaga gggtctgaaa | 660 |
| agtgtgttca acgatacaac tgctttagaa cattccacaa ttgccattat ttctgcagta | 720 |
| tataatagtc aaggcaaagc ttcagggtat catttgtct ttccaccgta tggatcacga | 780 |
| tcagacctcc cgcaaaaagt tttttctata aaaaatgata cattcattag tagcgcattt | 840 |
| agaaacggga agggagggtc tttgaaacaa accaatatcc tttctacacg gaatactgct | 900 |
| ttaggctatt caccatgttc gtttaaccta gttaattggg tcgcgatagt ttcacagcct | 960 |
| gagtcggttt tcctttctcc agcaacgaaa ctagcaaaaa tcatcaccgg cactgtcatc | 1020 |
| gctattggtg tctttgtcat tttgttaacc cttcctctag cacactgggc agtgcaacca | 1080 |
| attgtacgtc tacaaaaggc aactgaatta attacagagg ggagaggcct tcgaccgagc | 1140 |
| acccaagaa cgataagcag agccagttca ttcaaaagag gatttagttc tggatttgct | 1200 |
| gttccttctt cgttattaca atttaatact gctgaagctg gcagcaccac aagcgtaagt | 1260 |
| ggccatggag gcagtggcca tggcagtggt gcagcttttt cagcaaatag tagcatgaaa | 1320 |
| agcgctataa accttggaaa tgagaaaatg tcacctccag aggaggagaa caaaataccg | 1380 |

-continued

```
aataaccaca ccgatgctaa aatatcaatg gatggctcgc taaatcacga tttgcttgga    1440
ccacattcct tgagacataa tgacactgac agaagttcca atagatctca cattctcaca    1500
acttctgcaa atttaactga agctaggcta ccagattata gaagactatt ttctgatgaa    1560 cttctccgatt taacagaaac cttcaatact atgacagacg cattagacca acattatgct   1620
cttctagaag aaagagttag ggcgaggaca aaacaactcg aagctgccaa gattgaggca    1680
gaggccgcaa atgaagcaaa aaccgtctttt attgccaata tttcgcacga attgagaacg   1740
cctttaaatg gtattctggg tatgacggct atttcaatgg aagaaaccga tgttaacaaa    1800
ataagaaata gtttaaaact cattttagta tcaggtgagc ttttgcttca tattctaacg    1860
gaattgttaa cttttccaa aaacgttctt caaagaacga aactggagaa aagagatttt     1920
tgcattaccg atgttgcctt acaaataaaa tcgatatttg gtaaagttgc aaaggatcag    1980
cgtgttcgtc tttcaatatc attgtttcct aatttgataa ggacaatggt tctttggggt    2040
gattccaaca gaattattca aattgtgatg aatctagtgt ccaatgcact aaagttcacc    2100
cctgtagatg gtaccgttga tgtaagaatg aaactgttgg gtgaatacga caaagaatta   2160
agcgagaaga agcaatacaa agaagtgtat atcaaaaaag ggacagaagt aaccgaaaat   2220
ttagaaacta cagataaata cgatcttcca actttatcga accataggaa aagtgtcgat    2280
ttagaatcca gcgctacttc cctaggaagt aatagagaca cttcgacaat tcaggaagag    2340
ataacaaaaa gaaatactgt tgcgaatgaa agtatctata agaaagtgaa tgacagggaa    2400
aaagcttcga atgatgatgt atcttctata gtatcaacaa ctaccagctc gtatgataac    2460
gctatcttca atagtcagtt caataaagca cctggctcag atgatgaaga aggtggtaac    2520
ctaggaagac ctatcgaaaa ccccaaaacg tgggttattt ctattgaagt ggaagacact    2580
gggcctggta ttgacccttc cttacaagaa tctgtatttc atccatttgt tcaaggtgat    2640
caaacattgt ccaggcaata tggtggtact ggcttaggtc tatcaatctg tagacagtta    2700
gcaaatatga tgcatggaac gatgaaatta gagtcgaaag taggtgttgg tagtaaattc    2760
acttttacct tgccattaaa tcaaactaaa gagatcagtt ttgcagatat ggagtttcct    2820
tttgaggacg aatttaatcc tgagagtaga agaacagaa gagtcaagtt tagtgttgct     2880
aaaagcatca agagccgaca atccacatca tctgttgcaa caccagctac aaatagaagt    2940
agcctaacca acgacgtgct accggaggta agaagtaaag gtaagcatga gacgaaagat    3000
gttggaaatc ctaacatggg aagagaagaa aaaaacgaca atggagggct tgaacaactg    3060
caggaaaaaa atattaaacc ttctatatgt cttacaggtg ctgaagttaa cgaacaaaat    3120
tccttgtctt ctaagcatcg ttctcgacat gaaggtctag ttctgtcaa tcttgataga    3180 ccatttttgc aaagtactgg tacagccaca tcaagtagaa acatccccac agtcaaagac    3240
gacgataaaa atgaaacaag tgtcaaaatt ttggttgtag aagataatca tgtaaatcag    3300
gaagttatca aaagaatgtt gaacttggag ggcattgaaa atattgaact ggcttgcgat    3360
ggccaagaag cattcgacaa agttaaagaa ttgacatcta agggcgaaaa ttataatatg    3420
attttcatgg atgtccagat gcctaaagtg gatggtttac tttctaccaa gatgataagg    3480
cgcgatttag gttataccctc acctattgtc gctctaaccg cttttgctga cgatagcaac   3540
attaaagaat gtttggaatc aggaatgaac ggattttttat cgaaaccaat caaaagacca    3600
aaattgaaaa ctattcttac tgagttttgt gcagcatatc agggaaagaa aaataacaaa    3660
tga                                                                   3663
```

<210> SEQ ID NO 51
<211> LENGTH: 2154
<212> TYPE: DNA
<213> ORGANISM: Saccharomyces cerevisiae

<400> SEQUENCE: 51

| | | |
|---|---|---|
| atggaacaga cacaaacagc agagggcact gacttactaa ttggtgacga aaagaccaac | 60 |
| gatttacctt ttgtgcagtt atttctggag gaaataggat gcactcaata cctggatagc | 120 |
| tttattcagt gcaaccttgt cacagaagaa gaaattaagt atctcgacaa ggatatcctc | 180 |
| attgctttgg gtgtaaacaa aataggagac agactcaaaa ttttaaggaa gtcaaaatcg | 240 |
| ttccagagag ataaacggat tgaacaggtg aatagattga aaaacctgat ggaaaaagta | 300 |
| agctctctat ccactgctac gctatccgatg aattcagaat tgattcctga aaagcactgt | 360 |
| gttatattta tcttaaacga tggttccgct aagaaagtta atgtaaatgg ttgctttaat | 420 |
| gcagattcta ttaagaaaag gctaatcaga agattgccac atgaattatt agccacaaac | 480 |
| tccaatggag aagtaactaa aatggtccaa gattatgatg tgtttgtctt agattatacc | 540 |
| aagaacgtac tgcatttgct atatgacgtg gaattagtca ctatttgcca cgcaaatgat | 600 |
| cgtgttgaga aaaataggct aatttttgtt tccaaagacc aaacaccaag tgataaagct | 660 |
| atatccacat ccaaaaaact atatctaaga acgttgagtg cattgagcca ggttgggcca | 720 |
| tcctcgtcaa atttgttggc acagaacaag ggggatttcgc ataacaatgc tgaagggaaa | 780 |
| ctccggatcg acaacacaga aaaggacaga attagacaga ttttttaatca gaggcctcct | 840 |
| agcgaattta tttctaccaa tttggccgga tattttcctc atacagacat gaagcggttg | 900 |
| caaaagacga tgagagagtc atttcgccat tcagcaaggc taagcattgc tcaaagaaga | 960 |
| cctttaagtg cagaatcaaa taatatcggt gacatactat tgaaacactc aaacgctgtt | 1020 |
| gatatggccc tattacaagg attagatcag acaagattaa gcagtaaact tgacacaact | 1080 |
| aaaattccga agcttgccca taaaaggcca gaagataatg atgccatatc taaccagtta | 1140 |
| gaactattaa gtgtagagtc tggtgaagaa gaagatcacg atttctttgg ggaggacagt | 1200 |
| gacattgttt cattaccgac gaaaattgcc acgcccaaga attggttaaa aggtgcttgc | 1260 |
| attggatcag gcagttttgg gagtgtttac ttgggcatga atgctcacac tggtgaacta | 1320 |
| atggcagtaa agcaagtgga gataaaaaat aataacattg tgttcccac agacaacaat | 1380 |
| aaacaagcca attctgatga gaataatgag caggaggaac aacaagagaa aatagaagat | 1440 |
| gttggggcgg taagtcatcc aaaaaccaat caaaatattc acagaaagat ggttgatgct | 1500 |
| ttacagcatg aaatgaattt attgaaggag ttacatcatg agaacattgt tacttattat | 1560 |
| ggtgcttctc aagaaggcgg aaatttaaat atttttcttg aatacgttcc tgggggttcg | 1620 |
| gtttcctcca tgctgaataa ttacggtcca tttgaggaat cactgattac taatttcact | 1680 |
| aggcaaatac tgattggggt tgcgtatttg cataagaaga acattattca cagagatatc | 1740 |
| aagggtgcaa atatttgat tgatatcaaa ggttgcgtaa aaattactga ttttggtatt | 1800 |
| tcaaaaaaat tatcacccttt gaataaaaaa caaaataaga gagcttctttt gcaaggttcc | 1860 |
| gtattctgga tgtcaccaga ggtggtcaaa cagaccgcta ctactgctaa gcggatata | 1920 |
| tggtctacag gatgtgttgt cattgaaatg tttaccggta agcatccttt cccagatttt | 1980 |
| tctcaaaatgc aagcgatctt caaaataggc acaaacacga cccccgagat accttcctgg | 2040 |
| gctacgtcag aaggaaagaa tttcttaaga aaggcatttg agttggatta tcaatacagg | 2100 |
| cctagtgccc ttgaattgct gcagcatcca tggctggatg cacacataat ttga | 2154 |

<210> SEQ ID NO 52
<211> LENGTH: 4437
<212> TYPE: DNA
<213> ORGANISM: Saccharomyces cerevisiae

<400> SEQUENCE: 52

| | | | | | | |
|---|---|---|---|---|---|---|
| atgccctttt | tgaggaaaat | agcggggaca | gcacatacac | attctaggtc | tgattcgaac | 60 |
| tcatctgtga | aattcggcca | tcagccgact | agttcggtag | catcaaccaa | aagttcaagc | 120 |
| aaaagccctc | gtgcaacatc | tcgcaaaagc | atttatgatg | atattagaag | ccaatttccc | 180 |
| aacctaaccc | ccaactctac | ctcttctcag | ttttacgaaa | gcacgccagt | tatcgaacaa | 240 |
| tcctttaatt | ggacgacaga | tgaccacatc | tcagctggaa | cgcttgaaaa | cccaacgagc | 300 |
| tttacaaaca | gttcttataa | aaatgacaat | ggacctagta | gcctctctga | ttcgaggaaa | 360 |
| tcctccggtg | gcaatagcgt | aaatagtttg | tcctttgaca | agctaattct | atcgtgggat | 420 |
| cctacagacc | ctgatgaatg | gacaatgcat | cgcgtcacct | catggtttaa | atttcatgat | 480 |
| tttccagaat | cctggatatt | gttttcaaa | aagcatcaat | tgtttggtca | cagatttata | 540 |
| aagttgcttg | catatgataa | tttcgctgtt | tatgaaaagt | atttgccgca | gactaaaact | 600 |
| gcttcatata | ccaggtttca | gcagttattg | aaaaaaacaa | tgaccaagaa | cgtaacaaat | 660 |
| agccatattc | gtcagaagag | cgctagcaaa | cttaaaagtt | ccaggtcttc | cagcgaatcg | 720 |
| atcaaatcaa | aattaaaaaa | tagtaaatcg | caagaggata | tttcaaattc | tagatcaacg | 780 |
| tcagaatctg | cattgagccc | aacaaaatcg | ggcccttcca | agaccgatga | aagaatttt | 840 |
| ttacattcta | cttcaacaca | ccaaaaaacc | aaaagcgcaa | gttcactata | cagaagaagt | 900 |
| tttatatccc | taagaggctc | atcatcgagc | aatgcttcct | cagcaaaatc | accttcaaac | 960 |
| atcaagttaa | gtataccggc | tcggccgcac | tcaattattg | aatctaacag | tacacttacc | 1020 |
| aaatcggcga | gcccacctgc | atctccttcg | tatcctagca | tatttagaag | acatcacaaa | 1080 |
| agtagttcat | ctgagtcgtc | attattaaat | tccctttttg | gtagtggaat | aggcgaggaa | 1140 |
| gctccaacaa | agcctaatcc | acaaggtcat | agtctgtcta | gtgaaaattt | agctaaagga | 1200 |
| aaatctaaac | actatgaaac | taatgtgtct | tcacctttaa | aacaatcttc | actacccact | 1260 |
| tcggatgata | aagtaatttt | atggaataaa | ttcaaaagaa | agagccaaat | aggggttcct | 1320 |
| agcccaaata | cggtagctta | tgtaacgtct | caagaaactc | catccttaaa | atcgaattcg | 1380 |
| agtactgcta | ccttaaccgt | acaaacggca | gatgtaaata | taccatctcc | atcttcatca | 1440 |
| ccaccgccaa | tacccaaaac | tgcaaacaga | agtttggagg | tcatcagcac | agaagataca | 1500 |
| cctaaaattt | cttcaaccac | ggcgtctttt | aaagaaacgt | atcctgattg | tattaatcca | 1560 |
| gacaagacag | ttccagtgcc | ggtaaataat | caaaagtata | gtgtaaagaa | cttttactg | 1620 |
| gaccaaaaat | tttatcctct | gaagaaaaca | gggttaaatg | atagtgagaa | taaatatatt | 1680 |
| ctggttacca | agataatgt | tagttttgtt | ccgctaaact | taaaaagtgt | agcaaaatta | 1740 |
| tccagtttca | aagaatctgc | tctcacaaaa | ttgggaatca | atcacaaaaa | tgtcactttc | 1800 |
| catatgacag | actttgattg | cgatattggt | gctgcaattc | cagatgatac | tttggaattt | 1860 |
| ttgaaaaaaa | gcttgttttt | gaacacttct | ggaaaaattt | atatcaaaga | ccaaatgaag | 1920 |
| cttcaacaaa | aaccgaaacc | tgctcctctc | acctcagaaa | acaatgttcc | tttaaaatcg | 1980 |
| gtgaaaagta | agagttcaat | gaggtccgga | acaagcagtc | tgatagcatc | gacagatgat | 2040 |
| gtttccattg | tcacttcgtc | ttctgacata | acatcatttg | atgaacatgc | atcaggaagt | 2100 |

-continued

```
gggcgcaggt accccccaaac cccgagttat tactatgaca gagtttccaa tactaatcca    2160
actgaagaat tgaattattg gaatattaaa gaagttcttt ctcatgagga aaatgcacca    2220
aaaatggttt ttaaaacaag tccaaaatta gaactcaacc taccagataa aggaagtaaa    2280
ttaaatattc ctaccccat aacagaaaat gaaagcaaga gtagttttca agtgctaaga    2340
aaagatgagg ggactgaaat tgatttcaat catcgtaggg aatcgcctta tacaaaacca    2400
gaactggcac caaaaagaga agctcccaag cctcccgcaa atacttctcc tcagaggacc    2460
ttatcaactt ctaaacagaa taaaccgatc cgcctagtga gggcaagtac aaaaatttcg    2520
agaagcaaaa gatcgaaacc attgccgcca caattattat catctcctat agaagctagc    2580
agctcgtctc ctgattcgct tacttcctca tatactcctg cttcgactca tgttttgata    2640
ccgcaacctt ataagggtgc aaacgatgtt atgcgtaggt tgaaaacaga ccaggactcg    2700
acgagtactt ccccatcttt gaaaatgaaa cagaaagtga atcgctcaaa ttcaactgta    2760
tcgacttcaa attcaatttt ctattctcct tcaccattgt taaaaagagg taactcaaaa    2820
agagttgttt cgtcgacatc tgcggccgat atatttgaag agaatgacat aacattcgcg    2880
gatgctccgc cgatgtttga cagcgatgat agtgatgacg attctagttc atccgatgac    2940
attatctggt ccaagaaaaa aacagctcct gagactaata atgaaaacaa aaaggatgag    3000
aaaagcgata acagttctac gcattctgac gaaatattct atgattctca aacgcaggac    3060
aaaatggaga gaaagatgac ctttagacca tctccggagg tcgttatca aaatttagag    3120
aaattcttcc caagggctaa cttagataag ccaatcactg aaggaatagc ttcaccaaca    3180
tctccgaaat ccttagacag cctactttca ccaagaatg tggcttcatc gagaactgag    3240
ccaagcactc cttcccgtcc cgtccctcct gatagctcat acgagttcat acaggatgga    3300
cttaacggta aaaataaacc attgaatcaa gctaagcaca ctaaaagaac aaaaaccata    3360
agaaccattg cacatgaagc tagtttagca agaaaaaact ctgtaaaact aaaaagacag    3420
aacaccaaaa tgtggggtac aagaatggtc gaagtgaccg aaaaccatat ggtgtcaatt    3480
aataaagcca aaaattcgaa aggtgagtat aaggaattcg cctggatgaa gggtgaaatg    3540
atagggaagg gatctttcgg tgctgtttat ttatgtttaa acgttactac aggtgagatg    3600
atggccgtta agcaggttga ggtccccaag tatagctcac aaaatgaagc cattctaagt    3660
accgtggaag cattaagatc tgaagtgtcc acgttaaaag atttagatca tcttaatatt    3720
gttcaatact taggttttga gaataaaaac aatatttaca gtttgttttt agaatatgtt    3780
gctggtggct ccgtgggatc cttgattaga atgtatggaa gattcgatga accgttgatc    3840
aaacatttaa caacacaagt attaaaagga ttggcatacc tacactcgaa aggtattctc    3900
cacagggata tgaaggcaga caacttactt ttggatcaag atggtatctg caaaatcagt    3960
gacttcggaa tttcaagaaa atcaaaggac atatactcta attcggatat gaccatgcga    4020
ggaacagtct tctggatggc tcctgaaatg gttgatacaa agcaaggcta cagtgcaaaa    4080
gttgatatat ggtctctggg atgcatcgtt ctggaaatgt tgctggtaa gcgcccgtgg    4140
tccaacttag aagtcgtcgc agccatgttc aaaattggaa agtcaaaatc ggcaccacca    4200
attcctgagg acactttacc attgatatcg caaatcggac gaaattttct ggacgcatgc    4260
ttcgagataa atccagagaa aaggccaacc gctaacgagc ttctttctca tccttttagt    4320
gaagtaaatg aaacattcaa tttcaaatct accagactcg cgaagtttat aaagtcaaat    4380
gataagttaa actcttcaaa attaaggata acctctcagg agaataaaac tgaatag    4437
```

<210> SEQ ID NO 53
<211> LENGTH: 4740
<212> TYPE: DNA
<213> ORGANISM: Saccharomyces cerevisiae

<400> SEQUENCE: 53

| | | | | | |
|---|---|---|---|---|---:|
| atgtcgcatt | cagactactt | caattataag | ccttacggcg | attccacgga | aaagcccagc | 60 |
| agctccaaga | tgaggcagtc | atcttcatca | tcttcatcta | gactaaggtc | ggaaagttta | 120 |
| gggcgaaatt | ccaatactac | gcaggctcga | gtagcgtcat | cgcccatcag | cccagggctg | 180 |
| cattctaccc | agtactttag | atcaccaaac | gctgtttaca | gccctggaga | gtctccatta | 240 |
| aatacagtac | agctattcaa | tcgtcttccg | ggtatacctc | aaggtcagtt | ttttcatcaa | 300 |
| aatgccattt | ctgggtcctc | cagctcctcg | gcaagatcta | gtagacggcc | ctcgaatatt | 360 |
| ggtcttcctc | taccaaaaaa | tcctcagcag | tctctaccga | agttgtctac | tcaacctgtt | 420 |
| cctgtacata | agaaagttga | ggctagtaaa | acagagagcg | agattattaa | gaagcccgct | 480 |
| cccgtgaata | gtaatcaaga | tccattattg | acgaccccaa | cgttagtgat | atcaccagaa | 540 |
| ctggcttcac | taaatacaac | gaatacatcg | attatgtcaa | cgccacaaaa | tattacaaac | 600 |
| caaacttcga | caaacacat | tcccaccaga | tcgcaaccaa | atgggtcaac | aagttcctcc | 660 |
| actttgcagg | atattgtcac | gacaaatagc | tcgcaacggt | ctgtaggcca | ccatggtgga | 720 |
| agcacaacga | gcctccgaac | atacaaaaaa | caatatgtat | aaatgaaca | gttatattta | 780 |
| agaaaaatga | gaaaccgtgc | taatgatgat | tattacacta | gaggtatagt | cgcatcatcc | 840 |
| aactttgaag | atgacgaaga | aaattttagt | aacaaaggtg | aagatgactt | agaactagaa | 900 |
| atggatgatc | ttttaaaggt | agaaggtgag | gataaagata | acgacttcaa | ttttggttat | 960 |
| aattttatta | cgtcgagcac | aaaaaataat | gaaaatgttg | tttcgatgag | cctaaattat | 1020 |
| ctaaagggca | aattggattg | gttgagggat | gtgaacaatg | atcaaccgtg | tgaaatagaa | 1080 |
| gatgaggagt | ggcattccat | actggggagc | gaggatttgc | tgtcaaaatt | gttacaaaat | 1140 |
| cctatggtga | caaccgatt | tgaatggcaa | acaatgttat | ctaaggtact | gaagggagat | 1200 |
| attgtgagga | atgaaaaaac | gaagattgca | aatcaaggga | aaggccctgg | cttcaatact | 1260 |
| cagttttcag | atgacatttg | gattgagttg | aaggcatgga | tgaatgggag | gaccgtggaa | 1320 |
| gatcagaaca | aatctctgag | gatttttagg | gattctactg | actccgtatt | tcaagaaatc | 1380 |
| atggcctttta | aactagaaga | taatatgagc | gctgacgagg | ctgcagagac | tatcaaatca | 1440 |
| ctagtagaca | aatattatag | agtcttaaat | ctatggccta | acattaaaag | aatgcatgct | 1500 |
| gaaaaaccca | ttactaaaac | agaagcattc | aggaatcgaa | tagatacttt | gaatagttgg | 1560 |
| cttaatttca | aatttaactt | tgatactaat | attgcgtacc | tgaaaaaatg | gatagttggc | 1620 |
| aataaagagc | tagaaagcac | taccgaagtg | gataacacca | ccgtgaattt | ggatgatcca | 1680 |
| gccgttttcg | ccactaattg | taaacgcttt | gcggagcaaa | ttatgaagga | aaaggatatt | 1740 |
| gaactgatat | ttcaaaaaaa | aatattcttt | ccattagcac | catggatttt | gaaggccaaa | 1800 |
| ttttttcttct | tgaaatacca | aaaaacttgg | aatgaattga | atctatctta | tttggatcaa | 1860 |
| gatctggaat | ttttattgat | gtttccaatg | cgtttggtaa | agatataat | actaattcgc | 1920 |
| ctatcttacg | cgaagaaaat | acagaatcca | accttgatga | tgatcgatca | aatgatggac | 1980 |
| gattttagta | catatattaa | gttggcagtc | caaatgaaat | tcactgttgc | ttcttactgt | 2040 |
| aatgactggt | tttttaaagt | gaaaatcgat | cccgaatttg | atcataccgt | tgttgaagga | 2100 |
| ttggaatatt | ttttctccat | tttggaactg | agaatattat | atagtggcaa | aaactcattc | 2160 |

```
aagacttcta aagaacctga tctgttatta aatatattggg aaatgtttag aaacgtcggc   2220
tattatattg atgatgcagg cgaactgatc gcagcagaat ttacgaagtt gacacttaga   2280
ttggttcaca gattgcacgc ttacctttta aggcagcaaa acactccgcc aaaattagag   2340
aatgaagctg ctgctgaaaa atggctggtg caaatattcg aaatacttgg atccatgaaa   2400
agaaaactca atagattcac caatattttg acaaaagcat ttcaaaattt tgtccgctac   2460
aagatagaag atcacaacta tctgctaaag caactaaaag aaacaggcca ctttcttata   2520
tacacaggag gttacctaga gcaaaatggt acttatttaa ttggtagccc agagctatta   2580
ggctgtaaag atgatgatat tttaagaatc attaagaatt cagacatcgg ttgtgattta   2640
gtgcctaagc tagaaattaa taacagtctg acaatttata atgctttgga tgataattgg   2700
aactccaact catcactggg ttcagatatc tcgaatgatg taccccatt ttattatatc    2760
aaaaacgatt tgaccaccca gcctagatct tataacggta atagagtcaa tcgtgaaccg   2820
gatttttgaaa acagcaggag cacggaggaa gagttttatg aactggagac aagattgaac   2880
tctcttggtt atgtattggt attgactccg caagagccat tactttggga gggtgagatg   2940
tataatctat ccgataacaa aacaattaaa ccagagggat tgaacttgaa agtaattcct   3000
aattcaatag atttgatgtg ccaaggatcc agttatgcct tagaatacca atgtgacagg   3060
ttccaacaga tatctggtag ctcagttttct ttcttggaaa aaaaatcttc ctcagaaacg   3120
gttaaaaaca acttacaaag gataaataaa gcatatttca gatgcacgta cagtgttctg   3180
aagaactata caaagattgt gaccacgttc aagaaggtaa gtcctgtcaa tgatttattg   3240
aataatattt tccttttttgg gagggatttt ggtctgaact ttttgagaat taatgttgcc   3300
aacaatgaaa aaagatccat tataatactt ttaatgatgc ggttaagtat cggatggctg   3360
aagttcttag ctgaagactg tgatccgact gatcaaaggg tatttaggtg gtgtgtcacg   3420
tcaatggagt tcgcgatgca tatggtaagc ggttggaaca tactagctct tgatgaatgc   3480
caattttctt cttttaaaaca aaaaatttca gaatgcatgt cattacttat ttctcatttt   3540
gatataatag gcgcacgctc catagaagtt gagaaaatca atcaacaagc tagatcaaat   3600
cttgatttgg aagatgtgtt tgacgatgat atgatgctac aagtgaattc cgagttccga   3660
gtacaaagta taatggaatt ggaagaaagg ataaagcgga atcctcatca aactggtaaa   3720
gtaattgatg atagtgacaa aggtaacaag taccttgttt cttttggcatc ttccatatcg   3780
aacgtttcta tgagatggca aaagaggaac tttattggtg gcggtacttt tggaagggta   3840
tattctgctg ttgatttgga taatggtgag attttagcag tcaaggaaat caatattcaa   3900
gatagcaaat caatgcaaaa atattccccc ttaatcaagg aggaaatgag tgtcttagag   3960
atattgaacc atccaaatat agtttcatat tacggtgttg aagttcatcg tgataaagtt   4020
aacatcttta tggaatattg tgaaggcggt tccctagcag ctcttttgga gcatggtcgt   4080
attgaagatg aaatggtcac tcaagtctac actttacaat tgctagaagg acttgcatat   4140
ttgcatgaat ccggcattgt tcaccgtgat gttaaacccg aaaacatcct actagatttt   4200
aatggtgtta ttaagtatgt tgattttggt gctgctaaaa aaattgctaa taatggaact   4260
agattggcaa gtatgaacaa aatcgaaaac gcagatggtg aacacgaaga tgttacccat   4320
gtttctgatt caaaggcagt gaaaaataac gaaaatgctc tattagacat gatgggaact   4380
cctatgtaca tggctccaga atccatcact ggatctacca ccaaaggcaa acttggggca   4440
gacgatgttt ggtcgttagg ctgcgtggta ttagaaatga tcactggtag acggccatgg   4500
gctaacttag ataatgaatg ggctatcatg taccatgttg ctgcaggaca tacccccacaa   4560
```

<210> SEQ ID NO 54
<211> LENGTH: 1548
<212> TYPE: DNA
<213> ORGANISM: Saccharomyces cerevisiae

<400> SEQUENCE: 54

| | | | | | |
|---|---|---|---|---|---|
| atgtttcaac | gaaagacttt | acagagaagg | aacttgaaag | ggctcaatct | taacctgcac | 60 |
| ccagatgtgg | gcaataatgg | ccaattgcag | gaaaagacag | agactcacca | gggacaatct | 120 |
| cgaatagaag | gccacgtgat | gtctaacatt | aatgcaatac | agaataatag | caacctgttt | 180 |
| ttgcgaagag | gcataaaaaa | aaaactgacg | ttggatgcgt | ttggtgatga | ccaagctata | 240 |
| tcgaaaccaa | acactgtggt | aatacagcaa | ccgcaaaatg | aacctgtttt | agttctgtct | 300 |
| tctctatcac | aatcccgtg | tgtatcatca | tcatcatctt | tgtccacgcc | atgcattata | 360 |
| gatgcgtaca | gtaataattt | cggattatcg | ccatcatcca | cgaattctac | tccctctacg | 420 |
| attcagggat | tgtccaatat | tgcaacacca | gttgaaaacg | aacattcgat | atcactacca | 480 |
| cctttggagg | aaagcctatc | gccagccgca | gcagatctga | agatacgtt | gtcgggaact | 540 |
| tcaaatggta | attatataca | actccaggac | ttggttcagt | tggggaaaat | tggtgctgga | 600 |
| aattctggaa | ctgtggtgaa | ggcactacat | gttcctgatt | ccaaaatagt | tgccaaaaaa | 660 |
| accattcctg | tggaacagaa | taacagtaca | atcatcaacc | aattagttag | ggaattatct | 720 |
| atcgtcaaaa | acgttaagcc | ccatgaaaac | attatcaccct | tctatggagc | ttattataac | 780 |
| cagcatataa | ataatgaaat | cataaattta | atggaatact | ctgattgtgg | ttctttagat | 840 |
| aaaatactgt | ccgtttataa | aaggtttgtt | caaagaggga | ctgtttcgag | taagaaaacc | 900 |
| tggttcaacg | aattaacaat | atcaaaaata | gcgtatggcg | tactaaatgg | cttggatcat | 960 |
| ttgtaccgac | aatataagat | cattcatcgt | gatatcaagc | cttccaatgt | tctgattaat | 1020 |
| agtaaggggc | agattaagtt | atgtgatttt | ggagtttcca | aaaaactaat | aaattctatc | 1080 |
| gctgatacat | tgttggaac | gtccacttat | atgtcaccag | agaggataca | aggaaacgtt | 1140 |
| tattctatca | aggggacgt | ttggtcattg | ggcttaatga | tcatcgagct | ggtaactgga | 1200 |
| gagtttcccc | taggtgggca | taacgataca | cctgatggca | tattggattt | gctgcaacgt | 1260 |
| attgtcaacg | agccttcacc | aagattaccc | aagaccgta | tctattccaa | ggaaatgaca | 1320 |
| gattttgtca | ataggtgttg | tattaagaat | gaaagggaaa | ggtcatcgat | tcatgaattg | 1380 |
| ctacatcatg | atcttataat | gaaatacgta | tcaccgtcta | aagatgataa | atttagacat | 1440 |
| tggtgtagaa | aaataaaatc | taaaataaag | gaagacaaga | gaattaaaag | agaagccttg | 1500 |
| gaccgtgcca | agttagaaaa | gaaacaatcg | gaaagatcaa | cccattga | | 1548 |

<210> SEQ ID NO 55
<211> LENGTH: 1521
<212> TYPE: DNA
<213> ORGANISM: Saccharomyces cerevisiae

<400> SEQUENCE: 55

| | | | | | |
|---|---|---|---|---|---|
| atggcttcaa | tgttcagacc | accagaatcc | aataggagtc | accaaaagac | tccaaaatta | 60 |
| acgcttccag | taaatttagt | tcaaaatgcg | aaatccacta | atgatgggca | acatctcaac | 120 |

```
cggtcaccgt actcgtcagt gaacgaaagc ccatactcca acaatagcac ttcagctact    180
tccactacgt catccatggc ttcaaattcc actttgttgt acaatagatc atctactaca    240
actattaaaa atagaccggt accacctcca ttacctcccc tagtactaac gcaaaaaaaa    300
gacggtatag aatatagagt tgccggcgat agtcagcttt ctgaaagatt ttctaatttg    360
catgttgata taacttacaa ggaactacta tctagtgctc caatttccac taagttatcc    420
aacatagata ccacttttat caagaaagat ctcgacacac cagaaggcga ggattcatac    480
ccctcgacac ttctttctgc gtacgacttc agcagtagcg ggagcaactc cgcccctta    540 agtgcaaata acataatttc ttgttccaac ttaatacaag gaaagacgt agaccagtta     600 gaggaagaag catggaggtt tgggcatctc aaggatgaga ttactacact aggaattcta    660
ggagaaggcg cgggtggttc tgtagccaag tgccgattaa aaatggaaa aaaggttttt     720 gcgttgaaga caatcaacac tatgaatact gacccagaat atcaaaagca atattcaga    780 gagctacaat ttaataagag ttttaagtcc gattatattg tgcagtacta tggtatgttt    840
accgacgaac agagttcttc aatatacatt gccatgaat atatgggagg aaaatcactg     900
gaggcaacgt ataaaaattt gttgaaacgt ggcggtagaa taagtgagag ggtgatagga    960
aagatagcag aatctgtctt aagaggttta tcatacttac acgaaaggaa agtcatccac   1020
agggacatta aaccccaaaa cattcttctt aatgaaaaag gggaaatcaa attatgcgat   1080
ttcggtgtca gtggggaggc tgttaactct ttagcgatga catttactgg aacgtcattt   1140
tatatggccc cagaacgaat acaaggccaa ccatacagcg taacctgtga tgtatggtcc   1200
ttaggattaa ctcttctgga ggttgctgga gggagatttc catttgaatc tgacaaaata   1260
acgcaaaacg tggctcctat agaattattg acgatgatcc tgacgttttc tccccagttg   1320
aaagatgagc cagaactaga catatcctgg agcaagacat ttagatcttt tatcgactat   1380
tgtttaaaaa aagatgccag agagaggcct tctcccaggc aaatgttaaa gcatccctgg   1440
attgtagggc aaatgaaaaa aaaagtcaac atggaacggt ttgtaaagaa atgctgggaa   1500
aaggaaaagg atgggatata a                                             1521

<210> SEQ ID NO 56
<211> LENGTH: 2007
<212> TYPE: DNA
<213> ORGANISM: Saccharomyces cerevisiae

<400> SEQUENCE: 56
atggaagaca agtttgctaa cctcagtctc catgagaaaa ctggtaagtc atctatccaa      60
ttaaacgagc aaacaggctc agataatggc tctgctgtca agagaacatc ttcgacgtcc    120
tcgcactaca ataacatcaa cgctgacctt catgctcgtg taaagcttt tcaagaacaa     180 cgtgcattga aaggtctgc cagcgtgggc agtaatcaaa gcgagcaaga caaaggcagt    240
tcacaatcac ctaaacatat tcagcagatt gttaataagc cattgccgcc tcttcccgta    300
gcaggaagtt ctaaggtttc acaaagaatg agtagccaag tcgtgcaagc gtcctccaag    360
agcactctta agaacgttct ggacaatcaa gaaacacaaa acattaccga cgtaaatatt    420
aacatcgata caaccaaaat taccgccaca acaattggtg taaatactgg cctacctgct    480
actgacatta cgccgtcagt ttctaatact gcatcagcaa cacataaggc gcaattgctg    540
aatcctaaca gaagggcacc aagaaggccg ctttctaccc agcaccctac aagaccaaat    600
gttgccccgc ataaggcccc tgctataatc aacacaccaa acaaagtttt aagtgcccgt    660
cgagggctca aattaccacc aggaggaatg tcattaaaaa tgcccactaa aacagctcaa    720
```

```
cagccgcagc agtttgcccc aagcccttca acaaaaaac atatagaaac cttatcaaac      780
agcaaagttg ttgaagggaa aagatcgaat ccgggttctt tgataaatgg tgtgcaaagc      840
acatccacct catcaagtac cgaaggccca catgacactg taggcactac acccagaact      900
ggaaacagca acaactcttc aaattctggt agtagtggtg gtggtggtct tttcgcaaat      960
ttctcgaaat acgtggatat caaatccggc tctttgaatt ttgcaggcaa actatcgcta     1020
tcctctaaag gaatagattt cagcaatggt tctagttcga gaattacatt ggacgaacta     1080
gaattttttgg atgaactggg tcatggtaac tatggtaacg tctcaaaggt actgcataag     1140
cccacaaatg ttattatggc gacgaaggaa gtccgtttgg agctagatga ggctaaattt     1200
agacaaattt taatggaact agaagttttg cataaatgca attctcccta tattgtggat     1260
ttttatggtg cattctttat tgagggcgcc gtctacatgt gtatgaaata catggatggt     1320
ggttccttgg ataaaatata cgacgaatca tctgaaatcg gcggcattga tgaacctcag     1380
ctagcgttta ttgccaatgc tgtcattcat ggactaaaag aactcaaaga gcagcataat     1440
atcatacaca gagatgtcaa accaacaaat attttatgtt cagccaacca aggcaccgta     1500
aagctgtgcg atttcggtgt ttctggtaat ttggtggcat cttttagcgaa gactaatatt     1560
ggttgtcagt catacatggc acctgaacga atcaaatcgt tgaatccaga tagagccacc     1620
tataccgtac agtcagacat ctggtctttta ggtttaagca ttctggaaat ggcactaggt     1680
agatatccgt atccaccaga aacatacgac aacattttct ctcaattgag cgctattgtt     1740
gatgggccgc caccgagatt accttcgat aaattcagtt ctgacgcaca agattttgtt     1800
tctttatgtc tacaaaagat tccggaaaga agacctacat acgcagcttt aacagagcat     1860
ccttggttag taaaatacag aaaccaggat gtccacatga gtgagtatat cactgaacga     1920
ttagaaaggc gcaacaaaat cttacgggaa cgtggtgaga atggtttatc taaaaatgta     1980
ccggcattac atatgggtgg tttatag                                          2007
```

<210> SEQ ID NO 57
<211> LENGTH: 1539
<212> TYPE: DNA
<213> ORGANISM: Saccharomyces cerevisiae

<400> SEQUENCE: 57

```
atggtagcaa caataatgca gacgacaaca actgtgctga cgacagtcgc cgcaatgtct       60
actaccttag catcaaatta catatcttcg caagctagtt cctcgacgag tgtaacaaca      120
gtaacgacaa tagcgacatc aatacgctct acaccgtcta atctactctt ttctaatgtg      180
gcggctcagc caaaatcatc ttcagcaagc acaattgggc tttcaatcgg acttcccatc      240
ggaatattct gtttcggatt acttatcctt ttgtgttatt tctaccttaa aaggaattcg      300
gtgtccattt caaatccacc catgtcagct acgattccaa gggaagagga atattgtcgc      360
cgcactaatt ggttctcacg gttattttgg cagagtaagt gtgaggatca gaattcatat      420
tctaatcgtg atattgagaa gtataacgac acccagtgga cctcgggtga taacatgtct      480
tcaaaaatac agtacaaaat ttccaaaccc ataataccgc agcatatact gacacctaag      540
aaaacggtga agaacccata tgcttggtct ggtaaaaaca tttcgttaga ccccaaagtg      600
aacgaaatgg aggaagagaa agttgtggat gcattcctgt atactaaacc accgaatatt      660
gtccatattg aatccagcat gccctcgtat aatgatttac cttctcaaaa acggtgtcc      720
tcaaagaaaa ctgcgttaaa aacgagtgag aaatggagtt acgaatctcc actatctcga      780
```

```
tggttcttga ggggttctac atactttaag gattatggct tatcaaagac ctctttaaag      840
accccaactg gggctccaca actgaagcaa atgaaaatgc tctcccggat aagtaagggt      900
tacttcaatg agtcagatat aatgcctgac gaacgatcgc ccatcttgga gtataataac      960
acgcctctgg atgcaaatga cagtgtgaat aacttgggta ataccacgcc agattcacaa     1020
atcacatctt atcgcaacaa taacatcgat ctaatcacgg caagacccca ttcagtgata     1080
tacggtacta ctgcacaaca aactttggaa accaacttca atgatcatca tgactgcaat     1140
aaaagcactg agaaacacga gttgataata cccaccccat caaaaccact aagaaaagg      1200 aaaaaaagaa gacaaagtaa aatgtatcag catttacaac atttgtcacg ttctaaacca     1260
ttgccgctta ctccaaactc caaatatat ggggaggcta gcgtccaatt agggaagaca      1320
tatacagtta ttcaggatta cgagcctaga ttgacgacg aaataagaat ctcgctgggt      1380
gaaaaagtta aaattctggc cactcatacc gatggatggt gtctggtaga aagtgtaat      1440 acacaaaagg gttctattca cgtcagtgtt gacgataaaa gatacctcaa tgaagataga     1500
ggcattgtgc ctggtgactg tctccaagaa tacgactga                            1539

<210> SEQ ID NO 58
<211> LENGTH: 1455
<212> TYPE: DNA
<213> ORGANISM: Saccharomyces cerevisiae

<400> SEQUENCE: 58
atggctgata agatagagag gcatactttc aaggtcttca atcaagattt cagtgtagat       60
aagaggtttc aacttatcaa agaaataggg catggagcat acggcatagt gtgttcagcg      120
cggtttgcag aagctgccga agataccaca gttgccatca agaaagtgac aaacgttttt      180
tcgaagacct tactatgtaa aagatcccta cgtgagctaa agcttttgag acatttcaga      240
ggccacaaaa atattacatg tctttatgat atggatattg ttttttatcc agacgggtct      300
atcaatggac tatatcttta tgaggaactt atggaatgtg atatgcacca aatcatcaaa      360
tccggtcaac ctttgacgga tgctcactat caaagtttca cataccaaat attatgtggt      420
ttaaagtata ttcattctgc agatgtcttg catcgtgatt tgaagcccgg caatttgctt      480
gtcaatgcag attgtcaatt gaaaatctgt gattttgggt tagctagagg ttattcggag      540
aatcctgtcg aaaacagtca atttttgacg gagtacgtgg ccactagatg gtatagagct      600
ccggaaataa tgttgagtta ccaaggatat accaaggcga ttgacgtatg gtcagctggc      660 tgtatttttag cggagtttct tggtggaaag ccaatcttca aggaaagga ttacgttaat      720 caattgaatc aaatattaca agttttaggg acaccccag acgaaacttt aagaaggatt      780
ggttctaaaa atgttcagga ctacatacat caattaggtt tcattccaaa agtacctttt      840
gtcaatttat acccaaatgc caattcacaa gcattagact tattggagca aatgctcgcg      900
tttgaccctc aaaagagaat taccgtggat gaggccctgg agcatcctta cttgtctata      960
tggcatgatc cagctgacga acctgtgtgt agtgaaaaat tcgaatttag ttttgaatcg     1020
gttaatgata tggaggactt aaaacaaatg gttatacaag aagtgcaaga tttcaggctg     1080
tttgtgagac aaccgctatt agaagagcaa aggcaattac aattacagca gcagcaacag     1140
cagcagcaac agcaacagca acagcaacag cagccttcag atgtggataa tggcaacgcc     1200
gcagcgagtg aagaaaatta tccaaaaacg atggccacgt ctaattctgt tgcgccacaa     1260
caagaatcat ttggtattca ctcccaaaat ttgccaggc atgatgcaga tttcccacct     1320
cgacctcaag agagtatgat ggagatgaga cctgccactg gaaataccgc agatattccg     1380
```

| | |
|---|---|
| cctcagaatg ataacggcac gcttctagac cttgaaaaag agctggagtt tggattagat | 1440 |
| agaaaatatt tttag | 1455 |

<210> SEQ ID NO 59
<211> LENGTH: 1308
<212> TYPE: DNA
<213> ORGANISM: Saccharomyces cerevisiae

<400> SEQUENCE: 59

| | |
|---|---|
| atgaccacta acgaggaatt cattaggaca cagatattcg gtacagtttt cgagatcaca | 60 |
| aatagataca atgatttaaa ccccgttggg atggggggcat ttgggttggt ttgctcagcc | 120 |
| acggacactt tgacatctca gccagttgcc attaagaaaa tcatgaaacc ttttccact | 180 |
| gcagtgctgg ccaaaaggac atatcgtgaa ctaaaactac taaaacatct aagcacgag | 240 |
| aacttgattt gccttcagga catatttctt tctccattgg aagatatata ttttgtcacg | 300 |
| gaattacaag gaacagattt acatagactc ttgcaaacaa gacccttgga aaagcaattt | 360 |
| gttcagtatt tcctatacca aattctaagg ggtttaaaat acgttcactc cgcgggcgtc | 420 |
| attcatagag atttgaaacc gagcaacatt ctgattaatg aaaactgtga tttgaagatt | 480 |
| tgcgatttcg gtctagcaag aattcaagac cctcaaatga caggctatgt ttccactaga | 540 |
| tactacaggg cacctgaaat catgctaacg tggcaaaaat atgacgtcga ggtcgacatt | 600 |
| tggtccgctg gttgtatttt tgccgaaatg attgaaggta agcctttgtt ccctgggaaa | 660 |
| gatcatgttc accaattttc gatcatcact gacttgttgg gatctccgcc aaaggatgtg | 720 |
| ataaatacta tttgttccga aaatactcta aaatttgtta cttcgttacc acacagagat | 780 |
| ccaattccat tttctgaaag atttaaaaca gtcgaacctg atgccgtaga cctttttggaa | 840 |
| aaaatgctgg tttttgatcc taagaagaga atcactgcgg cggatgcctt ggctcatcct | 900 |
| tattcggctc cttaccacga tccaacggat gaaccagtag ccgatgccaa gttcgattgg | 960 |
| cactttaatg acgctgatct gcctgtcgat acctggcgtg ttatgatgta ctcagaaatc | 1020 |
| ctagacttcc ataagattgg tggcagtgat ggacagattg atatatctgc cacgtttgat | 1080 |
| gaccaagttg ctgcagccac cgctgccgcg gcgcaggcac aggctcaggc tcaggctcaa | 1140 |
| gttcagttaa acatggctgc gcattcgcat aatggcgctg gcactactgg aaatgatcac | 1200 |
| tcagatatag ctggtggaaa caagtcagc gatcatgtag ctgcaaatga caccattacg | 1260 |
| gactacggta accaggccat acagtacgct aatgagttcc aacagtaa | 1308 |

<210> SEQ ID NO 60
<211> LENGTH: 7416
<212> TYPE: DNA
<213> ORGANISM: Candida albicans

<400> SEQUENCE: 60

| | |
|---|---|
| atgtctatga acttttttaa ttcaagcgaa cctgcaaggg accacaaacc ggaccaggaa | 60 |
| aaggaaacag taatgacgac agaacattat gaatttgaac gaccagatgt caaagctata | 120 |
| cgaaatttca aattcttcag gctggacgaa acagaaaccca aaaaggacc aaaccttcat | 180 |
| atttcggatc tatcccctct tgaatcacaa tctgtgcccc cttcagcctt aagtttaaat | 240 |
| cattcgataa taccagacca atatgaacga cgtcaggata caccggatcc tatacacact | 300 |
| cctgaaattt cattaagtga ttatttatat gatcagacat tgagtcccca aggttttgac | 360 |
| aatagccgtg aaaatttcaa catccacaaa acaatcgcca gtttattcga agataactca | 420 |

```
tctgttgtat cacaagaatc tactgatgac accaagacaa cattatcact ggaaacatgt    480
gatagctttt cattgaataa cgcatcatat ttgaccaaca ttaactttgt gcaaaatcat    540
ttacaatacc ttagtcaaaa tgttttggga aatcgcactt ccaacagctt accgccatca    600
tcatcatcac agatagactt tgatgcctcc aatttgacac ccgattcgat accagggtac    660
attctcaaca agaaacttgg ctctgttcat caactgacag acctggtata caacgctatc    720
aagattcctc aaaacgaaga atacaactgt tgcactaaag cttctgctag tcaaaatcca    780
acaaatttga attctaaagt gatagtgagg ctatcaccta atattttttca aaacttgtca    840 ctttcgcgtt ttcttaatga gtggtacata ttatctggga agcacagttc aaaagagcac    900
caaatatggt ccaatgagtc tctcacaaat gaatacgtac aagacaaaac aattccgaca    960
tttgataaag aaagtgcacg ttttagacca acgttgccca taaatatacc aggtatcttg   1020
tacccgcaag agataataaa cttttgtgtg aacagccatg attatccact gaacacccca   1080
tcacagtcca ctgatcaaaa aagatttgcc atggtgtacc aagacaacga ttacaagaca   1140
ttcaaagaac tcagcatgtt cactttgcac gagctacaaa ctagacaggg gtcgtattcg   1200
tccaacgagt cacgcgaaaa atccagcagt ggctttaata taggtgtcaa tgcaaccacc   1260
actgaagctg ggtctttgga atcttttagt aatctaatgc agaatcacca tcttggtgca   1320
acttcaacca acggagaccc atttcactca aaactagcaa agtttgagta tggagttttcc  1380 aaatccccta tgaagcttat agagattttg actgatataa tgagagttgt cgagacaata   1440
agtgttattc atgaactagg atttgttcac aatggcctaa ctagcagcaa tttattgaag   1500
tcagagaaaa atgtcagaga tataaaaata acaggatggg ggtttgcatt cagtttttact  1560 gaaaattgca gccagggtta cagaaataaa cacttggcac aagtccaaga tttaatacct   1620
tacatggcac cagaggtgtt ggctattaca aattcggttg tggattatcg gtcggacttt   1680
tactcgttag gggtaataat gtatgagtta gttttgggta ttttgccatt caaaaatagc   1740
aacccccaga aattgatcag aatgcatact tttgaaaacc caatagctcc cagtgctcta   1800
gcaccaggtt ggatttcaga gaaattgagt ggcgttatta tgaaattgtt agagaagcac   1860
ccacataaca gatacaccga ctgccactca ttgctccacg atttaattga agttaaaaat   1920
atgtacatta gcaaattatt ggattcaggg gaaacaatcc ccaatagtaa cctaaatttta  1980 agtgatcgcc agtactattt gactaaagaa aatttacttc atcccgagaa aatgggaatt   2040
actcctgtac ttgggttgaa agaaagttttt attggaagaa gagatttctt gcaaaatgtt   2100
actgaagttt acaataacag caaaaatggg attgatttac ttttttatatc cggtgaaagc   2160 ggaagaggta aaacgataat attacaagat cttcgagcag cagcagtttt gaaacaagac   2220 tttttattact catggaagtt tagtttttttt ggagcagata cacatgtgta ccggtttctt   2280
gttgaaggtg ttcaaaagat tattacccag attctaaatt cttcagaaga aattcaaaat   2340
acatggagag atgtgatttt gacacacatt cctatagatc taagcatatt attttatttg   2400
attcctgagc taaaagtact attggggaaa aaatacactt ccatttacaa acataaaatt   2460
ggaatgggga tgctaaagag aagtttcaaa gaagaccaaa cactgagact agagattaaa   2520
ttgagacaaa tactaaaaga attttttcaaa cttgtagcga acaaggctt gtctatttttt  2580 ttagatgatg tacagtggtg ttcagaagag tcctggaggt tattatgtga tgtattagat   2640
tttgattcat ctggagaggt gcgagagagc tataacatca aaatagttgt gtgctatgct   2700
ttgaatgcag accatttaga gaatgttaat atcgagcata aaaagatttc ttttttgccga   2760 tatgccaaac aaagccactt aaatttgcgt gagtttagta tacctcatat cccacttgaa   2820
```

```
gacgctattg aattttttgtg tgaaccttac acgagactgc acgatcatga atgtaacagt    2880
aaaaagtctg atgtaattgc caatttaaac tgcacaaatg aatatcctca gaacacttgc    2940
aaagtcatcc ccagtataat ccaagagttg tatcaatcat cagaagggaa tgttttgctt    3000
ttgatattcc taacaagaat gacaaagcta tctggcaaag ttcccttttca acgattttcg    3060 gtcaaaaatt catatctata tgatcaccta ctgaatagta actatggaac tacaagaaaa    3120
gagattctta caaattattt gaatatggga actaactcag acacaagagc cttgcttaaa    3180
gttgcagcgt taatctccaa tggatcggga ttctttttttt cagatttaat tgtagccacc    3240
gacttgccca tggctgaagc gtttcagttg ttacaaatat gtattcattc cagaataatt    3300
gttcctacta gcacatatta taaaatacct atggatttaa tagcctctga ccagactcca    3360
tttgatttaa cagatgataa tatttggaaa ctagccactt tatgcagcta caagttctat    3420
catgattcta tttgtactca tataatcaaa gaattaaacg ccagtggcga attcaaagaa    3480
ctttctcggt tatgtgggtt gagattttac aatacaatta caaagaacg tttattaaat    3540 attggtggct atcttcaaat ggctactcac tttagaaact catacgaggt ggcaggtccc    3600
gaagaaaatg aaaagtatgt tgaagttttg gtccaggcag gacgatatgc catatcgaca    3660
tataatatga agttgtctca atggtttttc aatgttgttg gcgaattggt atataatctt    3720
gattcgaaaa ctcagttaaa atccgtgtta acaatagccg agaatcattt taattctcgt    3780
gaatttgaac aatgcctaag tgtggttgaa aatgcacaga ggaaatttgg ttttgacagg    3840
ttgatatttt ccattcaaat agtccgttgc aaaattgaat taggtgatta tgacgaagca    3900
catcgaattg caattgaatg tcttaaggaa ttaggtgttc cattagatga cgatgacgaa    3960
tatacaagtg aaaacctgct tgagacgtgt ttgggaaaaa ttccgctctc tgttgctgac    4020
attagaggta ttttgaagat taaaagatgc aagaattcaa gaacattgct aatgtatcag    4080
ttaatttcag agctaattgt actattcaag cttcaaggta aagacaaagt gagaaggttt    4140
ctcacagctt atgcgatgag tcaaattcat actcaagggt cttctcctta ttgtgcagta    4200
attcttatag actttgcaca atcatttgtc aacgaaacca caacttcagg aatgcttaaa    4260
gcaaaagaac tcagtattgt catgttgtca ttgattaata gagcaccaga aatatcttta    4320
tcatatgttc agtctatttta tgaatattat ttcagttgtc atgctgtatt ttttgaatca    4380
attgaaaaaa tgctggatct tatacatcca ggtaacgcta gttcccattg cacaagactg    4440
tcttattatt catcttttca tttgatagtt aatgtttcca agattttctt ttcatgtatg    4500
aatggagaaa gtttcaaaat gttctcaaca ttcaagtgta atcctatttt aacaggggat    4560
ccccaaatgc ctgaaatgga caattttttta tacgatagtg aaatgttact gctggacat    4620 tcagaattga atgaatttat gagaaaatat cagtcattca accaaacttc cgttggtaaa    4680
ttttgctact atttaattgt actacttgta atgtcacgtg aacacagatt tgacgaggct    4740
gccgatttgg ttttgaaagt tttggaagac ttactggaaa aattgcctgt atcttttttg    4800
catcatcaat attacttaat atgtggtaaa gtgtttgctt atcaccagac caaaaccccca    4860 gaaagtgagg aacaagtgga acgtattttg gctcgtcaat ttgaaagata tgaattgtgg    4920
gcactgacga ataagccgac ccttctacca cggtacttgt tgttgagtac ctacaaacag    4980
attagagaaa accatgttga caagttagaa atactagatt catttgagga ggcgttacag    5040
acggcccata aatttcataa tgtatatgat atgtgctgga tcaatttgga atgtgcaaga    5100
tggttaatta gcataaaacca aaaaaggcac agaatctcaa gaatggttaa acaaggtctt    5160
```

```
aaaattttga gaagcttgga attaaataat catttaagat tagctgaatt tgaatttgat    5220
gaatacattg aggacgaaga tcacagaaat aaatgggcag ggttaactaa taatccaaca    5280
ttggatactg ttactacctg gcaacaacag aacatgcccg ataaggtatc tccatgcaat    5340
gacaagcagt tggtccacgg aaaacaattt ggcaaaaaag agtttgatag ccatttgctc    5400
agattgcact ttgatggcca atatacaggc ctagatttga attcagctat tcgtgaatgt    5460
ctagcaatat ccgaagcttt agacgaaaat tccattctca caaagttgat ggcatctgcc    5520
atcaagtatt caggtgccac atatggggta attgtcacga agaaaaacca ggagacacct    5580
tttcttagaa caattggctc gcagcacaat attcacacat aaacaacat gccaatttcc     5640 gacgacattt gtcctgctca gttgattcgt catgtattgc atacaggaga aacggtgaac    5700
aaagctcatg atcacatagg atttgctaac aagtttgaga atgaatactt tcaaacaaca    5760
gataaaaagt attcagttgt gtgtttgcca ttaaagagtc tgcttggatt atttggtgca    5820
ctttatctag aaggtagtga tggtgatttt ggacatgaag atttgttcaa tgaaaggaaa    5880
tgtgatttgt tacaactttt ttgcacacaa gcagctgtgg ctttgggtaa ggagcgtttg    5940
cttttgcaaa tggaactagc aaaaatggca gcagaagacg ccactgatga aaaagccagt    6000
tttttggcaa acatgtcaca tgaaatacga accccattca attcgttatt gtcatttgct    6060 attttttgt tagataccaa attggattct actcaaagag aatatgtcga ggcaattcag     6120
agctccgcaa tgataacgtt gaatattatt gatgggatac ttgcgttttc caaaattgag    6180
catggatcct ttacattaga aaatgccccc ttttctttga atgattgtat cgagactgct    6240
attcaagtaa gtggggaaac aattttgaat gaccagattg agttggtgtt ttgtaacaat    6300
tgtccagaga ttgaatttgt ggttggtgat ctaacgaggt tcagacaaat tgtgatcaat    6360
ttggtgggta atgctattaa gtttacaacc aaaggtcatg ttttgatttc ttgtgatagc    6420
cgaaaaatta cggacgacag atttgagatc aatgtgtcag ttgaggattc aggaattgga    6480
atttccaaaa aatctcaaaa taaagtgttt ggagcatttt ctcaagtaga tggttccgca    6540
agacgagaat atggtggctc tggattaggt ttagctatat caaagaaatt gactgaacta    6600
atgggtggca caattagatt tgaaagtgag gaagggattg gcacaacgtt ttatgttagc    6660
gtcattatgg acgcaaaaga atactcatcc ccgccattta gtttaaataa aaaatgtttg    6720
atttacagcc agcattgtct tactgccaag tcaatttcaa atatgcttaa ttattttgga    6780
tcaacagtta aagtcactaa tcagaagtct gagttttcaa cttccgtgca agccaacgac    6840 atcattttc ttgatcgcgg aatggaacct gatgttagtt gcaaaaccaa agtcattccc     6900
atcgacccaa aacctttcaa aagaaacaaa ctcattagta ttctcaaaga acaaccaagt    6960
ttgcccacca aagtgtttgg aaacaacaaa tctaatttat caaaacaata ccctctaaga    7020
atattattag cagaagacaa tcttttgaac tataaagtat gtttgaagca tttggataaa    7080
ttggggtaca aggcagatca tgccaaagat ggagtagtag ttttggataa atgtaaagaa    7140
ctactagaaa aagacgaaaa atatgatgtc atattgatgg atattcaaat gcctcgtaag    7200
gacggtatta cagctacaag ggatttgaaa acattgtttc acacacaaaa aaaggaaagt    7260
tggttacccg tgatcgtagc attgacagct aatgttgctg gagacgacaa aaagaggtgt    7320
ctagaagagg gaatgtttga ttttataacc aaacccattt taccagatga acttagacgt    7380
attttaacaa aagtagggga aacagtgaat atgtaa                              7416

<210> SEQ ID NO 61
<211> LENGTH: 5020
```

<212> TYPE: DNA
<213> ORGANISM: Saccharomyces pombe

<400> SEQUENCE: 61

| | | | | | |
|---|---|---|---|---|---:|
| atgaggccac | ctgacgatca | aatcaacaat | aacgttggtt | ctaattctca | cttggaaaag | 60 |
| ttgaaagagg | taagtgattt | caatacttgg | attctccttt | tttaaatatg | aaataaaatg | 120 |
| tgatatctct | tgttacttaa | ttaatttaaa | ttactaacgt | ttgaataagg | ccatggacca | 180 |
| ccagctgcaa | aaatcatcaa | aaattgtagg | atcgtttact | aattctcaaa | actcttctgt | 240 |
| tggctctgtt | cattctccga | tacttgaatc | tcccaccagt | ttaaataggc | agcatcgaaa | 300 |
| ttcattttct | ttcaataatg | tatcttctcc | ttcactagag | gatgagcgac | ttattaattt | 360 |
| tccccgagta | aatccaaatc | gattgatgac | atccaaacgt | cccaatgagt | tatttaaaac | 420 |
| ctcctcaatg | agttcagatt | gctattctcc | tcaaaaatct | agggaatcac | taaattcatt | 480 |
| atgccattca | cctgctccat | ccgtttcttc | ttgtggaaat | gctttgaaca | acgataatac | 540 |
| ttctgcttcg | cactcactaa | ctgatgagca | accatttgaa | acagattcat | ccgctaactt | 600 |
| atttaagcag | ttacaggaga | agcgtaaccg | taccattgga | aatgtgtatg | aaatggcttg | 660 |
| cttattggtc | tttaaaaccg | gtttgatgaa | tttctggaaa | aacattattg | acttttttcgc | 720 |
| tcagcagttt | ttttccactc | aaatatctgt | tgtagaaccg | cgtgacccttt | ctgacatata | 780 |
| caatactcct | tggcaactca | gatgttatta | cgatggcggt | tcccattatg | atccgtatag | 840 |
| taaccctata | agtgttaatg | acaaccttgc | tagcagttct | tatgttaccg | tagttgcttc | 900 |
| ggatggttca | aagggtatta | tatacaaaga | tccagcttct | cttaaacatg | aagggggattt | 960 |
| gcttattgat | agcaaagttg | tacaaacagt | cttggagcgt | gcgacattgc | ttgtatatac | 1020 |
| acgtaaacaa | cagcacattg | ttaaaaacac | caaggttcat | gataatgatt | actttagttc | 1080 |
| tatacctaat | gttgatgata | ttcgcagcat | taagaattca | tggaaagttt | ttcatgatga | 1140 |
| aaaacttaat | gaattgaaaa | agcaggttga | aattagtgct | tctgcagctc | agttaaatgg | 1200 |
| actttatcca | cagaaaaaga | gagcatttgt | ttcacatttc | agtcagaatc | gtaaaccgta | 1260 |
| ttcccaaagt | gacatttcaa | aagcacaaag | ttcgtctttt | tcggaagaac | cttcaaacat | 1320 |
| ttatgatgag | tatgaacaaa | atttactttc | tccttggtca | agatctccag | ttgctagtcc | 1380 |
| ctccattcaa | acagatccta | ataggaatcc | attcttccaa | aattgcttgc | aagaatcttc | 1440 |
| tttcgctact | gaatcgtcaa | cagagaagtc | tgcttcagag | tccgtatcag | aaacagctgt | 1500 |
| taatgatgat | tgtaaaggta | tgaatttttc | tggtaacagg | cgtcaagaag | atcatttgaa | 1560 |
| cgacttcacc | agttttccta | ctgaaactgc | tgtcagtatt | gtacatgttc | ctctgatgtt | 1620 |
| tccttgttcg | gatcaaactt | caagccgtgg | gagagctcca | attgcaattc | tttctttcaa | 1680 |
| gtccaattta | gttccttatc | cggaaaattt | aatagcctcc | atagaacgtt | tgatacccttt | 1740 |
| tattttttct | tcatactcaa | attctcaatc | tgttccgtta | cttccttgtc | ctacacaaag | 1800 |
| gcatctatta | tttaacacgt | ctagcactga | caataccaag | gagttgagta | tgagcgcgag | 1860 |
| ctccgaaaac | tctgattgtc | ctcataaaga | aggagagtgc | gtaggcagct | tttgcaatat | 1920 |
| caatgctaaa | ggatcttctc | ttaataacat | acctaaattg | cctaggtttg | taccagttcc | 1980 |
| ttctgaattt | tttaaaaaaa | accagcgatc | atgggttact | ttaaagaagc | atcgtttgct | 2040 |
| agctagattg | aagtctcgaa | ttagcaaaaa | gaattctaaa | gtgaacgaga | atttgagatt | 2100 |
| ctcgctaaat | gatggtgaaa | attattcaaa | tgaaactatt | actctaaaga | aggatgaaat | 2160 |
| tgttttagat | aaatcaaaat | catatgcctg | ttgcacttct | gaatctcaca | agtatgtgca | 2220 |

-continued

| | |
|---|---|
| agggcattgt ggtggtcaag cgcctccttt tcccttacta aaggttataa ttgattctat | 2280 |
| accggttcat gtgtttactg cggatccggg aagtggaaaa ctcacatggg ttaatagaaa | 2340 |
| aactcttctt tactgtggtt taaatatgaa tgagcaaata gagctacaat ttagtcgaat | 2400 |
| tcatcctgat gatctgccaa acttttttaaa tgactggaaa tcttcattat tctctggtag | 2460 |
| tggtttttat catgaaattc gtttgcaaag gtttgataat gtttatcgat actttatctg | 2520 |
| tcgcgcggtt cctttacggg attgcactgg atctgtgcta cattttttttg gaacaatgac | 2580 |
| ggatgtccat gatcaaaagt tggcagaacg agaactacaa aaacaatcag ctatagccgc | 2640 |
| aaatgaaaac agctacaggt ctttagctga agcttctcct caaattgttt ttgccgcaaa | 2700 |
| tggtaaaaat ggaattattt atgcaaatgc gcagtggtta agttattcag gtctttcact | 2760 |
| ggaatcttca ttgggacttg ggttttttatc tgctgtatat cacgctgatc gcaagaaatg | 2820 |
| tttattgcct gaatctttgg agggaacgtt taataaccaa gacgaaagta atggtaccaa | 2880 |
| aacgtttgcg gcggagatac gttttagatc taccgatggt cattatagat ggcatttggt | 2940 |
| gaaatctgtt tgcgtaaata attctgctga tacgtctact aatctctggt taggaacttg | 3000 |
| tactgatatt cacgatcata aaatgttgga agaaaagctc caagaatcta acattgaagc | 3060 |
| tcaaagaatt gttcggagca aaatgcagta tcttttccaat atgtctcatg aaattcgaac | 3120 |
| ccctcttatc ggtattacag gcatggtaag cttcttgttg gaaactcaaa tgtctgccga | 3180 |
| acagctgagt tatgcacgta ttattcagca atcagctaag tctcttttga ctgttatcaa | 3240 |
| tgatattttg gaccttagta aagtcagagc tggaatgatg aagctaacta gccaacgctt | 3300 |
| ttctgtacga gctatgatgg aagatgcaaa cgaaactcta ggtaccctcg cttttttcaaa | 3360 |
| gggaatagaa ttgaactaca cggttgacat tgatgttcct gatatagtat ttggggataa | 3420 |
| tatgagaatg aggcaagttg ctttgaatgt gatcggaaat gctattaaat ttacgaatgt | 3480 |
| tggtgaagtt tttactcgtt gttccgttga aaagattgat tactcaacca atactgttgt | 3540 |
| tttaaagtgg gaatgcattg ataccggtca agggtttaac agagatgatc aattacaaat | 3600 |
| gtttaaaccg ttttctcaag tagagagttc tacattacca agacatggtg gctcaggtct | 3660 |
| tggattagtt atttcaaaag agcttgttga gctacataat ggtagtatgt cctgtcaaag | 3720 |
| tagaagaggc gtgggaacgc gctttatgtg gactgcaacg tttacaatgg ataaaactcc | 3780 |
| tctaaaattt gaaccccccag atggttgttg tccagtctgt tttttgtccat acgaaaaaag | 3840 |
| caaacaaagc acagaagact attattgcgc agacgatgga aacgataaaa gcgcgacgaa | 3900 |
| ttttgtaaaa ttggccgtaa ataaagcaga tcccggaaga gaaagcaacc gacgtaaact | 3960 |
| tgaatcggac aaaaatgttc aatccaacaa atatgtgaat cctttcgctt ctgaatcgga | 4020 |
| attttgtcga tgcggcgcat ctgctgatcc atacacagtt ctattttgga gactctatag | 4080 |
| aaacaaacct tctgggatca agttggataa aagtgcttta gccgttgttg tatcacacac | 4140 |
| taaatacagt agtgaagcga ttggcaacat gcttcaatca attatcgata taagctcatt | 4200 |
| taaagatatc gtaaggtatg gaaataccta tgaagccttt gaagaattgc tagagaatcc | 4260 |
| tatgcaatcc aaggtcaccc atattatatt aaatcttccg gacatagaag catatgtttt | 4320 |
| atttgtcaaa tcactgcaac tttgtagtct atacaaggat acaaaattta ttttggtgac | 4380 |
| ttccactcga caaaaagaat cattatctaa gattttttca gatagcgagg attgtaattc | 4440 |
| ggaaagcatc cattacgttt taaaacttgt gaaaccatcc aagttttttc cattatttta | 4500 |
| ttctgattct gaggaaaagg ggaaaatcgg tgcacttaat gatatgactc gaaaggctgc | 4560 |
| aatggagcag aaggctgatg ctgaaacact ccgatataat ctggcaaagt ctggctttag | 4620 |

```
cgtgttgttg gcggaagaca acattatcaa tattaaggtt ataagccgtt accttgaaag   4680
aattggtgtc aaattcaagg tcaccatgga cggtttgcaa tgtgttgaag aatggaaacg   4740
tgaaaagcct aatttttact ctcttattct aatggattta caaatgcctg ttatggatgg   4800
ttaccaggca tgtaatgaaa ttcgtaaata cgaattggaa aacgattacc ctaaagttcc   4860
tatagttgca cttagtgcga atgctttacc tcatgttgtt ttaagctgca agatagtgg    4920 ttttgattct taccttgcca aacctattac tttgcaacac ttgtccttaa tcatatctgg   4980
catacttaat tatacgaacc aatcaaagtt acacaaatga                         5020
```

<210> SEQ ID NO 62
<211> LENGTH: 504
<212> TYPE: DNA
<213> ORGANISM: Saccharomyces cerevisiae

<400> SEQUENCE: 62

```
atgtctacta ttccctcaga aatcatcaat tggaccatct taaatgaaat tatatctatg    60
gatgacgatg attccgattt ttctaaaggt ctaattattc aatttatcga ccaggcacaa   120
acaacttttg ctcaaatgca acgacagctg gacggtgaaa aaaatcttac cgaattagac   180
aatctgggcc atttttaaa gggttcttct gctgcattag gcttacaaag aattgcctgg    240
gtttgtgaaa gaattcaaaa cttgggaaga aaaatggaac atttcttccc caacaagacc   300
gaattggtca acactctgag cgataaatcg attattaatg gaatcaatat tgatgaagat   360
gacgaggaaa taaagataca agtggacgat aaagacgaaa attccatata tctcatcttg   420
atagcaaaag ctttgaacca gtctaggttg gagttcaaac tggcgagaat tgagttatct   480
aaatattaca acacaaacct ataa                                          504
```

<210> SEQ ID NO 63
<211> LENGTH: 888
<212> TYPE: DNA
<213> ORGANISM: Saccharomyces pombe

<400> SEQUENCE: 63

```
atgagtgtat atcgtgataa catgtatatg aaatacgacc gaaacttcga aaatcgtgtc    60
gcccgaagaa tggacaggc gcgtaacgct agtcttgcta agactcttca cgattctggc    120
atagctgaac gtgcacgctc tccttcaggg tcagcgatcc cccatgctta tcgggttatg   180
aatggttctg gagcgaatga cacttcttta ccactgacct caaatcctgc ttatgttgct   240
ctaacgtcac gtatatcttc gagcaaaagt gaaaacaatc aacaattggc tgctaatgag   300
acggctggcg cacctgaagg cacggaggag accgttgaca tctccaattc tattagcgat   360
gaccatgcga atgccaaaaa tcttcccgct gcttcagtca aagctttggt tggggctggt   420
gtcttgtcgg atgaactttc agtaattgct tacgatatgt catttgagga tgaactcatc   480
caagacaaac agctcattga tcattccgtt tttgaccagt tgcttgagat ggatgatgat   540
gatgagcatg aatttagtaa gagtattgtt tggaattatt ttgagcaggc agagactacc   600
attgccgacc tccaaaaggc cctagaggct aaggatttga agaagctttc ctcgttgggg   660
catttcctta aaggatcttc agctgtattg ggccttacaa aaatgagaaa ggtttgtgaa   720
cgtatccaaa attacggatc tctacgcagt cgtgatggtg taatgaaatt accgagcgag   780
gaaattgcat tggatttgat tagcaaatct ctgtcggttg tgaacgactt ttataaggat   840
gctcgagctt acttacttga cttttatgaa aaaaattctt ctacataa                888
```

<210> SEQ ID NO 64
<211> LENGTH: 2139
<212> TYPE: DNA
<213> ORGANISM: Saccharomyces cerevisiae

<400> SEQUENCE: 64

| | | | | | |
|---|---|---|---|---|---|
| atgctcaatt | ctgcgttact | gtggaaggtt | tggctacgaa | tagacaactc | cactgatgaa | 60 |
| gtaaaccaac | caattgctgt | acagttcgat | gaaatagata | ctgttgatga | tttgaagagc | 120 |
| aggttttttc | agaaactgag | ttcgactcga | tggcgagaaa | ttaacgataa | tgcttccatt | 180 |
| gcaataggcc | tctacgcacc | taaatttgac | aatcaagccg | acaataccag | tagtaacaac | 240 |
| actaacgata | atagttgtcg | aagtaagagt | aacggtgctg | gaagtggcgc | caacctttcc | 300 |
| gttaatagca | ataccaagag | ttcagtgagc | cccacagcag | gatcatttgg | tctttcaaaa | 360 |
| gaccttgcaa | aggacaggaa | tgttctccag | catcctaaac | ctacgcagaa | aagaggagca | 420 |
| ttatacgacg | cctttgccgc | cgtgccgaca | gtggccgcga | ctaccaatgt | ggattttcct | 480 |
| cccaacgagg | cgccaatgct | aagcccgcaa | agaccatact | ctactagtcc | taaacagttt | 540 |
| ccagcaacaa | ctaaaagtcc | gttactgcga | tttgcctcag | tctcacccta | ccctaaattt | 600 |
| cattctgata | atcaaattat | ggcatcagct | ggtcttacat | acgtctcacc | gcataataaa | 660 |
| aataaataca | aaggccgtt | gattagaaaa | ggtttaaatt | ttaccacaga | atcagttaat | 720 |
| gattgcactt | ataaaatcat | ctttgaaccg | gatgaattgg | ctattaacat | atataaggaa | 780 |
| ctattcggaa | ccatgggttc | ccaacctgca | tcgcagcctt | tgctgatatt | ttcgaatgtt | 840 |
| aatttacgcc | aggatgtacc | gcctttagat | atcttaaatg | ttgtagacta | tgttcctacg | 900 |
| aatgaagaaa | tttcgcagca | gaaaactcaa | ccaacagacc | atggggccgt | tggtgttttt | 960 |
| catctagacg | accatatttc | tccgggcgaa | caaggtctta | agcaaacaat | tggtgataaa | 1020 |
| gcagatctta | aggtaaaga | tggcaatagc | agccctcagg | aatttaaatt | aataactgat | 1080 |
| gaagagcaat | tgagaagagc | gtcacaagaa | ctgaaggatg | aggaaaagga | tgccgagtct | 1140 |
| ccttggcaag | caatcttgct | gttaccaaaa | ggttataaag | gaggggtaga | ttttcgaaat | 1200 |
| aaaccagtgg | cccacacgga | ttcatctttc | aataatgaag | acacaattac | tcattcagag | 1260 |
| ttagaagtga | acaccggatc | cccttcgcaa | gaaagcggat | cacttaatga | agctggtata | 1320 |
| ggcataacgc | aacccatgtc | ggaagtacaa | agaagaaaag | aagacgttac | gcccgcatca | 1380 |
| ccaatattaa | caagtagtca | aacgccgcat | tactcaaact | cgctttataa | cgcacctttt | 1440 |
| gctgtttcct | ctccaccaga | tcctttacca | aacctttta | ccaccacaag | tgaaaaagtt | 1500 |
| ttccccaaaa | ttaatgtttt | aatagttgaa | gacaacgtca | tcaaccaagc | tatcttaggt | 1560 |
| tcctttctga | ggaaacacaa | aatctcatat | aaactggcta | aaaatggtca | agaagctgtt | 1620 |
| aatatttgga | aggaaggcgg | tcttcattta | atatttatgg | atttacagct | gcctgtcttg | 1680 |
| tctggtatag | aagctgccaa | gcagattagg | gacttcgaaa | acaaaatgg | cattggcatt | 1740 |
| caaaaaagtc | tcaataactc | acactccaat | cttgaaaaag | gtacttcaaa | gagattctct | 1800 |
| caggcgcccg | tgattattgt | agcattgacc | gcatctaact | ctcagatgga | taaaagaaaa | 1860 |
| gcacttcttt | ctggttgtaa | cgactacctg | actaaaccag | tgaatttaca | ctggcttagt | 1920 |
| aagaaaatta | cagagtgggg | atgtatgcaa | gccttgattg | attttgacag | ctggaagcag | 1980 |
| ggagaaagcc | ggatgaccga | cagtgttttg | gttaaatctc | cacagaaacc | tattgcacct | 2040 |
| tccaaccctc | actcattcaa | acaagcgaca | tctatgaccc | ctacacacag | cccagtaaga | 2100 |
| aaaaattcaa | acctctcgcc | cactcaaata | gaattgtga | | | 2139 |

<210> SEQ ID NO 65
<211> LENGTH: 1569
<212> TYPE: DNA
<213> ORGANISM: Saccharomyces pombe

<400> SEQUENCE: 65

| | | | | | |
|---|---|---|---|---|---|
| atgcgcattt | ggtttaaaaa | agttccagat | gggattactt | cctccgttat | attgtctgaa | 60 |
| gatcatctgg | ttgacgattt | aaaagatgcc | atcgctcgga | aattccctat | tcgtatcagt | 120 |
| cagtattatg | atgcacctga | gctttcgatt | cgtgtagtag | ctccaccaaa | tgcatcatcg | 180 |
| gagttgcaat | ctagagaact | cagtcccaac | gaaagcatat | tatttgtcat | ggaaacttat | 240 |
| tatcctcatg | gtcaggattt | taacgacgcg | cttctagtag | cgtcgccgga | tacctcagtt | 300 |
| gccttaagat | atcgctcttc | tcaactctca | tcctctacat | ttgaatcaac | acctcccgtt | 360 |
| ttttctgaat | acccacctaa | cataatccct | accccagcga | acgaaacagt | cccgcgtatc | 420 |
| aaacagccat | ccattgctct | tgattcactt | gagagcccgg | tttctgcccc | ttcacgacat | 480 |
| caaagtactt | attcttataa | aggaggtcct | ttaaattata | atttacgaaa | tgcatcccga | 540 |
| actaggtccc | atcaaactct | tccttcctct | aatgtaaata | aaactggcgt | actacttttg | 600 |
| cctcgttctt | ctagacagca | aacattggct | tcaagaccct | ctttaccaga | tctaacttca | 660 |
| gctgacaagt | cgcaaccatc | agacgaagcc | gaatccatta | ctagaaaaaa | ttctattgga | 720 |
| atgtcgactc | ggtctgatga | atcaacagct | gaaaaattgg | cgaaagccga | agtcgcgaca | 780 |
| cccactaata | gtagaagtat | tagtcattca | tcgctttata | cgaaacaatc | tggtaccgca | 840 |
| ggagtccttc | ccgcggttaa | tgctgatatt | gacgcagcaa | ataggatgaa | ccctgatatc | 900 |
| agttctcaat | ttcctatagc | agacaacaaa | gatcccttaa | atgctgatac | acaagcccat | 960 |
| ttaggatttc | cttctaatca | aatagatgga | attgttggta | cttcaccagt | caatgttcta | 1020 |
| acaagtcccg | gcataggtgc | gaaagcacct | tttgctagtc | tacttgaagg | agtgattcct | 1080 |
| ccaattaacg | ttttgattgt | tgaagataat | attattaatc | aaaaaatcct | agagactttt | 1140 |
| atgaagaagc | gcaatatttc | ctcggaggtt | gctaaagatg | gcttgaagc | actcgagaag | 1200 |
| tggaaaaaga | atcttttca | cttgattcta | atggacatcc | aacttccac | gatgtccggt | 1260 |
| attgaagtca | cccaagaaat | taggagactt | gagcggttaa | acgcaattgg | agttggtgct | 1320 |
| ccaaaattga | cacaaccgat | acctgaaaag | gatcagctaa | atgaaaacaa | atttcaatct | 1380 |
| cctgtgatta | tagtggcact | tactgcttct | agcctaatgg | ctgatcgaaa | cgaggcttta | 1440 |
| gctgctggtt | gcaatgattt | tcttacaaag | cctgtctctt | tagtttggct | agagaaaaaa | 1500 |
| attacggagt | ggggctgtat | gcaagcgctt | attgattgga | atggttggtg | ccgttttcgc | 1560 |
| ggtcgatga | | | | | 1569 |

<210> SEQ ID NO 66
<211> LENGTH: 2025
<212> TYPE: DNA
<213> ORGANISM: Candida albicans

<400> SEQUENCE: 66

| | | | | | |
|---|---|---|---|---|---|
| atgaattttc | tctataacaa | ttcagattat | agtagcacat | cacatactat | gaagtcacca | 60 |
| ctggcatata | atcagtttcc | taaactacag | gcaagcaatt | cgacagctgg | taacaataat | 120 |
| acagccacaa | cagcaacggc | agcagcggca | gcagcatcag | catcagcatc | agcatcagtt | 180 |
| acaccacaat | tgatatcacc | aacaacgttg | accacaccac | agaacaagta | taaacgtgga | 240 |

```
ggattggata atacgcttcc caaaatagaa actactagaa agaacagacc ggatgatggc    300
aattcaatca cgcccagcaa ttcgatcaat agtggtacaa caaagttaac cttaccacca    360
cgacgagttt gggttaagaa accgcaaaca aacaacccaa ccacggtact tgttatgtg     420 aatgatataa ttgatgattt aaaagtagca gtggtaacaa atatccaaa taccattggc     480 aggtacgagg atgctgccga tttgcttgtt aagatagatt tgaacaacat cagagtgcca    540
gtttccccca gtgttaatcg agtgtcgcaa agaactccat tgataattg tataattttg     600 gaaccagatc agaacgtttg gcaaatacta gacaattatt ttcctaatgg aatggccatg    660
cacgatgcct tgataattga gacaccaaca ttcaaaccag accatcaaat gctaacacca    720
ataacagcca atatgaacaa taatagtaac acttttatac cttttcaaga acgtcaatcg    780
agtatcggga caacaacaa caacaacagt aatgtaaaca caacaataa agcacaagca     840 gtcaaacacc cgcaaccaat gcaaccaaac aatactcgtg taggtttaca caagtcttat    900
gccatgaata ggtcgagttt cctgaccaat aacaaccctg tcccatctat catcaaggat    960
agatcggtgt caccatcaaa cttgggagtt tcaagaaact ctcctgtttc ccataaaaga   1020
tcatattcaa atccagtttc ttcaccaaat tctgttgcta cacaagctaa taatccgctg   1080
gcagttttac tattacccag gaatttctca ttagctaata ataatagtaa tcaagcactg   1140
caaagtagtg gtggaacacc tgccaaaaaa gttttatccg aggacggaag taaatcggtc   1200
aatgacaaga cagaagaagt tgtatcatcc aaattgaaac caaacgataa caataaaagc   1260
tatcaagcta aacagcaaga acaacaaact gccgaacagt ctgaaaatgg ctttagtgaa   1320
acttcagcat cgcctgaagc ggttcataat tctaaagcag caccattacc gttgaccaaa   1380
tcatcaacaa ctgctaccac aacctcttcc aactccatta gtaataacaa taatactagc   1440
agcaaaggaa agccaagtca atccaaatta aaagcagcta atgatccaac gccgacggat   1500
atagtgttac cgtctatttc tgtattggta gttgaagata tgccatcaa tcaagctatt    1560 ttgggagcat ttttacgtaa acgtaaaatt cattatcaaa ttgcaaaaaa tggccaagaa   1620
gcaatagata aatggaaaaa gggagggttt cacttggtat tgatggatat tcaattgcca   1680
gtgaaatcag ggattgaagc aactaaagaa atcagacact tggagaaatt gaacaggatt   1740
ggtgtatttc atgaaaacga aattgggaaa aatgtaataa ttaatgaaga agatagattg   1800
acttccaata cgtttagatc tccggtgatt atagttgctt taaccgccag ttcaaattct   1860
tctgtggata agactaatgc tttaacagca ggctgtaatg attatttaac caaaccagtc   1920
aatttagttt ggttacagaa taaaatcaca gagtgggggt gcatgcaagc attgattgat   1980
tttgacggat ggaaagataa gaatcgaaga ttaaacaaag cttga                   2025
```

<210> SEQ ID NO 67
<211> LENGTH: 1869
<212> TYPE: DNA
<213> ORGANISM: Saccharomyces cerevisiae

<400> SEQUENCE: 67

```
atgagctttt ccaccataaa tagcaacgtc aataaaacca ccggcgatag caataataac     60
accaccgaga acagttcgac tgcagacctt ttaggaatgg acttgttgca gagcgggcct    120
cgactgatga acacgatgca gccaaacaac tcttctgaca tgctgcacat taacaacaag    180
actaataacg ttcaacaacc agctggaaac acaaatatca gcagtgctaa tgcggagcca    240
aaggctccag caaatgagtt cgtaagaaaa ctgttcagga tactgaaaaa caatgaatat    300
cctgacattg taacttggac tgagaacggc aaaagtttcg tcgttttgga cacaggaaag    360
```

-continued

```
ttcactacgc atatattgcc taatcacttc aaacattcaa attttgcatc ttttgtaagg      420
caactaaaca agtatgactt tcacaaggtt aagagaagtc ccgaggaaag acagagatgt      480
aaatatggcg aacaaagttg ggagtttcag catccagaat ttagagtcca ttacggaaaa      540
ggtctcgata acatcaaaag gaaaattccg gcgcaaagga aagtgctttt ggatgaatct      600
caaaaggctc ttttgcattt caatagtgaa ggcactaacc ccaacaatcc ttctgggtct      660
cttttgaatg aatccaccac agagctgttg ttaagcaata ccgtaagtaa agatgcattt      720
ggaaatctaa gaaggcgagt agacaaacta caaaaggagt tggatatgtc caaaatggag      780
agttatgcta ctaaagtaga actacaaaag ttgaactcga aatacaatac ggttatcgaa      840
agtttgataa cattcaagac cataaatgaa aatttactca acaacttcaa cactctgtgt      900
tccactttgg caaataatgg tattgaagtg ccaatatttg cgacaatgg  aaaccgtaac      960 ccaactggta ataccaaccc agcaacaaca acagctatcc aaagcaacaa caacaccaac    1020
aatgcttctc cggcaacatc tacagtttcc ttacaactac ctaatttacc cgatcagaat    1080
agcctaacac caaatgctca aaataacaca gtcacgctac gaaaaggttt ccatgtactg    1140
ttggtggaag atgacgcagt gtctatacag ttgtgttcaa aattttttacg gaaatatggc    1200 tgtactgtcc aagttgtcag cgacggtctt tcagctatct caacactaga gaagtatagg    1260
tatgatttgg ttttaatgga cattgttatg ccaaacctag atggtgccac agcgacatcc    1320
attgtcagaa gttttgataa tgagactccc atcattgcca tgacaggtaa cattatgaat    1380
caagacttga tcacatactt acaacatgga atgaatgata tcttggccaa accattcacg    1440
agggatgatt tacactcaat tttaatacgt tatctaaagg accgtattcc tttatgcgaa    1500
cagcaattac cacctcgcaa ctcttcgcca caaactcatt ccaacaccaa tactgctaat    1560
tcgaatccta atacgattaa tgaacagtcg ttagccatgt taccacaaga taatccgtca    1620
actactaccc ctgttacccc aggtgcctct atatcttctg cacagcatgt tcaacaaggt    1680
caacaagaac agcagcatca aatttttccat gctcagcagc agcagcagca tcacaacgcc    1740
attgctaatg ctaggtcaga cgtagccata ccgaatttgg aacatgaaat caacactgta    1800
ccacattcct caatgggttc cactccgcaa ttaccacaat ctacacttca agaaaaccag    1860
ctatcataa                                                               1869
```

<210> SEQ ID NO 68
<211> LENGTH: 2669
<212> TYPE: DNA
<213> ORGANISM: Saccharomyces pombe

<400> SEQUENCE: 68

```
atgccgtctt cgaacggatc ctccgacttt gtatgttggt tcctttttcc gatgaatttt       60
ttataattat aaaatttcac gtttcgtgat aaaactatgt tttctcatac taacgttgtt      120
gaattaggtg cgaaaactct tcaacatgtt ggaagaaccc gaatataggc atatcctgcg      180
ctggagcgat tctggggatt cttttattgt gttggatgta agaaatcctt gaaaatttgt      240
ttgctggatg taaagagag  aagaaaggaa gaatgagtta tcattatatt tatcgccgcc      300
attgttgtta tttaaccaga gaaagcattc tactttatt  gttatcctc gaaaagctag      360 taaaagaggg gagatttttt ttgaaggttt gctaaaaaat aatttttttta ctattcttga      420 tttgtttcct ttttctttct gattacaact tgaattaaaa aggattgaca atgatgggaa      480
aggaatcttt tgaggcagca agagattcct atcgcaacaa tcgggttgtt ttattacaaa      540
```

| aatcgctttt cttttgaaa taaaacaatt ctattcgttg ttttcttttt agtattacca | 600 |
| atgttacgct gaaaaacgtc cagtttgccc gtaaacctga gtcgtcgaat ttgctttgtt | 660 |
| tccataccct agtactttgt cctttttttt cgcattgcat ctcgattttt tcgaacagac | 720 |
| ttattccttg tcatcatctt ttttgagtaa tagtttttac atctcttaga gaccaatttt | 780 |
| atttttaggc cttaccttct ttttaaactt tggcttttga ctagctattc ttctagtctt | 840 |
| atgttttttt ttctcttacg tttgcatttt tctcctttct ttgtcactct aatctacttt | 900 |
| tccgcattca aaattccttt ttccccttc ccctttgttt ccctgagttt atcactaact | 960 |
| tactgctttt tagaccaacg agtttacaaa gaccattctg cctcgccact tcaaacatag | 1020 |
| taactttgca agttttgtcc gacaactcaa caagtatgag atatttttat ttatttattt | 1080 |
| ttttttaca cttgctaatc gtctagatat gattttcaca aagtacggca cgaagaaggc | 1140 |
| gcgccgagta tatatggtga aggggtatgt catatgggtt aaggatttag gggcttcata | 1200 |
| cttgttgaat aggtttgaga acaaacttg tcttcattcc atcatacttg taaaaaagcc | 1260 |
| atccctcctt ttagaatttc tattatacta atcattctct tctttaggct tgggagtttc | 1320 |
| gtcatgacga ctttcagctt catcataagg acctgctcga caatattaag cgaaaggctc | 1380 |
| cgtccaagcg caatttagct aacgagaaca ctgctccagt tattgaaaac ctaaaacagc | 1440 |
| aggtggattc tatattagac tttcaaaaat tacttgatag aaatctttcg ggtcttgcca | 1500 |
| caagttacca aacgatactt cttaaaatgt ttgaactcaa gcggggggatt gagtctagag | 1560 |
| atttgcttat gagtagcatc atatcttacc tctgcgattt agagggatct actcaacggc | 1620 |
| aagctaatcc cggagccatg tttgttccct ctcatcctct ccaggagtta ttaaatgcat | 1680 |
| accaagcgtt agcgaagggc caagttgcaa ctacttctcc acaacagata ccaaatcaaa | 1740 |
| ttcaacaggc ttccgctgct actaccgctt cttcaaagat gactgttgac accaatcttg | 1800 |
| gcacagcaca accttctttg tataatactc cttcatctga ttatgaactg gcaaatcagg | 1860 |
| aaaagccggc agactccatg gcctctgccg cctctctaaa tacccctta tcatctaatg | 1920 |
| accattcttt gaatccacac gcccatggct catatccgat gtacgaaaaa tttcaaccga | 1980 |
| ttcagcatcc aaatccagga agctttacca cccatcttga ctccaatgct tccatggcaa | 2040 |
| agtcattttc tcaaatttca aacgattccc ttgccaaagc tagttcagta gcaacgtcca | 2100 |
| tgtctcaaat gggcgctgct gttccaacta ctggcttgtg gaagcggcaa ccaaggattt | 2160 |
| tacttgtcga agatgatgaa cttttctcgta gaatgactat caaatttttta acttcatttg | 2220 |
| attgccaggt cgatgtagct gtcgatgaa ttggtgccgt aaataaagct aatgctggtg | 2280 |
| gattcgatct catcttaatg gactttatac ttcctaattt ggatggactg tctgtaacct | 2340 |
| gtttaattcg tcaatacgat cataacacac cgattttggc tataacttca aatatatcga | 2400 |
| tgaatgatgc agttacctac tttaatcatg gtgtaacaga tctattagtt aagccattta | 2460 |
| caaagttgac tctacttcaa cttttaaaaa agcaacttt gaatcttta caagcggata | 2520 |
| actcaattaa tatgtctgat gttccctcca cgaaagaagc taaagacgat aaggctcctg | 2580 |
| tgacatttta cttagagaat gatgctccta tgtatcctca acagatgtta caggatccca | 2640 |
| ttcaagcaga cttacagcat ccacattga | 2669 |

<210> SEQ ID NO 69
<211> LENGTH: 1680
<212> TYPE: DNA
<213> ORGANISM: Candida albicans

<400> SEQUENCE: 69

```
atgtcttcat tacaacaacc catacccca aactcaacac ttgcgacaac ggcgagctcc      60
aaccaaagtg gctctaatga tttttgtcaag aaattgtttc taatgctaca agaagatagc    120
tataaagaag ttgtacgatg gactgtcaaa ggtgatagtt ttgtggtgat taacaccaac    180
gagtttacca agatatact accaaaacat ttcaagcact caaactttgc cagttttgta    240
cgtcagttga acaagtatga tttccataaa gtaaagatct caaacgaagc aaaggctagc   300
tacccgtatg gagaagatgc ttgggagttc aaacaccctg aatttaggat aaacgacgcc  360
gaggcattgg aaaatattaa aaggaaagga ccaacagcga aaaagtctgc ttcaaatgtt   420
acaatcaaga cagaagcaaa caataatgga acacagccta catgcaatca caattactcc   480
cagcttgttt ccgctacaaa tcatttaaag gagcaagttg aaagtctaaa gaacgataaa   540
catagcttgt atcaagagat cagtgtgttg aaagaaaat acaagacggt ggttgaaaat   600
attgttgcaa taaatacatt caacgaaagg tattaccgtt caatgaacgt attgataaat   660
tctatagtgc aaaatggaat gaagttgcct ccattggatt tcccgcctcc agtgcaacta   720
ggtcctgatt ctgggatagg tagtaattta ggtccaatat catcagatac agcattacct   780
agcatatctc atcatcttct gtcacctttg ccacatcatc aacaattatt gaatcgaacc   840
atacgtccaa tatcgagtcc tattgacgga ataccttttgg tcaagcttca acaacagtca   900
cttggacaga atcttcaggc accgattgga acaccatcag cagtcccttt ctctgaagaa   960
gcatcttcaa gtattcaagc cgcgaccccca gcaccattgg cgcaaccagt tgctcaaccg  1020
atcaaccagc cgccgccgcc accaccacca ccagcaacac agcagcaacc actaccacca  1080
ccgccgccac cagcaacagc tacatcccaa attcctagtg cacctccacc tccgacacaa  1140
caacaagtgg ggacaagttc ttcgagtgtt cctacgatat caccgaaatc tcaagggatc  1200
gttgttagca attctgcatc acctaccaca tcagctcaga tcagtacaac tagtgtaccc  1260
aatccaaagt ttcatgtttt actagtggaa gatgataatg tttgtattca attgtgtcgc  1320
aaaattcctg taaagtatgg atgtctggtt actgttgtga ccgatggttt gaacgctata  1380
tcgacagttg agcacacgaa atatgatttg gttttaatgg atattgttat gccaaaccta  1440
gacggggcaa cggccacaag tgtgattcgt tctttcgata caaaaacccc aatcattgcc   1500
atgacaggaa acattgagga taacgattttg gtgacatatt tgcagaatgg tatgtcggat  1560
attttggcca agccatttac aaaagatgat ttatatgcaa tattgtcgaa gcatttatta  1620
gatcctaaag aaaataagca agataatgaa cctacggtaa agaaacagaa attgagttaa  1680
```

<210> SEQ ID NO 70
<211> LENGTH: 5313
<212> TYPE: DNA
<213> ORGANISM: Saccharomyces cerevisiae

<400> SEQUENCE: 70

```
atgttcaata gaagtaacac cgcaggcgga tctcaggcta tgaaagaggg acttggcata      60
aacaagctct ccccgatatc atcgaattcg aacccaagct cattgacttc ctccaattat    120
gaaaaatatc tgcagctggc cacagagaag aatccgtgta tgatcttgga gctggaactg   180
gacggcaagg tgcgatatgg ctctccacag tggaacacga tcacaggagt cgccgatgat  240
agtggctctt ctccgacgta cattgcagac cttattctcg gatccgatca agataaaggt  300
gtctttcaaa aggccacaga catgctgctc atgaatgatg acaccagttg cactataacg  360
ttcaagataa aggcagccga ctatgaaggt agcgcaggct gtgacgatga aagtacgata  420
```

```
acgaccttgg aagcacgtgg tatcttaatc agggatggcc acacacagtt gccctctcac    480
acgatgtgga tagtcaagcc tcgcacaaac gactggtcag acttttatgc caacgaagac    540
gctcaagacg acatggtcat ccagttatcc gataattgcg acgatatcga tatccaactt    600
cccgaagagt tcgccaagac gcttgggttc ggcgctaaga tcttcgtgca gtacttgaag    660
agaatacgac tggaaatgat aatagacgag ttcaatctac ctctgccaaa aatggaacta    720
tgccgggtct gtgagaactt tgtccctgtt tggtggttgg agacccattc gcaaagttgc    780
gtttgcgagc atagaacgga atcgctcata caattactac acgataatct tcttgagcaa    840
caggcgatct tggcaaactt cacgaaagat tcagagtata agggcagtca gatacaggta    900
cgttccaaca acttccttaa ccaagtttta gactccttaa gagagctgtg tcaggacgcc    960
atagatatca acccgagtga aatggttcct gatctttacc acagtctttc aacatttcct   1020
caagataatg gtaataataa caataataat aataataata ataataataa caatgctttg   1080
ttagatcaat tccctatcca aaaagataca gttagcttga attcatattt tcagttttcc   1140
ccaaggacta accacaacat tcaaaacgtc acgtcgtggc aatcaagatt ttttctcaat   1200
gatgatcagg atcctggact agctcttttg attcacgata ctctggactt ggcaaggaaa   1260
aaagtggatg ccgtgttgag gttggataac gcaatgacct attctttaaa gattaaaaac   1320
gaggtcaaca actatgtggt acaactgatc cgcgagcaaa ttgaaataaa taagcatgca   1380
atcctaactc acccaatgaa tttaaggtct tcttccatat ttcattcccc actgccgcaa   1440
attcactctc aacaaccaga agccgagaat ctcatatatt cctcctctac tcccctgcaa   1500
gtccaacacg accaatgtgc gtcctttgaa gcaccctcca gtctcatct ggagcctatt    1560
ccttttcccgg tttcttccat tgaagaaaca ccaactgcaa atgatatcag gcatccttct   1620
cctttgcccc gtagttgtag caacaccgtt atgaaactac cgacacctcg aaggaaactt   1680
gactcaaacg gattattctc tgatgcctat ttaaacgctg acatcattcc gaacccaagt   1740
atcgaatcca cgatatctat tgatagagat aataacacta atagtagggg tagtagtatg   1800
aaacagtatg gtattggtga agccaccgac tctcggacta gtaactcgga aagaccttct   1860
tcctcttcgt caaggctggg gataagatca agatccataa caccaagaca aaagatagaa   1920
tactcacatg tagataatga tgaccgcacc aacgaaatgc tgtctagaga taaagattct   1980
cttcaacctc aaccttccgt agataccacc ataacatcct ctactcaggc gaccaccacg   2040
ggtaccaaga ctaatagtaa caattccaca aactcagtat taccaaaact aatgacaagt   2100
atttccttga ccccaaggcg tggttcacca tcatttggta atctcgcaag ccattctatg   2160
cagcagacaa acagttttaa actgattcat gataaatcgc cgatatcttc acctttcaca   2220
ttctccaagg atttttttaac cccagagcag caccccttcca atattgccag aacagatagt   2280
atcaataatg caatgttaac ttcaccgaat atgccattat caccccttt attggccaca    2340
aaccaaactg ttaaatctcc aacgcctagc ataaaagatt acgatatctt gaaaccaatc   2400
agcaaaggtg cttatggtag tgtttatcta gcacggaaaa aactcacagg agattatttt   2460
gctataaagg ttctaaggaa atcagatatg attgccaaaa atcaagtaac aaatgtcaaa   2520
tccgagagag caatcatgat ggttcaaagt gataagccct atgttgcgag actatttgct   2580
agtttccaaa ataaagataa cctttttctta gtgatggaat atttaccagg tggagatttg   2640
gccactttaa tcaagatgat ggggtatctg cccgatcaat gggccaagca atacctaacc   2700
gaaatcgttg tcggtgtgaa tgatatgcat caaaatggga tcattcatca tgacttaaag   2760
cctgaaaatc tactaattga taatgcaggt catgtgaaat taacagattt cggtttatca   2820
```

```
agagctggtc tgattcgccg tcacaagttt gtcccacata agtcgtcgct aagtatcagt   2880
tccactttac caatcgataa cccagcaaat aattttacca tgaacaacaa caatagtaat   2940
cattctcaat tatcaacccc agatagcttc acatcagatc ataagcagta taatagaagc   3000
aagaagtcat cactaggtca gcaatacgaa cactcagaat actcaagtac ttccaattcc   3060
cactcaatga cgccaacgcc cagtacgaac actgttgttt atccttcata ttaccgtggg   3120
aaggacagat cacacggaag ttcgaacatc gatctcccag cgtcccttag aagaagtgaa   3180
tctcaattat catttccct ccttgatatt tctcgttcta gtactcctcc tttagcaaat    3240
cccacaaatt cgaacgctaa taatattatg agaaggaaat cactcactga gaataaatcc   3300
ttttctaatg acctattatc ttcagatgct atcgcagcta ccaatacgaa tattaactcg   3360
aataataaca tttccctttc gccagcacct tcggatttag ctttgtttta tcctgatgat   3420
agcaagcaaa ataagaaatt ttttgggact cccgattatc tcgctccaga aactattgaa   3480
ggaaagggtg aagataacaa gcaatgcgac tggtggtcag ttggttgtat attttttcgaa  3540 ttacttttag ggtatcctcc attccatgca gaaacaccag atgctgtttt taagaaaatt   3600
ctatcaggag tcattcaatg gccagagttt aaaaatgaag aagaagagcg agaattccta   3660
acaccagagg caaaagattt gatagaaaaa ttgttggttg tggatcctgc gaaaagactg   3720
ggtgcgaaag gaattcaaga aattaaagat caccttatt tcaagaatgt ggattgggat    3780
catgtttacg atgaggaagc ttcttttgtc cctacaatag acaatccaga agatactgat   3840
tattttgacc taaggggtgc agagctccaa gattttggag acgatatcga aaacgataat   3900
gccaatattt tgtttggtaa acatggcatt aacaccgatg tttctgaatt atctgcagct   3960
aatctctctc caccattgaa tcataaaaat attttatccc gtaaactatc gatgagtaac   4020
accactaata ggagctcaaa taattccaac agtagcgtgc atgactttgg tgcacataca   4080
ccggttaata aattaagtat tgcttctgta ttagagtcag tacctcaaga aacaggatat   4140 attcaccta acgggaccgg tacaactact acaagtgcca aaaactcacc caatctgaag   4200
aatttgtcac tggctatacc tccacatatg agggatcgca gatcaagtaa attgaatgat   4260
tcacaaacgg aatttggttc ttttaatttc aggaattat cggctcttga taagctaat    4320 aaagatgcta taaatagact gaaaagtgaa cattttttctg aacaacctgg ggttcacaga   4380
agaacctctt ctgcgtcact aatggggtca tcctcagacg gatcagtgtc aactccaggg   4440
agtaacgctt caaacactac atctggtggc aagttgaaaa tacataagcc taccatatcc   4500
ggttctcctt caacatttgg cacatttccc aaaacatttt tgaggtctga ttcattctcc   4560
acaagatcat attctcctga acgaagtatt agtatcgact cgtcaacatt atcaaggaag   4620
ggtagtataa tcggggataa ccaacaaaca acagcaaata gctcggattc acctacgatg   4680
actaaattca gtcgccact atcacctgct aataccacca ccgtgagctc atatttttca    4740
agacagaggt ttctatcaaa gagttttttcg caacggacca attccagtga tctctcggca   4800
gaggaaagcg accgactaca ggctatatca agagttaact ctttaagaaa caggaggcgt   4860
agtggccgaa agagctcgag cacttctgag attggatacc acatggatgt tcttgtttgt   4920
gagcctatac cgattcatag atatcgggtt actaaagact tagaaaattt gggctgtacc   4980
gtcgtcagtg ttggtgccgg tgatgaacta gttagtagag ccactagtgg tgtaagtttt   5040
gacttaatta tgcagccctt gaagcttcca aaacttggtg ctattgacat tgttcaacta   5100
ctaaagcaaa caaatggtgc taattcgaca acaccaattg tggccataac aaattatttt   5160
```

| | |
|---|---|
| caggaggcgg caaccagtag agtctttgac gatgttttag aaaaaccggt aaaacttgac | 5220 |
| gagctaaaaa aattggtggc taagtacgca ctgaaaaagt ctcaagaaga tgaagagcat | 5280 |
| actatattga gcgattctga tgaaacgcac tga | 5313 |

```
<210> SEQ ID NO 71
<211> LENGTH: 4017
<212> TYPE: DNA
<213> ORGANISM: Saccharomyces pombe

<400> SEQUENCE: 71
```

| | |
|---|---|
| atgaagcata taaaaaacga acgcgaagaa gtcttcttgg aagatgacca agctcaacat | 60 |
| tcccaggcag agcttctcag ctcaaaagat gagaaccttc aaccttccat tcctttatct | 120 |
| cccgttgcat tcgagcttga cttttccgga aactttcaat ttattagcga taactcatcc | 180 |
| gaacttttgg atatacccaa agacaagatc attgggcatt ctgtagcaga agtccttggt | 240 |
| accgatggat acaatgcgtt tatgagagcc gttaactgtc ttttgaagga tgactctcat | 300 |
| agctatcatg ttcggttcca acattcaatt aacgctaatc atgccaatca aaactattac | 360 |
| accgctaaag gagatcttcc aagcgatgaa aaaattacaa aaccttttga tgctattgga | 420 |
| attctcattc gtcatcctgg gtccgcaatt cccgcacaca cgatgtgggt tgtgaaccca | 480 |
| gctaccaatt cccttggtag tgtatctcct cttgtaacta aattattgga tgtcatcggt | 540 |
| ttcggtgcca gtcttttaga caaatattta tgcgacttaa ggacttccta tcacaagcat | 600 |
| aacagcttag atgcgttacc acttccgacc ccagagtttt gccaaatatg tgaacgtgaa | 660 |
| atacaatcat ggttttctga gttgcactcc aagttttgtc ttagcacaag cacctatgaa | 720 |
| tctgttgtac aggctgctca ggattccttg ctttatttcc ggagtacctt actggaaatt | 780 |
| caggaaggaa tgcagaaaga ttcaagtctt gttcccgtat acaaaaatga accgcttatt | 840 |
| gttgatgcgg atgattattt ttttaccgat gagaataaac aaacattatc actatgttca | 900 |
| ttcttaagtc aggttatgta ctacttggaa gtggctatcg acattactat tcctccagtg | 960 |
| aaaatcattg tgaattttga taaagtggat tctcttcgtg ttcagtctcc gcggtcagaa | 1020 |
| aaagctacta tcgagcttga taattataac ccgtccttag aaaattgctc atccgcagtg | 1080 |
| attgctctct gggaggacat aaagacagca gttgatacta aaattactgg agttttgcgt | 1140 |
| cttcgaaatg caatctatta ctctgaacgt attcgtttgg aaattgacca tcatgttcaa | 1200 |
| gaaattattg atgatgtcgt atcgaatttg gtaacaaatc attcctctac ttctttagga | 1260 |
| cacttggaat ctaaattagc gccttcaatt acctttcctg atgcctgcga tgcactcgag | 1320 |
| gcagaggaat gcattactcg acccgggagc gctacaaata caccacaatc tgatagaagc | 1380 |
| cttgatatca atgatctttc aagatcctct tcttattcaa ggcatcttag ccatgtttct | 1440 |
| cttagtaatc cagattttgc aattggttcg cctatgagtc aagatagttc aaattattct | 1500 |
| tctccgttac atagaagaaa agcatctgat tccaatttct ccgatcctcg ttttgatgat | 1560 |
| ttaaagtatc tttctccaaa ttcgagtcca agatttgtgg cttctgatgg tccgaatcgc | 1620 |
| ccagcatcta acggtcgttc gtctttgttt tctcgtggaa gggccagcaa ccttggagat | 1680 |
| gtgggactac gtctaccatc accatcaccct cgtatacata cgattgtacc caactctgcc | 1740 |
| cctgagcatc cttctatcaa tgactacaaa atattgaagc cgattagcaa aggtgcgttt | 1800 |
| ggctctgtgt atctggctca gaaaagaact actggtgatt attttgctat taaaatatta | 1860 |
| aaaaaatcga atatgatagc aaagaatcaa gttatcaatg ttagagctga acgtgctatt | 1920 |
| ctcatgtctc aaggcgaatc accatttgtt gccaagttgt attacaccctt tcaatcaaaa | 1980 |

```
gactaccttt atttagttat ggaatatctt aacggcggag actgtggttc acttctgaaa    2040
accatgggtg tattagattt ggattggatt cgaacttata tagctgaaac tgttctttgt    2100
ctaggtgatc ttcatgatcg tggaataatt catcgtgata tcaaacctga aaacctactc    2160
atatcacaga acggacattt aaagctcaca gatttcggtt tgagtcgggt cggttatatg    2220
aaaagacaca ggagaaaaca gagttcttca attcctgtac ttgacttgag agatcgctct    2280
agtgctatat ctgatttatc acttagtact gcttcatcgg tactagaagc acagtctttg    2340
ataacaccag agcgtcccaa acggccttca ttaaatgaaa agcttctttc tttagatggt    2400
actagtattc gacttgctgg acaaagtttc aattacgaga cagcgctga ggattctccc     2460 actgcaacaa atactcctac ttctcaggta gacgaatcca acattttccg tagcacagat    2520
tcgcctcgag ttcaaccgtt ttttgaaaat aaagatccct ctaagcgatt tattggtaca    2580
cctgattata tagcacccga agttatcctt ggaaatcctg gtattaaagc gagtgattgg    2640
tggtccttgg gttgcgttgt ttttgagttt ttatttggat accccccgtt taacgcggaa    2700
acgcctgacc aagtctttca aaatattctt gctaggcgca tcaattggcc tgccgaagtt    2760
tttactgctg aaagtagtgt tgctttggat ttgattgatc gccttctatg tatgaatccg    2820
gcaaataggc ttggtgccaa cggagtagag gagataaaag cacatccttt tttcaagtct    2880
gttaactggg atactatctt agaagaggac cctccatttg taccaaaacc tttttctcct    2940
gaagacactg tgtattttga ttctagggga cttaaaggat ttgatttcag tgaatattac    3000
aatcaaccta cggtgacaga agcacaaaaa ttggaagaag aaagacctgc atcctctata    3060
ccccagcatg tgtctggtaa tcgtaaaggt cgtttacgaa gcaatacgat tagtactcct    3120
gaatttggaa gttttacata tcgaaacttg gattttctta ataaagctaa ccggaatact    3180
attcaaaaac ttagaaagga gcatatggct gttaaatcag caaagacttc tgttgatgac    3240
acctttagtc agtacatgag taggtttaaa gccaaacttt caacttctca aagtgtaggt    3300
cctgttaagt cttcgcgtcg agcttcaatg gctgactatg aggcatccac cacgacaaga    3360
gtgcaagata ttactacaga ttcaattgat tcaattgatg attttgattc tctgaaagaa    3420
ggtcggatgc tttcattttt tgataattta gcgttagaag atcataaggg tgtttcaagc    3480
actatgtcag catcacaatc gcaatcaagc atgcacacgg cgttaccaga cgttacagag    3540
ggtacctcat cagatgaaca tactacaatt cagaagggca ggattgacaa cttacaagct    3600
cagagtttaa ctcataagcg aaatgccatt tcttatccag ggttatttca gcttgaccgt    3660
ttacaaatga taattcctaa ggatgaaatt gaacttgcgg agatcttgaa aaaaattttt    3720
ccaaagttaa cgcttgttct aatagatgat ccatggagca ttcttaagaa gcttttgcag    3780
aacgagcaat taacgtcgt attcttacat tttggaaatg ataaagtatc ttcttcccga    3840
ttaatgtatt cagtgcgaac cagtgctact ataaattcaa gggtgccgtt tgtatacatt    3900
tgcgaggacg agacttgcat tccgactgat ttacaatctg atggagtttt gttgaaaccc    3960
attacttgtg agaacattga aagctgtcta cgaaagttag atgtttggca ctcttga      4017
```

<210> SEQ ID NO 72
<211> LENGTH: 5772
<212> TYPE: DNA
<213> ORGANISM: Candida albicans

<400> SEQUENCE: 72

```
atgtcgaata ctcccaataa atcaacacct gaacctgaaa gtactgtctt tcacggatcg     60
```

| | |
|---|---|
| atatttgaac atcctcattt gcatcatagt gtatcagaga ggtcaatatc accacgccac | 120 |
| gtatcaaaag aaagtcaaaa ccacaaccac aaccaccaac aacaacaaca agcatctaac | 180 |
| agtctcaact tctcagatca agtatcagga tatgattatc catcggcaac tattgaagaa | 240 |
| caaatagatt tacgactcgc gtcgtctaat aatcctacta ttgttatgga attagacttg | 300 |
| gatggaaata tccgttattt aagtaaaaat tgggaatata ttgttggaac aaatatcaag | 360 |
| aaaattgtta atcgacacat ttcgaaaatt ataattggta ataatgatga tgattctcaa | 420 |
| gtatttaaca ttgctataga tgccatgact cgagaagata ttagttataa agtgaaattt | 480 |
| ataactgcta caaatcatac tcaaagaaat aaagatggtg aagaagtcta taatgattta | 540 |
| aatgatttat tattaagtcg gtctcacgat gatgaacaat cagggatttt aactcctcat | 600 |
| aattctatgg aagatatggc taaaaacgat aatatacctg taaataatta ttttgaaaaa | 660 |
| caacaacaac aacagcagca gcagcaacag cagcaacagc aacatttaga actgtcacaa | 720 |
| caagaacctg aaaaaattga cacttctgat acttctagta ctttatcatc agaaatatct | 780 |
| aatgatggag aaattatcga attggaagca caaggtatat taattcatga tgccaaaaca | 840 |
| aaattaccaa cccattcaat gtggactata agacctttta aagagattga tttagaattg | 900 |
| acattaccta ttgctttaat cgatttatta gggtttggat cagaaatatt tgaaggatat | 960 |
| ttggttagtc ttaaaaattt agggataatc gatgaagaaa gtgttccaca accgaaaatg | 1020 |
| atcttgtgca gaatttgtga aaccaatata cctgcttggt ttatcgaaaa acattctgac | 1080 |
| ttatgtgttt tggaacatag ggccgctgag aaattacaac aatatcatga tgctattggt | 1140 |
| gaacaaaaag aattggtgat tcgtatatcg gaaagtttag ctgtttccaa tcaactgctt | 1200 |
| ccattattgt cgtcatcact gggaggttct tgttctggat tgaatactcc accaccacaa | 1260 |
| ttattgacaa atcaatcact tttagcatct tcagcatctt tagtatcatc ggcttcatct | 1320 |
| agttcatctg aaggagaaag ttcaagtctg tcttcacatt taatttttaga atataagggg | 1380 |
| ttaccattac caaatatgtc agattatcca tcaccaaaat tggctaataa aatattgacg | 1440 |
| aaaaatttcc aatcgaaaaa caaacatgca ttaatgtttt ctaaaaaatt cccgtttgga | 1500 |
| atttttacaaa gaatagtaga attatgtgat gaggcattat tagtaaatcc tccttcaaca | 1560 |
| aatgaagaca atattttagc attttctcct gggtccgaaa aggcattgaa tgttgtcatg | 1620 |
| agttcaagct ttttgaaaac ttctgatgtg gcaattaaac aattaattga agatactcaa | 1680 |
| gaattgatta atgataaaat ggaaacttta tcgagattag tttcaatttt acaatttctg | 1740 |
| gagaaaatca aacatgaagt agatactttg gtgttatgta cagttcgaga aactgttgaa | 1800 |
| aaaatcaaga atcaaactat tttggaatca agagaatgta caccaattaa taatgatagt | 1860 |
| ctgataagta ttaatgaaga agtggtgccg tcaaggttag aaacttcaaa catcaaagac | 1920 |
| caacaacaga cacaaattga agaaccacca ccaccacaac aacaccaac acaaaatata | 1980 |
| caagacaatt accaggagca acctatttct gaaacactta atttgacaac aacaacaaca | 2040 |
| acagcatcaa ctttacaagc gccaaagcct cacaagagta ttagtccaat tatttctgat | 2100 |
| ttgcttacac ctggtgaaaa tgtaataact cctaaagata tactattgaa agaatctaaa | 2160 |
| tcatacaata cctcaatgtc agcttcacct ttgaatcggt ctggttctag tttatgtacc | 2220 |
| ccaagaccac aatcaatggt agcaccagtt tcaacttcta actcttcaag agatttatta | 2280 |
| gaatcgattc aagtattaga tttatcgaaa cgatcatcag aaaacaattc ccaatattca | 2340 |
| tcaccaagac gtcattatc tccagcacca ccaccatacg ttgagaaatc caattttaaca | 2400 |
| acattacaga aaaatactgc tgccacacca attgcatcac catcattaac aactatggaa | 2460 |

```
gatattaatg catctgctac tactactact actactaaca ttggtggtta tggaggacta   2520
ggggataaaa aaatcactca tttgtcattg aatacacaag tgccgagtca accatcatcg   2580
gcaatgagtt ctagtgtaaa gagtgcaact atacgaccac cattatcacc attattagta   2640
tctacacaac aaccacaacc tcgattaagt actggcggca ttcgagatta tcaagtgatt   2700
aaacctatta gtaaaggggc atttggatca gttttttag gtaaacggaa attgacaggt   2760
gattatgtgg cgattaaatg tttgaaaaaa agagatatga ttgctaaaaa tcaagtttta   2820
aatgttaaat ctgaacgagc agtaatgatg agacaatctg attcacctta tgttgctcaa   2880
ttatatagta gtttccaatc gcgagattat ttatatttag tgatggaata tttaaatgga   2940
ggagattgtg caaatttgct aaaacgttg ggtgtcattg gagtcgattg gacaccaaga   3000
tatattgctg aaataattgt gggtgttgat gatttacaca atagaggaat tattcatcga   3060
gatttgaaac cagataatat tttaattgat aaaaatggac atttgaaatt gactgatttt   3120
ggtttatctc gattaggtgt tgttggaaga caacaaacac aacaacatcg taaaagcagt   3180
accaatgaac aaggtattga attatttaga agtatgttac tggaagaatc aaatcaaaag   3240
aaagttaatc ctgggatagg tactccattt tcattatcac caagtttaga acaatcaaga   3300
gtgtctttta atagtcagca acaacaacaa caacaacaac aaatgggagt acctgctggt   3360
aatgccccat cagtgtcttc attagcagca ggtgaaaatt ttgttttatc tagtacatct   3420
ccaactttgg cttatttaga aagttttaat tcactttcat cagtatcaac tcctacgggt   3480
gccacacaac aacaacaaca acagcaacca ccgccaaaac cttttgttaa atcatccaat   3540
ggaagatctg gttcaagtgg atttgattca ccaatattaa aaccaataat tccaagaaca   3600
gaatcagaat catcatttgc cattatggat gatgaaccta gtcctggacc tacaactgat   3660
tatgcattat ataatcccga taattataaa aatgagggtg ctacagcaac aacagcaaca   3720
gcagcaacag caggaactgg aggtggagga gatgtcaatg ctggtgatgg cggcggtgct   3780
aatattaaaa agtttgttgg tacacctgat tatttggcac cagaaatcat taaaggatca   3840
ggagaaaatg aatcatctga ttggttttct gttggagtta taatgtttga atttctttat   3900
ggatatccgc catttcatgc tgatactccg gaaaaagttt tcaataatat tttactgggg   3960
aaaattgatt ggccagaatt aacacctgaa gaagatatga aattttgtcc acctgatgct   4020
aaagatttaa ttaataaatt attagtaatg aatcctgaag aaagattagg atttaatgga   4080
gctgatgaaa ttaaaaatca tccctatttt aaaaatattc attgggatac attatttgaa   4140
gaaccagctc catttacacc aatgttagat gatccagaac tgactgatta ttttgattca   4200
agaggagcaa tgatgactca atttcctaaa gaagaggacc tgcaactgct gctgctgctg   4260
caactgctgg atggtgaaac caaccagaa gaaaatgaaa atgaaaaaga tattgtcgtc   4320
accacaaaca caagatcatc atctacggga catattattc atcgacaaaa agtcttgat   4380
cggaatagta gtattagtag taatgattct ggatcattat cattacctgg atcttcaagt   4440
attaataata ttactcctac cactacaaaa aaggaaagaa gaagtagtaa attggctgat   4500
cctagtgaat ttggttcatt ccatttccga aatttggctg ttttggaaag acaaaataaa   4560
gatgttatta atcgattgaa aacagagcat ttagaacatc gtggtagttt ttctacttct   4620
tcatcatcag aatcaacacc aacaggaaga ctgagaggat tttcatttgg taatgctggt   4680
aatagtggta gttccagtag tggtggaggt ggaggtggag gtggagttgg acaagtggc   4740
tcaccatttta aacgtccaat ttctccacca tcgtttaatg ccaatcaatc aagtggatta   4800
```

| | |
|---|---|
| ggactgccag ttataactac atcatcagga gcaatgggaa ttatcaatac aacaaatcca | 4860 |
| gtcaacatta ccactactag tagtaatcat aatcatcata atagtttttaa tactgttggt | 4920 |
| ggtcttggaa ttggtacagc tacagctaca actgcggctg caactacagc tactacaaca | 4980 |
| acaggtagta ttcgatcagc atcacctcat cgattatttg aaagtccgaa tattcccaaa | 5040 |
| catgaacgta taccatcagc tacaagtgca tattctagtg gtgatgaaat aatgataagt | 5100 |
| ccactgttaa tgattcatca tgatgataga aatcatcatt caagaagtag tagtttgcca | 5160 |
| tatctacaaa ctattactaa acaacccagt ttcctgtatt tgaatcataa tcatataatt | 5220 |
| cgagattttt catcgccaaa ttcatcagat ctggaagata ctactaaatc aaatgcatta | 5280 |
| ttacgagttc aaagaagacg tgaaagttca cgtatgtcaa cagagttatt actgggcact | 5340 |
| aatactggtg gtggtggtgg tgccggtggt ggaaccacta gtagcaataa tagcagtgta | 5400 |
| attgttgctg atcttgatgt attatattgt gaacctattt ctgtgattcg tcatagtgtg | 5460 |
| gtgaaattat tagaaaaagc gggatgtata gtggtctcgg ttacagatgg agaagaatta | 5520 |
| attaaacgag caacatcaca agttaaattt gatttgattt tcactggatt gaaaatatca | 5580 |
| aaagttgatg ctatagatgc tgttaaatta attaaattta ctagtgggaa aaatcgtaat | 5640 |
| acaccaataa ttgggattac cgagaataag aataaaattg atgatgatat tactactagt | 5700 |
| agtacatttg attatattat tgaacctaat cttgaagcaa tttctaaagt ttgtcggata | 5760 |
| ttacgtagtt aa | 5772 |

<210> SEQ ID NO 73
<211> LENGTH: 3996
<212> TYPE: DNA
<213> ORGANISM: Saccharomyces cerevisiae

<400> SEQUENCE: 73

| | |
|---|---|
| atgatgatgg atatactgaa tacacagcaa caaaaagcgg ctgaaggcgg gagagttctg | 60 |
| gctcctcata ccatctcaag taagctcgtg aagagattat caagtcattc cagccataaa | 120 |
| ctatcaagat ctgatttgaa agcattgggt ggctcggaaa caataagcga cggccccagt | 180 |
| cagctgactt taaggaccg atacgttttc aatgaatcgc tatacttgaa aaagctaaaa | 240 |
| aagaccgctt tagatgacta ctacacgagg ggcataaaac tcactaaccg ctacgaggaa | 300 |
| gacgacggtg atgacgaaat tattcggttg tctaatggcg acagaattga tgaagacctg | 360 |
| cactcaggtg tcaagttttt ctccactaca ccttattgca ggaaaatgag gtcagacagt | 420 |
| gatgaactag cttggaatga aattgcgacc gaacggttca aatggcagtc aatgctggcc | 480 |
| agagtgctga agggagatat tgttaaaggt gaaaagacga ggattgctaa ccaagtcaag | 540 |
| aaaccagggt taaataagga gctctcagat gagatatggc tcgaattgaa ggcatggctg | 600 |
| aatgggagga ccatgcaaga gatggaacag tcgcttacat atttaagaga tagttcagat | 660 |
| tccgtttttg aagagataat gaagtttcaa attccacagg gcaagatatt gagcctggat | 720 |
| gcactggagg ccatcttaca agacctcatg aacagatatc acagcgttgt ctcttattgg | 780 |
| cctaacttga aaaaaatgta taggataaaa ccaatcacca atactgcaga atttaccgct | 840 |
| agaatagacg taatgaattc ttggctgaac tttaaaacga acttaacgtt gaggaggcaa | 900 |
| gagttggacg actggataaa ccgtttctca ccgataagta gttcggataa ttgccaagag | 960 |
| gattttgatg gtgtgcccca atggaactgc aaaatgaaga ttcttgcaga acaattgatg | 1020 |
| aaggaaaaga catcgagtc tatattccaa aaaaaaattt tctatccgct atcaccttgg | 1080 |
| atgttcaaac tgaaactaca ttttatagtc tacagagaaa ctttgacaaa gatgaacata | 1140 |

```
aaatatcctt atgaaaggtt aagatcacta ctggcgttcc ccgtctattt aatcaaagaa    1200
gttattttga ctagattgtc atatgcacga aagcttaaaa atccaacaat gatgatgatc    1260
gatcaaatga tcgatgattt taacgctttt attcgacttt ctgtgcaatt gaagtacaca    1320
ctgacaaaat attgctccaa tttgccgttc gatgtggatt ttgacccgac gttcgaaaat    1380
actgtaatag aagccattcg ttatttattt tttctgttga atttaaagtt gattgattcc    1440
agtaaacaaa atttcaaagc acccgatcta ctcttgaaat actgggatca cctaaaaaac    1500
accggtcact atattaacgg tgcagaaacc gtgattccaa atgaatttct caagttaact    1560
ttgagactcg tacataaatt gcaattctat cttttgaaac aacaaaactt cccaccaaca    1620
tttgctaacg cttcagaagc agaaaaatgg ctaagttcca ttttcgaaaa tttgggtgcc    1680
atgaaaagaa agctgaacag gttcagcaat attctagtca aggcgttcca aaattctgct    1740
gtttatcaga ttaatcataa tgcacaactt gttaaaaagt aaaagatgc tcactatttt     1800 ttggtatact ccggtaacac ttttgagtct agtggtgtat atatgtttgc tgctcctgaa    1860
ttattaggtt gtgacaatga taccatctta agaattttgc gaaataaatc cattggctgt    1920
gatttggtcc caaagcttga cattggaaat aatttgaatg tgtatgatat aacaacaaaa    1980
gaaacagatt tgaacattct agtatcgaaa ggggaggatt ccaaaggaat tccttactac    2040
cgagtagtag caaattcgtc aagtgatttg gacaggcatg ctcatcagtc caaaaagaag    2100 aattttttcaa cagacccttt tgatcagcac cttgatgaaa agaacaatga agttttttgaa   2160 ttggaagttg ctttgagctc attgggtgca ctagttgtac tatatcctgg agagccagta    2220
gtttgggatg gaccagtata taagcttcca ggtaacaacc ttttttgcatc caacgaaatg   2280 gatttaggga aaattggtaa cccaaatacg ttgattttac tcaatcaagg ttctaattat    2340
gcactgactt atcaaatcga caagtttaat caaacggtag gtgattctgt ttcattcata    2400
gagaaacgtt gttcactcaa ttcaattgaa tcctccctac aaaaaatcaa taaggcatat    2460
tacaaactta cttatacagt attgaacaac tacaaaggaa ttctaggtag ctttatgaag    2520
caatgtccgg gaaatgagtt gttaaattcg atattcatgt ttggaaggga ttttggaaga    2580
agtttcctta aatataacgc ctttagctca agaggaagt acgttatcat ctttctgatg     2640
gttaaattag aatgaactg gttgaaattc cttgttgaag agtgtgatcc taccgatcag     2700
cgaactttcc gatggtgcgt tcttgcaatg gattttgcga tgcagatgac tagtggttat    2760
aatatcctgg cgctgaatgt aaagcaattt caagaactga aggagagggt atcagtatgt    2820
atgtcattat taatttcaca tttcgacgtt atgggtgcac gagccactga agctgaaaat    2880
ggcatgcaac aggcaagatt gaatattgat actgaagaga atattgatga agaggccacc    2940
ctagaaataa acagcaggtt gagactgaa gctataaaga cgttggaaaa gactatgaag     3000
aggaatccca ggcaaatggg taaggtattg gatgctacag atcagggaaa caaatacccta   3060 ctatcgctag catcctcatt atcgaatgta tcaatgaggt ggcaaaaaag aagcttcatt    3120
ggcggtggaa catttggaca ggtatactct gcaattaatc tggaaaacgg tgaaatctta    3180
gctgttaagg aaataaagat acacgatacc acaacaatga agaagatttt tcccctgatt    3240
aaagaagaga tgaccgtatt ggaaatgtta accatcctaa atattgtcca gtactatggt    3300
gtcgaagtac atcgcgataa agttaacatc ttcatggaat actgtgaggg tggttctttta   3360 gcctcgttat tggatcatgg aagaattgaa gatgaaatgg taacacaagt gtacacattc    3420
gaactattag aaggtttggc atatttgcac caatctggcg tggtgcatcg cgacattaaa    3480
```

| | |
|---|---:|
| ccggagaata tcttgctgga tttcaatgga atcataaaat atgtggattt tggtacggca | 3540 |
| cgtaccgttg taggatctag gactagaact gtgcggaacg cagccgttca agattttgga | 3600 |
| gtagaaacaa agtccctcaa tgaaatgatg gggacaccga tgtatatggc tccagagact | 3660 |
| atttcaggct cggcagttaa gggaaaactt ggagcggacg atgtatgggc attaggatgt | 3720 |
| gttgtgctag aaatggccac aggtagacga ccttggtcta acttggataa tgaatgggcc | 3780 |
| atcatgtacc acgttgctgc aggtcgaata ccgcaactac caatagaga cgaaatgact | 3840 |
| gcagcgggaa gagccttctt ggaaaggtgt ttggttcaag accccactat gagggctact | 3900 |
| gctgtggaac tactgataga cccttggatg atacaaatcc gtgaaatagc atttggcaac | 3960 |
| tcagagaaag atcaagtacc tatcctaagc tcatag | 3996 |

<210> SEQ ID NO 74
<211> LENGTH: 6933
<212> TYPE: DNA
<213> ORGANISM: Saccharomyces pombe

<400> SEQUENCE: 74

| | |
|---|---:|
| atgagcttgt acaagtcatt ggacgttgca attgattatg caatttctca gttgggagag | 60 |
| ttccagttcc aaccaattcg tacgcaatcg aacccttctt ctcttctttc tgcgtgcttg | 120 |
| gtgcgtgccg tccatgtaga aacaaggcga aagtaattt ttaagttttc ccaacaaact | 180 |
| ttcaagctag agaatgaata cttttttgttg cgtcagttgt catctcatcc aaatggaaga | 240 |
| aattatgcta ttgctcccgc atatatatta ctgttgaacg aaaccttagg tgcgcttatt | 300 |
| tacgatgatc ctgggcctaa cattctggat gagtggttag ggaatcctaa ccсttttggat | 360 |
| ctaaaattat ttctcaagtt tgcccttggc gtttcttacg tcttatgttt tttacatgaa | 420 |
| aaaaaaatcg tgcatggcga aattcgtctt gacactttcc attatgattt gaatgcccct | 480 |
| attcatgcaa agttgcttac catcgggagt agcgtatccc ctatcagatt taccttgtct | 540 |
| tccttaaact ggaagcgtct ttatcaagtc cagaatatat gtcacaaact tcagtttttt | 600 |
| agtcctgaac aaattggaaa tgtggggcga ccgttagatt ccaggtccga tatctattct | 660 |
| ttgggtattc tttttttatgt tatcttgacc aagcaatatc cctggggtgg gcaatctatg | 720 |
| agaattgttc aatcgattca tatgagacag tttccttctg tattgcctcg tcgtcctgat | 780 |
| gcctttccag cgcttgatca attgattcaa aaaatgactg ccaagtctat gaactcaaga | 840 |
| atttcttctg ctaccgatt tgtgttatacg attgttgagt taatgcaaga attttctaca | 900 |
| atcacctctt ctcctttgct ggaccaaaaa ttgttatcta taaataaacc acagcaagaa | 960 |
| aagcttaagt ttcctaaatt actattgacc aattcttcag attacgtccg gatcttccac | 1020 |
| gagcttgtag cttttttcttc aaaacgcgat cttctaacga gtgctaagcg tgttgataaa | 1080 |
| cttccaaagc aacaccttttt caaatatcgt ccagtagata atgaggctac atattgccaa | 1140 |
| gttgttacag ttaccggtga aagggctct ggaaaaagta atttgcttaa tgctgtcgcc | 1200 |
| gatgaagcaa gaaaatttgg atattttgca atgagctctt ttaaaggtca tcattttttct | 1260 |
| ccatattctg ccatttttaa atgtgtctct ttaattatgc aacagactct tcgtgaagaa | 1320 |
| aaacagctag ttactgatta ctttacatcg ctgtgggaat tcttggatt tcaattgatt | 1380 |
| tacatgggag aactatttga atatgttcca gaattaaact cgctactatc tccgaaatat | 1440 |
| aatctacatt gcaaaagaga aaactatttc aagttaaaaa agagagatcc ccaacaattc | 1500 |
| cgcagtgcaa gcggtcgttt aggattttatg gtttgtcttc tagaaatact aagcttcact | 1560 |
| tccagagttc gacctgtcat tataatattg gatgaattac atttggctga tcatccttcg | 1620 |

```
ctctctttga taattggcat gatttctcat agacttccta tcttactaat tttggcttgg    1680
gatgaacctg tgatgtttaa agattttcg aaatgtcttc atgaggcccc atatgcgatg    1740
gtcactgata ttagaatgaa ccttttgat cgtaaaaata taactgaatt tttagatagc    1800
actttagagt ctccaactca agctttgggt ccgttagtgc tattgatgca aaagcttagt    1860
aagggaaatc cgttggtgct aaaaagtctt ctactcattg cctttgctaa taatggcttt    1920
gcctttcatc caaaatcctc ttcttggact tatgatctgc ctgttatcaa ccgaagcttt    1980
gaagctcttt cttcttatga tataccacca ttactggcat cattgttgga tgctttactc    2040
cctgccagat gtattgagtt tcttttatgg gctgcattgt tggtcgagcc gtttccgttt    2100
gaattgcttc gattaattac cacatcaatg catttgttta tcccaaaaga agagatattg    2160
gattttcctc tcaatgtttt acaatttgat aatgataacg aaagttgtca attttctgaa    2220
acattttttc gtgagggcat actatcaaaa atcagtttaa aagggccga atcaatgcat    2280 gcccagattg ctaaagaatt aatcactggt actgctaagg aatttatga tatccgtact    2340 gtgcatcaca tacttaaagg tttaggtgtt attaaaaagt tcgataatac caagccatat    2400
atattggcgc taaaggaatc agccgatgct ttgatgcaat ttggttcata tgagtatgct    2460
acggaattgt tgaaaagttg cctattcctt ttacctcgca acttttggaa tagcaagttg    2520
tacacaagga aagatctaat ttcgattcac attagcctag ccatgtgtta ttggtggtcc    2580
aaagatcatg aaaatgctat taagtattg aaaaatccaa agctaagctc ttcaaatgta    2640
tatgattatt tgccagcatt caggttatta actaagatcg aatactacaa atatcaatcc    2700
ttacgatcaa ttgataaggc gcaggaactt ctatctaatt taggtctgaa gttgaaggaa    2760
cctaccgatg atgtattaag ggagttttac gatagacttt ctacgaaatt tttggaatgc    2820
gattttctag ttaagcaatc tgagccatta gaccgaaaaa gaattgatgc tatcagcgta    2880 attcttcgg aatgtggatt tgttcttttc aatttctctc aaccttacta ttattatttc    2940
tcctttttac ttgcagaaat gtacttaagg tacgaaaatc catctttaag atatagtgta    3000
atgttttggg cttcttattg ttttgtaact agaagaaaac ccgaattttt acttcgcatc    3060
tcacaagttg attcagattt gtttgtaatt aaggatcgca gtgcggtagc ccatgctgaa    3120
ctcatctact gggggcttaa aagagaactt tgtagtactg aaactggttc agcagttaca    3180
cttgaaagta tactattaca atgcgttatg tttggtgata aaatttatgg agcttattgt    3240
cttgcctgtc taatggcgca acgtgtcttc cgtggtgacc atattcacca gttattactt    3300
gatcaagaaa actcagaaac attgcttctc ctatgggatt gtgagccacc attcacatat    3360
tatcttatgc tcatacgaaa ttcacttta gctctctttg ggttaacaaa caatgatgat    3420
cctaacaata tccttactac aaagcaaaga actcaaaaag atcttcacga taaacttacg    3480
tccaagaaag ttccgtgtac ttttttgctgt tggtactacg ctggaattat ttttcttaat    3540
actttgtttc atcactacga gtatgtcatg tcaattgctc aagaagttag aaaattggta    3600
gacggcaagc tgtatgaacg ctattatttg ataacccgtt catttattgg cgttgcggct    3660
ttacaacttt tattttataa aaagaatatc tcggagtttg agcgtgaaaa agtcgaggat    3720
gtggcccatt gggcgcaatc tagcttgtct gaaatggcaa atgtttcca tgcggagctg    3780 tacaagttat gggtatgtct tttggagggc ttgcgccaac gtaaccttgg caattacatg    3840
gaggcattaa gacttttga gaaggtcaca agcatgggtg cttcggtttt ttctcccatt    3900
gaatttccat ttgtgttgga actaattggg gaattttatt atggaagggg ccataagttt    3960
```

```
ctcgccaagt cttacataac tcgagcgctc agttgcctta aaaatattgg ttgttatggg      4020
gttgaaaata agttgagaag tagatattct gacttaattt ccgatgttga atctcgtgga      4080
actacggttg tatcaatagc aactaccact ggcgactatg ctgagaagct caaacttctt      4140
aggaatcagg acattaacga ttttagtcta ggtcttgcgt cttattctga tattttttgat     4200
aaacctctgg taaccttgcc tgtgaaaaaa agcagtgctg ttgatgaatc agaaaatgat      4260
ttttacgacc gaaacgatga ggaatctttt gacattgtat ctttagtttc tgttataaaa      4320
tgtggtcaac ttttatcgag taaattaagg ttaggtcctt tgcttacaac tgtcataaaa      4380
ctagttatcg aatactctca agccaagcat gctgctataa tcttgaaaga cgcttcaaat      4440
tacacactcg ctgctcatgg caatgtggag aaagccgaat catttgaacc tcctgtcatt      4500
ttgagccaat cggacgtcaa aattccagat tctttacttt ccgaagtatt tgaccattgc      4560
cgaatcgtct cactgtacac agtttctgct tcgcaagatg cagagctgtt aagatggttg      4620
caagaagagc atgatatgga ttttttttgcc ataatccccc ttcaatttaa agaatcggta     4680
ataggtgctt tgtatctatg tctttcgcgt agagctattc gtacaggaaa tgttacattt      4740
ttgaaacttt tgtcccagca aattgcaatt agcgtttcga atgctttact ttttcagagt      4800
ttgcgtcgca cgataacaga taatgttact cttatcgaac ttcaacgatt atcataccaa      4860
cggtataagg caatagagga aaaatgcata accctttttag actcactacc ttgtatagtt    4920
tggacgctag attccgacat tggcgaaata gagtacacta atgcgtcgaa acggaattat      4980
tttggtgttc ccgaagattg tcatgattca ctcagttgga aaacattcat acacccggac     5040
catcatcacc aatttcaaga aaaattattg aaccttaaaa ctctagagct tggcgacatt     5100
gaattgcttc tacgaatgga agatggaaat taccattggc atttgtgtcg tggattgtca     5160
tttaaagaag atgctaatgc taaaaagtgg atagttgttt gtatagatat taatgatgaa     5220
aaggaagctc gtgaagctgc aatgcatgct gtcaatctaa aaactaattt tcttgccaat     5280
atgtctcatg aactgagaac tccgttttcg agttttttatg ggatgctttc tctgcttagt    5340
gataccaaat taaatgaaga gcagtatgac atagttagca ctgctaaaca gagttgcaca     5400
tcgttggtcc aaattataga tgatctattg aacttcagcg aattgaagtc aggcaaaatg     5460
aaacttgagc ctgacaaagt cttttgatgtt gaagagaata ttgcagattg cattgagtta   5520
gtataccctt ctctttcttc taaacctgtt caaatttcat acgacatata tccgaatgtt     5580
ccagctttat tggctggtga ttctgcaaag cttcgacaag ttattaccaa tctccttgga     5640
aattccgtaa agtttacaac ggagggtcat attttgttac gttgtatggc tattgatgag     5700
gaaataaatg cagaagaaaa tcaatgcaaa ttgagatttg agattgagga cactggaatt     5760
ggacttaaag aagagcaact taaactgctt tttaatcctt tcactcaagt cgatggtagc     5820
actactagaa tctatggagg ttcaggcctt gggctctcta tttgccttca aatatgcaaa     5880
ataatggatg gagacatcgg tgttcagtct gtttatggag aaggttctac attctggttc    5940
catgtccaat tgcgtaacgt tacttctaag ttatctcaga acatttcga agaaagccat      6000
gagagatttg ctaatattcg acaatctctt aagaatgcta aaatacttgt agttaaatca     6060
tttactacat cacgatctat tttcaggtct cttttctcct tagctgtagt tgatacaact     6120
actatttaca gtgatatcga acagcagtta attgattctt tagataagcg acaaccttat     6180
gactttcttt gtatcgaagc tgccagcggc cagacggaac aaataattac tcagatactt    6240
agtaatcaaa aattgaacaa ggtattactt attgttctgt taccgtcgat tcaacgaacg    6300
aaagtacgat ctgacggcga tccattcata acctctttaa ataaaaacca aagcagaata   6360
```

-continued

| | |
|---|---|
| ttttgcttca gggagccaat acgcatttca aagttactac aaaactttcc cgcattacta | 6420 |
| agtaaatggt caactcctac caaacttgtc gagccctctc aatttcgagc atcacctagg | 6480 |
| aaggtcgatc aagcagttgt tcttcctagc gaagagaagg agattcttca gaaaaagtat | 6540 |
| gcgctaatag ctgaagataa tttgattgct agaaagttgc tcacgaaaca attaagcaat | 6600 |
| ttaggattcc aagttcatgc cgcggtagat ggcgttgaat tggttaaaat gtatgaggct | 6660 |
| aaacaatttg ttttatag tgtaatattt gctgattacc atatgcccat ccagatggt | 6720 |
| gcagaagcag ttatggatat ccgtgcttac gaacgtgaaa ataattgctc aactccaatc | 6780 |
| ccagtcattg ctttaacagc tgatatacag aaatctgcaa acagcgatg cttagaggtt | 6840 |
| ggaatgaatt tttatttgac caaaccattt actcaaaaac aattagtcaa tgccgttcgc | 6900 |
| gaatttgtgc ttttggagaa gagtgctcgt tga | 6933 |

<210> SEQ ID NO 75
<211> LENGTH: 7035
<212> TYPE: DNA
<213> ORGANISM: Saccharomyces pombe

<400> SEQUENCE: 75

| | |
|---|---|
| atgtattctc agcatgaact tcgtaataaa gtcagcctag cactctcgag tctacttagg | 60 |
| tacacgtttg aattgacgcc tttttttgaa ctgtacgaag ctgatttcgc atatgctttg | 120 |
| tatgctggct ttgaactggc cacaaatcga aggtggttg gaaagttctc atttcaaaat | 180 |
| gttcatcttg aaaacgagta taacatactt acggaaattg caaagatga aagggcatcg | 240 |
| aaatttagcc ctactcctat tgagtttacc tctttcccc atattgattt atctgcttgt | 300 |
| attgcttatg actttggcca cggagctgaa ttatcgacaa gttatgccta ttttagagag | 360 |
| aacccagcag aatttgttcg cttttgtatt gcaatttgta aatgcattga atacttgcac | 420 |
| tcaaaaggaa tggtacatgg agaaatacgt ctggatagtt tcatcccat aagctcttac | 480 |
| gacaatgttt acatgctcac tgtgggatca ggcgctagct attttcataa ttgtttacaa | 540 |
| gcgcataatt ggcgtaaata ttccgaagac tcagaatcga tgtccagaat tttgtttatc | 600 |
| agtcccgagc aaacgggcag aacttcatac agtgtcggat atcgtacaga tatatatagt | 660 |
| ttaggggttt tattttttcca ttacctttca gattgttctc cttatacggg atcttttgta | 720 |
| caacgaattc gatctatttt gacagaacct ttacccgaca tcagtaaatc atgtcccaaa | 780 |
| cttccgcatt tgatttttaa aattattgaa aaaatgacac gaaaaaaccc agatgaaaga | 840 |
| tacacttcct gttctggtat cgttaacgac ttggaagctt gcttggatga tattgacaaa | 900 |
| gggttaatac tcaatgatca tgttttggaa aaaacaggac gtacatcttt attctatttg | 960 |
| ccttgttcta tatatggtcg tgaacatgaa atcaaattaa tcagaaaaat cttaagaaat | 1020 |
| tccccgcgcg caataaatca ccaagacaaa aaggatttgg agacatttaa tccatattat | 1080 |
| ttaaatgcga tagaatctga gagctcttct caatccctct ctttatccca aagggcttct | 1140 |
| gaagttatgc cactggtaat acttatcaca ggatgtgagg gtattggaga tcaagcttgg | 1200 |
| attcaaacta tttgtgatcg acgtgaaggg tatatggcta tcacaaaatt tgaagtatca | 1260 |
| caatcaattg tatactctgc gattgtttca gctgttgccg agtttattcg gcaaatcctt | 1320 |
| gctgaagatc agcttttact taataatttt tttgaagagc ttaagaataa attagaatcg | 1380 |
| gatttgtatt tgctcgattc ggttttcgat tggtaccag aaattagaag tttattacaa | 1440 |
| cagttttcga cttcttctgg taatactaga aaaacgtctt tgttgggctc gaatcattct | 1500 |

```
agctattccg ataaacttgg gtctcctaca attctctcaa cttcgttttc acttgcaagg   1560
ccatatcctg agccggctct tgtaagtcct tcgactgaaa ggccccctag gtcaagtttt   1620
tctgccgcct tgatgaccct gctaaatatc attgctagtt ttaaaaaagt aacgatggtt   1680
atagagaata ttcatcttgc tgatgagtct tctttaatta ttctccagaa aatcgtttac   1740
tctgatcttc cacttacctt gatgattact tgcgataaag aaaacgatca tgtaattaac   1800
aggtttcgtt tagcgaatga caggatacac gaaatcgagt taaaaccact gtctttttaat  1860 gctgtgaatt cctatgttca ggctactttg catcgaaccg atgatggatt agcaagattt   1920
tcttcttacg tttatcacat tagcaaaggt gtgcctttac ttgtgagaaa tgtactactg   1980
agtatttatg aaaacaagat aatttacttt gattggaaaa aaaatcgatg ggaagtaaat   2040
tacgacgaaa tgtacactct tgacaatgat tattctgagc ccgatgcatt tatgacggcc   2100
aagaaaaaaa tcagtaaact gaacgactct tctcgtgcta tccttggttg ggctagtctt   2160
ttgggcccat cttttttcttt tgcaactgta aagaagcttt gtaaggatac cgataatatt   2220
gaattaaatg tggaggctct tcagtccgca ttaagagaag gtataattta cgccacttct   2280
tctgatgaca cgtatacgtt ttcaaggtct atttatgtta aagcgatgcg tgatttgctt   2340
aatgaagcaa aaatacagat tatgcatgca tgtcttattg acgtttgtct taaaaatcga   2400
gatcgttata acatcttcga tatcgctttt catatcaatg ccgcttttga ttttgttaag   2460
ggtgataaac gatctgttga atattgccat tatttgcact tggctgccga agaggcttta   2520
aagattggag ctaatcaaga ggcgcttgac ttatataaca gatgtataaa aatgatacca   2580
cacgaaattc ctgaggaaag tgatgatagt tatattcgct gccagcttat tggtatgtat   2640
gttggatgcg ctgaagctta ttgggtaaat gataatttcg atacagcttc agaaatgtta   2700
aaactagcag aggagaaagc ttgtaataac tcggaggttt ttcctgcaag ttttttgtac   2760
tctcggattt tattcgaagg ggtgcatata gaagagtgca ctcaatatgt attatcttgt   2820
ttgaagccac ttgggtatga gttaaagcga cattctctcg aagattcaaa gtcaattatt   2880
tcagcactga tcccacgtat tattgacaaa attactaaaa gctcagagga atctcagtca   2940
tcaacagatg acgatgaccg gagaattttc gaaatacttt cttttttata cgtcggttca   3000
gtcgctactt cttactttcc agagaccgca gaaatggcca ttgattttgg aatagcacaa   3060
gtcgaatttt ttttaagtac tgttgtcaat tcgttctccg cttttgcctt agtttatttt   3120
gctattcttg caaattcttt acttgagcct tcagaagata ttctcttcat cggtaattat   3180
ggagagaaac tgaatcgtga agctgagaat cctataatat tttcacgtac tgaatatttg   3240
tatgttcaat ctcttggttt tatagacagt accacgaaag agagaagact tactattgat   3300
tatttggaca gaaattgtgt cacttgcagt gataaacacg ttattattag tctgcttttta  3360 gtgtcatcat gggagaaatt tctaacttcc aacaactatt caaattactt ggcagatttt   3420
gaaactactc atgcgcaaat tatggaaatg aagccttggg ttggtgatac ctcattaata   3480
acacaattaa agcgattttt gatgtgctta caggataaca tcaaattgga tttaatcaag   3540
tcaaagagtt ttttgtcgga tcataatatc caattatcat ccccagcagc acaagaatct   3600
gcgaaacttg cattcagcct tcacggatgg attaactcat ggtatcttct ggctcttgtg   3660
atgcatggtg aatgggatat ggctatcagt tatggagaga ttttaaacg tgaatttaaa   3720 aatgcgcttt taacttcttc tagggtattt ggaattttta tgtttacttg gtctttggtc   3780
aacaagatgc tcatttgtcc cgaattcact aagcaaaaaa aatattatga gcagtataaa   3840
gaaaatcttg gatttttga tagcctatgc attggtgata acgaatgtat cactcgtgta   3900
```

```
tattttctttt tattaaaagc atgtggttta ataatgaatg ggctgaattt tgaagcatca    3960
gttatgctgg aggaagtcat ctctttaaca gaaaaacttg aactttttt gttacaggca     4020 tttgcatttg aaactgttgg aagcatttt gtgtctatgg aactatatac ttctgctact     4080
caatacttgg aagaggctat tcgaaattat gctgctctgg gtgttaaaca aaaagctagg    4140
catttgaggg ataagttcgg tgatttgttg gtttcgaaca acttacaggt ttcgattgat    4200
gaagctacac aaacagattt ccctttggtg tttagtcctg agcgctcaag tattgacata    4260
aatgctagta gtatgcgttc tgaaaaagcg tcctttgaga ttccttttcc tgaagagcag    4320
attgatgatg atgtttctcc agtagcccaa gattcttctc tggaagagtt acttatatct    4380
ttggacatca tcgatctaac ctcagtaatg agatcctgcc aaacgattgc cagtgaaatt    4440
gagttgactg gtttgctctc gactatgaca cagagaatgt tggaagattc ttcagctaac    4500
gctgctgtta tagcaattcg tgatgacgtt ggctttaaaa ttgcagctta tcgtacggga    4560
gagcttaacg aagttttgc tcccccgatg cctattacag aagatcaaac gtacgttcct    4620
tctagagtga taaattatgt tgtccatacg caaaaagctt tgttttcgaa taatataaac    4680
catgaatttg atttgcagca ggagcgttgg aatatcgaaa atcatatggg gagaagcgta    4740
attgctattc ctttatacca aaagaaggag gttttgcga tactctactt gcaaggccct    4800
ccatcagcat ttcattctcg acatatgtcg gtactatcaa tccttgggc tcaggcaagt    4860 ttcgcaattg tgaatatatc tttgtttcat aaggtgaaag aggcaactaa tgttaatacg    4920
attatcatta aagcccagag agaagcatta aatttggtgc aaaaatcgga ggctaaaatat   4980 cgcagctttg tcgatacaat gccttgcttg ttatcaaaat tagaatttga tgaagagtta    5040
aggattgagc ttttggaag ttttggaaa gaatattgtg gtgaattaaa tataaacgac     5100
ccaaatacat ggaaggaata tgttcatctt gacgatcacc ttaaattaca ggatttcctg    5160
ctctctcact tgcacaatcc tcttcctttt gaactagaaa taagaattaa aggaaggat    5220 ggagtttatc gatggaatct tacacgctgt acccctacga cgaacgaaaa aaatagaact    5280
agttttttgt gtgcaacaat tgatattgac gatcaaaaga aggcacgagc taccgcatta    5340
gaactggcac gtttgcgttc gaatttcttg gcgaacattt cacacgaatt aagaacacct    5400 tttttctggct tctacggcat gcttttctctc ttagatgata caaatttaga ttctgagcaa    5460
agggatattg ttagtgctgc tcgtataagc tgtgaaatgc ttcttcgggt aatcaacgat    5520
ttgttgaatt ttagcaaaact tgaagcgggc aaagtcactt tagaatctga ccttgaattt    5580
tctttagaat ctgtcgtttg tgattgtatg caatctgtat attcagcttg tgccgagaaa    5640
ggtatcaatt tatcttataa tgtttctcca gatattcctt ttttcacagc gggagacggc    5700
atgaaaattg acaaatgtt aaagagtatc cttgataatt cggtaaaaac agttaacaat    5760
ggatttatcc gtgttagggc cttttttggct ggttcatcga aaaagaatga tagggaccag    5820
ttacaaattg cgtttattgt agaggatact cgcgaagaaa gcaatgctat tttttttggct    5880 aatatgatca attccttgaa tcgtggctgt aacgactatt tacccatgga tttaagtggt    5940
accgcacttg gaatgtccac gtgtttacaa ctttgcaaaa taatgggtgg atcagtaagt    6000
gtagaggtat cacaaaataa ccctacattt aaaatttgtt atgatctgaa aattcatgaa    6060
cttggaaagg aaagatacga cattatagct actcctctat ttcaaaacct aacagagttc    6120
aatgatctca taaaatcaaa agttgctatc cgagtttcta aaacttctac tgagtatgac    6180
aacattacta catatcttca agctgcgaga aaggttttgc atgttttaa gggattacaa    6240
```

-continued

```
gacctagcat caatttttga cttaagccct gactctgcac ttctccgctg ttccgttgtg        6300
gtagtggatg tttattcgat ggatgatgtt aaggcagtcg aaaaaatatt gaaaagctat        6360
ccggatgtac atgtcatata tttgtgctgt gatccctcta gattgaacat cgagcaggaa        6420
ctacagaaac cttcaggaag atcgtttgca tgtaaaaaaa gatggggatt tcttcaaatg        6480
ccttgtacta gagaaaactt cctcaaggtt acattacaag tgtttaagtc taatgaagat        6540
acttgtaact tttactctta tgttaatgag tacggtgaat ccccaaaacc agatgacgat        6600
atggaccggt taaacaaatg tgttggatca aagattttaa ttgctgaaga caccccata         6660 gtgcgtatga ctttaaaaaa gcaactagag catttaggaa tggatgttga tgccgcagaa        6720
gatggaaagg aaactcttca aattttttgag agtcaccccg acaactatta ccaagtttgt       6780
tttgttgatt atcatatgcc tgtatatgat ggcttagagg taaccagaag gatgagaaag        6840
atagagcgta agcatggttg tgcacctctt cccatctttg ctttgaccgc cgatatgcag        6900
cctaccatgg aaactcagtt tcaagaagtt ggaataacgc attatctcag taaacctttc        6960
aagaaagaaa cactaattaa aatgcttctg caatatttag ttaacggaac tgatggaaat        7020
gctaatactt cataa                                                         7035

<210> SEQ ID NO 76
<211> LENGTH: 3894
<212> TYPE: DNA
<213> ORGANISM: Aspergillus niger

<400> SEQUENCE: 76
atggctggcg cggacgaaac gctcgcggcc gctgctgcca ttttgagagg tcttgcgaaa          60
gaaactcctt cctccagcgc tcctcccttc gacttcgaat ctcccatcc tcccgccaat         120 ggctacgaca caaaactcgc aaaattaccc ggggaaacga gttcagcaaa gcggctttt          180 gaacaggagt tggaagcttt ggtccgacga gtccgtcatc tggaattcca aaatacaaca        240
caacaacaac aacaacaaca accccatgga tccagacgat cggccatcga accggaagac        300
cacgaagtgg aggaagacat cgacgatgag gagagtgacg aagatgagga actgaattca        360
aggacacgtt tggtacgcga ggaggacatc agctacctac ggaatcatgt tcaaaaacaa        420
gcggaggaaa taagtttcca gaaggatatc attgctcagg tccgtgacga attacaacaa        480
caggaggagc aaaacacgac gggctttgac caaggtcgaaa acgaagatgt ggtcttgctg       540
gagcgggagc tacgcaagca ccagcaggcc aacgaagcgt tccaaaaggc actacgggaa       600
atcggcggca tcattaccca ggtcgcaaac ggtgacctgt ccatgaaggt gcagattcac        660
ccgttggaga tggaccccga aattgccact ttcaagcgta cgatcaacac catgatggac        720
caactacaag tcttcggtag cgaggtgtcg cgagtcgcac gagaggtcgg aacagagggc        780
atactcggtg gtcaggctca gatcaccggg gtgcatggta tctggaagga gttgacggag        840
aacgtcaaca taatggccaa gaatctcacc gatcaggtcc gtgagatcgc tgcagtcacg        900
acagcggtcg cccacggtga cctgagccag aagattgaaa gtcgggccca gggtgaaatc        960
ttggaactgc aacagactat caacaccatg gtggaccaac taaggacatt tgcaacggaa        1020
gtcacccgcg tcgcgcgtga tgtcggtacg aaggtgtgc ttggtggaca ggcccaaatt        1080 gaagggtgc aaggcatgtg aacgaactc acggtgaatg tcaacgccat ggcgaacaat        1140
cttacgacgc aagtgcgtga tatcgccacg gttaccaagg ctgtggcgaa gggtgacttg       1200
acgcagaagg ttcaggcgaa ctgcaaggga gagatcgcag agttgaagaa tatcatcaat        1260
tccatggttg accaactaag gcagtttgca caagaagtca ccaagatcgc caaggaggtc       1320
```

```
ggtacggatg gtgtccttgg tggtcaagcc accgtcaacg atgtggaggg cacatggaag    1380
gatctgaccg aaaacgtcaa ccgtatggcc aacaatctga ccacccaggt cagggagatc    1440
gccgacgtga ccaccgccgt cgccaagggt gatttgacaa agaaggtgac ggctaatgtt    1500
caaggtgaaa tactggactt gaagagcacg atcaacggca tggtggaccg gctaaatacc    1560
tttgcctttg aagtcagcaa ggtcgcgcgt gaagtcggca cggatggtac actgggtggt    1620
caagccaagg ttgataatgt ggaaggaaaa tggaaggatc taaccgacaa tgtgaacacc    1680
atggcccaga atctgacgtc ccaggtgcgg agtatatcgg acgttacgca agcaattgca    1740
aagggtgacc ttagcaagaa gatcgaggtc catgcacaag agagatact cacccctgaag    1800
gtcaccatca accacatggt tgaccgacta gccaaattcg cgactgaact gaagaaggtg    1860
gcgcgcgatg ttggggttga tggcaagatg ggtggtcagg ctaacgtcga agggatcgct    1920
ggaacatgga aggaaatcac ggaggacgtg aatacgatgg ccgagaacct gacgtctcag    1980
gtgcgcgcat tcggtgagat tacgatgcc gccacggacg tgatttcac caagctcatc     2040
acggtcaacg catccggcga aatggatgag ttgaagcgga agatcaacaa gatggtttcc    2100
aacctccgag acagtatcca acgtaacacg gccgccaggg aagctgcaga attggcgaac    2160
cgcaccaaat ccgagttcct cgcaaacatg agtcacgaga tccggacgcc catgaacggt    2220
atcattggta tgacgcagtt gaccttggac acggatgatc tcaagcccta tacccgagag    2280
atgttgaatg tcgtgcacaa cctggccaac agcttgctca ccatcattga tgacatactc    2340
gatatctcca agatcgaagc gaaccgtatg gtgattgaga gcatcccgtt caccgtgagg    2400
ggaaccgtct tcaacgccct gaagacgtta gccgtcaagg ccaacgagaa gttcctgagt    2460
ttgacgtacc aggtgacaa caccgttcct gactatgtca tcggtgatcc cttccgtctg     2520
cggcagatta tccttaacct tgtcggcaat gccatcaagt tcaccgagca tggcgaagtc    2580
aaacttacta tctgcaaatc cgaccgagag cagtgcgcag cagacgaata tgcgtttgaa    2640
ttctccgtct cggatacagg tattggtatt gaggaagaca agctagatct catcttcgac    2700
accttccagc aggcggacgg atcgaccacg cggaggtttg gtggaactgg tcttggtctg    2760
tccatttcca agcgcctcgt gaacctgatg ggtggtgatg tctgggtcac ttcggaatac    2820
ggccatggca gtaccttcca cttcacttgc gttgttaaac tggcggacca gtctttgagc    2880
gtcatcgcct cgcagctgtt gccgtacaag aaccaccgtg tcctctttat cgacaagggc    2940
gagaatggtg ccaggccga gaatgtgatg aagatgctca agcaaatcga cctggaaccg     3000
ttagtggtgc ggaacgagga tcatgtcccg ccgcctgaga ttcaggaccc gtcgggcaag    3060
gagtccggcc atgcctatga tgtgataatc gtggactcgg tggccactgc tcggctgctg    3120
cggacgttcg atgacttcaa gtacgttcct attgtcttgg tgtgccgct ggtctgcgtc     3180
agcttgaagt ctgcccttga cctcggtatc agctcctata tgaccacgcc atgccagcca    3240
attgatctcg gtaacggtat gctgcctgct cttgaaggac ggtctacgcc catcaccacg    3300
gaccactccc ggtcgttcga catccttctg gcggaggata cgacgtcaa tcagaagttg     3360
gctgtgaaga tacttgagaa acacaaccac aacgtttccg tcgtcagtaa cggtctcgaa    3420
gccgtagaag ccgtaaagca acggcgctac gatgtcattc tgatggatgt tcagatgcca    3480
gtcatgggtg gtttcgaagc cacaggcaag atccgcgagt atgagaggga agtggtctc     3540
agccggacac cgatcatcgc gctaactgca cacgccatgc tgggcgatcg agagaagtgt    3600
attcaagccc agatggatga gtacttgtcg aaaccctga agcagaacca gatgatgcag      3660
```

```
accattctca aatgtgctac attaggtggt tctcttttgg agaagagcag gagtcgcgaa    3720
tctcaagtag tggtgaaatg cacccggtcc atcacagtgg gcctgatggc aagagccaac    3780
agcgtccggg gttggaacct cgatccgtca ccgcaaccag cactattaac cgtggtggtg    3840
gcctcgcaag cccaaacgtt gaccgagcgg atgagcttgc cgtcgaaagg gtga          3894
```

<210> SEQ ID NO 77
<211> LENGTH: 1206
<212> TYPE: DNA
<213> ORGANISM: Aspergillus niger

<400> SEQUENCE: 77

```
atgagcttcc gtcaagccct cagacccttc cgtcgcacca tgtccggtga aaagatctac      60
gaaggcgtat tcgccgtcca caaaccccaa ggcgtctcct ccgccgacgt cgtccgcacc     120
ctccaaacgc acttcaaccc ctccacgctc ttcgccccct ggctgctga cgagcgcgcc     180 cgtcgcgccc gcgaaagcac ctaccagcgc aagcgccgcc gcaccagcg tctcgacgtg     240 aagatcggcc acggaggcac cctcgacccc ctcgcgaccg gcattctcgt cgcgggagtc     300
ggcaagggca cgaaacacct gaacgagttc ctaggatgca cgaagcaata tgagaccgtt     360
gtgctgttcg cgccgagac agatacctat gatcggctgg ggaaggtggt gcgcaaggcg     420
ccctacgagc atgtgacaag ggagatggtg gagaaggcac tggagcagtt ccgtgggaag     480
attatgcaga ggccgccaat tttctcggcg ctgaaggtga atggcaagaa gctttatgag     540
tatgcccgcg agggcaagga ccgccgatt gagatccaga gaggccggt cgaggtgacg     600 gatttgagga ttgtcgagtg gtacgagcct ggaacgcatg agtttaagtg gcctgaggtt     660
gaggcagacg gggaggagaa ggctgttgcg gagaagttgt tggcgaagga ggatgagttg     720
ccgattgtgg agagggaggc ggatggtgaa ggagaggcct ctgcgaagag aaagtccccg     780
cctgcggagg atgctaagga ggagaaggta gagggtggtg atactgagtc tgctccctcg     840
gctaagaagc agaaggttgc tgatggcgag gctgcgcctg ttgcgccggc cgagcaggag     900
gcgtcggatg ctcccaatgc tgaagccgtg gaatcctcgg aatccaagcc ccagtcccag     960
ccccagccgg ctgcggtgaa gatcaccatg acggtgtcat ctggcttcta tgtgcgctcc    1020
ttggcgcacg atctgggcaa ggcggtcgga agctgcgggc tgatgtcctc gctgatccgg    1080
tctcgtcagg ctcagttcga gcttcacccg gacaaggtgc tcgagtataa ggacctcgag    1140
gccggcgagg aggtctgggg ccccaaggtc cagcgattcc tcgaggactg ggaggagaag    1200
cgactg                                                              1206
```

<210> SEQ ID NO 78
<211> LENGTH: 3303
<212> TYPE: DNA
<213> ORGANISM: Aspergillus niger

<400> SEQUENCE: 78

```
atgactatcc cactgagtcg actatccacc gtggatccgc ggcaaccagg aattagtggc      60
cataatcggg gcctcttgaa cgccgacgtc gtcccgatca acgacaagca gaaagtcttt     120
cttgccggtt ctggccctcc gtcgccaatg catcgcgtac aacctctgga cggatcgcat     180
ggtccgccca gtgctccagc agtctacgag cagccatggc gccctccgta tcgtcttct     240 tatgacggac atcccgcgga ccagcgtcgc acatcgaatg ctcctcagcc tgcgctccca     300
ccccacggat acccgatgaa cccaaaccgt gagctgccgc agctcccacc agaagtccca     360
tatggccgac agggcagttt gcctggcccc gtgcatacc ctccagaagc ccccactcct     420
```

```
catcccagct tcgtcctat gaatggaact ccccatgagg ccgcccctca ttcagcaccc      480
cccgactatc gctcacggat gtcttttaca cctcaggagc ctcacagcaa tggggacgct      540
ccgctccccg cccacacgtt accccccgact cagtatccca ctccggttcc gcatttgtcg     600
catactccta cgccgtacga ttcaggtctt tacggaaacc aggcgtacgg gatacgccag     660
cagcgaaagg ccgctcgggc gcaacaggcc tgcgatcagt gccgaacgag aaaggccaag     720
tgcgatgaag gccggcctgc ttgtagccat gcaaggaga  acaacttgat atgtgtttat     780
aaagaagttc cccctcacaa gcaagaaaag gcaacacagc ttcttctgga ccgtatctct     840
cagttggaag acggtctcat cgaaaaaatc gatcgcatta atgcactcca ggtcgagcac     900
acgaatcaac tcactcagct gtatcctcgg ttgaaagagg ctaaagcgat aagcaccaag     960
gagacgacag agaagcaagc cattcctcgg atatcgaaag cggatatacc tgatatctta    1020
caaaaaacgg aaaccaaaga agaagacatg aacgcgatcg tcggacagga gcttgaaaga    1080
gccgaagggg aagtgattcc acagggtgaa gacggtgatc tttcaattcc cgttgagcat    1140
accactgcag cccacaagtt gctttcgtgg ccgtctatca aggctcttct cgaaccgaga    1200
gagtacgatg aagattatgt tatgaagctg gaagaggagc gaggattgat tctcgtttac    1260
ggccgcggtg aaggacacga tactagtgaa agcccagcaa tgacattctc atcatcatcg    1320
tcccggtcca actgggatca aagttacagc aatggtgctc ctgctagcgg ccagtggaac    1380
ccaggcgctg tccaaaatgg cactcatctc aaaccactcg acccagtat  tgatgatttc    1440
gggatattca gcactgatgc caaaaccgtt cgtcgttatc atcaaagcta cctgaaccac    1500
atgcataagc ttcatccatt tatcaacctg accgaattga gcgcaagcat cgaatcattc    1560
attcagaaat actgctcacc tgacgtttct gttccggtaa acatcctgaa cagccatacg    1620
cccggcgaca ttcacgcgg  tgcgaaaagg aagcgttctt gcgatacgct acatggtggc    1680
ggatgcgaca tccagtttt  tcctggtgcc aaacacgaag gctctagcgg acgtcgcgtg    1740
gagaagtcac tggaaaatgc tattgttctc ttggttcttg cacttggcag tatttgtgaa    1800
gttccgggag ccatccctgg tccagttact gacacgcccg tggactttca aaaggagcgg    1860
attcctggac cctctacacg cagcatgcta tcatcggcag atacagaact agttatgcag    1920
tcccagggaa gtttcttctc gcagacaagt aaccattcat tttcatctgc taccgggggg    1980
cagaaggctg cttccgatcg gtcgccatac ccggataata gtcacttaag gaacgtggat    2040
gtcattcctg gcttggcata ttatgcgtac gccgcacaga tcttggggag tttgcaaggc    2100
gcgaacgggc tgtaccatgt tcaagcagcc ttactagcag gactttatgc gggacaatta    2160
gcacatcctt tccagagcca tggatggatc taccaggcgg ccagagcatg ccaagtgctt    2220
gtccgatcga aacggtatga acaaatgaat gacggcccgc tgaaagacct atataacttt    2280
gcgtactgga cctgcctgca gctcgagagc gacatccttg ccgaactaga tcttccggct    2340
agtggtatat ctcgcgcgga agcacggatt gagttgccaa agggccgaac tctctctcta    2400
cctaacgacc ctgctgctcc gaacaccatg atgatgtttt tctactctgc ccagatccat    2460
ttgagaaagg ttctgaaccg tgttcacacc gatctataca agtcgaaag  taagttgatc    2520
ttaggcaggc aggagccctt ggctaatgag aacaggtggt ctgctaacgt acaggagatt    2580
ctgagcatga accttgaact gtggagaagc agcttacctg acataatgag atggaaggac    2640
acggaccctc cacatgagga tattaatgtg gctcggatgc gagctaagta ctacggtgca    2700
cgatacatta tccatcgtcc actccttta  tgggctctgc atcattcaca tcccaccgaa    2760
```

| | |
|---|---:|
| aacggtcgat cggcatcagt ggattcccct acaggatcag cgatgtcggg agccaagtcg | 2820 |
| cagcaggttt cgccctcaat ggcgcacagc caacgtgcta tcaatatggc acgattgtct | 2880 |
| agtgatgttg gccctatggg tcgatcggca ccgacgccaa cccccgctcc gacaggatcg | 2940 |
| cgaccagcac tcgcatatcg cgacctcaat ccgaagttac gaagagcgtg caaagtatgc | 3000 |
| atagactccg ccatattgag taccgaggcc tttgatggca tcacaggccg gccggtagta | 3060 |
| actaatatct tcggcacagc tcatgctcaa ttcggtaaca tgctggtatt gtcgccacg | 3120 |
| tatatgtcaa gtctctcaga gctggttgat cggaacgacc tcgatcggtt atttaagcga | 3180 |
| accatacgct ttctcctcca aagccgcgag atatcgccaa ccctacgagc cgatgcaaag | 3240 |
| attctcagcg agatatacga aagatctttt ggggagccag ctgatatcgt ggctccgtta | 3300 |
| taa | 3303 |

<210> SEQ ID NO 79
<211> LENGTH: 6084
<212> TYPE: DNA
<213> ORGANISM: Aspergillus niger

<400> SEQUENCE: 79

| | |
|---|---:|
| atggctgctg ctacgattga gttaccgttt atttcgtcgc actacgccat tgccgagtcg | 60 |
| acattgagca ccctcaccac agctcctacg gtcgagctag tcaaccagct cttggaagct | 120 |
| atcactacga aagcacgcga gcatgacgag ctcaagtctg acaagatacg cctcgaggtg | 180 |
| gaactcgata atgccgttcg ctccagagaa aacaaaatca aggttctgaa gagctcggtc | 240 |
| gagaaaggtc atgccgaagt cgaggaaaca aggaagaaac ttcacgagtc cgaaaacact | 300 |
| cgttctaccc tggaatccga gatcgctaca ctcaagtcgt cctccacgtc aaacgagtct | 360 |
| gaagccagct cattgaagtc tcgtatctcg tcgctcgaag cttctaacag agacactctc | 420 |
| tcactcctcg aatccaagtc cgcagcatat gacaagcttg ccgaggagct ctcaacacaa | 480 |
| cacaagaaga caatcgaatt gagacgcgaa cttttccaccg ccgagcagaa cctccaagcc | 540 |
| gccaactctg cttccgccag cgctaagttc cgtgagcaga gtctccagca ggatttggaa | 600 |
| ttgacaaaga aaacaacga gtggttcgag acggaattga agaccaagtc cgccgaatat | 660 |
| ctgaaatttc gcaaggagaa gagcgcccgg atttcggagc ttcagcgtga aaacgaggag | 720 |
| atcagtgcaa acgttgactc cttgagacga agcgagaatg cccttaagag ccgcctggat | 780 |
| gaggtggaac agcgttatga agaggctctt tccagcatca accagctcag agaagacgct | 840 |
| atcaaggcga ccgagtcgtt cagaatcgaa ttggacagtg caagtagact agccgagttg | 900 |
| cagtcgaatg ctgcagagac ttcgaagcag cgtgccaagg aatgtcaact cgctctggat | 960 |
| aaagcaaggg aagatgctgc ggagcagatt tcccgactcc gagtggagat tgaaaccgaa | 1020 |
| catgccgaca agaagctgc tgaacgccgc gttgctgagc ttgagctcac ggtcagccag | 1080 |
| ctcgaatccg atggttttgc tggaagaaga tccatgagcc ctgcactgaa tggcgcaggg | 1140 |
| cccagcaccc caatgcgtcc cagtacccca gttggcgcgt tttcacctag agcgtcgcgc | 1200 |
| ggaaagggag gactcacact gacgcagatg tataccgagt acgacaagat gagaatttcg | 1260 |
| ctggccatga gcaaaaaac aaaccaagaa cttcagcaa ctctagacga gatggtccaa | 1320 |
| gatctcgagg ccagcaagcc tgaaatcgat gagctgcgtg cggaccacgg tagacttgaa | 1380 |
| aatgctgttg ttgagatgtc taacatactg gaaactgctg gaaggaacg agacgatgca | 1440 |
| actaaggagg caagaaagtg gcaaggccag gtggagggat tgcccgggga gggagacatt | 1500 |
| ttgcgccagc aactcagaga cctgagctcc cagattaagg tcttggtttt ggaaaatgca | 1560 |

```
attctgaagg aaggcgaaac aacgtacgat agagaggaac tcgagaagat tgcgcgccag    1620
gagatcgatg actcctctgc tgatctcaac ccaaccggac ggttcatcag tcgcaatctg    1680
atgacgttca aggatctcca cgagctccaa gagcagaatg tcactctccg tcgtatgctg    1740
agagagcttg gggataagat ggagggtgca gaagctcgcg agcaggatgc catccgtcaa    1800
caagagcaag aagagttgaa ggacctgaga atccgggtgc agacttaccg tgacgagatc    1860
gctaacctcg tcgctcaaac aaagagctat gttaaggaga gagatacgtt ccggagcatg    1920
cttacccgcc gccgtcagac tgttggcgat gcttctgtct tctcccaatc tcttcctctg    1980
ggcgcagctc ctcccgcttc tgaagagcca gccaaggatg ttccagacta cgctgatctg    2040
ttgcgcaagg tgcaggcaca cttcgacagc ttccgcgagg agtccgccac cgaccatgca    2100
gctttgaagc aacaggtcaa tgagttgtcc aggaagaaca gtgaattgat gagcgaaatt    2160
agccgctcta gcagtcagct tgttgccgcc acacagagag cggagcttct tcagggtaac    2220
ttcgatatgc tcaagaacga aaacgcgaaa atgcagaaac gctacgctac cctcctggag    2280
aacgctaacc ggcaggatat caggactcag caagctgccg aagatctggt ggagacgaag    2340
ggcctcgttg agagccttca acgggaaaat gccaacctca aggcagaaaa ggatctctgg    2400
aagaatatcg agaagagact catcgaggat aacgagacac tacgtaacga gagaggtcga    2460
cttgattctc ttaacgcgaa cctccaaacc attctcaatg agcgggaaca taccgatgct    2520
gagagtcgcc gtcgtttgca aagcagtgtg gagtctctcg aatcggagct tcaatccacc    2580
aagcggaagc ttaacgatga ggttgaggaa ggaaagaagg catcgctgcg tagggaatac    2640
gaacatgagc aaagtcagaa gcgaattgac gacttggtga cgagcttggg cgcagctcgg    2700
gaggagttag tggctgcgaa gacgacaaga gatcacttgc aatcgagagt cgatgaactc    2760
actgtcgagc tgcgtagcgc cgaagagcgc ctccaggtcg tgcagactaa gcccagtgtg    2820
tctgctgctc ctactgaagc gcctgcggtt ccggaggaag gccaggagag tggcctgaca    2880
cgcgagcagg aacttggtat tgaagtttcc gagctccgtc gtgatttgga gttgacaaag    2940
aatgagcttc agcacgctga agagcgggtg gaggattata aggctatcag tcagcagagc    3000
gaagagcgtc tgcagtctgt cactgagacc caggaacagt atcgggagga aacggagcgt    3060
ctcatcgaag agaaggataa gaagattcag gacctcgaaa agcgcatcga agaaatttcc    3120
gccgagcttt cgactacgaa cggcgaactt accaaattgc gtgacgagca aggggaggct    3180
agccgacatt tggaggagca gaaggccgcg ctggaagcag agatcacaag gctgaaggac    3240
gagaatgaaa ggcagatcgc ttctgcccaa ttccaccagg aagatctcaa ggcacaagct    3300
gaaatcgcgc agcatgccca gcagaactat gagagcgaac tgctcaagca tgctgaagcc    3360
gcgaagaatc tacaattggt ccggtccgaa gctaaccagt tgaagctgga agttgtcgaa    3420
ctgcggacac aggccgacac tttcaagaag gaccttgctc agaaggagga aagctggacc    3480
gagatcaagg ataggtatga gagcgagctt acggaactgc aaaagcgccg cgaggaagtt    3540
ctccaccaga actctttgtt gcatacccaa ctcgagaata ttacaaacca gatcgcagcc    3600
ctccagcgtg accgggctaa cattcctgag ggagatgagg acggagaggc cggcgcgccc    3660
aacctcgaag gcctccaggg ggtgatcaag ttcctgcgtc gggagaagga gatcgttgat    3720
gtgcagtacc atctgtcaac ccaggaaagc aagcgtcttc gtcagcaact cgactacact    3780
cagacccagc ttgacgaggc ccggcttaag ctcgagcagc agcgtcgcgc ggctgccgac    3840
agtgaacata gcgccctcag ccacaacaag ctgatggaga ccctgaacga actgaatctg    3900
```

```
ttccgcgaga gtagtgttac gctgcgtaac caggttaagc aggcggaaac ctcacttgcg    3960
gagaagtcct ctcgcatcga agaacttgtt cagcaaatac agccgctaga gactagaatc    4020
agggaactgg agaacactgt agagacaaag gatggagagc tgaagttgct acaggatgat    4080
agggaccggt ggcagcaacg tacgcagaat atcctgcaga agtacgaccg ggtagatccc    4140
gcggaaatgg aaggtctgaa ggagaagctc gagactttgg aaaaggagcg ggatgaggcc    4200
attgctgccc gggacactct acagacccag gctgctgctt cccagaaca gctgaagcat    4260
gcggaggatc gcgtgcaaga actgcgcacg aagctcacgg accaattcaa ggctcggtcc    4320
aaggagttga ctggccgtat aaacgctaaa caggtggagc tcaacacggt tatgcaggag    4380
aaggaagtca ttcaagaaga actcaagacg actcgggagg aattgaatga gctgaagacg    4440
aagatggccg agcaacccgc agctcctgct gccccagctg ttgaaggagc tactggtgtt    4500
gactcaacgc ctgcctctca gttccctgcg ccaacaacgc agccgcctgc cgcttctgac    4560
gatcaacgcg tgaaggctct ggaagagaag gtgcagcgcc tcgaggcagc tcttgcggag    4620
aaggagacgg cgttgaccgc gaaggaaacg gagcacgagg cgaagatcaa ggagcggtcc    4680
gacaagctga aggagatgtt caacagtaag ctggctgaga ttcgagctgc gcaccggcaa    4740
gaagttgagc ggttgaaatc cagtcaacca gccgctcctc aagaacctgg aaccccagct    4800
cccaaacccg agcaggtgcc agcaacgccg gcgactcctg cggctgctcc tgcgacaccc    4860
tccaaggaca ctgggctgcc tgaactgaca gatgcgcaag ccagggagct cgttgccaag    4920
aacgagacga ttcgtaacat cattcggagc aacatccgca cccaggtggc taagcaaaag    4980
gaatccgaca agcaggaaag ccaggccaac caggaggcta tgagcacact ggagcagaag    5040
tttaacgaag agagagaagc gttgaagaag gcccacgaag agggtgtgga ggagaagatc    5100
aaggctgctg tcgagttgtc ggacaagaaa tcactggcga aactaagcat gctggacacc    5160
cggtaccgga cagcccaggc caagatcgat gtggttcaga aggctgctac ggagacgcct    5220
cagaagcctg ttgtcgaagt ctgggaggtc gcaaagacca ctagagcgcc tccagcggcg    5280
caggccaagc ccgcccaggt ggcatctcct gcgcctgcac cgtctcccgc gcccgctgcg    5340
gcccaggcaa caccggtggt gccatcgccg tcgcctgccc caacggctac tcctgcggcc    5400
acacccgcag ctacgcctgc agctgcaccc caggcccagc ctgtggagcc tgcagcagca    5460
tccacagccg agccagcttc tgctgaatct acgccgcaga caggtgcccc agcgcagcag    5520
caaccgcagc aacaacctgc gcctgaacag gccgcacaac aacaagctgc acctgcgacg    5580
gctcagccag ctaccaatgc tcctccaaac ccattcggtc agagccagaa caagcagccc    5640
tcgtcgttgc ccagcaagcc cccagccggt aatgcttctg gccttatgcg agcactgacg    5700
tccggactgc ccgtcgcgcg aggcggcagg gccggcggcc gcggtgggtc gcaagcgaat    5760
actttcggtc agcaacaggg acaacagcaa caggcgcaag gtcaggctca agcccagcag    5820
caagctccta gccagcgcgg ctctggtcta ccccggggtc gtggcggacg cggaggccat    5880
ggacgcggcg gaaaccaaaa tgtacagccc acgaatgccg ctcagcaagg acaggctagc    5940
ccaggtcgct cgctgaatgc cggtgctcgc cagttcgtcc ctcagggcaa caagcgtgct    6000
cgcgaggatg gagaagctgg aggcgaagga gcaaccagtg gaggaaagcg catgagggga    6060
ggaggtcata cccgggggtc atag                                          6084
```

MANIPULATION OF GENES INVOLVED IN SIGNAL TRANSDUCTION TO CONTROL FUNGAL MORPHOLOGY DURING FERMENTATION AND PRODUCTION

CROSS-REFERENCE TO RELATED APPLICATIONS

This application is a Continuation of U.S. application Ser. No. 16/433,624, filed Jun. 6, 2019 (now U.S. Pat. No. 11,028,401 issued Jun. 8, 2021), which claims the benefit of priority to U.S. Provisional Application Ser. No. 62/681,604, filed Jun. 6, 2018, each of which is herein incorporated by reference in its entirety for all purposes.

FIELD

The present disclosure is directed to regulating hyphal growth of fungal cells in various growth conditions. The disclosed regulation of hyphal growth entails the genetic manipulation of filamentous fungi to generate fungal production strains with restricted hyphal growth under production conditions. The resultant fungal production strains are well-suited for growth in submerged cultures, e.g., for the large-scale production of products of interest (e.g., antibiotics, metabolites, proteins, etc.) for commercial applications.

STATEMENT REGARDING SEQUENCE LISTING

The Sequence Listing associated with this application is provided in text format in lieu of a paper copy and is hereby incorporated by reference into the specification. The name of the text file containing the Sequence Listing is ZYMR_015_02US_SeqList_ST25.txt. The text file is 314,221 bytes, was created on Apr. 30, 2021, and is being submitted electronically via EFS-Web.

BACKGROUND

Eukaryotic cells are preferred organisms for the production of polypeptides and secondary metabolites, hi fact, filamentous fungi are capable of expressing native and heterologous proteins to high levels, making them well-suited for the large-scale production of enzymes and other proteins for industrial, pharmaceutical, animal health and food and beverage applications. However, use of filamentous fungi for large-scale production of products of interest often requires genetic manipulation of said fungi as well as use of automated machinery and equipment and certain aspects of the filamentous fungal life cycle can make genetic manipulation and handling difficult.

For example, DNA introduced into a fungus integrates randomly within a genome, resulting in mostly random integrated DNA fragments, which quite often can be integrated as multiple tandem repeats (see, for example, Casqueiro et al., 1999, J. Bacteriol. 181:1181-1188). This uncontrolled "at random multiple integration" of an expression cassette can be a potentially detrimental process, which can lead to unwanted modification of the genome of the host.

Additionally, present transfection systems for filamentous fungi can be very laborious (see for review Fincham, 1989, Microbiol. Rev. 53:148-170) and relatively small scale in nature. This can involve protoplast formation, viscous liquid handling (i.e., polyethylene glycol solutions), one-by-one swirling of glass tubes and subsequent selective plating. Further, conditions for protoplasting can be difficult to determine and yields can often be quite low. Moreover, the protoplasts can contain multiple nuclei such that introduction of a desired genetic manipulation can lead to the formation of heterokaryotic protoplasts that can be difficult to separate from homokaryotic protoplasts.

Further, typical filamentous fungal cells, including those derived from protoplasts, grow as long fibers called hyphae that can form dense networks of hyphae called mycelium. These hyphae can contain multiple nuclei that can differ from one another in genotype. The hyphae can differentiate and form asexual spores that can be easily dispersed in the air. If the hyphae contain nuclei of different genotypes, the spores will also contain a mixture of nuclei. Due to this aspect of fungal growth, genetic manipulation inherently results in a mixed population that must be purified to homogeneity in order to assess any effect of the genetic changes made. Further, in an automated environment, the spores can cause contamination of equipment that could negatively impact the ability to purify strains and may contaminate any other work performed on the equipment.

To mitigate the aerial dispersal of spores, the filamentous fungi can be grown in submerged cultures. However, the mycelium formed by hyphal filamentous fungi growth in submerged cultures can affect the rheological properties of the broth. Generally, the higher the viscosity of the broth, the less uniform the distribution of oxygen and nutrients, and the more energy required to agitate the culture. In some cases, the viscosity of the broth due to hy phal filamentous fungal growth becomes sufficiently high to significantly interfere with the dissolution of oxygen and nutrients, thereby adversely affecting the growth of the fungi and ultimately the yield and productivity of any desired product of interest.

Thus, there is a great need in the art for new methods of engineering filamentous fungi, which do not suffer from the aforementioned drawbacks inherent, with traditional strain building programs in fungi and greatly accelerate the process of discovering and consolidating beneficial mutations.

The current invention overcomes many of the challenges inherent in genetically manipulating filamentous fungi in an automated, high-throughput platform. The methods provided herein are designed to generate fungal production strains with a desired morphology by incorporating genetic changes using automated co-transformation combined with automated screening of transformants thereby allowing exchange of genetic traits between two strains without going through a sexual cross.

SUMMARY OF THE DISCLOSURE

In one aspect, provided herein is a variant strain of filamentous fungus derived from a parental strain, wherein cells of the variant, strain possess a non-mycelium, pellet forming phenotype as compared to cells of the parental strain when grown in a submerged culture due to the variant strain possessing a genetic alteration in one or more genes of an osmotic response pathway that causes cells of the variant strain to produce a reduced or substantially reduced amount and/or less or substantially less active form of functional protein encoded by the one or more genes of the osmotic response pathway as compared to cells of the parental strain when grown under submerged culture conditions. In some cases, the variant strain sporulates normally as compared to the parental strain when grown under non-submerged growth conditions. In some cases, the filamentous fungus is selected from *Achlya, Acremonium, Aspergillus, Aureobasidium, Bjerkandera, Ceriporiopsis, Cephalosporium,*

Chrysosporium, Cochliobolus, Corynascus, Cryphonectria, Cryptococcus, Coprinus, Coriolus, Diplodia, Endolhis, Fusarium, Gibberella, Gliocladium, Humicola, Hypocrea, Myceliophthora (e.g., Myceliophthora thermophila), Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verlicillium, Volvariella species or teleomorphs, or anamorphs, and synonyms or taxonomic equivalents thereof. In some cases, the filamentous fungus is Aspergillus niger (A. niger) or teleomorphs or anamorphs thereof. In some cases, the one or more genes of the osmotic response pathway are filamentous fungal orthologues of yeast osmotic response pathway genes found in Table 7. In some cases, the one or more genes of the osmotic response pathway are A. niger orthologues of yeast osmotic response pathway genes found in Table 7. In some cases, the one or more genes of the osmotic response pathway are selected from genes with nucleic acid sequences of SEQ ID NO: 9, 10, 11, 12, 13 or any combination thereof. In some cases, the one or more genes of the osmotic response pathway is an A. niger orthologue of a Saccharomyces cerevisiae (S. cerevisiae) SLN1 gene or a Neurospora crassa (N. crassa) nik1 gene. In some cases, the A. niger orthologue of the S. cerevisiae SLN1 gene or the N. crassa nik1 gene is a non-SNP containing version of the nucleic acid sequence of SEQ ID NO: 7. In some cases, the genetic alteration is selected from replacement of a native promoter of the one or more genes with a promoter that weakly expresses the one or more genes as compared to the native promoter, replacement of the one or more genes with a mutated form of the one or more genes, replacement of the one or more genes with a selectable marker, or a combination thereof. In some cases, the promoter that weakly expresses the one or more genes as compared to the native promoter is selected from an amyB promoter or a manB promoter. In some cases, the promoter that weakly expresses the one or more genes as compared to the native promoter comprises, consist essentially of or consists of a nucleic acid sequence selected from SEQ ID NO: 1 or SEQ ID NO: 2. In some cases, the selectable marker is selected from an auxotrophic marker gene, a colorimetric marker gene, antibiotic resistance gene, or a directional marker gene. In some cases, the colorimetric marker gene is an aygA gene. In some cases, the auxotrophic marker gene is selected from an argB gene, a trpC gene, a pyrG gene, or a met3 gene. In some cases, the directional marker gene is selected from an aeetamidase (amdS) gene or a nitrate reductase gene (niaD). In some cases, the antibiotic resistance gene is a ble gene, wherein the Me gene confers resistance to pheomycin. In some cases, the mutated form of the one or more genes of the osmotic stress response pathway comprises a single nucleotide polymorphism. In some cases, the mutated form of the one or more genes of the osmotic response pathway is an A. niger orthologue of a S. cerevisiae SLN1 gene or a N. crassa nik1 gene, wherein the mutated form of the A. niger orthologue of the S. cerevisiae SLN1 gene or the N, crassa nik1 gene is a nucleic acid sequence of SEQ ID NO. 7. In some cases, the variant strain further comprises a genetic alteration of one or more genes selected from a non-SNP containing version of the genes with nucleic acid sequences of SEQ ID NO: 5, 6, 8 or any combination thereof. In some cases, the genetic alteration is selected from replacement of a native promoter of the one or more genes with a promoter that weakly expresses the one or more genes as compared to the native promoter, replacement of the one or more genes with a mutated form of the one or more genes, replacement of the one or more genes with a selectable marker, or a combination thereof. In some cases, the promoter that weakly expresses the one or more genes as compared to the native promoter is selected from an amyB promoter or a manB promoter. In some cases, the promoter that weakly expresses the one or more genes as compared to the native promoter comprises, consist essentially of or consists of a nucleic acid sequence selected from SEQ ID NO: 1 or SEQ ID NO: 2. In some cases, the selectable marker is selected from an auxotrophic marker gene, a colorimetric marker gene, antibiotic resistance gene, or a directional marker gene. In some cases, the colorimetric marker gene is an aygA gene. In some cases, the auxotrophic marker gene is selected from an argB gene, a trpC gene, a pyrG gene, or a met3 gene. In some cases, the directional marker gene is selected from an acetamidase (amdS) gene or a nitrate reductase gene (niaD). In some cases, the antibiotic resistance gene is a ble gene, wherein the ble gene confers resistance to pheomycin. In some cases, the mutated form of the one or more genes comprises a single nucleotide polymorphism. In some cases, the mutated form of the one or more genes is a nucleic acid sequence selected from SEQ ID NO: 5, 6 or 8.

In another aspect, provided herein is a filamentous fungal host cell comprising a promoter operably linked to a gene that regulates morphology of the host cell, wherein the promoter is heterologous to the gene, wherein the promoter has a nucleic sequence selected from the group consisting of SEQ ID NOs. 1-4. In some cases, the filamentous fungal host cell has a non-mycelium, pellet morphology when grown under submerged culture conditions in fermentation media as compared to a reference filamentous fungal host cell without the promoter operably linked to the gene that regulates morphology of the host cell. In some cases, the fermentation media comprises at least 14 ppb of manganese. In some cases, the fermentation media is free or substantially free of chelating agents (e.g., less than 5%, 4%, 3%, 2%, or 1% of the amount or concentration of chelating agent found in fermentation media known in the art for producing a product of interest such as, for example, citric acid). In some cases, the fermentation media is free of chelating agents. In some cases, the filamentous fungal host cell produces an amount of a product of interest that is at least equal to the amount produced by the reference filamentous fungal host cell without the promoter operably linked to the gene that regulates morphology of the host-cell. In some cases, the product of interest is citric acid or an enzyme of interest. In some cases, the gene that regulates morphology is selected from one or more genes of an osmotic response pathway, non-SNP containing versions of the genes with nucleic acid sequences SEQ ID NO: 5, 6, 8, or any combination thereof. In some cases, the gene that regulates morphology is a wild-type or mutated form of the gene. In some cases, the filamentous fungal host cell is selected from Achlya, Acremonium, Aspergillus, Aureohasidium, Bjerkandera, Ceriporiopsis, Cephalosporium, Chrysosporium, Cochliobolus, Corynascus, Cryphonectria, Cryptococcus, Coprims, Coriolus, Diplodia, Endothis, Fusarium, Gibberella, Gliocladium, Humicola, Hypocrea, Myceliophthora (e.g., Myceliophthora thermophila), Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillinm, Volvariella species or teleomorphs, or anamorphs, and synonyms or taxonomic equivalents thereof. In some cases, the filamentous fungal host cell is A. niger or teleomorphs or anamorphs thereof. In some cases, the one or more genes of the osmotic response pathway are filamentous fungal orthologues of yeast osmotic response pathway genes found in Table 7. In some cases, the one or more genes of the osmotic response pathway are *A. niger* orthologues of yeast osmotic response pathway genes found in Table 7. In some cases, the one or more genes of the osmotic response pathway are selected from genes with nucleic acid sequences of SEQ ID NO: 9, 10, 11, 12, 13 or any combination thereof. In some cases, the one or more genes of the osmotic response pathway is an *A. niger* orthologue of a *S. cerevisiae* SLN1 gene or a *N. crassa* nik1 gene. In some cases, the *A. niger* orthologue of the *S. cerevisiae* SEN1 gene or the *N. crassa* nik1 gene is a non-SNP containing version of nucleic acid sequence of SEQ ID NO: 7. In some cases, the *A. niger* orthologue of the *S. cerevisiae* SLN1 gene or the *N. crassa* nik1 gene is a nucleic acid sequence of SEQ ID NO: 7. In some cases, the promoter is selected from the nucleic acid sequence of SEQ ID NO: 1 or 2.

In yet another aspect, provided herein is a filamentous fungus host, cell comprising a heterologous modification of one or more genes of the host cell's osmotic response pathway, wherein the modified one or more genes has reduced activity and/or reduced expression relative to a parental filamentous fungal host cell lacking the modified one or more genes of the host cell's osmotic response pathway. In some cases, the filamentous fungal host cell has a non-mycelium, pellet morphology when grown under submerged culture conditions in fermentation media. In some cases, the filamentous fungal host cell is selected from *Achlya, Acremonium, Aspergillus, Aureobasidium, Bjerkcmdera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Promotes, Tolypocladium, Trichoderma, Verticillium, Volvariella* species or teleomorphs, or anamorphs, and synonyms or taxonomic equivalents thereof. In some cases, the filamentous fungal host cell is *A. niger* or teleomorphs or anamorphs thereof. In some cases, the one or more genes of the osmotic response pathway are filamentous fungal orthologues of yeast osmotic response pathway genes found in Table 7. In some cases, the one or more genes of the osmotic response pathway are *A. niger* orthologues of yeast osmotic response pathway genes found in Table 7. In some cases, the one or more genes of the osmotic response pathway are selected from genes with nucleic acid sequences of SEQ ID NO: 9, 10, 11, 12, 13 or any combination thereof. In some cases, the one or more genes of the osmotic response pathway is an *A. niger* orthologue of the *S. cerevisiae* SLN1 gene or the *N. crassa* nik1 gene. In some cases, the *A. niger* orthologue of the *S. cerevisiae* SLN1 gene or the *N. crassa* nik1 gene is a non-SNP containing version of a nucleic acid sequence of SEQ ID NO: 7. In some cases, the heterologous modification is selected from replacement of a native promoter of the one or more genes with a promoter that weakly expresses the one or more genes as compared to the native promoter, replacement of the one or more genes with a mutated form of the one or more genes, replacement of the one or more genes with a selectable marker, or a combination thereof. In some cases, the promoter that weakly expresses the one or more genes as compared to the native promoter is selected from an amyB promoter or a manB promoter. In some cases, the promoter that weakly expresses the one or more genes as compared to the native promoter comprises, consist essentially of or consists of a nucleic acid sequence selected from SEQ ID NO: 1 or SEQ ID NO: 2. In some cases, the selectable marker is selected from an auxotrophic marker gene, a colorimetric marker gene, antibiotic resistance gene, or a directional marker gene. In some cases, the colorimetric marker gene is an aygA gene. In some cases, the auxotrophic marker gene is selected from an argB gene, a trpC gene, a pyrG gene, or a met3 gene. In some cases, the directional marker gene is selected from an acetamidase (amdS) gene or a nitrate reductase gene (niaD), In some cases, the antibiotic resistance gene is a ble gene, wherein the ble gene confers resistance to pheomycin. In some cases, the mutated form of the one or more genes of the osmotic stress response pathway comprises a single nucleotide polymorphism. In some cases, the one or more genes of the osmotic stress pathway is an *A. niger* orthologue of the *S. cerevisiae* SLN1 gene of the *N. crassa* nik1 gene, wherein the mutated form of the *A. niger* orthologue of the *S. cerevisiae* SLN1 gene or the *N. crassa* nik1 gene is the nucleic acid sequence of SEQ ID NO: 7. In some cases, the filamentous fungal host cell further comprises a genetic alteration of one or more genes selected from a non-SNP containing version of the genes with nucleic acid sequences of SEQ ID NO: 5, 6, 8 or any combination thereof. In some cases, the genetic alteration is selected from replacement of a native promoter of the one or more genes with a promoter that weakly expresses the one or more genes as compared to the native promoter, replacement of the one or more genes with a mutated form of the one or more genes, replacement of the one or more genes with a selectable marker, or a combination thereof. In some cases, the promoter that weakly expresses the one or more genes as compared to the native promoter is selected from an amyB promoter or a manB promoter. In some cases, the promoter that weakly expresses the one or more genes as compared to the native promoter comprises, consist essentially of or consists of a nucleic acid sequence selected from SEQ ID NO: 1 or SEQ ID NO: 2. In some cases, the selectable marker is selected from an auxotrophic marker gene, a colorimetric marker gene, antibiotic resistance gene, or a directional marker gene. In some cases, the colorimetric marker gene is an aygA gene. In some cases, the auxotrophic marker gene is selected from an argB gene, a trpC gene, a pyrG gene, or a met3 gene. In some cases, the directional marker gene is selected from an acetamidase (amdS) gene or a nitrate reductase gene (niaD). In some cases, the antibiotic resistance gene is a ble gene, wherein the Me gene confers resistance to pheomycin. In some cases, the mutated form of the one or more genes comprises a single nucleotide polymorphism. In some cases, the mutated form of the one or more genes is a nucleic acid sequence selected from SEQ ID NO: 5, 6 or 8.

In still another aspect, provided herein is a fermentation broth comprising at least 14 ppb of manganese and a filamentous fungal cell comprising a non-mycelium pellet phenotype, wherein the broth is free or substantially free of a chelating agent (e.g., less than 5%, 4%, 3%, 2%, or 1% of the amount or concentration of chelating agent found in fermentation broth known in the art for producing a product of interest such as, for example, citric acid), and wherein the filamentous fungal cell comprises one or more genetically altered genes from an osmotic response pathway of the filamentous fungal cell. In some cases, the one or more genetically altered genes from the osmotic response pathway are operably linked to a heterologous promoter. In some cases, the heterologous promoter is selected from SEQ ID NO: 1 or 2. In some cases, the one or more genetically altered genes from the osmotic response pathway comprises a mutation. In some cases, the mutation in a SNP. In some cases, the filamentous fungal host, cell is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof. In some cases, the filamentous fungal host cell is *A. niger* or teleomorphs or anamorphs thereof. In some cases, the one or more genetically altered genes of the osmotic response pathway are genetically altered filamentous fungal orthologues of yeast osmotic response pathway genes found in Table 7. In some cases, the one or more genetically altered genes of the osmotic response pathway are genetically altered *A. niger* orthologues of yeast osmotic response pathway genes found in Table 7. In some cases, the one or more genetically altered genes of the osmotic response pathway are genetically altered forms of genes with nucleic acid sequences selected from 8EQ ID NO: 9, 10, 11, 12, 13 or any combination thereof. In some cases, the one or more genetically altered genes of the osmotic response pathway is a genetically altered *A. niger* orthologue of the *S. cerevisiae* SLN1 gene or the *A. crassa* nik1 gene. In some cases, the genetically altered *A. niger* orthologue of the *S. cerevisiae* SLN1 gene or the *N. crassa* nik1 gene is a gene with a nucleic acid sequence of SEQ ID NO: 7.

In one aspect, provided herein is a method for generating a promoter swap filamentous fungal strain library, comprising the steps of: a. providing one or more target genes that play a role in morphology to a base filamentous fungal strain, and a promoter ladder, wherein said promoter ladder comprises a plurality of promoters exhibiting different expression profiles in the base filamentous fungal strain; and b. engineering the genome of the base filamentous fungal strain, to thereby create an initial promoter swap filamentous fungal strain library comprising a plurality of individual filamentous fungal strains with unique genetic variations found within each strain of said plurality of individual filamentous fungal strains, wherein each of said unique genetic variations comprises one or more of the promoters from the promoter ladder operably linked to one of the one or more target genes that play a role in the osmotic stress response to the base filamentous fungal strain. In some cases, the promoter ladder comprises the promoters found in Table 2. In some cases, the one or more target genes that play a role in morphology comprise a disruption. In some cases, the disruption is a SNP, a missense mutation, a nonsense mutation, a deletion and/or an insertion. In some cases, the one or more target genes that play a role in morphology are selected from one or more genes of an osmotic response pathway, non-SNP containing versions of genes with nucleic acid sequences SEQ ID NO: 5, 6, 8, or any combination thereof. In some cases, the filamentous fungal host cell is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof. In some cases, the filamentous fungal host cell is *A. niger* or teleomorphs or anamorphs thereof. In some cases, the one or more genes of the osmotic response pathway are filamentous fungal orthologues of yeast osmotic response pathway genes found in Table 7. In some cases, the one or more genes of the osmotic response pathway are *A. niger* orthologues of yeast osmotic response pathway genes found in Table 7. In some cases, the one or more genes of the osmotic response pathway are selected from genes with nucleic acid sequences of SEQ ID NO: 9, 10, 11, 12, 13 or any combination thereof. In some cases, the one or more genes of the osmotic response pathway is an *A. niger* orthologue of a *S. cerevisiae* SLN1 gene or a *N. crassa* nik1 gene. In some cases, the *A. niger* orthologue of the *S. cerevisiae* SLN1 gene or the *N. crassa* nik1 gene is a non-SNP containing version of nucleic acid sequence of SEQ ID NO: 7. In some cases, the *A. niger* orthologue of the *S. cerevisiae* SLN1 gene or the *N. crassa* nik1 gene is a nucleic acid sequence of SEQ ID NO: 7.

In another aspect, provided herein is a promoter swap method for improving the morphological phenotype of a production filamentous fungal strain, comprising the steps of: a. providing a plurality of target genes that play a role in morphology to a base filamentous fungal strain, and a promoter ladder, wherein said promoter ladder comprises a plurality of promoters exhibiting different expression profiles in the base filamentous fungal strain; b. engineering the genome of the base filamentous fungal strain, to thereby create an initial promoter swap filamentous fungal strain library comprising a plurality of individual filamentous fungal strains with unique genetic variations found within each strain of said plurality of individual filamentous fungal strains, wherein each of said unique genetic variations comprises one or more of the promoters from the promoter ladder operably linked to one of the plurality of target genes that play a role in morphology to the base filamentous fungal strain; c. screening and selecting individual filamentous fungal strains of the initial promoter swap filamentous fungal strain library for morphological phenotypic improvements over a reference filamentous fungal strain, thereby identifying unique genetic variations that confer morphological phenotypic improvements; d. providing a subsequent plurality of filamentous fungal microbes that each comprise a combination of unique genetic variations from the genetic variations present in at least two individual filamentous fungal strains screened in the preceding step, to thereby create a subsequent promoter swap filamentous fungal strain library; e. screening and selecting individual filamentous fungal strains of the subsequent promoter swap filamentous fungal strain library for morphological phenotypic improvements over the reference filamentous fungal strain, thereby identifying unique combinations of genetic variation that confer additional morphological phenotypic improvements; and f. repeating steps d)-e) one or more times, in a linear or non-linear fashion, until an filamentous fungal strain exhibits a desired level of improved morphological phenotype compared to the morphological phenotype of the production filamentous fungal strain, wherein each subsequent iteration creates a new promoter swap filamentous fungal strain library of microbial strains, where each strain in the new library comprises genetic variations that are a combination of genetic variations selected from amongst at least two individual filamentous fungal strains of a preceding library. In some cases, the subsequent promoter swap filamentous fungal strain library is a full combinatorial library of the initial promoter swap filamentous fungal strain library. In some cases, the subsequent promoter swap filamentous fungal strain library is a subset of a full combinatorial library of the initial promoter swap filamentous fungal strain library. In some cases, the subsequent promoter swap filamentous fungal strain library is a full combinatorial library of a preceding promoter swap filamentous fungal strain library. In some cases, the subsequent promoter swap filamentous fungal strain library is a subset of a full combinatorial library of a preceding promoter swap filamentous fungal strain library. In some cases, the promoter ladder comprises the promoters found in Table 2. In some cases, the one or more target genes that play a role in morphology comprise a disruption. In some cases, the disruption is a SNP, a missense mutation, a nonsense mutation, a deletion and/or insertion. In some cases, the one or more target genes that play a role in morphology are selected from one or more genes of an osmotic response pathway, non-SNP containing versions of genes with nucleic acid sequences SEQ ID NO: 5, 6, 8, or any combination thereof. In some cases, the filamentous fungal host cell is selected from Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora (e.g., Myceliophthora thermophila), Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella species or teleomorphs, or anamorphs, and synonyms or taxonomic equivalents thereof. In some cases, the filamentous fungal host cell is A. niger or teleomorphs or anamorphs thereof. In some cases, the one or more genes of the osmotic response pathway are filamentous fungal orthologues of yeast osmotic response pathway genes found in Table 7. In some cases, the one or more genes of the osmotic response pathway are A. niger orthologues of yeast osmotic response pathway genes found in Table 7. In some cases, the one or more genes of the osmotic response pathway are selected from genes with nucleic acid sequences of SEQ ID NO: 9, 10, 11, 12, 13 or any combination thereof. In some cases, the one or more genes of the osmotic response pathway is an A. niger orthologue of a S. cerevisiae SLN1 gene or a N. crassa nik1 gene. In some cases, the A. niger orthologue of the S. cerevisiae SLN1 gene or the N. crassa nik1 gene is a non-SNP containing version of nucleic acid sequence of SEQ ID NO: 7. In some cases, the A. niger orthologue of the S. cerevisiae SLN1 gene or the N. crassa nik1 gene is a nucleic acid sequence of SEQ ID NO: 7. In some cases, the morphological phenotypic improvement comprises conferring the ability to form a non-mycelium pellet morphology when grown under submerged culture conditions. In some cases, the submerged culture conditions comprise a culture medium comprising at least 14 ppb of manganese and is free or substantially free of chelating agents (e.g., less than 5%, 4%, 3%, 2%, or 1% of the amount or concentration of chelating agent found in fermentation media known in the art for producing a product of interest such as, for example, citric acid). In some cases, the fermentation media is free of chelating agents.

BRIEF DESCRIPTION OF THE FIGURES

FIG. 22 also shows that deletion of nikA leads to slower growth and lower citric acid production in the base strain.

FIG. 23A shows titers of citric acid that were quantified using an enzymatic assay (Megazyme; K-CITR) from cultures grown in Citric Acid Production media for 96 hours in shake flasks. Strains were grown in triplicate. Error bars indicate one standard deviation from the mean. FIG. 23B shows a graph of Oneway ANOVA with points of lines indicating 95% confidence intervals. Overall, FIG. 23A-B show's that introduction of the *Aspergillus* nikA gene comprising the point mutation into the base strain led to a 33% increase in citric acid titer.

DETAILED DESCRIPTION

Figure 1:
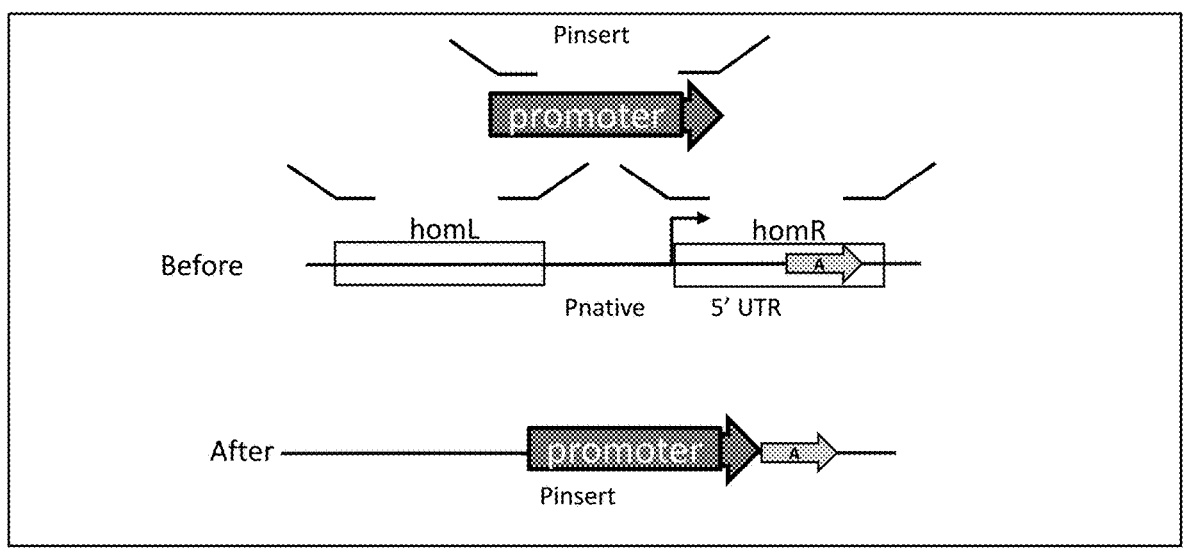
FIG. 1 illustrates an approach for promoter swapping in a filamentous fungal cell. In particular, a promoter swap design for a gene with an annotated promoter is shown.

The current disclosure overcomes many of the challenges inherent in genetically manipulating filamentous fungi in an automated, high-throughput platform. The methods provided herein are designed to generate fungal production strains with altered hyphal growth for more efficient growth in submerged cultures. The methods comprise incorporating genetic changes using automated co-transformation combined with automated screening of transformants thereby allowing exchange of genetic traits between two strains that affect the growth and morphology of the fungal cells without going through a sexual cross.

Definitions

While the following terms are believed to be well understood by one of ordinary skill in the art, the following definitions are set forth to facilitate explanation of the presently disclosed subject matter.

The term "a" or "an" refers to one or more of that entity, i.e., can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "cellular organism" "microorganism" or "microbe" should be taken broadly. These terms are used interchangeably and include, but are not limited to, the two prokaryotic domains, Bacteria and Archaea, as well as certain eukaryotic fungi and protists. In some embodiments, the disclosure refers to the "microorganisms" or "cellular organisms" or "microbes" of lists/tables and figures present in the disclosure. This characterization can refer to not only the identified taxonomic genera of the tables and figures, but also the identified taxonomic species, as well as the various novel and newly identified or designed strains of any organism in said tables or figures. The same characterization holds true for the recitation of these terms in other parts of the Specification, such as in the Examples.

The term "coenocyte" or "coenocytic organism" as used herein can refer to a multinucleate cell or an organism comprising a multinucleate cell. The multinucleate cell can result from multiple nuclear divisions without their accompanying cytokinesis, in contrast to a syncytium, which results from cellular aggregation followed by dissolution of the cell membranes inside the mass. Examples of coenocytic organisms as it pertains to the methods, compositions and systems provided herein can include protists (e.g., algae, protozoa, myxogastrids (slime molds), alveolates, plants, fungi (e.g., filamentous fungi), and/or metazoans (e.g., *Drosphila* spp).

The term "prokaryotes" is art recognized and refers to ceils that contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl), and extreme (hyper) *thermophilus* (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*), (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides*, Flavobacteria; (7) *Chlamydia*, (8) Green sulfur bacteria; (9) Green non-sulfur bacteria (also anaerobic phototrophs); (10) Radioresistant micrococci and relatives; (11) *Thermotoga* and *Thermosipho thermophiles*.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

The terms "genetically modified host cell," "recombinant host cell," and "recombinant strain" are used interchangeably herein and refer to host cells that have been genetically modified by the cloning and transformation methods of the present disclosure. Thus, the terms include a host cell (e.g., bacteria, yeast cell, fungal cell, CHO, human cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring organism from which it was derived. It is understood that in some embodiments, the terms refer not only to the particular recombinant host cell in question, but also to the progeny or potential progeny of such a host cell.

The term "wild-type microorganism" or "wild-type host cell" describes a cell that occurs in nature, i.e., a cell that has not been genetically modified.

The term "parent strain" or "parental strain" or "parent" may refer to a host cell from which mutant strains are derived. Accordingly, the "parent strain" or "parental strain" is a host cell or cell whose genome is perturbed by any manner known in the art and/or provided herein to generate one or more mutant strains. The "parent strain" or "parental strain" may or may not have a genome identical to that of a wild-type strain.

The term "genetically engineered" may refer to any manipulation of a host cell's genome (e.g. by insertion, deletion, mutation, or replacement of nucleic acids).

The term "control" or "control host cell" refers to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification(s) differentiating the treatment host cell. In some embodiments, the present disclosure teaches the use of parent strains as control host cells. In other embodiments, a host cell may be a genetically identical cell that lacks a specific promoter or SNP being tested in the treatment host cell.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present disclosure, in embodiments, relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype".

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment. The term "recombinant" refers to an organism having a new genetic makeup arising as a result of a recombination event.

As used herein, the term "phenotype" refers to the observable characteristics of an individual cell, cell culture, organism, or group of organisms, which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that re-arranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribonucleotides or deoxyribonucleotides, or analogs thereof.

This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "DNA scaffold" or "nucleic acid scaffold" refers to a nucleic acid scaffold that is either artificially produced or a naturally occurring sequence that is repurposed as a scaffold. In one embodiment of the present disclosure, the nucleic acid scaffold is a synthetic deoxyribonucleic acid scaffold. The deoxyribonucleotides of the synthetic scaffold may comprise purine and pyrimidine bases or other natural, chemically or biochemically modified, non-natural, or derivatized deoxyribonucleotide bases. As described in more detail herein, the nucleic acid scaffold of the present disclosure is utilized to spatially and temporally assemble and immobilize two or more proteins involved in a biological pathway, i.e. biosynthetic enzymes, to create a functional complex. The assembly and immobilization of each biological pathway protein on the scaffold occurs via the binding interaction between one of the protein-binding sequences, i.e., protein docking sites, of the scaffold and a corresponding DNA-binding portion of a chimeric biosynthetic enzyme. Accordingly, the nucleic acid scaffold comprises one or more subunits, each subunit comprising two or more protein-binding sequences to accommodate the binding of two or more different chimeric biological pathway proteins.

As used herein, a "DNA binding sequence" or "DNA binding site" refers to a specific nucleic acid sequence that is recognized and bound by a DNA-binding domain portion of a chimeric biosynthetic genes of the present disclosure. Many DNA-binding protein domains and their cognate binding partner recognition sites (i.e., protein binding sites) are well known in the art. For example, numerous zinc finger binding domains and their corresponding DNA protein binding target sites are known in the art and suitable for use in the present disclosure. Other DNA binding domains include, without limitation, leucine zipper binding domains and their corresponding DNA protein binding sites, winged helix binding domains and their corresponding DNA protein binding sites, winged helix-turn-helix binding domains and their corresponding DNA protein binding sites, HMG-box binding domains and their corresponding DNA protein binding sequences, helix-loop-helix binding domains and their corresponding DNA protein binding sequences, and helix-turn-helix binding domains and their corresponding DNA protein binding sequences. Other known DNA binding domains with known DNA protein binding sequences include the immunoglobulin DNA domain, B3 DNA binding domain, and TAL effector DNA binding domain. Nucleic acid scaffold subunits of the present disclosure may comprise any two or more of the aforementioned protein binding sites.

As used herein, the term "gene" refers to any segment of DNA associated with a biological function. Thus, genes include, but are not limited to, coding sequences and/or the regulatory sequences required for their expression Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "orthologue" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologues" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocol sin Molecular Biology (F. M Ausubel et al., eds., 1987) Supplement 30, section 7.718, Table 7.71. Some alignment programs are Mac Vector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "endogenous" or "endogenous gene," refers to the naturally occurring gene, in the location in which it is naturally found within the host cell genome. In the context of the present disclosure, operably linking a heterologous promoter to an endogenous gene means genetically inserting a heterologous promoter sequence in front of an existing gene, in the location where that gene is naturally present. An endogenous gene as described herein can include alleles of naturally occurring genes that have been mutated according to any of the methods of the present disclosure.

As used herein, the term "exogenous" is used interchangeably with the term "heterologous," and refers to a substance coming from some source other than its native source. For example, the terms "exogenous protein" or "exogenous gene" refer to a protein or gene from a non-native source or location, and that have been artificially supplied to a biological system.

As used herein, the term "heterologous modification" can refer to a modification coming from a source other than a source native to a particular biological system (e.g., a host cell as provided herein), or a modification from a source that is native to the particular biological system, but which is found in a non-native context/position/location. Thus, the modification is non-native or not naturally occurring in reference to a biological system (e.g., a host cell as provided herein, or non-native context/position/location within a host cell), in which said modification has been or will be introduced. The heterologous modification can therefore be considered artificially introduced to the biological system (e.g., a host cell as provided herein, or heterologous context/ position/location within a host). The modification can be a genetic or epigenetic variation, disruption or perturbation A genetic variation, disruption or perturbation can be, for example, replacement of a native promoter and/or terminator of a gene with a promoter and/or terminator that is not native to said host, or it can be a promoter and/or terminator from within the host organism that has been moved to a non-native heterologous context/position/location. A genetic variation, disruption or perturbation can be replacement of a native or naturally occurring gene with a non-native or naturally occurring gene such as, for example a selectable marker gene. Or, a genetic variation, disruption or perturbation can be replacement, or swapping, of a native or naturally occurring gene, with another native gene (e.g., promoter) from within the host genome, which is placed into a non-natural context/position/location. A genetic variation, disruption or perturbation can be replacement of a native or naturally occurring gene with a non-native or naturally occurring form of the gene. The non-native or naturally occurring form of the gene can be a mutant form of the gene not naturally found in a particular host cell and/or a mutant form of the gene not naturally found in a particular host cell operably linked to a heterologous promoter and/or terminator.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full-length molecule, up to and including the full-length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full-length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning. A Laboratory Manual ($3^{rd}$ ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g., at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 10 M Na+ ion, typically about 0.01 to 1.0 M Na+ ion concentration (or other salts) at pH 7.0 to 8.3 and the temperature is at least about 30° C. for short probes or primers (e.g., 10 to 50 nucleotides) and at least about 60° C. for long probes or primers (e.g., greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g., Ausubel et al., 1998 and Sambrook et al., 2001 In some embodiments, stringent conditions are hybridization in 0.25 M Na2HPO4 buffer (pH 7.2) containing 1 mM Na2EDTA, 0.5-20% sodium dodecyl sulfate at 45° C., such as 0.5%, 1%, 2%, 3%, 4%, 5%, 6%, 7%, 8%, 9%, 10%, 11%, 12%, 13%, 14%, 15%, 16%, 17%, 18%, 19% or 20%, followed by a wash in 5×SSC, containing 0.1% (w/v) sodium dodecyl sulfate, at 55° C. to 65° C.

As used herein, "promoter" refers to a DNA sequence capable of controlling the expression of a coding sequence or functional RNA. In some embodiments, the promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. A promoter for use in the methods and systems described herein can be inducible such that expression of a gene or genes under control of said promoter is regulated by the presence and/or absence of a specific agent. The inducible promoters can be any promoter whose transcriptional activity is regulated by the presence or absence of a chemical or a physical condition such as for example, alcohol, tetracycline, steroids, metal or other compounds known in the art or by the presence or absence of light or low or high temperatures. It is further recognized that since in most cases the exact boundaries of regulatory sequences have not been completely defined, DNA fragments of some variation may have identical promoter activity.

As used herein, "terminator" generally refers to a section of DNA sequence that marks the end of a gene in genomic DNA and is capable of stopping transcription. Terminators may be derived in their entirety from a native gene or be composed of different elements derived from different terminators found in nature, or even comprise synthetic DNA segments. It is understood by those skilled in the art that different terminators may direct the expression of a gene in different tissues or cell types, or at different stages of development, or in response to different environmental conditions.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source but arranged in a manner different than that found in nature. Such construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al, (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" means in this context the sequential arrangement of the promoter polynucleotide according to the disclosure with a further oligo- or polynucleotide, resulting in transcription of said further polynucleotide.

The term "product of interest" or "biomolecule" as used herein refers to any product produced by microbes from feedstock. In some cases, the product of interest may be a small molecule, enzyme, peptide, amino acid, organic acid, synthetic compound, fuel, alcohol, etc. For example, the product of interest or biomolecule may be any primary or secondary extracellular metabolite. The primary metabolite may be, inter alia, ethanol, citric acid, lactic acid, glutamic acid, glutamate, lysine, threonine, tryptophan and other amino acids, vitamins, polysaccharides, etc. The secondary metabolite may be, inter alia, an antibiotic compound like penicillin, or an immunosuppressant like cyclosporin A, a plant hormone like gibberellin, a statin drug like lovastatin, a fungicide like griseofulvin, etc. The product of interest or biomolecule may also be any intracellular component produced by a microbe, such as: a microbial enzyme, including, catalase, amylase, protease, pectinase, glucose isomerase, cellulase, hemicellulase, lipase, lactase, streptokinase, and many others. The intracellular component may also include recombinant proteins, such as: insulin, hepatitis B vaccine, interferon, granulocyte colony-stimulating factor, streptokinase and others. The product of interest may also refer to a "protein of interest".

The term "protein of interest" generally refers to any polypeptide that is desired to be expressed in a filamentous fungus. Such a protein can be an enzyme, a substrate-binding protein, a surface-active protein, a structural protein, or the like, and can be expressed at high levels, and can be for the purpose of commercialization. The protein of interest can be encoded by an endogenous gene or a heterologous gene relative to the variant strain and/or the parental strain. The protein of interest can be expressed intracellularly or as a secreted protein. If the protein of interest is not naturally secreted, the polynucleotide encoding the protein may be modified to have a signal sequence in accordance with techniques known in the art. The proteins, which are secreted may be endogenous proteins which are expressed naturally but can also be heterologous. Heterologous means that the gene encoded by the protein is not produced under native condition in the filamentous fungal host cell. Examples of enzymes which may be produced by the filamentous fungi of the disclosure are carbohydrases, e.g.

cellulases such as endoglucanases, beta-glucanases, cellobiohydrolases or beta-glucosidases, hemicellulases or pectinolytic enzymes such as xylanases, xylosidases, mannanases, galactanases, galactosidases, rhamnogalacturonases, arabanases, galacturonases, lyases, or amylolytic enzymes; phosphatases such as phytases, esterases such as lipases, proteolytic enzymes, oxidoreductases such as oxidases, transferases, or isomerases.

The term "carbon source" generally refers to a substance suitable to be used as a source of carbon for cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a product of interest (e.g., small molecule, peptide, synthetic compound, fuel, alcohol, etc.) in a fermentation process. However, a feedstock may contain nutrients other than a carbon source.

The term "volumetric productivity" or "production rate" is defined as the amount of product formed per volume of medium per unit of time Volumetric productivity can be reported in gram per liter per hour (g/L/h).

The term "specific productivity" is defined as the rate of formation of the product. Specific productivity is herein further defined as the specific productivity in gram product per gram of cell dry weight (CDW) per hour (g/g CDW/h). Using the relation of CDW to $OD_{600}$ for the given microorganism specific productivity can also be expressed as gram product per liter culture medium per optical density of the culture broth at 600 nm (OD) per hour (g/L/h/OD).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product.

The term "titre" or "titer" is defined as the strength of a solution or the concentration of a substance in solution. For example, the titre of a product of interest (e.g., small molecule, peptide, synthetic compound, fuel, alcohol, etc.) in a fermentation broth is described as g of product of interest in solution per liter of fermentation broth (g/L).

The term "total titer" is defined as the sum of all product of interest produced in a process, including but not limited to the product of interest in solution, the product of interest in gas phase if applicable, and any product of interest removed from the process and recovered relative to the initial volume in the process or the operating volume in the process.

As used herein, the term "HTP genetic design library" or "library" refers to collections of genetic perturbations according to the present disclosure. In some embodiments, the libraries of the present disclosure may manifest as i) a collection of sequence information in a database or other computer file, ii) a collection of genetic constructs encoding for the aforementioned series of genetic elements, or iii) host cell strains comprising said genetic elements. In some embodiments, the libraries of the present disclosure may refer to collections of individual elements (e.g., collections of promoters for PRO swap libraries, or collections of terminators for STOP swap libraries). In other embodiments, the libraries of the present disclosure may also refer to combinations of genetic elements, such as combinations of promoter::genes, gene:terminator, or even promoter:gene: terminators. In some embodiments, the libraries of the present disclosure further comprise meta data associated with the effects of applying each member of the library in host organisms. For example, a library as used herein can include a collection of promoter::gene sequence combinations, together with the resulting effect of those combinations on one or more phenotypes such as changes in morphology when grown in submerged cultures in a particular species, thus improving the future predictive value of using said combination in future promoter swaps.

As used herein, the term "SNP" can refer to Small Nuclear Polymorphism(s). In some embodiments, SNPs of the present disclosure should be construed broadly, and include single nucleotide polymorphisms, sequence insertions, deletions, inversions, and other sequence replacements. As used herein, the term "non-synonymous" or non-synonymous SNPs" refers to mutations that lead to coding changes in host cell proteins.

A "high-throughput (HTP)" method of genomic engineering may involve the utilization of at least one piece of automated equipment (e.g., a liquid handler or plate handler machine) to carry out at least one-step of said method.

The terms "substantially reduced" and "substantially less" are used interchangeably herein and, when referring to an expression level or amount or an activity level of a protein or enzyme, can refer to a lowering of said amount or activity by a percentage or range of percentages as compared to or versus a control or reference level or activity of said protein or enzyme. The terms "substantially reduced" and "substantially less" can refer to a lowering of an amount or level of a protein or enzyme or an activity of an enzyme by at least, at most, exactly or about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% as compared to or versus a control or reference (e.g., a control or reference level or activity of said protein or enzyme). The terms "substantially reduced" and "substantially less" can refer to a lowering of an amount or level of a protein or enzyme or activity of an enzyme (e.g., enzymatic activity) by 1%-5%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95% or 95%-100%, inclusive of the endpoints, as compared to or versus a control or reference (e.g., a control or reference level or activity of said protein or enzyme). The terms "substantially reduced" and "substantially less" can also mean that the amount of a protein or enzyme or the activity of an enzyme can be at least, at most, exactly or about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the amount of control or reference version of said protein or enzyme or the activity of said enzyme. The terms "substantially reduced" and "substantially less" can also mean that the amount of a protein or enzyme or the activity of an enzyme is 1%-5%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95% or 95%-100%, inclusive of the endpoints, of the amount of a control or reference version of said protein or enzyme or the activity of an enzyme. With regards to a level or amount of a protein or enzyme, the control or reference can be a level or amount of said protein or enzyme in a control or reference cell. In one embodiment, the tested protein or enzyme in a control of reference cell does not have a heterologous modification. With regards to activity of an enzyme, the control or reference can be the activity of said protein or enzyme in a control or reference cell. In one embodiment, the tested protein or enzyme in a control of reference cell does not have a heterologous modification.

The level or activity of a protein or enzyme provided herein can be measured within a cell or after extraction and/or isolation from a cell (e.g., in vitro). In some cases, the level or amount of a gene encoding a protein of interest is measured or determined. The level or amount of a gene provided herein can be measured within a cell or after extraction from a cell (e.g., in vitro). In some cases, the activity of an enzyme encoded by a gene provided herein is measured or determined. The activity (e.g., specific activity) of an enzyme encoded by a gene provided herein can be measured within a cell or after extraction from a cell (e.g., in vitro). The assay utilized to measure the level or amount of expression of a gene or protein provided herein can be high-throughput in nature. The assay utilized to measure the activity of an enzyme encoded by a gene provided herein can be high-throughput in nature.

The level or amount of a gene provided herein can be measured using any assay known in the art for measuring a level or amount of a gene at the nucleic acid level. Examples of suitable assays for determining or measuring the levels of nucleic acid (e.g., a gene provided herein) can be selected from microarray analysis, RT-PCR such as quantitative RT-PCR (qRT-PCR), serial analysis of gene expression (SAGE), RNA-seq, Northern Blot, digital molecular barcoding technology, for example, Nanostring Counter Analysis, and TaqMan quantitative PCR assays. Other methods of mRNA detection and quantification can be applied, such as mRNA in situ hybridization. mRNA in situ hybridization can be measured using QuantiGene ViewRNA (Affymetrix), which uses probe sets for each mRNA that bind specifically to an amplification system to amplify the hybridization signals, these amplified signals can be visualized using a standard fluorescence microscope or imaging system. This system for example can detect and measure transcript levels in heterogeneous samples.

The level or amount of a protein encoded by a gene provided herein can be measured using any assay known in the art for measuring a level or amount at the protein level. Examples of suitable assays for determining or measuring the levels of protein (e.g., encoded by a gene provided herein) can be selected from quantitative mass spectrometry or immunoassays including, for example, immunohistochemistry, ELISA, Western blot, immunoprecipitation, Luminex® assay, and the like, where a biomarker detection agent such as an antibody, for example, a labeled antibody, specifically binds a protein encoded by a gene provided herein and permits, for example, relative or absolute ascertaining of the amount of a protein in a sample or a cell. The level or amount of an enzyme encoded by a gene provided herein or of the gene itself that has been heterologously modified as provided herein can be compared to the level or amount of the same enzyme or gene that has not been heterologously modified as described herein and the percentage of the level or amount of the modified enzyme or gene vs. the non-modified enzyme or gene can be determined.

The activity of an enzyme encoded by a gene provided herein can be measured using any assay known in the art for measuring enzyme activity. Examples of suitable assays for determining enzyme activity can be any kinase assay known in the art such as, for example, biochemical kinase assays commercially available from EMD Millipore (e.g., FRET-based HTRF assays), eBioscience (e.g., Instant One cell signaling assays), Life Technologies (LanthaScreen or Omnia kinase assays), Symansis (e.g., Multikinase assay array), Abcam or Promega (e.g., the ADP-Glo Kinase Assay). The kinase activity assay can be radiometric based and employ the use of radioisotopes (e.g., $\lambda$-$^{32}$P-ladeled ATP or $^{32}$P orthophosphate) or be luminescence or fluorescence (e.g., ATP labeled with fluorophores) based assays. In one embodiment, a histidine kinase activity assay is employed to measure the activity of a histidine kinase such as the two-component histidine kinase encoded by the *A. niger* nikA gene (e.g., protein encoded by the SNP-containing nucleic acid sequence of SEQ ID NO. 7 or the non-SNP containing nucleic acid sequence of SEQ ID NOs. 14 or 76). The histidine kinase activity assay can be any histidine kinase activity assay known in the art. In one example, the activity of a kinase (e.g., a histidine kinase) encoded by a gene or nucleic acid sequence provided herein (e.g., nucleic acid sequences of SEQ ID NOs. 7, 4 or 76) can be determined using a radiometric kinase activity assay and analysis (i.e., polyacrylamide gel electrophoresis (PAGE) in combination with liquid scintillation counting) as described in Sankhe G D, Dixit N M, Saini D K 2018. Activation of bacterial histidine kinases, insights into the kinetics of the cis autophosphorylation mechanism. mSphere 3:e00111-18, which is herein incorporated by reference. In another example, the activity of a kinase (e.g., a histidine kinase) encoded by a gene or nucleic acid sequence provided herein (e.g., nucleic acid sequences of SEQ ID NOs. 7, 4 or 76) can be determined using phosphotransfer assays that employ radioisotopic labelling in combination with SDS-PAGE and autoradiography as described in Brown, J L et al. "Yeast Skn7p functions in a eukaryotic two-component regulatory pathway." The EMBO journal vol. 13, 21 (1994). 5186-94, Aoyama, K et al. "Spy1, a histidine-containing phosphotransfer signaling protein, regulates the fission yeast cell cycle through the Mcs4 response regulator." Journal of bacteriology vol. 182, 17 (2000): 4868-74, and Li, S et al. "The yeast histidine protein kinase, Sln1p, mediates phosphotransfer to two response regulators, Ssk1p and Skn7p." The EMBO journal vol. 17, 23 (1998): 6952-62, each of which is incorporated herein by reference. The activity of an enzyme encoded by a gene provided herein that has been heterologously modified as provided herein can be compared to the activity of the same enzyme that is encoded by a gene that has not been heterologously modified as described herein and the level or percentage of activity of the modified enzyme vs. the non-modified enzyme can be determined.

Overview

It is an object of the present invention to provide strains of filamentous eukaryotic organisms that possess a desired morphological phenotype when grown in production media for a product of interest as well as methods for generating said strains of filamentous eukaryotic organisms. A variant strain generated using the methods provided herein that possesses the desired morphological phenotype can produce a higher yield, titer or total titer of said product of interest as compared to a parental or control strain. A variant strain generated using the methods provided herein that possesses the desired morphological phenotype can produce said product of interest at a higher production rate than a parental or control strain. A variant strain generated using the methods provided herein that possesses the desired morphological phenotype can produce said product of interest with a higher volumetric productivity or specific productivity as compared to a parental or control strain. The filamentous eukaryotic organism can be any filamentous eukaryotic organism known in the art and/or provided herein such as, for example, Aspergillus niger (A. niger). The desired morphological phenotype can be a non-mycelium pellet phenotype when grown under submerged culture conditions in a desired production medium for a desired product of interest. The desired product or product of interest can be any product listed in Table 1. In one embodiment, the desired product of interest is an enzyme. The enzyme can be any enzyme known in the art to be produced by genetically engineered organisms. The enzyme can be any enzyme found in Table 1. In one embodiment, the desired product of interest is citric acid and the desired production medium is citric acid production (CAP) medium. In some cases, the filamentous eukaryotic strains (e.g., A. niger) comprising the desired morphological phenotype (e.g., non-mycelium, pellet morphology) can be grown in manganese comprising CAP media that is free or substantially free (e.g., less than 5%, 4%, 3%, 2%, or 1% of the amount or concentration of chelating agent found in fermentation broth known in the art for producing a product of interest such as, for example, citric acid) of chelating agents such as, for example, manganese chelators. The manganese can be in an amount of about 13 ppb or greater. The manganese can be in an amount of about 14 ppb or greater. In another embodiment, the provided strains of filamentous eukaryotic strains (e.g., A. niger) comprising the desired morphological phenotype (e.g., non-mycelium, pellet morphology) comprise one or more genes that play a role in controlling morphology that have been altered or disrupted. The disruption or alteration can be a mutation within the coding domain of the gene. The disruption or alteration can be an alteration in a genetic control element (e.g., promoter and/or terminator). The disruption or alteration can be a mutation within the coding domain of the gene in combination with an alteration in a genetic control element (e.g., promoter and/or terminator). The alteration in genetic control element can be replacement of an endogenous genetic control element with a non-native or heterologous genetic control element. In some cases, the genetic control element is a promoter. The promoter can be selected from a promoter listed in Table 2 The one or more genes that play a role in controlling morphology can be any gene known in the art to play a role in controlling the morphology of the filamentous eukaryotic organism (e.g., A. niger). Genes that play a role in controlling morphology can be genes that encode proteins that function in the physical structure of the cell as well as genes that are part of biochemical pathways that regulate or govern either, directly or indirectly, the expression of proteins that function in the physical structure of the cell. The one or more genes that play a role in controlling morphology can be any gene provided herein such as, for example, the SNP containing gene sequences represented by SEQ ID NOs: 5, 6, 7 or 8 or orthologues thereof from Table 4 alone or in combination with one or more genes found within the same pathways as said SNP containing gene sequences. In one embodiment, the one or more genes that play a role in controlling morphology are one or more genes from an osmotic response or osmotic stress response pathway. For example, the one or more genes or orthologues thereof can be selected from the osmotic response pathway genes shown in Table 7 In one embodiment, the one or more genes that play a role in controlling the morphology of an Aspergillus host cell (e.g., A. niger) are the orthologues of one or more of the yeast osmotic pathway genes shown in Table 7. For example, the A. niger orthologue of one or more genes of the yeast osmotic response pathway can be selected from the nucleic acid sequences represented by SEQ ID NOs. 9-32, 76 or any combination thereof. The methods for generating the strains of filamentous eukaryotic organisms that possess a desired morphological phenotype when grown in production media for a product of interest can comprise performing a PRO swap method, a SNP Swap method or a combination of a PRO swap and SNP swap method as provided herein. The SNP Swap and/or PRO swap methods can be performed as described in PCT/US2018/036360, filed on Jun. 6, 2018, which is herein incorporated by reference.

TABLE 1

A non-limiting list of the host cells and products of interest of the present disclosure.

| Product category | Products | Host category | Hosts |
|---|---|---|---|
| Flavor & Fragrance | Agarwood | Yeast | Saccharomyces cerevisiae |
| Flavor & Fragrance | Ambrox | Yeast | Saccharomyces cerevisiae |
| Flavor & Fragrance | Nootkatone | Yeast | Saccharomyces cerevisiae |
| Flavor & Fragrance | Patchouli oil | Yeast | Saccharomyces cerevisiae |
| Flavor & Fragrance | Saffron | Yeast | Saccharomyces cerevisiae |
| Flavor & Fragrance | Sandalwood oil | Yeast | Saccharomyces cerevisiae |
| Flavor & Fragrance | Valencene | Yeast | Saccharomyces cerevisiae |
| Flavor & Fragrance | Vanillin | Yeast | Saccharomyces cerevisiae |
| Food | CoQ10/Ubiquinol | Yeast | Schizosaccharomyces pombe |
| Food | Omega 3 fatty acids | Microalgae | Schizochytrium |
| Food | Omega 6 fatty acids | Microalgae | Schizochytrium |

TABLE 1-continued

A non-limiting list of the host cells and products of interest of the present disclosure.

| Product category | Products | Host category | Hosts |
|---|---|---|---|
| Food | Vitamin B2 | Filamentous fungi | Ashbya gossypii |
| Food | Erythritol | Yeast-like fungi | Torula coralhne |
| Food | Erythritol | Yeast-like fungi | Pseudozyma tsukubaensis |
| Food | Erythritol | Yeast-like fungi | Moniliella pollinis |
| Food | Steviol glycosides | Yeast | Saccharomyces cerevisiae |
| Organic acids | Citric acid | Filamentous fungi | Aspergillus niger |
| Organic acids | Citric Acid | Filamentous fungi | Aspergillus carbonarius |
| Organic acids | Citric Acid | Filamentous fungi | Aspergillus aculeatus |
| Organic acids | Citric acid | Yeast | Pichia guilliermondii |
| Organic acids | Gluconic acid | Filamentous fungi | Aspergillus niger |
| Organic acids | Itaconic acid | Filamentous fungi | Aspergillus terreus |
| Organic acids | Itaconic acid | Filamentous fungi | Aspergillus niger |
| Organic acids | LCDAs - DDDA | Yeast | Candida |
| Organic acids | Kojic Acid | Filamentous fungi | Aspergillus oryzae |
| Organic acids | Kojic Acid | Filamentous fungi | Aspergillus flavus |
| Organic acids | Kojic Acid | Filamentous fungi | Aspergillus tamarii |
| Organic acids | Malic Acid | Filamentous fungi | Aspergillus oryzae |
| Organic acids | Oxalic acid | Filamentous fungi | Aspergillus niger |
| Organic acids | Succinic acid | Filamentous fungi | Aspergillus saccarolyticus |
| Organic acids | Lactic acid | Filamentous fungi | Aspergillus niger |
| Organic acids | Lactic acid | Filamentous fungi | Aspergillus brasiliensis |
| Hypolipidemic agent | Lovastatin | Filamentous fungi | Aspergillus terreus |
| Melanogenesis inhibitor | Terrein | Filamentous fungi | Aspergillus terreus |
| Immunosuppresent drug | Cyclosporine A | Filamentous fungi | Aspergillus terreus |
| Antiproliferative agent | Asperfuranone | Filamentous fungi | Aspergillus terreus |
| Antiproliferative agent | Asperfuranone | Filamentous fungi | Aspergillus nidulans |
| Cholesterol-lowering agent | Pyripyropene | Filamentous fungi | Aspergillus fumigatus |
| Antibiotics | Penicillin | Filamentous fungi | Aspergillus oryzae |
| Antibiotics | Penicillin | Filamentous fungi | Aspergillus nidulans |
| Antimicrobial agent | Fumagillin | Filamentous fungi | Aspergillus fumigatus |
| Anticancer agent | Fumitremorgin C | Filamentous fungi | Aspergillus fumigatus |
| Anticancer agent | Spirotryprostatins | Filamentous fungi | Aspergillus fumigatus |
| Anticancer agent; Antimicrobial agent | Plinabulin | Filamentous fungi | Aspergillus ustus |
| Anticancer agent | Phenylahistin | Filamentous fungi | Aspergillus ustus |
| Anticancer agent | Stephacidin A & B | Filamentous fungi | Aspergillus ochraceus |
| Anticancer agent | Asperphenamate | Filamentous fungi | Aspergillus flavus |
| Cholecystokinin antagonist | Asperlicin | Filamentous fungi | Aspergillus alliaceus |
| Industrial enzyme | Alpha-amylase | Filamentous fungi | Aspergillus niger |
| Industrial enzyme | Alpha-amylase | Filamentous fungi | Aspergillus oryzae |
| Industrial enzyme | Aminopeptidase | Filamentous fungi | Aspergillus niger |
| Industrial enzyme | Aminopeptidase | Filamentous fungi | Aspergillus oryzae |
| Industrial enzyme | Aminopeptidase | Filamentous fungi | Aspergillus sojae |
| Industrial enzyme | AMP deaminase | Filamentous fungi | Aspergillus melleus |
| Industrial enzyme | Catalase | Filamentous fungi | Aspergillus niger |
| Industrial enzyme | Cellulase | Filamentous fungi | Aspergillus niger |
| Industrial enzyme | Chymosin | Filamentous fungi | Aspergillus niger |
| Industrial enzyme | Esterase | Filamentous fungi | Aspergillus niger |
| Industrial enzyme | Alpha-galactosidase | Filamentous fungi | Aspergillus niger |
| Industrial enzyme | Beta-glucanase | Filamentous fungi | Aspergillus niger |
| Industrial enzyme | Beta-glucanase | Filamentous fungi | Aspergillus aculeatus |
| Industrial enzyme | Glucose oxidase | Filamentous fungi | Aspergillus niger |
| Industrial enzyme | Glutaminase | Filamentous fungi | Aspergillus oryzae |
| Industrial enzyme | Glutaminase | Filamentous fungi | Aspergillus sojae |
| Industrial enzyme | Beta-D-Glucosidase | Filamentous fungi | Aspergillus niger |
| Industrial enzyme | Inulinase | Filamentous fungi | Aspergillus niger |
| Industrial enzyme | Lactase | Filamentous fungi | Aspergillus niger |
| Industrial enzyme | Lipase | Filamentous fungi | Aspergillus niger |
| Industrial enzyme | Lipase | Filamentous fungi | Aspergillus oryzae |
| Industrial enzyme | Xylanase | Filamentous fungi | Aspergillus niger |

It is a further object of the present invention to provide a filamentous fungus host cell comprising a heterologous modification of a gene from the host cell's osmotic response pathway. The gene can be any one of the genes from the filamentous fungus host cell's osmotic response pathway or a combination thereof. A modified gene from the osmotic pathway can have reduced expression and/or encode a protein with reduced activity as compared to a non-modified version of the gene. In one embodiment, the gene is a filamentous fungal orthologue of one of the yeast osmotic response pathway genes listed in Table 7. In one embodiment, the filamentous fungal host cell is an Aspergillus host cell (e.g., A. niger) and the gene is an A. niger orthologue of one or more of the yeast osmotic pathway genes shown in Table 7. For example, the A. niger orthologue of one or more genes of the yeast osmotic response pathway can be selected from the nucleic acid sequences represented by SEQ ID NOs. 9-32 or 76. In another embodiment, a plurality of filamentous fungal orthologues from the yeast osmotic response pathway genes listed in Table 7 are heterologously modified in a filamentous fungal host cell. In one embodiment, the filamentous fungal host cell comprises a heterologous modification of a filamentous fungus host cell orthologue of a S. cerevisiae SLN1 gene. The modified orthologue of a S. cerevisiae SLN1 gene can have reduced expression and/or encode an orthologue of an *S. cerevisiae* SLN1 protein with reduced activity relative to a parental filamentous fungal host cell lacking the heterologous modification. The filamentous fungal host cell can possess a non-mycelium, pellet forming phenotype. This pellet phenotype can be due to the filamentous fungal host cell possessing the heterologous modification in a gene or a plurality of genes from the osmotic response pathway (e.g., an orthologue of the *S. cerevisiae* SLN1 gene) that causes cells of the filamentous host cell to produce a reduced or substantially reduced amount and/or less or substantially less active form of functional orthologue of the modified gene (e.g., an orthologue of a *S. cerevisiae* SLN1 protein) or the modified plurality of genes of as compared to cells of that do not possess said heterologous modification or modifications. The amount of functional protein in the filamentous fungal host cell can be reduced by at least, at most, exactly or about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%, as compared to an amount of the respective functional protein in a parental or control strain. The amount of functional protein (e.g. molar amount) can be measured using any method known in the art such as, for example, ELISA, Luminex® assays, mass spectrometry and/or quantitative western blot analysis. The activity (e.g., specific activity) of functional protein in the filamentous fungal host cell can be reduced by at least, at most, exactly or about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%, as compared to the activity of the respective functional protein in a parental or control strain. The activity of functional protein can be measured using any enzyme activity method known in the art such as, for example, kinase assays Measuring enzymatic activity can be performed using any method known in the art and/or provided herein such as, for example, commercially available biochemical kinase activity assays available from Life Technologies, EMD Millipore, eBioscience, Abeam or Promega. The filamentous fungal host cell and any parental strain said filamentous fungal host cell is derived therefrom can be any filamentous fungus known in the art and/or provided herein such as, for example, *A. niger*. In one embodiment, the filamentous fungal host cell is *A. niger* and the gene from the osmotic response pathway with a heterologous modification is an *A. niger* orthologue of a *S. cerevisiae* SLN1 gene. The *A. niger* orthologue of the *S. cerevisiae* SLN1 gene can be any of the *A. niger* orthologues of the *S. cerevisiae* SLN1 gene listed in Table 6. In one embodiment, the *A. niger* orthologues of the *S. cerevisiae* SLN1 gene is the *A. niger* orthologue with the id ASPNIDRAFT 39736, which is the *Aspergillus* nikA gene (SEQ ID NO: 14). In another embodiment, the *A. niger* orthologues of the *S. cerevisiae* SLN1 gene is the *A. niger* orthologue with the nucleic acid sequence of SEQ ID NO: 76. The *Aspergillus* nikA gene is an orthologue or homologue of the *Neurospora crassa* (*N. crassa*) nik1 gene.

In one embodiment, the filamentous fungal host cell sporulates normally as compared to a parental strain when grown under non-submerged growth conditions such as, for example, on solid media In another embodiment, the filamentous fungal host cell sporulates normally as compared to the parental strain when grown under non-submerged growth conditions such as, for example, on solid media only when one, all or a combination of the SNP containing genes from Table 3 or orthologues thereof are also expressed in the filamentous fungal host cell. In one embodiment, the filamentous fungal host cell is *A. niger* and said *A. niger* host cell sporulates normally as compared to a parental strain when grown under non-submerged growth conditions such as, for example, on solid media only when one, all or a combination of the SNP containing genes from Table 3 are also expressed in said *A. niger* host cell. In yet another embodiment, the filamentous fungal host cell sporulates normally as compared to a parental strain when grown under non-submerged growth conditions such as, for example, on solid media only when one, all or a combination of orthologoues of the SNP containing genes from Table 4 are also expressed in the filamentous fungal host cell. In one embodiment, the filamentous fungal host cell is *A. niger* and said *A. niger* host cell sporulates normally as compared to a parental strain when grown under non-submerged growth conditions such as, for example, on solid media only when one, all or a combination of the SNP containing genes from Table 4 are also expressed in said *A. niger* host cell. The submerged culture conditions can comprise growing the variant strain in CAP medium. The CAP media can comprise manganese and be free or substantially free (e.g., less than 5%, 4%, 3%, 2%, or 1% of the amount or concentration of chelating agent found in fermentation broth known in the art for producing a product of interest such as, for example, citric acid) of chelating agents. The manganese can be present in an amount that is at least 13 ppb or higher. The manganese can be present in an amount that is at least 14 ppb or higher.

The genetic alteration or heterologous modification of a gene or each gene from a plurality of genes from the osmotic response pathway of a filamenotous fungus can be replacement of the wild-type form of the gene with a mutated form, replacement of the native promoter of the gene with a heterologous promoter that more weakly expresses the gene as compared to the native promoter, or a combination thereof. Alternatively, the genetic alteration or heterologous modification of a gene or each gene from a plurality of genes from the osmotic response pathway of a filamenotous fungus can be the removal gene (e.g., the gene of the orthologue of the *S. cerevisiae* SLN1 gene) and replacement with a selectable marker gene. The mutated form of a gene or each gene from a plurality of genes from the osmotic response pathway of a filamenotous fungus can comprise a SNP, a non-sense mutation, a missense mutation, a deletion, an insertion or any combination thereof. The gene or each gene of the plurality of genes from the osmotic response pathway can be any one of the genes from the filamentous fungus host cell's osmotic response pathway. In one embodiment, the gene or each gene of the plurality of genes from the osmotic response pathway is a filamentous fungal orthologue of one of the yeast osmotic response pathway genes listed in Table 7. In one embodiment, the gene from the osmotic response pathway is an orthologue of the yeast Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 gene or any combination thereof. The nucleic acid sequence of the yeast Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 gene can be selected from SEQ ID NO: 50-75. In one embodiment, the filamentous fungal host cell is *A. niger* and the orthologues of a yeast SLN1, Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 gene are *A. niger* orthologues or mutants thereof. For example, the *A. niger* orthologues can be selected from the nucleic acid sequences represented by SEQ ID NOs. 9-32 or 76. In one embodiment, the *A. niger* orthologues that are part of the osmotic response pathway can be selected from the nucleic acid sequences represented by SEQ ID NOs: 9, 10, 11, 12, 13 or any combination thereof. In one embodiment, the filamentous fungal host cell is *A. niger* and the gene from the osmotic response pathway is an *A. niger* orthologue of the *S. cerevisiae* SLN1 gene. In another embodiment, the filamentous fungal host cell is *A. niger* and the gene from the osmotic response pathway has the nucleic acid sequence of SEQ ID NO: 7 comprising a missense mutation that converts a histidine at the 272 amino acid position in the encoded protein into a tyrosine. In yet another embodiment, the filamentous fungal host cell is *A. niger* and the gene from the osmotic response pathway has the nucleic acid sequence of SEQ ID NO: 7 comprising a missense mutation that converts a histidine at the 272 amino acid position in the encoded protein into a tyrosine and that is operably linked to a promoter that more weakly expresses the nucleic acid sequence of SEQ ID NO.7. In still another embodiment, the filamentous fungal host cell is *A. niger* and the gene from the osmotic response pathway has the nucleic acid sequence of SEQ ID NO: 14 or 76 that is operably linked to a promoter that more weakly expresses the nucleic acid sequence of SEQ ID NO. 14 or 76. Further to any of the above embodiments, the heterologous promoter can be selected from a promoter listed in Table 2. In one embodiment, the heterologous promoter is a manB or amyB promoter. Further to this embodiment, the heterologous promoter can have the nucleic acid sequence of SEQ ID NO. 1 or SEQ ID NO. 2. In one embodiment, the promoter can be an inducible promoter. An inducible promoter can be used to ensure proper expression of a gene such as the orthologue of the *S. cerevisiae* SLN1 gene (e.g., the *A. niger* nikA gene) during sporulation, but reduced expression of said gene under specific conditions required for producing a desired product of interest (e.g., under fermentation conditions) in order to promote the non-mycelium, pellet phenotype under such conditions. The amyB promoter is an example of an inducible promoter that can be so utilized. The selectable marker can be selected from an auxotrophic marker gene, a colorimetric marker gene, antibiotic resistance gene, or a directional marker gene as provided herein.

In one embodiment, a filamentous fungal host cell provided herein or generated using the methods provided herein possesses a reduced or substantially reduced amount and/or less or substantially less active form of a functional orthologue of a *S. cerevisiae* SLN1 protein and further comprises a genetic disruption or alteration in one or more additional genes that are part of the same pathway (i.e., the osmotic response pathway) as the orthologue of the *S. cerevisiae* SLN1 protein. The one or more genes that are part of the same pathway can be orthologues of any of the genes from the yeast osmotic response pathway listed in Table 7. In one embodiment, the filamentous fungal host cell further comprises an orthologue of the *S. cerevisiae* Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 gene or any combination thereof. The nucleic acid sequence of the yeast Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 gene can be selected from SEQ ID NO: 50-75. In one embodiment, the filamentous fungal host cell is *A. niger* and the orthologues of the *S. cerevisiae* SLN1, Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 genes are *A. niger* orthologues or mutants thereof. For example, the *A. niger* orthologues can be selected from the nucleic acid sequences represented by SEQ ID NOs. 9-32 or 76. Further to this embodiment, the one or more genes that are part of the same pathway (i.e., osmotic response pathway) can be selected from the nucleic acid sequences represented by SEQ ID NOs: 9, 10, 11, 12, 13 or any combination thereof. The filamentous fungal host cell can further comprise a genetic disruption or alteration in one or more genes that are part of a different pathway or pathways that are known or suspected to play a role in controlling filamentous fungal morphology. The one or more genes that are part of the different pathway or pathways can be selected from orthologues of genes with nucleic acid sequences represented by SEQ ID NOs: 5, 6, 8 or any combination thereof. In one embodiment, the filamentous fungal host cell is *A. niger* and the one or more genes that are part of the different pathway or pathways are the *A. niger* genes with nucleic acid sequences represented by SEQ ID NOs: 5, 6, 8 or any combination thereof. In another embodiment, the filamentous fungal host coll is *A. niger* and the one or more genes that are part of the different pathway or pathways are the non-SNP containing versions of the *A. niger* genes with nucleic acid sequences represented by SEQ ID NOs: 5, 6, 8 or any combination thereof. The non-SNP containing versions of the *A. niger* genes with nucleic acid sequences represented by SEQ ID NOs: 5, 6, 8 can be the nucleic acid sequences of SEQ ID NO. 77-79, respectively.

The genetic disruption or alteration to the one or more genes that are part of the different pathway or pathways that are known or suspected to play a role in controlling filamentous fungal morphology can be replacement of the wild-type form of the gene with a mutated form of the gene, replacement of the native promoter of the gene with a heterologous promoter that alters the expression (e.g., higher or lower) of the gene as compared to the native promoter, or a combination thereof. The promoter can be a promoter listed in Table 2 In one embodiment, the promoter can be an inducible promoter. Alternatively, the genetic disruption or alteration to the one or more genes that are part of the different pathway that is known to play a role in controlling filamentous fungal morphology can be the removal of the gene and replacement with a selectable marker gene. The selectable marker can be selected from an auxotrophic marker gene, a colorimetric marker gene, antibiotic resistance gene, or a directional marker gene as provided herein.

Also provided herein, are methods for generating a filamentous fungus host cell that possesses a reduced or substantially reduced amount and/or less or substantially less active form of functional protein or a plurality of proteins that is or are part of said filamentous fungal host cell's osmotic response pathway. In one embodiment, said filamentous fungal host cell possesses a reduced or substantially reduced amount and/or less or substantially less active form of functional protein or a plurality of proteins that is or are orthologues of protein(s) from the yeast osmotic response pathway as known in the art and/or shown in Table 7. In one embodiment, said filamentous fungal host cell possesses a reduced or substantially reduced amount and/or less or substantially less active form of functional protein that is an orthologue of the S. cerevisiae SLN1 protein or the N. crassa Nik1 protein. In one embodiment, said filamentous fungal host cell possesses a reduced or substantially reduced amount and/or less or substantially less active form of functional protein of each of a plurality of genes from the yeast osmotic response pathway as shown in Table 7. In one embodiment, said filamentous fungal host cell is A. niger and said host cell possesses a reduced or substantially reduced amount and/or less or substantially less active form of functional protein that is an A. niger orthologue of each of the plurality of genes from the yeast osmotic response pathway Said A. niger orthologs can be selected from the nucleic acid sequences represented by SEQ ID NOs. 9-32 or 76. The methods can comprise performing a PRO swap method, a SNP Swap method or a combination of a PRO swap and SNP swap method as provided herein. The amount of functional protein in the filamentous fungal host cell can be reduced by at least, at most, exactly or about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%, as compared to an amount of the respective functional protein in a parental or control strain. The amount of functional protein (e.g., molar amount) can be measured using any method known in the art such as, for example, ELISA, Luminex® assays, mass spectrometry and/or quantitative western blot analysis. The activity (e.g., specific activity) of functional protein in the filamentous fungal host cell can be reduced by at least, at most, exactly or about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%, as compared to the activity of the respective functional protein in a parental or control strain. The activity of functional protein can be measured using any enzyme activity method known in the art such as, for example, kinase assays. Measuring enzymatic activity can be performed using any method known in the art and/or provided herein such as, for example, commercially available biochemical kinase activity assays available from Life Technologies, EMD Millipore, eBioscience, Abcam or Promega.

It is a further object of the present invention to provide a filamentous fungus host cell comprising a heterologous modification of the host cell's orthologue of an A. niger gene with a nucleic acid sequence selected from SEQ ID NO. 5, 6, 8, 77, 78, 79 or any combination thereof, whereby the modified orthologue of the A. Niger gene with a nucleic acid sequence selected from SEQ ID NO. 5, 6, 8, 77, 78, 79 or any combination thereof has reduced activity and/or reduced expression relative to a parental filamentous fungal host cell lacking the heterologous modification(s). The filamentous fungal host can possess a non-mycelium, pellet forming phenotype as compared to the cells of the parental strain when grown in a submerged culture due to the filamentous host cell possessing a heterologous modification to the orthologue of an A. niger gene with nucleic acid sequence of SEQ ID NO: 5, 6, 8, 77, 78, 79 or any combination thereof. Possession of an orthologue of an A. niger gene with a nucleic acid sequence of SEQ ID NO: 5, 6, 8 or any combination thereof can cause cells of the host cell to produce a reduced or substantially reduced amount and/or less or substantially less active form of functional protein encoded by orthologues of the A. niger genes with said SEQ ID NOs as compared to cells of a parental host cell when grown under submerged culture conditions. The filamentous host cell and parental strain of said filamentous fungal host cell can be any filamentous fungus known in the art and/or provided herein such as, for example, A. Niger. In one embodiment, the filamentous host cell strain sporulates normally as compared to a parental strain when grown under non-submerged growth conditions such as, for example, on solid media. In some cases, the orthologues of the A. Niger genes with SEQ ID NOs, 5, 6, 8, 77, 78, or 79 are further genetically altered. The further genetic alteration can be replacement of the native promoter of the gene with a heterologous promoter that more weakly expresses the gene as compared to the native promoter. Alternatively, the further genetic alteration can be the removal of the orthologues of the A. Niger genes with SEQ ID NO: 5, 6, 8, 77, 78 or 79 and replacement with a selectable marker gene. The selectable marker can be selected from an auxotrophic marker gene, a colorimetric marker gene, antibiotic resistance gene, or a directional marker gene as provided herein. The heterologous promoter can be selected from a promoter listed in Table 2. In one embodiment, the heterologous promoter is a manB or amyB promoter. Further to this embodiment, the heterologous promoter can have the nucleic acid sequence of SEQ ID NO: 1 or SEQ ID NO: 2. In one embodiment, the promoter is an inducible promoter. The submerged culture conditions can comprise growing the variant strain in CAP medium. The CAP media can comprise manganese and be substantially free or free of chelating agents. The manganese can be present in an amount that is at least 13 ppb or higher. The manganese can be present in an amount that is at least 14 ppb or higher. It should be understood that in embodiments where the filamentous fungal host cell is A. niger, the A. niger gene with a nucleic acid sequence selected from SEQ ID NO. 5, 6, 8 or wild-type versions thereof (e.g., nucleic acid sequences with SEQ ID NOs. 77-79) can comprise the heterologous modifications detailed herein.

The filamentous fungal host cell that possesses a substantially reduced or reduced amount and/or substantially less or less active form of functional protein encoded by orthologues of the A. niger genes with sequences selected from SEQ ID NOs: 5, 6, 8, 77, 78 or 79 can further comprise a genetic disruption or alteration in one or more genes that are part of the same pathway. The filamentous fungal host cell can further comprise a genetic disruption or alteration in one or more genes that are part of the different pathway that is known to play a role in controlling filamentous fungal morphology. The one or more genes that are part of the different pathway can be any of the genes provided herein such as the genes that are part of a host cells osmotic response pathway. The genetic disruption or alteration to the one or more genes that are part of the same pathway or are part of the different pathway that is known to play a role in controlling filamentous fungal morphology can be replacement of the wild-type form of the gene with a mutated form of the gene, replacement of the native promoter of the gene with a heterologous promoter that alters the expression (e.g., higher or lower) of the gene as compared to the native promoter, or a combination thereof. The promoter can be a promoter listed in Table 2. In one embodiment, the promoter is an inducible promoter. Alternatively, the genetic disruption or alteration to the one or more genes that are part of the same pathway or are part of the different pathway that is known to play a role in controlling filamentous fungal morphology can be the removal of the gene and replacement with a selectable marker gene. The selectable marker can be selected from an auxotrophic marker gene, a colorimetric marker gene, antibiotic resistance gene, or a directional marker gene as provided herein.

Also provided herein, are methods for generating the variant strain of filamentous fungus that possess a substantially reduced or reduced amount and/or substantially less or less active form of functional protein encoded by orthologues of the *A. niger* genes with SEQ ID NOs: 5, 6, 8, 77, 78 or 79 The methods can comprise performing a PRO swap method, a SNP Swap method or a combination of a PRO swap and SNP swap method as provided herein. The amount of functional protein encoded by the orthologues of the *A. niger* genes with SEQ ID NOs: 5, 6, 8, 77, 78 or 79 in the variant strain can be reduced by at least, at most, exactly or about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%, as compared to an amount of the respective functional protein in a parental or control strain. The amount of functional protein (e.g., molar amount) can be measured using any method known in the art such as, for example, an ELISA, Luminex® assays, mass spectrometry and/or quantitative western blot analysis. The activity (e.g., specific activity) of functional protein encoded by the orthologues of the *A. niger* genes with SEQ ID NOs: 5, 6, 8, 77, 78 or 79 in the variant strain can be reduced by at least, at most, exactly or about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%, as compared to the activity of the respective functional protein in a parental or control strain. The activity of functional protein can be measured using any enzyme activity method known in the art such as, for example, kinase assays. Measuring enzymatic activity can be performed using any method known in the art and/or provided herein such as, for example, commercially available biochemical kinase activity assays available from Life Technologies, EMD Millipore, eBioscience, Abcam or Promega.

It is yet another object of this invention to provide a filamentous fungal host cell comprising a promoter operably linked to a gene that regulates morphology of the host cell, wherein the promoter is heterologous to the gene, and wherein the promoter has a nucleic acid sequence selected from the group consisting of SEQ ID NOs. 1-4. The filamentous fungus host cell can be any filamentous fungus known in the art and/or provided herein such as, for example, *A. niger*. In some cases, the fungal host cell sporulates normally as compared to a parental strain of the host cell when grown under non-submerged growth conditions such as, for example, on solid media, but forms a non-mycelium, pellet morphology when grown under submerged culture conditions. In some cases, the host cell can comprise one or more genes that regulate morphology such that each of said one or more genes has a heterologous promoter linked thereto. The one or more genes that regulates morphology of the host cell can be any such gene as provided herein such as, for example, the SNP containing gene sequences represented by SEQ ID NOs. 5, 6, 7 or 8 or orthologues thereof from Table 4, either alone or in combination. In some cases, the SNP containing gene sequences represented by SEQ ID NOs. 5, 6, 7 or 8 or orthologues thereof from Table 4 can be in combination with one or more genes from the same pathway as the respective SNP containing gene sequence. In one embodiment, the one or more genes is a wild-type or non-SNP containing version of the gene with a nucleic acid sequence selected from SEQ ID NOs. 5, 6, 7 or 8 (e.g., nucleic acid sequences of SEQ ID NOs. 76-79) or orthologues thereof, either alone or in combination. In another embodiment, the wild-type or non-SNP containing version of the gene with a nucleic acid sequence selected from SEQ ID NOs. 5, 6, 7 or 8 (e.g., nucleic acid sequences of SEQ ID NOs. 76-79) or orthologues thereof can be in combination with one or more genes from the same pathway as the respective wild-type or non-SNP containing gene sequence. In one embodiment, the gene that regulates morphology of the host cell can be a gene from the host cell's osmotic response pathway. In another embodiment, a plurality of genes from the host cell's osmotic response pathway are used in combination to regulate the morphology of the host cell. In one embodiment, the gene that regulates morphology of the host cell can be an orthologue of the *S. cerevisiae* SLN1 gene or an orthologue of a gene from a yeast osmotic response pathway as shown in Table 7. In another embodiment, a plurality of orthologues from a yeast osmotic response pathway as shown in Table 7 are used in combination to regulate the morphology of the host cell. In one embodiment, the orthologue of a gene from a yeast osmotic response pathway can be selected from orthologues of yeast Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 genes or any combination thereof. In one embodiment, the orthologue of a gene from a yeast osmotic response pathway can have a sequence that is an orthologue of a nucleic acid sequence selected from SEQ ID NO. 50-75.

In one embodiment, the filamentous fungal host cell is *A. niger* and an *A. niger* orthologue of the *S. cerevisiae* SLN1 gene or the *N. crassa* nik1 gene is operably linked to a promoter that has a nucleic acid sequence selected from the group consisting of SEQ ID NOs. 1-4. In another embodiment, the filamentous fungal host cell is *A. niger* and an *A. niger* orthologue of the *S. cerevisiae* SLN1 gene or the *N. crassa* nik1 gene is operably linked to a promoter that has a nucleic acid sequence of SEQ ID NO. 1. In another embodiment, the filamentous fungal host cell is *A. niger* and an *A. niger* orthologue of the *S. cerevisiae* SLN1 gene or the *N. crassa* nik1 gene is operably linked to a promoter that has a nucleic acid sequence of SEQ ID NO. 2. The orthologue of the *S. cerevisiae* SLN1 gene or the *N. crassa* nik1 gene can be a wild-type or mutant form of the gene. In one embodiment, the filamentous fungal host cell is *A. niger* and the mutated *A. niger* ortholog of the *S. cerevisiae* SLN1 gene or the *N. crassa* nik1 gene has the nucleic acid sequence of SEQ ID NO: 7. In one embodiment, the filamentous fungal host cell is *A. niger* and the wild-type *A. niger* ortholog of the *S. cerevisiae* SLN1 gene or the *N. crassa* nik1 gene has the nucleic acid sequence of SEQ ID NO. 14 or 76. The submerged culture conditions can comprise growing the variant strain in CAP medium. The CAP media can comprise manganese and be free or substantially free (e.g., less than 5%, 4%, 3%, 2%, or 1% of the amount or concentration of chelating agent found in fermentation media known in the art for producing a product of interest such as, for example, citric acid) or free of chelating agents. The manganese can be present in an amount that is at least 13 ppb or higher. The manganese can be present in an amount that is at least 14 ppb or higher.

In one embodiment, the filamentous fungal host cell is *A. niger* and one or more orthologues from a yeast osmotic response pathway are operably linked to a promoter that has a sequence selected from the group consisting of SEQ ID NOs. 1-4. In another embodiment, the filamentous fungal host cell is *A. niger* and one or more of orthologues from a yeast osmotic response pathway are operably linked to a promoter that has a nucleic acid sequence of SEQ ID NO. 1 In yet another embodiment, the filamentous fungal host cell is *A. niger* and one or more of orthologues from a yeast osmotic response pathway are operably linked to a promoter that has a nucleic acid sequence of SEQ ID NO. 2. of The one or more orthologues can be selected from the *A. niger* orthologues listed in Table 7. For example, the *A. niger* orthologues can be selected from the nucleic acid sequences represented by SEQ ID NOs. 14-32, 76 or any combination thereof. In one embodiment, the one or more orthologues are selected from the nucleic acid sequences represented by SEQ ID NOs: 9, 10, 11, 12, 13 or any combination thereof. The submerged culture conditions can comprise growing the variant strain in CAP medium. The CAP media can comprise manganese and be free or substantially free (e.g., less than 5%, 4%, 3%, 2%, or 1% of the amount or concentration of chelating agent found in fermentation media known in the art for producing a product of interest such as, for example, citric acid) or free of chelating agents. The manganese can be present in an amount that is at least 13 ppb or higher. The manganese can be present in an amount that is at least 14 ppb or higher.

Filamentous Eukaryotic Microbes

In one embodiment, the methods and systems provided herein to generate the filamentous fungal host cells or strains with the desired pellet morphology use fungal elements derived from filamentous fungus that are capable of being readily separated from other such elements in a culture medium and are capable of reproducing itself. For example, the fungal elements can be a spore, propagule, hyphal fragment, protoplast or micropellet. In a preferred embodiment, the systems and methods provided herein utilize protoplasts derived from filamentous fungus. Suitable filamentous fungi host cells include, for example, any filamentous forms of the division Ascomycota, Deuteromycota, Zygomycota or Fungi imperfecti. Suitable filamentous fungi host cells include, for example, any filamentous forms of the subdivision Eumycotina. (see, e.g., Hawksworth el al., In Ainsworth and Bisby's Dictionary of The Fungi, 8$^{th}$ edition, 1995, CAB International, University Press, Cambridge, UK, which is incorporated herein by reference). In certain illustrative, but non-limiting embodiments, the filamentous fungal host cell may be a cell of a species of: Achlya, *Acremonium, Aspergillus, Aureobasidium, Bjerkandera, Ceriporiopsis, Cephalosporium, Chrysosporium, Cochhobolus, Corynascus, Cryphonectria, Cryptococcus, Coprinus, Coriolus, Diplodia, Endothis, Filibasidium, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophylium, Scytalidium, Sporotrichum, Talaromyces, Thermoascus, Thielavia, Tramates, Tolypocladium, Trichoderma, Verticillium, Volvariella*, or teleomorphs, or anamorphs, and synonyms or taxonomic equivalents thereof. In one embodiment, the filamentous fungus is selected from the group consisting of *A. nidulans, A. oryzae, A. sojae*, and *Aspergilli* of the *A. niger* Group. In a preferred embodiment, the filamentous fungus is *Aspergillus niger*.

In one embodiment, the filamentous fungus is a production strain selected from *Aspergillus foetidus* ACM 39% (=FRR 3558), *Magnaporthe grisea* Guy-11 or *Phanerochaete Chrysosporium* RP78 In a separate embodiment, the filamentous fungus is an *A. niger* production strain known in the art. Examples of *A. niger* production strains for use in the methods provided herein can include *A. niger* ATCC 11414, ATCC 1015, ACM 4992 (=ATCC 9142), ACM 4993 (=ATCC 10577), ACM 4994 (=ATCC 12846), ATCC26550, ATCC 11414, N402, CBS 513.88 or NRRL3 (ATCC 9029, CBS 120.49).

In another embodiment, specific mutants of the fungal species are used for the methods and systems provided herein to generate the filamentous fungal host cells or strains with the desired pellet morphology. In one embodiment, specific mutants of the fungal species are used which are suitable for the high-throughput and/or automated methods and systems provided herein. Examples of such mutants can be strains that protoplast very well; strains that produce mainly protoplasts with a single nucleus; strains that regenerate efficiently in microtiter plates, strains that regenerate faster and/or strains that take up polynucleotide (e.g., DNA) molecules efficiently, strains that have reduced random integration (e.g., disabled non-homologous end joining pathway) or combinations thereof. In yet another embodiment, a specific mutant strain for use in the methods and systems provided herein can be strains lacking a selectable marker gene such as, for example, uridine-requiring mutant strains. These mutant strains can be either deficient in orotidine 5 phosphate decarboxylase (OMPD) or orotate p-ribosyl transferase (OPRT) encoded by the pyrG or pyrE gene, respectively (T. Goosen et al., Curr Genet. 1987, 11:499 503; J. Begueret et al., Gene. 1984 32:487 92.

In still another embodiment, mutant strains for use in the methods and systems provided herein to generate the filamentous fungal host cells or strains with the desired pellet morphology are modified in their DNA repair system in such a way that they are extremely efficient in homologous recombination and/or extremely inefficient in random integration. The efficiency of targeted integration of a nucleic acid construct into the genome of the host cell by homologous recombination, i.e. integration in a predetermined target locus, can be increased by augmented homologous recombination abilities and/or diminished non-homologous recombination abilities of the host cell. Augmentation of homologous recombination can be achieved by overexpressing one or more genes involved in homologous recombination (e.g., Rad51 and/or Rad52 protein). Removal, disruption or reduction in non-homologous recombination or the non-homologous end joining (NHEJ) pathway in the host cells of the present disclosure can be achieved by any method known in that art such as, for example, by use of an antibody, a chemical inhibitor, a protein inhibitor, a physical inhibitor, a peptide inhibitor, or an anti-sense or RNAi molecule directed against a component of the non-homologous recombination (NHR) or NHEJ pathway (e.g., yeast KU70, yeast KU80 or homologues thereof) Inhibition of the NHEJ pathway can be achieved using chemical inhibitors such as described in Arras SMD, Fraser J A (2016), "Chemical Inhibitors of Non-Homologous End Joining Increase Targeted Construct Integration in *Cryptococcus neoformans*" PloS ONE 11 (9): e0163049, the contents of which are hereby incorporated by reference. Treatment with the chemical inhibitor(s) to facilitate disabling or reducing the NHEJ pathway can be before and/or during generation of protoplasts. Alternatively, a host-cell for use in the methods provided herein can be deficient in one or more genes (e.g., yeast ku70, ku80 or homologues thereof) of the NHR pathway. Examples of such mutants are cells with a deficient hdfA or hdfB gene as described in WO 05/95624. Examples of chemical inhibitors for use in inhibiting NHR in host cells for use in the methods provided herein can be W7, chlorpromazine, vanillin, Nu7026, Nu7441, mirin, SCR7, AG14361 or a combination thereof as described in Arras SDM et al (2016) Chemical Inhibitors of Non-Homologous End Joining Increase Targeted Construct Integration in *Cryptococcus neoformans*. PloS One 11(9).

In one embodiment, a mutant strain of filamentous fungal cell produced by the methods and systems provided herein have a disabled or reduced non-homologous end-joining (NHEJ) pathway and possess a yeast-like, non-mycelium forming phenotype when grown in culture (e.g., submerged culture). The yeast-like, non-mycelium forming phenotype when grown in submerged culture is due to the disruption of one or more genes shown to play a role in controlling or affecting fungal morphology as provided herein (e.g., genes with SEQ ID NOs: 5, 6, 7 or 8). The one or more genes shown to play a role in controlling or affecting fungal morphology as provided herein can be part of a host cell osmotic response pathway to osmotic stress. The NHEJ pathway in said mutant strain can be reduced or disabled due to treatment with a chemical inhibitor (e.g., W7, chlorpromazine, vanillin, Nu7026, Nu7441, mirin, SCR7, AG14361 or any combination thereof). In one embodiment, the chemical inhibitor is W7. The filamentous fungal host cell (e.g., *A. niger*) can be treated with a minimum inhibitory concentration (MIC) of W7 that can be host strain dependent. Said mutant strain(s) can be subsequently used to produce a desired product of interest such as, for example, any of the products listed in Table 1.

Morphology-Related Genes

The morphology related genes for use in the methods, strains and systems provided herein can be any gene known in the art that has been shown or is suspected to play a role in controlling or affecting the morphology of a filamentous eukaryotic microbe (e.g., filamentous fungal host cell or strain) The gene that regulates morphology of the host cell can be any such gene as provided herein. In one embodiment, a gene that plays a role in or regulates morphology of the host cell can be any gene that is part of a host cell pathway that governs said host cells response to osmotic stress. Accordingly, the gene can be any gene from the filamentous fungal host cell's osmotic response pathway or a combination of said genes. In one embodiment, the gene is an orthologue of a gene from the yeast osmotic response pathway as shown in Table 7, such as, for example, orthologues of a yeast (e.g., *S. cerevisiae*) Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 gene or any combination thereof. The nucleic acid sequence of the yeast Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 gene can be selected from SEQ ID NO: 50-75. In one embodiment, the gene is an orthologue of the *S. cerevisiae* SLN1 gene or the *N. crassa* nik1 gene. In one embodiment, the host cell is an *Aspergillus* (e.g., *A. niger*) and an orthologue of the *S. cerevisiae* SLN1 gene can be selected from the SLN1 orthologues listed in Table 6 or the nucleic acid sequence of SEQ ID NO 76. In one embodiment, the *A. niger* orthologue of the *S. cerevisiae* SLN1 gene has a nucleic acid sequence selected from SEQ ID NO: 14-17. In one embodiment, the *A. niger* orthologue of the *S. cerevisiae* SLN1 gene has a nucleic acid sequence selected from SEQ ID NO: 76. In one embodiment, the host cell is an *Aspergillus* (e.g., *A. niger*) and the gene is an *A. niger* orthologue of a yeast osmotic response pathway gene as listed in Table 7. In one embodiment, the gene is an orthologue of the *Neurospora crassa* (*N. crassa*) nik1. In one embodiment, the host cell is an *Aspergillus* (e.g., *A. niger*) and the orthologue of the *N. crassa* nik1 gene can be the nik1 ortholog listed in Table 6. In one embodiment, the host cell is an *Aspergillus* (e.g., *A. niger*) and the gene is the *Aspergillus* nikA gene. In another embodiment, the morphology related gene can be any gene from the same pathway as the orthologue of the *N. crassa* nik1 gene or the *Aspergillus* nikA gene. In another embodiment, the gene is an orthologue of the *A. niger* gene with nucleic acid SEQ ID NO: 5 or 77 and/or any gene in the same biochemical pathway of said orthologue of the *A. niger* gene with nucleic acid SEQ ID NO: 5 or 77 In another embodiment, the gene is an orthologue of the *A. niger* gene with nucleic acid SEQ ID NO: 6 or 78 and/or any gene in the same biochemical pathway of said orthologue of the *A. niger* gene with nucleic acid SEQ ID NO. 6 or 78. In another embodiment, the gene is an orthologue of the *A. niger* gene with nucleic acid SEQ ID NO: 8 or 79 and/or any gene in the same biochemical pathway of said orthologue of the *A. niger* gene with nucleic acid SEQ ID NO. 8 or 79. In another embodiment, the host cell is *A. niger* and the gene is the *A. niger* gene with nucleic acid SEQ ID NO: 5 or 77 and/or any gene in the same biochemical pathway of the *A. niger* gene with nucleic acid SEQ ID NO. 5 or 77. In another embodiment, the host cell is *A. niger* and the gene is the *A. niger* gene with nucleic acid SEQ ID NO. 6 or 78 and/or any gene in the same biochemical pathway of the *A. niger* gene with nucleic acid SEQ ID NO. 6 or 78. In another embodiment, the host cell is *A. niger* and the gene is the *A. niger* gene with nucleic acid SEQ ID NO: 8 or 79 and/or any gene in the same biochemical pathway of the *A. niger* gene with nucleic acid SEQ ID NO: 8 or 79.

The morphology related genes for use in the methods, strains and systems provided herein can be any gene known in the art that has been shown or is suspected to play a role in controlling or affecting the morphology of *A. niger*. In one embodiment, the gene is a SNP containing gene with a nucleic acid sequence selected from SEQ ID NOs: 5, 6, 7 or 8 (see Table 4). In one embodiment, the gene is a plurality of genes. The plurality of genes can be any combination of the SNP containing genes with a nucleic acid sequence selected from SEQ ID NOs. 5, 6, 7 or 8. The plurality of genes can be any combination of the SNP containing genes with a nucleic acid sequence selected from SEQ ID NOs: 5 and any gene present within the same biochemical pathway. The plurality of genes can be any combination of the SNP containing genes with a nucleic acid sequence selected from SEQ ID NOs: 6 and any gene present within the same biochemical pathway. The plurality of genes can be any combination of the SNP containing genes with a nucleic acid sequence selected from SEQ ID NOs: 7 and any gene present within the same biochemical pathway (i.e., osmotic response pathway). The plurality of genes can be any combination of the SNP containing genes with a nucleic acid sequence selected from SEQ ID NOs: 8 and any gene present within the same biochemical pathway. In one embodiment, the gene is a wild-type or non-SNP containing version of the gene with a nucleic acid sequence selected from SEQ ID NOs: 5, 6, 7 or 8 (see Table 4). In one embodiment, the gene is a wild-type or non-SNP containing version of the gene with a nucleic acid sequence selected from SEQ ID NOs: 76-79.

In one embodiment, the gene that regulates morphology of an *A. niger* host cell is an *A. niger* orthologue of the *S. cerevisiae* SLN1 gene. The *A. niger* orthologue of the *S. cerevisiae* SLN1 gene can be a wild-type form or a mutant form. The mutated form of the *A. niger* orthologue of the *S. cerevisiae* SLN1 gene can be FungiSNP_18 from Table 3 or 4 or with a nucleic acid sequence of SEQ ID NO: 7. In another embodiment, the morphology related gene can be any gene from the same pathway (i.e., osmotic response pathway) as the *A. niger* orthologue of the *S. cerevisiae* SLN1 gene. The genes that are part of the same pathway (i.e., osmotic response pathway) can be selected from *A. niger* orthologues of the *S. cerevisiae* Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 genes or any combination thereof. The nucleic acid sequence of the yeast Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 can be selected from SEQ ID NO: 50-75. The genes that are part of same pathway (i.e., osmotic response pathway) as an *A. niger* orthologue of the *S. cerevisiae* SLN1 gene (or the *N. crassa* nik1 gene) can have a nucleic acid sequence selected from SEQ ID NO: 18-32. The genes that are part of the same pathway (i.e., osmotic response pathway) can be selected from the nucleic acid sequences represented by SEQ ID NOs: 9, 10, 11, 12, 13 or any combination thereof.

The morphology-related genes can be any of the genes or orthologues thereof that are disclosed in Dai et al. ("Identification of Genes Associated with Morphology in *Aspergillus niger* by Using Suppression Subtractive Hybridization" Applied and Environmental Microbiology, April 2004, p 2474-2485), the contents of which are incorporated by reference in its entirety. The morphology-related gene can be selected from the gas1 gene, the sfb3 gene, the seb1 gene, the mpg1 gene, the crz1 gene, and the tps2 gene. The expression of any of the morphology related genes can be increased or decreased depending on if the gene promotes a filamentous or mycelial morphology or pellet morphology.

As described herein, the expression of any of the morphology related genes or mutant thereof (e.g., FungiSNPs 9, 12, 18 or 40 from Table 4) provided herein can be controlled by replacing the native promoter of the gene with a heterologous promoter that confers expression at a level (e.g., higher or lower) different from the native promoter. The heterologous promoter can be selected from Table 2 Replacement of the native promoter can be performed using a PRO swap method as provided herein.

Promoter Ladders

Promoters regulate the rate at which genes are transcribed and can influence transcription in a variety of ways. Constitutive promoters, for example, direct the transcription of their associated genes at a constant rate regardless of the internal or external cellular conditions, while regulatable, tunable or inducible promoters increase or decrease the rate at which a gene is transcribed depending on the internal and/or the external cellular conditions, e.g. growth rate, temperature, responses to specific environmental chemicals, and the like. Promoters can be isolated from their normal cellular contexts and engineered to regulate the expression of virtually any gene, enabling the effective modification of cellular growth, product yield and/or other phenotypes of interest.

Promoter sequences can be operably linked to the 5' termini of any sequences (e.g., morphology related genes) provided herein to be expressed in a filamentous fungal host cell as provided herein. A variety of known fungal promoters are likely to be functional in the host strains of the disclosure such as, for example, the promoter sequences of Cl endoglucanases, the 55 kDa cellobiohydrolase (CBH1), glyceraldehyde-3-phosphate dehydrogenase A, *C. lucknowense* GARG 27K and the 30 kDa xylanase (Xy1F) promoters from *Chrysosporium*, as well as the *Aspergillus* promoters described in, e.g., U.S. Pat. Nos. 4,935,349, 5,198,345; 5,252,726; 5,705,358; and 5,965,384; and PCT application WO 93/07277.

In one embodiment the promoters for use in the methods and systems provided herein for generating strains or host cells comprising the desired pellet morphology under specific growth conditions (i.e., submerged cultures) are inducible promoters. The inducible promoters can be any promoter whose transcriptional activity is regulated by the presence or absence of a chemical such as for example, alcohol, tetracycline, steroids, met als or other compounds known in the art. The inducible promoters can be any promoter whose transcriptional activity is regulated by the presence or absence of light or low or high temperatures. In one embodiment, the inducible promoters are selected from filamentous fungal genes such as the srpB gene, the amyB gene, the manB gene or the mbfA gene. In one embodiment, the inducible promoter is selected from the promoters listed in Table 2. In one embodiment, the inducible promoter is catabolite repressed by glucose. The catabolite repressed by glucose can be the amyB promoter from *A. oryzae*.

Figure 2:
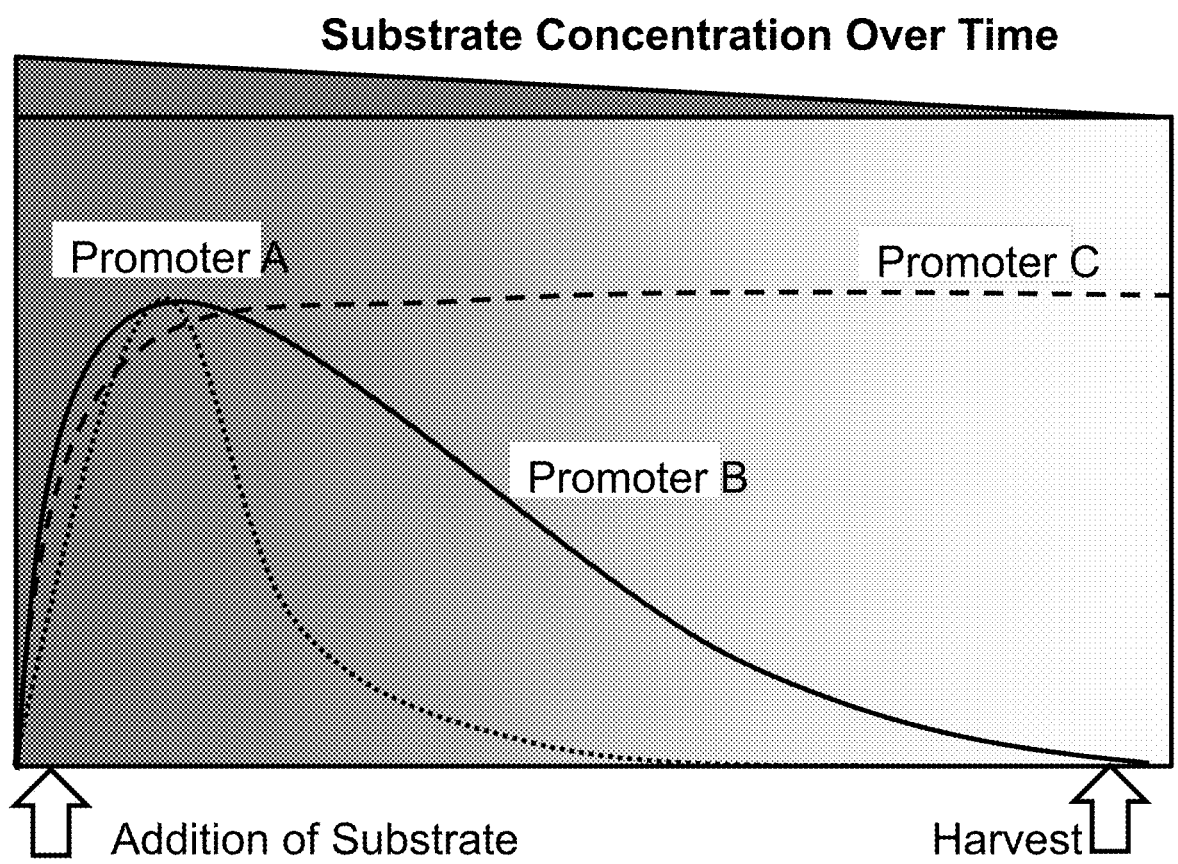
FIG. 2 illustrates expression profiles of illustrative promoters exhibiting a range of regulatory expression, according to the promoter ladders of the present disclosure. Promoter A expression peaks immediately upon addition of a selected substrate, but quickly returns to undetectable levels as the concentration of the substrate is reduced. Promoter B expression peaks immediately upon addition of the selected substrate and lowers slowly back to undetectable levels together with the corresponding reduction in substrate. Promoter C expression peaks upon addition of the selected substrate, and remains highly expressed throughout the culture, even after the substrate has dissipated.

In some embodiments, the present disclosure teaches the generation of promoter ladders for controlling the expression of one or more genes that control and/or play a role in controlling filamentous fungal growth and/or morphology. In some embodiments, the promoter ladders of the present disclosure comprise a collection of promoters that exhibit a continuous range of expression profiles. For example, in some embodiments, promoter ladders are created by: identifying natural, native, or wild-type promoters that exhibit a range of expression strengths in response to a stimuli, or through constitutive expression (see e.g., FIG. 2). These identified promoters can be grouped together as a promoter ladder.

In other embodiments, the present disclosure teaches the creation of promoter ladders exhibiting a range of expression profiles across different conditions. For example, in some embodiments, the present disclosure teaches creating a ladder of promoters with expression peaks spread throughout the different stages of a fermentation. In other embodiments, the present disclosure teaches creating a ladder of promoters with different expression peak dynamics in response to a specific stimulus (see e.g., FIG. 2). Persons skilled in the art will recognize that the regulatory promoter ladders of the present disclosure can be representative of any one or more regulatory profiles.

In some embodiments, the promoter ladders of the present disclosure are designed to perturb gene expression in a predictable manner across a continuous range of responses. In some embodiments, the continuous nature of a promoter ladder confers strain improvement programs with additional predictive power. For example, in some embodiments, swapping promoters for a gene shown to or suspected of controlling or affecting morphology can produce a host cell performance curve with respect to morphology, which identifies the most optimum expression ratio or profile of a specific gene for producing a strain or host cell with the desired pellet morphology under the desired growth condition; producing a strain in which the targeted gene is no longer a limiting factor for a particular reaction or genetic cascade, while also avoiding unnecessary over expression or misexpression under inappropriate circumstances. In some embodiments, promoter ladders are created by: identifying natural, native, or wild-type promoters exhibiting the desired profiles. In other embodiments, the promoter ladders are created by mutating naturally occurring promoters to derive multiple mutated promoter sequences. Each of these mutated promoters is tested for effect on target gene expression and the resulting morphological phenotypes. In some embodiments, the edited promoters are tested for expression activity across a variety of conditions, such that each promoter variant's activity is documented/characterized/annotated and stored in a database. The resulting edited promoter variants are subsequently organized into promoter ladders arranged based on the strength of their expression (e.g., with highly expressing variants near the top, and attenuated expression near the bottom, therefore leading to the term "ladder").

In some embodiments, the present disclosure teaches the generation and/or use of promoter ladders that are a combination of identified naturally occurring promoters and mutated variant promoters.

In some embodiments, the present disclosure teaches methods of identifying natural, native, or wild-type promoters that satisfied both of the following criteria: 1) represented a ladder of constitutive promoters; and 2) could be encoded by short DNA sequences, ideally less than 100 base pairs In some embodiments, constitutive promoters of the present disclosure exhibit constant gene expression across two selected growth conditions (typically compared among conditions experienced during industrial cultivation). In some embodiments, the promoters of the present disclosure will consist of a ~60 base pair core promoter, and a 5' UTR between 26- and 40 base pairs in length.

In some embodiments, one or more of the aforementioned identified naturally occurring promoter sequences are chosen for gene editing. In some embodiments, the natural promoters are edited via any of the mutation methods described supra. In other embodiments, the promoters of the present disclosure are edited by synthesizing new promoter variants with the desired sequence.

A non-exhaustive list of the promoters for use in the methods and systems for generating strains or host cells comprising the desired pellet morphology is provided in the Table 2. Each of the promoter sequences can be referred to as a heterologous promoter or heterologous promoter polynucleotide.

TABLE 2

Selected promoter sequences of the present disclosure.

| SEQ ID NO. | Promoter Short Name | Promoter Name |
| --- | --- | --- |
| 1 | manBp | manB promoter from Aspergillus niger |
| 2 | amyBp | amyB gene from Aspergillus oryzae |
| 3 | srpBp | srpB promoter from Aspergillus niger |
| 4 | mbfAp | mbfA promoter from Aspergillus niger |

In some embodiments, the promoters of the present disclosure exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a promoter from the above table.

Promoter Swapping

In some embodiments, the present disclosure teaches methods of selecting promoters with optimal expression properties to produce beneficial effects on overall-host strain phenotype (e.g., non-mycelium, pellet morphology under desired growth conditions (i.e., submerged culture in fermentation media)).

For example, in some embodiments, the present disclosure teaches methods of identifying one or more promoters and/or generating variants of one or more promoters within a host cell, which exhibit a range of expression strengths (e.g. promoter ladders discussed infra), or superior regulatory properties (e.g., tighter regulatory control for selected genes). A particular combination of these identified and/or generated promoters can be grouped together as a promoter ladder.

Also provided herein are promoter swapping methods to genetically engineer filamentous fungal cells to produce or express a desired trait such as, for example, a desired pellet morphology. In general, promoter swapping (i.e., PRO swap) entails systematically associating each promoter from a promoter ladder as described with a given gene of interest. Thus, for example, if one has promoters $P_1$-$P_8$ (representing eight promoters that have been identified and/or generated to exhibit a range of expression strengths) and associates the promoter ladder with a single gene of interest in a microbe (i.e. genetically engineer a microbe with a given promoter operably linked to a given target gene), then the effect of each combination of the eight promoters can be ascertained by characterizing each of the engineered strains resulting from each combinatorial effort, given that the engineered microbes have an otherwise identical genetic background except the particular promoter(s) associated with the target gene. The resultant microbes that are engineered via this process can form HTP genetic design libraries.

In a specific embodiment, the promoter swapping (PRO Swap) methods provided herein entail systematically associating each promoter from the promoter ladder depicted in Table 2 with a gene shown to or suspected to play a role or affect morphology of filamentous fungal cells when grown under specific conditions (referred to as target morphological genes) The perturbation of the gene can cause a desired morphological phenotype. The desired phenotype can be a non-mycelium, pellet morphology when grown in submerged cultures of a production media (e.g., CAP media). Thus, if one has promoters $P_1$-$P_4$ (representing the four promoters from Table 2 that have been identified and/or generated to exhibit a range of expression strengths) and associates the promoter ladder with a single target morphological gene of interest in a microbe (i.e. genetically engineer a microbe with a given promoter operably linked to a given target morphological gene), then the effect of each combination of the four promoters can be ascertained by characterizing each of the engineered strains resulting from each combinatorial effort, given that the engineered microbes have an otherwise identical genetic background except the particular promoter(s) associated with the specific target morphological gene. The resultant microbes that are engineered via this process can form HTP morphological genetic design libraries.

Further, one can utilize the same promoter ladder comprising promoters $P_1$-$P_4$ to engineer microbes, wherein each of the 4 promoters is operably linked to a plurality of different morphological target genes as provided herein. For example, the plurality can be 10 different morphological target genes. The result of this procedure would be 40 microbes that are otherwise assumed genetically identical, except for the particular promoters operably linked to a target morphological gene of interest. These 40 microbes could be appropriately screened and characterized and give rise to another HTP genetic design library. The characterization of the microbial strains in the HTP genetic design library produces information and data that can be stored in any data storage construct, including a relational database, an object-oriented database or a highly distributed NoSQL database. This data/information could be, for example, a given promoter's (e.g. $P_1$-$P_4$) effect when operably linked to a given morphological gene target. This data/information can also be the broader set of combinatorial effects that result from operably linking two or more of promoters $P_1$-$P_4$ to a given morphological gene target.

The aforementioned examples of four promoters and 10 target genes is merely illustrative, as the concept can be applied with any given number of promoters that have been grouped together based upon exhibition of a range of expression strengths and any given number of target morphological genes Persons having skill in the art will also recognize the ability to operably link two or more promoters in front of any gene target. Thus, in some embodiments, the present disclosure teaches promoter swap libraries in which 1, 2, 3 or more promoters from a promoter ladder are operably linked to one or more genes.

In summary, utilizing various promoters to drive expression of various genes in an organism is a powerful tool to optimize a trait of interest (e.g., pellet morphology under submerged culture conditions). The molecular tool of promoter swapping, as described herein, uses a ladder of promoter sequences (e.g., Table 2) that have been demonstrated to vary expression of at least one locus (e.g., FungiSNP_9, FungiSNP_12, FungiSNP_18 or FungiSNP_40) under at least one condition (e.g., submerged culture in CAP media). This ladder is then systematically applied to a group of genes (e.g., within the same pathway as FungiSNP18 as provided herein) in the organism using high-throughput genome engineering. This group of genes is determined to have a high likelihood of impacting the trait of interest based on any one of a number of methods. These could include selection based on known function, or impact on the trait of interest (i.e., morphology), or algorithmic selection based on previously determined beneficial genetic diversity. In some embodiments, the selection of genes can include all the morphological genes in a given host. In other embodiments, the selection of genes can be a subset of all morphological genes in a given host, chosen randomly or specifically selected based on known or suspected pathway function.

The resultant HTP genetic design microbial strain library of organisms containing a promoter sequence linked to a morphological gene is then assessed for performance in a high-throughput screening model, and promoter-gene linkages which lead to increased performance are determined and the information stored in a database. The collection of genetic perturbations (i.e. given promoter x operably linked to a given gene y) form a "promoter swap library," which can be utilized as a source of potential genetic alterations to be utilized in microbial engineering processing. Over time, as a greater set of genetic perturbations is implemented against a greater diversity of host cell backgrounds, each library becomes more powerful as a corpus of experimentally confirmed data that can be used to more precisely and predictably design targeted changes against any background of interest.

Transcription levels of genes in an organism are a key point of control for affecting organism behavior Transcription is tightly coupled to translation (protein expression), and which proteins are expressed in what quantities determines organism behavior. Cells express thousands of different types of proteins, and these proteins interact in numerous complex ways to create function. By varying the expression levels of a set of proteins systematically, function can be altered in ways that, because of complexity, are difficult to predict Some alterations may increase performance, and so, coupled to a mechanism for assessing performance, this technique allows for the generation of organisms with improved function.

In some embodiments, the promoter swap tool of the present disclosure is used to identify optimum expression of a selected morphological gene target. In some embodiments, the goal of the promoter swap may be to increase expression of a target morphological gene to reduce bottlenecks in a metabolic or genetic pathway. In other embodiments, the goal of the promoter swap may be to reduce the expression of the target morphological gene to avoid unnecessary energy expenditures in the host cell, when expression of said target morphological gene is not required.

In the context of other cellular systems like transcription, transport, or signaling, various rational methods can be used to try and find out, a priori, which proteins are targets for expression change and what that change should be. These rational methods reduce the number of perturbations that must be tested to find one that improves performance, but they do so at significant cost. Gene deletion studies identify proteins whose presence is critical for a particular function, and important genes can then be over-expressed. Due to the complexity of protein interactions, this is often ineffective at increasing performance. Different types of models have been developed that attempt to describe, from first principles, transcription or signaling behavior as a function of protein levels in the cell. These models often suggest targets where expression changes might lead to different or improved function. The assumptions that underlie these models are simplistic and the parameters difficult to measure, so the predictions they make are often incorrect, especially for non-model organisms. With both gene deletion and modeling, the experiments required to determine how to affect a certain gene are different than the subsequent work to make the change that improves performance. Promoter swapping sidesteps these challenges, because the constructed strain that highlights the importance of a particular perturbation is also, already, the improved strain.

In particular embodiments, promoter swapping for use in generating a filamentous fungal strain or host cell comprising a desired pellet morphology is a multi-step process comprising:

1. Selecting a set of "x" promoters to act as a "ladder." Ideally these promoters have been shown to lead to highly variable expression across multiple genomic loci, but the only requirement is that they perturb gene expression in some way. In one embodiment, the set of "x" promoters that acts as a ladder comprises the promoters in Table 2.

2. Selecting a set of "n" genes to target. This set can be every open reading frame (ORF) in a genome, or a subset of ORFs shown to play a role in controlling or affecting morphology. The subset can be chosen using annotations on ORFs related to function, by relation to previously demonstrated beneficial perturbations (previous promoter swaps or previous SNP swaps), by algorithmic selection based on peristatic interactions between previously generated perturbations, other selection criteria based on hypotheses regarding beneficial ORF to target, or through random selection. In one embodiment, the set of "n" genes can be orthologues of the S. cerevisiae SLN1 gene or N. crassa nik1 gene (e.g., A. niger orthologues listed in Table 6) and/or orthologues of one or more genes that are part of the same pathway (e.g., osmotic response pathway genes listed in Table 7). The orthologues of the S. cerevisiae SLN1 gene or N. crassa nik1 gene (e.g., A. niger orthologues listed in Table 6) and/or one or more genes that are part of the same pathway (e.g., osmotic response pathway genes listed in Table 7) can be wild-type are mutant forms of said genes. In one embodiment, the filamentous fungal strain or host cell is A. niger, and the set of "n" genes selected is the SNP containing genes found in Table 3 or Table 4. In another embodiment wherein A. niger is the host cell, the set of "n" genes selected is the non-SNPs or wildtype versions of the SNP containing genes found in Table 3 or Table 4. When A. niger is the host cell, the set of "n" genes can be the gene for FungiSNP_9 found in Tables 3 and 4 in addition to one or more genes that are part of the same pathway. When A. niger is the host cell, the set of "n" genes can be the gene for FungiSNP_12 found in Tables 3 and 4 in addition to one or more genes that are part of the same pathway. When A. niger is the host cell, the set of "n" genes can be the gene for FungiSNP_40 found in Tables 3 and 4 in addition to one or more genes that are part of the same pathway. In another embodiment, when A. niger is the host cell, the set of "n" genes can be the gene for FungiSNP_18 (i.e., a mutant form of the A. niger orthologue of the S. cerevisiae SLN1 gene or N. crassa nik1 gene) from Tables 3 and 4 in addition to one or more genes that are part of the same pathway (e.g., A. niger osmotic response pathway genes listed in Table 7). The A. niger orthologue of the S. cerevisiae SLN1 gene (or N. crassa nik1 gene) and/or the one or more genes in the same pathway can be wild-type or mutant forms of the gene (e.g., A. niger osmotic response pathway genes listed in Table 7). A mutant form of the A. niger orthologue of the S. cerevisiae SLN1 gene or N. crassa nik1 gene can be the form with SEQ ID NO: 7 The one or more genes in the pathway can be an A. niger orthologue of the yeast (e.g., S. cerevisiae) Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 genes or any combination thereof. The nucleic acid sequence of the yeast Ypd1, Skn7, Ssk1, Ste11, Bck1, Ste7, Mkk2/22, Pbs2, Fus1/Kss3, Mpk1, Hog1, Phk1/2, Chk1, Phk3, Spy1, Mcs4, SskA, Prr1, Rim15, Cek1, Rim15 and Ssk2/22 can be selected from SEQ ID NO: 50-75. The one or more genes that are part of the same pathway can be selected from the nucleic acid sequences represented by SEQ ID NOs: 9, 10, 11, 12, 13 or any combination thereof.

3. High-throughput strain engineering to rapidly- and in some embodiments, in parallel-carry out the following genetic modifications: When a native promoter exists in front of morphological target gene n and its sequence is known, replace the native promoter with each of the x promoters in the ladder (e.g., the promoter ladder found in Table 2). When the native promoter does not exist, or its sequence is unknown, insert each of the x promoters in the ladder in front of gene n (see e.g., FIG. 1). In this way a "library" (also referred to as a HTP genetic design library) of morphologically phenotypic strains is constructed, wherein each member of the library is an instance of x promoter operably linked to n morphological target gene, in an otherwise identical genetic context. As previously described combinations of promoters can be inserted, extending the range of combinatorial possibilities upon which the library is constructed.

4. High-throughput screening of the library of strains in a context where their performance against one or more metrics is indicative of the performance that is being optimized. The context can be growth in submerged cultures in media for a desired product of interest such as, for example, CAP media for the production of citric acid.

This foundational process can be extended to provide further improvements in strain performance by, inter alia: (1) Consolidating multiple beneficial perturbations into a single strain background, either one at a time in an interactive process, or as multiple changes in a single step. Multiple perturbations can be either a specific set of defined changes or a partly randomized, combinatorial library of changes. For example, if the set of targets is every gene in a pathway, then sequential regeneration of the library of perturbations into an improved member or members of the previous library of strains can optimize the expression level of each gene in a pathway regardless of which genes are rate limiting at any given iteration; (2) Feeding the performance data resulting from the individual and combinatorial generation of the library into an algorithm that uses that data to predict an optimum set of perturbations based on the interaction of each perturbation, and (3) Implementing a combination of the above two approaches.

The molecular tool, or technique, discussed above is characterized as promoter swapping, but is not limited to promoters and can include other sequence changes that systematically vary the expression level of a set of targets. Other methods for varying the expression level of a set of genes could include: a) a ladder of ribosome binding sites (or Kozak sequences in eukaryotes); b) replacing the start codon of each target with each of the other start codons (i.e start/stop codon exchanges discussed infra), c) attachment of various mRNA stabilizing or destabilizing sequences to the 5' or 3' end, or at any other location, of a transcript, d) attachment of various protein stabilizing or destabilizing sequences at any location in the protein.

The approach is exemplified in the present disclosure with industrial microorganisms but is applicable to any organism where desired traits can be identified in a population of genetic mutants. For example, this could be used for improving the performance of CHO cells, yeast, insect cells, algae, as well as multi-cellular organisms, such as plants.

SNP Swapping

In one embodiment, the methods and systems provided herein are utilized for SNP swapping in order to generate filamentous fungal libraries comprising filamentous fungal with individual SNPs or combinations of SNPs. SNP swapping is not a random mutagenic approach to improving a microbial strain, but rather involves the systematic introduction or removal of individual Small Nuclear Polymorphism nucleotide mutations (i.e., SNPs) (hence the name "SNP swapping") across strains. The SNPs or combination SNPs can each be in genes that have been shown to or are suspected of controlling or affecting filamentous fungal morphology.

The resultant microbes that are engineered via this process form HTP morphological genetic design libraries. The HTP genetic design library can refer to the actual physical microbial strain collection that is formed via this process, with each member strain being representative of the presence or absence of a given SNP, in an otherwise identical genetic background, said library being termed a "SNP swap microbial strain library." In the specific context of filamentous fungus (e.g., *A. niger*), the library can be termed a "SNP swap filamentous fungal strain library," or "SNP swap *A. niger* strain library," but the terms can be used synonymously, as filamentous fungus is a specific example of a microbe or coenocytic organism.

Furthermore, the HTP genetic design library can refer to the collection of genetic perturbations—in this case a given SNP being present or a given SNP being absent-said collection being termed a "SNP swap library." A SNP swap library for use in the methods provided herein can be the SNP library of Table 3 or Table 4.

TABLE 3

SNP containing genes potentially involved in citric acid production in *A. niger*.

| Mutation name | Location | Sequence change | orientation | Contig |
| --- | --- | --- | --- | --- |
| FungiSNP_01 | 50669-680224 | ~>~ | 680224 | chr_1_1 |
| FungiSNP_02 | 1172974 | G > A | + | chr_1_1 |
| FungiSNP_03 | 367948 | C > T | + | chr_1_2 |
| FungiSNP_04 | 549014 | C > G | − | chr_1_2 |
| FungiSNP_05 | 1330718 | G > A | + | chr_1_2 |
| FungiSNP_06 | 662258 | G> | + | chr_2_1 |
| FungiSNP_07 | 673547 | G > A | − | chr_2_1 |
| FungiSNP_08 | 946654 | T> | + | chr_2_1 |
| FungiSNP_09 | 641661 | T > A | − | chr_2_2 |
| FungiSNP_10 | 2316591 | G > A | + | chr_2_2 |
| FungiSNP_11 | 935908 | A > G | − | chr_3_1 |
| FungiSNP_12 | 205638 | T > A | + | chr_3_2 |
| FungiSNP_13 | 268107 | T > C | + | chr_3_3 |
| FungiSNP_14 | 186943 | A > T | + | chr_3_4 |
| FungiSNP_15 | 276232 | C > T | + | chr_3_4 |
| FungiSNP_16 | 1287891 | T > C | − | chr_4_1 |
| FungiSNP_17 | 1639965 | A > T | + | chr_4_1 |
| FungiSNP_18 | 1826343 | G > A | − | chr_4_1 |
| FungiSNP_19 | 1358794 | C > A | + | chr_4_2 |
| FungiSNP_20 | 1466380 | CTA> | + | chr_4_2 |
| FungiSNP_21 | 1700330 | C > A | − | chr_4_2 |
| FungiSNP_22 | 2873296 | A > G | + | chr_4_2 |
| FungiSNP_23 | 815022 | G > A | + | chr_5_2 |
| FungiSNP_24 | 831672 | G > A | − | chr_5_2 |
| FungiSNP_25 | 1507652 | >A | + | chr_5_2 |
| FungiSNP_26 | 442488 | T > C | + | chr_6_1 |
| FungiSNP_27 | 93202-103239 | ~>~ | + | chr_6_2 |
| FungiSNP_28 | 972833 | A > T | + | chr_6_2 |
| FungiSNP_29 | 972932 | A> | + | chr_6_2 |
| FungiSNP_30 | 1183094 | G> | + | chr_6_2 |
| FungiSNP_31 | 1701762 | T > G | + | chr_6_2 |
| FungiSNP_32 | 236406 | G > A | − | chr_7_1 |
| FungiSNP_33 | 2350056 | A> | + | chr_7_1 |
| FungiSNP_34 | 375013 | C > T | + | chr_8_1 |
| FungiSNP_35 | 1272037 | C > T | + | chr_8_1 |
| FungiSNP_36 | 281612 | T > C | + | chr_8_2 |

TABLE 3-continued

SNP containing genes potentially involved in citric acid production in *A. niger*.

| Mutation name | Location | Sequence change | orientation | Contig |
| --- | --- | --- | --- | --- |
| FungiSNP_37 | 565087 | A > G | + | chr_8_2 |
| FungiSNP_38 | 865958 | A> | + | chr_8_2 |
| FungiSNP_39 | 947633 | A> | + | chr_8_2 |
| FungiSNP_40 | 2482267 | G > A | + | chr_8_2 |
| FungiSNP_41 | 2486601 | G> | + | chr_8_2 |
| FungiSNP_42 | 2709491 | T > C | + | chr_8_2 |
| FungiSNP_43 | 2708043 | >A | ~ | chr_8_2 |

TABLE 4

Gene description/putative function for subset of SNP containing genes from Table 3 with SNPs that are located within coding domains.

| ATCC 1015 (fungidb.org ID) | Name | Description/ Putative Function | Altered Morphological Phenotype in SNPSWP, knock-out and/or knock-in experiments |
| --- | --- | --- | --- |
| ASPNIDRAFT_212500 (SEQ ID NO: 46) | FungiSNP_02 | Aromatic amino acid aminotransferase and related protein | |
| ASPNIDRAFT_44864 (SEQ ID NO: 33) | FungiSNP_06 | Taurine catabolism dioxygenase TauD/TfdA | |
| ASPNIDRAFT_44868 (SEQ ID NO: 45) | FungiSNP_07 | alpha/beta hydrolase | |
| ASPNIDRAFT_196832 (SEQ ID NO: 42) | FungiSNP_09 (SEQ ID NO: 5; A > T SNP at nucleotide 706) | pseudouridylate synthase activity (PUS4 in yeast) | x |
| ASPNIDRAFT_212853 (SEQ ID NO: 41) | FungiSNP_11 | Serine/threonine protein kinase | |
| ASPNIDRAFT_119127 (SEQ ID NO: 47) | Fungi SNP_12 (SEQ ID NO: 6; T > A SNP at nucleotide 2728) | Transcription factor | x |
| ASPNIDRAFT_123785 (SEQ ID NO: 40) | FungiSNP_16 | Serine/threonine protein kinase | |
| ASPNIDRAFT_39736 (SEQ ID NO: 14) | FungiSNP_18 (SEQ ID NO: 7; C > T SNP at nucleotide 814) | Sensory transduction histidine kinase/two component histidine kinase | x |
| ASPNIDRAFT_55560 (SEQ ID NO: 36) | FungiSNP_20 | mannitol-1-phosphate 5-dehydrogenase | |
| ASPNIDRAFT_206922 (SEQ ID NO: 48) | FungiSNP_21 | Tomosyn and related SNARE-interacting protein | |
| ASPNIDRAFT_53655 (SEQ ID NO: 39) | FungiSNP_23 | unknown function | |
| ASPNIDRAFT_121820 (SEQ ID NO: 44) | FungiSNP_24 | Cytochrome c heme-binding site | |
| ASPNIDRAFT_131243 (SEQ ID NO: 37) | FungiSNP_30 | Monooxygenase involved | |

TABLE 4-continued

Gene description/putative function for subset of SNP containing genes from Table 3 with SNPs that are located within coding domains.

| ATCC 1015 (fungidb.org ID) | Name | Description/ Putative Function | Altered Morphological Phenotype in SNPSWP, knock-out and/or knock-in experiments |
|---|---|---|---|
| ASPNIDRAFT_127977 (SEQ ID NO: 38) | FungiSNP_32 | in coenzyme Q (ubiquinone) biosynthesis extracellular unknown protein | |
| ASPNIDRAFT_38583 (SEQ ID NO: 43) | FungiSNP_36 | unknown function | |
| ASPNIDRAFT_52574 (SEQ ID NO: 49) | FungiSNP_40 (SEQ ID NO: 8; G > A SNP at nucleotide 3680) | Uncharacterized conserved coiled-coil protein | x |
| ASPNIDRAFT_47328 (SEQ ID NO: 34) | FungiSNP_41 | Magnesium-dependent phosphatase | |
| ASPNIDRAFT_37842 (SEQ ID NO: 35) | FungiSNP_43 | GTPase-activating protein | |

In some embodiments, SNP swapping involves the reconstruction of host organisms with optimal combinations of target SNP "building blocks" with identified beneficial performance effects. In one embodiment, the SNP swapping entails reconstruction of a filamentous fungal host cell (e.g., *A. niger*) with optimal combinations of morphological target genes with identified beneficial effects of fungal morphology in defined culture conditions (e.g., submerged cultures). Thus, in some embodiments, SNP swapping involves consolidating multiple beneficial mutations into a single strain background, either one at a time in an iterative process, or as multiple changes in a single step. Multiple changes can be either a specific set of defined changes or a partly randomized, combinatorial library of mutations.

In other embodiments, SNP swapping also involves removing multiple mutations identified as detrimental from a strain, either one at a time in an iterative process, or as multiple changes in a single step. In one embodiment, SNP swapping involves removing multiple mutations in morphological target genes that are identified as being detrimental to a strain forming a desired morphology (e.g., pellet morphology in submerged cultures of production media). Multiple changes can be either a specific set of defined changes or a partly randomized, combinatorial library of mutations. In some embodiments, the SNP swapping methods of the present disclosure include both the addition of beneficial SNPs and removing detrimental and/or neutral mutations.

SNP swapping is a powerful tool to identify and exploit both beneficial and detrimental mutations in a lineage of strains subjected to mutagenesis and selection for an improved trait of interest (e.g., pellet morphology in submerged cultures of production media). SNP swapping utilizes high-throughput genome engineering techniques to systematically determine the influence of individual mutations in target morphological genes in a mutagenic lineage. Genome sequences are determined for strains across one or more generations of a mutagenic lineage with known performance improvements. High-throughput genome engineering is then used systematically to recapitulate mutations from improved strains in earlier lineage strains, and/or revert mutations in later strains to earlier strain sequences. The performance of these strains is then evaluated and the contribution of each individual mutation on the improved phenotype of interest (e.g., pellet morphology in submerged cultures of production media) can be determined. As aforementioned, the microbial strains that result from this process are analyzed/characterized and form the basis for the SNP swap genetic design libraries that can inform microbial strain improvement across host strains.

Removal of detrimental mutations can provide immediate performance improvements, and consolidation of beneficial mutations in a strain background not subject to mutagenic burden can rapidly and greatly improve strain performance. The various microbial strains produced via the SNP swapping process form the HTP genetic design SNP swapping libraries, which are microbial strains comprising the various added/deleted/or consolidated SNPs, but with otherwise identical genetic backgrounds.

As discussed previously, random mutagenesis and subsequent screening for performance improvements is a commonly used technique for industrial strain improvement, and many strains currently used for large scale manufacturing have been developed using this process iteratively over a period of many years, sometimes decades. Random approaches to generating genomic mutations such as exposure to UV radiation or chemical mutagens such as ethyl methanesulfonate were a preferred method for industrial strain improvements because: 1) industrial organisms may be poorly characterized genetically or metabolically, rendering target selection for directed improvement approaches difficult or impossible; 2) even in relatively well characterized systems, changes that result in industrial performance improvements are difficult to predict and may require perturbation of genes that have no known function, and 3) genetic tools for making directed genomic mutations in a given industrial organism may not be available or very slow and/or difficult to use.

However, despite the aforementioned benefits of this process, there are also a number of known disadvantages Beneficial mutations are relatively rare events, and in order to find these mutations with a fixed screening capacity, mutations rates must be sufficiently high. This often results in unwanted neutral and partly detrimental mutations being incorporated into strains along with beneficial changes. Over time this 'mutagenic burden' builds up, resulting in strains with deficiencies in overall robustness and key traits such as growth rates. Eventually 'mutagenic burden' renders further improvements in performance through random mutagenesis increasingly difficult or impossible to obtain. Without suitable tools, it is impossible to consolidate beneficial mutations found in discrete and parallel branches of strain lineages.

SNP swapping is an approach to overcome these limitations by systematically recapitulating or reverting some or all mutations observed when comparing strains within a mutagenic lineage. In this way, both beneficial ('causative') mutations can be identified and consolidated, and/or detrimental mutations can be identified and removed. This allows rapid improvements in strain performance that could not be achieved by further random mutagenesis or targeted genetic engineering.

Removal of genetic burden or consolidation of beneficial changes into a strain with no genetic burden also provides a new, robust starting point for additional random mutagenesis that may enable further improvements.

In addition, as orthogonal beneficial changes are identified across various, discrete branches of a mutagenic strain lineage, they can be rapidly consolidated into better performing strains. These mutations can also be consolidated into strains that are not part of mutagenic lineages, such as strains with improvements gained by directed genetic engineering.

Other approaches and technologies exist to randomly recombine mutations between strains within a mutagenic lineage. These include techniques such as protoplast fusion and whole genome shuffling that facilitate genomic recombination across mutated strains. For some industrial microorganisms such as yeast and filamentous fungi, natural mating cycles can also be exploited for pairwise genomic recombination. In this way, detrimental mutations can be removed by 'back-crossing' mutants with parental strains and beneficial mutations consolidated. However, these approaches are subject to many limitations that are circumvented using the SNP swapping methods of the present disclosure.

For example, as these approaches rely on a relatively small number of random recombination crossover events to swap mutations, it may take many cycles of recombination and screening to optimize strain performance. In addition, although natural recombination events are essentially random, they are also subject to genome positional bias and some mutations may be difficult to address. These approaches also provide little information about the influence of individual mutations without additional genome sequencing and analysis. SNP swapping overcomes these fundamental limitations as it is not a random approach, but rather the systematic introduction or removal of individual mutations across strains.

In some embodiments, the SNP swapping methods of the present disclosure comprise the step of introducing one or more SNPs identified in a mutated strain to a reference strain or wild-type strain ("wave up") This can be done in order to determine whether or not a specific SNP and/or the gene containing the contributes to strains displaying a desired trait (e.g., pellet morphology in submerged cultures of production media).

In other embodiments, the SNP swapping methods of the present disclosure comprise the step of removing one or more SNPs identified in a mutated strain ("wave down"). This can be done in order to determine whether or not a specific SNP and/or the gene containing the contributes to strains displaying a desired trait (e.g., pellet morphology in submerged cultures of production media).

In some embodiments, each generated strain comprising one or more SNP changes (either introducing or removing) is cultured and analyzed under one or more criteria of the present disclosure (e.g., pellet morphology in submerged cultures of production media). Data from each of the analyzed host strains is associated, or correlated, with the particular SNP, or group of SNPs present in the host strain, and is recorded for future use. Thus, the present disclosure enables the creation of large and highly annotated HTP genetic design microbial strain libraries that are able to identify the effect of a given SNP on any number of microbial genetic or phenotypic traits of interest (e.g., pellet morphology in submerged cultures of production media). The information stored in these HTP genetic design libraries informs the machine learning algorithms of the HTP genomic engineering platform and directs future iterations of the process, which ultimately leads to evolved microbial organisms that possess highly desirable properties/traits.

In another embodiment, the HTP genetic design microbial strain libraries comprising strains of filamentous fungal cells comprising one or more SNPs of morphological target genes generated using the SNP swapping methods provided herein are subjected to swapping methods with libraries of genetic control elements as provided herein. The genetic control elements can be promoters or terminators. The promoters or terminators can be part of promoter or terminator libraries. In one embodiment, the HTP genetic design microbial strain libraries comprising strains of filamentous fungal cells comprising one or more SNPs of morphological target genes generated using the SNP swapping methods provided herein are subjected to promoter swapping methods as provided herein using promoter libraries. The promoter libraries can be the promoter library of Table 2. Further to this embodiment, the promoter swapping method performed on the HTP genetic design microbial strain libraries comprising strains of filamentous fungal cells comprising one or more SNPs of morphological target genes generated using the SNP swapping methods provided herein generates new HTP genetic design microbial strain libraries which can be screened for expression of a desired trait (e.g., pellet morphology in submerged cultures of production media).

Protoplasting Methods

In one embodiment, the methods and systems provided herein to generate the filamentous fungal host cells or strains with the desired pellet morphology require the generation of protoplasts from filamentous fungal cells. Suitable procedures for preparation of protoplasts can be any known in the art including, for example, those described in EP 238,023 and Yelton et al. (1984, Proc. Natl. Acad. Sci. USA 81:1470-1474). In one embodiment, protoplasts are generated by treating a culture of filamentous fungal cells with one or more lytic enzymes or a mixture thereof. The lytic enzymes can be a beta-glucanase and/or a polygalacturonase. In one embodiment, the enzyme mixture for generating protoplasts is VinoTaste concentrate. Many of the parameters utilized to pre-cultivate cultures of coenocytic organisms (e.g., filamentous fungal cells) and subsequently generate and utilize protoplasts therefrom for use in the methods and compositions provided herein can be varied. For example, there can be variations of inoculum size, inoculum method, pre-cultivation media, pre-cultivation times, pre-cultivation temperatures, mixing conditions, washing buffer composition, dilution ratios, buffer composition during lytic enzyme treatment, the type and/or concentration of lytic enzyme used, the time of incubation with lytic enzyme, the protoplast washing procedures and/or buffers, the concentration of protoplasts and/or polynucleotide and/or transformation reagents during the actual transformation, the physical parameters during the transformation, the procedures following the transformation up to the obtained transformants. In some cases, these variations can be utilized to optimize the number of protoplasts and the transformation efficiency. In one embodiment, the coenocytic organism is a filamentous fungal cell as provided herein (e.g., *A. niger*). Further to this embodiment, the pre-cultivation media can be YPD or complete media. The volume of pre-cultivation media can be at least, at most or about 50 ml, 100 ml, 150 ml, 200 ml, 250 ml, 300 ml, 350 ml, 400 ml, 450 ml, 500 ml, 550 ml, 600 ml, 650 ml, 700 ml, 750 ml, 800 ml, 850 ml, 900 ml, 950 ml or 1000 ml. The volume of pre-cultivation media can be from about 50 ml to about 100 ml, about 100 ml to about 150 ml, about 150 ml to about 200 ml, about 200 ml to about 250 ml, about 250 ml to about 300 ml, about 300 ml to about 350 ml, about 350 ml to about 400 ml, about 400 ml to about 450 ml, about 450 ml to about 500 ml, about 500 ml to about 550 ml, about 550 ml to about 600 ml, about 600 ml to about 650 ml, about 650 ml to about 700 ml, about 700 ml to about 750 ml, about 750 ml to about 800 ml, about 800 ml to about 850 ml, about 850 ml to about 900 ml, about 900 ml to about 950 ml or about 950 ml to about 1000 ml. In some cases, a plurality of cultures are cultivated and subsequently subjected to protoplasting. The plurality of cultures can be 2, 3, 4, 5, 6, 7, 8, 9, 10, 12, 14, 16, 18, 20, 25, 50, 75, 100, 150, 200, 300, 400, 500 or more In one embodiment, a pre-cultivation preparation is prepared by inoculating 100 ml of rich media (e.g., YPD or complete media) with $10^6$ spores/ml and incubating the pre-cultivation preparation between 14-18 hours at 30° C. In another embodiment, a pre-cultivation preparation is prepared by inoculating 500 ml of rich media (e.g., Yeast Mold Broth, YPD or complete media) with at least $10^6$ spores/ml and incubating the pre-cultivation preparation between 14-18 hours at 30° C. Prior to protoplasting, the coenocytic organism can be isolated by any method known in the art such as, for example centrifugation. In one embodiment, the coenocytic organism is filamentous fungus (e.g., *A. niger*) Further to this embodiment, Yeast Mold Broth (YMB) is inoculated with $10^6$ spores/ml of the filamentous fungal cells and grown for 16 hours at 30° C. Further still to this embodiment, the filamentous fungal cells grown in the precultivation preparation can be isolated by centrifugation. The pre-cultivation preparations provided herein for use in the methods and compositions provided herein can produce an amount of hyphae for subsequent protoplasting of about, at least or more than 0.5 g, 1 g, 1.5 g, 2 g, 2.5 g, 3 g, 3.5 g, 4 g or 5 g of wet weight. Pre-cultivation/cultivation of the coenocytic organism (e.g., filamentous fungus) can be part of a workflow in a high-throughput system (HTP) such as described in 62/515,907 filed Jun. 6, 2017. The HTP system can be automated or semi-automated Pre-cultivation of the organism can entail inoculating a small-scale volume (e.g., 100 ml) of sporulation media (PDA media) with $10^6$ spores/ml of the organism (e.g., *A. niger*) and growing for 14-16 hours at 30° C. During pre-cultivation, the workflow can contain a step whereby an enzyme solution for generating protoplasts from the pre-cultivated organism (e.g., *A. niger*) is generated. The enzyme solution can consist of Vinotaste pro (Novozymes) enzyme mix in phosphate buffer comprising 1.2 M $MgSO_4$ Following pre-cultivation, hyphae can be collected following filtration through a Miracloth and a large-scale culture can be cultivated by inoculating about 500 ml of complete media in a 2.8 L flask with 10 ul to 20 ml of the collected hyphae. Inoculum size can be variable based on the OD of the culture obtained from the pre-cultivation step. The large-scale culture can be grown for 6-18 hours at either 30° C. or 18° C. at 80% humidity with shaking at 200 rpms. Following cultivation, the culture(s) can be isolated by centrifugation following by one or more washes and resuspended. In one embodiment, the cultures are resuspended in a protoplasting buffer as described herein and subjected to protoplasting as described herein. Centrifugation can be performed in 500 ml centrifuge tubes at 4° C. for 10-15 minutes at 5500-6100×g. Each of the one or more washes can be performed in 10-50 ml of wash buffer (e.g., water with 10% glycerol) followed by centrifugation at 4° C. for 10-15 minutes at 5500-6100×g.

Following isolation as described above, the coenocytic organism (e.g., filamentous fungal cells such as *A. niger*) can be resuspended in protoplasting buffer such that the protoplasting buffer comprises one or enzymes as provided herein (e.g., VinoTaste pro concentrate (Novozymes)) for generating protoplasts. In one embodiment, the protoplasting buffer has a high concentration of osmolite (e.g., greater than or equal to 1 M of an osmolite such as $MgSO_4$) In embodiments utilizing a protoplasting buffer with a high osmolite concentration (e.g., 1.2 M $MgSO_4$), the incubation time for the enzymatic treatment (e.g., VinoTaste pro concentrate (Novozymes)) can be from about 14-16 hours at about 30° C. The volume of protoplasting buffer used for resuspension can be 50 ml, 100 ml, 150 ml, 200 ml, 250 ml, 300 ml, 350 ml, 400 ml, 450 ml, 500 ml, 550 ml, 600 ml, 650 ml, 700 ml, 750 ml, 800 ml, 850 ml, 900 ml, 950 ml or 1000 ml. The volume of protoplasting buffer used for resuspension can be can be from about 50 ml to about 100 ml, about 100 ml to about 150 ml, about 150 ml to about 200 ml, about 200 ml to about 250 ml, about 250 ml to about 300 ml, about 300 ml to about 350 ml, about 350 ml to about 400 ml, about 400 ml to about 450 ml, about 450 ml to about 500 ml, about 500 ml to about 550 ml, about 550 ml to about 600 ml, about 600 ml to about 650 ml, about 650 ml to about 700 ml, about 700 ml to about 750 ml, about 750 ml to about 800 ml, about 800 ml to about 850 ml, about 850 ml to about 900 ml, about 900 ml to about 950 ml or about 950 ml to about 1000 ml. In one embodiment, filamentous fungal cells are grown in 500 ml of rich media (e.g., YPD or complete media) and hyphae (can be about 1 g wet mass) are isolated by filtration through a Miracloth, rinsing with 100 ml of wash buffer (e.g., 100 mM sodium phosphate buffer with 1.2 M $MgSO_4$. pH 5.5) and resuspended in about 500 ml of protoplasting buffer (e.g., 100 mM sodium phosphate buffer with 1.2 M $MgSO_4$ pH 5.5) comprising a protoplasting enzyme mixture (e.g., VinoTaste pro concentrate (Novozymes)) in a 1 L bottle. The hyphae in the enzyme solution can be incubated for 14-16 hours at 30° C. with shaking at 140 rpm with continued monitoring of protoplast formation via microscopic examination.

In one embodiment, one or more chemical inhibitors of the NHEJ pathway are added to a protoplasting buffer as provided. The one or more chemical inhibitors can be selected from W7, chlorpromazine, vanillin, Nu7026, Nu7441, mirin, SCR7, AG14361 or any combination thereof. Addition of the one or more chemical inhibitors to the protoplasting buffer can occur at any point during the protoplasting procedure In one embodiment, treatment with the one or more chemical inhibitors is for the entire protoplasting procedure. In a separate embodiment, treatment with the one or more chemical inhibitors is for less than the entire protoplasting procedure. Treatment with the one or more chemical inhibitors can be for about 1, 5, 10, 15, 20, 30, 45, 60, 90, 120, 150, 180, 210, 240, 270 or 300 minutes. In one embodiment, the co-enocytic cells (e.g., filamentous fungal cells) are treated with W-7. In another embodiment, the co-enocytic cells (e.g., filamentous fungal cells) are treated with SCR-7.

Following enzymatic treatment, the protoplasts can be isolated using methods known in the art. Prior to isolation of protoplasts, undigested hyphal fragments can be removed by filtering the mixture through a porous barrier (such as Miracloth) in which the pores range in size from 20-100 microns in order to produce a filtrate of filtered protoplasts. In one embodiment, the filtered protoplasts are then centrifuged at moderate levels of centripetal force to cause the protoplasts to pellet to the bottom of the centrifuge tube. The centripetal force can be from about 500-1500×g. In a preferred embodiment, the centripetal force used is generally below 1000×g (e.g., 800×g for 5 minutes). In a separate embodiment, a buffer of substantially lower osmotic strength is gently applied to the surface of the protoplasts (e.g., filtered protoplasts) following generation of protoplasts in a protoplasting buffer comprising a high concentration of osmolite. Examples of buffers of substantially lower osmotic strength include buffers (e.g., Tris buffer) comprising 1M Sorbitol, 1M NaCl, 0.6M Ammonium Sulfate or 1M KCl. In one embodiment, the lower osmotic strength buffer for use in the methods provided herein is a Sorbitol-Tris (ST) buffer that comprises 0.4 M sorbitol and has a pH of 8. This layered preparation can then be centrifuged, which can cause the protoplasts to accumulate at a layer in the tube in which they are neutrally buoyant. Protoplasts can then be isolated from this layer for further processing (e.g., storage and/or transformation). In yet another embodiment, the protoplasts (e.g., filtered protoplasts) generated in a protoplasting buffer comprising a high concentration of osmolite (e.g., 100 mM phosphate buffer comprising 1.2M $MgSO_4$, pH 5.5) are transferred to an elongated collection vessel (e.g., graduated cylinder) and a buffer of lower osmolarity as provided herein (e.g., 0.4M ST buffer, pH 8) is overlaid on the surface of the protoplasts (e.g., filtered protoplasts) to generate a layer at which the protoplasts are neutrally buoyant. The combination of the buffers of differing osmolarity in the elongated collection vessel (e.g., graduated cylinder) can facilitate the protoplasts 'floating' to the surface of the elongated collection vessel (e.g., graduated cylinder). Once at the top of the collection vessel, the protoplasts can be isolated. In one embodiment, a 500 ml pre-cultivation preparation of coenocytic organisms (e.g., filamentous fungal cells such as *A. niger*) grown and subjected to protoplasting as provided herein yields about 25 ml of protoplasts.

Following protoplast isolation, the remaining enzyme containing buffer can be removed by resuspending the protoplasts in an osmotic buffer (e.g., 1M sorbitol buffered using 10 mM TRIS, pH 8) and recollected by centrifugation. This step can be repeated. After sufficient removal of the enzyme containing buffer, the protoplasts can be further washed in osmotically stabilized buffer also containing Calcium chloride (e.g., 1M sorbitol buffered using 10 mM TRIS, pH 8, 50 mM $CaCl_2$) one or more times.

Following isolation and washing, the protoplasts can be resuspended in an osmotic stabilizing buffer. The composition of such buffers can vary depending on the species, application and needs. However, typically these buffers contain either an organic component like sucrose, citrate, mannitol or sorbitol between 0.5 and 2 M. More preferably between 0.75 and 1.5 M; most preferred is 1 M Otherwise these buffers contain an inorganic osmotic stabilizing component like KCl, $(NH_4)_2SO_4$ $MgSO_4$, NaCl or $MgCl_2$ in concentrations between 0.1 and 1.5 M. Preferably between 0.2 and 0.8 M; more preferably between 0.3 and 0.6 M, most preferably 0.4 M. The most preferred stabilizing buffers are STC (sorbitol, 0.8 M; $CaCl_2$, 25 mM, Tris, 25 mM, pH 8.0) or KCl-citrate (KCl, 0.3-0.6 M, citrate, 0.2% (w/v)). The protoplasts can be used in a concentration between $1 \times 10^5$ and $1 \times 10^{10}$ cells/ml or between $1-3 \times 10^7$ protoplasts per ml. Preferably, the concentration is between $1 \times 10^6$ and $1 \times 10^9$; more preferably the concentration is between $1 \times 10^7$ and $5 \times 10^8$; most preferably the concentration is $1 \times 10^8$ cells/ml. To increase the efficiency of transfection, carrier DNA (as salmon sperm DNA or non-coding vector DNA) may be added to the transformation mixture. DNA is used in a concentration between 0.01 and 10 ug; preferably between 0.1 and 5 ug, even more preferably between 0.25 and 2 ug, most preferably between 0.5 and 1 ug.

In one embodiment, following generation and subsequent isolation and washing, the protoplasts are mixed with one or more cryoprotectants. The cryoprotectants can be glycols, dimethyl sulfoxide (DMSO), polyols, sugars, 2-Methyl-2,4-pentanediol (MPD), polyvinylpyrrolidone (PVP), methylcellulose, C-linked antifreeze glycoproteins (C-AFGP) or combinations thereof. Glycols for use as cryoprotectants in the methods and systems provided herein can be selected from ethylene glycol, propylene glycol, polypropylene glycol (PEG), glycerol, or combinations thereof. Polyols for use as cryoprotectants in the methods and systems provided herein can be selected from propane-1,2-diol, propane-1,3-diol, 1,1,1-tris-(hydroxymethyl)ethane (THME), and 2-ethyl-2-(hydroxymethyl)-propane-1,3-diol (EHMP), or combinations thereof. Sugars for use as cryoprotectants in the methods and systems provided herein can be selected from trehalose, sucrose, glucose, raffinose, dextrose or combinations thereof. In one embodiment, the protoplasts are mixed with DMSO. DMSO can be mixed with the protoplasts at a final concentration of at least, at most, less than, greater than, equal to, or about 1%, 2%, 3%, 4%, 5%, 6%, 7%, 8%, 9%, 10%, 12.5%, 15%, 20%, 25%, 30%, 35%, 40%, 45%, 50%, 55%, 60%, 65%, 70%, or 75% w/v or v/v. The protoplasts/cryoprotectant (e.g., DMSO) mixture can be distributed to microtiter plates prior to storage. The protoplast/cryoprotectant (e.g., DMSO) mixture can be stored at any temperature provided herein for long-term storage (e.g., several hours, day(s), week(s), month(s), year(s)) as provided herein such as, for example −20° C. or −80° C. In one embodiment, an additional cryoprotectant (e.g., PEG) is added to the protoplasts/DMSO mixture In yet another embodiment, the additional cryoprotectant (e.g., PEG) is added to the protoplast/DMSO mixture prior to storage. The PEG can be any PEG provided herein and can be added at any concentration (e.g., w/v or v/v) as provided herein. In one embodiment, the PEG solution is prepared as 40% w/v in STC buffer. 20% v/v of this 40% PEG-STC can then be added to the protoplasts. For example, 800 microliters of $1.25 \times 10^7$ protoplasts would have 200 microliters of 40% PEG-STC giving a final volume of 1 ml. Seventy microliters of DMSO can then be added to this 1 ml to bring this prep to 7% v/v DMSO.

Any pre-cultivation, cultivation and/or protoplasting protocol provided herein can be performed in a high-throughput manner. For example, pre-cultivation, cultivation and protoplasting can be performed as part of a workflow such that said workflow represents a portion of a high-throughput (HTP) protocol such as that described in 62/515,907 filed Jun. 6, 2017. The high-throughput protocol can utilize automated liquid handling for any and/or all steps.

Transformation Methods

In some embodiments, the vectors or constructs of the present disclosure may be introduced into the host cells (e.g., filamentous fungal cells or protoplasts derived therefrom) using any of a variety of techniques, including transformation, transfection, transduction, viral infection, gene guns, or Ti-mediated gene transfer (see Christie, P. J., and Gordon, J. E., 2014 "The *Agrobacterium* Ti Plasmids" Microbiol SPectr. 2014; 2(6); 10. 1128). Particular methods include calcium phosphate transfection, DEAE-Dextran mediated transfection, lipofection, or electroporation (Davis, L., Dibner, M., Battey, I., 1986 "Basic Methods in Molecular Biology"). Other methods of transformation include, for example, lithium acetate transformation and electroporation see, e.g., Gietz et al., Nucleic Acids Res. 27:69-74 (1992); Ito et al., J. Bacterol. 153:163-168 (1983); and Becker and Guarente, Methods in Enzymology 194:182-187 (1991). In some embodiments, transformed host cells are referred to as recombinant host strains.

In some embodiments, the present disclosure teaches high-throughput transformation of cells using the 96-well plate robotics platform and liquid handling machines such as that described in 62/515,907 filed Jun. 6, 2017.

In one embodiment, the methods and systems provided herein require the transfer of nucleic acids (e.g., heterologous promoter-target morphology gene fusion or SNP such as, for example, from Table 3 or Table 4) to protoplasts derived from filamentous fungal cells as described herein. In another embodiment, the transformation utilized by the methods and systems provided herein is high-throughput in nature and/or is partially or fully automated as described herein. The partially or fully automated method can entail the use of automated liquid handling one or more liquid handling steps as provided herein. Further to this embodiment, the transformation is performed by adding constructs or expression constructs as described herein to the wells of a microtiter plate followed by aliquoting protoplasts generated by the methods provided herein to each well of the microtiter plate. Suitable procedures for transformation/transfection of protoplasts can be any known in the art including, for example, those described in international patent applications PCT/NL99/00618, PCT/EP99/202516, Finkelstein and Ball (eds), Biotechnology of filamentous fungi, technology and products, Butterworth-Heinemann (1992), Bennett and Lasure (eds.) More Gene Manipulations in fungi. Academic Press (1991), Turner, in: Puhler (ed), Biotechnology, second completely revised edition, VHC (1992) protoplast fusion, and the Ca-PEG mediated protoplast transformation as described in EP635574B. Alternatively, transformation of the filamentous fungal host cells or protoplasts derived therefrom can also be performed by electroporation such as, for example, the electroporation described by Chakraborty and Kapoor, Nucleic Acids Res 18:6737 (1990), *Agrobacterium tumefaciens*-mediated transformation, biolistic introduction of DNA such as, for example, as described in Christiansen et al., Curr. Genet. 29:100 102 (1995); Durand et al., Curr. Genet. 31:158 161 (1997); and Barcellos et al., Can. J. Microbiol. 44:1137 1141 (1998) or "magneto-biolistic" transfection of cells such as, for example, described in U.S. Pat. Nos. 5,516,670 and 5,753,477. In one embodiment, the transformation procedure used in the methods and systems provided herein is one amendable to being high-throughput and/or automated as provided herein such as, for example, PEG mediated transformation.

Transformation of the protoplasts generated using the methods described herein can be facilitated through the use of any transformation reagent known in the art. Suitable transformation reagents can be selected from Polyethylene Glycol (PEG), FUGENE® HD (from Roche), Lipofectamine® or OLIGOFECTAMINE® (from Invitrogen), TRANSPASS®D1 (from New England Biolabs), LYPOVEC® or LIPOGEN® (from Invivogen). In one embodiment, PEG is the most preferred transformation/transfection reagent. PEG is available at different molecular weights and can be used at different concentrations. Preferably, PEG 4000 is used between 10% and 60%, more preferably between 20% and 50%, most preferably at 40%. In one embodiment, the PEG is added to the protoplasts prior to storage as described herein.

Looping Out of Selected Sequences

In some embodiments, the present disclosure teaches methods of looping out selected regions of DNA from the host organisms. The looping out method can be as described in Nakashima et al. 2014 "Bacterial Cellular Engineering by Genome Editing and Gene Silencing." Int. J. Mol. Sci. 15(2), 2773-2793. In some embodiments, the present disclosure teaches looping out selection markers from positive transformants. Looping out deletion techniques are known in the art, and are described in (Tear et al. 2014 "Excision of Unstable Artificial Gene-Specific inverted Repeats Mediates Scar-Free Gene Deletions in *Escherichia coli*." Appl. Biochem. Biotech. 175:1858-1867). The looping out methods used in the methods provided herein can be performed using single-crossover homologous recombination or double-crossover homologous recombination. In one embodiment, looping out of selected regions as described herein can entail using single-crossover homologous recombination as described herein.

Figure 6:
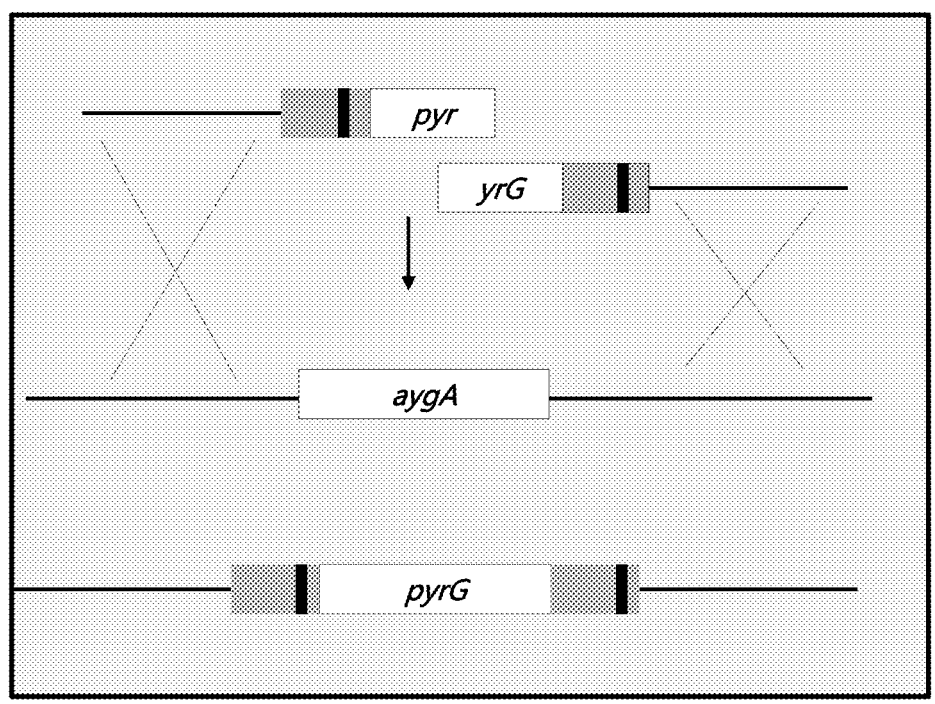
FIG. 6 is a representation of how SNPs are targeted to a specific locus in filamentous fungi using a split marker system. The marker gene (pyrG in this example) is amplified into two components that are unable to complement the mutation in the target strain without homologous recombination, which restores gene function. Flanking these fragments is a direct repeat of DNA that each of which contains the SNPs to be targeted to the locus. Non-repeat DNA sequence on each construct facilitates proper integration through native homologous recombination pathways.

First, loop out constructs are inserted into selected target regions within the genome of the host organism (e.g., via homologous recombination, CRISPR, or other gene editing technique). In one embodiment, double-crossover homologous recombination is used between a construct or constructs and the host cell genome in order to integrate the construct or constructs such as depicted in FIG. 6. The inserted construct or constructs can be designed with a sequence which is a direct repeat of an existing or introduced nearby host sequence, such that the direct repeats flank the region of DNA slated for looping-out and deletion. In one embodiment, the construct for use in the loop-out process comprises a mutated form of a gene shown to or suspected to play role in controlling or affecting morphology split between direct repeats that flank a selectable marker gene (e.g., pyrG gene in FIG. 6). In another embodiment, the construct for use in the loop-out process comprises a gene shown to or suspected to play role in controlling or affecting morphology operably linked to a heterologous promoter split between direct repeats that flank a selectable marker gene (e.g., pyrG gene in FIG. 6). In yet another embodiment, the construct for use in the loop-out process comprises a mutated form of a gene shown to or suspected to play role in controlling or affecting morphology operably linked to a heterologous promoter split between direct repeats that flank a selectable marker gene (e.g., pyrG gene in FIG. 6). In each of the embodiments, as shown in FIG. 6, the direct repeats can be flanked by sequence that facilitates that sequence being integrated into a specific locus (e.g., the locus for the gene shown to or suspected to play role in controlling or affecting morphology) in the host cell genome. The gene shown to or suspected to play role in controlling or affecting morphology can be any such gene provided herein such as, for example, the *S. cerevisiae* SLN1 gene, the *N. crassa* nik1 gene or an orthologue thereof (e.g., an *A. Niger* orthologue of the *S. cerevisiae* SLN1 gene or *N. crassa* nik1 gene). In one embodiment, the SLN1/nik1 gene or orthologue thereof can comprise a genetic perturbation. The genetic perturbation can be a mutation such as, for example, a single nucleotide polymorphism (SNP). In one embodiment, the mutated form of this gene can be the *A. niger* orthologue of the *S. cerevisiae* or *N. crassa* gene with the nucleic acid sequence of FungiSNP_18 (i.e., SEQ ID NO. 7) In another embodiment, the gene or each of a plurality of genes shown to or suspected of playing a role in controlling or affecting morphology can be any genes or genes from an osmotic response pathway of a filamentous fungal host cell such as an orthologue or orthologues of a gene or genes from a yeast osmotic response pathway listed in Table 7. Other examples of genes shown to or suspected to play a role in controlling or affecting morphology can be the wild-type versions of the *A. niger* genes with a nucleic acid sequence of SEQ ID NO: 5, 6 or 8 (e.g., nucleic acid SEQ ID NO. 77, 78 or 79) or orthologues thereof. The heterologous promoter can be any promoter provided herein In one embodiment, the heterologous promoter is selected from Table 2. Once inserted, cells containing the loop out construct or constructs can be counter selected for deletion of the selection region (e.g., see FIG. 7; lack of resistance to the selectable marker gene).

Persons having skill in the art will recognize that the description of the loopout procedure represents but one illustrative method for deleting unwanted regions from a genome. Indeed, the methods of the present disclosure are compatible with any method for genome deletions, including but not limited to gene editing via CRISPR, TALENS, FOK, or other endonucleases. Persons skilled in the art will also recognize the ability to replace unwanted regions of the genome via homologous recombination techniques Constructs for Transformation In one embodiment, the methods and systems provided herein entail the transformation or transfection of filamentous fungal cells or protoplasts derived therefrom with at least one nucleic acid. The transformation or transfection can be using of the methods and reagents described herein. The generation of the protoplasts can be performed using any of the methods provided herein. The protoplast generation and/or transformation can be high-throughput and/or automated as provided herein. The nucleic acid can be DNA, RNA or cDNA The nucleic acid can be a polynucleotide. The nucleic acid or polynucleotide for use in transforming a filamentous fungal cell or protoplast derived therefrom using the methods and systems provided herein can be an endogenous gene or a heterologous gene relative to the variant strain and/or the parental strain. The endogenous gene or heterologous gene can comprise a mutation and/or be under the control of or operably linked to one or more genetic control or regulatory elements. As provided herein, the endogenous gene or heterologous gene can encode a protein that has been shown to or is suspected to play a role in controlling or affecting morphology. For example, the gene can be an S. cerevisiae SLN1 gene, a N. crassa nik1 gene or an orthologue thereof (e.g., A. niger orthologue of the S. cerevisiae SLN1 gene or N. crassa nik1 gene) and/or any gene within the same pathway (e.g., any gene or orthologue thereof selected from the osmotic response pathway genes found in Table 7). The mutation can be any mutation provided herein such as, for example, an insertion, deletion, substitution and/or single nucleotide polymorphism (SNP). The one or more genetic control or regulatory elements can be a promoter sequence and/or a terminator sequence. The endogenous gene or heterologous gene can be present on one expression construct or split across multiple expression constructs. When split across multiple expression constructs, each portion of the endogenous gene or heterologous gene can comprise a mutation and/or be under the control of or operably linked to one or more genetic control or regulatory elements. In one embodiment, an endogenous gene or heterologous gene is bipartite, wherein said endogenous gene or heterologous gene is split into two portions such that each of said two portions is present on a separate construct. In one embodiment, the gene is FungiSNP_9 (SEQ ID NO: 5), FungiSNP_12 (SEQ ID NO: 6), FungiSNP_18 (SEQ ID NO: 7) or FungiSNP_40 (SEQ ID NO: 8). In another embodiment, the gene is FungiSNP_9 (SEQ ID NO 5), FungiSNP_12 (SEQ ID NO. 6), FungiSNP_18 (SEQ ID NO: 7) or FungiSNP_40 (SEQ ID NO: 8) fused to or operably linked to any of the promoters from Table 2. In one embodiment, the gene is FungiSNP_18 (SEQ ID NO: 7). In another embodiment, the gene is FungiSNP_18 (SEQ ID NO: 7) fused to or operably linked to the man8p or amy8p promoter from Table 2. In another embodiment, the gene is wt or non-SNP FungiSNP_9 (SEQ ID NO: 77), wt or non-SNP FungiSNP_12 (SEQ ID NO: 78), wt or non-SNP FungiSNP_18 (SEQ ID NO: 76) or wt or non-SNP FungiSNP_40 (SEQ ID NO: 79). In another embodiment, the gene is wt or non-SNP FungiSNP_9 (SEQ ID NO: 77), wt or non-SNP FungiSNP_12 (SEQ ID NO: 78), wt or non-SNP FungiSNP_18 (SEQ ID NO: 76) or wt or non-SNP FungiSNP_40 (SEQ ID NO: 79) fused to or operably linked to any of the promoters from Table 2 In one embodiment, the gene is wt or non-SNP FungiSNP_18 (SEQ ID NO: 14 or 76). In another embodiment, the gene is FungiSNP_18 (SEQ ID NO: 14 or 76) fused to or operably linked to the man8p or amy8p promoter from Table 2.

In one embodiment, a protoplast generated from a filamentous fungal cell is co-transformed with two or more nucleic acids or polynucleotides. Further to this embodiment, at least one of the two or more polynucleotides is an endogenous gene or a heterologous gene relative to the filamentous fungal strain from which the protoplast was generated and at least one of the two or more polynucleotides is a gene for a selectable marker. As provided herein, the endogenous gene or heterologous gene can encode a protein that has been shown to or is suspected to play a role in controlling or affecting morphology. For example, the gene can be an S. cerevisiae SLN1 gene, a N. crassa nik1 gene or an orthologue thereof (e.g., A. niger orthologue of the S. cerevisiae SLN1 gene or N. crassa nik1 gene) and/or any gene within the same pathway (e.g., any gene or orthologue thereof selected from the osmotic response pathway genes found in Table 7). The selectable marker gene can be any selectable marker as provided herein. As described herein, each of the two or more nucleic acids or polynucleotides can be split into separate portions such that each separate portion is present on a separate construct.

In one embodiment, each nucleic acid or polynucleotide for use in transforming or transfecting a filamentous fungal cell or protoplast derived therefrom comprises sequence homologous to DNA sequence present in a pre-determined target locus of the genome of the filamentous fungal cell or protoplast derived therefrom that is to be transformed on either a 5', a 3' or both a 5' and a 3' end of the nucleic acid or polynucleotide. The nucleic acid or polynucleotide can be an endogenous gene or heterologous gene relative to the filamentous fungal cell used for transformation or a selectable marker gene such that sequence homologous to a pre-determined locus in the filamentous fungal host cell genome flanks the endogenous, heterologous, or selectable marker gene. As provided herein, the endogenous gene or heterologous gene can encode a protein that has been shown to or is suspected to play a role in controlling or affecting morphology. For example, the gene can be an S. cerevisiae SLN1 gene, N. crassa nik1 gene or an orthologue thereof (e.g., A. niger orthologue of the S. cerevisiae SLN1 gene or N. crassa nik1 gene) and/or any gene within the same pathway (e.g., any gene or orthologue thereof selected from the osmotic response pathway genes found in Table 7). In one embodiment, each nucleic acid or polynucleotide is cloned into a cloning vector using any method known in the art such as, for example, pBLUESCRIPT® (Stratagene). Suitable cloning vectors can be the ones that are able to integrate at the pre-determined target locus in the chromosomes of the filamentous fungal host cell used. Preferred integrative cloning vectors can comprise a DNA fragment, which is homologous to the DNA sequence to be deleted or replaced for targeting the integration of the cloning vector to this pre-determined locus. In order to promote targeted integration, the cloning vector can be linearized prior to transformation of the host cell or protoplasts derived therefrom. Preferably, linearization is performed such that at least one but preferably either end of the cloning vector is flanked by sequences homologous to the DNA sequence to be deleted or replaced. In some cases, short homologous stretches of DNA may be added for example via PCR on both sides of the nucleic acid or polynucleotide to be integrated. The length of the homologous sequences flanking the nucleic acid or polynucleotide sequence to be integrated is preferably less than 2 kb, even preferably less, than 1 kb, even more preferably less than 0.5 kb, even more preferably less than 0.2 kb, even more preferably less than 0.1 kb, even more preferably less than 50 bp and most preferably less than 30 bp. The length of the homologous sequences flanking the nucleic acid or polynucleotide sequence to be integrated can vary from about 30 bp to about 1000 bp, from about 30 bp to about 700 bp, from about 30 bp to about 500 bp, from about 30 bp to about 300 bp, from about 30 bp to about 200 bp, and from about 30 bp to about 100 bp. The nucleic acids or polynucleotides for use in transforming filamentous fungal cells or protoplasts derived therefrom can be present as expression cassettes. In one embodiment, the cloning vector is pUC19. Further to this embodiment, a cloning vector containing a marker sequence as provided herein can be associated with targeting sequence by building the construct through using a Gibson assembly as known in the art. Alternatively, the targeting sequence can be added by fusion PCR. Targeting sequence for co-transformation that is not linked to a marker may be amplified from genomic DNA.

In theory, all loci in the filamentous fungi genome could be chosen for targeted integration of the expression cassettes comprising nucleic acids or polynucleotides provided herein. Preferably, the locus wherein targeting will take place is such that when the wild type gene present at this locus has been replaced by the gene comprised in the expression cassette, the obtained mutant will display a change detectable by a given assay such as, for example a selection/counterselection scheme as described herein. In one embodiment, the protoplasts generated from filamentous fungal cells as described herein are co-transformed with a first construct or expression cassette and a second construct or expression cassette such that the first construct or expression cassette is designed to integrate into a first locus of the protoplast genome, while the second construct or expression cassette is designed to integrate into a second locus of the protoplast genome. To facilitate integration into the first locus and second locus, the first construct or expression cassette is flanked by sequence homologous to the first locus, while the second construct or expression cassette is flanked by sequence homologous to the second locus. In one embodiment, the first construct or expression cassette comprises sequence for an endogenous gene, while the second construct comprises sequence for a selectable marker gene. Further to this embodiment, the second locus contains sequence for an additional selectable marker gene present in the protoplast genome used in the methods and systems provided herein, while the first locus contains sequence for the endogenous target gene present in the protoplast genome used in the methods and systems provided herein In a separate embodiment, the first construct or expression cassette comprises sequence for an endogenous gene or a heterologous gene, while the second construct comprises sequence for a first selectable marker gene. Further to this separate embodiment, the second locus contains sequence for a second selectable marker gene that is present in the protoplast genome used in the methods and systems provided herein, while the first locus contains sequence for a third selectable marker gene that is present in the protoplast genome used in the methods and systems provided herein. In each of the above embodiments, the endogenous gene and/or heterologous gene can comprise a mutation (e.g., SNP) and/or a genetic control or regulatory element as provided herein. As provided herein, the endogenous gene or heterologous gene can encode a protein that has been shown to or is suspected to play a role in controlling or affecting morphology. For example, the gene can be an *S. cerevisiae* SLN1 gene, *N. crassa* nik1 gene or an orthologue thereof (e.g., *A. niger* orthologue of the *S. cerevisiae* SLN1 gene or *N. crassa* nik1 gene) and/or any gene within the same pathway (e.g., any gene or orthologue thereof selected from the osmotic response pathway genes found in Table 7).

Purification of Homokaryotic Protoplasts

As will be appreciated by those skilled in the art, protoplasts derived from filamentous fungal can often contain more than one nucleus such that subsequent transformation with a construct (e.g., insert DNA fragment) as provided herein can produce protoplasts that are heterokaryotic such that the construct (e.g., insert DNA fragment) is incorporated into only a subset of the multiple nuclei present in the protoplast. In order to reduce the number or percentage of heterokaryotic protoplasts following transformation, strategies can be employed to increase the percentage of mononuclear protoplasts in a population of protoplasts derived from filamentous fungal host cells prior to transformation such as, for example, using the method described in Roncero et al., 1984, Mutat. Res. 125:195, the contents of which are herein incorporated by reference in its entirety.

Aside from or in addition to employing strategies to increase the number or percentage of mononuclear protoplasts prior to transformation, strategies can be employed to drive protoplasts (and the colonies derived therefrom following regeneration of said protoplasts) to being homokaryotic post-transformation regardless of whether they are mono- or multi-nucleate. As provided herein, increasing the number or percentage of protoplasts (and the colonies derived therefrom) that are homokaryotic for a desired or target gene of interest (e.g., target morphology gene) can entail subjecting the colonies derived from the transformed protoplast or population of transformed protoplasts to selection and/or counter-selection based on the presence and/or absence of one or more selectable markers. The one or more selectable markers can be any selectable marker or combination of selectable markers as provided herein and the selection and/or counter-selection scheme can any such scheme as provided herein.

Identification of Homokaryotic Transformants

Homokaryotic transformants produced by the methods provided herein can be identified through the use of phenotypic screening, sequence-based screening or a combination thereof. In other words, phenotypic screening, sequence-based screening or a combination thereof can be used to detect the presence or absence of a parental genotype in a colony derived from a protoplast following transformation of said protoplast with a construct (e.g., insert DNA fragment). Identification or detection of homokaryotic transformants can occur before and/or following subjecting said transformants to a selection and/or counter-selection scheme as provided herein in keeping with the introduction and/or loss of one or more selectable marker genes. Phenotypic screening can be used to identify a transformant with a discernable phenotype (change in growth and/or colorimetric change), while sequence-based screening can be used to identify transformants with or without a discernable phenotype following transformation and integration of a construct or constructs as provided herein.

Sequence-Based Screening

As described herein, sequence-based screening can be used to determine the presence or absence of a desired or target construct in a transformant. In this manner, sequence-based sequencing can be used to assess whether or not integration of a desired gene or construct has occurred in a specific transformant. Sequence-based screening can be used to determine the percentage of nuclei in a multinucleate cell or population of multinucleate cells that contain a desired gene, mutation or construct. Further, sequence-based screening can be used to determine the percentage of a population of transformants that has experienced a desired target integration. The construct can be any construct or a plurality of constructs as described herein. In some cases, the results of sequence-based screening can be used to select purification schemes (e.g., homokaryotic purification) if the percentage or ratio of nuclei comprising a desired gene, mutation or construct vs. nuclei lacking said desired gene, mutation or construct is below a certain threshold.

In general, sequence-based screening can entail isolating transformants that may contain a desired mutation or construct. Each transformant may contain one or a plurality of nuclei such that the one or each of the plurality of the nuclei contain fragments of nucleic acid (e.g., one or more constructs or genes comprising a mutation) introduced during transformation. The transformation can be targeted transformations of protoplasts with specific fragments of DNA (e.g., one or more constructs or genes comprising a mutation) as provided herein.

In some cases, following isolation, sequence-based screening entails propagating the transformants that contain a mixture of nuclei with both the target gene (introduced construct) and the wild-type or parental gene on media that impacts the purity of the target gene (i.e., selective media) or may be completely non-selective for any particular phenotype or trait, thereby generating colonies derived from the transformants. In one embodiment, each isolated transformant or a portion of a colony derived therefrom is transferred to or placed in a well of a microtiter plate such as, for example, an Omnitray comprising agar wherein the transformant or a portion of a colony derived therefrom sporulate. The microtiter plate can be a 96 well, 384 well or 1536 well microtiter plate.

Following isolation alone or in combination with propagation, nucleic acid (e.g., DNA) can be extracted from the transformant or colonies or spores derived therefrom. Nucleic acid isolation can be from spores derived from transformants and can be performed in a microtiter plate format and can utilize automated liquid handling. Extraction of the nucleic acid can be performed using any known nucleic acid extraction method known in the art and/or commercially available kit such as for example Prepman™ (ThermoFischer Scientific) In one embodiment, nucleic acid extracted from spores derived from transformants is performed using a boil prep method that allows for amplification of DNA. The boil prep method can include the inoculation of spores into a small amount of growth media. In one embodiment, the spores are separated into 96 wells in a plate suitable for PCR wherein each well comprises the small amount of growth media. The spores can be allowed to grow for between 10 and 16 hours, which can help the spores discard pigments that may inhibit PCR. Additionally, the growth can also facilitate several rounds of nuclear division which can serve to increase the genomic DNA content of each well Subsequently, the overnight "mini cultures" can then be supplemented with a buffer that assists in cell lysis as well as stabilizes the DNA that will be released during lysis. One example of a suitable buffer can be PrepMan Ultra (Thermo Fisher). Other examples of suitable buffers can include Tris buffered solutions that contain a small amount of ionic detergent. The min-culture-buffer mixtures can then be heated in a thermocycler to 99 degrees C. for any of a range of incubation times of between 15 minutes and 1 hour.

Following nucleic acid extraction, sequence-based screening can be performed to assess the percentage or ratio of target or mutant nuclei comprising an introduced target gene or construct to parent nuclei (i.e., non-transformed nuclei) The sequence-based screening can be any method known in the art that can be used to determine or detect the sequence of a nucleic acid. The method used to perform sequence-based screening can be selected from nucleic acid sequencing methods or hybridization based assays or methods. The nucleic acid sequencing assay or technique utilized by the methods provided herein can be a next generation sequencing (NGS) system or assay. The hybridization based assay for detecting a particular nucleic acid sequence can entail the use of microarrays or the nCounter system (Nanostring). Prior to conducting sequence-based screening, the extracted nucleic acid can be amplified using PCR with primer pair(s) directed to the target gene.

In embodiments utilizing nucleic acid sequencing methodologies, the primer pairs utilized in the PCR can comprise adapter sequences that can be subsequently used in a secondary amplification using coded indexing primers. Amplicons generated by the secondary amplification reaction can then be sequenced using multiplex sequencing with sequencing primers directed to the coded indexed primers. The sequencing can be performed using any type of sequencing known in the art. In one embodiment, the sequencing is next generation sequencing (NGS). The NGS can be any known NGS method known in the art such as, for example, Illumina NGS. Data from the multiplex sequencing reactions can then be used to determine the presence or absence of the target nuclei. In some cases, the data from the multiplex sequencing reactions can also be used to determine the ratio of parental nuclei to mutant nuclei for a transformant within the target well. Further to this embodiment, a standard curve can be generated in order to quantify the percentage or ratio of parent to mutant nuclei. The standard curve can be generated by amplifying and sequencing nucleic acid isolated from strains containing known ratios of a parent to mutant nuclei and subsequently using the ratio of parent to mutant amplicons that appear in the known ratio to determine an approximation of the purity of a test sample. The strains used to generate the standard curve can be processed (e.g., isolated, propagated and extracted) in the same set of plates as the test sample.

In one embodiment, sequence-based sequencing is used following selection and/or counter-selection in order to assess or determine the homokaryotic status of each transformant. Sequence-based sequencing post selection and/or counter-selection can use multiplex sequencing as described herein and can be automated or semi-automated Sequence-based sequencing post selection and/or counter-selection can also utilize generation of a standard curve as described herein as means of determining the presence and/or amount (e.g., ratio) a transformant is heterokaryotic.

Use of Sequence-Based Screening to Determine Purity of Transformants

As discussed herein, protoplasts generated from coenocytic host cells (e.g., filamentous fungal host cells) in the methods, systems and workflows provided herein can be multinucleate. Subsequently, protoplasts transformed with one or more constructs such as those provided herein can contain only a portion or percentage of their multiple nuclei with a particular construct or constructs integrated into their genome. Depending on the nature of the transformed constructs, colonies derived from the transformed protoplast may not produce a discernable phenotype due to the presence of the mixed population of nuclei present in the colony. Accordingly, the use of sequence-based screening can be essential for determining the percentage of the nuclei in a mixed population of nuclei that contain a desired construct or constructs vs. those that do not contain a desired construct or constructs. In one embodiment, NGS based screening is used to identify transformants or strains derived therefrom that contain a desired percentage of nuclei with an introduced construct or constructs. The desired percentage can be a threshold percentage, whereby transformants or strains derived therefrom at or above said threshold percentage produce a desired trait (e.g., pellet morphology). The desired percentage can be 50%, 55%, 60%, 65%, 70%, 75%, 80%, 85%, 90%, 95%, 99% or 100%. The percentage can be determined by utilizing a standard curve as described herein Phenotypic Screening As described herein, phenotypic screening can be used in combination with sequence-based screening or transformants. In some cases, the results of sequence-based screening can be used to determine purification schemes in order to ensure the isolation of homokaryotic transformants. Further, sequence-based screening can be utilized following phenotypic screening/purification in order to assess if the isolates obtained by phenotypic screening/purification are homokaryotic.

Phenotypic screening of transformants generated using the methods, compositions or systems provided herein can employ the use of one or more selectable markers. A selectable marker can often encode a gene product providing a specific type of resistance foreign to the non-transformed strain. This can be resistance to heavy metals, antibiotics or biocides in general. Prototrophy can also be a useful selectable marker of the non-antibiotic variety. Auxotrophic markers can generate nutritional deficiencies in the host cells, and genes correcting those deficiencies can be used for selection.

There is a wide range of selection markers in use in the art and any or all of these can be applied to the methods and systems provided herein. The selectable marker genes for use herein can be auxotrophic markers, prototrophic markers, dominant markers, recessive markers, antibiotic resistance markers, catabolic markers, enzymatic markers, fluorescent markers, luminescent markers or combinations thereof. Examples of these include, but are not limited to: amdS (acetamide/fluoroacetamide), ble (belomycin-phleomycin resistance), hyg (hygromycinR), nat (nourseotricin R), pyrG (uracil/5FOA), niaD (nitrate/chlorate), sutB (sulphate/selenate), eGFP (Green Fluorescent Protein) and all the different color variants, aygA (colorimetric marker), met3 (methionine/selenate), pyrE (orotate P-ribosyl transferase), trpC (anthranilate synthase), argB (ornithine carbamoyltransferase), bar (phosphinothricin acetyl transferase), mutant acetolactate synthase (sulfonylurea resistance), and neomycin phosphotransferase (aminoglycoside resistance).

Another embodiment of the present disclosure entails the use of two or more selection markers active in filamentous fungi. There is a wide range of combinations of selection markers that can be used and all of these can be applied in the selection/counterselection scheme provided herein. For example, the selection/counterselection scheme can utilize a combination of auxotrophic markers, prototrophic markers, dominant markers, recessive markers, antibiotic resistance markers, catabolic markers, enzymatic markers, fluorescent markers, and luminescent markers. A first marker can be used to select in the forward mode (i.e., if active integration has occurred), while additional markers can be used to select in the reverse mode (i.e., if active integration at the right locus has occurred). Selection/counterselection can be carried out by cotransformation such that a selection marker can be on a separate vector or can be in the same nucleic acid fragment or vector as the endogenous or heterologous gene as described herein.

In one embodiment, the homokaryotic protoplast purification scheme of the present disclosure entails co-transforming protoplasts generated form filamentous fungal host cells with a first construct comprising sequence for an endogenous morphological gene or heterologous morphological gene and a second construct comprising sequence for a first selectable marker gene such that the first construct is directed to a first locus of the protoplast genome that comprises sequence for a target gene to be removed or inactivated, while the second construct is directed to a second locus of the protoplast genome that comprises sequence for a second selectable marker gene. In one embodiment, the first construct comprises sequence for an endogenous gene or heterologous gene and the target gene to be removed or inactivated is for a third selectable marker gene. In a separate embodiment, the first construct comprises a sequence for an endogenous gene and the target gene to be removed or inactivated is the copy of the endogenous gene present in the genome of the protoplast prior to transformation. As described herein, the endogenous gene or heterologous gene of the first construct can comprise a mutation (e.g., SNP) and/or a genetic regulatory or control element (e.g., promoter and/or terminator). The first, second and/or third selectable marker can be any auxotrophic markers, prototrophic markers, dominant markers, recessive markers, antibiotic resistance markers, catabolic markers, enzymatic markers, fluorescent markers, luminescent markers known in the art and/or described herein. To be directed to a specific locus each of the constructs is flanked by nucleotides homologous to the desired locus in the protoplast genome as described herein.

In one embodiment, the second construct comprises an expression cassette that encodes a recyclable or reversible marker. The recyclable or reversible marker can be a disruption neo-pyrG-neo expression cassette. The neo-pyrG-neo construct can be co-transformed with the first construct as described in the above embodiments in a ura-strain of filamentous fungal host cell (e.g., *A. niger*) and homokaryotic transformants can be selected by plating on uracil deficient medium and selecting pure yellow uracil prototrophs as described above. Subsequently, use of pyrG selection can be regenerated by plating said homokaryotic transformants on 5-FOA containing medium and selecting transformants that grow on said 5-FOA medium, which indicates that said transformants have undergone an intrachromosomal recombination between the neo repeats that results in excision of the pyrG gene.

Figure 7:
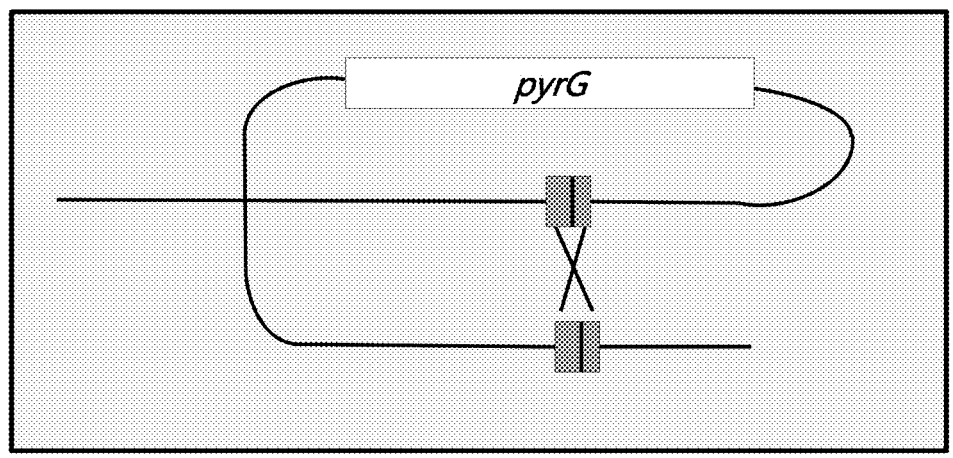
FIG. 7 illustrates that, the direct repeats flanking the marker gene are unstable and will result in marker removal through homologous recombination between the direct repeats. Essentially, the loop-out is facilitated by direct repeats that were incorporated into the transforming DNA. Essentially, the loop-out is facilitated by direct repeats that were incorporated into the transforming DNA. Cells counter selected for the selection marker contain deletions of the loop DNA flanked by the direct repeat regions.

In a further embodiment, instead of using co-transformation as provided herein, the homokaryotic protoplast purification scheme of the present disclosure entails transforming protoplasts generated form filamentous fungal host cells with a deletion construct comprising sequence for a specific gene such that the construct is directed to a desired locus of the protoplast genome that comprises sequence for a target gene to be removed or inactivated. To be directed to a specific locus the constructs is flanked by nucleotides homologous to the desired locus in the protoplast genome as described herein. The desired locus can be the locus from a morphological target gene or mutant thereof as provided herein (e.g., *A. niger* orthologue of the *S. cerevisiae* SLN1 or a mutant thereof such as, for example, FungiSNP_18 or any orthologue of the *S. cerevisiae* SLN1). Use of this type of construct/transformation can be used to provide information on the role a particular gene plays in the morphology of the transformed host cell or strain In one embodiment, confirmation of correct integration of the deletion construct into the protoplast genome is confirmed by sequencing the genome of the protoplast using such as, for example next generation sequencing (NGS). The NGS system or method used can be any NGS system or method known in the art such as for example Illumina NGS. In one case, the filamentous fungal host cell is pyrG negative and the deletion construct comprises a selectable marker gene, while the target gene is a a morphological target gene or mutant thereof as provided herein (e.g., *A. niger* orthologue of the *S. cerevisiae* SLN1 or a mutant thereof such as, for example, FungiSNP_18 or any orthologue of the *S. cerevisiae* SLN1). Accordingly, purification of homokaryotic protoplast transformants entails growing said transformants on minimal media lacking uracil. In another case, the filamentous fungal host cell is pyrG positive and the deletion construct comprises a SNP (e.g., SNP from Table 3 or Table 4 of a fusion between a promoter from Table 2 and a SNP from Table 3 or Table 4), while the target gene is a selectable marker gene. Accordingly, purification of homokaryotic protoplast transformants entails growing said transformants on minimal media comprising FOA In yet another embodiment, a mutated morphological target gene (e.g., a SNP from Table 3 or Table 4) is integrated into a target locus (e.g., the locus from the morphological target gene) in the genome of a coenocytic organism (e.g., filamentous fungi such as *A. niger*) via transformation and integration of multiple portions of the mutated gene such that each of the multiple portions of the mutated gene are present on a separate construct. Each of the multiple constructs can comprise a unique portion of the mutated gene plus an overlapping portion of the mutated gene that is also present on one of the other multiple constructs in order to facilitate recombination of the multiple constructs to produce a functional copy of the mutated gene in the organism's genome. To facilitate integration of each portion of the mutated gene into the desired locus of the organism, each of the multiple constructs can further comprise nucleotides homologous to the desired locus in the organism's genome that flank the portion of the mutated gene in the construct. In some cases, the mutated gene is split across two constructs and is introduced into the organism via bipartite transformation of the two constructs. One example of this concept is depicted in FIG. 6. As shown in FIG. 6, the pyrG marker gene is split into two constructs such that each of the constructs comprises a unique portion of the pyrG and a portion that overlaps with the other construct. Further, each construct further comprises sequence homologous to the aygA marker gene in the host organism genome that flanks a terminator repeat (e.g., direct repeat (DR)) comprising sequence of a target morphological gene that flanks the unique portion of the pyrG marker gene. The target morphological gene can be a mutant form (e.g., comprise a SNP) or a wild-type form. The target morphological gene can be a mutant form (e.g., comprise a SNP) or a wild-type form that can be fused to a heterologous promoter (e.g., promoter from Table 2). Recombination of the two constructs following transformation using any of the methods provided herein results in insertion of the whole pyrG marker gene comprising the two DRs. Transformants containing the wholly integrated pyrG marker gene and transformants who have lost the pyrG marker gene via loop-out (as shown in FIG. 7) can be detected via selection/counterselection as described herein. In particular, loop-outs can be selected by growing the transformants on media with FOA.

As can be understood by one skilled in the art, the concepts depicted in FIGS. 6 and 7 can be used to introduce combinations of mutations (e.g., SNPs) into a target gene and subsequently test the phenotypic effects of said combination. The phenotypic effect can be generation of a strain or host cell that has a desired morphological phenotype. The desired morphological phenotype can be that said strain or host cell displays a non-mycelium, pellet morphology when grown in production media under submerged culture conditions. Said strain or host cell can grow and sporulate normally when grown on solid media. Further, as described herein, it is contemplated that further mutations can be introduced using a similar technique in order to build strains containing specific combinations of mutations.

In a further embodiment, combinatorial SNPSWP in fungi (e.g., *A. niger*) is performed whereby multiple mutations of a target gene are introduced in various combinations with inducible promoters into a protoplast genome by the integration into the parental gene of two separate constructs each comprising a mutation fused to an inducible promoter and a portion of a split marker gene (divergent pyrG genes) in a single transformation Upon successful recombination between the overlapping portions of the respective pyrG gene containing constructs and between the homologous portions of the target gene in the constructs and host genome, expression of each of the whole pyrG genes can be controlled via catabolite repression by glucose. Accordingly, transformants can be selected by growing the transformants on glucose such that the growth of transformants in which the desired recombination and integration events have occurred will be favored. Further, loop-outs can be facilitated by growing the transformants on media with FOA.

Another embodiment entails integration of a mutation (e.g., SNP) in a target gene (e.g., aygA) using a loop-in single crossover event with a construct comprising a copy of the target gene with a mutation and one or more selectable markers (e.g., antibiotic resistance gene ($amp^R$) and auxotrophic marker gene (pyrG)).

HTP Automated Systems

In some embodiments, the methods and systems provided herein for generating filamentous fungal strains or host cell that possess the desired pellet morphology under submerged culture conditions comprise automated steps. For example, the generation of protoplasts, transformation of protoplasts and/or purifying homokaryotic protoplasts via selection/counterselection as described herein can be automated. As described herein, the methods and system can contain a further step of screening purified homokaryotic transformants for the showing the desired pellet morphology under submerged culture conditions. The automated methods of the disclosure can comprise a robotic system. The systems outlined herein can be generally directed to the use of 96- or 384-well microtiter plates, but as will be appreciated by those in the art, any number of different plates or configurations may be used. In addition, any or all of the steps outlined herein may be automated; thus, for example, the systems may be completely or partially automated. The automated methods and systems can be high-throughput. For purposes of this disclosure, high-throughput screening can refer to any partially- or fully-automated method that is capable of evaluating about 1,000 or more transformants per day, and particularly to those methods capable of evaluating 5,000 or more transformants per day, and most particularly to methods capable of evaluating 10,000 or more transformants per day.

As described herein, the methods and system provided herein can comprise a screening step such that a transformant generated and purified as described herein is screened or tested for the desired pellet morphology in submerged cultures. The generated strains or host cells comprising the desired pellet morphology can subsequently used to generate products of interest. The product of interest can be any product of interest provided herein such as, for example, an alcohol, pharmaceutical, metabolite, protein, enzyme, amino acid, or acid (e.g., citric acid). Accordingly, the methods and systems provided herein can further comprise culturing a clonal colony or culture comprising the desired pellet morphology purified according to the methods of the invention, under conditions permitting expression and secretion of the product of interest and recovering the subsequently produced product of interest. As described herein, the product of interest can an exogenous and/or heterologous protein or a metabolite produced as the result of the expression of an exogenous and or heterologous protein.

In some embodiments, the automated systems of the present disclosure comprise one or more work modules. For example, in some embodiments, the automated system of the present disclosure comprises a DNA synthesis module, a vector cloning module, a strain transformation module, a screening module, and a sequencing module.

As will be appreciated by those in the art, an automated system can include a wide variety of components, including, but not limited to: liquid handlers; one or more robotic arms, plate handlers for the positioning of microplates; plate sealers, plate piercers, automated lid handlers to remove and replace lids for wells on non-cross contamination plates; disposable tip assemblies for sample distribution with disposable tips, washable tip assemblies for sample distribution; 96 well loading blocks; integrated thermal cyclers; cooled reagent racks; microtiter plate pipette positions (optionally cooled); stacking towers for plates and tips; magnetic bead processing stations; filtrations systems; plate shakers; barcode readers and applicators; and computer systems.

In some embodiments, the robotic systems of the present disclosure include automated liquid and particle handling enabling high-throughput pipetting to perform all the steps in the process of gene targeting and recombination applications. This includes liquid and particle manipulations such as aspiration, dispensing, mixing, diluting, washing, accurate volumetric transfers; retrieving and discarding of pipette tips, and repetitive pipetting of identical volumes for multiple deliveries from a single sample aspiration. These manipulations are cross-contamination-free liquid, particle, cell, and organism transfers. The instruments perform automated replication of microplate samples to filters, membranes, and/or daughter plates, high-density transfers, full-plate serial dilutions, and high capacity operation.

The automated system can be any known automated high-throughput system known in the art. For example, the automated system can be the automated microorganism handling tool is described in Japanese patent application publication number 11-304666. This device is capable of the transfer of microdroplets containing individual cells, and it is anticipated that the fungal strains of the present invention, by virtue of their morphology, will be amenable to micromanipulation of individual clones with this device. An additional example of an automated system for use in the methods and system of the present disclosure is the automated microbiological high-throughput screening system described in Beydon et al., J. Biomol. Screening 5:13 21 (2000). The automated system for use herein can be a customized automated liquid handling system. In one embodiment, the customized automated liquid handling system of the disclosure is a TECAN machine (e.g., a customized TECAN Freedom Evo).

In some embodiments, the automated systems of the present disclosure are compatible with platforms for multi-well plates, deep-well plates, square well plates, reagent troughs, test tubes, mini tubes, microfuge tubes, cryovials, filters, micro array chips, optic fibers, beads, agarose and acrylamide gels, and other solid-phase matrices or platforms are accommodated on an upgradeable modular deck. In some embodiments, the automated systems of the present disclosure contain at least one modular deck for multi-position work surfaces for placing source and output samples, reagents, sample and reagent dilution, assay plates, sample and reagent reservoirs, pipette tips, and an active tip-washing station.

In some embodiments, the automated systems of the present disclosure include high-throughput electroporation systems for transforming the protoplasts. In some embodiments, the high-throughput electroporation systems are capable of transforming cells in 96 or 384-well plates. In some embodiments, the high-throughput electroporation systems include VWR® High-throughput Electroporation Systems, BTX™, Bio-Rad® Gene Pulser MXcell™ or other multi-well electroporation system.

In some embodiments, the automated systems comprise an integrated thermal cycler and/or thermal regulators that are used for stabilizing the temperature of heat exchangers such as controlled blocks or platforms to provide accurate temperature control of incubating samples from 0° C. to 100° C.

In some embodiments, the automated systems of the present disclosure are compatible with interchangeable machine-heads (single or multi-channel) with single or multiple magnetic probes, affinity probes, replicators or pipetters, capable of robotically manipulating liquid, particles, cells, and multi-cellular organisms. Multi-well or multi-tube magnetic separators and filtration stations manipulate liquid, particles, cells, and organisms in single or multiple sample formats.

In some embodiments, the automated systems of the present disclosure are compatible with camera vision and/or spectrometer systems. Thus, in some embodiments, the automated systems of the present disclosure are capable of detecting and logging color and absorption changes in ongoing cellular cultures.

In some embodiments, the automated system of the present disclosure to generate the filamentous fungal host cells or strains with the desired pellet morphology is designed to be flexible and adaptable with multiple hardware add-ons to allow the system to carry out multiple applications. The automated system for use in the methods provided herein can comprise software program modules. The software program modules can allow creation, modification, and running of methods. The systems can further comprise diagnostic modules. The diagnostic modules can allow setup, instrument alignment, and motor operations. The systems can still further comprise customized tools, labware, liquid and particle transfer patterns and/or a database(s). The customized tools, labware, and liquid and particle transfer patterns can allow different applications to be programmed and performed. The database can allow method and parameter storage. Further, robotic and computer interfaces present in the system can allow communication between instruments.

Persons having skill in the art will recognize the various robotic platforms capable of carrying out the HTP methods of the present disclosure to generate the filamentous fungal host cells or strains with the desired pellet morphology.

Computer System Hardware

Figure 10:
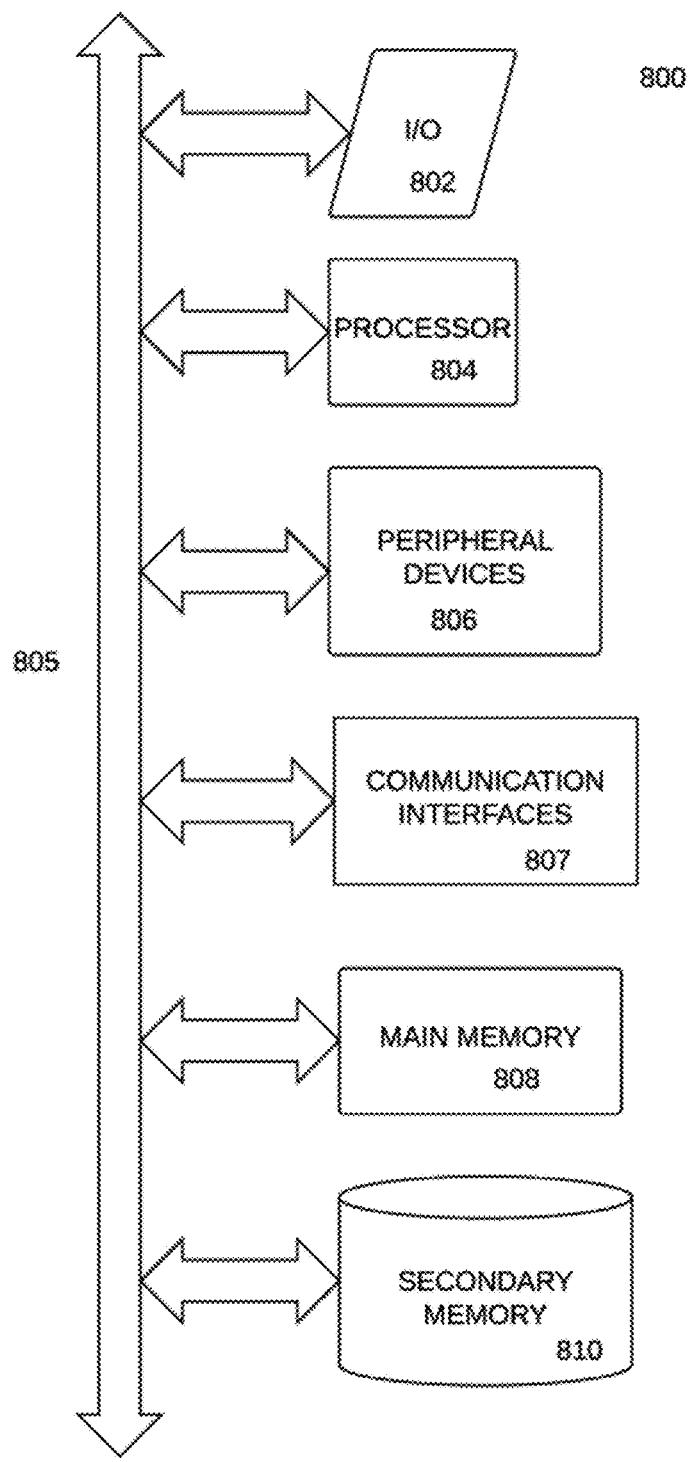
FIG. 10 diagrams an embodiment of a computer system, according to embodiments of the present disclosure.

FIG. 10 illustrates an example of a computer system 800 that may be used to execute program code stored in a non-transitory computer readable medium (e.g., memory) in accordance with embodiments of the disclosure. The computer system includes an input/output subsystem 802, which may be used to interface with human users and/or other computer systems depending upon the application. The I/O subsystem 802 may include, e.g., a keyboard, mouse, graphical user interface, touchscreen, or other interfaces for input, and, e.g., an LED or other flat screen display, or other interfaces for output, including application program interfaces (APIs). Other elements of embodiments of the disclosure, such as the components of the LIMS system, may be implemented with a computer system like that of computer system 800.

Program code may be stored in non-transitory media such as persistent storage in secondary memory 810 or main memory 808 or both. Main memory 808 may include volatile memory such as random access memory (RAM) or non-volatile memory such as read only memory (ROM), as well as different levels of cache memory for faster access to instructions and data. Secondary memory may include persistent storage such as solid state drives, hard disk drives or optical disks. One or more processors 804 reads program code from one or more non-transitory media and executes the code to enable the computer system to accomplish the methods performed by the embodiments herein Those skilled in the art will understand that the processors) may ingest source code and interpret or compile the source code into machine code that is understandable at the hardware gate level of the processors) 804. The processor(s) 804 may include graphics processing units (GPUs) for handling computationally intensive tasks. Particularly in machine learning, one or more CPUs 804 may offload the processing of large quantities of data to one or more GPUs 804.

The processor(s) 804 may communicate with external networks via one or more communications interfaces 807, such as a network interface card, WiFi transceiver, etc. A bus 805 communicatively couples the I/O subsystem 802, the processors) 804, peripheral devices 806, communications interfaces 807, memory 808, and persistent storage 810. Embodiments of the disclosure are not limited to this representative architecture. Alternative embodiments may employ different arrangements and types of components, e.g., separate buses for input-output components and memory subsystems.

Those skilled in the art will understand that some or all of the elements of embodiments of the disclosure, and their accompanying operations, may be implemented wholly or partially by one or more computer systems including one or more processors and one or more memory systems like those of computer system 800. In particular, any robotics and other automated systems or devices described herein may be computer-implemented. Some elements and functionality may be implemented locally and others may be implemented in a distributed fashion over a network through different servers, e.g., in client-server fashion, for example. In particular, server-side operations may be made available to multiple clients in a software as a service (SaaS) fashion.

The term component in this context refers broadly to software, hardware, or firmware (or any combination thereof) component. Components are typically functional components that can generate useful data or other output using specified input(s). A component may or may not be self-contained. An application program (also called an "application") may include one or more components, or a component can include one or more application programs.

Some embodiments include some, all, or none of the components along with other modules or application components Still yet, various embodiments may incorporate two or more of these components into a single module and/or associate a portion of the functionality of one or more of these components with a different component.

The term "memory" can be any device or mechanism used for storing information. In accordance with some embodiments of the present disclosure, memory is intended to encompass any type of, but is not limited to: volatile memory, nonvolatile memory, and dynamic memory. For example, memory can be random access memory, memory storage devices, optical memory devices, magnetic media, floppy disks, magnetic tapes, hard drives, SIMMs, SDRAM, DIMMs, RDRAM, DDR RAM, SODIMMS, erasable programmable read-only memories (EPROMs), electrically erasable programmable read-only memories (EEPROMs), compact disks, DVDs, and/or the like. In accordance with some embodiments, memory may include one or more disk drives, flash drives, databases, local cache memories, processor cache memories, relational databases, flat databases, servers, cloud based platforms, and/or the like. In addition, those of ordinary skill in the art will appreciate many additional devices and techniques for storing information can be used as memory.

Memory may be used to store instructions for running one or more applications or modules on a processor. For example, memory could be used in some embodiments to house all or some of the instructions needed to execute the functionality of one or more of the modules and/or applications disclosed in this application.

Cell Culture and Fermentation

Cells of the present disclosure can be cultured in conventional nutrient media modified as appropriate for any desired biosynthetic reactions or selections. In some embodiments, the present disclosure teaches culture in inducing media for activating promoters. In some embodiments, the present disclosure teaches media with selection agents, including selection agents of transformants (e.g., antibiotics), or selection of organisms suited to grow under inhibiting conditions (e.g., high ethanol conditions) In some embodiments, the present disclosure teaches growing cell cultures in media optimized for cell growth. In other embodiments, the present disclosure teaches growing cell cultures in media optimized for product yield. In some embodiments, the present disclosure teaches growing cultures in media capable of inducing cell growth and also contains the necessary precursors for final product production (e.g., high levels of sugars for ethanol production).

Culture conditions, such as temperature, pH and the like, are those suitable for use with the host cell selected for expression, and will be apparent to those skilled in the art. As noted, many references are available for the culture and production of many cells, including cells of bacterial, plant, animal (including mammalian) and archaebacterial origin. See e.g., Sambrook, Ausubel (all supra), as well as Berger, *Guide to Molecular Cloning Techniques, Methods in Enzy-*

*mology* volume 152 Academic Press, Inc., San Diego, Calif.; and Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY, Humason (1979) *Animal Tissue Techniques*, fourth edition W.H. Freeman and Company, and Ricciardelle et al., (1989) *In Vitro Cell Dev. Biol.* 25:1016-1024, all of which are incorporated herein by reference. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*, Fundamental Methods Springer Lab Manual, Springer-Verlag (Berlin Heidelberg N.Y.); Jones, ed. (1984) *Plant Gene Transfer and Expression Protocols*, Humana Press, Totowa, N.J. and *Plant Molecular Biology* (1993) R. R. D. Croy, Ed Bios Scientific Publishers, Oxford, U K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* from Sigma-Aldrich, Inc (St Louis, Mo.) ("Sigma-LSRCCC") and, for example, *The Plant Culture Catalogue* and supplement also from Sigma-Aldrich, Inc (St Louis, Mo.) ("Sigma-PCCS"), all of which are incorporated herein by reference.

The culture medium to be used must in a suitable manner satisfy the demands of the respective strains. Descriptions of culture media few various microorganisms are present in the "Manual of Methods for General Bacteriology" of the American Society for Bacteriology (Washington D.C., USA, 1981).

The present disclosure furthermore provides a process for fermentative preparation of a product of interest, comprising the steps of: a) culturing a microorganism according to the present disclosure in a suitable medium, resulting in a fermentation broth; and b) concentrating the product of interest in the fermentation broth of a) and/or in the cells of the microorganism.

In some embodiments, the present disclosure teaches that the microorganisms produced may be cultured continuously—as described, for example, in WO 05/021772- or discontinuously in a batch process (batch cultivation) or in a fed-batch or repeated fed-batch process for the purpose of producing the desired organic-chemical compound. A summary of a general nature about known cultivation methods is available in the textbook by Chmiel (Bioprozeßtechnik. 1: Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

In some embodiments, the cells of the present disclosure are grown under batch or continuous fermentations conditions.

Classical batch fermentation is a closed system, wherein the compositions of the medium is set at the beginning of the fermentation and is not subject to artificial alternations during the fermentation. A variation of the batch system is a fed-batch fermentation which also finds use in the present disclosure. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art.

Continuous fermentation is a system where a defined fermentation medium is added continuously to a bioreactor and an equal amount of conditioned medium is removed simultaneously for processing and harvesting of desired biomolecule products of interest. In some embodiments, continuous fermentation generally maintains the cultures at a constant high density where cells are primarily in log phase growth. In some embodiments, continuous fermentation generally maintains the cultures at a stationary or late log/stationary, phase growth. Continuous fermentation systems strive to maintain steady state growth conditions.

Methods for modulating nutrients and growth factors for continuous fermentation processes as well as techniques for maximizing the rate of product formation are well known in the art of industrial microbiology.

For example, a non-limiting list of carbon sources for the cultures of the present disclosure include, sugars and carbohydrates such as, for example, glucose, sucrose, lactose, fructose, maltose, molasses, sucrose-containing solutions from sugar beet or sugar cane processing, starch, starch hydrolysate, and cellulose; oils and fats such as, for example, soybean oil, sunflower oil, groundnut oil and coconut fat; fatty acids such as, for example, palmitic acid, stearic acid, and linoleic acid; alcohols such as, for example, glycerol, methanol, and ethanol, and organic acids such as, for example, acetic acid or lactic acid.

A non-limiting list of the nitrogen sources for the cultures of the present disclosure include organic nitrogen-containing compounds such as peptones, yeast extract, meat extract, malt extract, corn steep liquor, soybean flour, and urea; or inorganic compounds such as ammonium sulfate, ammonium chloride, ammonium phosphate, ammonium carbonate, and ammonium nitrate. The nitrogen sources can be used individually or as a mixture.

A non-limiting list of the possible phosphorus sources for the cultures of the present disclosure include, phosphoric acid, potassium dihydrogen phosphate or dipotassium hydrogen phosphate or the corresponding sodium-containing salts.

The culture medium may additionally comprise salts, for example in the form of chlorides or sulfates of metals such as, for example, sodium, potassium, magnesium, calcium and iron, such as, for example, magnesium sulfate or iron sulfate, which are necessary for growth.

Finally, essential growth factors such as amino acids, for example homoserine and vitamins, for example thiamine, biotin or pantothenic acid, may be employed in addition to the abovementioned substances.

In some embodiments, the pH of the culture can be controlled by any acid or base, or buffer salt, including, but not limited to sodium hydroxide, potassium hydroxide, ammonia, or aqueous ammonia, or acidic compounds such as phosphoric acid or sulfuric acid in a suitable manner. In some embodiments, the pH is generally adjusted to a value of from 6.0 to 8.5, preferably 6.5 to 8.

In some embodiments, the cultures of the present disclosure may include an anti-foaming agent such as, for example, fatty acid polyglycol esters. In some embodiments the cultures of the present disclosure are modified to stabilize the plasmids of the cultures by adding suitable selective substances such as, for example, antibiotics.

In some embodiments, the culture is carried out under aerobic conditions. In order to maintain these conditions, oxygen or oxygen-containing gas mixtures such as, for example, air are introduced into the culture. It is likewise possible to use liquids enriched with hydrogen peroxide. The fermentation is carried out, where appropriate, at elevated pressure, for example at an elevated pressure of from 0.03 to 0.2 MPa. The temperature of the culture is normally from 20° C. to 45° C. and preferably from 25° C. to 40° C., particularly preferably from 30° C. to 37° C. In batch or fed-batch processes, the cultivation is preferably continued until an amount of the desired product of interest (e.g., an organic-chemical compound) sufficient for being recovered has formed. This aim can normally be achieved within 10 hours to 160 hours. In continuous processes, longer cultivation times are possible. The activity of the microorganisms results in a concentration (accumulation) of the product of interest in the fermentation medium and/or in the cells of said microorganisms.

In some embodiments, the culture is carried out under anaerobic conditions.

In some embodiments, provided herein is a fermentation media for growing filamentous fungal strains or host cells generated using the methods provided herein that comprises manganese and is substantially free (less than 5%, 4%, 3%, 2%, or 1% of the amount or concentration of chelating agent found in fermentation media known in the art for producing a product of interest such as, for example, citric acid) or free of chelating agents such that said filamentous fungal strains or host cells maintain a non-mycelium, pellet morphology when grown in said fermentation media. The fermentation media can be citric acid production media. The manganese can be present at about 14, 15, 16, 17, 18, 19, 20, 25, 30, 35, 40, 45, 50, 55, 60, 65, 70, 75, 100, 250, 500, 750, or 1000 ppb. The manganese can be present at greater than 13, 14, 15, 16, 17, 18, 19, 20, 25, 30, 35, 40, 45, 50, 55, 60, 65, 70, 75, 100, 250, 500, 750, or 1000 ppb. The fermentation media can comprise no chelating agents. The fermentation media can comprise about 50%, 55%, 60%, 65%, 70%, 75%, 80%, 85%, 90%, 95% or 99% less chelating agents than normal fermentation media. The chelating agents can be manganese chelators. The filamentous fungal strain or host cell can comprise one or more genetically altered target morphology genes. The target morphology genes can be any morphology related genes provided herein In one embodiment, the target morphology gene is an *A. niger* two-component histidine kinase gene (e.g., *A. niger* nikA gene; SEQ ID NO: 14). The genetic alteration can be a mutant form of the target morphology related gene and/or substitution of native promoter or terminator with a heterologous promoter or terminator. In one embodiment, the mutant form of the target morphology gene is Fungi SNP_9 (SEQ ID NO: 5), FungiSNP_12 (SEQ ID NO: 6), FungiSNP_18 (SEQ ID NO: 7) or FungiSNP_40 (SEQ ID NO: 8). In another embodiment, the mutant form of the target morphology gene is FungiSNP_9 (SEQ ID NO 5), FungiSNP_12 (SEQ ID NO: 6), FungiSNP_18 (SEQ ID NO: 7) or FungiSNP_40 (SEQ ID NO: 8) fused to or operably linked to any of the promoters from Table 2 In one embodiment, the target morphology gene is the mutant form of an *A. niger* orthologue of the *S. cerevisiae* SLN 1 protein or *N. crassa* Nik1 protein encoded by SEQ ID NO: 7. Further to this embodiment, the gene for the mutant form of *A. niger* orthologue of the *S. cerevisiae* SLN1 gene or *N. crassa* nik1 gene is fused to a man8p or amy8p promoter. The man8p promoter or amy8p promoter can be from Table 2.

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will be recognized by those skilled in the art.

A brief table of contents (i.e., Table 5) is provided below solely for the purpose of assisting the reader. Nothing in this table of contents is meant to limit the scope of the examples or disclosure of the application.

TABLE 5

Table of Contents For Example Section

| Example # | Title | Brief Description |
|---|---|---|
| 1 | HTP Genomic Engineering of filamentous fungi: identification of genes that affect filamentous fungal morphology | Describes SNP swap method for generating filamentous fungal strains with non-mycelium, pellet phenotype in submerged CAP culture |
| 2 | HTP Genomic Engineering of filamentous fungi: confirmation of role the identified genes play in filamentous fungal morphology | Describes confirmation genes that play a role in morphology of filamentous fungal strains in submerged CAP culture by knocking out putative morphologically related genes |
| 3 | HTP Genomic Engineering of filamentous fungi: altering filamentous fungal cell morphology by altering gene expression | Describes a PROSWP library being utilized in filamentous fungi to control expression of putative morphologically related genes |
| 4 | Examination of the growth of morphological mutant filamentous fungal strain in submerged culture lacking chelating agents | Describes growth of morphological mutant generated in Examples 1-3 in CAP medium lacking chelating agents |
| 5 | HTP Genomic Engineering of filamentous fungi: examination of gene that affects filamentous fungal morphology and its role in citric acid production and osmotic stress response | Describes SNP swap method for generating filamentous fungal strains with non-mycelium, pellet phenotype in submerged CAP culture by altering expression of candidate osmotic response pathway gene |

Example 1: HTP Genomic Engineering of Filamentous Fungi: Identification of Genes that Affect Filamentous Fungal Morphology This example demonstrates the use of SNP Swap libraries in a SNPSWAP method in the filamentous fungi, *Aspergillus niger*, in order to identify genes that play a role in controlling fungal cell morphology. In particular, this example describes the identification of a group of genes that confer a non-mycelium forming, pellet-like morphological phenotype in *A. niger* mutant strains, where the cells maintain a tighter, less elongated phenotype with each cell having multiple tips when grown in submerged cultures. This type of growth can be favorable to stirred tank fermentation.

*Aspergillus niger* is a species of filamentous fungi used for the large-scale production of citric acid through fermentation. Multiple strains of this species have been isolated and shown to have varying capacity for production of citric acid and other organic acids. The *A. niger* strain ATCC 1015 was identified as a producer of citric acid in the early twentieth century. An isolate of this strain named ATCC 11414, was later found to exhibit increased citric acid yield over its parent. For example, *A. niger* strain ATCC 1015 on average produces 7 grams of citric acid from 140 grams of glucose in media containing ammonium nitrate but lacking both iron and manganese cations. Isolate strain ATCC 11414 on the other hand, exhibits a 10-fold yield increase (70 grams of citric acid) under the same conditions. Moreover, strain ATCC 11414 spores germinate and grow better in citric acid production media than do spores of strain 1015.

In order to identify potential genetic sources for these phenotypic differences, the genomes of both the ATCC 1015 and ATCC 11414 strains were sequenced and analyzed. The resulting analysis identified 43 SNPs distinguishing the 1015 and 11414 strains (see Table 3). Of these 43 SNPs, 18 were found to be in the coding domains of their respective genes (see Table 4).

In order to identify genes that play a potential role in controlling the morphology/growth of filamentous fungi under different culture conditions, the 43 SNPs from Table 3 were used in a SNP swap process as described herein in order to systematically introduce each individual SNP from Table 3 into the base 1015 strain and examine phenotype differences from a morphological standpoint between resulting parent and mutant strains. Conversely, the same type of process was performed in the 11414 production strain, whereby each of the SNPs from Table 3 already present in the genome of 11414 was systemically replaced with wild-type versions of each gene and any resulting difference in morphology between the parent and mutant strains were noted.

Constructs for Transforming Protoplasts

Figure 4:
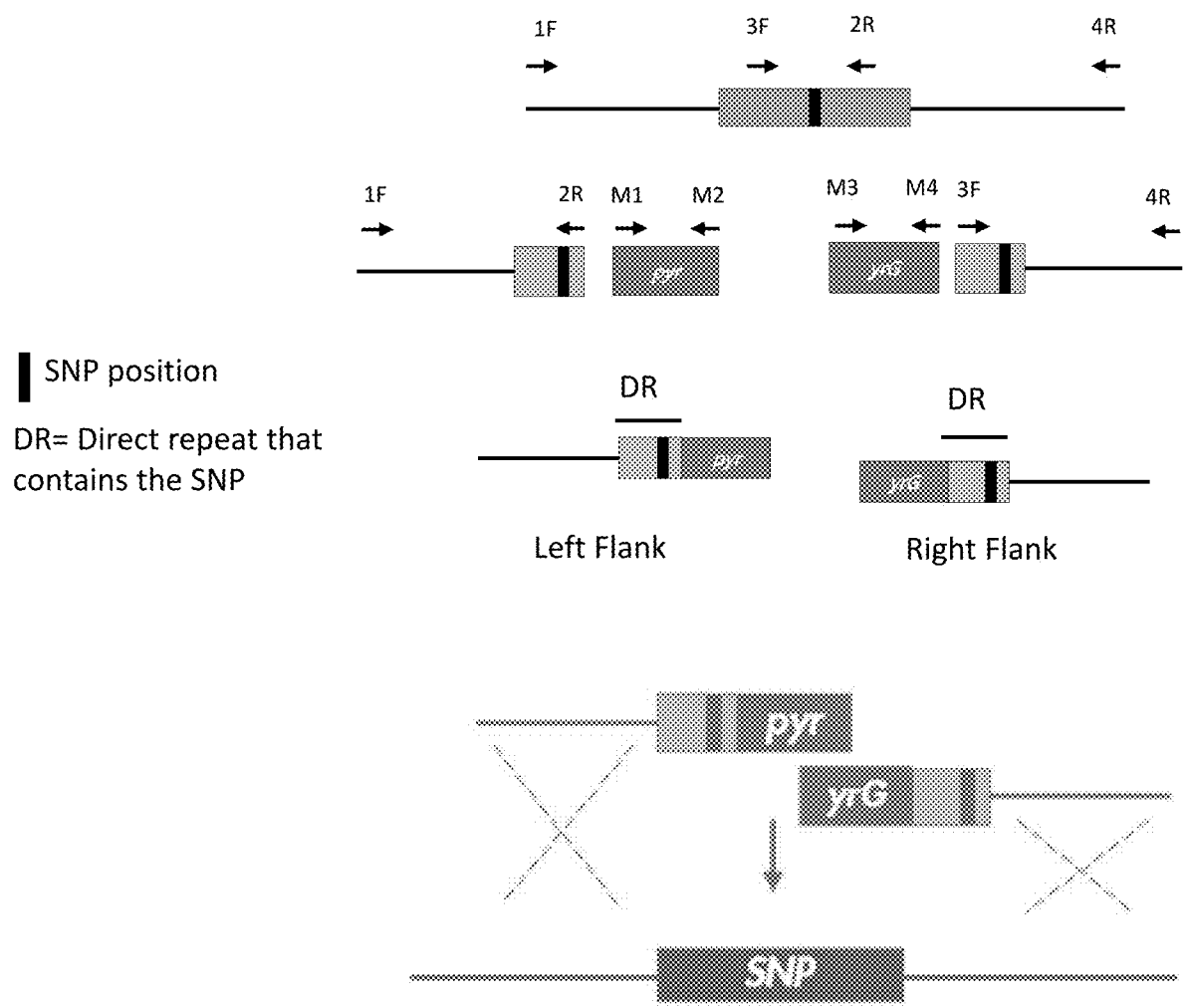
FIG. 4 illustrates the use of fusion PCR to generate split-marker constructs for use in the present invention.
Figure 5:
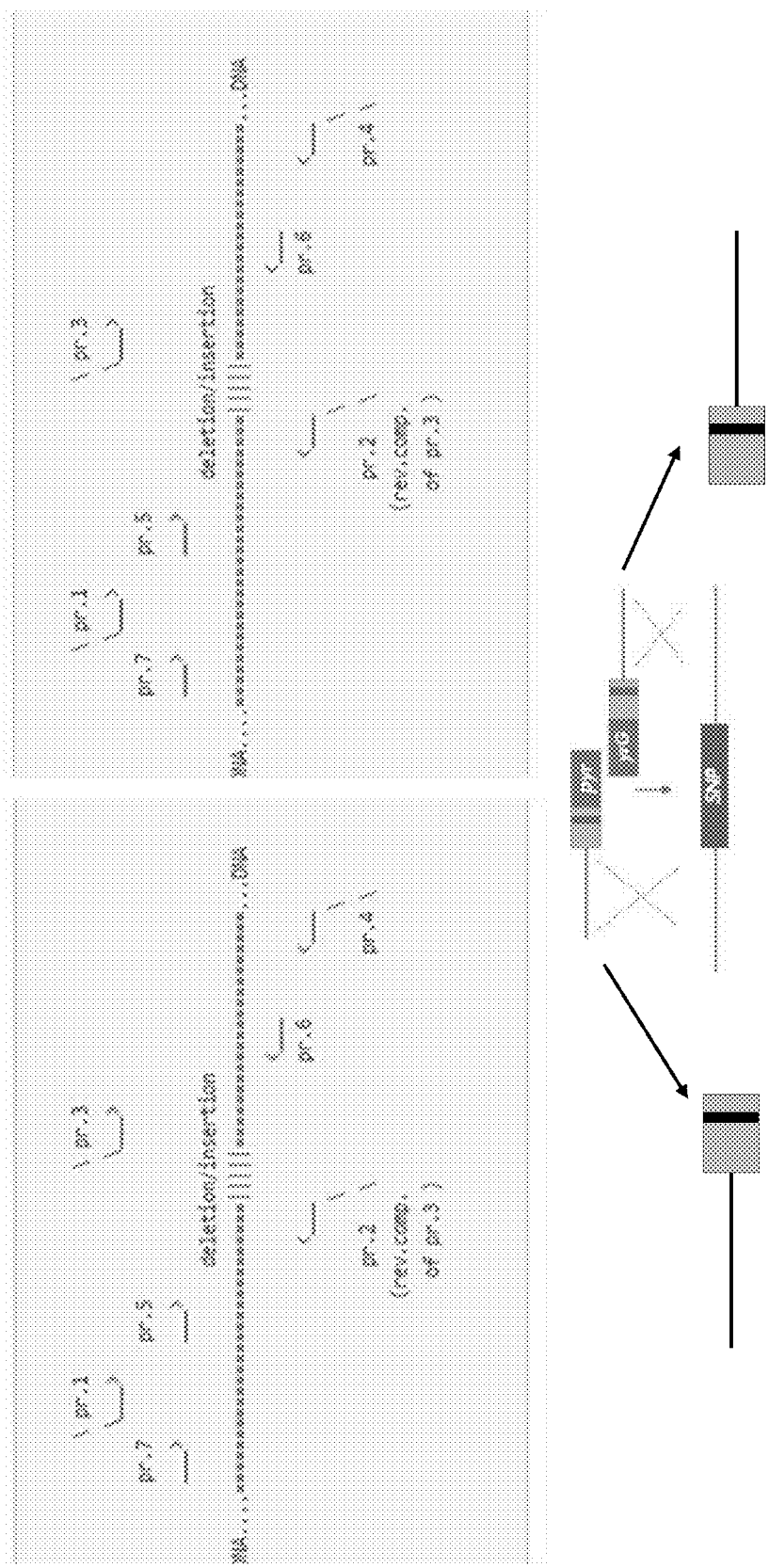
FIG. 5 illustrates quality control analysis of split-marker constructs generated as depicted in FIG. 4.
Figure 5:
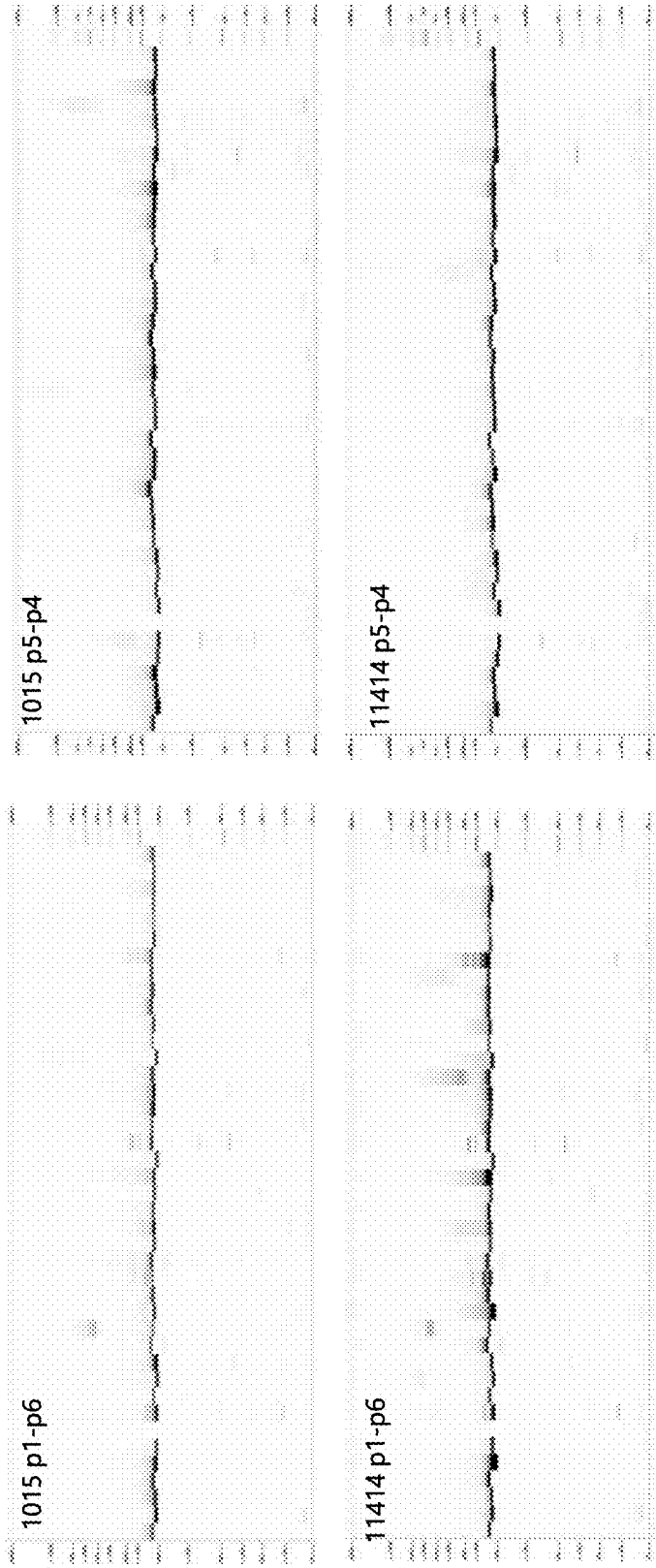

In this Example, each strain (i.e., 1015 and 11414) was co-transformed with two constructs ("split-marker constructs"), wherein each of the two constructs contained an overlapping portion of a selectable marker (i.e., pyrG in FIGS. 4 and 5) and were flanked by direct repeat sequence as shown in FIGS. 4 and 5. The split-marker constructs were generated using fusion PCR and were quality controlled (QC d) using a fragmenta analyzer as shown in FIG. 5. Moreover, each of these constructs further comprised sequence flanking the direct repeat portions of each construct in order to direct integration in the host cell genome at the respective target gene for each SNP from Table 3. For the 1015 base strain protoplasts, the direct repeats in the split constructs comprised one of the SNPs from Table 3 (see FIG. 6). In contrast, for the 11414 production strain protoplasts, the direct repeats did not comprise a SNP from Table 3.

The *A. niger* base strain 1015 and production strain 11414 were cultivated, converted to protoplasts, transformed and screened as described in 62/515,907 filed Jun. 6, 2017. In summary, each of these steps were as follows:

Generation of Protoplasts 500 milliliters of complete media was inoculated with $10^6$ conidia/ml and grown overnight at 150 rpm at 30° C. for both the/l. *niger* 1015 base strain and *A. niger* 11414 production strain. Following the overnight growth, the mycelia were harvested by filtering each culture through Miracloth. Subsequently, the mycelia were rinsed thoroughly with sterile water. Harvested and washed mycelia from both strains were then each separately subjected to enzymatic digestion with a VinoTaste Pro (VTP) enzymatic cocktail.

Enzymatic digestion of the mycelia for both strains was performed by first making 50 ml of 60 mg/ml of VTP in protoplasting buffer (1.2M magnesium sulfate, 50 mM phosphate buffer, pH 5). After dissolving the VTP, the buffer was placed in clean Oakridge tubes and spun at 15,000×g for 15 minutes. The solution was then filter sterilized after centrifugation. Once made, some of the harvested mycelia was added to the VTP solution and the mycelia was digested at 30° C. at 80 rpm for ~2-4 hours. At various intervals during VTP digestion, small samples were examined under 400× magnification for the presence of protoplasts (i.e., large round cells that are larger than conidia and are sensitive to osmotic lysis). When most or all of the mycelia for each strain were digested, the culture from each strain was filtered through sterile Miracloth and the filtrates were collected in a graduated cylinder. The filtered protoplasts were transferred to a graduated cylinder and a buffer of lower osmolite concentration (5 ml of 0.4M ST buffer (0.4M Sorbitol, 100 mM Tris, pH 8) was gently overlaid. The overlaid samples were then spun at 800×g for 15 minutes at 4° C. and protoplasts were then removed with a pipette and mixed gently with 25 ml of ST solution (1.0 M sorbitol, 50 mM Tris, Ph 8.0) and respun at 800×g for 10 minutes. The protoplasts should pellet at the bottom of the tube. The protoplasts from each strain were then each separately resuspended in 25 ml of ST solution and collected by centrifugation at 800×g for 10 minutes.

Transformation of Protoplasts

Following centrifugation, the protoplasts from both strains were ultimately resuspended in a buffer containing calcium chloride Subsequently, protoplasts from both strains were subjected to traditional PEG Calcium mediated transformations using automated liquid handlers, which combined the DNA from the split constructs described above with the protoplast-PEG mixtures in the 96 wells.

Screening for Transformants

As described above, the split marker constructs utilized in this Example contained direct repeats flanking the pyrG marker gene, which were subsequently used for looping out the marker gene. As a result, strains containing the loop out construct were counter selected for deletion of the selection region (e.g., see FIG. 4 and FIG. 7; absence of pyrG gene). Correct integration was further assessed by sequence-based screening as described herein. Further, the mutant strains were screened using NGS in order to assess the homokaryotic nature of the transformants as provided herein. Homokaryotic or substantially homokaryotic mutant strains were plated on minimal media with (see FIGS. 13 and 14) or without (see FIG. 15) various supplements in order to assess said strain's ability to grow under low pH (FIG. 13) or osmotic stress (FIG. 14) or sporulate (FIG. 15). In addition, the mutant strains were grown as submerged cultures in CAP media in order to assess their phenotype in submerged production media.

Results

Individual integration of 4 of the SNPs shared between Tables 3 and 4 into the base *A. niger* strain 1015, generated a morphological phenotype. In particular, integration of FungiSNP_9 (SEQ ID NO. 5), FungiSNP_12 (SEQ ID NO. 6), FungiSNP_18 (SEQ ID NO. 7) or FungiSNP_40 (SEQ ID NO: 8) into the 1015 genome generated mutant strains produced a non-mycelium, pellet morphology when grown as a submerged culture in CAP media.

The role of the genes containing the 4 SNPs in affecting fungal morphology was further demonstrated in the wave down experiments, whereby removal of each of these 4 SNPs rescued the observed morphological phenotypes. The sequences of the 4 SNPs can be found in the attached sequence listing, while their putative or known protein function can be found in Table 4.

Figure 13:
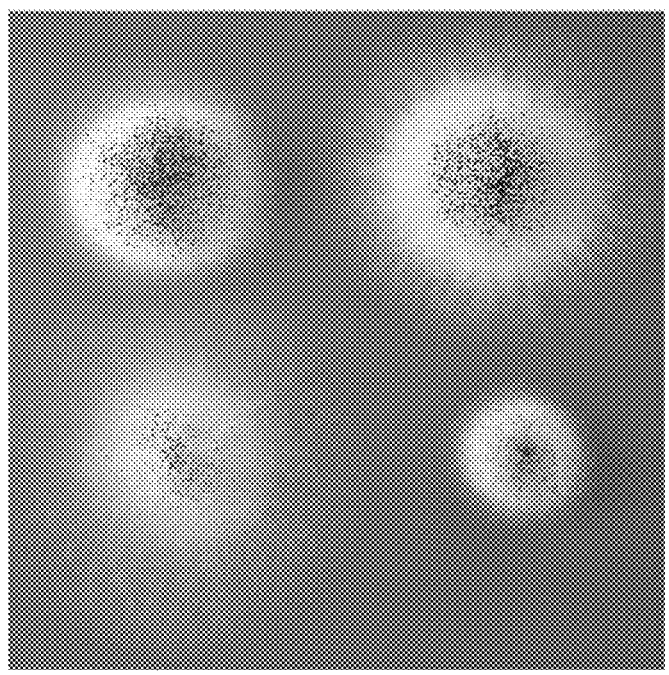
FIG. 13 illustrates that strains that contain the Base SNP18 grow faster on low pH media.
Figure 13:
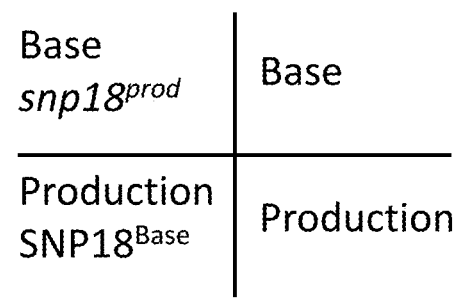

As shown in FIG. 13, strains that contain the Base SNP18 grow faster on low pH media. The presence of FungiSNP_18 from the production strain (11414) in the base strain (i.e., Base snp $18^{prod}$ in FIG. 13) reduced radial growth of the resultant colony on pH2 media as compared to the base (i.e., Base from FIG. 13). In contrast, the presence of the wild-type version of FungiSNP_18 from the base strain in the production strain (i.e., Production SNP18$^{Base}$ in FIG. 13) allowed for radial growth in said strain as compared to the Base and Production strains from FIG. 13. Further, it seems that other SNPs present in the production strain also contribute to lower radial growth (see Production in smaller than snp18$^{prod}$ in FIG. 13).

Figure 14:
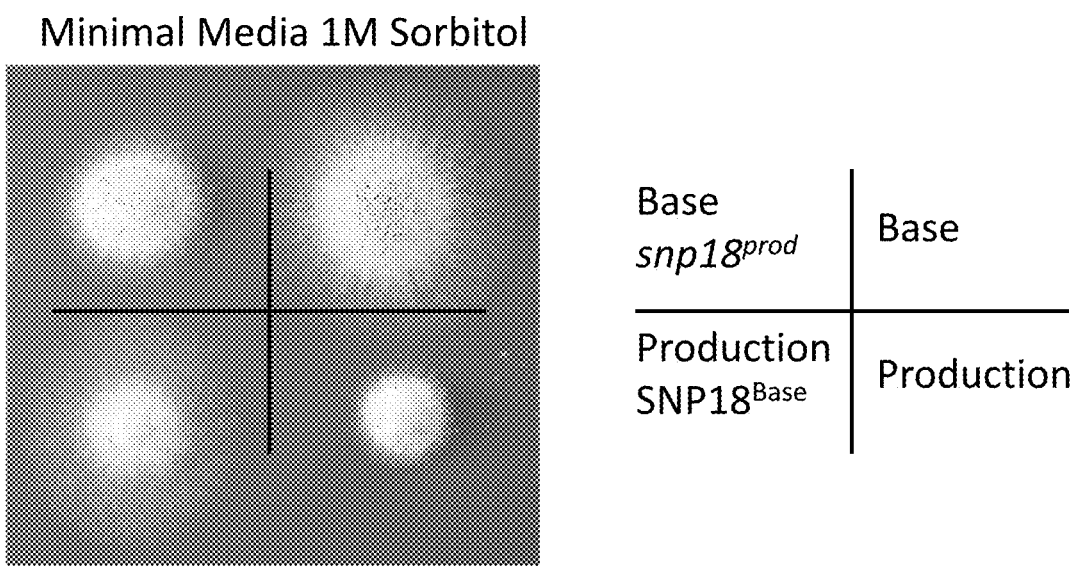
FIG. 14 illustrates that strains that contain the Base SNP 18 grow faster on media that provide osmotic stress.
Figure 15:
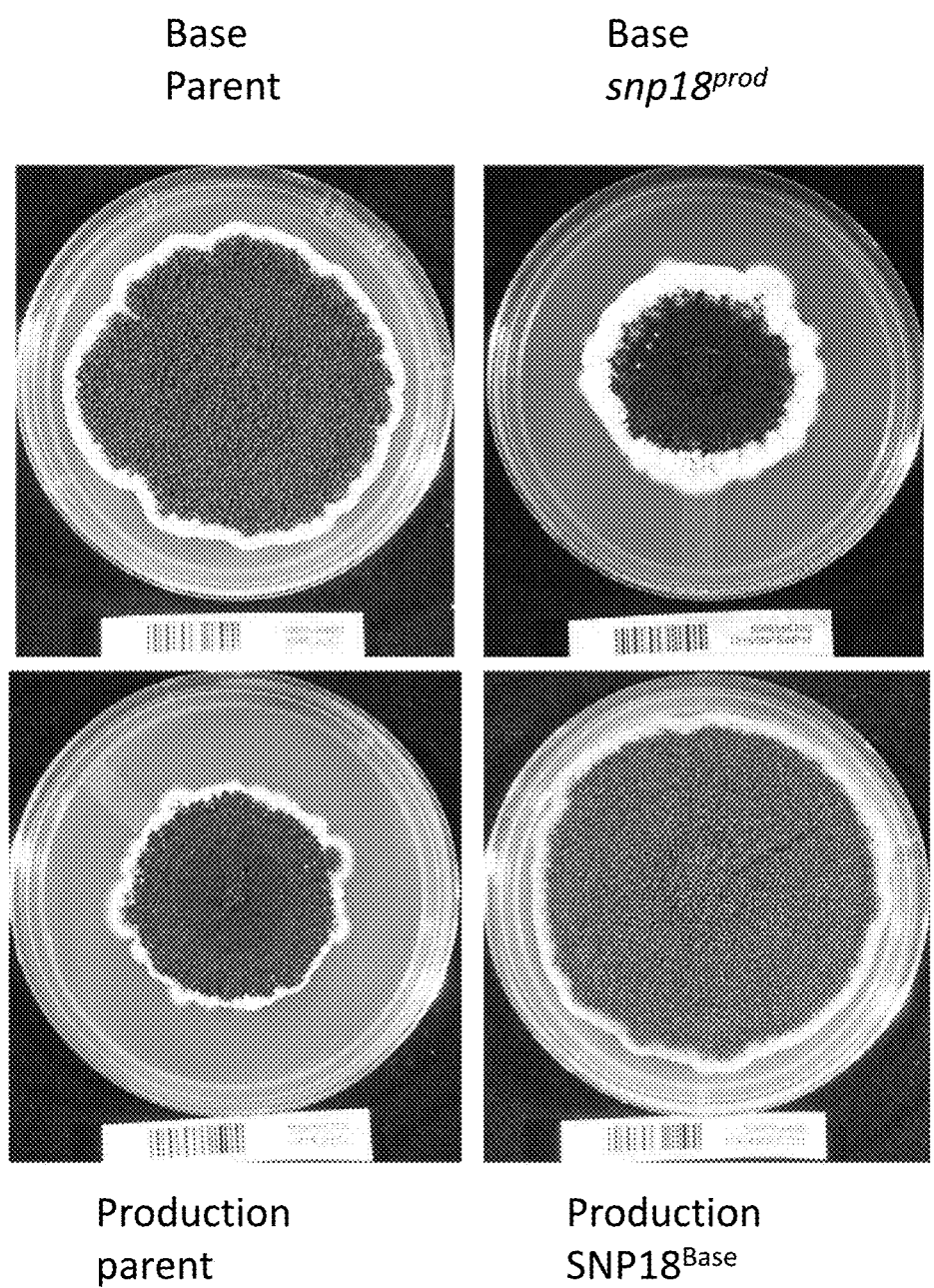
FIG. 15 illustrates that exchanging FungiSNP_18 between the base and production strains has an impact, on sporulation and radial growth rate.

As shown in FIG. 14, strains that contain the base SNP18 (i.e., wild-type version of FungiSNP_18) grow faster on media which provide osmotic stress. The presence of FungiSNP_18 from the production strain (11414) in the base strain (i.e., Base snp18$^{prod}$ in FIG. 14) reduced radial growth of the resultant colony under osmotic stress as compared to the base (i.e., Base from FIG. 14). In contrast, the presence of the wild-type version of FungiSNP_18 from the base strain in the production strain (i.e., Production SNP18$^{Base}$ in FIG. 14) allowed for radial growth in said strain as compared to the Base and Production strains from FIG. 14. Further, it seems that other SNPs present in the production strain also contribute to lower radial growth (see Production in smaller than Base snp18$^{prod}$ in FIG. 14).

Interestingly, base strains containing each of FungiSNP_9, FungiSNP_12, or FungiSNP_40 grew normally and sporulated normally when not grown in submerged cultures (e.g., on plates). Expressing FungiSNP_18 in the base strain (i.e., 1015) did show an effect on radial growth rate (reduced) and sporulation as shown in FIG. 15.

Example 2: HTP Genomic Engineering of Filamentous Fungi: Confirmation of Role the Identified Genes Play in Filamentous Fungal Morphology-Deletion of the Identified Morphological Control Genes This example demonstrates confirmation of the role of the 4 genes identified in Example 1 as playing a role in fungal morphology. In particular, this example describes knocking out or deleting each of the 4 genes using HTP methods as described herein in *A. niger* strains 1015 and 11414.

Figure 8:
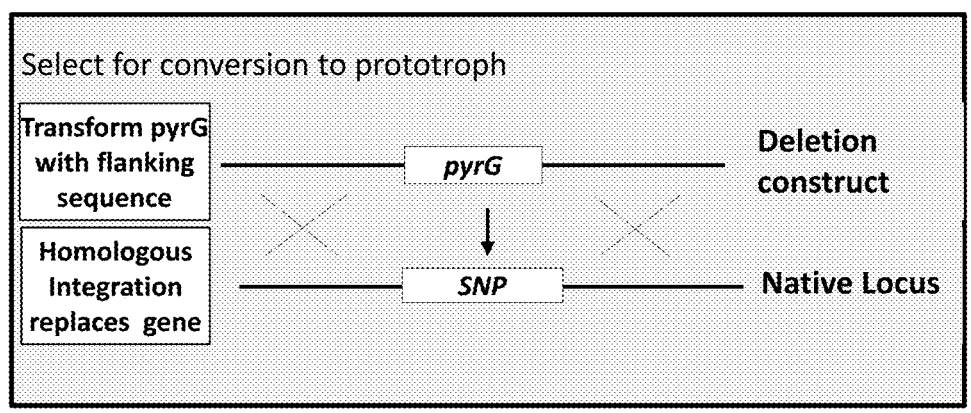
FIG. 8 illustrates using deletion constructs for assessing deletion phenotypes for each SNP from Table 3 as described in Example 2. The deletion phenotype can be used to inform pathway analysis

The *A. niger* base strain 1015 and production strain 11414 were cultivated, converted to protoplasts, transformed and screened as described in Example 1.
Constructs for Transforming Protoplasts In this Example, protoplasts from each strain (i.e., 1015 and 11414) were transformed with a series of single constructs whereby each construct in the series contained a selectable marker gene (i.e., pyrG) flanked by sequence complementary to genomic sequence flanking one of the 4 genes of interest identified in Example 1 in order to direct integration of the marker gene into the host cell genome. As shown in FIG. 8, integration of the marker gene into the locus of one of the 4 genes (one of the 4 wild-type genes in the 1015 strain and one the of 4 SNPs in the 11414 strain) essentially served to remove said wildtype gene or SNP containing gene from the locus of the respective strain.

Figure 16:
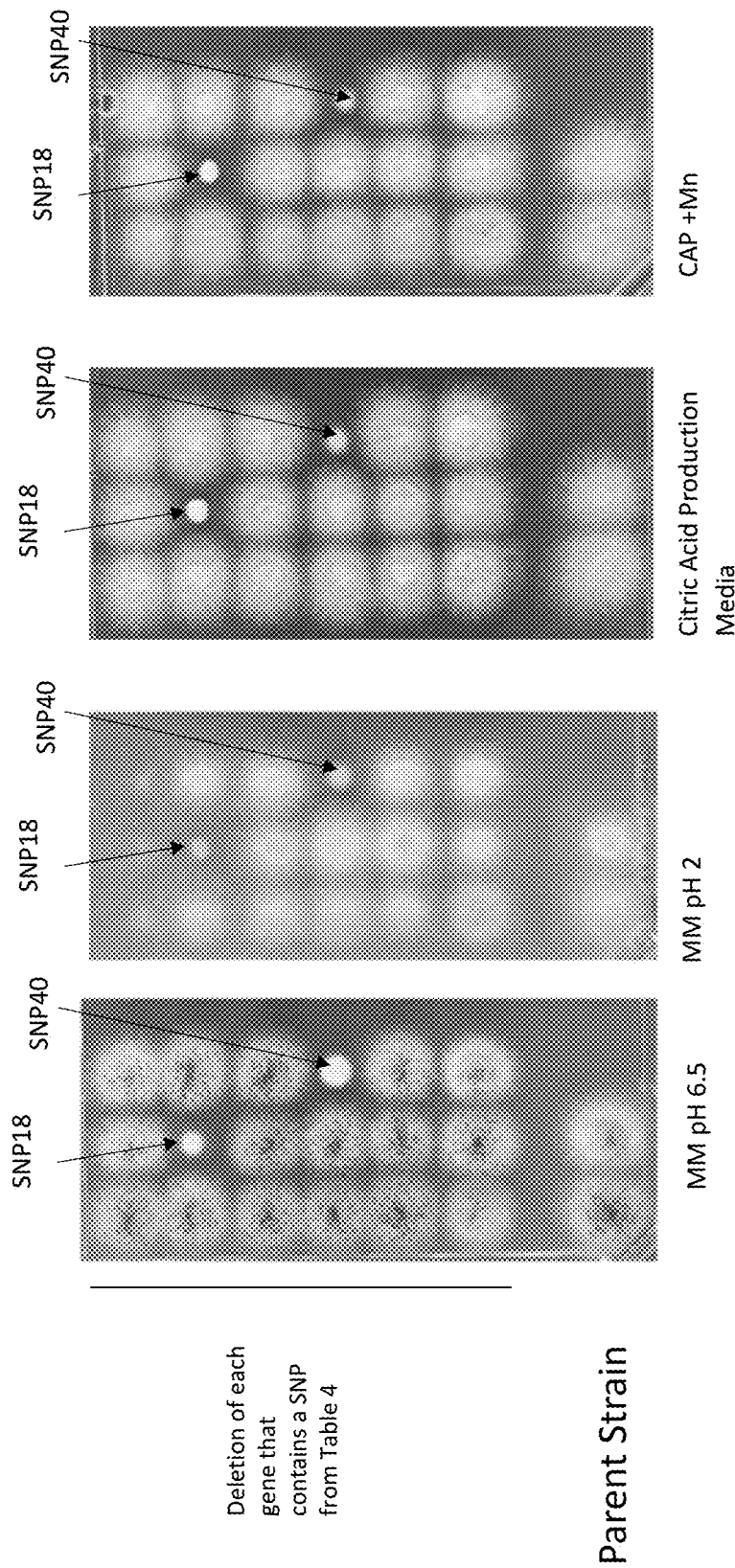
FIG. 16 illustrates deletion in the base strain of all coding sequences that contain SNPs (i.e., the Fungi SNPs from Table 4) in the production strain.

Following growth, the mutant strains were screened using NGS in order to assess the homokaryotic nature of the transformants as provided herein. Homokaryotic or substantially homokaryotic mutant strains were plated on media in order to assess said strains ability to sporulate or grown as submerged cultures in CAP media in order to assess their phenotype in submerged production media.
Results Removal of each of the 4 genes from the base 1015 strain as well as the 11414 production strain confirmed the results from Example 1 in that each of said 4 genes clearly play a role in affecting fungal morphology. In particular, as in Example 1, removal of the non-SNP containing version of the gene containing FungiSNP_18 in the 1015 strain or the gene containing FungiSNP_18 in the 11414 strain, produced the most striking phenotype whereby under submerged culture conditions, said strains had a pellet like morphology. Further, as shown in FIG. 16, deletion of FungiSNP18 and FungiSNP40 genes resulted in a tight morphology under all conditions. This data may indicate that the SNPs are not loss of function mutations given that the deletion phenotypes are more pronounced (stronger impact on morphology) than the SNPs themselves. Thus, it seems that altering the expression of these genes may impact morphology in a manner that is desirable for growth in fermenters.

Figure 17:
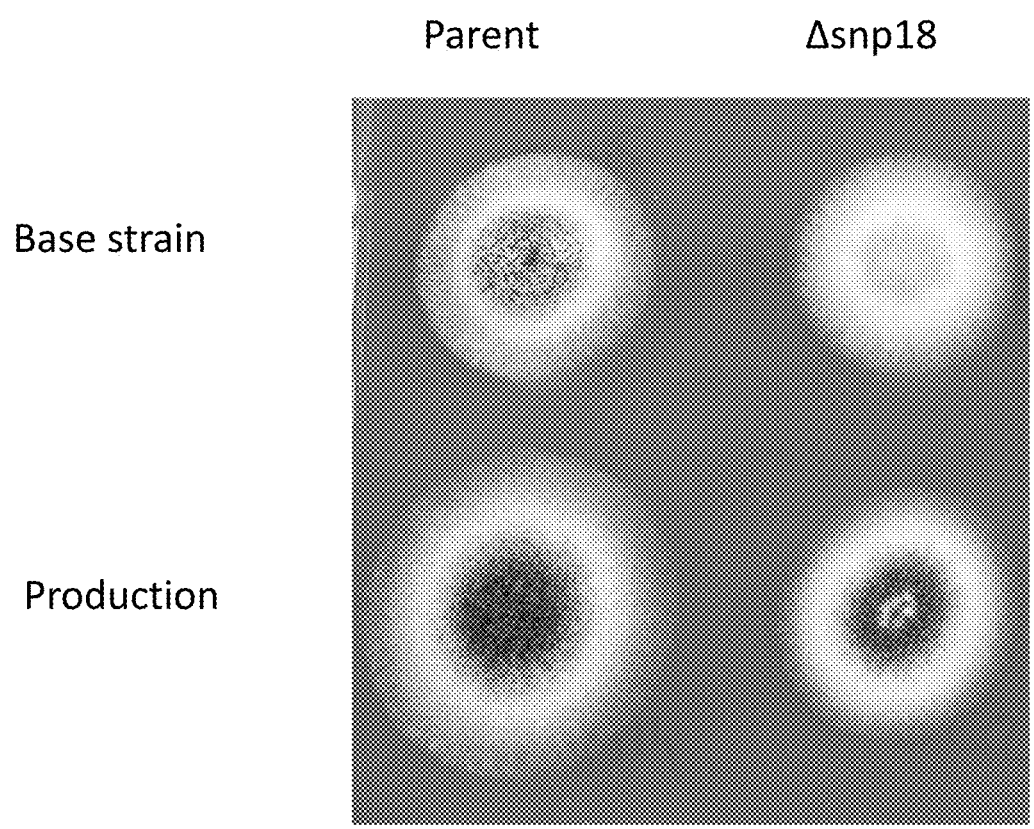
FIG. 17 illustrates that the gene that contains FungiSNP_18 is dispensable for sporulation in the production strain but not in the base strain.

Interestingly, deletion of the non-SNP containing version of the gene containing FungiSNP_18 in the 1015 strain produced a negative sporulation phenotype in the resultant variant 1015 strain such that said variant 1015 strain lost the ability to sporulate (see FIG. 17) This loss of sporulation was not observed in the 11414 strain in which the Fungi SNP_18 gene was removed. Given that the genetic backgrounds of the 11414 and 1015 strains are identical aside from the SNPs present in Tables 3 and 4, this suggested that the presence of one, all or some combination of the SNPs from Table 3 or 4 in the 11414 genetic background is enough to rescue the negative sporulation phenotype produced when FungiSNP_18 is removed. Put another way, there are other mutations (SNPs) that act epistatically to maintain sporulation in the production strain in the absence of SNP18 activity.

It should be noted that the loss of sporulation was not observed in either the variant 11414 or 1015 strains produced by removing FungiSNP_9, FungiSNP_12 or FungiSNP_40 or their non-SNP containing versions, respectively.

It should be further noted that the observed morphological phenotypes under submerged culture conditions in this Example were more striking than in Example 1 for each of the 4 genes, which could be due to the experimental design whereby successful transformants essentially displayed a deletion phenotype. Moreover, the phenotypes in the 11414 strain were also more pronounced which could be due to contributions to the phenotype by one or more of the other SNPs present in this strain vs. the 1015 base strain.

Example 3: HTP Genomic Engineering of Filamentous Fungi: Altering Filamentous Fungal Cell Morphology by Altering Gene Expression This example demonstrates the use of an automated, HTP PROSWP method in filamentous fungal cells in order to test the effects of modulating the expression of the FungiSNP_9, FungiSNP_12, FungiSNP_18 and FungiSNP_40 genes identified from Examples 1 and 2 that are thought to play a role in controlling filamentous fungal morphology.

Figure 18:
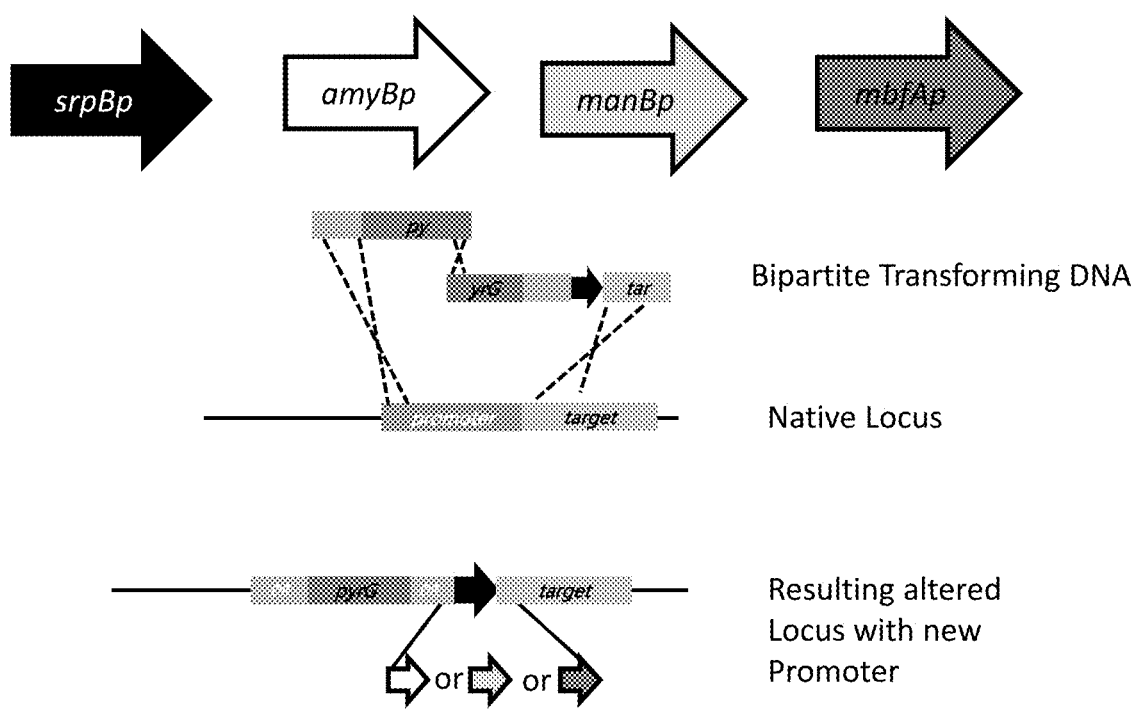
FIG. 18 illustrates the design of the bipartite constructs and general scheme employed for conducting the PROSWP experiments described in Example 3.

In this Example, the expression of the FungiSNP_18 gene (i.e., SEQ ID NO: 7) identified in Examples 1 and 2 was modulated in both the *A. niger* 1015 base strain and the *A. niger* 11414 production strain by replacing the annotated native promoter with one of the four promoters from Table 2 using the PROSWP method described herein. More specifically, for each of the strains (i.e., the 1015 parent strain or the 11414 parent strain) for each FungiSNP, a set of (4) variant or mutant strains were generated, where a 1$^{st}$ variant strain expresses a first construct comprising said candidate FungiSNP (FungiSNP_9 (SEQ ID NO: 5);_12 (SEQ ID NO: 6);_18 (SEQ ID NO: 7),_40 (SEQ ID NO. 8)) gene under the control of the srp8p promoter described in Table 2, a 2nd variant strain had said candidate FungiSNP gene under the control of the amy8p promoter described in Table 2, a 3rd variant strain had said candidate FungiSNP gene under the control of the man8p promoter described in Table 2 and a 4th variant strain had said candidate FungiSNP gene under the control of the mbfAp promoter described in Table 2. Each of the constructs used to generate the variants further comprised sequence flanking the candidate FungiSNP gene and promoter that served to direct integration of the construct into the locus of the respective candidate FungiSNP. A general description of the bipartite construct design and integration scheme used in this Example is shown in FIG. 18.

Figure 3:
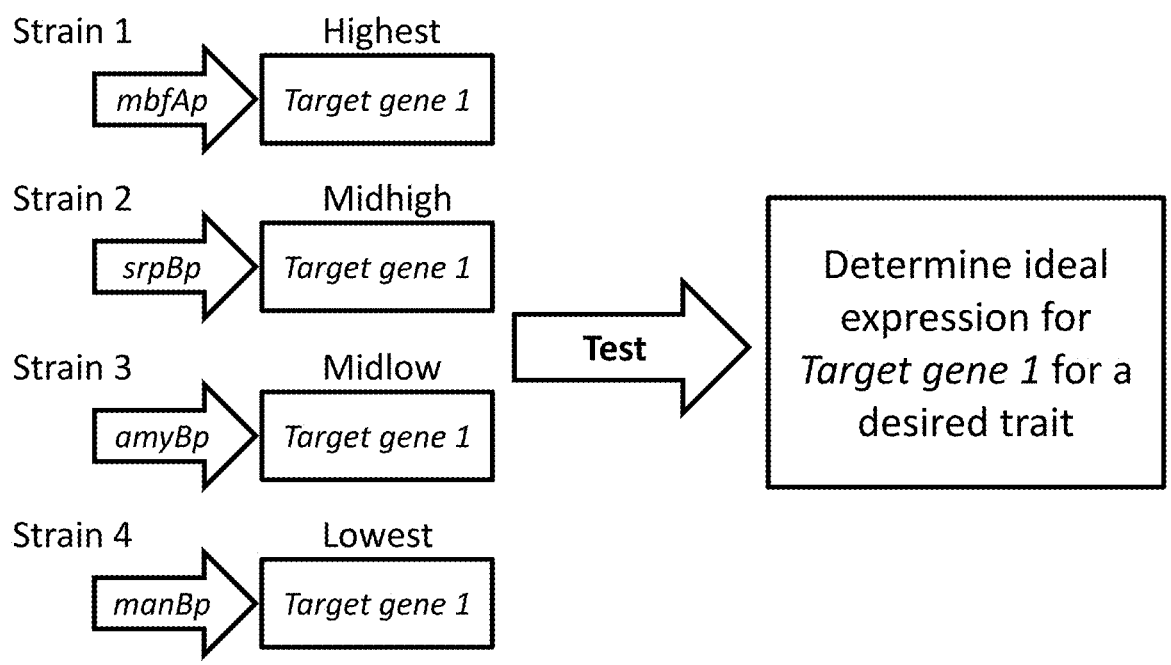
FIG. 3 illustrates four different promoters being placed in front of a target gene to generate 4 different strains. These strains can then be compared in a test for a desired trait and an ideal level of expression can be determined.

Following their generation, each construct for each candidate FungiSNP used to generate the (4) variant strains was individually transformed into protoplasts generated for both the *A. niger* 1015 base strain as well as the *A. niger* 11414 production strain. The protoplasts for both strains were cultivated, converted to protoplasts, transformed and screened to select for substantially homokaryotic protoplasts using phenotypic and/or sequence-based screening as described in the Examples above. Accordingly, the transformation of each individual construct led to the generation of the 4 variant or mutant strains for each of the parental strains for each candidate FungiSNP as generally depicted in FIG. 3. The morphological phenotype of each of these strains was then observed and compared with the morphological phenotype of a mutant strain comprising the identified gene under the control of the native promoter for said gene. An ideal level of expression was then determined for each of the identified genes.

Results

Figure 19:
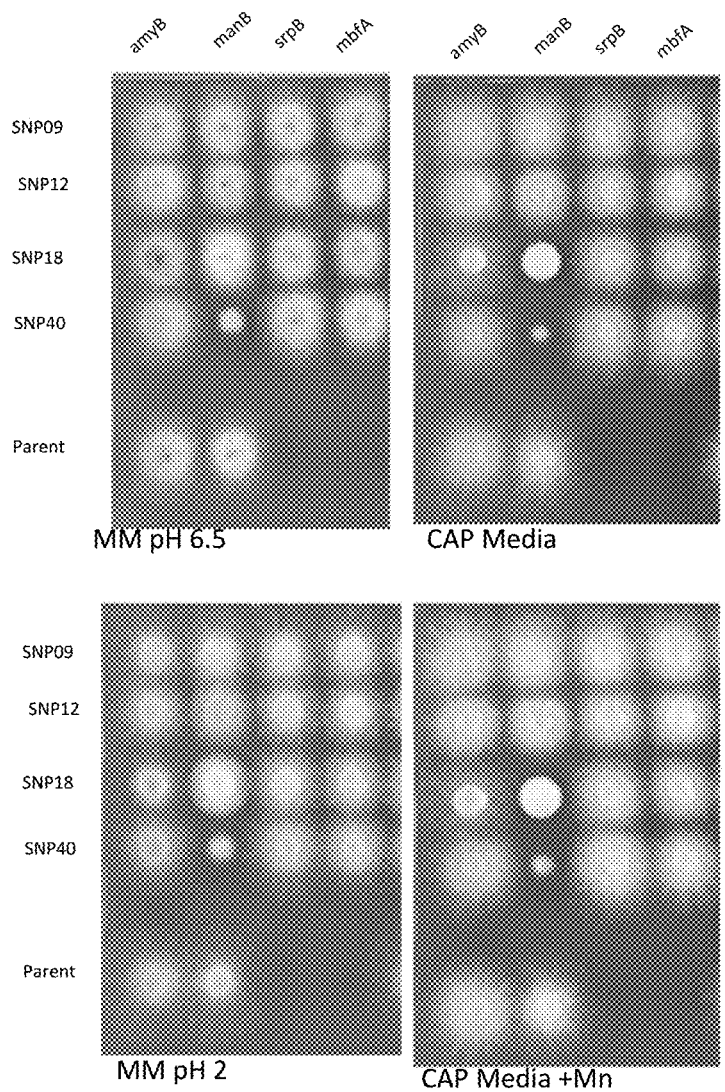
FIG. 19 illustrates that weaker promoters used in Example 3 impact morphology. The strain containing FungiSNP_18 (SNP18) under the weak manB promoter has tighter colony morphology than strains containing other promoter combinations. The impact of SNP 18 control is more pronounced under osmotic stress than under low pH.

Overall, promoter swapping for each morphology control gene target (i.e., FungiSNP_9, _12, _18 and _40) with the different promoters from Table 2 revealed that controlling expression of these genes impacted morphology (see FIG. 19). The strain containing SNP18 under the weak manB promoter had tighter colony morphology than strains containing other promoter combinations. The impact of SNP18 control was more pronounced under osmotic stress than under low pH. Further, the strain containing SNP40 under the weak manB promoter had a drastic effect on colony morphology than strains containing other promoter combinations under all growth conditions tested.

Figure 20:
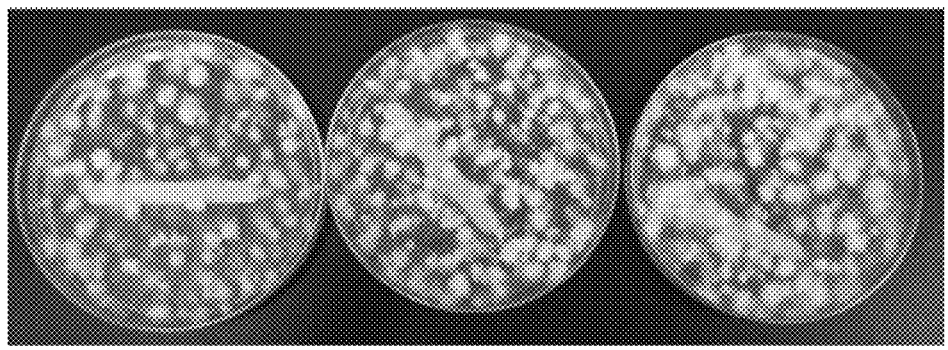
FIG. 20 illustrates the PROSWP of FungiSNP_12 (snp_12). Lower strength promoters operably linked to snp_12 result in yellow pigment in hyphae and some altered morphology (observed at the edge of colonies). This yellow pigment is common in a variety of mutants and is thought to be a sign of metabolic stress.
Figure 20:

As shown in FIG. 20, promoter swapping of morphology control gene target 12 (FungiSNP_12; SEQ ID NO: 6) with the different promoters from Table 2 revealed that lower strength promoters resulted in yellow pigment in hyphae and some altered morphology observed at the edge of colonies. The presence of the yellow pigment indicated that the variant or mutant strains were experiencing metabolic stress.

Figure 9:
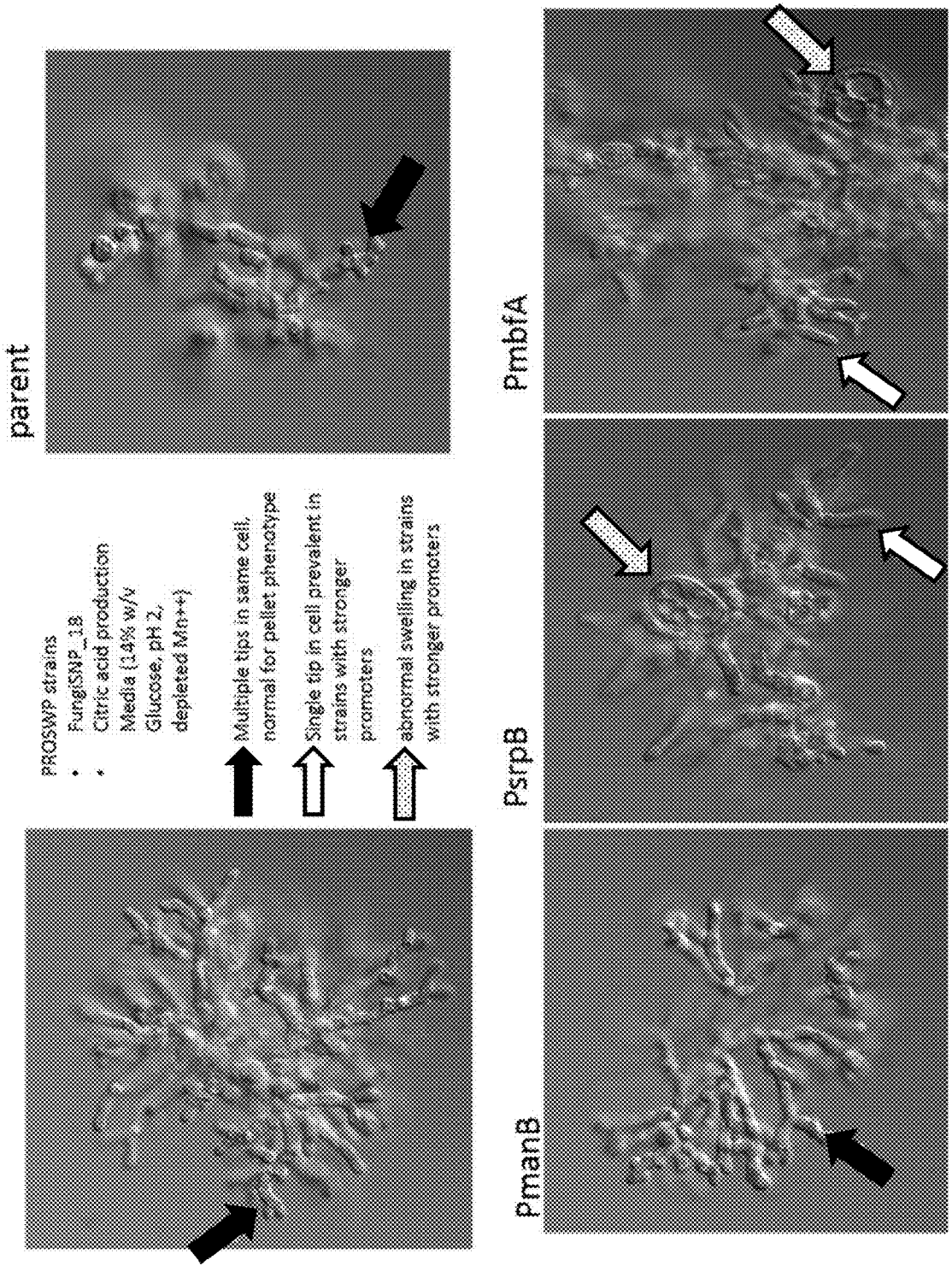
FIG. 9 illustrates promoter swapping of a morphology gene (i.e., FungiSNP_18; SEQ ID NO: 7). Different promoters controlling expression of this gene impact morphology. The strains containing the manB fusion and the amyB fusion retain the multiple tips vs, the 11414 parent strain, whereas those with higher expression srpB and mbfA lack the multiple tip phenotype. The strains were grown in citric acid production media (14% w/v Glucose, pH 2, depleted Mn++) at 30° C. for 48 hours. When allowed to incubate for 168 hours, the strains with higher expression promoters as well as the parent control all contained long filamentous hyphae. The strains with the lower level of expression from the promoter fusion, amyB and manB, remained pelleted.
Figure 11:
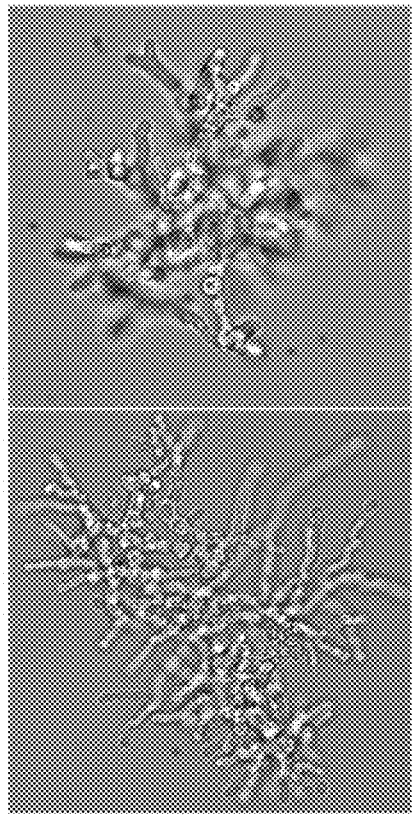
FIG. 11 illustrates promoter swapping of morphology gene target 18 (FungiSNP_18) in the base 1015 strain and 11414 production strain. The gene product associated with FungiSNP 18 is a signaling kinase that responds to osmotic stress (i.e., *A. niger* orthologue of *S. cerevisiae* SLN1). This figure shows that when the gene expression of said gene is reduced by replacing the native promoter with a weaker promoter, the cells maintain a tighter, less elongated phenotype, which is referred to herein as a 'pellet' phenotype (see right hand panels for the cells expressing the manB(p) snp18 gene in the base 1015 strain and 11414 production strain). The strains were grown in citric acid production media (14% w/v Glucose, pH 2, depleted Mn++) at 30° C. for 24 hours. This type of growth can be favorable to stirred tank fermentation.
Figure 11:
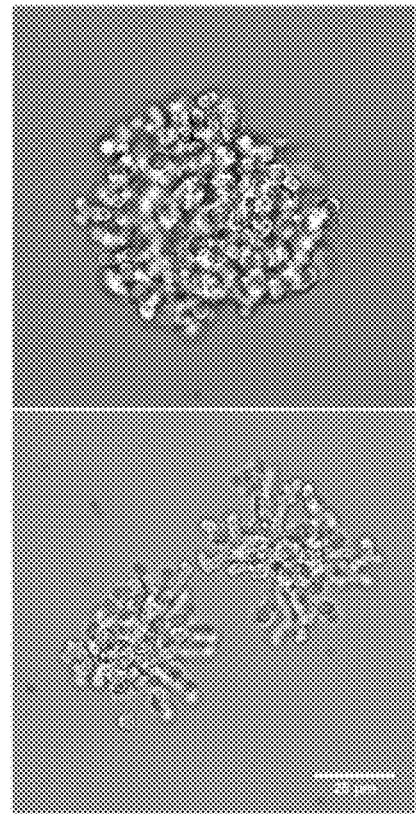
Figure 21:
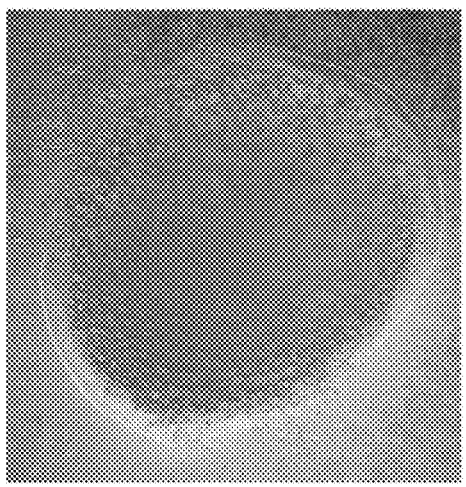
FIG. 21 illustrates that when driven by weaker promoters, FungiSNP18 (snp 18) has more severe morphological phenotype in the base strain than in the production strain.
Figure 21:
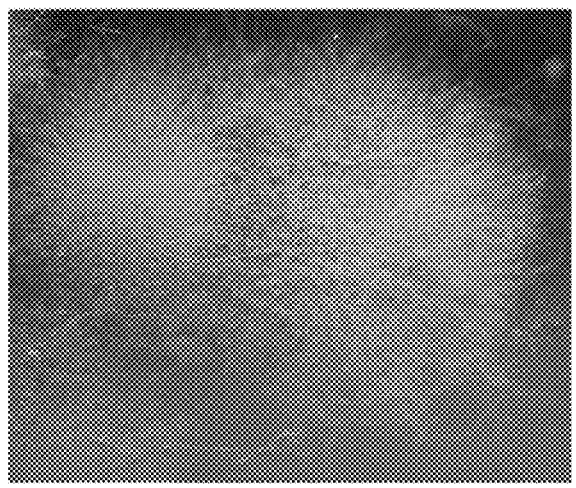

Moreover, promoter swapping of morphology control gene target 18 (FungiSNP_18; SEQ ID NO. 7) with the different promoters from Table 2 revealed that controlling expression of this gene with the two weaker promoters impacted morphology (see FIGS. 9,11 and 21). For example, the strains containing the manB fusion and the amyB fusion retained a multiple tip, pellet phenotype, whereas those with higher expression srpB and mbfA lacked the multiple tip phenotype and instead showed abnormal swelling (see FIG. 9). The images in FIG. 11 are of strains grown in citric acid production media at 30° C. for 24 hours. The images in FIG. 9 are of parent 11414 strains as well as 11414 strains expressing various non-native promoter-FungiSNP_18 fusions grown in citric acid production media at 30° C. for 48 hours. When allowed to incubate for 168 hours, the strains with higher expression promoters as well as the parent strain control all contained long filamentous hyphae. The strains with the lower level of expression from the promoter fusion, amyB and manB, remained pelleted. It should be noted that, as shown in FIG. 21, when driven by weaker promoters, SNP18 has more severe morphological phenotype in the base strain than in the production strain.

Figure 12:
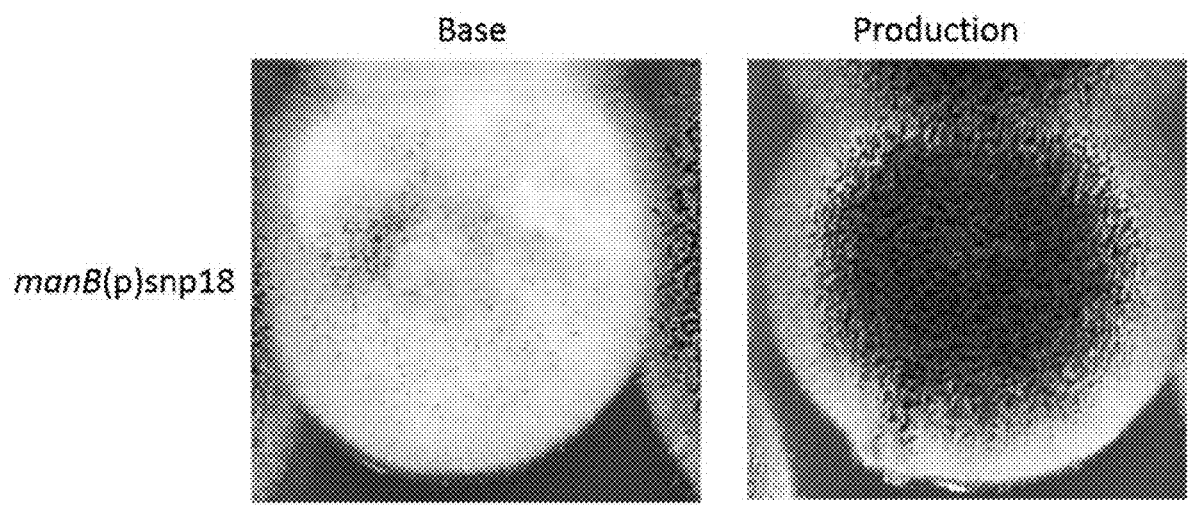
FIG. 12 illustrates that reduced levels of the FungiSNP_18 gene product in the base strain (i.e., *A. niger* 1015) by introducing the Fungi SNP 18 gene (SEQ ID NO: 7) under the control of the manB(p) promoter (SEQ ID NO: 1) results in inability to sporulate in the base strain genetic background. This phenotype was not observed when the same construct was introduced to the production strain (i.e., *A. niger* 11414)

Similar to the results of the deletion experiments from Example 2, reduction of the expression of the FungiSNP_18 gene in the 1015 strain resulted in cells that experienced a loss of sporulation as shown in FIG. 12. This loss of sporulation was not observed in the 11414 mutant strains. Again, given that the genetic backgrounds of the 11414 and 1015 strains are identical aside from the SNPs present in Tables 3 and 4, this suggested that the presence of one, all or some combination of the SNPs from Table 3 or 4 in the 11414 genetic background is enough to rescue the negative sporulation phenotype produced when expression of the FungiSNP_18 is reduced.

Example 4: Examination of the Growth of Morphological Mutant Filamentous Fungal Strain in Submerged Culture Lacking Chelating Agents This example demonstrates the ability of *A. niger* strains expressing the FungiSNP_18 gene under the control of a lower expression promoter (i.e., man8p promoter) to grow in pellet morphology in CAP media comprising varying levels of manganese and lacking chelating agents under submerged culture conditions.

The morphology of citric acid production strains of *Aspergillus niger* is sensitive to a variety of factors, including the concentration of manganese ($Mn^{2+}$). Upon increasing the $Mn^{2+}$ concentration in *A. niger* (ATCC 11414) cultures to 14 ppb or higher, the morphology switches from pelleted to filamentous, accompanied by a rapid decline in citric acid production. Conversely, low concentrations and/or omission of $Mn^{2+}$ from the nutrient medium of *Aspergillus niger* can result in abnormal morphological development which is characterized by increased spore swelling, and squat, bulbeous hyphae. As a result, chelating agents are often added to production media in order to keep the concentration in an acceptable range; however, the presence of chelating agents can often limit the production of desired end products and it is often necessary to subsequently remove said chelating agents at added additional costs.

Accordingly, in this Example, *A. niger* 11414 and 1015 mutant strains comprising the FungiSNP_18 gene under the control of the man8p promoter (SEQ ID NO: 1) as well as *A. niger* 11414 and 1015 parent strains are grown under submerged culture conditions in media containing varying levels of Mn2+ and lacking chelating agents in order to determine if the man8p-FungiSNP_18 fusion confers on the resulting strain the ability to maintain a pellet morphology in the presence of Mn2+.

The mutant 11414 and 1015 strains comprising the man8p-FungiSNP_18 fusion gene are generated as described in the above Examples. Further, the mutant strains as well as the parental strains are grown in CAP media supplemented with no $Mn^{2+}$, or $Mn^{2+}$ at 10 ppb, 11 ppb, 12 ppb, 13 ppb, 14 ppb, 15 ppb or 1000 ppb for 72 hours at 30° C. with shaking at 250 rpm in order to assess the effects of $Mn^{2+}$ on morphological development of each strain.

Example 5: HTP Genomic Engineering of Filamentous Fungi: Confirmation of Gene that Affect Filamentous Fungal Morphology This example demonstrates the use of the SNPSWAP method in the filamentous fungi, *Aspergillus niger*, in order to confirm that the *Aspergillus* nikA gene plays a role in an osmotic response pathway and can affect fungal cell morphology as well as aid in citric acid production. Further this example was used to confirm that fungiSNP_18 in Table 4 is *Aspergillus* nikA, which is the *A. niger* orthologue of *N. crassa* nik1.

Methods

In this Example, protoplasts from an *A. niger* base strain (i.e., ATCC 1015) and production strain (i.e., ATCC 11414) were generated, transformed and subjected to a SNPSWP as described in Example 1 and WO 2018/226900 filed Jun. 6, 2018, which is incorporated by reference herein. In summary, protoplasts generated from the base strain were transformed with either a single construct that contained a selectable marker gene (i.e., pyrG) flanked by sequence complementary to genomic sequence flanking the nikA gene in the base strain in order to direct integration of the marker gene into the base strain genome or co-transformed with two constructs ("split-marker constructs") as described in Example 1. As described in Example 1, each of the two constructs contained an overlapping portion of a selectable marker (i.e., pyrG in FIGS. 4 and 5) and were flanked by direct repeat sequence as shown in FIGS. 4 and 5 that contained the SNP18 point mutation (i.e., nikA$^{PROD}$ in FIG. 22 and Base_nikA—in FIG. 23A-B) The split-marker constructs were generated using fusion PCR and were quality controlled (QC'd) using a fragmenta analyzer as shown in FIG. 5. Moreover, each of these constructs further comprised sequence flanking the direct repeat portions of each construct in order to direct integration in the base strain genome at the nikA locus.

Figure 23A:
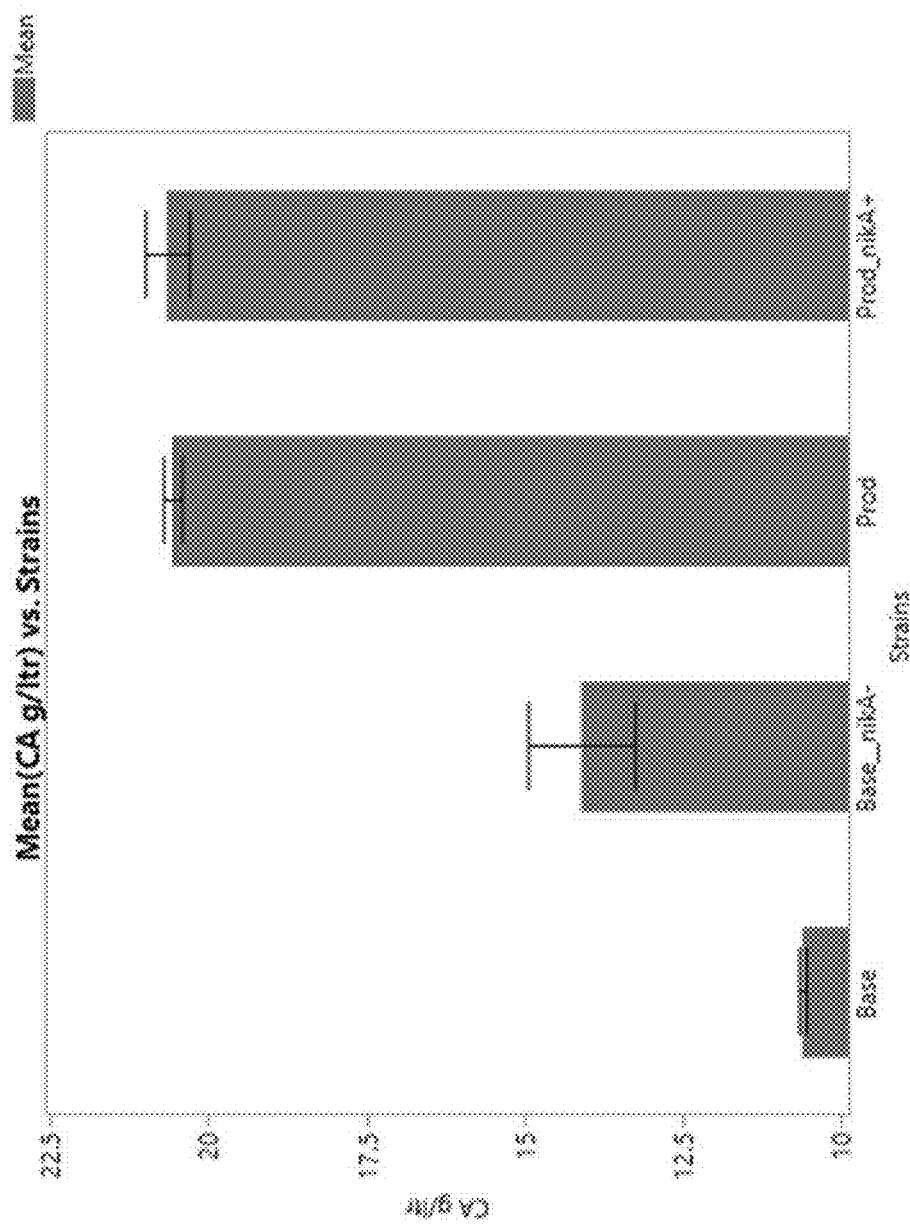
FIG. 23A-B illustrates that inserting the *Aspergillus* nikA gene comprising the point mutation described in FIG. 22 into the base strain increases citric acid titer by 33% in shake flasks.
Figure 23B:
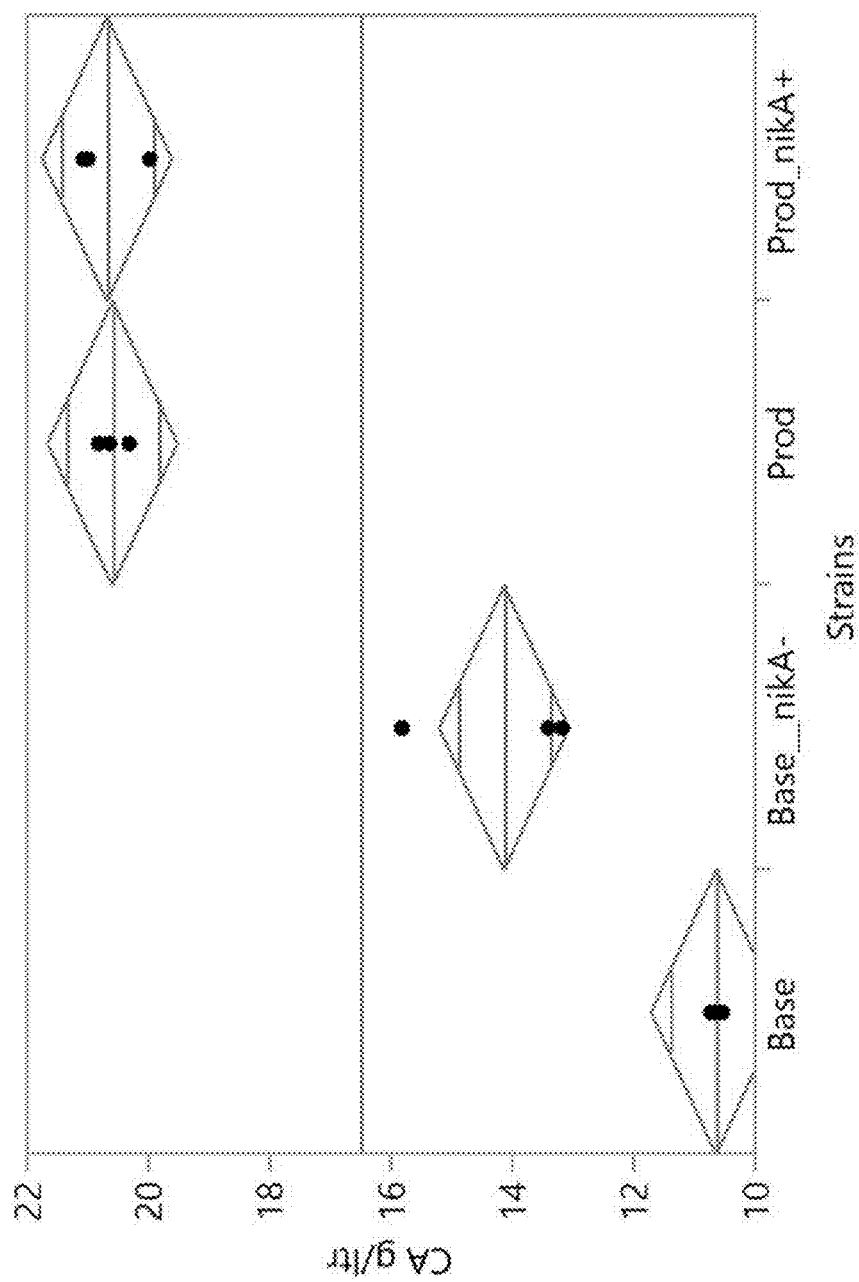

Additionally, in order to examine the effect of the wild-type nikA in the production strain genomic background (see. FIG. 23A-B), the wild-type nikA gene was introduced into protoplasts generated from the production strain (i.e., *A. niger* ATCC 11414) using a split-marker construct with direct repeats that did not comprise the SNP18 point mutation and sequence flanking the direct repeat portions in order to direct integration in the production strain genome at the nikA locus.

Citric Acid Production

Wild-type ATCC 1015 strains, ATCC 1015 strains with the SNP18 mutations (i.e., nikA$^{PROD}$) or ATCC 1015 strains without nikA (i.e., nikAΔpyrG) as well as ATCC 11414 production strains with the nikA point mutation (i.e., SNP18; Prod in FIG. 23A-B) or with wild-type nikA gene (i.e., Prod_nikA+ in FIG. 23A-B) were grown in 100 mL of Citric Acid Production media (CAP; 140 g glucose, 3.1 g NH4NO3, 0.15 g KH2PO4, 0.15 g NaCl, 2.2 g MgSO4_7H2O, 6.6 mg ZnSO4_7H2O, 0.1 mg FeCl3) to induce high levels of citric acid production. Cultures were grown in triplicate, in 250 mL flasks shaking at 250 rotations per minute, at 30° C. for 96 hours. Mycelia was removed from the supernatant using Miracloth (Millipore; #475855), and titers of citric acid were determined from the supernatant using an enzymatic assay (Megazyme; K-CITR).

Osmotic Stress Response

For microscopic examination, wild-type ATCC 1015 strain, ATCC 1015 strains with the SNP18 mutations (i.e., nikA$^{PROD}$) or ATCC 1015 strains without nikA (i.e., nikAΔpyrG) were point inoculated with 1,000 spores on slides overlaid with agar media. The media used was Minimal Media (MM; contains glucose, nitrogen source, and required salts only; low osmotic stress) and MM with 1.0 M Sorbitol (high osmotic stress). Slides were grown overnight at 30 C and imaged using an upright Olympus microscope (BX53). Images were obtained under 400× magnification.

For examination of the osmotic stress response on plates, wild-type ATCC 1015 strain, ATCC 1015 strains with the SNP18 mutations (i.e., nikA™$^{00}$) or ATCC 1015 strains without nikA (i.e., nikAΔpyrG) were point inoculated with 1,000 spores on MM with 0.05 g/L of Bromocresol green (BGC), which is a pH indicator used to visualize changes in pH. BGC is blue at pH 6.5, and gradually turns yellow as the pH drops toward pH 2. Plates were grown at 30 C for 48 hours. Yellow regions in plates were confirmed to contain citric acid by extracting agar fragments and analysis with enzymatic assay (Megazyme).

Results

Figure 22:
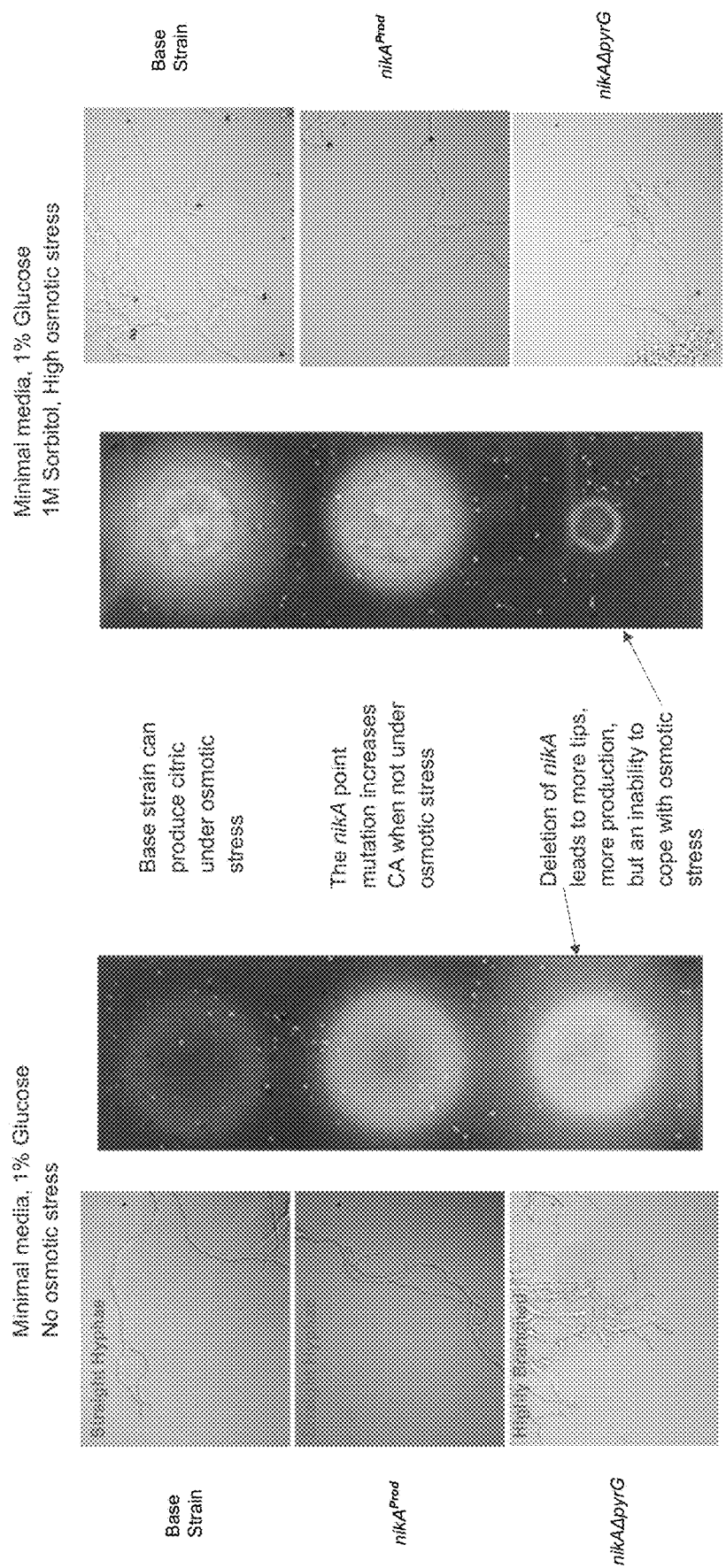
FIG. 22 illustrates that introduction of an *Aspergillus* nikA (also known as Two-component system protein C (TcsC)) gene containing a point mutation (i.e., SNP from Table 3 for FungiSNP_18; C>T nucleotide change in coding domain as shown in SEQ ID NO. 76 vs. SEQ ID NO. 7) into the base strain leads to higher citric production and retention of proper osmotic response.

With regard to the osmotic stress response, as shown in FIG. 22, via microscopy, the mutation of the nikA gene results in an increase in hyphal tip cells, with the deletion of nikA resulting in the largest increase. Strains examined on plates containing minimal media with a pH dye indicator that can visualize a drop in pH that corresponds to citric acid production, surprisingly, showed that under the conditions tested, the deletion strain produced the most citric acid. This was most likely due to the increase in hyphal tip cells observed in these strains. In contrast, when the strains tested were subjected to osmotic stress (right side of FIG. 22) the deletion strain formed a smaller colony and the increase in citric acid production was no longer observed. Interestingly, the point mutation resulted in a decrease in nikA activity while maintaining the ability to respond to osmotic stress. This showed that lowering the activity of nikA (by lowering gene expression or mutation) led to a desirable change in morphology while maintaining the ability to respond to osmotic stress. However, this data also showed that deletion of nikA may improve fermentations that does not put cells under osmotic stress.

With regard to citric acid production, as shown in FIG. 23A-B, the point mutation of the nikA/sln1 gene (i.e., SNP18; SEQ ID NO: 7) in the base strain was enough to lead to a 33% increase in citric acid titer over the course of the fermentation. This increase appears to be the result of a change in morphology, leading to greater numbers of hyphal tip cells.

TABLE 6

*S. cervisiae* Sln1 & *N. crassa* nik1 orthologues in *A. niger* ATCC 1015

| | Query Coverage | Percent Identity |
|---|---|---|
| *S. cerevisiae* SLN1 orthologues in *A. niger* ATCC 1015 strain | | |
| ASPNIDRAFT_183029 (SEQ ID NO: 15) | 41% | 32.20% |
| ASPNIDRAFT_41708 (SEQ ID NO: 16) | 53% | 21.62% |
| ASPNIDRAFT_37188 (SEQ ID NO: 17) | 33% | 31.90% |
| ASPNIDRAFT_39736 (SEQ ID NO: 14) | 33% | 30.93% |
| *N. crassa* Nik1 orthologues in *A. niger* ATCC 1015 strain | | |
| ASPNIDRAFT_39736 (SEQ ID NO: 14) | 95% | 68.86% |

TABLE 7

Osmotic Pathway Genes

| Yeast Osmotic Response Pathway Genes (Genus species) | Orthologues in ATCC 1015 (fungidb.org ID) | SEQ ID NO of orthologues in ATCC 1015 |
|---|---|---|
| Sln1 (S. cerevisiae; SEQ ID NO: 50) | ASPNIDRAFT_39736; ASPNIDRAFT_183029; ASPNIDRAFT_41708; ASPNIDRAFT_37188 | SEQ ID NO: 14; SEQ ID NO: 15; SEQ ID NO: 16; SEQ ID NO: 17 |
| Ste11 (S. cerevisiae; SEQ ID NO: 51) | ASPNIDRAFT_214017 | SEQ ID NO: 18 |
| Bck1 (S. cerevisiae; SEQ ID NO: 52) | ASPNIDRAFT_55574 | SEQ ID NO: 19 |
| Ssk2 (S. cerevisiae; SEQ ID NO: 53); Ssk22 (S. cerevisiae; SEQ ID NO: 73); | ASPNIDRAFT_38443 | SEQ ID NO: 20 |
| Ste7 (S. cerevisiae; SEQ ID NO: 54) | ASPNIDRAFT_209137 | SEQ ID NO: 21 |
| Mkk2/22 (S. cerevisiae; SEQ ID NO: 55) | ASPNIDRAFT_211983 | SEQ ID NO: 22 |
| Pbs2 (S. cerevisiae; SEQ ID NO: 56) | ASPNIDRAFT_51782 | SEQ ID NO: 23 |
| Fus1/Kss3 (S. cerevisiae; SEQ ID NO: 57) | ASPNIDRAFT_207710 | SEQ ID NO: 24 |
| Mpk1 (S. cerevisiae; SEQ ID NO: 58) | ASPNIDRAFT_205706 | SEQ ID NO: 25 |
| Hog1 (S. cerevisiae; SEQ ID NO: 59) | ASPNIDRAFT_52673 | SEQ ID NO: 26 |
| Phk1 (S. pombe; SEQ ID NO: 74); Phk2 (S. pombe; SEQ ID NO: 75); Chk1 (C. albicans; SEQ ID NO: 60) | ASPNIDRAFT_37188 | SEQ ID NO: 27 |
| Phk3 (S. pombe; SEQ ID NO: 61) | ASPNIDRAFT_174806 | SEQ ID NO: 28 |
| Ypd1p (S. cerevisiae; SEQ ID NO: 62); Spy1 (S. pombe; SEQ ID NO: 63) | ASPNIDRAFT_214261 | SEQ ID NO: 29 |
| Ssk1p (S. cerevisiae; SEQ ID NO: 64); Mcs4 (S. pombe; SEQ ID NO: 65); SskA (C. albicans; SEQ ID NO: 66) | ASPNIDRAFT_120745 | SEQ ID NO: 30 |
| Skn7 (S. cerevisiae; SEQ ID NO: 67); Prr1 (S. pombe; SEQ ID NO: 68); Skn7 (C. albicans; SEQ ID NO: 69) | ASPNIDRAFT_37857 | SEQ ID NO: 31 |
| Rim15p (S. cerevisiae; SEQ ID NO: 70); Cek1 (S. pombe; SEQ ID NO: 71); Rim15 (C. albicans; SEQ ID NO: 72) | ASPNIDRAFT_200656 | SEQ ID NO: 32 |

Further Numbered Embodiments of the Disclosure

Other subject matter contemplated by the present disclosure is set out in the following numbered embodiments:

1. A variant strain of filamentous fungus derived from a parental strain, wherein the cells of the variant strain possess a non-mycelium, pellet forming phenotype as compared to the cells of the parental strain when grown in a submerged culture due to the variant strain possessing a genetic alteration in a Aspergillus niger (A. niger) orthologue of a Saccharomyces Cerevisiae (S. cerevisiae) SLN1 gene or a Neurospora crassa (N. crassa) nik1 gene that causes cells of the variant strain to produce a reduced amount and/or less active form of functional A. niger orthologue of an S. cerevisiae SLN1 protein or a N. crassa Nik1 protein as compared to cells of the parental strain when grown under submerged culture conditions.

2. The variant strain of embodiment 1, wherein the variant strain sporulates normally as compared to the parental strain when grown under non-submerged growth conditions.

3. The variant strain of embodiment 1 or 2, wherein the genetic alteration comprises replacement of a native promoter for the A. niger orthologue of the S. cerevisiae SLN1 gene or the N. crassa nik1 gene with a promoter that more weakly expresses the gene for the A. niger orthologue of the S. cerevisiae SLN1 protein or the N. crassa Nik1 protein as compared to the native promoter.

4. The variant strain of embodiment 3, wherein the promoter that more weakly expresses the gene for the A. niger orthologue of the S. cerevisiae SLN1 protein or the N. crassa Nik1 protein is selected from an amyB promoter or a manB promoter.

5. The variant strain of embodiment 3 or 4, wherein the promoter that more weakly expresses the gene for the A. niger orthologue of the S. cerevisiae SLN1 protein or the N. crassa Nik1 protein is selected from the promoter of SEQ ID NO: 1 or SEQ ID NO: 2.

6. The variant strain of any one of the above embodiments, wherein the genetic alteration comprises replacement of a native form of the A. niger orthologue of the S. cerevisiae SLN1 gene or the N. crassa nik1 gene with a mutated A. niger orthologue of the S. cerevisiae SLN1 gene or the N. crassa nik1 gene, wherein the mutated A. niger orthologue of the S. cerevisiae SLN1 gene or the N. crassa nik1 gene encodes a mutated A. niger orthologue of the S. cerevisiae SLN1 protein or the N. crassa Nik1 protein.

7. The variant strain of embodiment 6, wherein the mutated A. niger orthologue of the S. cerevisiae SLN1 gene or the N. crassa nik1 gene comprises a single nucleotide polymorphism.

8. The variant strain of embodiment 6 or 7, wherein the mutated A. niger orthologue of the S. cerevisiae SLN1 gene or the N. crassa nik1 gene comprises the nucleic sequence of SEQ ID NO: 7.

9. The variant strain of embodiment 1 or 2, wherein the genetic alteration comprises replacement of a native form of the A. niger orthologue of the S. cerevisiae SLN1 gene or the N. crassa nik1 gene with a selectable marker gene, thereby removing the native form of the A. niger orthologue of the S. cerevisiae SLN1 gene or the N. crassa nik1 gene from the genome of the variant strain.

10. The variant strain of any of the above embodiments, further comprising disruption of (me or more genes within a signaling cascade of which the A. niger orthologue of the S. cerevisiae SLN1 protein or the N. crassa Nik1 protein is a component.

11. The variant strain of embodiment 10, wherein the one or more genes are selected from genes with nucleic acid sequences of SEQ ID NO: 9, 10, 11, 12, 13 or any combination thereof.

12. The variant strain of any one of the above embodiments, further comprising a disruption of one or more genes selected from a non-SNP containing version of the genes with nucleic acid sequences of SEQ ID NO: 5, 6, 8 or any combination thereof.

13. The variant of any one of embodiments 10-12, wherein the disruption is selected from replacement of a native promoter of the one or more genes with a promoter that weakly expresses the one or more genes as compared to the native promoter, replacement of the one or more genes with a mutated form of the one or more genes, replacement of the one or more genes with a selectable marker, or a combination thereof.

14. The variant of embodiment 13, wherein the promoter that weakly expresses the one or more genes as compared to the native promoter is selected from an amyB promoter or a manB promoter.

15. The variant strain of embodiment 13 or 14, wherein the promoter that weakly expresses the one or more genes as compared to the native promoter is selected from the promoter of SEQ ID NO: 1 or SEQ ID NO: 2.

16. The variant of embodiment 13, wherein the mutated form of the one or more genes is selected from nucleic acid sequence SEQ ID NO. 5, 6, or 8.

17. The variant of any one of the above embodiments, wherein the selectable marker is selected from an auxotrophic marker gene, a colorimetric marker gene, antibiotic resistance gene, or a directional marker gene.

18. The variant of embodiment 17, wherein the colorimetric marker gene is an aygA gene.

19. The variant of embodiment 17, wherein the auxotrophic marker gene is selected from an argB gene, a trpC gene, a pyrG gene, or a met3 gene.

20. The variant of embodiment 17, wherein the directional marker gene is selected from an acetamidase (amdS) gene or a nitrate reductase gene (niaD).

21. The variant of embodiment 17, wherein the antibiotic resistance gene is a ble gene, wherein the ble gene confers resistance to pheomycin.

22. The variant strain of any one of the above embodiments, wherein the filamentous fungus is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprimus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scyalidium, Sporotrichum, Talaromyces, Thermoascm, Thielavia, Tramates, Tolypocladium, Trichoderma, Verticillium, Volvariella* species or teleomorphs, or anamorphs, and synonyms or taxonomic equivalents thereof.

23. The variant strain of any one of the above embodiments, wherein the filamentous fungus is *A. niger* or teleomorphs or anamorphs thereof.

24. A filamentous fungal host cell comprising a promoter operably linked to a gene that regulates morphology of the host cell, wherein the promoter is heterologous to the gene, wherein the promoter has a nucleic sequence selected from the group consisting of SEQ ID NOs. 1-4.

25. The filamentous fungal host cell of embodiment 24, wherein the filamentous fungal host cell has a non-mycelium, pellet morphology when grown under submerged culture conditions in fermentation media as compared to a reference filamentous fungal host cell without the promoter operably linked to the gene that regulates morphology of the host cell.

26. The filamentous fungal host cell of embodiment 25, wherein the fermentation media comprises at least 14 ppb of manganese.

27. The filamentous fungal host cell of embodiment 25 or 26, wherein the fermentation media is free of chelating agents.

28. The filamentous fungal host cell of any one of embodiments 24-27, wherein the filamentous fungal host cell produces an amount of a product of interest that is at least equal to the amount produced by the reference filamentous fungal host cell without the promoter operably linked to the gene that regulates morphology of the host cell.

29. The filamentous fungal host cell of any one of embodiments 24-28, wherein the gene that regulates morphology is selected from a *A. niger* orthologue of a *S. cerevisiae* SLN1 gene or a *N. crassa* nik1 gene, non-SNP containing versions of the genes with nucleic acid sequences SEQ ID NO: 5, 6, 8, or any combination thereof 30. The filamentous fungal host cell of any one of embodiments 24-29, wherein the gene that regulates morphology is a wild-type or mutated form of the gene.

31. The filamentous fungal host cell of any one of embodiments 24-30, wherein the gene that regulates morphology is the *A. niger* orthologue of the *S. cerevisiae* SLN1 gene or the *N. crassa* nik1 gene and the promoter is selected from SEQ ID NO: 1 or 2.

32. The filamentous fungal host cell of any one of embodiments 24-30, wherein the gene that regulates morphology is SEQ ID NO. 7.

33 The filamentous fungal host cell of any one of embodiments 24-32, wherein the filamentous fungal host cell is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

34. The filamentous fungal host cell of any one of embodiments 24-33, wherein the filamentous fungal host cell is *A. niger* or teleomorphs or anamorphs thereof.

35. A fermentation broth comprising at least 14 ppb of manganese and a filamentous fungal cell comprising a non-mycelium pellet phenotype, wherein the broth is free of a chelating agent, and wherein the filamentous fungal comprises a genetically altered *A. niger* orthologue of a *S. cerevisiae* SLN1 gene or a *N. crassa* nik1 gene.

36. The fermentation broth of embodiment 35, wherein the genetically altered *A. niger* orthologue of the *S. cerevisiae* SLN1 gene or the *N. crassa* nik1 gene comprises a heterologous promoter operably linked to the *A. niger* orthologue of the *S. cerevisiae* SLN1 gene or the *N. crassa* nik1 gene.

37. The fermentation broth of embodiment 36, wherein the heterologous promoter is selected from SEQ ID NO: 1 or 2.

38. The fermentation broth of any one of embodiments 35-37, wherein the genetically altered *A. Niger* orthologue of the *S. cerevisiae* SLN1 gene or the *N. crassa* nik1 gene comprises a mutation.

39. The fermentation broth of embodiment 38, wherein the mutation in a SNP.

40. The fermentation broth of embodiment 38 or 39, wherein the *A. Niger* orthologue of the *S. cerevisiae* SLN1 gene or the *N. crassa* nik1 gene has a nucleic acid sequence of SEQ ID NO. 7.

41. The fermentation broth of any one of embodiments 35-40, further comprising disruption of one or more genes within a signaling cascade of which the *A. Niger* orthologue of the *S. cerevisiae* SLN1 protein or the *N. crassa* Nik1 protein is a component, wherein the one or more genes are selected from genes with nucleic acid sequences of SEQ ID NO: 9, 10, 11, 12, 13 or any combination thereof.

42. The fermentation broth of any one of embodiments 35-40, further comprising a disruption of one or more genes selected from the group consisting of non-SNP containing versions of the genes with nucleic acid sequences of SEQ ID NO. 5, 6, 8 or any combination thereof.

43. The fermentation broth of any one of embodiments 35-42, wherein the filamentous fungal host cell is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

44. The fermentation broth of any one of embodiments 35-43, wherein the filamentous fungal host cell is *A. niger* or teleomorphs or anamorphs thereof.

45. A method for generating a promoter swap filamentous fungal strain library, comprising the steps of:
  a. providing one or more target genes that play a role in morphology to a base filamentous fungal strain, and a promoter ladder, wherein said promoter ladder comprises a plurality of promoters exhibiting different expression profiles in the base filamentous fungal strain; and
  b. engineering the genome of the base filamentous fungal strain, to thereby create an initial promoter swap filamentous fungal strain library comprising a plurality of individual filamentous fungal strains with unique genetic variations found within each strain of said plurality of individual filamentous fungal strains, wherein each of said unique genetic variations comprises one or more of the promoters from the promoter ladder operably linked to one of the one or more target genes that play a role in morphology to the base filamentous fungal strain.

46. The method of embodiment 45, wherein the promoter ladder comprises the promoters found in Table 2.

47. The method of embodiment 45 or 46, wherein the one or more target genes that play a role in morphology comprise a disruption.

48. The method of embodiment 47, wherein the disruption is a single nucleotide polymorphism (SNP), missense mutation, nonsense mutation, deletion and/or insertion.

49. The method of any one of embodiments 45-48, wherein the one or more target genes that play a role in morphology are selected from a *A. niger* orthologue of a *S. cerevisiae* SLN1 gene or a *N. crassa* nik1 gene, non-SNP containing versions of the genes with nucleic acid sequences SEQ ID NO: 5, 6, 8 or any combination thereof.

50. The method of any one of embodiments 45-49, wherein the one or more target genes that play a role in morphology is the *A. niger* orthologue of the *S. cerevisiae* SLN1 gene or the *N. crassa* nik1 gene.

51. The method of any one of embodiments 45-50, wherein the one or more target genes that play a role in morphology is the gene represented by SEQ ID NO: 7.

52. The method of any one of embodiments 45-51, wherein the filamentous fungal strain is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

53. The method of any one of embodiments 45-52, wherein the filamentous fungal strain is an *A. niger* strain.

54. A promoter swap method for improving the morphological phenotype of a production filamentous fungal strain, comprising the steps of:
  a. providing a plurality of target genes that play a role in morphology to a base filamentous fungal strain, and a promoter ladder, wherein said promoter ladder comprises a plurality of promoters exhibiting different expression profiles in the base filamentous fungal strain;
  b. engineering the genome of the base filamentous fungal strain, to thereby create an initial promoter swap filamentous fungal strain library comprising a plurality of individual filamentous fungal strains with unique genetic variations found within each strain of said plurality of individual filamentous fungal strains, wherein each of said unique genetic variations comprises one or more of the promoters from the promoter ladder operably linked to one of the target genes that play a role in morphology to the base filamentous fungal strain;
  c. screening and selecting individual filamentous fungal strains of the initial promoter swap filamentous fungal strain library for morphological phenotypic improvements over a reference filamentous fungal strain, thereby identifying unique genetic variations that confer morphological phenotypic improvements;
  d. providing a subsequent plurality of filamentous fungal microbes that each comprise a combination of unique genetic variations from the genetic variations present in at least two individual filamentous fungal strains screened in the preceding step, to thereby create a subsequent promoter swap filamentous fungal strain library;
  e. screening and selecting individual filamentous fungal strains of the subsequent promoter swap filamentous fungal strain library for morphological phenotypic improvements over the reference filamentous fungal strain, thereby identifying unique combinations of genetic variation that confer additional morphological phenotypic improvements, and f. repeating steps d)-e) one or more times, in a linear or non-linear fashion, until an filamentous fungal strain exhibits a desired level of improved morphological phenotype compared to the morphological phenotype of the production filamentous fungal strain, wherein each subsequent iteration creates a new promoter swap filamentous fungal strain library of microbial strains, where each strain in the new library comprises genetic variations that are a combination of genetic variations selected from amongst at least two individual filamentous fungal strains of a preceding library.

55. The promoter swap method for improving the morphological phenotype of a production filamentous fungal strain of embodiment 54, wherein the subsequent promoter swap filamentous fungal strain library is a full combinatorial library of the initial promoter swap filamentous fungal strain library.

56. The promoter swap method for improving the morphological phenotype of a production filamentous fungal strain of embodiment 54, wherein the subsequent promoter swap filamentous fungal strain library is a subset of a full combinatorial library of the initial promoter swap filamentous fungal strain library.

57. The promoter swap method for improving the morphological phenotype of a production filamentous fungal strain of embodiment 54, wherein the subsequent promoter swap filamentous fungal strain library is a full combinatorial library of a preceding promoter swap filamentous fungal strain library.

58. The promoter swap method for improving the morphological phenotype of a production filamentous fungal strain of embodiment 54, wherein the subsequent promoter swap filamentous fungal strain library is a subset of a full combinatorial library of a preceding promoter swap filamentous fungal strain library 59. The promoter swap method for improving the morphological phenotype of a production filamentous fungal strain of any one of embodiments 54-58, wherein the promoter ladder comprises the promoters found in Table 2.

60. The promoter swap method for improving the morphological phenotype of a production filamentous fungal strain of any one of embodiments 54-59, wherein the one or more target genes that play a role in morphology comprise a disruption 61. The promoter swap method for improving the morphological phenotype of a production filamentous fungal strain of any one of embodiments 54-60, wherein the disruption is a SNP, missense mutation, nonsense mutation, deletion and/or insertion.

62. The promoter swap method for improving the morphological phenotype of a production filamentous fungal strain of any one of embodiments 54-60, wherein the one or more target genes that play a role in morphology are selected from a *A. Niger* orthologue of a *S. cerevisiae* SLN1 gene or a *N. crassa* nik1 gene, non-SNP containing versions of the genes with nucleic acid sequences SEQ ID NO: 5, 6, 8 or any combination thereof.

63. The promoter swap method for improving the morphological phenotype of a production filamentous fungal strain of embodiment 62, wherein the *A. niger* orthologue of the *S. cerevisiae* SLN1 gene or the *N. crassa* nik1 gene comprises the sequence of SEQ ID NO: 7.

64. The promoter swap method for improving the morphological phenotype of a production filamentous fungal strain of any one of embodiments 54-63, wherein the filamentous fungal strain is selected from *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

65. The promoter swap method for the morphological phenotype of a production filamentous fungal strain, of any one of embodiments 54-64, wherein the filamentous fungal strain is an *A. niger* strain.

66. The promoter swap method for the morphological phenotype of a production filamentous fungal strain, of any one of embodiments 54-65, wherein the morphological phenotypic improvement comprises conferring the ability to form a non-mycelium pellet morphology when grown under submerged culture conditions.

67. The promoter swap method for the morphological phenotype of a production filamentous fungal strain, of embodiment 66, wherein the submerged culture conditions comprise a culture medium comprising at least 14 ppb of manganese and is free of chelating agents.

68. A filamentous fungus host cell comprising a heterologous modification of the host cell's orthologue of a *S. cerevisiae* SLN1 gene or a *N. crassa* nik1 gene, whereby the protein encoded by the modified orthologue of the *S. cerevisiae* SLN1 gene or the *N. crassa* nik1 gene has reduced activity and/or reduced expression relative to a parental filamentous fungal host cell lacking the heterologous modification.

69. The filamentous fungus host cell of embodiment 68, wherein the filamentous fungal host cell has a non-mycelium, pellet morphology when grown under submerged culture conditions in fermentation media.

70. The filamentous fungus host cell of embodiment 68 or 69, wherein the heterologous modification comprises replacement of a native promoter for the orthologue of the *S. cerevisiae* SLN1 gene or the *N. crassa* nik1 gene with a promoter that more weakly expresses the orthologue of the *S. cerevisiae* SLN1 gene or the *N. crassa* nik1 gene as compared to the native promoter.

71. The filamentous fungus host cell of any one of the embodiments 68-70, wherein the heterologous modification comprises replacement of the orthologue of the *S. cerevisiae* SLN1 gene or the *N. crassa* nik1 gene with a mutated version of the orthologue of the *S. cerevisiae* SLN1 gene or the *N. crassa* nik1 gene.

72. The filamentous fungus host cell of embodiment 71, wherein the mutated version of the orthologue of the *S. cerevisiae* SLN1 gene or the *N. crassa* nik1 gene comprises a single nucleotide polymorphism (SNP).

73. The filamentous fungus host cell of embodiment 68 or 69, wherein the heterologous modification comprises replacement of the orthologue of the *S. cerevisiae*

SLN1 gene or the *N. crassa* nik1 gene with a selectable marker gene, thereby removing the native orthologue of the *S. cerevisiae* SLN1 gene or the *N. crassa* nik1 gene from the genome of the filamentous fungus host cell.

74. The filamentous fungus host cell of any one of the embodiments 68-73 further comprising a heterologous modification of one or more genes within a biochemical pathway of which the orthologue of the *S. cerevisiae* SLN1 gene or the *N. crassa* nik1 gene is a component.

75. The filamentous fungus host cell of embodiment 74, wherein the one or more genes are selected from the orthologue of the *S. cerevisiae* Ssk1 gene, the orthologue of the *S. cerevisiae* Ssk2 gene, the orthologue of the *S. cerevisiae* Ypd1 gene, the orthologue of the *S. cerevisiae* Skn7 gene or any combination thereof.

76. The filamentous fungus host cell of embodiment 68 or 69, wherein the filamentous fungal host cell is selected from Achlya, *Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladiunt, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

77. The filamentous fungus host cell of embodiment 68 or 69, wherein the filamentous fungal host cell is *A. niger* or teleomorphs or anamorphs thereof.

78. The filamentous fungus host cell of embodiment 77, wherein the heterologous modification comprises replacement of a native promoter for the *A. niger* orthologue of the *S. cerevisiae* SLN1 gene or the *N. crassa* nik1 gene with a promoter that more weakly expresses the *A. niger* orthologue of the *S. cerevisiae* SLN1 gene or the *N. crassa* nik1 gene as compared to the native promoter.

79. The filamentous fungus host cell of embodiment 78, wherein the promoter that more weakly expresses the gene for the *A. niger* ortholog of the *S. cerevisiae* SLN1 protein or the *N. crassa* Nik1 protein is selected from an amyB promoter or a manB promoter.

80. The filamentous fungus host cell of embodiment 78, wherein the promoter that more weakly expresses the gene for the *A. niger* ortholog of the *S. cerevisiae* SLN1 protein or the *N. crassa* Nik1 protein is selected from the promoter of SEQ ID NO. 1 or SEQ ID NO: 2.

81. The filamentous fungus host cell of embodiment 77 or 78, wherein the heterologous modification comprises replacement of the *A. niger* orthologue of the *S. cerevisiae* SLN1 gene or the *N. crassa* nik1 gene with a mutated version of the *A. niger* orthologue of the *S. cerevisiae* SLN1 gene or the *N. crassa* nik1 gene.

82. The filamentous fungus host cell of embodiment 81, wherein the mutated version of the *A. niger* orthologue of the *S. cerevisiae* SLN1 gene or the *N. crassa* nik1 gene comprises a SNP.

83. The filamentous fungus host cell of embodiment 82, wherein the mutated *A. niger* ortholog of the *S. cerevisiae* SLN1 gene or the *N. crassa* nik1 gene comprises the sequence of SEQ ID NO: 7.

84. The filamentous fungus host cell of embodiment 77, wherein the heterologous modification comprises replacement of the *A. niger* orthologue of the *S. cerevisiae* SLN1 gene or the *N. crassa* nik1 gene with a selectable marker gene, thereby removing the native *A. niger* orthologue of the *S. cerevisiae* SLN1 gene or the *A. crassa* nik1 gene from the genome of the filamentous fungus host cell 85. The filamentous fungus host cell of embodiment 77, further comprising a heterologous modification of one or more genes within a biochemical pathway of which the *A. niger* orthologue of the *S. cerevisiae* SLN1 gene or the *A. crassa* nik1 gene is a component.

86. The filamentous fungus host cell of embodiment 85, wherein the one or more genes are selected from the *A. niger* orthologue of the *S. cerevisiae* Ypd1 gene with SEQ ID NO. 9, the *A. niger* orthologue of the *S. cerevisiae* Ssk1 gene with SEQ ID NO. 10, the *A. niger* orthologue of the *S. cerevisiae* Skn7 gene with SEQ ID NO. 11 or 12, the *A. niger* orthologue of the *S. cerevisiae* Ssk2 gene with SEQ ID NO. 13 or any combination thereof.

87. The filamentous fungus host cell of embodiment 77, further comprising a disruption of one or more genes selected from a non-SNP containing version of a gene with nucleic acid sequence of SEQ ID NO: 5, 6, 8 or any combination thereof.

88. The filamentous fungus host cell of embodiment 87, wherein the disruption is selected from replacement of a native promoter of the one or more genes with a promoter that weakly expresses the one or more genes as compared to the native promoter, replacement of the one or more genes with a mutated form of the one or more genes, replacement of the one or more genes with a selectable marker, or a combination thereof.

89. The filamentous fungus host cell of embodiment 88, wherein the promoter that weakly expresses the one or more genes as compared to the native promoter is selected from an amyB promoter or a manB promoter.

90. The filamentous fungus host cell of embodiment 88, wherein the promoter that weakly expresses the one or more genes as compared to the native promoter is selected from the promoter of SEQ ID NO: 1 or SEQ ID NO. 2.

91. The filamentous fungus host cell of embodiment 88, wherein the mutated form of the one or more genes is selected from SEQ ID NO. 5, 6, or 8.

92 The filamentous fungus host cell of embodiment 73, 84 or 88, wherein the selectable marker is selected from an auxotrophic marker gene, a colorimetric marker gene, antibiotic resistance gene, or a directional marker gene.

93. The filamentous fungus host cell of embodiment 92, wherein the colorimetric marker gene is an aygA gene.

94. The filamentous fungus host cell of embodiment 92, wherein the auxotrophic marker gene is selected from an argB gene, a trpC gene, a pyrG gene, or a met3 gene.

95. The filamentous fungus host cell of embodiment 92, wherein the directional marker gene is selected from an acetamidase (amdS) gene or a nitrate reductase gene (niaD).

96. The filamentous fungus host cell of embodiment 92, wherein the antibiotic resistance gene is a ble gene, wherein the ble gene confers resistance to pheomycin.

97. A variant strain of filamentous fungus derived from a parental strain, wherein cells of the variant strain possess a non-mycelium, pellet forming phenotype as compared to cells of the parental strain when grown in a submerged culture due to the variant strain possessing a genetic alteration in one or more genes of an osmotic response pathway that causes cells of the variant strain to produce a reduced amount and/or less active form of functional protein encoded by the one or more genes of the osmotic response pathway as compared to cells of the parental strain when grown under submerged culture conditions.

98. The variant strain of embodiment 97, wherein the variant strain sporulates normally as compared to the parental strain when grown under non-submerged growth conditions.

99. The variant strain of any one of the above embodiments, wherein the filamentous fungus is selected from Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora (e.g., Myceliophthora thermophila), Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella species or teleomorphs, or anamorphs, and synonyms or taxonomic equivalents thereof.

100. The variant strain of any one of the above embodiments, wherein the filamentous fungus is Aspergillus niger (A. niger) or teleomorphs or anamorphs thereof.

101. The variant strain of any one of the above embodiments, wherein the one or more genes of the osmotic response pathway are filamentous fungal orthologues of yeast osmotic response pathway genes found in Table 7.

102. The variant strain of embodiment 100, wherein the one or more genes of the osmotic response pathway are A. niger orthologues of yeast osmotic response pathway genes found in Table 7.

103. The variant strain of embodiment 100, wherein the one or more genes of the osmotic response pathway are selected from genes with nucleic acid sequences of SEQ ID NO: 9, 10, 11, 12, 13 or any combination thereof 104. The variant strain of embodiment 100, wherein the one or more genes of the osmotic response pathway is an A. niger orthologue of a Saccharomyces cerevisiae (S. cerevisiae) SLN1 gene or a Neurospora crassa (N. crassa) nik1 gene.

105. The variant of embodiment 104, wherein the A. niger orthologue of the S. cerevisiae SLN1 gene or the N. crassa nik1 gene is a non-SNP containing version of the nucleic acid sequence of SEQ ID NO. 7

106. The variant strain of any one of the above embodiments, wherein the genetic alteration is selected from replacement of a native promoter of the one or more genes with a promoter that weakly expresses the one or more genes as compared to the native promoter, replacement of the one or more genes with a mutated form of the one or more genes, replacement of the one or more genes with a selectable marker, or a combination thereof.

107. The variant strain of embodiment 106, wherein the promoter that weakly expresses the one or more genes as compared to the native promoter is selected from an amyB promoter or a manB promoter.

108. The variant strain of embodiment 106 or 107, wherein the promoter that weakly expresses the one or more genes as compared to the native promoter comprises, consist essentially of or consists of a nucleic acid sequence selected from SEQ ID NO: 1 or SEQ ID NO: 2.

109. The variant strain of embodiment 106, wherein the selectable marker is selected from an auxotrophic marker gene, a colorimetric marker gene, antibiotic resistance gene, or a directional marker gene.

110. The variant strain of embodiment 109, wherein the colorimetric marker gene is an aygA gene.

111. The variant strain of embodiment 109, wherein the auxotrophic marker gene is selected from an argB gene, a trpC gene, a pyrG gene, or a met3 gene 112. The variant strain of embodiment 109, wherein the directional marker gene is selected from an acetamidase (amdS) gene or a nitrate reductase gene (niaD).

113. The variant strain of embodiment 109, wherein the antibiotic resistance gene is a ble gene, wherein the ble gene confers resistance to pheomycin.

114. The variant strain of embodiment 106, wherein the mutated form of the one or more genes of the osmotic stress response pathway comprises a single nucleotide polymorphism.

115. The variant strain of embodiment 114, wherein the mutated form of the one or more genes of the osmotic response pathway is an A. niger orthologue of a S. cerevisiae SLN1 gene or a N. crassa nik1 gene, wherein the mutated form of the A. niger orthologue of the S. cerevisiae SLN1 gene or the N. crassa nik1 gene is a nucleic acid sequence of SEQ ID NO 7

116. The variant strain of any one of the above embodiments, further comprising a genetic alteration of one or more genes selected from a non-SNP containing version of the genes with nucleic acid sequences of SEQ ID NO: 5, 6, 8 or any combination thereof.

117. The variant strain of embodiment 116, wherein the genetic alteration is selected from replacement of a native promoter of the one or more genes with a promoter that weakly expresses the one or more genes as compared to the native promoter, replacement of the one or more genes with a mutated form of the one or more genes, replacement of the one or more genes with a selectable marker, or a combination thereof.

118. The variant strain of embodiment 117, wherein the promoter that weakly expresses the one or more genes as compared to the native promoter is selected from an amyB promoter or a manB promoter.

119. The variant strain of embodiment 117 or 118, wherein the promoter that weakly expresses the one or more genes as compared to the native promoter comprises, consist essentially of or consists of a nucleic acid sequence selected from SEQ ID NO: 1 or SEQ ID NO: 2.

120. The variant strain of embodiment 117, wherein the selectable marker is selected from an auxotrophic marker gene, a colorimetric marker gene, antibiotic resistance gene, or a directional marker gene.

121. The variant strain of embodiment 120, wherein the colorimetric marker gene is an aygA gene 122. The variant strain of embodiment 120, wherein the auxotrophic marker gene is selected from an argB gene, a trpC gene, a pyrG gene, or a met3 gene.

123. The variant strain of embodiment 120, wherein the directional marker gene is selected from an acetamidase (amdS) gene or a nitrate reductase gene (niaD).

124. The variant strain of embodiment 120, wherein the antibiotic resistance gene is a ble gene, wherein the ble gene confers resistance to pheomycin.
125. The variant strain of embodiment 117, wherein the mutated form of the one or more genes comprises a single nucleotide polymorphism.
126. The variant strain of embodiment 125, wherein the mutated form of the one or more genes is a nucleic acid sequence selected from SEQ ID NO: 5, 6 or 8.
127. A filamentous fungal host cell comprising a promoter operably linked to a gene that regulates morphology of the host cell, wherein the promoter is heterologous to the gene, wherein the promoter has a nucleic sequence selected from the group consisting of SEQ ID NOs. 1-4.
128. The filamentous fungal host cell of embodiment 127, wherein the filamentous fungal host cell has a non-mycelium, pellet morphology when grown under submerged culture conditions in fermentation media as compared to a reference filamentous fungal host cell without the promoter operably linked to the gene that regulates morphology of the host cell.
129. The filamentous fungal host cell of embodiment 128, wherein the fermentation media comprises at least 14 ppb of manganese.
130. The filamentous fungal host cell of embodiment 127 or 128, wherein the fermentation media is free of chelating agents.
131. The filamentous fungal host cell of any one of embodiments 127-130, wherein the filamentous fungal host cell produces an amount of a product of interest that is at least equal to the amount produced by the reference filamentous fungal host cell without the promoter operably linked to the gene that regulates morphology of the host cell.
132. The filamentous fungal host cell of embodiment 131, wherein the product of interest is citric acid or an enzyme of interest.
133. The filamentous fungal host cell of any one of embodiments 127-132, wherein the gene that regulates morphology is selected from one or more genes of an osmotic response pathway, non-SNP containing versions of the genes with nucleic acid sequences SEQ ID NO: 5, 6, 8, or any combination thereof.
134. The filamentous fungal host cell of any one of embodiments 127-133, wherein the gene that regulates morphology is a wild-type or mutated form of the gene.
135. The filamentous fungal host cell of any one of embodiments 127-134, wherein the filamentous fungal host cell is selected from Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora (e.g., Myceliophthora thermophila), Mucor, Neurospora. Penicillium, Podospora, Phlebia, Piromyces, Pyricularia, Rhizomucor, Rhizopus, Schizophyllum, Scytalidium, Sporotrichum, Talaromyces, Thermoascus, Thielavia, Promotes, Tolypocladium, Trichoderma, Verticillium, Volvariella species or teleomorphs, or anamorphs, and synonyms or taxonomic equivalents thereof.
136. The filamentous fungal host cell of any one of embodiments 127-135, wherein the filamentous fungal host cell is A. niger or teleomorphs or anamorphs thereof
137. The filamentous fungal host cell of any one of embodiments 133-136, wherein the one or more genes of the osmotic response pathway are filamentous fungal orthologues of yeast osmotic response pathway genes found in Table 7.
138. The filamentous fungal host cell of embodiment 136, wherein the one or more genes of the osmotic response pathway are A. niger orthologues of yeast osmotic response pathway genes found in Table 7.
139. The filamentous fungal host cell of embodiment 136, wherein the one or more genes of the osmotic response pathway are selected from genes with nucleic acid sequences of SEQ ID NO. 9, 10, 11, 12, 13 or any combination thereof.
140. The filamentous fungal host cell of embodiment 136, wherein the one or more genes of the osmotic response pathway is an A. niger orthologue of a S. cerevisiae SLN1 gene or a N. crassa nik1 gene.
141. The filamentous fungal host cell of embodiment 140, wherein the A. niger orthologue of the S. cerevisiae SLN1 gene or the N. crassa nik1 gene is a non-SNP containing version of nucleic acid sequence of SEQ ID NO: 7.
142. The filamentous fungal host cell of embodiment 140, wherein the A. niger orthologue of the S. cerevisiae SLN1 gene or the N. crassa nik1 gene is a nucleic acid sequence of SEQ ID NO: 7.
143. The filamentous fungal host cell of any one of embodiments 127-142, wherein the promoter is selected from the nucleic acid sequence of SEQ ID NO. 1 or 2
144. A filamentous fungus host cell comprising a heterologous modification of one or more genes of the host cell's osmotic response pathway, wherein a protein encoded by the modified one or more genes has reduced activity and/or reduced expression relative to a parental filamentous fungal host cell lacking the modified one or more genes of the host cell's osmotic response pathway.
145. The filamentous fungus host cell of embodiment 144, wherein the filamentous fungal host cell has a non-mycelium, pellet morphology when grown under submerged culture conditions in fermentation media.
146. The filamentous fungal host cell of embodiment 144 or 145, wherein the filamentous fungal host cell is selected from Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora (e.g., Myceliophthora thermophila), Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella species or teleomorphs, or anamorphs, and synonyms or taxonomic equivalents thereof
147. The filamentous fungal host cell of embodiment 144 or 145, wherein the filamentous fungal host cell is A. niger or teleomorphs or anamorphs thereof.
148. The filamentous fungal host cell of any one of embodiments 144-147, wherein the one or more genes of the osmotic response pathway are filamentous fungal orthologues of yeast osmotic response pathway genes found in Table 7.

149. The filamentous fungal host cell of embodiment 147, wherein the one or more genes of the osmotic response pathway are *A. niger* orthologues of yeast osmotic response pathway genes found in Table 7.
150. The filamentous fungal host cell of embodiment 147, wherein the one or more genes of the osmotic response pathway are selected from genes with nucleic acid sequences of SEQ ID NO: 9, 10, 11, 12, 13 or any combination thereof.
151. The filamentous fungal host cell of embodiment 147, wherein the one or more genes of the osmotic response pathway is an *A. niger* orthologue of the *S. cerevisiae* SLN1 gene or the *N. crassa* nik1 gene.
152. The filamentous fungal host cell of embodiment 151, wherein the *A. niger* orthologue of the *S. cerevisiae* SLN1 gene or the *N. crassa* nik1 gene is a non-SNP containing version of a nucleic acid sequence of SEQ ID NO: 7.
153. The filamentous fungal host cell of any one of embodiments 144-152, wherein the heterologous modification is selected from replacement of a native promoter of the one or more genes with a promoter that weakly expresses the one or more genes as compared to the native promoter, replacement of the one or more genes with a mutated form of the one or more genes, replacement of the one or more genes with a selectable marker, or a combination thereof.
154. The filamentous fungal host cell of embodiment 153, wherein the promoter that weakly expresses the one or more genes as compared to the native promoter is selected from an amyB promoter or a manB promoter.
155. The filamentous fungal host cell of embodiment 153 or embodiment 154, wherein the promoter that weakly expresses the one or more genes as compared to the native promoter comprises, consist essentially of or consists of a nucleic acid sequence selected from SEQ ID NO: 1 or SEQ ID NO. 2
156. The filamentous fungal host cell of embodiment 153, wherein the selectable marker is selected from an auxotrophic marker gene, a colorimetric marker gene, antibiotic resistance gene, or a directional marker gene.
157. The filamentous fungal host cell of embodiment 156, wherein the colorimetric marker gene is an aygA gene
158. The filamentous fungal host cell of embodiment 156, wherein the auxotrophic marker gene is selected from an argB gene, a trpC gene, a pyrG gene, or a met3 gene.
159. The filamentous fungal host cell of embodiment 156, wherein the directional marker gene is selected from an acetamidase (amdS) gene or a nitrate reductase gene (niaD).
160. The filamentous fungal host cell of embodiment 156, wherein the antibiotic resistance gene is a ble gene, wherein the ble gene confers resistance to pheomycin
161. The filamentous fungal host cell of embodiment 153, wherein the mutated form of the one or more genes of the osmotic stress response pathway comprises a single nucleotide polymorphism.
162. The filamentous fungal host cell of embodiment 161, wherein the one or more genes of the osmotic stress pathway is an *A. niger* orthologue of the *S. cerevisiae* SLN1 gene of the *N. crassa* nik1 gene, wherein the mutated form of the *A. niger* orthologue of the *S. cerevisiae* SLN1 gene or the *N. crassa* nik1 gene is the nucleic acid sequence of SEQ ID NO. 7.
163. The filamentous fungal host cell of any one of embodiments 144-162, further comprising a genetic alteration of one or more genes selected from a non-SNP containing version of the genes with nucleic acid sequences of SEQ ID NO: 5, 6, 8 or any combination thereof.
164. The filamentous fungal host cell of embodiment 163, wherein the genetic alteration is selected from replacement of a native promoter of the one or more genes with a promoter that weakly expresses the one or more genes as compared to the native promoter, replacement of the one or more genes with a mutated form of the one or more genes, replacement of the one or more genes with a selectable marker, or a combination thereof.
165. The filamentous fungal host cell of embodiment 164, wherein the promoter that weakly expresses the one or more genes as compared to the native promoter is selected from an amyB promoter or a manB promoter.
166. The filamentous fungal host cell of embodiment 164 or embodiment 165, wherein the promoter that weakly expresses the one or more genes as compared to the native promoter comprises, consist essentially of or consists of a nucleic acid sequence selected from SEQ ID NO: 1 or SEQ ID NO. 2
167. The filamentous fungal host cell of embodiment 164, wherein the selectable marker is selected from an auxotrophic marker gene, a colorimetric marker gene, antibiotic resistance gene, or a directional marker gene.
168. The filamentous fungal host cell of embodiment 167, wherein the colorimetric marker gene is an aygA gene.
169. The filamentous fungal host cell of embodiment 167, wherein the auxotrophic marker gene is selected from an argB gene, a trpC gene, a pyrG gene, or a met3 gene.
170. The filamentous fungal host cell of embodiment 167, wherein the directional marker gene is selected from an acetamidase (amdS) gene or a nitrate reductase gene (niaD).
171. The filamentous fungal host cell of embodiment 167, wherein the antibiotic resistance gene is a ble gene, wherein the ble gene confers resistance to pheomycin.
172. The filamentous fungal host cell of embodiment 164, wherein the mutated form of the one or more genes comprises a single nucleotide polymorphism.
173. The filamentous fungal host cell of embodiment 172, wherein the mutated form of the one or more genes is a nucleic acid sequence selected from SEQ ID NO: 5, 6 or 8.
174. A fermentation broth comprising at least 14 ppb of manganese and a filamentous fungal cell comprising a non-mycelium pellet phenotype, wherein the broth is free of a chelating agent, and wherein the filamentous fungal cell comprises one or more genetically altered genes from an osmotic response pathway of the filamentous fungal cell.
175. The fermentation broth of embodiment 174, wherein the one or more genetically altered genes from the osmotic response pathway are operably linked to a heterologous promoter.
176. The fermentation broth of embodiment 175, wherein the heterologous promoter is selected from SEQ ID NO. 1 or 2.
177. The fermentation broth of any one of embodiments 174-176, wherein the one or more genetically altered genes from the osmotic response pathway comprises a mutation.
178. The fermentation broth of embodiment 177, wherein the mutation in a SNP.
179. The fermentation broth of any one of embodiments 174-178, wherein the filamentous fungal host cell is selected from Achlya, *Acremonium, Aspergillus,*

*Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella* species or teleomorphs, or anamorphs, and synonyms or taxonomic equivalents thereof.

180. The fermentation broth of any one of embodiments 174-178, wherein the filamentous fungal host cell is *A. niger* or teleomorphs or anamorphs thereof.

181. The fermentation broth of any one of embodiments 174-180, wherein the one or more genetically altered genes of the osmotic response pathway are genetically altered filamentous fungal orthologues of yeast osmotic response pathway genes found in Table 7.

182. The fermentation broth of embodiment 180, wherein the one or more genetically altered genes of the osmotic response pathway are genetically altered *A. niger* orthologues of yeast osmotic response pathway genes found in Table 7.

183. The fermentation broth of embodiment 180, wherein the one or more genetically altered genes of the osmotic response pathway are genetically altered forms of genes with nucleic acid sequences selected from SEQ ID NO. 9, 10, 11, 12, 13 or any combination thereof.

184. The fermentation broth of embodiment 180, wherein the one or more genetically altered genes of the osmotic response pathway is a genetically altered *A. niger* orthologue of the *S. cerevisiae* SLN1 gene or the *N. crassa* nik1 gene.

185. The fermentation broth of embodiment 184, wherein the genetically altered *A. niger* orthologue of the *S. cerevisiae* SLN1 gene or the *N. crassa* nik1 gene is a gene with a nucleic acid sequence of SEQ ID NO. 7.

186. A method for generating a promoter swap filamentous fungal strain library, comprising the steps of:
   a. providing one or more target genes that play a role in morphology to a base filamentous fungal strain, and a promoter ladder, wherein said promoter ladder comprises a plurality of promoters exhibiting different expression profiles in the base filamentous fungal strain; and
   b. engineering the genome of the base filamentous fungal strain, to thereby create an initial promoter swap filamentous fungal strain library comprising a plurality of individual filamentous fungal strains with unique genetic variations found within each strain of said plurality of individual filamentous fungal strains, wherein each of said unique genetic variations comprises one or more of the promoters from the promoter ladder operably linked to one of the one or more target genes that play a role in the osmotic stress response to the base filamentous fungal strain.

187. The method of embodiment 186, wherein the promoter ladder comprises the promoters found in Table 2.

188. The method of embodiment 186 or 187, wherein the one or more target genes that play a role in morphology comprise a disruption.

189. The method of embodiment 188, wherein the disruption is a SNP, a missense mutation, a nonsense mutation, a deletion and/or an insertion.

190. The method of any one of embodiments 186-189, wherein the one or more target genes that play a role in morphology are selected from one or more genes of an osmotic response pathway, non-SNP containing versions of genes with nucleic acid sequences SEQ ID NO: 5, 6, 8, or any combination thereof.

191. The method of any one of embodiments 180-190, wherein the filamentous fungal host cell is selected from *Achlya, Acremonium, Aspergillus, Aureobasidium, Bjerkandera, Ceriporiopsis, Cephalosporium, Chrysosporium, Cochliobolus, Corymscus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Promotes, Tolypocladium, Trichoderma, Verticillium, Volvariella* species or teleomorphs, or anamorphs, and synonyms or taxonomic equivalents thereof.

192. The method of any one of embodiments 180-190, wherein the filamentous fungal host cell is *A. niger* or teleomorphs or anamorphs thereof.

193. The method of any one of embodiments 190-192, wherein the one or more genes of the osmotic response pathway are filamentous fungal orthologues of yeast osmotic response pathway genes found in Table 7.

194. The method of embodiment 192, wherein the one or more genes of the osmotic response pathway are *A. niger* orthologues of yeast osmotic response pathway genes found in Table 7.

195. The method of embodiment 192, wherein the one or more genes of the osmotic response pathway are selected from genes with nucleic acid sequences of SEQ ID NO: 9, 10, 11, 12, 13 or any combination thereof 196. The method of embodiment 192, wherein the one or more genes of the osmotic response pathway is an *A. niger* orthologue of a *S. cerevisiae* SLN1 gene or a *N. crassa* nik1 gene 197. The method of embodiment 196, wherein the *A. niger* orthologue of the *S. cerevisiae* SLN1 gene or the *N. crassa* nik1 gene is a non-SNP containing version of nucleic acid sequence of SEQ ID NO: 7.

198. The method of embodiment 192, wherein the *A. niger* orthologue of the *S. cerevisiae* SLN1 gene or the *N. crassa* nik1 gene is a nucleic acid sequence of SEQ ID NO: 7.

199. A promoter swap method for improving the morphological phenotype of a production filamentous fungal strain, comprising the steps of:
   a. providing a plurality of target genes that play a role in morphology to a base filamentous fungal strain, and a promoter ladder, wherein said promoter ladder comprises a plurality of promoters exhibiting different expression profiles in the base filamentous fungal strain;
   b. engineering the genome of the base filamentous fungal strain, to thereby create an initial promoter swap filamentous fungal strain library comprising a plurality of individual filamentous fungal strains with unique genetic variations found within each strain of said plurality of individual filamentous fungal strains, wherein each of said unique genetic variations comprises one or more of the promoters from the promoter ladder operably linked to one of the plurality of target genes that play a role in morphology to the base filamentous fungal strain;

c. screening and selecting individual filamentous fungal strains of the initial promoter swap filamentous fungal strain library for morphological phenotypic improvements over a reference filamentous fungal strain, thereby identifying unique genetic variations that confer morphological phenotypic improvements;

d. providing a subsequent plurality of filamentous fungal microbes that each comprise a combination of unique genetic variations from the genetic variations present in at least two individual filamentous fungal strains screened in the preceding step, to thereby create a subsequent promoter swap filamentous fungal strain library;

e. screening and selecting individual filamentous fungal strains of the subsequent promoter swap filamentous fungal strain library for morphological phenotypic improvements over the reference filamentous fungal strain, thereby identifying unique combinations of genetic variation that confer additional morphological phenotypic improvements; and f. repeating steps d)-e) one or more times, in a linear or non-linear fashion, until an filamentous fungal strain exhibits a desired level of improved morphological phenotype compared to the morphological phenotype of the production filamentous fungal strain, wherein each subsequent iteration creates a new promoter swap filamentous fungal strain library of microbial strains, where each strain in the new library comprises genetic variations that are a combination of genetic variations selected from amongst at least two individual filamentous fungal strains of a preceding library.

200. The promoter swap method for improving the morphological phenotype of a production filamentous fungal strain of embodiment 199, wherein the subsequent promoter swap filamentous fungal strain library is a full combinatorial library of the initial promoter swap filamentous fungal strain library.

201. The promoter swap method for improving the morphological phenotype of a production filamentous fungal strain of embodiment 199, wherein the subsequent promoter swap filamentous fungal strain library is a subset of a full combinatorial library of the initial promoter swap filamentous fungal strain library.

202. The promoter swap method for improving the morphological phenotype of a production filamentous fungal strain of embodiment 199, wherein the subsequent promoter swap filamentous fungal strain library is a full combinatorial library of a preceding promoter swap filamentous fungal strain library.

203. The promoter swap method for improving the morphological phenotype of a production filamentous fungal strain of embodiment 199, wherein the subsequent promoter swap filamentous fungal strain library is a subset of a full combinatorial library of a preceding promoter swap filamentous fungal strain library.

204. The promoter swap method for improving the morphological phenotype of a production filamentous fungal strain of any one of embodiments 199-203, wherein the promoter ladder comprises the promoters found in Table 2.

205. The promoter swap method for improving the morphological phenotype of a production filamentous fungal strain of any one of embodiments 199-204, wherein the one or more target genes that play a role in morphology comprise a disruption.

206. The promoter swap method for improving the morphological phenotype of a production filamentous fungal strain of any one of embodiments 199-205, wherein the disruption is a SNP, a missense mutation, a nonsense mutation, a deletion and/or insertion.

207. The promoter swap method for improving the morphological phenotype of a production filamentous fungal strain of any one of embodiments 199-205, wherein the one or more target genes that play a role in morphology are selected from one or more genes of an osmotic response pathway, non-SNP containing versions of genes with nucleic acid sequences SEQ ID NO: 5, 6, 8, or any combination thereof.

208. The promoter swap method for improving the morphological phenotype of a production filamentous fungal strain of any one of embodiments 199-207, wherein the filamentous fungal host cell is selected from Achlya, Acremonium, Aspergillus, Aureobasidium, Bjerkandera, Ceriporiopsis, Cephalosporium, Chrysosporinm, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora (e.g., Myceliophthora thermophila), Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella species or teleomorphs, or anamorphs, and synonyms or taxonomic equivalents thereof.

209. The promoter swap method for improving the morphological phenotype of a production filamentous fungal strain of any one of embodiments 199-207, wherein the filamentous fungal host cell is *A. niger* or teleomorphs or anamorphs thereof.

210. The promoter swap method for improving the morphological phenotype of a production filamentous fungal strain of any one of embodiments 207-209, wherein the one or more genes of the osmotic response pathway are filamentous fungal orthologues of yeast osmotic response pathway genes found in Table 7.

211. The promoter swap method for improving the morphological phenotype of a production filamentous fungal strain of embodiment 209, wherein the one or more genes of the osmotic response pathway are *A. niger* orthologues of yeast osmotic response pathway genes found in Table 7.

212. The promoter swap method for improving the morphological phenotype of a production filamentous fungal strain of embodiment 209, wherein the one or more genes of the osmotic response pathway are selected from genes with nucleic acid sequences of SEQ ID NO: 9, 10, 11, 12, 13 or any combination thereof.

213. The promoter swap method for improving the morphological phenotype of a production filamentous fungal strain of embodiment 209, wherein the one or more genes of the osmotic response pathway is an *A. niger* orthologue of a *S. cerevisiae* SLN1 gene or a *N. crassa* nik1 gene.

214. The promoter swap method for improving the morphological phenotype of a production filamentous fungal strain of embodiment 213, wherein the *A. niger* orthologue of the *S. cerevisiae* SLN1 gene or the *N. crassa* nik1 gene is a non-SNP containing version of nucleic acid sequence of SEQ ID NO. 7.

215. The promoter swap method for improving the morphological phenotype of a production filamentous fungal strain of embodiment 213, wherein the *A. niger* orthologue of the *S. cerevisiae* SLN1 gene or the *N. crassa* nik1 gene is a nucleic acid sequence of SEQ ID NO: 7.

216. The promoter swap method for the morphological phenotype of a production filamentous fungal strain of any one of embodiments 199-215, wherein the morphological phenotypic improvement comprises conferring the ability to form a non-mycelium pellet morphology when grown under submerged culture conditions.

217. The promoter swap method for the morphological phenotype of a production filamentous fungal strain of embodiment 216, wherein the submerged culture conditions comprise a culture medium comprising at least 14 ppb of manganese and is free of chelating agents.

218. The variant strain of any one of embodiments 1-23, wherein the amount of functional *A. niger* orthologue of an *S. cerevisiae* SLN1 protein or a *N. crassa* Nik1 protein produced by the variant strain is reduced by at least 10%, 20%, 30%, 40%, 50%, 60%, 70%, 80%, 90%, 95% or 99% as compared to an amount of functional *A. niger* orthologue of an *S. cerevisiae* SLN1 protein or a *N. crassa* Nik1 protein produced by cells of the parental strain when grown under submerged culture conditions 219. The variant strain of any one of embodiments 1-23 or 218, wherein the amount of functional *A. niger* orthologue of an *S. cerevisiae* SLN1 protein or a *N. crassa* Nik1 protein produced by the variant strain and/or parental strain is measured using quantitative mass spectrometry or an immunoassay, wherein the immunoassay is selected from a Luminex assay, an ELISA or a quantitative Western blot analysis.

220. The variant strain of any one of embodiments 1-23, wherein the activity of functional *A. niger* orthologue of an *S. cerevisiae* SLN1 protein or a *N. crassa* Nik1 protein produced by the variant strain is reduced by at least 10%, 20%, 30%, 40%, 50%, 60%, 70%, 80%, 90%, 95% or 99% as compared to the activity of functional *A. niger* orthologue of an *S. cerevisiae* SLN1 protein or a *N. crassa* Nik1 protein produced by cells of the parental strain when grown under submerged culture conditions.

221. The variant strain of any one of embodiments 1-23 or 220, wherein the activity of the functional *A. niger* orthologue of an *S. cerevisiae* SLN1 protein or a *N. crassa* Nik1 protein produced by the variant strain and/or parental strain is measured using a kinase assay.

222. The filamentous fungus host cell of any one of embodiments 68-96, wherein the expression of the protein encoded by the modified orthologue of the *S. cerevisiae* SLN1 gene or the *N. crassa* Nik1 gene is reduced by at least 10%, 20%, 30%, 40%, 50%, 60%, 70%, 80%, 90%, 95% or 99% relative to the expression of a protein encoded by an orthologue of the *S. cerevisiae* SLN1 gene or the *N. crassa* Nik1 gene in the parental filamentous fungal host cell lacking the heterologous modification.

223. The filamentous fungus host cell of any one of embodiments 68-96 or 222, wherein the expression of the protein encoded by the modified orthologue of the *S. cerevisiae* SLN1 gene or the *N. crassa* Nik1 gene or the orthologue of the *S. cerevisiae* SLN1 gene or the *N. crassa* Nik1 gene in the filamentous fungus host cell and/or the parental filamentous fungal host cell lacking the heterologous modification is measured using quantitative mass spectrometry or an immunoassay, wherein the immunoassay is selected from a Luminex assay, an ELISA or a quantitative Western blot analysis.

224. The filamentous fungus host cell of any one of embodiments 68-96, wherein the activity of the protein encoded by the modified orthologue of the *S. cerevisiae* SLN1 gene or the *N. crassa* Nik1 gene is reduced by at least 10%, 20%, 30%, 40%, 50%, 60%, 70%, 80%, 90%, 95% or 99% relative to the activity of a protein encoded by an orthologue of the *S. cerevisiae* SLN1 gene or the *N. crassa* Nik1 gene in the parental filamentous fungal host cell lacking the heterologous modification.

225. The filamentous fungus host cell of any one of embodiments 68-96 or 224, wherein the activity of the protein encoded by the modified orthologue of the *S. cerevisiae* SLN1 gene or the *N. crassa* Nik1 gene or the orthologue of the *S. cerevisiae* SLN1 gene or the *N. crassa* Nik1 gene in the filamentous fungus host cell and/or the parental filamentous fungal host cell lacking the heterologous modification is measured using a kinase assay.

226. The variant strain of any one of embodiments 97-126, wherein the amount of functional protein encoded by the one or more genes of the osmotic response pathway that is produced by the variant strain is reduced by at least 10%, 20%, 30%, 40%, 50%, 60%, 70%, 80%, 90%, 95% or 99% as compared to an amount of functional protein encoded by the one or more genes of the osmotic response pathway that is produced by the parental strain when grown under submerged culture conditions.

227. The variant strain of any one of embodiments 97-126 or 226, wherein the amount of functional protein encoded by the one or more genes of the osmotic response pathway produced by the variant and/or parental strain is measured using quantitative mass spectrometry or an immunoassay, wherein the immunoassay is selected from a Luminex assay, an ELISA or a quantitative Western blot analysis.

228. The variant strain of any one of embodiments 97-126, wherein the activity of functional protein encoded by the one or more genes of the osmotic response pathway that is produced by the variant strain is reduced by at least 10%, 20%, 30%, 40%, 50%, 60%, 70%, 80%, 90%, 95% or 99% as compared to the activity of functional protein encoded by the one or more genes of the osmotic response pathway that is produced by the parental strain when grown under submerged culture conditions.

229. The variant strain of any one of embodiments 97-126 or 228, wherein the activity of a functional protein encoded by the one or more genes of the osmotic response pathway produced by the variant strain and/or the parental strain is measured using a kinase assay.

230. The filamentous fungus host cell of any one of embodiments 144-173, wherein the expression of the protein encoded by the modified one or more genes is reduced by at least 10%, 20%, 30%, 40%, 50%, 60%, 70%, 80%, 90%, 95% or 99% relative to the expression of a protein encoded by the modified one or more genes in the parental filamentous fungal host cell lacking the modified one or more genes of the host cell's osmotic response pathway.

231. The filamentous fungus host cell of any one of embodiments 144-173 or 230, wherein the expression of the protein encoded by the modified one or more genes in the filamentous fungus host cell and/or the parental filamentous fungal host cell lacking the modified one or more genes of the host cell's osmotic response pathway is measured using quantitative mass spectrometry or an immunoassay, wherein the immunoassay is selected from a Luminex assay, an ELISA or a quantitative Western blot analysis.

232. The filamentous fungus host cell of any one of embodiments 144-173, wherein the activity of the protein encoded by the modified one or more genes is reduced by at least 10%, 20%, 30%, 40%, 50%, 60%, 70%, 80%, 90%, 95% or 99% relative to the activity of a protein encoded by the modified one or more genes in the parental filamentous fungal host cell lacking the modified one or more genes of the host cell's osmotic response pathway 233. The filamentous fungus host cell of any one of embodiments 144-173 or 232, wherein the activity of the protein encoded by the modified one or more genes in the filamentous fungus host cell and/or the parental filamentous fungal host cell lacking the modified one or more genes of the host cell's osmotic response pathway is measured using a kinase activity.

TABLE 8

SEQUENCES OF THE DISCLOSURE WITH SEQ ID NO IDENTIFIERS

| NAME (SHORT NAME) | SOURCE | NUCLEIC ACID SEQ ID NO. | DESCRIPTION |
|---|---|---|---|
| manBp | Aspergillus niger | 1 | manB promoter from Aspergillus niger |
| amyBp | Aspergillus oryzae | 2 | amyB gene from Aspergillus oryzae |
| srpBp | Aspergillus niger | 3 | srpB promoter from Aspergillus niger |
| mbfAp | Aspergillus niger | 4 | mbfA promoter from Aspergillus niger |
| FungiSNP_9 | Aspergillus niger | 5 | SNP containing sequences for morphology related gene |
| FungiSNP_12 | Aspergillus niger | 6 | SNP containing sequences for morphology related gene |
| FungiSNP_18 | Aspergillus niger | 7 | A. niger SNP-containing orthologue of S. cerevisiae SLN1 gene or the N. crassa nik1 gene; A. niger SNP-containing version of nikA gene (the SNP is a missesnse mutation that converst a histidine at the 272 amino acid position into a tyrosine) |
| FungiSNP_40 | Aspergillus niger | 8 | SNP containing sequences for morphology related gene |
| Ypd1 orthologue | Aspergillus niger | 9 | Sequence for a version of an A. niger orthologue of S. cerevisiae Ypd1 gene |

TABLE 8-continued

SEQUENCES OF THE DISCLOSURE WITH SEQ ID NO IDENTIFIERS

| NAME (SHORT NAME) | SOURCE | NUCLEIC ACID SEQ ID NO. | DESCRIPTION |
|---|---|---|---|
| Ssk1 orthologue | Aspergillus niger | 10 | Sequence for a version of an A. niger orthologue of S. cerevisiae Ssk1 gene |
| Skn7 orthologue #1 | Aspergillus niger | 11 | Sequence for a version of an A. niger orthologue of S. cerevisiae Skn7 gene |
| Skn7 orthologue #2 | Aspergillus niger | 12 | Sequence for a version of an A. niger orthologue of S. cerevisiae Skn7 gene |
| Ssk2 orthologue | Aspergillus niger | 13 | Sequence for a version of an A. niger orthologue of S. cerevisiae Ssk2 gene |
| SLN1/nik1 orthologue (ASPNI-DRAFT_39736) | Aspergillus niger | 14 | A. niger orthologue of S. cerevisiae SLN1 gene; A. niger orthologue of N. crassa nik1 gene; non-SNP containing version of A. niger nikA gene (ASPNI-DRAFT_39767); Non-SNP containing sequences for morphology related gene for FungiSNP_18 |
| SLN1 orthologue (ASPNI-DRAFT_183029) | Aspergillus niger | 15 | A. niger orthologue of S. cerevisiae SLN1 gene |
| SLN1 orthologue (ASPNI-DRAFT_41708) | Aspergillus niger | 16 | A. niger orthologue of S. cerevisiae SLN1 gene |
| SLN1 orthologue (ASPNI-DRAFT_37188) | Aspergillus niger | 17 | A. niger orthologue of S. cerevisiae SLN1 gene |
| ASPNI-DRAFT_214017 | Aspergillus niger | 18 | A. niger orthologue of S. cerevisiae Ste11 gene |
| ASPNI-DRAFT_55574 | Aspergillus niger | 19 | A. niger orthologue of S. cerevisiae Bck1 gene |
| ASPNI-DRAFT_38443 | Aspergillus niger | 20 | A. niger orthologue of S. cerevisiae Ssk2/22 gene |
| ASPNI-DRAFT_209137 | Aspergillus niger | 21 | A. niger orthologue of S. cerevisiae Ste7 gene |
| ASPNI-DRAFT_211983 | Aspergillus niger | 22 | A. niger orthologue of S. cerevisiae Mkk2/22 gene |
| ASPNI-DRAFT_51782 | Aspergillus niger | 23 | A. niger orthologue of S. cerevisiae Pbs2 gene |
| ASPNI-DRAFT_207710 | Aspergillus niger | 24 | A. niger orthologue of S. cerevisiae Fus1/Kss3 gene |
| ASPNI-DRAFT_205706 | Aspergillus niger | 25 | A. niger orthologue of S. cerevisiae Mpk1 gene |
| ASPNI-DRAFT_52673 | Aspergillus niger | 26 | A. niger orthologue of S. cerevisiae Hog1 gene |
| ASPNI-DRAFT_37188 | Aspergillus niger | 27 | A. niger orthologue of S. pombe Phk1/2 (S. pombe); C. albicans Chk1 gene |
| ASPNI-DRAFT_174806 | Aspergillus niger | 28 | A. niger orthologue of S. pombe Phk3 gene |
| ASPNI-DRAFT_214261 | Aspergillus niger | 29 | A. niger orthologue of S. cerevisiae Ypd1 gene; S. pombe Spy1 gene. |
| ASPNI-DRAFT_120745 | Aspergillus niger | 30 | A. niger orthologue of S. cerevisiae Ssk1 gene; S. pombe Mcs4 gene; C. albicans SskA gene |

TABLE 8-continued

SEQUENCES OF THE DISCLOSURE WITH SEQ ID NO IDENTIFIERS

| NAME (SHORT NAME) | SOURCE | NUCLEIC ACID SEQ ID NO. | DESCRIPTION |
|---|---|---|---|
| ASPNI-DRAFT_37857 | Aspergillus niger | 31 | A. niger orthologue of S. cerevisiae Skn7 gene; S. pombe Prr1 gene; C. albicans Skn7 gene |
| ASPNI-DRAFT_200656 | Aspergillus niger | 32 | A. niger orthologue of S. cerevisiae Rim15 gene S. pombe Cek1 gene; C. albicans Rim15 gene |
| ASPNI-DRAFT_44864 | Aspergillus niger | 33 | Non-SNP containing sequences for morphology related gene for FungiSNP_06 |
| ASPNI-DRAFT_47328 | Aspergillus niger | 34 | Non-SNP containing sequences for morphology related gene for FungiSNP_41 |
| ASPNI-DRAFT_37842 | Aspergillus niger | 35 | Non-SNP containing sequences for morphology related gene for FungiSNP_43 |
| ASPNI-DRAFT_55560 | Aspergillus niger | 36 | Non-SNP containing sequences for morphology related gene for FungiSNP_20 |
| ASPNI-DRAFT_131243 | Aspergillus niger | 37 | Non-SNP containing sequences for morphology related gene for FungiSNP_30 |
| ASPNI-DRAFT_127977 | Aspergillus niger | 38 | Non-SNP containing sequences for morphology related gene for FungiSNP_32 |
| ASPNI-DRAFT_53655 | Aspergillus niger | 39 | Non-SNP containing sequences for morphology related gene for FungiSNP_23 |
| ASPNI-DRAFT_123785 | Aspergillus niger | 40 | Non-SNP containing sequences for morphology related gene for FungiSNP_16 |
| ASPNI-DRAFT_212853 | Aspergillus niger | 41 | Non-SNP containing sequences for morphology related gene for FungiSNP_11 |
| ASPNI-DRAFT_196832 | Aspergillus niger | 42 | Non-SNP containing sequences for morphology related gene for FungiSNP_09 |
| ASPNI-DRAFT_38583 | Aspergillus niger | 43 | Non-SNP containing sequences for morphology related gene for FungiSNP_36 |
| ASPNI-DRAFT_121820 | Aspergillus niger | 44 | Non-SNP containing sequences for morphology related gene for FungiSNP_24 |
| ASPNI-DRAFT_44868 | Aspergillus niger | 45 | Non-SNP containing sequences for morphology related gene for FungiSNP_07 |
| ASPNI-DRAFT_212500 | Aspergillus niger | 46 | Non-SNP containing sequences for morphology related gene for FungiSNP_02 |
| ASPNI-DRAFT_119127 | Aspergillus niger | 47 | Non-SNP containing sequences for morphology related gene for FungiSNP_12 |
| ASPNI-DRAFT_206922 | Aspergillus niger | 48 | Non-SNP containing sequences for morphology related gene for FungiSNP_21 |
| ASPNI-DRAFT_52574 | Aspergillus niger | 49 | Non-SNP containing sequences for morphology related gene for FungiSNP_40 |
| SLN1 | S. cerevisiae | 50 | |
| Ste 11 | S. cerevisiae | 51 | |
| Bck 1 | S. cerevisiae | 52 | |
| Ssk2 | S. cerevisiae | 53 | |
| Ste7 | S. cerevisiae | 54 | |
| Mkk2/22 | S. cerevisiae | 55 | |
| Pbs2 | S. cerevisiae | 56 | |
| Fus1/Kss3 | S. cerevisiae | 57 | |
| Mpk1 | S. cerevisiae | 58 | |
| Hog1 | S. cerevisiae | 59 | |
| Chk1 | C. albicans | 60 | |
| Phk3 | S. pombe | 61 | |
| Ypd1 | S. cerevisiae | 62 | |
| Spy1 | S. pombe | 63 | |
| Ssk1 | S. cerevisiae | 64 | |
| Mcs4 | S. pombe | 65 | |
| SskA | C. albicans | 66 | |
| Skn7 | S. cerevisiae | 67 | |
| Prr1 | S. pombe | 68 | |
| Skn7 | C. albicans | 69 | |
| Rim15 | S. cerevisiae | 70 | |
| Cek1 | S. pombe | 71 | |
| Rim15 | C. albicans | 72 | |
| Ssk22 | S. cerevisiae | 73 | |
| Phk1 | S. pombe | 74 | |
| Phk22 | S. pombe | 75 | |
| Non-SNP containing FungiSNP_18 | Aspergillus niger | 76 | Another version of non-SNP containing sequences for morphology related gene for FungiSNP_18 |
| Non-SNP containing FungiSNP_09 | Aspergillus niger | 77 | Another version of non-SNP containing sequences for morphology related gene for FungiSNP_09 |
| Non-SNP containing FungiSNP_12 | Aspergillus niger | 78 | Another version of non-SNP containing sequences for morphology related gene for FungiSNP_12 |
| Non-SNP containing FungiSNP_40 | Aspergillus niger | 79 | Another version of non-SNP containing sequences for morphology related gene for FungiSNP_40 |

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as an acknowledgment or any form of suggestion that they constitute valid prior art or form part of the common general knowledge in any country in the world.

In addition, the following particular applications are incorporated herein by reference: U.S. application Ser. No. 15/396,230 (U S. Pub. No. US 2017/0159045 A1) filed on Dec. 30, 20016; PCT/US2016/065465 (WO 2017/100377 A1) filed on Dec. 7, 2016; U.S. application Ser. No. 15/140,296 (US 2017/0316353 A1) filed on Apr. 27, 2016; PCT/US2017/029725 (WO 2017/189784 A1) filed on Apr. 26, 2017; PCT/US2016/065464 (WO 2017/100376 A2) filed on Dec. 7, 2016; U.S. Prov. App. No. 62/431,409 filed on Dec. 7, 2016; U.S. Prov. App. No. 62/264,232 filed on Dec. 7, 2015, and U.S. Prov. App. No. 62/368,786 filed on Jul. 29, 2016. In addition, the following particular applications are incorporated herein by reference: PCT/US2017/069086 (WO 2018/12607), filed on Dec. 29, 2017, PCT/US2018/036360 (WO 2018/226900), filed on Jun. 6, 2018; U.S. Prov. App No. 62/441,040, filed on Dec. 30, 2016 and U.S. Prov. App. No. 62/515,907, filed on Jun. 6, 2017.

What is claimed is:

1. An engineered *Aspergillus* strain capable of responding to osmotic stress substantial similar to a parental strain of *Aspergillus* from which the engineered *Aspergillus* strain is generated, wherein the engineered *Aspergillus* strain comprises a heterologous modification of an *Aspergillus niger* (*A. niger*) orthologue of a *Saccharomyces cerevisiae* (*S. cerevisiae*) sln1 gene that produces a reduced amount and/or less active form of the polypeptide encoded by the *A. niger* orthologue of the *S. cerevisiae* sln1 gene in the engineered *Aspergillus* strain as compared to cells of the parental *Aspergillus* strain.

2. The engineered *Aspergillus* strain of claim 1, wherein the heterologous modification comprises replacement of the *A. niger* orthologue of the *S. cerevisiae* sln1 gene of the parental *Aspergillus* strain with a single nucleotide polymorphism (SNP) containing version of the *A. niger* orthologue of the *S. cerevisiae* sln1 gene wherein the SNP containing version of the *A. niger* orthologue of the *& cerevisiae* sln1 gene comprises a nucleotide substitution at position 814 of the *A. niger* orthologue of the *S. cerevisiae* sln1 gene of the parental *Aspergillus* strain.

3. The engineered *Aspergillus* strain of claim 2, wherein the SNP containing version of the *A. niger* orthologue of the *S. cerevisiae* sln1 gene comprises a cytosine to thymine substitution at nucleotide position 814 of the *A. niger* orthologue of the *S. cerevisiae* sln1 gene of the parental *Aspergillus* strain.

4. The engineered *Aspergillus* strain of claim 2, wherein the SNP containing version of the *A. niger* orthologue of the *S. cerevisiae* sln1 gene comprises the nucleic acid sequence of SEQ ID NO: 7.

5. The engineered *Aspergillus* strain of claim 2, wherein the *A. niger* orthologue of the *S. cerevisiae* sln1 gene of the parental *Aspergillus* strain comprises the nucleic acid sequence of SEQ ID NO: 76.

6. The engineered *Aspergillus* strain of claim 2, wherein the SNP-containing version of the *A. niger* orthologue of the *S. cerevisiae* sln1 gene encodes a polypeptide comprising a histidine to tyrosine substitution at amino acid position 272 of an *A. niger* orthologue of *S. cerevisiae* SLN.

7. The engineered *Aspergillus* strain of claim 1, wherein the engineered *Aspergillus* strain is capable of producing an increased level of citric add as compared to the parental strain.

8. The engineered *Aspergillus* strain of claim 1, wherein the engineered *Aspergillus* strain is capable of producing at least about 33% more citric acid as compared to the parental *Aspergillus* strain.

9. The engineered *Aspergillus* strain of claim 1, wherein the heterologous modification comprises replacement of the native promoter of the *A. niger* orthologue of the *S. cerevisiae* sln1 gene of the parental *Aspergillus* strain with a promoter that more weakly expresses the *A. niger* orthologue of the *S. cerevisiae* sln1 gene as compared to the native promoter of the *A. niger* orthologue of the *S. cerevisiae* sln1 gene.

10. The engineered *Aspergillus* strain of claim 9, wherein the promoter that more weakly expresses the *A. niger* orthologue of the *S. cerevisiae* sln1 gene as compared to the native promoter of the *A. niger* orthologue of the *S. cerevisiae* sln1 gene is selected from an amyB promoter and a manB promoter.

11. The engineered *Aspergillus* strain of claim 9, wherein the promoter that more weakly expresses the *A. niger* orthologue of the *S. cererisiae* sln1 gene as compared to the native promoter of the *A. niger* orthologue of the *S. cerevisiae* sln1 gene has the nucleic acid sequence of SEQ ID NO: 1 or 2.

12. The engineered *Aspergillus* strain of claim 9, further comprising a heterologous modification of one or more genes selected from a non-SNP containing version of the genes with nucleic acid sequences of SEQ ID NO: 77, 78, 79 and any combination thereof.

13. The engineered *Aspergillus* strain of claim 12, wherein the heterologous modification is selected from replacement of a native promoter of the one or more genes with a promoter that weakly expresses the one or more genes as compared to the native promoter, replacement of the one or more genes with a mutated form of the one or more genes, replacement of the one or more genes with a selectable marker, and a combination thereof.

14. The engineered *Aspergillus* strain of claim 13, wherein the promoter that weakly expresses the one or more genes as compared to the native promoter is selected from an amyB promoter and a manB promoter.

15. The engineered *Aspergillus* strain of claim 13, wherein the promoter that weakly expresses the one or more genes as compared to the native promoter is selected from the promoter of SEQ ID NO: 1 and SEQ ID NO: 2.

16. The engineered *Aspergillus* strain of claim 13, wherein the mutated form of the one or more genes has a nucleic acid sequence selected from the nucleic acid sequence of SEQ ID NO: 5, 6, and 8.

17. The engineered *Aspergillus* strain of claim 1, wherein the reduced amount and/or less active form of the polypeptide encoded by the heterologously modified *A. niger* orthologue of the *S. cerevisiae* sln1 gene results in a non-mycelium, multi-hyphal tip, pellet phenotype when grown in submerged liquid culture conditions.

18. A method for generating the engineered strain of *Aspergillus* of claim 1, the method comprising: transforming cells of a parental strain of *Aspergillus* with a nucleic acid construct comprising a heterologously modified *A. niger* orthologue of the *S. cerevisiae* sln1 gene as compared to the *A. niger* orthologue of the *S. cerevisiae* sln1 gene of the parental strain flanked by sequence complementary to a locus for the *A. niger* orthologue of the *S. cerevisiae* sln1 gene in the genome of the parental *Aspergillus* strain that facilitates integration of the heterologously modified *A. niger* orthologue of the *S. cerevisiae* sln1 gene into the genomic locus of the *A. niger* orthologue of the *S. cerevisiae* sln1 gene, wherein integration of the heterologously modified *A. niger* orthologue of the *S. cerevisiae* sln1 gene in the transformed cells results in production of a reduced amount and/or less active form of functional *S. cerevisiae* sln1 orthologue of the *S. cerevisiae* SLN1 as compared to cells of the parental *Aspergillus* strain which retains a substantially similar osmotic response to the parental *Aspergillus* strain, thereby generating the engineered strain of *Aspergillus*.

19. The method of claim 18, wherein the nucleic acid construct comprises from 5' to 3, a first portion of the sequence complementary to the locus for the *A. niger* orthologue of the *S. cerevisiae* sln1 gene, a first direct repeat sequence comprising a first copy of the heterologously modified *A. niger* orthologue of the *S. cerevisiae* sln1 gene, a selectable marker gene, a second direct repeat sequence comprising a second copy of the heterologously modified *A. niger* orthologue of the *S. cerevisiae* sln1 gene, and a second portion of the sequence complementary to the locus for the *A. niger* orthologue of the *S. cerevisiae* sln1 gene, wherein the direct repeats provide an unstable integration that can result in loss of the selectable marker gene.

20. The method of claim 19, wherein the nucleic acid construct is split into construct A and construct B, wherein construct A comprises from 5' to 3', the first portion of the sequence complementary to the locus for the *A. niger* orthologue of the *S. cerevisiae* sln1 gene, the first direct repeat sequence comprising a first copy of the heterologously modified *A. niger* orthologue of the *S. cerevisiae* sln1 gene, and a first portion of the selectable marker gene, while construct B comprises from 5' to 3', a second portion of the selectable marker gene, the second direct repeat sequence comprising the second copy of the heterologously modified *A. niger* orthologue of the *S. cerevisiae* sln1 gene, and the second portion of the sequence complementary to the locus for the *S. cerevisiae* sln1 orthologue of the *S. cerevisiae* sln1 gene, wherein the first portion and the second portion of the selectable marker gene comprises overlapping complementary sequence.

21. The method of claim 18, wherein the heterologous modified *A. niger* orthologue of the *S. cerevisiae* sln1 gene is a single nucleotide polymorphism (SNP) containing version of the endogenous *A. niger* orthologue of the *S. cerevisiae* sln1 gene of the parental *Aspergillus* strain, wherein the SNP containing version of the *A. niger* orthologue of the *S. cerevisiae* sln1 gene comprises a nucleotide substitution at position 814 of the *A. niger* orthologue of the *S. cerevisiae* sln1 gene of the parental *Aspergillus* strain.

22. The method of claim 21, wherein the SNP containing version of the *A. niger* orthologue of the *S. cerevisiae* sln1 gene comprises a cytosine to thymine substitution at nucleotide position 814 of the *A. niger* orthologue of the *S. cerevisiae* sln1 gene of the parental *Aspergillus* strain.

23. The method of claim 21, wherein the SNP containing version of the *A. niger* orthologue of the *S. cerevisiae* sln1 gene comprises a nucleic acid sequence of SEQ ID NO: 7.

24. The method of claim 21, wherein the *A. niger* orthologue of the *S. cerevisiae* sln1 gene of the parental *Aspergillus* strain comprises a nucleic acid sequence of SEQ ID NO: 76.

25. The method of claim 21, wherein the SNP-containing version of the *A. niger* orthologue of the *S. cerevisiae* sln1 gene encodes a polypeptide comprising a histidine to tyrosine substitution at amino acid position 272 of the *A. niger* orthologue of the *S. cerevisiae* SLN1.

26. The method of claim 18, wherein the heterologous modified *A. niger* orthologue of the *S. cerevisiae* sln1 gene comprises replacement of the native promoter of the endogenous *A. niger* orthologue of the *S. cerevisiae* sln1 gene of the parental with a promoter that more weakly expresses the *A. niger* orthologue of the *S. cerevisiae* sln1 gene as compared to the native promoter of the *A. niger* orthologue of the *S. cerevisiae* sln1 gene.

27. The method of claim 18, wherein the promoter that more weakly expresses the *A. niger* orthologue of the *S. cerevisiae* sln1 gene as compared to the native promoter of the *A. niger* orthologue of the *S. cerevisiae* sln1 gene b selected from an amyB promoter or a manB promoter.

28. The method of claim 18, wherein the promoter that more weakly expresses the *A. niger* orthologue of *S. cerevisiae* sln1 gene as compared to the native promoter of the *A. niger* orthologue of *S. cerevisiae* sln1 gene has a nucleic acid sequence of SEQ ID NO: 1 or 2.

29. An engineered *Aspergillus* strain comprising a heterologous modification of a nikA gene that produces a reduced amount and/or less active form of a polypeptide encoded by the nikA gene in the engineered *Aspergillus* strain as compared to cells of die parental *Aspergillus* strain, wherein the heterologous modification comprises replacement of the nikA gene of the parental *Aspergillus* strain with a single nucleotide polymorphism (SNP) containing version of the nikA gene, wherein the SNP containing version of the nikA gene comprises a nucleotide substitution at position 814 of the nikA gene of the parental *Aspergillus* strain.

* * * * *

UNITED STATES PATENT AND TRADEMARK OFFICE
CERTIFICATE OF CORRECTION

Page 1 of 2

PATENT NO. : 11,299,741 B2
APPLICATION NO. : 17/245928
DATED : April 12, 2022
INVENTOR(S) : Kenneth S. Bruno et al.

It is certified that error appears in the above-identified patent and that said Letters Patent is hereby corrected as shown below:

In the Claims

At Column 327, Claim number 1, Line number 66:
"to osmotic stress substantial similar to a parental strain of"
Should read:
-- to osmotic stress substantially similar to a parental strain of --

At Column 329, Claim number 2, Line number 11:
"version of the *A. niger* orthologue of the & *cerevisiae* sln1"
Should read:
-- version of the *A. niger* orthologue of the *S. cerevisiae* sln1 --

At Column 329, Claim number 6, Line number 34:
"of an *A. niger* orthologue of *S. cerevisiae* SLN."
Should read:
-- of an *A. niger* orthologue of *S. cerevisiae* SLN1. --

At Column 329, Claim number 7, Line number 37:
"increased level of citric add as compared to the parental"
Should read:
-- increased level of citric acid as compared to the parental --

At Column 329, Claim number 11, Line number 59:
"orthologue of the *S. cererisiae* sln1 gene as compared to the"
Should read:
-- orthologue of the *S. cerevisiae* sln1 gene as compared to the --

Signed and Sealed this
Twentieth Day of September, 2022

Katherine Kelly Vidal
*Director of the United States Patent and Trademark Office*

CERTIFICATE OF CORRECTION (continued)
U.S. Pat. No. 11,299,741 B2

At Column 330, Claim number 18, Line number 42:
"and/or less active form of functional *S. cerevisiae* sln1"
Should read:
-- and/or less active form of functional *A. niger* --

At Column 331, Claim number 20, Line number 6:
"for the S. *cerevisiae* sln1 orthologue of the *S. cerevisiae* sln1"
Should read:
-- for the S. *cerevisiae* sln1 orthologue of the *A. niger* --

At Column 332, Claim number 27, Line number 14:
"the *A. niger* orthologue of the *S. cerevisiae* sln1 gene b"
Should read:
-- the *A. niger* orthologue of the *S. cerevisiae* sln1 gene is --

At Column 332, Claim number 29, Line number 26:
"pared to cells of die parental *Aspergillus* strain, wherein the"
Should read:
-- pared to cells of the parental *Aspergillus* strain, wherein the --